United States Patent
Jones et al.

(10) Patent No.: US 11,033,490 B2
(45) Date of Patent: Jun. 15, 2021

(54) TREATMENT OF A DISEASE OF THE GASTROINTESTINAL TRACT WITH A JAK INHIBITOR AND DEVICES

(71) Applicant: Progenity, Inc., San Diego, CA (US)

(72) Inventors: Mitchell Lawrence Jones, La Jolla, CA (US); Sharat Singh, Rancho Santa Fe, CA (US); Christopher Loren Wahl, San Diego, CA (US); Harry Stylli, La Jolla, CA (US)

(73) Assignee: Progenity, Inc., San Diego, CA (US)

( * ) Notice: Subject to any disclaimer, the term of this patent is extended or adjusted under 35 U.S.C. 154(b) by 68 days.

(21) Appl. No.: 16/468,158

(22) PCT Filed: Dec. 14, 2017

(86) PCT No.: PCT/US2017/066492
§ 371 (c)(1),
(2) Date: Jun. 10, 2019

(87) PCT Pub. No.: WO2018/112245
PCT Pub. Date: Jun. 21, 2018

(65) Prior Publication Data
US 2020/0197295 A1 Jun. 25, 2020

Related U.S. Application Data

(60) Provisional application No. 62/583,832, filed on Nov. 9, 2017, provisional application No. 62/545,380, filed on Aug. 14, 2017, provisional application No. 62/478,919, filed on Mar. 30, 2017, provisional application No. 62/434,374, filed on Dec. 14, 2016.

(51) Int. Cl.
*A61K 9/00* (2006.01)
*A61K 31/519* (2006.01)

(52) U.S. Cl.
CPC .......... *A61K 9/0009* (2013.01); *A61K 9/0004* (2013.01); *A61K 9/0053* (2013.01); *A61K 31/519* (2013.01)

(58) Field of Classification Search
CPC .. A61K 9/0053; A61K 9/0004; A61K 9/4808; A61K 9/08; A61K 9/10; A61K 31/519; A61K 31/00; A61P 35/00; A61M 31/00
See application file for complete search history.

(56) References Cited

U.S. PATENT DOCUMENTS

| | | | |
|---|---|---|---|
| 3,773,919 A | 11/1973 | Boswell et al. |
| 4,120,649 A | 10/1978 | Schechter |
| 4,190,328 A | 2/1980 | Levine et al. |
| 4,223,680 A | 9/1980 | Jobsis |
| 4,292,961 A | 10/1981 | Kawashima |
| 4,522,811 A | 6/1985 | Eppstein et al. |
| 4,665,077 A | 5/1987 | Stringfellow et al. |
| 4,676,980 A | 6/1987 | Segal et al. |
| 4,816,567 A | 3/1989 | Cabilly et al. |
| 4,987,071 A | 1/1991 | Cech et al. |
| 5,114,721 A | 5/1992 | Cohen et al. |
| 5,116,742 A | 5/1992 | Cech et al. |
| 5,314,805 A | 5/1994 | Haugland et al. |
| 5,318,557 A | 6/1994 | Gross |
| 5,516,636 A | 5/1996 | McCapra |
| 5,705,622 A | 1/1998 | McCapra |
| 5,759,808 A | 6/1998 | Casterman et al. |
| 5,763,602 A | 6/1998 | Li et al. |
| 6,171,586 B1 | 1/2001 | Lam et al. |
| 6,251,581 B1 | 6/2001 | Ullman et al. |
| 6,267,958 B1 | 7/2001 | Andya et al. |
| 6,331,530 B1 | 12/2001 | Breslow et al. |
| 6,506,559 B1 | 1/2003 | Fire et al. |
| 6,693,113 B2 | 2/2004 | Lindstrom et al. |
| 7,217,531 B2 | 5/2007 | Singh et al. |
| 7,709,273 B2 | 5/2010 | Singh et al. |
| 8,247,180 B2 | 8/2012 | Pidaparthi et al. |
| 8,394,034 B2 | 3/2013 | Iddan et al. |
| 8,615,284 B2 | 12/2013 | Arneson et al. |
| 8,907,081 B2 | 12/2014 | Vail et al. |
| 9,296,725 B2 | 3/2016 | Harrison et al. |
| 9,309,240 B2 | 4/2016 | Blench et al. |
| 9,324,145 B1 | 4/2016 | Cherevatsky et al. |
| 9,593,313 B2 | 3/2017 | Capron et al. |
| 10,172,598 B2 | 1/2019 | Amoako-Tuffour et al. |
| 2003/0056235 A1 | 3/2003 | Fire et al. |
| 2003/0117491 A1 | 6/2003 | Avni et al. |
| 2003/0191430 A1 | 10/2003 | D'Andrea et al. |
| 2005/0049462 A1 | 3/2005 | Kanazawa |
| 2005/0065441 A1 | 3/2005 | Glukhovsky |
| 2005/0260186 A1 | 11/2005 | Bookbinder et al. |
| 2005/0266074 A1* | 12/2005 | Zilberstein ............. A61B 6/425 424/464 |
| 2006/0069317 A1 | 3/2006 | Horn et al. |
| 2006/0104968 A1 | 5/2006 | Bookbinder et al. |
| 2006/0269485 A1 | 11/2006 | Friedman et al. |
| 2007/0027362 A1 | 2/2007 | Handa et al. |
| 2007/0059316 A1 | 3/2007 | Pallenberg et al. |
| 2008/0051633 A1 | 2/2008 | Blijevsky |
| 2008/0208077 A1 | 8/2008 | Iddan et al. |

(Continued)

FOREIGN PATENT DOCUMENTS

| | | |
|---|---|---|
| CN | 104473611 | 4/2015 |
| EP | 0340109 | 11/1989 |
| JP | 2005-073888 | 3/2005 |
| JP | 2008-500126 | 1/2008 |
| JP | 2015-509744 | 4/2015 |
| JP | 2017-516962 | 6/2017 |
| KR | 100931946 | 12/2009 |
| WO | WO 1988009810 | 12/1988 |
| WO | WO 1990008187 | 7/1990 |
| WO | WO 1990011294 | 10/1990 |

(Continued)

OTHER PUBLICATIONS

Davoodi et al. "Drug delivery systems for programmed and on-demand release," in Advanced Drug Delivery Reviews 132 (2018) 104-138).*

(Continued)

*Primary Examiner* — Blessing M Fubara
(74) *Attorney, Agent, or Firm* — Fish & Richardson P.C.

(57) ABSTRACT

This disclosure features methods and compositions for treating diseases of the gastrointestinal tract with a JAK inhibitor.

18 Claims, 56 Drawing Sheets
Specification includes a Sequence Listing.

(56) References Cited

U.S. PATENT DOCUMENTS

| | | | |
|---|---|---|---|
| 2010/0045786 | A1 | 2/2010 | Kitamura |
| 2011/0125031 | A1 | 5/2011 | Blit et al. |
| 2012/0136209 | A1 | 5/2012 | Kostenich et al. |
| 2013/0013031 | A1 | 1/2013 | Ben-Yehuda et al. |
| 2013/0078248 | A1* | 3/2013 | Gschwind ............... A61P 5/00 424/136.1 |
| 2013/0129675 | A1 | 5/2013 | Priebe et al. |
| 2013/0143915 | A1 | 6/2013 | Ellard et al. |
| 2013/0158344 | A1 | 6/2013 | Taniguchi |
| 2013/0231340 | A1 | 9/2013 | Reader |
| 2014/0296666 | A1 | 10/2014 | Rabinovitz et al. |
| 2015/0118264 | A1 | 4/2015 | Baumhof et al. |
| 2016/0090598 | A1 | 3/2016 | Oestergaard et al. |
| 2016/0213234 | A1 | 7/2016 | Poon et al. |
| 2016/0249793 | A1 | 9/2016 | Wang |
| 2016/0251376 | A1 | 9/2016 | Dahlgren et al. |
| 2016/0376261 | A1* | 12/2016 | Aktoudianakis ..... C07D 413/14 514/234.5 |
| 2017/0006202 | A1 | 1/2017 | Otani et al. |
| 2017/0296092 | A1 | 10/2017 | Jones et al. |
| 2018/0049725 | A1 | 2/2018 | Jones et al. |
| 2018/0070857 | A1 | 3/2018 | Jones et al. |
| 2018/0070928 | A1 | 3/2018 | Jones et al. |
| 2018/0164221 | A1 | 6/2018 | Singh et al. |
| 2018/0168488 | A1 | 6/2018 | Jones et al. |
| 2018/0193003 | A1 | 7/2018 | Jones et al. |
| 2018/0206726 | A1 | 7/2018 | Singh et al. |
| 2018/0279908 | A1 | 10/2018 | Jones et al. |
| 2019/0307434 | A1 | 10/2019 | Jones et al. |

FOREIGN PATENT DOCUMENTS

| | | |
|---|---|---|
| WO | WO 1991001133 | 2/1991 |
| WO | WO 1992021307 | 12/1992 |
| WO | WO 1996027011 | 9/1996 |
| WO | WO 1999042838 | 8/1999 |
| WO | WO 2001045789 | 6/2001 |
| WO | WO 2004066903 | 8/2004 |
| WO | WO 2006044908 | 4/2006 |
| WO | WO 2007024715 | 3/2007 |
| WO | WO 2008024188 | 2/2008 |
| WO | WO 2008053396 | 5/2008 |
| WO | WO 2008104968 | 9/2008 |
| WO | WO 2011004395 | 1/2011 |
| WO | WO 2011016002 | 2/2011 |
| WO | WO 2012158648 | 11/2012 |
| WO | WO 2013088444 | 6/2013 |
| WO | WO 2013120184 | 8/2013 |
| WO | WO 2013188783 | 12/2013 |
| WO | WO 2014188377 | 11/2014 |
| WO | WO 2015061665 | 4/2015 |
| WO | WO 2015099749 | 7/2015 |
| WO | WO 2015103072 | 7/2015 |
| WO | WO 2015112575 | 7/2015 |
| WO | WO 2016049602 | 3/2016 |
| WO | WO 2016193964 | 12/2016 |

OTHER PUBLICATIONS

Xitian et al. "A novel remote controlled capsule for site-specific drug delivery in human GI tract." In International Journal of Pharmaceutics, 382 (2009) 160-164).*

Yungliang et al. (Glatirameracetate ameliorates inflammatory bowel disease in mice through induction of Qa-1-restricted CD8+ regulatory cells, in European J. Immunol. 2013, 43:125-136).*

Abubaker et al., "Inhibition of the JAK2/STAT3 pathway in ovarian cancer results in the loss of cancer stem cell-like characteristics and a reduced tumor burden," BMC Cancer, 2014, 14:317, 22 pages.

Akahane et al., "Anti-Leukemic Activity of the TYK2 Selective Inhibitor Ndi-031301 in T-Cell Acute Lymphoblastic Leukemia," Molecular Pharmacology, Drug Resistance-Lymphoid and Other Diseasses: Poster I, Blood, 2016, 128:1596, 3 pages.

Al-Lazikani et al., "Standard conformations for the canonical structures of immunoglobulins," J. Mol. Biol., 1997, 273:927-948.

Andersen et al., "RNAi using a chitosan/siRNA nanoparticle system: in vitro and in vivo applications," Chitosan/siRNA Nanoparticles, Chapter 6, Methods Mol. Biol., 2009, 555:77-86.

Ashino et al., "JAK1/3 signaling pathways are key initiators of TH2 differentiation and lung allergic responses," J. Allergy Clin. Immunol., 2014, 133(4):1162-1174.

Aslam and Majeed, "Ingestible electronically controlled drug-capsule in the gut," J. Drug Delivery & Therapeutics, 2012, 2(3):1-3.

Baffert et al., "Potent and selective inhibition of polycythemia by the quinoxaline JAK2 inhibitor NVP-BSK805," Mol. Cancer Ther., 2010, 9(7):1945-1955.

Barbeau et al., "Application Note: Screening for inhibitors of TNFa/sTNFR1 Binding using AlphaScreen Technology," Perkin Elmer Technical Note ASC-016, 2002, 5 pages.

Bartel and Szostak, "Isolation of new ribozymes from a large pool of random sequences," Science, 1993, 261:1411-1418.

Bartoli et al., "Efficacy of endoscopic placement of a drug eluting platform with infliximab for the treatment of mucosal lesions in a rat model of experimental colitis," United European Gastroenterology Journal, 2017, 5(5):Suppl. 1, A101.

Basar et al., "Ingestible Wireless Capsule Technology: A Review of Development and Future Indication," International Journal of Antennas and Propagation, 2012, Article ID 807165, 14 pages.

Beattie et al., "Intestinally-restricted Janus Kinase inhibition: a potential approach to maximize the therapeutic index in inflammatory bowel disease therapy," Journal of Inflammation, 2017, 14:28, 11 pages.

Berleman and Auer, "The role of bacterial outer membrane vesicles for intra- and interspecies delivery," Environmental Microbiology, 2012, 15(2):347-354.

Bernkop-Schnurch, "Thiomers: a new generation of mucoadhesive polymer," Adv. Drug Deliv. Rev., 2005, 57(11):1569-1582.

Best et al., "Rederived values of the eight coefficients of the Crohn's Disease Activity Index (CDAI)," Gastroenterology, 1979, 77:843-846.

Bissonnette et al., "A randomized, double-blind, placebo-controlled, dose-escalation study of the safety and efficacy of INCB039110, an oral janus kinase 1 inhibitor, in patients with stable, chronic plaque psoriasis," J. Dermatolog. Treat., 2016, 27(4):332-338.

Boland et al., "Update on Janus Kinase Antagonists in Inflammatory Bowel Disease," Gatstroenterol. Clin. North Am., 2014, 43(3):603-317.

Bordonaro et al., "Comprehensive suppression of all apoptosis-induced proliferation pathways as a proposed approach to colorectal cancer prevention and therapy," PLoS One, 2014, 9(12):e115068.

Brennan et al., "Preparation of bispecific antibodies by chemical recombination of monoclonal immunoglobulin G1 fragments," Science, 1985, 229:81-83.

Brown et al., "Naphthyl ketones: a new class of Janus kinase 3 inhibitors," Bioorg. Med. Chem. Lett., 2000, 10(6):575-579.

Brunius, "Technical aspects of the use of 3',6'-diacetylfluorescein for vital fluorescent staining of bacteria," Current Microbiol., 1980, 4:321-323.

Buyens et al., "Liposome based systems for systemic siRNA delivery: stability in blood sets the requirements for optimal carrier design," J. Control Release, 2012, 158(3):362-370.

Calama et al., "Tofacitinib ameliorates inflammation ion a rat model of airway neutrophilia induced by inhaled LPS," Pulm. Pharmacol. Ther., 2017, 43:60-67.

Cao et al., "Pharmacokinetics, Pharmacodynamics, and Safety of ASP015K (Peficitinib), a New Janus Kinase Inhibitor, in Healthy Subjects," Clin. Pharmacol. Drug Dev., 2016, 5(6):435-449.

Caplen, "A new approach to the inhibition of gene expression," Trends Biotech., 2002, 20:49-51.

Capron et al., "Mo1696. Treatment With P28GST, a Recombinant Enzyme From Schistosome Helminth Parasite Prevents Hapten-Induced Colitis by Inducing a Regulatory Th2 Response," Gastroenterology, 2014, 146(5):S-638.

CAS 457081-03-7, 1 page.

(56) References Cited

OTHER PUBLICATIONS

Chang and Lichtenstein, "Drug Insight: antagonists of tumor-necrosis factor-α in the treatment of inflammatory bowel disease," Nat. Clin. Pract. Gastroenterol. Hepatology, 2006, 3:220-228.

Cheal et al., "Preclinical evaluation of multistep targeting of diasialoganglioside GD2 using an IgG-scFv bispecific antibody with high affinity for GD2 and DOTA metal complex," Mol. Cancer Ther., 2014, 13(7):1803-1812.

Chelius et al., "Structural and functional characterization of the trifunctional antibody catumaxomab," Mabs, 2010, 2(3):309-319.

Choung et al., "Serologic microbial associated markers can predict Crohn's disease behaviour years before disease diagnosis," Aliment. Pharmacol. Ther., 2016, 43(12):1300-1310.

Chow et al., "Emerging treatment options for myelofibrosis: focus on pacritinib," OncoTargets Ther., 2016, 9:2655-2665.

Ciuti et al., "Frontiers of robotic endoscopic capsules: a review," Journal of Micro-Bio Robotics, 11:1-18, 2016.

Coffey et al., "The novel kinase inhibitor PRT062070 (Cerdulatinib) demonstrates efficacy in models of autoimmunity and B-cell cancer," J. Pharmacol. Exp. Ther., 2014, 351(3):538-548.

Collard et al., "The pharmacokinetics of oclacitinib maleate, a Janus kinase inhibitor, in the dog," J. Vet. Pharmacol. Ther., 2013, 37(3):279-285.

Collins and Franzblau, "Microplate alamar blue assay versus BACTEC 460 system for high-throughput screening of compounds against *Mycobacterium tuberculosis* and *Mycobacterium avium*," Antimicrob. Agents Chemother., 1997, 41(5):1004-1009.

Cook et al., "Role of altered growth factor receptor-mediated JAK2 signaling in growth and maintenance of human acute myeloid leukemia stem cells," Blood, 2014, 123:2826-2837.

Cosgrove et al., "A blinded, randomized, placebo-controlled trial of the efficacy and safety of the Janus kinase inhibitor oclacitinib (Apoquel®) in client-owned dogs with atopic dermatitis," Vet. Dermatol., 2013, 24(6):587-597.

Cuesta et al., "Multivalent antibodies: when design surpasses evolution," Trends in Biotechnol., 2010, 28(7):355-362.

Cutolo and Meroni, "Clinical utility of the oral JAK inhibitor tofacitinib in the treatment of rheumatoid arthritis," J. Inflamm. Res., 2013, 6:129-137.

Danese et al., "JAK inhibition using tofacitinib for inflammatory bowel disease treatment: a hub for multiple inflammatory cytokines," Am. J. Physiol. Gastrointest. Liver Physiol., 2016, 310(3):G155-G162.

Daperno et al., "Development and validation of a new, simplified endoscopic activity score for Crohn's disease: the SES-CD," Gastrointest. Endosc., 2004, 60(4):505-512.

Davies, "A comparison of fluorochromes for direct viable counts by image analysis," Lett. Appl. Microbiol., 1991, 13:58.

Deeg et al., "Phase II study of SB1518, an orally available novel JAK2 inhibitor, in patients with myelofibrosis," J. Clin. Oncol., 2011, 29:Abstract 6515, 2 pages.

Degryse and Cools, "JAK kinase inhibitors for the treatment of acute lymphoblastic leukemia," J. Hematol. Oncol., 2015, 8:91, 5 pages.

Deuse et al., "Novel immunosuppression: R348, a JAK3- and Syk-inhibitor attenuates acute cardiac allograft rejection," Transplantation, 2008, 85(6):885-892.

Diaz et al., "Lestaurtinib Inhibition of the JAK/STAT Signaling Pathway in Hodgkin Lymphoma Inhibits Proliferation and Induces Apoptosis," PLoS One, 2011, 6(4):e18856.

Driss et al., "The schistosome glutathione S-transferase P28GST, a unique helminth protein, prevents intestinal inflammation in experimental colitis through a Th2-type response with mucosal eosinophils," Mucosal Immunology, 2016, 9:322-335.

Dugan et al., "A selective, orally bioavailable 1,2,4-triazolo[1,5-a]pyridine-based inhibitor of Janus kinase 2 for use in anticancer therapy: discovery of CEP-33779," J. Med. Chem., 2012, 55(11):5243-5254.

Dumoulin et al., "A camelid antibody fragment inhibits the formation of amyloid fibrils by human lysozyme," Nature, 2003, 424:783-788.

Durie et al., "Prevention of collagen-induced arthritis with an antibody to gp39, the ligand for CD40," Science, 1993, 261:1328-1330.

Durmus et al., "P-glycoprotein (MDR1/ABCB1) and breast cancer resistance protein (BCRP/ABCG2) restrict brain accumulation of the JAK1/2 inhibitor, CYT387," Pharmacol. Res., 2013, 76:9-16.

Elluri et al., "Outer Membrane Vesicles Mediate Transport of Biologically Active Vibrio cholerae Cytolysin (VCC) from *V. cholerae* Strains," PloS One, 2014, 9:e106731, 13 pages.

Elwood et al., "Evaluation of JAK3 Biology in Autoimmune Disease Using a Highly Selective, Irreversible JAK3 Inhibitor," J. Pharmacol. Exp. Ther., 2017, 361(2):229-244.

Farmer et al., "Discovery of VX-509 (Decernotinib): A Potent and Selective Janus Kinase 3 Inhibitor for the Treatment of Autoimmune Diseases," J. Med. Chem., 2015, 58(18):7195-7216.

Faure et al., "Serotonin signaling is altered in irritable bowel syndrome with diarrhea but not in functional dyspepsia in pediatric age patients," Gastroenterology, 2010, 139(1):249-258.

Finck et al., "Treatment of murine lupus with CTLA4Ig," Science, 1994, 265:1225-1227.

Finn et al., "Synthesis and properties of DNA-PNA chimeric oligomers," Nucleic Acids Res., 1996, 24:3357-3363.

Fleischmann et al., "A Randomized, Double-Blind, Placebo-Controlled, Twelve-Week, Dose-Ranging Study of Decernotinib, an Oral Selective JAK-3 Inhibitor, as Monotherapy in Patients With Active Rheumatoid Arthritis," Arthritis Rheumatol., 2015, 67(2):334-343.

Forsyth et al., "SAR and in vivo evaluation of 4-aryl-2-aminoalkylpyrimidines as potent and selective Janus kinase 2 (JAK2) inhibitors," Bioorg. Med. Chem. Lett., 2012, 22(24):7653-7658.

Foster et al., "The Pharmacological Profile of TOP1288, a Narrow Spectrum Kinase Inhibitor (NSKI) in Clinical Development as an Anti-Inflammatory Treatment for Ulcerative Colitis" Gastroenterology, 2017, 152(5):S766.

Fridman et al., "Selective inhibition of JAK1 and JAK2 is efficacious in rodent models of arthritis: preclinical characterization of INCB028050," J. Immunol., 2010, 84(9):5298-5307.

Furqan et al., "Dysregulation of JAK-STAT pathway in hematological malignancies and JAK inhibitors for clinical application," Biomark Res., 2013, 1(1):5, 10 pages.

Furumoto and Gadina, "The arrival of JAK inhibitors: advancing the treatment of immune and hematologic disorders," BioDrugs, 2013, 27(5):431-438.

Gadina, "Advances in kinase inhibition: treating rheumatic diseases and beyond," Curr. Opin. Rheumatol., 2014, 26(2):237-243.

Gadina et al., "Decernotinib: A Next-Generation Jakinib," Arthritis Rheumatol., 2016, 68(1):31-34.

Gant et al., "The application of flow cytometry to the study of bacterial responses to antibiotics," J. Med. Microbiol., 1993, 39:147-154.

Gasink et al., "Abstract 1679: Evaluation of an Interim Crohn's Disease Outcome Measure (PRO-2) Based on 2 Patient-Reported Components (Stool Frequency, Abdominal Pain) of the Crohn's Disease Activity Index (CDAI) in the Ustekinumab CERTIFI Study," ACG Annual Meeting, 2014, S497.

Gautier et al., "α-DNA IV: α-anomeric and β-anomeric tetrathymidylates covalently linked to intercalating oxazolopyridocarbazole. Synthesis, physicochemical properties and poly (rA) binding," Nucleic Acids Res., 1987, 15:6625-6641.

Genovese et al., "Efficacy of VX-509 (decernotinib) in combination with a disease-modifying antirheumatic drug in patients with rheumatoid arthritis: clinical and MRI findings," Ann. Rheum. Dis., 2016, 75(11):1979-1983.

Genovese et al., "Peficitinib, a JAK Inhibitor, in Combination With Limited Conventional Synthetic Disease-Modifying Antirheumatic Drugs in the Treatment of Moderate-to-Severe Rheumatoid Arthritis," Arthritis Rheumatol., 2017, 69(5):932-942.

Geyer et al., "JAK2 inhibitors and their impact in myeloproliferative neoplasms," Hematology, 2012, 7(Suppl):S129-132.

(56) References Cited

OTHER PUBLICATIONS

Ghoreschi et al., "Modulation of Innate and Adaptive Immune Responses by Tofacitinib (CP-690,550)," J. Immunol., 2011, 186(7):4234-4243.
Ghosal, "Importance of secreted bacterial RNA in bacterial-host interactions in the gut," Microbial Pathogenesis, 2017, 104:161-163.
Gillooly et al., "BMS-986165 is a highly potent and selective allosteric inhibitor of Tyk2, blocks IL-12, IL-23 and type I interferon signaling and provides for robust efficacy in preclinical models of systemic lupus erythematosus and inflammatory bowel disease," 2016 ACR/ARHP Annual Meeting, Abstract 11L, 3 pages.
Gonzales et al., "Oclacitinib (APOQUEL(®)) is a novel Janus kinase inhibitor with activity against cytokines involved in allergy," J. Vet. Pharmacol. Ther., 2014, 37(4):317-324.
Goodgame, "Viral infections of the gastrointestinal tract," Curr. Gastroenterol. Rep., 1(4):292-300, 1999.
Gruber et al., "Efficient tumor cell lysis mediated by a bispecific single chain antibody expressed in *Escherichia coli*," J. Immunol., 1994, 152:5368-5374.
Guo et al., "Extracellular domain of 4-1BBL enhanced the antitumoral efficacy of peripheral blood lymphocytes mediated by anti-CD3 x anti-PGP bispecific diabody against human multidrug-resistant leukemia," Cell. Immunol. 251(2):102-108, 2008.
Gupta et al., "A phase 1/2, open-label study evaluating twice-daily administration of momelotinib in myelofibrosis," Haematologica, 2017, 102(1):94-102.
Guschin et al., "A major role for the protein tyrosine kinase JAK1 in the JAK/STAT signal transduction pathway in response to interleukin-6," EMBO J., 1995, 14:1421-1429.
Hammond et al., "Post-transcriptional gene silencing by double-stranded RNA," Nature Rev. Gen., 2001, 2:110-119.
Hanauer et al., "Maintenance infliximab for Crohn's disease: the ACCENT I randomised trial," Lancet., 2002, 359:1541-1549.
Harding et al., "Biopolymer Mucoadhesives," Biotechnol. Genet. Eng. News, 1999, 16(1):41-86.
Harrison et al., "JAK Inhibition with Ruxolitinib versus Best Available Therapy for Myelofibrosis," N. Engl. J. Med., 2012, 366:787-798.
Haselhoff and Gerlach, "Simple RNA enzymes with new and highly specific endoribonuclease activities," Nature, 1988, 334:585-591.
Hasler et al., "VNAR single-domain antibodies specific for BAFF inhibit B cell development by molecular mimicry," Mol. Immunol., 2016, 75:28-37.
Helene, "The anti-gene strategy: control of gene expression by triplex-forming-oligonucleotides," Anticancer Drug Des., 1991, 6(6):569-584.
Helene et al., "Control of gene expression by triple helix-forming oligonucleotides. The antigene strategy," Ann. NY Acad. Sci., 1992, 660:27-36.
Hexner et al., "Lestaurtinib (CEP701) is a JAK2 inhibitor that suppresses JAK2/STAT5 signaling and the proliferation of primary erythroid cells from patients with myeloproliferative disorders," Blood, 2008, 111:5663-5671.
Hexner et al., "Phase I dose escalation study of lestaurtinib in patients with myelofibrosis," Leuk. Lymphoma, 2015, 56(9):2543-2551.
Hirsch et al., "Easily reversible desthiobiotin binding to streptavidin, avidin, and other biotin-binding proteins: uses for protein labeling, detection, and isolation," Anal. Biochem., 2002, 308(2):343-357.
Hoentjen and van Bodegraven, "Safety of anti-tumor necrosis factor therapy in inflammatory bowel disease," World J. Gastroenterol., 2009, 15(17):2067-2073.
Holliger et al., ""Diabodies": small bivalent and bispecific antibody fragments.," Proc. Natl. Acad. Sci. USA, 1993, 90:6444-6448.
Holt et al., "Domain antibodies: proteins for therapy," Trends Biotechnol., 2003, 21(11):484-490.
Hsu and Armstrong, "JAK Inhibitors: Treatment Efficacy and Safety Profile in Patients with Psoriasis," J. Immunol. Res., 2014, Article ID 283617, 8 pages.

Hu et al., "Enhanced antitumor activity of cetwdmab in combination with the Jak inhibitor CYT387 against non-small-cell lung cancer with various genotypes," Mol. Pharm., 2016, 13(2):689-697.
Hudson and Kortt, "High avidity scFv multimers: diabodies and triabodies," J. Immunol. Methods, 1999, 23(1-2):177-189.
Huston et al., "Engineered antibodies take center stage," Human Antibodies, 2001, 10(3-4):127-142.
Hyrup and Nielsen, "Peptide nucleic acids (PNA): synthesis, properties and potential applications," Bioorganic Medicinal Chem., 1996, 4(1):5-23.
Inoue et al., "Sequence-dependent hydrolysis of RNA using modified oligonucleotide splints and RNase H," FEBS Lett., 1987, 215:327-330.
Inoue et al., "Synthesis and hybridization studies on two complementary nona(2'-O-methyl)ribonucleotides," Nucleic Acids Res., 1987, 15:6131-6148.
International Preliminary Report on Patentability in PCT Appln. No. PCT/US2017/025117, dated Jun. 18, 2019, 12 pages.
International Preliminary Report on Patentability in PCT Appln. No. PCT/US2017/066492, dated Jun. 18, 2019, 20 pages.
International Search Report an Written Opinion in Application No. PCT/US2017/025117, dated Jul. 4, 2017, 19 pages.
International Search Report and Written Opinion in PCT Appln. No. PCT/US2017/066492, dated May 28, 2018, 30 pages.
Ioannidis et al., "Discovery of 5-Chloro-N2-[(1S)-1-(5-fluoropyrimidin-2-yl)ethyl]-N4-(5-methyl-1H-pyrazol-3-yl)pyrimidine-2,4-diamine (AZD1480) as a Novel Inhibitor of the Jak/Stat Pathway," J. Med. Chem., 2011, 54:262-276.
Ishizaki et al., "Tyk2 is a therapeutic target for psoriasis-like skin inflammation," Int. Immunol., 2013, 26(5):257-267.
Ito et al., "A novel JAK inhibitor, peficitinib, demonstrates potent efficacy in a rat adjuvant-induced arthritis model," J. Pharmacol. Sci., 2017, 133(1):25-33.
Jamieson et al., "Effect of treatment with a JAK2-selective inhibitor, fedratinib, on bone marrow fibrosis in patients with myelofibrosis," J. Transl. Med., 2015, 13:294, 8 pages.
Janeway, "Immunotherapy by peptides?" Nature, 1989, 341:482-483.
Jang et al., "Discovery of Tyk2 inhibitors via the virtual site-directed fragment-based drug design," Bioorg. Med. Chem. Lett., 2015, 25(18):3947-3952.
Jayaraman et al., "Metabolism and Disposition of Pacritinib (SB1518), an Orally Active Janus Kinase 2 Inhibitor in Preclinical Species and Humans," Drug Metab. Lett., 2015, 9(1):28-47.
Jiang et al., "The JAK2 inhibitor AZD1480 inhibits hepatitis A virus replication I nHuh7 cells," Biochem. Biophys. Res. Commun., 2015, 458(4):908-912.
Jones and Senft, "An improved method to determine cell viability by simultaneous staining-with fluorescein diacetate—propidium iodide," J. Histochem. Cytochem., 1985, 33:77-79.
Jones et al., "Design and Synthesis of a Pan-Janus Kinase Inhibitor Clinical Candidate (PF-06263276) Suitable for Inhaled and Topical Delivery for the Treatment of Inflammatory Diseases of the Lungs and Skin" J. Med. Chem., 2017, 60(2):767-786.
Jostins et al., "Host-microbe interactions have shaped the genetic architecture of inflammatory bowel disease," Nature, 491:119-124, 2012.
Kahl et al., "Safety, tolerability, efficacy and pharmacodynamics of the selective JAK1 inhibitor GSK2586184 in patients with systemic lupus erythematosus," Lupus, 2016, 25(13):1420-1430.
Kanofsky, "Singlet oxygen production by chloroperoxidase-hydrogen peroxide-halide systemes," J. Biol. Chem., 1984, 259:5596-5600.
Kaprelyants and Kell, "Rapid assessment of bacterial viability and vitality by rhodamine 123 and flow cytometry," J. Appl. Bacteriol., 1992, 72:410-422.
Khanna et al., "A retrospective analysis: the development of patient reported outcome measures for the assessment of Crohn's disease activity," Aliment. Pharmacol. Ther., 2015, 41:77-86.
Khanna et al., "A systematic review of measurement of endoscopic disease activity and mucosal healing in Crohn's disease: recommendations for clinical trial design," Inflamm. Bowel Dis., 2014, 20:1850-1861.

(56) References Cited

OTHER PUBLICATIONS

Kharenko et al., "Mucoadhesive drug delivery systems (review)," Pharmaceutical Chemistry Journal, 2009, 43(4):200-208.
Kim et al., "Benzimidazole Derivatives as Potent JAK1-Selective Inhibitors," J. Med. Chem., 2015, 58(18):7596-7602.
Kim et al., "Can Crohn's disease activity index differentiate clinical remission induced by placebo versus biologics treatment?—Analyses of sic clinical trials for Crohn's disease," Gastroenterology, 2014, 146:(5 Suppl. 1): S-368.
Kim et al., "Effective Therapeutic Approach for Head and Neck Cancer by an Engineered Minibody Targeting the EGFR Receptor," PLoS One, 2014, 10(1):e113442, 16 pages.
Kimura et al., "Accumulation of advanced glycation end products of the Maillard reaction with age in human hippocampal neurons," Neurosci. Lett., 1996, 208:53-56.
Kohler and Milstein, "Continuous cultures of fused cells secreting antibody of predefined specificity," Nature, 1975, 256:495-497.
Komrokji et al., "Results of a phase 2 study of pacritinib (SB1518), a JAK2/JAK2(V617F) inhibitor, in patients with myelofibrosis," Blood, Clinical Trials and Observations, 2015, 125(17):2649-2655.
Kontermann and Brinkmann, "Bispecific antibodies," Drug Discovery Today, 2015, 20(7):838-847.
Koppikar et al., "Efficacy of the JAK2 inhibitor INCB16562 in a murine model of MPLW515L-induced thrombocytosis and myelofibrosis," Blood, 2010, 115(4):2919-2927.
Koppikar et al., "Heterodimeric JAK-STAT activation as a mechanism of persistence to JAK2 inhibitor therapy," Nature, 2012, 489(7414):155-159.
Korzenik et al., "Sargramostim for active Crohn's disease" N. Engl. J. Med., 2005, 352:2193-2201.
Kostelny et al., "Formation of a bispecific antibody by the use of leucine zippers," J. Immunol., 1992, 148(5):1547-1553.
Kremer et al., "A Phase IIb Study of ABT-494, a Selective JAK-1 Inhibitor, in Patients With Rheumatoid Arthritis and an Inadequate Response to Anti-Tumor Necrosis Factor Therapy," Arthritis Rheumatol., 2016, 68(12):2867-2877.
Kubo et al., "Baricitinib for the treatment of rheumatoid arthritis," Expert. Rev. Clin. Immunol., 2016, 12(9):911-919.
Kulp and Kuehn, "Biological functions and biogenesis of secreted bacterial outer membrane vesicles," Annual Review of Microbiology, 2010, 64:163-184.
Lai et al., "Identification of chemical inhibitors to human tissue transglutaminase by screening existing drug libraries," Chem. Biol., 2008, 15(9):969-978.
Lemaitre et al., "Specific antiviral activity of a poly(L-lysine)-conjugated oligodeoxyribonucleotide sequence complementary to vesicular stomatitis virus N protein mRNA initiation site," Proc. Natl. Acad. Sci. USA, 1987, 84:648-652.
Lennard-Jones, "Classification of inflammatory bowel disease," Scand. J. Gastroenterol. Suppl., 1989, 170:2-6.
Letsinger et al., "Cholesteryl-conjugated oligonucleotides: synthesis, properties, and activity as inhibitors of replication of human immunodeficiency virus in cell culture," Proc. Natl. Acad. Sci. USA, 1989, 86:6553-6556.
Li et al., "3-O-methylthespesilactam, a new small-molecule anti-cancer pan-JAK inhibitor against A2058 human melanoma cells," Biochem. Pharmacol., 2013, 86(10):1411-1418.
Li et al., "INCB16562, a JAK1/2 Selective Inhibitor, Is Efficacious against Multiple Myeloma Cells and Reverses the Protective Effects of Cytokine and Stromal Cell Support," Neoplasia, 2010, 12(1):28-38.
Li et al., "Selection of similar single domain antibodies from two immune VHH libraries obtained from two alpacas by using different selection methods," Immunol. Lett., 2017, 188:89-95.
Liang et al., "Lead identification of novel and selective TYK2 inhibitors," Eur. J. Med. Chem., 2013, 67:175-187.
Lichtenstein et al., "Management of Crohn's disease in adults," Am. J. Gastroenterol., 2009, 104:465-483.
Lin et al., "Lipid-based nanoparticles in the systemic delivery of siRNA," Nanomedicine, 2014, 9(1):105-120.
Lindmark et al., "Outer membrane vesicle-mediated release of cytolethal distending toxin (CDT) from Campylobacter jejuni," BMC Microbiology, 2009, 9:220, 10 pages.
Ludbrook et al., "Investigation of selective JAK1 inhibitor GSK2586184 for the treatment of psoriasis in a randomized placebo-controlled phase IIa study," Br. J. Dermatol., 2016, 174(5):985-995.
Lv et al., "Concise review: the surface markers and identity of human mesenchymal stem cells," Stem Cells, 2014, 32:1408-1419.
Ma et al., "Cerdulatinib, a novel dual SYK/JAK kinase inhibitor, has broad anti-tumor activity in both ABC and GCB types of diffuse large B cell lymphoma," Oncotarget, 2015, 6(41):43881-43896.
Ma et al., "Discovery and characterization of LY2784544, a small-molecule tyrosine kinase inhibitor of JAK2V617F," Blood Cancer J., 2013, 3:e109, 11 pages.
Mace et al., "Single agent BMS-911543 Jak2 inhibitor has distinct inhibitory effects on STAT5 signaling in genetically engineered mice with pancreatic cancer," Oncotarget, 2015, 6(42):44509-44522.
Mackay and Mackay, "The role of BAFF in B-cell maturation, T-cell activation and autoimmunity," Trends Immunol., 2002, 23:113-115.
Mackay-Wiggan et al., "Oral ruxolitinib induces hair regrowth in patients with moderate-to-severe alopecia areata," JCI Insight, 2016, 1(15):e89790, 10 pages.
Mag and Engels, "Synthesis and selective cleavage of oligodeoxyribonucleotldes containing non-chiral internucieotlde phosphoramidate linkages," Nucleic Acids Res. 1989, 17:5973-5988.
Mahajan et al., "VX-509 (decernotinib) is a potent and selective janus kinase 3 inhibitor that attenuates inflammation in animal models of autoimmune disease," J. Pharmacol., 2015, 353(2):405-414.
Maher, "DNA triple-helix formation: an approach to artificial gene repressors," BioEssays, 1992, 14(12):807-815.
Mary and Modigliani, "Development and validation of an endoscopic index of the severity for Crohn's disease: a prospective multicentre study. Groupe d'Etudes Thérapeutiques des Affections Inflammatoires du Tube Digestif (GETAID)," Gut, 1989, 39:983-989.
Mascarenhas et al., "Primary analysis of a phase II open-label trial of INCB039110, a selective JAK1 inhibitor, in patients with myelofibrosis" Haematologica, 2017, 102(2):327-335.
Masse et al., "Identification of highly potent and selective Tyk2 inhibitors for the treatment of autoimmune diseases through structure-based drug design (THER2P.961)," J. Immunol., 2015, 194(1):67.
McCafferty et al., "Phage antibodies: filamentous phage displaying antibody variable domains," Nature, 1990, 348:552-554.
McFeters et al., "Acridine orange staining reaction as an index of physiological activity in *Escherichia coli*," J. Microbiol. Methods, 1991, 13:87-97.
Menet, "Toward selective TYK2 inhibitors as therapeutic agents for the treatment of inflammatory diseases," Pharm. Pat. Anal., 2014, 3(4):449-466.
Menet et al., "Triazolopyridines as Selective JAK1 Inhibitors: From Hit Identification to GLPG0634," J. Med. Chem., 2014, 57(22):9323-9342.
Meyer et al., "CHZ868, a Type II JAK2 Inhibitor, Reverses Type I JAK Inhibitor Persistence and Demonstrates Efficacy in Myeloproliferative Neoplasms," Cancer Cell, 2015, 28(1):15-28.
Milstein and Cuello, "Hybrid hybridomas and their use in immunohistochemistry," Nature, 1983, 305:537-539.
Minturn et al., "Phase I trial of lestaurtinib for children with refractory neuroblastoma: a new approaches to neuroblastoma therapy consortium study," Cancer Chemother. Pharmacol., 2011, 68(4):1057-1065.
Mitchell et al., "Development and a Practical Synthesis of the JAK2 Inhibitor LY2784544," Org. Process Res. Dev., 2012, 16(1):70-81.
Mohamed et al., "Intestinal stem cells and stem cell-based therapy for intestinal diseases," Cytotechnology, 2015, 67(2):177-189.
Mohamed et al., "Pharmacokinetics, Safety and Tolerability of ABT-494, a Novel Selective JAK 1 Inhibitor, in Healthy Volunteers and Subjects with Rheumatoid Arthritis," Clin. Pharmacokinet., 2016, 55(12):1547-1558.

(56) References Cited

OTHER PUBLICATIONS

Mohan et al., "Interaction between CD40 and its ligand gp39 in the development of murine lupus nephritis," J. Immunol., 1995, 154:1470-1480.
Moisan et al., "White-to-brown metabolic conversion of human adipocytes by JAK inhibition," Nat. Cell Biol., 2015, 17(1):57-67.
Monaghan et al., "The novel JAK inhibitor CYT387 suppresses multiple signalling pathways, prevents proliferation and induces apoptosis in phenotypically diverse myeloma cells," Leukemia, 2011, 25(12):1891-1899.
Morrison et al., "Chimeric human antibody molecules: mouse antigen-binding domains with human constant region domains," Proc. Natl. Acad. Sci. USA, 1984, 81:6851-6855.
Muller et al., "The serotonin system in autism spectrum disorder: From biomarker to animal models," Neuroscience, 2016, 321:24-41.
Nakagawa et al., "Pyridone 6, a Pan-JAK Inhibitor, Ameliorates Allergic Skin Inflammation of NC/Nga Mice via Suppression of Th2 and Enhancement of Th17," J. Immunol., 2011, 187(9):4611-4620.
Namour et al., "Pharmacokinetics and Pharmacokinetic/Pharmacodynamic Modeling of Filgotinib (GLPG0634), a Selective JAK1 Inhibitor, in Support of Phase IIB Dose Selection," Clin. Pharmacokinet., 2015, 54(8):859-874.
Natsume et al., "Fucose removal from complex-type oligosaccharide enhances the antibody-dependent cellular cytotoxicity of single-gene-encoded bispecific antibody comprising of two single-chain antibodies linked to the antibody constant region," J. Biochem., 2006, 140(3):359-368.
Nociari et al., "A novel one-step, highly sensitive fluorometric assay to evaluate cell-mediated cytotoxicity," J. Immunol. Methods, 1998, 213(2):157-167.
Norman, "Selective JAK inhibitors in development for rheumatoid arthritis," Exp. Opin. Investig. Drugs, 2014, 23(8):1067-1077.
Offner et al., "T cell receptor peptide therapy triggers autoregulation of experimental encephalomyelitis," Science, 1991, 251:430-432.
Oi et al., "STAT3 inhibitor, cucurbitacin I, is a novel therapeutic agent for osteosarcoma," Int. J. Oncol., 2016, 49(6):2275-2284.
O'Shea and Plenge, "JAK and STAT signaling molecules in immunoregulation and immunemediated disease," Immunity, 2012, 36:542-550.
O'Shea et al., "Janus kinase Inhibitors in autoimmune diseases," Ann. Rheum. Dis., 2013, 72(2):ii111-ii115.
O'Shea et al., "The JAK-STAT pathway: impact on human disease and therapeutic intervention," Annu. Rev. Med., 2015, 66(1):311-328.
Osorio et al., "Growth Factor and Th2 Cytokine Signaling Pathways Converge at STAT6 to Promote Arginase Expression in Progressive Experimental Visceral Leishmaniasis," PLoS Pathogens, 2014, 10(6):e1004165.
Paddison et al., "Stable suppression of gene expression by RNAi in mammalian cells," Proc. Natl. Acad. Sci. USA., 2002, 99:1443-1448.
Panes et al., "Randomized trial of tofacitinib in active ulcerative colitis: analysis of efficacy base on patient-reported outcomes," BMC Gastroenterology, 2015, 15:14, 10 pages.
Papp et al., "A phase 2a randomized, double-blind, placebo-controlled, sequential dose-escalation study to evaluate the efficacy and safety of ASP015K, a novel Janus kinase inhibitor, in patients with moderate-to-severe psoriasis," Br. J Dermatol., 2015, 173(3):767-776.
Pardanani et al., "CYT387, a selective JAK1/JAK2 inhibitor: in vitro assessment of kinase selectivity and preclinical studies using cell lines and primary cells from polycythemia vera patients," Leukemia, 2009, 23:1441-1445.
Pardanani et al., "Safety and efficacy of CYT387, a JAK1 and JAK2 inhibitor, in myelofibrosis," Leukemia, 2013, 27(6):1322-1327.
Pardanani et al., "Safety and efficacy of TG101348, a selective JAK2 inhibitor, in myelofibrosis," J. Clin. Oncol., 2011, 29:789-796.

Patil and Panyam, "Polymeric Nanoparticles for siRNA Delivery and Gene Silencing," Pharmaceutical Nanotechnol., 2009, 367:195-203.
Patterson et al., "Protein kinase inhibitors in the treatment of inflammatory and autoimmune diseases," Clin. Exp. Immunol., 2014, 176:1-10.
Pedranzini et al., "Pyridone 6, a pan-Janus-activated kinase inhibitor, induces growth inhibition of multiple myeloma cells," Cancer Res., 2006, 66(19):9714-9721.
Peppas et al., "Hydrogels as mucoadhesive and bioadhesive materials: a review," Biomaterials, 1996, 17(16):1553-1561.
Perepelyuk et al., "siRNA-Encapsulated Hybrid Nanoparticles Target Mutant K-ras and Inhibit Metastatic Tumor Burden in a Mouse Model of Lung Cancer," Mol. Ther. Nucleic Acids, 2017, 6:259-268.
Perry-O'Keefe et al., "Peptide nucleic acid pre-gel hybridization: An alternative to Southern hybridization," Proc. Natl. Acad. Sci. USA, 1996, 93:14670-14675.
Petersen et al., "A PNA-DNA linker synthesis of N-((4,4'-Dimethoxytrityloxy)Ethyl)-N-(Thymin-1-Ylacetyl)Glycine," Bioorganic & Medicinal Chemistry Letters, 1995, 5(11):1119-1124.
Pieri et al., "Safety and efficacy of ruxolitinib in splanchnic vein thrombosis associated with myeloproliferative neoplasms," Am. J. Hematol., 2017, 92(2):187-195.
Pleschberger et al., "Generation of a Functional Monomolecular Protein Lattice Consisting of an S-Layer Fusion Protein Comprising the Variable Domain of a Camel Heavy Chain Antibody" Bioconjugate Chem., 2003, 14(2):440-448.
Plimack et al., "AZD1480: A Phase I Study of a Novel JAK2 Inhibitor in Solid Tumors," Oncologist, 2013, 18(7):819-820.
Poljak, "Production and structure of diabodies," Structure, 1994, 2(12):1121-1123.
Purandare et al., "Characterization of BMS-911543, a functionally selective small-molecule inhibitor of JAK2," Leukemia, 2012, 26(2):280-288.
Qi et al., "JSI-124 (Cucurbitacin I) Inhibits Tumor Angiogenesis of Human Breast Cancer Through Reduction of STAT3 Phosphorylation," Am. J. Chin. Med., 2015, 43(2):337-347.
Qin et al., "Inhibition of the JAK/STAT Pathway Protects Against α-Synuclein-Induced Neuroinflammation and Dopaminergic Neurodegeneration," J. Neurosci., 2016, 36(18):5144-5159.
Regula et al., "Targeting key angiogenic pathways with a bispecific CrossMAb optimized for neovascular eye diseases," EMBO Mol. Med., 2017, 9(7):985.
Reinheimer and Demkow, "Comparison of rapid tests for assessing UHT milk sterility," J. Dairy Res., 1990, 57:239-243.
Reusch et al., "A novel tetravalent bispecific TandAb (CD30/CD16A) efficiently recruits NK cells for the lysis of CD30+ tumor cells," mAbs, 2014, 6(3):728-739.
Ringel et al., "Effects of Jak2 type 1 inhibitors NVP-BSK805 and NVP-BVB808 on Jak2 mutation-positive and Bcr-Abl-positive cell lines," Acta Haematol., 2014, 132(1):75-86.
Rosenthal and Mesa, "Janus kinase inhibitors for the treatment of myeloproliferative neoplasms," Exp. Opin. Pharmacother., 2014, 15(9):1265-1276.
Ross et al., "Estimation of cell survival by flow cytometric quantification of fluorescein diacetate/propidium iodide viable cell number," Cancer Research, 1989, 49:3776-3782.
Roszak and Colwell, "Survival strategies of bacteria in the natural environment," Microbiol. Rev., 1987, 51:365-379.
Rudolph et al., "The JAK inhibitor ruxolitinib impairs dendritic cell migration via off-target inhibition of ROCK," Leukemia, 2016, 30(10):2119-2123.
Sahay et al., "Efficiency of siRNA delivery by lipid nanoparticles is limited by endocytic recycling," Nature Biotechnol., 2013, 31:653-658.
Salamat-Miller et al., "The use of mucoadhesive polymers in buccal drug delivery," Adv. Drug Deliv. Reviews, 2005, 57(11):1666-1691.
Sandborn et al., "Adalimumab induction therapy for Crohn disease previously treated with infliximab: a randomized trial," Ann. Intern. Med., 2007, 146:829-838.
Sandborn et al., "Natalizumab induction and maintenance therapy for Crohn's disease," N. Engl. J. Med., 2005, 353:1912-1925.

(56) References Cited

OTHER PUBLICATIONS

Sandborn et al., "Tofacitinib, an Oral Janus Kinase Inhibitor, in Active Ulcerative Colitis," New England J. Med., 2012, 367:616-624.
Sandler et al., "Development of a Crohn's index for survey research," J. Clin. Epidemiol., 1988, 41:451-458.
Santos et al., "Phase 2 study of CEP-701, an orally available JAK2 inhibitor, in patients with primary or post-polycythemia vera/essential thrombocythemia myelofibrosis," Blood, 2010, 115:1131-1136.
Sanz et al., "Antibodies and gene therapy: teaching old 'magic bullets' new tricks," Trends in Immunol., 2004, 25(2):85-91.
Sayyah et al., "Z3, a novel Jak2 tyrosine kinase small-molecule inhibitor that suppresses Jak2-mediated pathologic cell growth," Mol. Cancer. Ther., 2008, 7(8):2308-2318.
Scarabel et al., "Strategies to optimize siRNA delivery to hepatocellular carcinoma cells," Expert Opin. Drug Deliv., 2017, 14(6):797-810.
Schnitzler et al., "Long-term outcome of treatment with infliximab in 614 patients with Crohn's disease: results from a single-centre cohort," Gut, 2009, 58:492-500.
Schoonooghe et al., "Efficient production of human bivalent and trivalent anti-MUC1 Fab-scFv antibodies in Pichia pastoris," BMC Biotechnol., 2009, 9:70, 14 pages.
Schwartz et al., "Type I/II cytokines, JAKs, and new strategies for treating autoimmune diseases," Nat. Rev. Rheum., 2016, 12:25-36.
Seavey et al., "Therapeutic efficacy of CEP-33779, a novel selective JAK2 inhibitor, in a mouse model of colitis-induced colorectal cancer," Mol. Cancer Ther., 2012, 11(4):984-993.
Seo et al., "Cucurbitacin B and cucurbitacin I suppress adipocyte differentiation through inhibition of STAT3 signaling," Food Chem. Toxicol., 2014, 64:217-224.
Shalaby et al., "Development of humanized bispecific antibodies reactive with cytotoxic lymphocytes and tumor cells overexpressing the HER2 protooncogene," J. Exp. Med., 1992, 175:217-225.
Sharp, "RNA interference—2001," Genes Dev., 2001, 15:485-490.
Shen et al., "Outer membrane vesicles of a human commensal mediate immune regulation and disease protection," Cell Host Microbe., 2012, 12(4):509-520.
Shen et al., "P036. Colon targeted delivery of tofacitinib inhibits oxazolone-induced colitis in mice, despite low systemic exposure," Journal of Crohn's and Colitis, 2016, 10(Suppl. 1):S107.
Shide et al., "R723, a selective JAK2 inhibitor, effectively treats JAK2V617F-induced murine myeloproliferative neoplasm," Blood, 2011, 117(25):6866-6875.
Shimizu, "Smart pills for oral drug delivery," Intl. Pharm. Industry, 2014, 6(3):72-74.
Shimokawa et al., "Advanced glycosylation end products in adrenal lipofuscin," J. Gerontol., 1998, 53A:B49-B51.
Simon et al., "Determining target engagement in living systems," Nature Chemical Biology, 9(4):200-205, 2013.
Sjostrom et al., "Membrane vesicle-mediated release of bacterial RNA," Scientific Reports, 2015, 5:15329, 10 pages.
Smith et al., "Single-agent CEP-701, a novel FLT3 inhibitor, shows biologic and clinical activity in patients with relapsed or refractory acute myeloid leukemia," Blood, 2004, 103:3669-3676.
Smolen et al., "Patient-reported outcomes form a randomised phase III study of baricitinib in patients with rheumatoid arthritis and an inadequate response to biological agents (RA-BEACON)," Ann. Rheum. Dis., 2016, 76(4):694-700.
Sokolowska-Wedzina et al., "High-affinity internalizing human scFv-Fc antibody for targeting FGFR1-overexpressing lung cancer," Mol. Cancer Res., 2017, 15(8):1040-1050.
Sonbol et al., "Comprehensive review of JAK inhibitors in myeloproliferative neoplasms," Ther. Adv. Hematol., 2013, 4(1):15-35.
Stijlemans et al., "Efficient Targeting of Conserved Cryptic Epitopes of Infectious Agents by Single Domain Antibodies," J. Biol. Chem., 2004, 279:1256-1261.
Stocks, "Intrabodies: production and promise," Drug Discov. Today, 2004, 9(22):960-966.
Stump et al., "A highly selective, orally active inhibitor of Janus kinase 2, CEP-33779, ablates disease in two mouse models of rheumatoid arthritis," Arthritis Res. Ther., 2011, 13(2):R68.
Suresh et al., "Bispecific monoclonal antibodies from hybrid hybridomas," Methods in Enzymology, 1986, 121:210-288.
Takeuchi et al., "Efficacy and safety of the oral Janus kinase inhibitor peficitinib (ASP015K) monotherapy in patients with moderate to severe rheumatoid arthritis in Japan: a 12-week, randomised, double-blind, placebo-controlled phase IIb study," Ann. Rheum. Dis., 2016, 75(6):1057-1064.
Tanaka, "Recent progress and perspective in JAK inhibitors for rheumatoid arthritis: from bench to bedside," J. Biochem., 2015, 158(3):173-179.
Tangsangasaksri et al., "siRNA-Loaded Polyion Complex Micelle Decorated with Charge-Conversional Polymer Tuned to Undergo Stepwise Response to Intra-Tumoral and Intra-Endosomal pHs for Exerting Enhanced RNAi Efficacy," BioMacromolecules, 2016, 17:246-255.
Teng and Maya, "Absolute bioavailability and regional absorption of ticagrelor in healthy volunteers," Journal of Drug Assessment, 2014, 3(1):43-50.
Than et al., "A review of localization systems for robotic endoscopic capsules," IEEE Trans. Biomed. Eng., 2012, 59(9):2387-2399.
Thia et al., "Short CDAI: development and validation of a shortened and simplified Crohn's disease activity index," Inflamm. Bowel Dis., 2011, 17:105-111.
Thoma et al., "Identification of a Potent Janus Kinase 3 Inhibitor with High Selectivity within the Janus Kinase Family," J. Med. Chem., 2011, 54(1):284-288.
Tiede et al., "Affimer proteins are versatile and renewable affinity reagents," eLife, 2017, 6:e24903, 35 pages.
Timmins et al., "Formulation technology can enable oral delivery of new generation medicines for inflammatory bowel disease," European Industrial Pharmacy, 2016, 31(52):4-18.
Tominaga et al., "A water-soluble tetrazolium salt useful for colorimetric cell viability assay," Anal. Commun., 1999, 36:47-50.
Truelove et al., "Cortisone in ulcerative colitis," L.J. Br. Med. J., 1955, 2:1041-1048.
Tsai et al., "CD19xCD3 DART protein mediates human B-cell depletion in vivo in humanized BLT mice," Mol. Ther. Oncolytics, 2016, 3:15024, 9 pages.
Tsuruta et al., "Liposome encapsulated doxorubicin transfer to the pelvic lymph nodes by endoscopic administration into the bladder wall: a preliminary report," J. Urol., 1997, 157(5):1652-1654.
Tutt et al., "Trispecific F(ab')3 derivatives that use cooperative signaling via the TCR/CD3 complex and CD2 to activate and redirect resting cytotoxic T cells," J. Immunol., 1991, 147:60-69.
Tyner et al., "CYT387, a novel JAK2 inhibitor, induces hematologic responses and normalizes inflammatory cytokines in murine myeloproliferative neoplasms," Blood, 2010, 115(25):5232-5240.
van Assche et al., "The second European evidence-based Consensus on the diagnosis and management of Crohn's disease: Special situations," J. Crohns Colitis., 2010, 4:63-101.
van der Krol et al., "Modulation of eukaryotic gene expression by complementary RNA or DNA sequences," Bio/Techniques, 1988, 6:958-976.
van der Schaar et al., "A novel ingestible electronic drug delivery and monitoring device," Gastrointestinal Endoscopy, 2013, 78(3):520-528.
van Rompaey et al., "Preclinical characterization of GLPG0634, a selective inhibitor of JAK1, for the treatment of inflammatory diseases," J. Immunol., 2013, 191(7):3568-3577.
van Vollenhoven et al., "DRESS syndrome and reversible liver function abnormalities in patients with systemic lupus erythematosus treated with the highly selective JAK-1 inhibitor GSK2586184," Lupus, 2015, 24(6):648-649.
Velayudhan et al., "Demonstration of Functional Similarity of Proposed Biosimilar ABP 501 to Adalimumab," BioDrugs, 2016, 30:339-351.
Velotta et al., "A Novel JAK3 Inhibitor, R348, Attenuates Chronic Airway Allograft Rejection," Transplantation, 2009, 87(5):653-659.

(56) References Cited

OTHER PUBLICATIONS

Vermeire et al., "Clinical remission in patients with moderate-to-severe Crohn's disease treated with filgotinib (the FITZROY study): results from a phase 2, double-blind, randomised, placebo-controlled trial," Lancet, 2017, 389(10066):266-275.
Verstovsek et al., "A phase I, open-label, multi-center study of the JAK2 inhibitor AZD1480 in patients with myelofibrosis," Leuk. Res., 2015, 39(2):157-163.
Verstovsek et al., "Phase 1/2 study of pacritinib, a next generation JAK2/FLT3 inhibitor, in myelofibrosis or other myeloid malignancies," J. Hematol. Oncol., 2016, 9(1):137, 12 pages.
Verstovsek et al., "Phase I evaluation of XL019, an oral, potent, and selective JAK2 inhibitor," Leuk. Res., 2014, 38(3):316-322.
Verstovsek et al., "Phase I Study of LY2784544, a JAK2 Selective Inhibitor, in Patients With Myelofibrosis (MF), Polycythemia Vera (PV), and Essential Thrombocythemia (ET)," Blood, 2013, 122:665, 3 pages.
Visser, "Oxygen requirements of yeasts," Appl. Environ. Microbiol., 1990, 56(12):3785-3792.
Wai et al., "The release of outer membrane vesicles from the strains of enterotoxigenic *Escherichia coli*," Microbiology and Immunology, 1995, 39:451-456.
Walmsley et al., "A simple clinical colitis activity index," Gut, 1998, 43:29-32.
Wan et al., "Discovery of a Highly Selective JAK2 Inhibitor, BMS-911543, for the Treatment of Myeloproliferative Neoplasms," ACS Med. Chem. Lett., 2015, 6(8):850-855.
Wang et al., "Crosstalk between nucleotide synthesis pathways with cellular immunity in constraining hepatitis E virus replications," Antimicrob. Agents Chemother., 2016, 60(5):2834-2848.
Wernig et al., "Efficacy of TG101348, a selective JAK2 inhibitor, in treatment of a murine model of JAK2V617F-induced polycythemia vera," Cancer Cell, 2008, 13(4):311-320.
Wheeler et al., "Intrabody and intrakine strategies for molecular therapy," Mol. Ther., 2006, 8(3):355-366.
White et al., "Assessment of neuronal viability with Alamar blue in cortical and granule cell cultures," J. Neurosci., Methods, 1996, 70:195-200.
Works et al., "Inhibition of TYK2 and JAK1 Ameliorates Imiquimod-Induced Psoriasis-like Dermatitis by Inhibiting IL-22 and the IL-23/IL-17 Axis," J. Immunol., 2014, 193(7):3278-3287.
Wu et al., "Simultaneous targeting of multiple disease mediators by a dual-variable-domain immunoglobulin," Nat. Biotechnol., 2007, 25(11):1290-1297.
Wu et al., "Activity of the Type II JAK2 Inhibitor CHZ868 in B Cell Acute Lymphoblastic Leukemia," Cancer Cell, 2015, 28(1):29-41.
Wu et al., "Improved siRNA delivery efficiency via solvent-induced condensation of micellar nanoparticles," Nanotechnology, 2017, 28(20):204002, 19 pages.
Xu et al., "Constitutive mobilization of CD34+ cells into the peripheral blood in idiopathic myelofibrosis may be due to the action of a number of proteases," Blood, 2005, 105:4508-4515.
Yan et al., "Inhibition of STAT3 with orally active JAK inhibitor, AZD1480, decreases tumor growth in Neuroblastoma and Pediatric Sarcomas in vitro and in vivo," Oncotarget, 2013, 4(3):433-445.
Yang et al., "Impact of PEG chain length on the physical properties and bioactivity of PEGylated chitosan/siRNA nanoparticles in vitro and in vivo," ACS Appl. Mater. Interfaces, 2017, 9(14):12203-12216.
Yokoyama et al., "Tofacitinib, a janus kinase inhibitor demonstrates efficacy in an IL-15 transgenic mouse model that recapitulates pathologic manifestations of celiac disease," J. Clin. Immunol., 2013, 33(3):586-594.
Yoshida et al., "Immunohistochemical study of human advanced glycation end-products (AGE) and growth factors in cardiac tissues of patients on maintenance dialysis and with kidney transplantation," Clin. Nephrol., 1998, 49:273-280.
Yoshida et al., "Low dose CP-690,550 (tofacitinib), a pan-JAK inhibitor, accelerates the onset of experimental autoimmune encephalomyelitis by potentiating Th17 differentiation," Biochem. Biophys. Res. Commun., 2012, 418(2):234-240.
Zapata et al., "Engineering linear F(ab')2 fragments for efficient production in *Escherichia coli* and enhanced antiproliferative activity," Protein Eng., 1995, 8(10):1057-1062.
Zhang et al., "JAK2 inhibitor TG101348 overcomes erlotinib-resistance in non-small cell lung carcinoma cells with mutated EGF receptor," Oncotarget, 2015, 6(16):14329-14343.
Zhi-Jun et al., "A dye-based lymphocyte proliferation assay that permits multiple immunological analyses: mRNA, cytogenetic, apoptosis, and immunophenotyping studies," J. Immunol. Methods, 1997, 210:25-39.
Zon, "Oligonucleotide analogues as potential chemotherapeutic agents," Pharm. Res., 1988, 5:539-549.
Chen et al., "Developing assessment system for wireless capsule endoscopy videos based on event detection," Proc. SPIE, Mar. 2009, 7260(72601G), 11 pages.
Lee et al., "Automatic classification of digestive organs in wireless capsule endoscopy videos," Proceedings of the 2007 ACM symposium on Applied computing, Mar. 2007, 1041-1045.

* cited by examiner

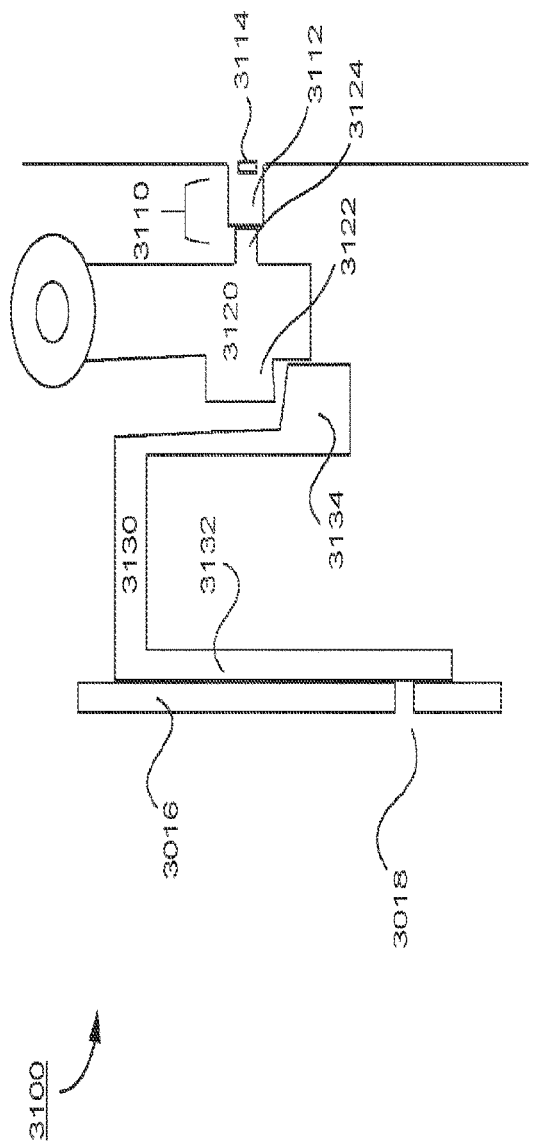
FIG. 23
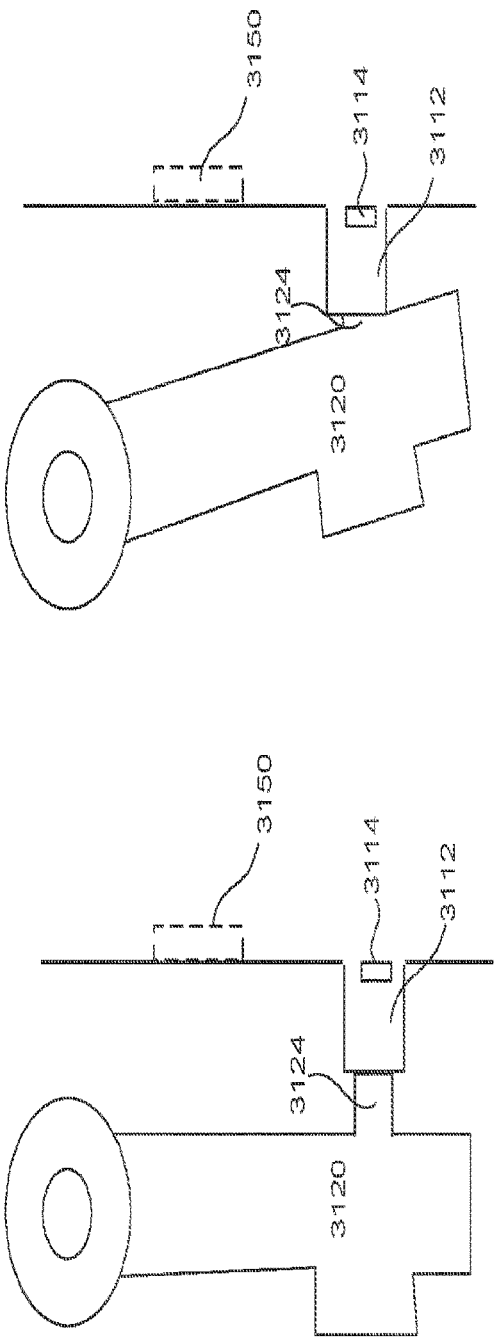
FIG. 24B
FIG. 24A

^Outlier removed from Group 5

| Time | SQ Adalimumab Plasma concentration µgs/ml | Topical Adalimumab Plasma concentration µgs/ml |
|---|---|---|
| 6hrs | 16 +/-8 | 0.01 |
| 12hrs | 13 +/-4 | 0.01 |
| 24hrs | 13 +/-3 | 0.01 |
| 48hrs | 16 +/-5 | 0.01 |

FIG. 52

SEQUENCE LISTING

```
<160> NUMBER OF SEQ ID NOS: 15

<210> SEQ ID NO 1
<211> LENGTH: 5118
<212> TYPE: DNA
<213> ORGANISM: Homo sapiens

<400> SEQUENCE: 1
ggggcgggac gggaggcggt gcgtcgctga gcgcaggccg cggcggccgc ggagtatcct      60
ggagctgcag acagtgcggg cctgcgccca gtcccggctg tcctcgccgc gacccctcct     120
cagccctggg cgcgcgcacg ctggggcccc gcggggctgg ccgcctagcg agcctgccgg     180 tcgacccag ccagcgcagc gacggggcgc tgcctggccc aggcgcacac ggaagtgcgc      240
ttctctgaag tagctttgga aagtagagaa gaaaatccag tttgcttctt ggagaacact     300
ggacagctga ataaatgcag tatctaaata taaaagagga ctgcaatgcc atggctttct     360
gtgctaaaat gaggagctcc aagaagactg aggtgaacct ggaggcccct gagccagggg     420
tggaagtgat cttctatctg tcggacaggg agcccctccg gctgggcagt ggagagtaca     480
cagcagagga actgtgcatc agggctgcac aggcatgccg tatctctcct ctttgtcaca     540
acctctttgc cctgtatgac gagaacacca agctctggta tgctccaaat cgcaccatca     600
ccgttgatga caagatgtcc ctccggctcc actaccggat gaggttctat ttcaccaatt     660
ggcatggaac caacgacaat gagcagtcag tgtggcgtca ttctccaaag aagcagaaaa     720
atggctacga gaaaaaaaag attccagatg caacccctct ccttgatgcc agctcactgg     780
agtatctgtt tgctcaggga cagtatgatt tggtgaaatg cctggctcct attcgagacc     840
ccaagaccga gcaggatgga catgatattg agaacgagtg tctagggatg gctgtcctgg     900
ccatctcaca ctatgccatg atgaagaaga tgcagttgcc agaactgccc aaggacatca     960
```

-continued

```
gctacaagcg atatattcca gaaacattga ataagtccat cagacagagg aaccttctca    1020
ccaggatgcg gataaataat gttttcaagg atttcctaaa ggaatttaac aacaagacca    1080
tttgtgacag cagcgtgtcc acgcatgacc tgaaggtgaa atacttggct accttggaaa    1140
ctttgacaaa acattacggt gctgaaatat ttgagacttc catgttactg atttcatcag    1200
aaaatgagat gaattggttt cattcgaatg acggtggaaa cgttctctac tacgaagtga    1260
tggtgactgg gaatcttgga atccagtgga ggcataaacc aaatgttgtt tctgttgaaa    1320
aggaaaaaaa taaactgaag cggaaaaaac tggaaaataa acacaagaag gatgaggaga    1380
aaaacaagat ccgggaagag tggaacaatt tttcttactt ccctgaaatc actcacattg    1440
taataaagga gtctgtggtc agcattaaca agcaggacaa caagaaaatg gaactgaagc    1500
tctcttccca cgaggaggcc ttgtcctttg tgtccctggt agatggctac ttccggctca    1560
cagcagatgc ccatcattac ctctgcaccg acgtggcccc cccgttgatc gtccacaaca    1620
tacagaatgg ctgtcatggt ccaatctgta cagaatacgc catcaataaa ttgcggcaag    1680
aaggaagcga ggagggatg tacgtgctga ggtggagctg caccgacttt gacaacatcc    1740
tcatgaccgt cacctgcttt gagaagtctg agcaggtgca gggtgcccag aagcagttca    1800
agaactttca gatcgaggtg cagaagggcc gctacagtct gcacggttcg gaccgcagct    1860
tccccagctt gggagacctc atgagccacc tcaagaagca gatcctgcgc acggataaca    1920
tcagcttcat gctaaaacgc tgctgccagc ccaagccccg agaaatctcc aacctgctgg    1980
tggctactaa gaaagcccag gagtggcagc ccgtctaccc catgagccag ctgagtttcg    2040
atcggatcct caagaaggat ctggtgcagg gcgagcacct gggagaggc acgagaacac    2100
acatctattc tgggaccctg atggattaca aggatgacga aggaacttct gaagagaaga    2160
agataaaagt gatcctcaaa gtcttagacc ccagccacag ggatatttcc ctggcctttct    2220
tcgaggcagc cagcatgatg agacaggtct cccacaaaca catcgtgtac ctctatggcg    2280
tctgtgtccg cgacgtggag aatatcatgg tggaagagtt tgtggaaggg ggtcctctgg    2340
atctcttcat gcaccggaaa agcgatgtcc ttaccacacc atggaaattc aaagttgcca    2400
aacagctggc cagtgccctg agctacttgg aggataaaga cctggtccat ggaaatgtgt    2460
gtactaaaaa cctcctcctg gcccgtgagg gcatcgacag tgagtgtggc ccattcatca    2520
agctcagtga ccccggcatc cccattacgg tgctgtctag caagaatgc attgaacgaa    2580
tcccatggat tgctcctgag tgtgttgagg actccaagaa cctgagtgtg gctgctgaca    2640
agtggagctt tggaaccacg ctctgggaaa tctgctacaa tggcgagatc cccttgaaag    2700
acaagacgct gattgagaaa gagagattct atgaaagccg gtgcaggcca gtgacaccat    2760
catgtaagga gctggctgac ctcatgaccc gctgcatgaa ctatgacccc aatcagaggc    2820
cttttcttccg agccatcatg agagacatta ataagcttga gagcagaat ccagatattg    2880
tttcagaaaa aaaaccagca actgaagtgg accccacaca ttttgaaaag cgcttcctaa    2940
agaggatccg tgacttggga gagggccact ttggaaggt tgagctctgc aggtatgacc    3000
ccgaagggga caatacaggg gagcaggtgg ctgttaaatc tctgaagcct gagagtggag    3060
gtaaccacat agctgatctg aaaaaggaaa tcgagatctt aaggaacctc tatcatgaga    3120
acattgtgaa gtacaaagga atctgcacag aagacggagg aaatggtatt aagctcatca    3180
tggaatttct gccttcggga agccttaagg aatatcttcc aaagaataag aacaaaataa    3240
acctcaaaca gcagctaaaa tatgccgttc agatttgtaa ggggatggac tatttgggtt    3300
ctcggcaata cgttcaccgg gacttggcag caagaaatgt ccttgttgag agtgaacacc    3360
```

```
aagtgaaaat tggagacttc ggtttaacca aagcaattga aaccgataag gagtattaca    3420
ccgtcaagga tgaccgggac agccctgtgt tttggtatgc tccagaatgt ttaatgcaat    3480 ctaaattta  tattgcctct gacgtctggt cttttggagt cactctgcat gagctgctga    3540
cttactgtga ttcagattct agtcccatgg ctttgttcct gaaaatgata ggcccaaccc    3600
atggccagat gacagtcaca agacttgtga atacgttaaa agaaggaaaa cgcctgccgt    3660
gcccacctaa ctgtccagat gaggtttatc aacttatgag gaaatgctgg gaattccaac    3720
catccaatcg gacaagcttt cagaaccttta ttgaaggatt tgaagcactt ttaaaataag    3780
aagcatgaat aacatttaaa ttccacagat tatcaagtcc ttctcctgca acaaatgccc    3840
aagtcatttt ttaaaaattt ctaatgaaag aagtttgtgt tctgtccaaa aagtcactga    3900
actcatactt cagtcacatat acatgtataa ggcacactgt agtgcttaat atgtgtaagg    3960
acttcctctt taaatttggt accagtaact tagtgacaca taatgacaac caaaatattt    4020
gaaagcactt aagcactcct ccttgtggaa agaatatacc accatttcat ctggctagtt    4080
caccatcaca actgcattac caaaaggga ttttgaaaa cgaggagttg accaaaataa    4140
tatctgaaga tgattgcttt tccctgctgc cagctgatct gaaatgtttt gctggcacat    4200
taatcataga taaagaaaga ttgatggact tagccctcaa atttcagtat ctatacagta    4260
ctagaccatg cattcttaaa atattagata ccaggtagta tatattgttt ctgtacaaaa    4320
atgactgtat tctctcacca gtaggactta aactttgttt ctccagtggc ttagctcctg    4380
ttcctttggg tgatcactag cacccatttt tgagaaagct ggttctacat gggggatag    4440 ctgtggaata gataatttgc tgcatgttaa ttctcaagaa ctaagcctgt gccagtgctt    4500
tcctaagcag tatacctta atcagaactc attcccagaa cctggatgct attacacatg    4560
cttttaagaa acgtcaatgt atatccttt ataactctac cactttgggg caagctattc    4620
cagcactggt tttgaatgct gtatgcaacc agtctgaata ccacatacgc tgcactgttc    4680 ttagagggt tccatactta ccaccgatct acaagggttg atccctgttt ttaccatcaa    4740
tcatcaccct gtggtgcaac acttgaaaga cccggctaga ggcactatgg acttcaggat    4800
ccactagaca gttttcagtt tgcttggagg tagctgggta atcaaaaatg tttagtcatt    4860
gattcaatgt gaacgattac ggtctttatg accaagagtc tgaaaatctt tttgttatgc    4920
tgtttagtat tcgtttgata ttgttacttt tcacctgttg agcccaaatt caggattggt    4980
tcagtggcag caatgaagtt gccatttaaa tttgttcata gcctacatca ccaaggtctc    5040
tgtgtcaaac ctgtggccac tctatatgca ctttgtttac tctttataca aataaatata    5100
ctaaagactt tacatgca                                                 5118

<210> SEQ ID NO 2
<211> LENGTH: 5021
<212> TYPE: DNA
<213> ORGANISM: Homo sapiens

<400> SEQUENCE: 2
agaagcggag cgtatacgga ggaggcggga tgcatttctg catcgagcgc acaaagttat      60
ctaaaacagt tcatgctgct gaaaacctcc ttcctggcag atgtccctca accctactgg     120
tgcctggctt ctgagacaca cgcttctctg aagtagcttt ggaaagtaga aagaaaatc      180 cagtttgctt cttggagaac actggacagc tgaataaatg cagtatctaa atataaaaga     240
ggactgcaat gccatggctt tctgtgctaa aatgaggagc tccaagaaga ctgaggtgaa     300
cctggaggcc cctgagccag gggtggaagt gatcttctat ctgtcggaca gggagcccct     360
```

-continued

```
ccggctgggc agtggagagt acacagcaga ggaactgtgc atcagggctg cacaggcatg      420
ccgtatctct cctctttgtc acaacctctt tgccctgtat gacgagaaca ccaagctctg      480
gtatgctcca atcgcacca tcaccgttga tgacaagatg tccctccggc tccactaccg      540
gatgaggttc tatttcacca attggcatgg aaccaacgac aatgagcagt cagtgtggcg      600
tcattctcca agaagcaga aaaatggcta cgagaaaaaa aagattccag atgcaacccc      660
tctccttgat gccagctcac tggagtatct gtttgctcag ggacagtatg atttggtgaa      720
atgcctggct cctattcgag accccaagac cgagcaggat ggacatgata ttgagaacga      780
gtgtctaggg atggctgtcc tggccatctc acactatgcc atgatgaaga agatgcagtt      840
gccagaactg cccaaggaca tcagctacaa gcgatatatt ccagaaacat gaataagtc      900
catcagacag aggaaccttc tcaccaggat gcggataaat aatgttttca aggatttcct      960
aaaggaattt aacaacaaga ccatttgtga cagcagcgtg tccacgcatg acctgaaggt     1020
gaaatacttg gctaccttgg aaactttgac aaaacattac ggtgctgaaa tatttgagac     1080
ttccatgtta ctgatttcat cagaaaatga gatgaattgg tttcattcga atgacggtgg     1140
aaacgttctc tactacgaag tgatggtgac tgggaatctt ggaatccagt ggaggcataa     1200
accaaatgtt gtttctgttg aaaaggaaaa aaataaactg aagcggaaaa aactggaaaa     1260
taaacacaag aaggatgagg agaaaaacaa gatccgggaa gagtggaaca attttttctta    1320
cttccctgaa atcactcaca ttgtaataaa ggagtctgtg gtcagcatta caagcagga     1380
caacaagaaa atggaactga agctctcttc ccacgaggag gccttgtcct ttgtgtccct     1440
ggtagatggc tacttccggc tcacagcaga tgcccatcat tacctctgca ccgacgtggc     1500
cccccgttg atcgtccaca acatacagaa tggctgtcat ggtccaatct gtacagaata     1560
cgccatcaat aaattgcggc aagaaggaag cgaggagggg atgtacgtgc tgaggtggag     1620
ctgcaccgac tttgacaaca tcctcatgac cgtcacctgc tttgagaagt ctgagcaggt     1680
gcagggtgcc cagaagcagt tcaagaactt tcagatcgag gtgcagaagg ccgctacag      1740
tctgcacggt tcggaccgca gcttccccag cttgggagac ctcatgagcc acctcaagaa     1800
gcagatcctg cgcacggata acatcagctt catgctaaaa cgctgctgcc agcccaagcc     1860
ccgagaaatc tccaacctgc tggtggctac taagaaagcc caggagtggc agcccgtcta     1920
ccccatgagc cagctgagtt cgatcggat cctcaagaag gatctggtgc agggcgagca     1980
ccttgggaga ggcacgagaa cacacatcta ttctgggacc ctgatggatt acaaggatga     2040
cgaaggaact tctgaagaga agaagataaa agtgatcctc aaagtcttag accccagcca     2100
cagggatatt tccctggcct tcttcgaggc agccagcatg atgagacagg tctcccacaa     2160
acacatcgtg tacctctatg gcgtctgtgt ccgcgacgtg gagaatatca tggtggaaga     2220
gtttgtggaa gggggtcctc tggatctctt catgcaccgg aaaagcgatg tccttaccac     2280
accatggaaa ttcaaagttg ccaaacagct ggccagtgcc ctgagctact ggaggataa     2340
agacctggtc catggaaatg tgtgtactaa aaacctcctc ctggcccgtg agggcatcga     2400
cagtgagtgt ggcccattca tcaagctcag tgaccccggc atccccatta cggtgctgtc     2460
taggcaagaa tgcattgaac gaatccatg gattgctcct gagtgtgttg aggactccaa     2520
gaacctgagt gtggctgctg acaagtggag ctttggaacc acgctctggg aaatctgcta     2580
caatggcgag atccccttga agacaagac gctgattgag aaagagagat tctatgaaag     2640
ccggtgcagg ccagtgacac catcatgtaa ggagctggct gacctcatga cccgctgcat     2700
gaactatgac cccaatcaga ggccttcctt ccgagccatc atgagagaca ttaataagct     2760
```

```
tgaagagcag aatccagata ttgtttcaga aaaaaaacca gcaactgaag tggaccccac   2820 acatttgaa aagcgcttcc taaagaggat ccgtgacttg ggagagggcc actttgggaa    2880
ggttgagctc tgcaggtatg accccgaagg ggacaataca ggggagcagg tggctgttaa   2940
atctctgaag cctgagagtg gaggtaacca catagctgat ctgaaaaagg aaatcgagat   3000
cttaaggaac ctctatcatg agaacattgt gaagtacaaa ggaatctgca cagaagacgg   3060
aggaaatggt attaagctca tcatggaatt tctgccttcg ggaagcctta aggaatatct   3120
tccaaagaat aagaacaaaa taaacctcaa acagcagcta aaatatgccg ttcagatttg   3180
taaggggatg gactatttgg gttctcggca atacgttcac cgggacttgg cagcaagaaa   3240
tgtccttgtt gagagtgaac accaagtgaa aattggagac ttcggtttaa ccaaagcaat   3300
tgaaaccgat aaggagtatt acaccgtcaa ggatgaccgg gacagccctg tgttttggta   3360
tgctccagaa tgtttaatgc aatctaaatt ttatattgcc tctgacgtct ggtcttttgg   3420
agtcactctg catgagctgc tgacttactg tgattcagat tctagtccca tggctttgtt   3480
cctgaaaatg ataggcccaa cccatggcca gatgacagtc acaagacttg tgaatacgtt   3540
aaaagaagga aaacgcctgc cgtgcccacc taactgtcca gatgaggttt atcaacttat   3600
gaggaaatgc tgggaattcc aaccatccaa tcggacaagc tttcagaacc ttattgaagg   3660
atttgaagca cttttaaaat aagaagcatg aataacattt aaattccaca gattatcaag   3720
tccttctcct gcaacaaatg cccaagtcat ttttttaaaa tttctaatga agaagtttg    3780 tgttctgtcc aaaaagtcac tgaactcata cttcagtaca tatacatgta taaggcacac   3840
tgtagtgctt aatatgtgta aggacttcct ctttaaattt ggtaccagta acttagtgac   3900
acataatgac aaccaaaata tttgaaagca cttaagcact cctccttgtg aaagaatat    3960 accaccattt catctggcta gttcaccatc acaactgcat taccaaaagg ggattttga    4020 aaacgaggag ttgaccaaaa taatatctga agatgattgc ttttccctgc tgccagctga   4080
tctgaaatgt tttgctggca cattaatcat agataaagaa agattgatgg acttagccct   4140
caaatttcag tatctataca gtactagacc atgcattctt aaaatattag ataccaggta   4200
gtatatattg tttctgtaca aaatgactg tattctctca ccagtaggac ttaaactttg    4260
tttctccagt ggcttagctc ctgttccttt gggtgatcac tagcacccat ttttgagaaa   4320
gctggttcta catgggggga tagctgtgga atagataatt tgctgcatgt taattctcaa   4380
gaactaagcc tgtgccagtg cttttcctaag cagtatacct ttaatcagaa ctcattccca   4440
gaacctggat gctattacac atgcttttaa gaaacgtcaa tgtatatcct tttataactc   4500
taccactttg gggcaagcta ttccagcact ggttttgaat gctgtatgca accagtctga   4560
ataccacata cgctgcactg ttcttagagg gttccatac ttaccaccga tctacaaggg    4620
ttgatccctg ttttaccat caatcatcac cctgtggtgc aacacttgaa agacccggct    4680
agaggcacta tggacttcag gatccactag acagttttca gtttgcttgg aggtagctgg   4740
gtaatcaaaa atgtttagtc attgattcaa tgtgaacgat tacggtcttt atgaccaaga   4800
gtctgaaaat cttttttgtta tgctgtttag tattcgtttg atattgttac ttttcacctg   4860
ttgagcccaa attcaggatt ggttcagtgg cagcaatgaa gttgccattt aaatttgttc   4920
atagcctaca tcaccaaggt ctctgtgtca aacctgtggc cactctatat gcacttttgtt  4980 tactcttat acaaataaat atactaaaga ctttacatgc a                       5021
```

```
<210> SEQ ID NO 3
<211> LENGTH: 5024
<212> TYPE: DNA
<213> ORGANISM: Homo sapiens

<400> SEQUENCE: 3
atctatcaca tggcagagat agaataaaaa cagaaaaatg gcgacggtca cgttgtggcg      60
agccttgctg cgtcattaga taatcctcat gcaaatagcg ggaagaacaa aggaagggga     120
gcccgggacc cccgggggcg cagcgcttct ctgaagtagc tttggaaagt agagaagaaa     180
atccagtttg cttcttggag aacactggac agctgaataa atgcagtatc taaatataaa     240
agaggactgc aatgccatgg ctttctgtgc taaaatgagg agctccaaga agactgaggt     300
gaacctggag gcccctgagc caggggtgga agtgatcttc tatctgtcgg acagggagcc     360
cctccggctg ggcagtggag agtacacagc agaggaactg tgcatcaggg ctgcacaggc     420
atgccgtatc tctcctcttt gtcacaacct ctttgccctg tatgacgaga acaccaagct     480
ctggtatgct ccaaatcgca ccatcaccgt tgatgacaag atgtccctcc ggctccacta     540
ccggatgagg ttctatttca ccaattggca tggaaccaac gacaatgagc agtcagtgtg     600
gcgtcattct ccaaagaagc agaaaaatgg ctacgaaaa aaaagattc cagatgcaac      660 ccctctcctt gatgccagct cactggagta tctgtttgct cagggacagt atgatttggt     720
gaaatgcctg gctcctattc gagaccccaa gaccgagcag gatggacatg atattgagaa     780
cgagtgtcta gggatggctg tcctggccat ctcacactat gccatgatga agaagatgca     840
gttgccagaa ctgcccaagg acatcagcta aagcgatat attccagaaa cattgaataa      900
gtccatcaga cagaggaacc ttctcaccag gatgcggata atatgtttt tcaaggattt      960 cctaaaggaa tttaacaaca agaccatttg tgacagcagc gtgtccacgc atgacctgaa    1020
ggtgaaatac ttggctacct tggaaacttt gacaaaacat tacggtgctg aaatatttga    1080
gacttccatg ttactgattt catcagaaaa tgagatgaat tggtttcatt cgaatgacgg    1140
tggaaacgtt ctctactacg aagtgatggt gactgggaat cttggaatcc agtggaggca    1200
taaaccaaat gttgtttctg ttgaaaagga aaaaataaa ctgaagcgga aaaaactgga     1260
aaataaacac aagaaggatg aggagaaaaa caagatccgg gaagagtgga caattttttc    1320
ttacttccct gaaatcactc acattgtaat aaaggagtct gtggtcagca ttaacaagca    1380
ggacaacaag aaaatggaac tgaagctctc ttcccacgag gaggccttgt cctttgtgtc    1440
cctggtagat ggctacttcc ggctcacagc agatgcccat cattacctct gcaccgacgt    1500
ggcccccccg ttgatcgtcc acaacataca gaatggctgt catggtccaa tctgtacaga    1560
atacgccatc aataaattgc ggcaagaagg aagcgaggag gggatgtacg tgctgaggtg    1620
gagctgcacc gactttgaca acatcctcat gaccgtcacc tgctttgaga agtctgagca    1680
ggtgcagggt gccagaagc agttcaagaa ctttcagatc gaggtgcaga agggccgcta     1740
cagtctgcac ggttcggacc gcagcttccc cagcttggga gacctcatga gccacctcaa    1800
gaagcagatc ctgcgcacgg ataacatcag cttcatgcta aaacgctgct gccagcccaa    1860
gccccgagaa atctccaacc tgctggtggc tactaagaaa gcccaggagt ggcagcccgt    1920
ctaccccatg agccagctga gtttcgatcg gatcctcaag aaggatctgg tgcagggcga    1980 gcacttggg agaggcacga gaacacacat ctattctggg accctgatgg attacaagga     2040
tgacgaagga acttctgaag agaagaagat aaaagtgatc ctcaaagtct tagacccag      2100 ccacagggat atttccctgg ccttcttcga ggcagccagc atgatgagac aggtctccca    2160
```

```
caaacacatc gtgtacctct atggcgtctg tgtccgcgac gtggagaata tcatggtgga    2220
agagtttgtg aaggggggtc ctctggatct cttcatgcac cggaaaagcg atgtccttac    2280
cacaccatgg aaattcaaag ttgccaaaca gctggccagt gccctgagct acttggagga    2340
taaagacctg gtccatggaa atgtgtgtac taaaaacctc ctcctggccc gtgagggcat    2400
cgacagtgag tgtggcccat tcatcaagct cagtgacccc ggcatcccca ttacggtgct    2460
gtctaggcaa gaatgcattg aacgaatccc atggattgct cctgagtgtg ttgaggactc    2520
caagaacctg agtgtggctg ctgacaagtg gagctttgga accacgctct gggaaatctg    2580
ctacaatggc gagatcccct tgaaagacaa gacgctgatt gagaaagaga gattctatga    2640
aagccggtgc aggccagtga caccatcatg taaggagctg gctgacctca tgacccgctg    2700
catgaactat gaccccaatc agaggccttt cttccgagcc atcatgagag acattaataa    2760
gcttgaagag cagaatccag atattgtttc agaaaaaaaa ccagcaactg aagtggaccc    2820
cacacatttt gaaaagcgct tcctaaagag gatccgtgac ttgggagagg gccactttgg    2880
gaaggttgag ctctgcaggt atgaccccga agggacaat acaggggagc aggtggctgt    2940
taaatctctg aagcctgaga gtggaggtaa ccacatagct gatctgaaaa aggaaatcga    3000
gatcttaagg aacctctatc atgagaacat tgtgaagtac aaaggaatct gcacagaaga    3060
cggaggaaat ggtattaagc tcatcatgga atttctgcct tcgggaagcc ttaaggaata    3120
tcttccaaag aataagaaca aaataaacct caaacagcag ctaaaatatg ccgttcagat    3180
ttgtaagggg atggactatt tgggttctcg gcaatacgtt caccgggact ggcagcaag    3240 aaatgtcctt gttgagagtg aacaccaagt gaaaattgga gacttcggtt taaccaaagc    3300
aattgaaacc gataaggagt attacaccgt caaggatgac cgggacagcc ctgtgttttg    3360
gtatgctcca gaatgtttaa tgcaatctaa attttatatt gcctctgacg tctggtcttt    3420
tggagtcact ctgcatgagc tgctgactta ctgtgattca gattctagtc ccatggcttt    3480
gttcctgaaa atgataggcc caacccatgg ccagatgaca gtcacaagac ttgtgaatac    3540
gttaaaagaa ggaaaacgcc tgccgtgccc acctaactgt ccagatgagg tttatcaact    3600
tatgaggaaa tgctgggaat tccaaccatc caatcggaca agctttcaga accttattga    3660
aggatttgaa gcacttttaa aataagaagc atgaataaca tttaaattcc acagattatc    3720
aagtccttct cctgcaacaa atgcccaagt catttttaa aaatttctaa tgaaagaagt    3780
ttgtgttctg tccaaaaagt cactgaactc atacttcagt acatatacat gtataaggca    3840
cactgtagtg cttaatatgt gtaaggactt cctcttaaa tttggtacca gtaacttagt    3900
gacacataat gacaaccaaa atatttgaaa gcacttaagc actcctcctt gtggaaagaa    3960
tataccacca tttcatctgg ctagttcacc atcacaactg cattaccaaa agggattttt    4020
tgaaaacgag gagttgacca aaataatatc tgaagatgat tgcttttccc tgctgccagc    4080
tgatctgaaa tgttttgctg gcacattaat catagataaa gaagattga tggacttagc    4140 cctcaaattt cagtatctat acagtactag accatgcatt cttaaaatat tagataccag    4200
gtagtatata ttgttttctgt acaaaaatga ctgtattctc tcaccagtag gacttaaact    4260
ttgtttctcc agtggcttag ctcctgttcc tttgggtgat cactagcacc cattttttgag    4320 aaagctggtt ctacatgggg ggatagctgt ggaatagata atttgctgca tgttaattct    4380
caagaactaa gcctgtgcca gtgctttcct aagcagtata cctttaatca gaactcattc    4440
ccagaacctg gatgctatta cacatgcttt taagaaacgt caatgtatat cctttttataa    4500 ctctaccact ttggggcaag ctattccagc actggttttg aatgctgtat gcaaccagtc    4560
```

| | |
|---|---|
| tgaataccac atacgctgca ctgttcttag agggtttcca tacttaccac cgatctacaa | 4620 |
| gggttgatcc ctgttttttac catcaatcat caccctgtgg tgcaacactt gaaagacccg | 4680 |
| gctagaggca ctatggactt caggatccac tagacagttt tcagtttgct tggaggtagc | 4740 |
| tgggtaatca aaaatgttta gtcattgatt caatgtgaac gattacggtc tttatgacca | 4800 |
| agagtctgaa aatcttttttg ttatgctgtt tagtattcgt ttgatattgt tactttttcac | 4860 |
| ctgttgagcc caaattcagg attggttcag tggcagcaat gaagttgcca tttaaatttg | 4920 |
| ttcatagcct acatcaccaa ggtctctgtg tcaaacctgt ggccactcta tatgcactttt | 4980 |
| gtttactctt tatacaaata aatatactaa agactttaca tgca | 5024 |

<210> SEQ ID NO 4
<211> LENGTH: 5283
<212> TYPE: DNA
<213> ORGANISM: Homo sapiens

<400> SEQUENCE: 4

| | |
|---|---|
| atctatcaca tggcagagat agaataaaaa cagaaaaatg gcgacggtca cgttgtggcg | 60 |
| agccttgctg cgtcattaga taatcctcat gcaaatagcg ggaagaacaa aggaaggggga | 120 |
| gcccgggacc cccgggggcg caggatccgg cgggaggagt ctaagaggag gaggcggcgg | 180 |
| tgccggagga ggaggaggag ggagggagaa gagaggaaga ccggagtccc cgcggcggcg | 240 |
| gcggtccgga gagagggcga gccccgcgcg gcgccgggga ccgggcgcta ccacgaggcc | 300 |
| gggacgctgg agtctgggtt atctaaaaca gttcatgctg ctgaaaacct ccttcctggc | 360 |
| agatgtccct caaccctact ggtgcctggc ttctgagaca cacgcttctc tgaagtagct | 420 |
| ttggaaagta gagaagaaaa tccagtttgc ttcttggaga acactggaca gctgaataaa | 480 |
| tgcagtatct aaatataaaa gaggactgca atgccatggc tttctgtgct aaaatgagga | 540 |
| gctccaagaa gactgaggtg aacctggagg cccctgagcc aggggtggaa gtgatcttct | 600 |
| atctgtcgga cagggagccc ctccggctgg gcagtggaga gtacacagca gaggaactgt | 660 |
| gcatcagggc tgcacaggca tgccgtatct ctcctctttg tcacaacctc tttgccctgt | 720 |
| atgacgagaa caccaagctc tggtatgctc caaatcgcac catcaccgtt gatgacaaga | 780 |
| tgtccctccg gctccactac cggatgaggt tctatttcac caattggcat ggaaccaacg | 840 |
| acaatgagca gtcagtgtgg cgtcattctc caaagaagca gaaaaatggc tacgagaaaa | 900 |
| aaagattcc agatgcaacc cctctccttg atgccagctc actggagtat ctgtttgctc | 960 |
| agggacagta tgatttggtg aaatgcctgg ctcctattcg agaccccaag accgagcagg | 1020 |
| atggacatga tattgagaac gagtgtctag ggatggctgt cctggccatc tcacactatg | 1080 |
| ccatgatgaa gaagatgcag ttgccagaac tgcccaagga catcagctac aagcgatata | 1140 |
| ttccagaaac attgaataag tccatcagac agaggaacct tctcaccagg atgcggataa | 1200 |
| ataatgttttt caaggatttc ctaaaggaat ttaacaacaa gaccatttgt gacagcagcg | 1260 |
| tgtccacgca tgacctgaag gtgaaatact ggctaccctt ggaaactttg acaaacatt | 1320 |
| acggtgctga atatttgag acttccatgt tactgatttc atcagaaaat gagatgaatt | 1380 |
| ggtttcattc gaatgacggt ggaaacgttc tctactacga agtgatggtg actgggaatc | 1440 |
| ttggaatcca gtggaggcat aaaccaaatg ttgtttctgt tgaaaaggaa aaaaataaac | 1500 |
| tgaagcggaa aaaactggaa aataaacaca gaaggatga ggagaaaaac aagatccggg | 1560 |
| aagagtggaa caatttttct tacttccctg aaatcactca cattgtaata aaggagtctg | 1620 |
| tggtcagcat taacaagcag gacaacaaga aaatggaact gaagctctct tcccacgagg | 1680 |

-continued

```
aggccttgtc ctttgtgtcc ctggtagatg gctacttccg gctcacagca gatgcccatc    1740
attacctctg caccgacgtg gcccccccgt tgatcgtcca caacatacag aatggctgtc    1800
atggtccaat ctgtacagaa tacgccatca ataaattgcg gcaagaagga agcgaggagg    1860
ggatgtacgt gctgaggtgg agctgcaccg actttgacaa catcctcatg accgtcacct    1920
gctttgagaa gtctgagcag gtgcagggtg cccagaagca gttcaagaac tttcagatcg    1980
aggtgcagaa gggccgctac agtctgcacg gttcggaccg cagcttcccc agcttgggag    2040
acctcatgag ccacctcaag aagcagatcc tgcgcacgga taacatcagc ttcatgctaa    2100
aacgctgctg ccagcccaag ccccgagaaa tctccaacct gctggtggct actaagaaag    2160
cccaggagtg gcagcccgtc tacccccatga gccagctgag tttcgatcgg atcctcaaga    2220
aggatctggt gcagggcgag caccttggga gaggcacgag aacacacatc tattctggga    2280
ccctgatgga ttacaaggat gacgaaggaa cttctgaaga gaagaagata aaagtgatcc    2340
tcaaagtctt agaccccagc cacagggata tttccctggc cttcttcgag gcagccagca    2400
tgatgagaca ggtctcccac aaacacatcg tgtacctcta tggcgtctgt gtccgcgacg    2460
tggagaatat catggtggaa gagtttgtgg aaggggtcc tctggatctc ttcatgcacc    2520
ggaaaagcga tgtccttacc acaccatgga aattcaaagt tgccaaacag ctggccagtg    2580
ccctgagcta cttggaggat aaagacctgg tccatggaaa tgtgtgtact aaaaacctcc    2640
tcctggcccg tgagggcatc gacagtgagt gtggcccatt catcaagctc agtgaccccg    2700
gcatccccat tacggtgctg tctaggcaag aatgcattga acgaatccca tggattgctc    2760
ctgagtgtgt tgaggactcc aagaacctga gtgtggctgc tgacaagtgg agctttggaa    2820
ccacgctctg ggaaatctgc tacaatggcg agatccccct gaaagacaag acgctgattg    2880
agaaagagag attctatgaa agccggtgca ggccagtgac accatcatgt aaggagctgg    2940
ctgacctcat gacccgctgc atgaactatg accccaatca gaggcctttc ttccgagcca    3000
tcatgagaga cattaataag cttgaagagc agaatccaga tattgtttca gaaaaaaaac    3060
cagcaactga agtggacccc acacattttg aaaagcgctt cctaaagagg atccgtgact    3120
tgggagaggg ccactttggg aaggttgagc tctgcaggta tgaccccgaa ggggacaata    3180
caggggagca ggtggctgtt aaatctctga agcctgagag tggaggtaac cacatagctg    3240
atctgaaaaa ggaaatcgag atcttaagga acctctatca tgagaacatt gtgaagtaca    3300
aaggaatctg cacagaagac ggaggaaatg gtattaagct catcatggaa tttctgcctt    3360
cgggaagcct taaggaatat cttccaaaga ataagaacaa aataaacctc aaacagcagc    3420
taaaatatgc cgttcagatt tgtaagggga tggactattt gggttctcgg caatacgttc    3480
accgggactt ggcagcaaga aatgtccttg ttgagagtga acaccaagtg aaaattggag    3540
acttcggttt aaccaaagca attgaaaccg ataaggagta ttacaccgtc aaggatgacc    3600
gggacagccc tgtgttttgg tatgctccag aatgttttaat gcaatctaaa ttttatattg    3660
cctctgacgt ctggtctttt ggagtcactc tgcatgagct gctgacttac tgtgattcag    3720
attctagtcc catggctttg ttcctgaaaa tgataggccc aacccatggc cagatgacag    3780
tcacaagact tgtgaatacg ttaaaagaag gaaaacgcct gccgtgccca cctaactgtc    3840
cagatgaggt ttatcaactt atgaggaaat gctgggaatt ccaaccatcc aatcggacaa    3900
gctttcagaa ccttattgaa ggatttgaag cacttttaaa ataagaagca tgaataacat    3960
ttaaattcca cagattatca agtccttctc ctgcaacaaa tgcccaagtc attttttaaa    4020
aatttctaat gaaagaagtt tgtgttctgt ccaaaaagtc actgaactca tacttcagta    4080
```

```
catatacatg tataaggcac actgtagtgc ttaatatgtg taaggacttc ctctttaaat    4140
ttggtaccag taacttagtg acacataatg acaaccaaaa tatttgaaag cacttaagca    4200
ctcctccttg tggaaagaat ataccaccat ttcatctggc tagttcacca tcacaactgc    4260
attaccaaaa ggggattttt gaaaacgagg agttgaccaa ataatatct gaagatgatt     4320
gcttttccct gctgccagct gatctgaaat gttttgctgg cacattaatc atagataaag    4380
aaagattgat ggacttagcc ctcaaatttc agtatctata cagtactaga ccatgcattc    4440
ttaaaatatt agataccagg tagtatatat tgtttctgta caaaaatgac tgtattctct    4500
caccagtagg acttaaactt tgtttctcca gtggcttagc tcctgttcct ttgggtgatc    4560
actagcaccc atttttgaga aagctggttc tacatggggg gatagctgtg aatagataa    4620
tttgctgcat gttaattctc aagaactaag cctgtgccag tgctttccta agcagtatac    4680
ctttaatcag aactcattcc cagaacctgg atgctattac acatgctttt aagaaacgtc    4740
aatgtatatc cttttataac tctaccactt tggggcaagc tattccagca ctggttttga    4800
atgctgtatg caaccagtct gaataccaca tacgctgcac tgttcttaga gggttttccat   4860
acttaccacc gatctacaag ggttgatccc tgttttttacc atcaatcatc accctgtggt   4920
gcaacacttg aaagacccgg ctagaggcac tatggacttc aggatccact agacagtttt    4980
cagtttgctt ggaggtagct gggtaatcaa aaatgtttag tcattgattc aatgtgaacg    5040
attacggtct ttatgaccaa gagtctgaaa atctttttgt tatgctgttt agtattcgtt    5100
tgatattgtt acttttcacc tgttgagccc aaattcagga ttggttcagt ggcagcaatg    5160
aagttgccat ttaaatttgt tcatagccta catcaccaag gtctctgtgt caaacctgtg    5220
gccactctat atgcactttg tttactcttt atacaaataa atatactaaa gactttacat    5280
gca                                                                 5283

<210> SEQ ID NO 5
<211> LENGTH: 5199
<212> TYPE: DNA
<213> ORGANISM: Homo sapiens

<400> SEQUENCE: 5
atctatcaca tggcagagat agaataaaaa cagaaaaatg gcgacggtca cgttgtggcg     60
agccttgctg cgtcattaga taatcctcat gcaaatagcg ggaagaacaa aggaaggggga   120
gcccgggacc cccgggggcg caggatccgg cgggaggagt ctaagaggag gaggcggcgg   180
tgccggagga ggaggaggag ggagggagaa gagaggaaga ccggagtccc cgcggcggcg    240
gcggtccgga gagagggcga gccccgcgcg gcgccgggga ccgggcgcta ccacgaggcc    300
gggacgctgg agtctgggcg cttctctgaa gtagctttgg aaagtagaga agaaaatcca    360
gtttgcttct tggagaacac tggacagctg aataaatgca gtatctaaat ataaaagagg    420
actgcaatgc catggctttc tgtgctaaaa tgaggagctc caagaagact gaggtgaacc    480
tggaggcccc tgagccaggg gtggaagtga tcttctatct gtcggacagg gagcccctcc    540
ggctgggcag tggagagtac acagcagagg aactgtgcat cagggctgca caggcatgcc    600
gtatctctcc tctttgtcac aacctctttg ccctgtatga cgagaacacc aagctctggt    660
atgctccaaa tcgcaccatc accgttgatg acaagatgtc cctccggctc cactaccgga   720
tgaggttcta tttcaccaat tggcatgaa ccaacgacaa tgagcagtca gtgtggcgtc    780
attctccaaa gaagcagaaa atggctacg agaaaaaaaa gattccagat gcaacccctc   840
tccttgatgc cagctcactg gagtatctgt ttgctcaggg acagtatgat ttggtgaaat    900
```

```
gcctggctcc tattcgagac cccaagaccg agcaggatgg acatgatatt gagaacgagt    960
gtctagggat ggctgtcctg gccatctcac actatgccat gatgaagaag atgcagttgc   1020
cagaactgcc caaggacatc agctacaagc gatatattcc agaaacattg aataagtcca   1080
tcagacagag gaaccttctc accaggatgc ggataaataa tgttttcaag gatttcctaa   1140
aggaatttaa caacaagacc atttgtgaca gcagcgtgtc cacgcatgac ctgaaggtga   1200
aatacttggc taccttggaa actttgacaa acattacgg tgctgaaata tttgagactt   1260
ccatgttact gatttcatca gaaaatgaga tgaattggtt tcattcgaat gacggtggaa   1320
acgttctcta ctacgaagtg atggtgactg ggaatcttgg aatccagtgg aggcataaac   1380
caaatgttgt ttctgttgaa aaggaaaaaa ataaactgaa gcggaaaaaa ctggaaaata   1440
aacacaagaa ggatgaggag aaaaacaaga tccgggaaga gtggaacaat ttttcttact   1500
tccctgaaat cactcacatt gtaataaagg agtctgtggt cagcattaac aagcaggaca   1560
acaagaaaat ggaactgaag ctctcttccc acgaggaggc cttgtccttt gtgtccctgg   1620
tagatggcta cttccggctc acagcagatg cccatcatta cctctgcacc gacgtggccc   1680
ccccgttgat cgtccacaac atacagaatg gctgtcatgg tccaatctgt acagaatacg   1740
ccatcaataa attgcggcaa gaaggaagcg aggaggggat gtacgtgctg aggtggagct   1800
gcaccgactt tgacaacatc ctcatgaccg tcacctgctt tgagaagtct gagcaggtgc   1860
agggtgccca gaagcagttc aagaactttc agatcgaggt gcagaagggc cgctacagtc   1920
tgcacggttc ggaccgcagc ttccccagct gggagacct catgagccac ctcaagaagc   1980
agatcctgcg cacggataac atcagcttca tgctaaaacg ctgctgccag cccaagcccc   2040
gagaaatctc caacctgctg gtggctacta agaaagccca ggagtggcag cccgtctacc   2100
ccatgagcca gctgagtttc gatcggatcc tcaagaagga tctggtgcag ggcgagcacc   2160
ttgggagagg cacgagaaca cacatctatt ctgggaccct gatggattac aaggatgacg   2220
aaggaacttg tgaagagaag aagataaaag tgatcctcaa agtcttagac cccagccaca   2280
gggatatttc cctggccttc ttcgaggcag ccagcatgat gagacaggtc tcccacaaac   2340
acatcgtgta cctctatggc gtctgtgtcc gcgacgtgga gaatatcatg gtggaagagt   2400
ttgtggaagg gggtcctctg gatctcttca tgcaccggaa aagcgatgtc cttaccacac   2460
catgaaaatt caaagttgcc aaacagctgg ccagtgccct gagctacttg gaggataaag   2520
acctggtcca tggaaatgtg tgtactaaaa acctcctcct ggcccgtgag ggcatcgaca   2580
gtgagtgtgg cccattcatc aagctcagtg accccggcat ccccattacg gtgctgtcta   2640
ggcaagaatg cattgaacga atcccatgga ttgctcctga gtgtgttgag gactccaaga   2700
acctgagtgt ggctgctgac aagtggagct ttggaaccac gctctgggaa atctgctaca   2760
atggcgagat ccccttgaaa gacaagacgc tgattgagaa agagagattc tatgaaagcc   2820
ggtgcaggcc agtgacacca tcatgtaagg agctggctga cctcatgacc cgctgcatga   2880
actatgaccc caatcagagg cctttcttcc gagccatcat gagagacatt aataagcttg   2940
aagagcagaa tccagatatt gtttcagaaa aaaaaccagc aactgaagtg daccccacac   3000
atttttgaaaa gcgcttccta agaggatccg tgacttggg agagggccac tttgggaagg   3060
ttgagctctg caggtatgac cccgaagggg acaatacagg ggagcaggtg gctgttaaat   3120
ctctgaagcc tgagagtgga ggtaaccaca tagctgatct gaaaaaggaa atcgagatct   3180
taaggaacct ctatcatgag aacattgtga agtacaaagg aatctgcaca gaagacggag   3240
gaaatggtat taagctcatc atggaatttc tgccttcggg aagccttaag gaatatcttc   3300
```

-continued

```
caaagaataa gaacaaaata aacctcaaac agcagctaaa atatgccgtt cagatttgta    3360
aggggatgga ctatttgggt tctcggcaat acgttcaccg ggacttggca gcaagaaatg    3420
tccttgttga gagtgaacac caagtgaaaa ttggagactt cggtttaacc aaagcaattg    3480
aaaccgataa ggagtattac accgtcaagg atgaccggga cagccctgtg ttttggtatg    3540
ctccagaatg tttaatgcaa tctaaatttt atattgcctc tgacgtctgg tcttttggag    3600
tcactctgca tgagctgctg acttactgtg attcagattc tagtcccatg gctttgttcc    3660
tgaaaatgat aggcccaacc catggccaga tgacagtcac aagacttgtg aatacgttaa    3720
aagaaggaaa acgcctgccg tgcccaccta actgtccaga tgaggtttat caacttatga    3780
ggaaatgctg ggaattccaa ccatccaatc ggacaagctt tcagaacctt attgaaggat    3840
ttgaagcact tttaaaataa gaagcatgaa taacatttaa attccacaga ttatcaagtc    3900
cttctcctgc aacaaatgcc caagtcattt tttaaaaatt tctaatgaaa gaagtttgtg    3960
ttctgtccaa aaagtcactg aactcatact tcagtacata tacatgtata aggcacactg    4020
tagtgcttaa tatgtgtaag gacttcctct ttaaatttgg taccagtaac ttagtgacac    4080
ataatgacaa ccaaaatatt tgaaagcact taagcactcc tccttgtgga agaatatac    4140
caccatttca tctggctagt tcaccatcac aactgcatta ccaaaagggg attttgaaa    4200
acgaggagtt gaccaaaata atatctgaag atgattgctt ttccctgctg ccagctgatc    4260
tgaaatgttt tgctggcaca ttaatcatag ataaagaaag attgatggac ttagccctca    4320
aatttcagta tctatacagt actagaccat gcattcttaa aatattagat accaggtagt    4380
atatattgtt tctgtacaaa aatgactgta ttctctcacc agtaggactt aaactttgtt    4440
tctccagtgg cttagctcct gttcctttgg gtgatcacta gcacccattt ttgagaaagc    4500
tggttctaca tggggggata gctgtggaat agataaattg ctgcatgtta attctcaaga    4560
actaagcctg tgccagtgct ttcctaagca gtatacctt aatcagaact cattcccaga    4620
acctggatgc tattacacat gcttttaaga aacgtcaatg tatatccttt tataactcta    4680
ccactttggg gcaagctatt ccagcactgg ttttgaatgc tgtatgcaac cagtctgaat    4740
accacatacg ctgcactgtt cttagagggt ttccatactt accaccgatc tacaagggtt    4800
gatccctgtt tttaccatca atcatcaccc tgtggtgcaa cacttgaaag acccggctag    4860
aggcactatg gacttcagga tccactagac agttttcagt ttgcttggag gtagctgggt    4920
aatcaaaaat gtttagtcat tgattcaatg tgaacgatta cggtctttat gaccaagagt    4980
ctgaaaatct ttttgttatg ctgtttagta ttcgtttgat attgttactt ttcacctgtt    5040
gagcccaaat tcaggattgg ttcagtggca gcaatgaagt tgccatttaa atttgttcat    5100
agcctacatc accaaggtct ctgtgtcaaa cctgtggcca ctctatatgc actttgttta    5160
ctctttatac aaataaatat actaaagact ttacatgca                           5199
```

<210> SEQ ID NO 6
<211> LENGTH: 5202
<212> TYPE: DNA
<213> ORGANISM: Homo sapiens

<400> SEQUENCE: 6

```
ggggcgggac gggaggcggt gcgtcgctga gcgcaggccg cggcggccgc ggagtatcct      60
ggagctgcag acagtgcggg cctgcgccca gtcccggctg tcctcgccgc gacccctcct     120
cagccctggg cgcgcgcacg ctgggcgccc gggggctgg ccgcctagcg agcctgccgg     180
tcgacccag ccagcgcagc gacggggcgc tgcctggccc aggcgcacac ggaagtgtta      240
```

```
tctaaaacag ttcatgctgc tgaaaacctc cttcctggca gatgtccctc aaccctactg    300
gtgcctggct tctgagacac acgcttctct gaagtagctt tggaaagtag agaagaaaat    360
ccagtttgct tcttggagaa cactggacag ctgaataaat gcagtatcta aatataaaag    420
aggactgcaa tgccatggct ttctgtgcta aaatgaggag ctccaagaag actgaggtga    480
acctggaggc ccctgagcca ggggtggaag tgatcttcta tctgtcggac agggagcccc    540
tccggctggg cagtggagag tacacagcag aggaactgtg catcagggct gcacaggcat    600
gccgtatctc tcctctttgt cacaacctct ttgccctgta tgacgagaac accaagctct    660
ggtatgctcc aaatcgcacc atcaccgttg atgacaagat gtccctccgg ctccactacc    720
ggatgaggtt ctatttcacc aattggcatg aaccaacga caatgagcag tcagtgtggc    780
gtcattctcc aaagaagcag aaaaatggct acgagaaaaa aaagattcca gatgcaaccc    840
ctctccttga tgccagctca ctggagtatc tgtttgctca gggacagtat gatttggtga    900
aatgcctggc tcctattcga dacccccaaga ccgagcagga tggacatgat attgagaacg    960
agtgtctagg gatggctgtc ctggccatct cacactatgc catgatgaag aagatgcagt    1020
tgccagaact gcccaaggac atcagctaca agcgatatat tccagaaaca ttgaataagt    1080
ccatcagaca gaggaacctt ctcaccagga tgcggataaa taatgttttc aaggatttcc    1140
taaaggaatt taacaacaag accatttgtg acagcagcgt gtccacgcat gacctgaagg    1200
tgaaatactt ggctaccttg gaaactttga caaaacatta cggtgctgaa atatttgaga    1260
cttccatgtt actgatttca tcagaaaatg agatgaattg gtttcattcg aatgacggtg    1320
gaaacgttct ctactacgaa gtgatggtga ctgggaatct tggaatccag tggaggcata    1380
aaccaaatgt tgtttctgtt gaaaaggaaa aaaataaact gaagcggaaa aaactggaaa    1440
ataaacacaa gaaggatgag gagaaaaaca agatccggga gagtggaac aatttttctt    1500 acttccctga aatcactcac attgtaataa aggagtctgt ggtcagcatt aacaagcagg    1560
acaacaagaa aatggaactg aagctctctt cccacgagga ggccttgtcc tttgtgtccc    1620
tggtagatgg ctacttccgg ctcacagcag atgcccatca ttacctctgc accgacgtgg    1680
cccccccgtt gatcgtccac aacatacaga atggctgtca tggtccaatc tgtacagaat    1740
acgccatcaa taaattgcgg caagaaggaa gcgaggaggg gatgtacgtg ctgaggtgga    1800
gctgcaccga cttgacaac atcctcatga ccgtcacctg cttgaggaag tctgagcagg    1860
tgcagggtgc ccagaagcag ttcaagaact ttcagatcga ggtgcagaag gccgctaca    1920 gtctgcacgg ttcggaccgc agcttcccca gcttgggaga cctcatgagc cacctcaaga    1980
agcagatcct gcgcacggat aacatcagct tcatgctaaa acgctgctgc cagcccaagc    2040
cccgagaaat ctccaacctg ctggtggcta ctaagaaagc ccaggagtgg cagcccgtct    2100
accccatgag ccagctgagt ttcgatcgga tcctcaagaa ggatctggtg cagggcgagc    2160
accttgggag aggcacgaga acacacatct attctggac cctgatggat tacaaggatg    2220
acgaaggaac ttctgaagag aagaagataa aagtgatcct caaagtctta daccccagcc    2280
acagggatat ttccctggcc ttcttcgagg cagccagcat gatgagacag gtctcccaca    2340
aacacatcgt gtacctctat ggcgtctgtg tccgcgacgt ggagaatatc atggtggaag    2400
agtttgtgga aggggtcctc tggatctct tcatgcaccg gaaaagcgat gtccttacca    2460
caccatggaa attcaaagtt gccaaacagc tggccagtgc cctgagctac ttggaggata    2520
aagacctggt ccatgaaat gtgtgtacta aaaacctcct cctggcccgt gagggcatcg    2580
acagtgagtg tggcccattc atcaagctca gtgaccccgg catccccatt acggtgctgt    2640
```

```
ctaggcaaga atgcattgaa cgaatcccat ggattgctcc tgagtgtgtt gaggactcca   2700
agaacctgag tgtggctgct gacaagtgga gctttggaac cacgctctgg gaaatctgct   2760
acaatggcga gatcccttg aaagacaaga cgctgattga aaagagaga ttctatgaaa     2820 gccggtgcag gccagtgaca ccatcatgta aggagctggc tgacctcatg acccgctgca   2880
tgaactatga ccccaatcag aggcctttct tccgagccat catgagagac attaataagc   2940
ttgaagagca gaatccagat attgtttcag aaaaaaaacc agcaactgaa gtggacccca   3000
cacattttga aaagcgcttc ctaaagagga tccgtgactt gggagagggc cactttggga   3060
aggttgagct ctgcaggtat gaccccgaag gggacaatac aggggagcag gtggctgtta   3120
aatctctgaa gcctgagagt ggaggtaacc acatagctga tctgaaaaag gaaatcgaga   3180
tcttaaggaa cctctatcat gagaacattg tgaagtacaa aggaatctgc acagaagacg   3240
gaggaaatgg tattaagctc atcatggaat ttctgccttc gggaagcctt aaggaatatc   3300
ttccaaagaa taagaacaaa ataaacctca acagcagct aaaatatgcc gttcagattt     3360
gtaaggggat ggactatttg ggttctcggc aatacgttca ccgggacttg gcagcaagaa   3420
atgtccttgt tgagagtgaa caccaagtga aaattggaga cttcggttta accaaagcaa   3480
ttgaaaccga taaggagtat tacaccgtca aggatgaccg ggacagccct gtgttttggt   3540
atgctccaga atgtttaatg caatctaaat tttatattgc ctctgacgtc tggtcttttg   3600
gagtcactct gcatgagctg ctgacttact gtgattcaga ttctagtccc atggctttgt   3660
tcctgaaaat gataggccca acccatggcc agatgacagt cacaagactt gtgaatacgt   3720
taaaagaagg aaaacgcctg ccgtgcccac ctaactgtcc agatgaggtt tatcaactta   3780
tgaggaaatg ctgggaattc caaccatcca atcggacaag ctttcagaac cttattgaag   3840
gatttgaagc acttttaaaa taagaagcat gaataacatt taaattccac agattatcaa   3900
gtccttctcc tgcaacaaat gcccaagtca ttttttaaaa atttctaatg aaagaagttt   3960
gtgttctgtc caaaaagtca ctgaactcat acttcagtac atatacatgt ataaggcaca   4020
ctgtagtgct taatatgtgt aaggacttcc tcttttaaatt tggtaccagt aacttagtga   4080
cacataatga caaccaaaat atttgaaagc acttaagcac tcctccttgt ggaaagaata   4140
taccaccatt tcatctggct agttcaccat cacaactgca ttaccaaaag gggattttg    4200 aaaacgagga gttgaccaaa ataatatctg aagatgattg cttttccctg ctgccagctg   4260
atctgaaatg ttttgctggc acattaatca tagataaaga aagattgatg gacttagccc   4320
tcaaatttca gtatctatac agtactagac catgcattct taaaatatta gataccaggt   4380
agtatatatt gtttctgtac aaaaatgact gtattctctc accagtagga cttaaacttt   4440
gtttctccag tggcttagct cctgttcctt tgggtgatca ctagcaccca ttttttgagaa  4500 agctggttct acatgggggg atagctgtgg aatagataat ttgctgcatg ttaattctca   4560
agaactaagc ctgtgccagt gctttcctaa gcagtatacc tttaatcaga actcattccc   4620
agaacctgga tgctattaca catgctttta agaaacgtca atgtatatcc ttttataact   4680
ctaccacttt ggggcaagct attccagcac tggttttgaa tgctgtatgc aaccagtctg   4740
aataccacat acgctgcact gttccttagag ggtttccata cttaccaccg atctacaagg   4800
gttgatccct gttttaccaa tcaatcatca ccctgtggtg caacacttga aagacccggc   4860
tagaggcact atggacttca ggatccacta gacagttttc agtttgcttg gaggtagctg   4920
ggtaatcaaa aatgtttagt cattgattca atgtgaacga ttacggtctt tatgaccaag   4980
agtctgaaaa tcttttttgtt atgctgttta gtattcgttt gatattgtta cttttcacct   5040
```

-continued

| | |
|---|---|
| gttgagccca aattcaggat tggttcagtg gcagcaatga agttgccatt taaatttgtt | 5100 |
| catagcctac atcaccaagg tctctgtgtc aaacctgtgg ccactctata tgcactttgt | 5160 |
| ttactctta tacaaataaa tatactaaag actttacatg ca | 5202 |

<210> SEQ ID NO 7
<211> LENGTH: 4937
<212> TYPE: DNA
<213> ORGANISM: Homo sapiens

<400> SEQUENCE: 7

| | |
|---|---|
| agaagcggag cgtatacgga ggaggcggga tgcatttctg catcgagcgc acaaagcgct | 60 |
| tctctgaagt agctttggaa agtagagaag aaaatccagt ttgcttcttg gagaacactg | 120 |
| gacagctgaa taaatgcagt atctaaatat aaaagaggac tgcaatgcca tggctttctg | 180 |
| tgctaaaatg aggagctcca agaagactga ggtgaacctg gaggcccctg agccaggggt | 240 |
| ggaagtgatc ttctatctgt cggacaggga gcccctccgg ctgggcagtg agagtacac | 300 |
| agcagaggaa ctgtgcatca gggctgcaca ggcatgccgt atctctcctc tttgtcacaa | 360 |
| cctctttgcc ctgtatgacg agaacaccaa gctctggtat gctccaaatc gcaccatcac | 420 |
| cgttgatgac aagatgtccc tccggctcca ctaccgatg aggttctatt tcaccaattg | 480 |
| gcatggaacc aacgacaatg agcagtcagt gtggcgtcat tctccaaaga agcagaaaaa | 540 |
| tggctacgag aaaaaaaaga ttccagatgc aaccctctc cttgatgcca gctcactgga | 600 |
| gtatctgttt gctcagggac agtatgattt ggtgaaatgc ctggctccta ttcgagaccc | 660 |
| caagaccgag caggatggac atgatattga gaacgagtgt ctagggatgg ctgtcctggc | 720 |
| catctcacac tatgccatga tgaagaagat gcagttgcca gaactgccca aggacatcag | 780 |
| ctacaagcga tatattccag aaacattgaa taagtccatc agacagagga accttctcac | 840 |
| caggatgcgg ataaataatg tttttcaagga tttcctaaag gaatttaaca acaagaccat | 900 |
| tgtgacagc agcgtgtcca cgcatgacct gaaggtgaaa tacttggcta ccttggaaac | 960 |
| tttgacaaaa cattacggtg ctgaaatatt tgagacttcc atgttactga tttcatcaga | 1020 |
| aaatgagatg aattggttc attcgaatga cggtggaaac gttctctact acgaagtgat | 1080 |
| ggtgactggg aatcttggaa tccagtggag gcataaacca aatgttgttt ctgttgaaaa | 1140 |
| ggaaaaaaat aaactgaagc ggaaaaaact ggaaaataaa cacaagaagg atgaggagaa | 1200 |
| aaacaagatc cgggaagagt ggaacaattt ttcttacttc cctgaaatca ctcacattgt | 1260 |
| aataaaggag tctgtggtca gcattaacaa gcaggacaac aagaaaatgg aactgaagct | 1320 |
| ctcttcccac gaggaggcct tgtcctttgt gtccctggta gatggctact ccggctcac | 1380 |
| agcagatgcc catcattacc tctgcaccga cgtggccccc ccgttgatcg tccacaacat | 1440 |
| acagaatggc tgtcatggtc caatctgtac agaatacgcc atcaataaat tgcggcaaga | 1500 |
| aggaagcgag gagggatgt acgtgctgag gtggagctgc accgactttg acaacatcct | 1560 |
| catgaccgtc acctgctttg agaagtctga gcaggtgcag ggtgcccaga agcagttcaa | 1620 |
| gaactttcag atcgaggtgc agaagggccg ctacagtctg cacggttcgg accgcagctt | 1680 |
| ccccagcttg ggagacctca tgagccacct caagaagcag atcctgcgca cggataacat | 1740 |
| cagcttcatg ctaaaacgct gctgccagcc caagccccga gaaatctcca acctgctggt | 1800 |
| ggctactaag aaagcccagg agtgcagcc cgtctacccc atgagccagc tgagtttcga | 1860 |
| tcggatcctc aagaaggatc tggtgcaggg cgagcacctt gggagaggca cgagaacaca | 1920 |
| catctattct gggaccctga tggattacaa ggatgacgaa ggaacttctg aagagaagaa | 1980 |

-continued

```
gataaaagtg atcctcaaag tcttagaccc cagccacagg gatatttccc tggccttctt    2040
cgaggcagcc agcatgatga gacaggtctc ccacaaacac atcgtgtacc tctatggcgt    2100
ctgtgtccgc gacgtggaga atatcatggt ggaagagttt gtggaagggg gtcctctgga    2160
tctcttcatg caccggaaaa gcgatgtcct taccacacca tggaaattca agttgccaa    2220
acagctggcc agtgccctga gctacttgga ggataaagac ctggtccatg gaaatgtgtg    2280
tactaaaaac ctcctcctgg cccgtgaggg catcgacagt gagtgtggcc attcatcaa    2340
gctcagtgac cccggcatcc ccattacggt gctgtctagg caagaatgca ttgaacgaat    2400
cccatggatt gctcctgagt gtgttgagga ctccaagaac ctgagtgtgg ctgctgacaa    2460
gtggagcttt ggaaccacgc tctgggaaat ctgctacaat ggcgagatcc ccttgaaaga    2520
caagacgctg attgagaaag agagattcta tgaaagccgg tgcaggccag tgacaccatc    2580
atgtaaggag ctggctgacc tcatgacccg ctgcatgaac tatgaccccca atcagaggcc    2640
tttcttccga gccatcatga gagacattaa taagcttgaa gagcagaatc cagatattgt    2700
ttcagaaaaa aaaccagcaa ctgaagtgga ccccacacat tttgaaaagc gcttcctaaa    2760
gaggatccgt gacttgggag agggccactt tgggaaggtt gagctctgca ggtatgaccc    2820
cgaaggggac aatacagggg agcaggtggc tgttaaatct ctgaagcctg agagtggagg    2880
taaccacata gctgatctga aaaggaaat cgagatctta aggaacctct atcatgagaa    2940
cattgtgaag tacaaaggaa tctgcacaga agacggagga aatggtatta agctcatcat    3000
ggaatttctg ccttcgggaa gccttaagga atatcttcca agaataaga acaaaataaa    3060
cctcaaacag cagctaaaat atgccgttca gatttgtaag gggatggact atttgggttc    3120
tcggcaatac gttcaccggg acttggcagc aagaaatgtc cttgttgaga gtgaacacca    3180
agtgaaaatt ggagacttcg gtttaaccaa agcaattgaa accgataagg agtattacac    3240
cgtcaaggat gaccgggaca gccctgtgtt ttggtatgct ccagaatgtt aatgcaatc    3300
taaattttat attgcctctg acgtctggtc ttttggagtc actctgcatg agctgctgac    3360
ttactgtgat tcagattcta gtcccatggc tttgttcctg aaaatgatag gcccaaccca    3420
tggccagatg acagtcacaa gacttgtgaa tacgttaaaa gaaggaaaac gcctgccgtg    3480
cccacctaac tgtccagatg aggtttatca acttatgagg aaatgctggg aattccaacc    3540
atccaatcgg acaagctttc agaaccttat tgaaggattt gaagcacttt taaaataaga    3600
agcatgaata acatttaaat tccacagatt atcaagtcct tctcctgcaa caaatgccca    3660
agtcattttt taaaaatttc taatgaaaga agtttgtgtt ctgtccaaaa agtcactgaa    3720
ctcatacttc agtacatata catgtataag gcacactgta gtgcttaata tgtgtaagga    3780
cttcctcttt aaatttggta ccagtaactt agtgacacat aatgcaaacc aaaatatttg    3840
aaagcactta agcactcctc cttgtggaaa gaatatacca ccatttcatc tggctagttc    3900
accatcacaa ctgcattacc aaaaggggat ttttgaaaac gaggagttga ccaaaataat    3960
atctgaagat gattgctttt ccctgctgcc agctgatctg aaatgttttg ctggcacatt    4020
aatcatagat aaagaaagat tgatggactt agccctcaaa tttcagtatc tatacagtac    4080
tagaccatgc attcttaaaa tattagatac caggtagtat atattgtttc tgtacaaaaa    4140
tgactgtatt ctctcaccag taggacttaa actttgtttc tccagtggct tagctcctgt    4200
tcctttgggt gatcactagc acccattttt gagaaagctg gttctacatg gggggatagc    4260
tgtggaatag ataatttgct gcatgttaat tctcaagaac taagcctgtg ccagtgcttt    4320
cctaagcagt ataccttttaa tcagaactca ttcccagaac ctggatgcta ttacacatgc    4380
```

| | | | |
|---|---|---|---|
| ttttaagaaa cgtcaatgta tatccttta taactctacc actttggggc aagctattcc | | | 4440 |
| agcactggtt ttgaatgctg tatgcaacca gtctgaatac cacatacgct gcactgttct | | | 4500 |
| tagagggttt ccatacttac caccgatcta caagggttga tccctgtttt taccatcaat | | | 4560 |
| catcaccctg tggtgcaaca cttgaaagac ccggctagag cactatgga cttcaggatc | | | 4620 |
| cactagacag ttttcagttt gcttggaggt agctgggtaa tcaaaaatgt ttagtcattg | | | 4680 |
| attcaatgtg aacgattacg gtctttatga ccaagagtct gaaaatcttt ttgttatgct | | | 4740 |
| gtttagtatt cgtttgatat tgttactttt cacctgttga gcccaaattc aggattggtt | | | 4800 |
| cagtggcagc aatgaagttg ccatttaaat ttgttcatag cctacatcac caaggtctct | | | 4860 |
| gtgtcaaacc tgtggccact ctatatgcac tttgtttact ctttatacaa ataaatatac | | | 4920 |
| taaagacttt acatgca | | | 4937 |

<210> SEQ ID NO 8
<211> LENGTH: 5115
<212> TYPE: DNA
<213> ORGANISM: Homo sapiens

<400> SEQUENCE: 8

| | | | |
|---|---|---|---|
| ggggcgggac gggaggcggt gcgtcgctga gcgcaggccg cggcggccgc ggagtatcct | | | 60 |
| ggagctgcag acagtgcggg cctgcgccca gtcccggctg tcctcgccgc gaccctcct | | | 120 |
| cagccctggg cgcgcgcacg ctgggcgccc gcggggctgg ccgcctagcg agcctgccgg | | | 180 |
| tcgaccccag ccagcgcagc gacggggcgc tgcctggccc aggcgcacac ggaagtgcgc | | | 240 |
| ttctctgaag tagctttgga aagtagagaa gaaaatccag tttgcttctt ggagaacact | | | 300 |
| ggacagctga ataaatgcag tatctaaata taaagagga ctgcaatgcc atggcttct | | | 360 |
| gtgctaaaat gaggagctcc aagaagactg aggtgaacct ggaggcccct gagccagggg | | | 420 |
| tggaagtgat cttctatctg tcggacaggg agcccctccg gctgggcagt ggagagtaca | | | 480 |
| cagcagagga actgtgcatc agggctgcac aggcatgccg tatctctcct ctttgtcaca | | | 540 |
| acctctttgc cctgtatgac gagaacacca agctctggta tgctccaaat cgcaccatca | | | 600 |
| ccgttgatga caagatgtcc ctccggctcc actaccggat gaggttctat ttcaccaatt | | | 660 |
| ggcatggaac caacgacaat gagcagtcag tgtggcgtca ttctccaaag aagcagaaaa | | | 720 |
| atggctacga gaaaaaaag attccagatg caaccctct ccttgatgcc agctcactgg | | | 780 |
| agtatctgtt tgctcaggga cagtatgatt tggtgaaatg cctggctcct attcgagacc | | | 840 |
| ccaagaccga gcaggatgga catgatattg agaacgagtg tctagggatg gctgtcctgg | | | 900 |
| ccatctcaca ctatgccatg atgaagaaga tgcagttgcc agaactgccc aaggacatca | | | 960 |
| gctacaagcg atatattcca gaaacattga ataagtccat cagacagagg aaccttctca | | | 1020 |
| ccaggatgcg gataaataat gttttcaagg atttcctaaa ggaatttaac aacaagacca | | | 1080 |
| tttgtgacag cagcgtgtcc acgcatgacc tgaaggtgaa atacttggct accttggaaa | | | 1140 |
| cttttgacaaa acattacggt gctgaaatat ttgagacttc catgttactg atttcatcag | | | 1200 |
| aaaatgagat gaattggttt cattcgaatg acggtggaaa cgttctctac tacgaagtga | | | 1260 |
| tggtgactgg gaatcttgga atccagtgga ggcataaacc aaatgttgtt tctgttgaaa | | | 1320 |
| aggaaaaaaa taaactgaag cggaaaaaac tggaaaataa acacaagaag gatgaggaga | | | 1380 |
| aaaacaagat ccgggaagag tggaacaatt ttcttacttt ccctgaaatc actcacattg | | | 1440 |
| taataaagga gtctgtggtc agcattaaca gcaggacaa caagaaaatg gaactgaagc | | | 1500 |
| tctcttccca cgaggaggcc ttgtcctttg tgtccctggt agatggctac ttccggctca | | | 1560 |

-continued

```
cagcagatgc ccatcattac ctctgcaccg acgtggcccc cccgttgatc gtccacaaca   1620
tacagaatgg ctgtcatggt ccaatctgta cagaatacgc catcaataaa ttgcggcaag   1680
aaggaagcga ggaggggatg tacgtgctga ggtggagctg caccgacttt gacaacatcc   1740
tcatgaccgt cacctgcttt gagaagtctg aggtgcaggg tgcccagaag cagttcaaga   1800
actttcagat cgaggtgcag aagggccgct acagtctgca cggttcggac cgcagcttcc   1860
ccagcttggg agacctcatg agccacctca agaagcagat cctgcgcacg ataacatca   1920
gcttcatgct aaaacgctgc tgccagccca gccccgaga atctccaac ctgctggtgg   1980
ctactaagaa agcccaggag tggcagcccg tctaccccat gagccagctg agtttcgatc   2040
ggatcctcaa gaaggatctg gtgcagggcg agcaccttgg gagaggcacg agaacacaca   2100
tctattctgg gaccctgatg gattacaagg atgacgaagg aacttctgaa gagaagaaga   2160
taaaagtgat cctcaaagtc ttagacccca gccacaggga tatttccctg gccttcttcg   2220
aggcagccag catgatgaga caggtctccc acaaacacat cgtgtacctc tatggcgtct   2280
gtgtccgcga cgtggagaat atcatggtgg aagagtttgt ggaaggggt cctctggatc   2340
tcttcatgca ccggaaaagc gatgtcctta ccacaccatg gaaattcaaa gttgccaaac   2400
agctggccag tgccctgagc tacttggagg ataaagacct ggtccatgga aatgtgtgta   2460
ctaaaaacct cctcctggcc cgtgagggca tcgacagtga gtgtggccca ttcatcaagc   2520
tcagtgaccc cggcatcccc attacggtgc tgtctaggca agaatgcatt gaacgaatcc   2580
catggattgc tcctgagtgt gttgaggact ccaagaacct gagtgtggct gctgacaagt   2640
ggagctttgg aaccacgctc tgggaaatct gctacaatgg cgagatcccc ttgaaagaca   2700
agacgctgat tgagaaagag agattctatg aaagccggtg caggccagtg acaccatcat   2760
gtaaggagct ggctgacctc atgacccgct gcatgaacta tgaccccaat cagaggcctt   2820
tcttccgagc catcatgaga gacattaata gcttgaaga gcagaatcca gatattgttt   2880
cagaaaaaaa accagcaact gaagtggacc ccacacattt tgaaaagcgc ttcctaaaga   2940
ggatccgtga cttgggagag ggccactttg ggaaggttga gctctgcagg tatgaccccg   3000
aaggggacaa tacaggggag caggtggctg ttaaatctct gaagcctgag agtgggaggta   3060
accacatagc tgatctgaaa aaggaaatcg agatcttaag gaacctctat catgagaaca   3120
ttgtgaagta caaaggaatc tgcacagaag acggaggaaa tggtattaag ctcatcatgg   3180
aatttctgcc ttcgggaagc cttaaggaat atcttccaaa gaataagaac aaaataaacc   3240
tcaaacagca gctaaaatat gccgttcaga tttgtaaggg gatggactat ttgggttctc   3300
ggcaatacgt tcaccgggac ttggcagcaa gaaatgtcct tgttgagagt gaacaccaag   3360
tgaaaattgg agacttcggt ttaaccaaag caattgaaac cgataaggag tattacaccg   3420
tcaaggatga ccgggacagc cctgtgtttt ggtatgctcc agaatgttta atgcaatcta   3480
aattttatat tgcctctgac gtctggtctt tggagtcac tctgcatgag ctgctgactt   3540
actgtgattc agattctagt cccatggctt tgttcctgaa aatgataggc ccaacccatg   3600
gccagatgac agtcacaaga cttgtgaata cgttaaaaga aggaaaacgc ctgccgtgcc   3660
cacctaactg tccagatgag gtttatcaac ttatgaggaa atgctgggaa ttccaaccat   3720
ccaatcggac aagctttcag aaccttattg aaggatttga agcactttta aaataagaag   3780
catgaataac atttaaattc cacagattat caagtccttc tcctgcaaca aatgcccaag   3840
tcatttttta aaaatttcta atgaaagaag tttgtgttct gtccaaaaag tcactgaact   3900
catacttcag tacatataca tgtataaggc acactgtagt gcttaatatg tgtaaggact   3960
```

-continued

```
tcctctttaa atttggtacc agtaacttag tgacacataa tgacaaccaa aatatttgaa 4020
agcacttaag cactcctcct tgtggaaaga atataccacc atttcatctg gctagttcac 4080
catcacaact gcattaccaa aaggggattt ttgaaaacga ggagttgacc aaaataatat 4140
ctgaagatga ttgcttttcc ctgctgccag ctgatctgaa atgttttgct ggcacattaa 4200
tcatagataa agaaagattg atggacttag ccctcaaatt tcagtatcta tacagtacta 4260
gaccatgcat tcttaaaata ttagatacca ggtagtatat attgtttctg tacaaaaatg 4320
actgtattct ctcaccagta ggacttaaac tttgtttctc cagtggctta gctcctgttc 4380
ctttgggtga tcactagcac ccatttttga gaaagctggt tctacatggg gggatagctg 4440
```

```
tggaatagat aatttgctgc atgttaattc tcaagaacta agcctgtgcc agtgctttcc 4500
taagcagtat acctttaatc agaactcatt cccagaacct ggatgctatt acacatgctt 4560
ttaagaaacg tcaatgtata tccttttata actctaccac tttggggcaa gctattccag 4620
cactggtttt gaatgctgta tgcaaccagt ctgaatacca catacgctgc actgttctta 4680
gagggtttcc atacttacca ccgatctaca agggttgatc cctgttttta ccatcaatca 4740
tcaccctgtg gtgcaacact tgaaagaccc ggctagaggc actatggact tcaggatcca 4800
ctagacagtt ttcagtttgc ttggaggtag ctgggtaatc aaaaatgttt agtcattgat 4860
tcaatgtgaa cgattacggt ctttatgacc aagagtctga aaatcttttt gttatgctgt 4920
```

```
ttagtattcg tttgatattg ttacttttca cctgttgagc ccaaattcag gattggttca 4980
gtggcagcaa tgaagttgcc atttaaattt gttcatagcc tacatcacca aggtctctgt 5040
gtcaaacctg tggccactct atatgcactt tgtttactct ttatacaaat aaatatacta 5100
aagactttac atgca 5115

<210> SEQ ID NO 9
<211> LENGTH: 5285
<212> TYPE: DNA
<213> ORGANISM: Homo sapiens

<400> SEQUENCE: 9
ctgcaggaag gagagaggaa gaggagcaga agggggcagc agcggacgcc gctaacggcc 60
tccctcggcg ctgacaggct gggccggcgc ccggctcgct tgggtgttcg cgtcgccact 120
tcggcttctc ggccggtcgg gcccctcggc ccgggcttgc ggcgcgcgtc ggggctgagg 180
gctgctgcgg cgcagggaga ggcctggtcc tcgctgccga gggatgtgag tgggagctga 240
gcccacactg gagggccccc gagggcccag cctggaggtc gttcagagcc gtgcccgtcc 300
cggggcttcg cagaccttga cccgccgggt aggagccgcc cctgcgggct cgagggcgcg 360
ctctggtcgc ccgatctgtg tagccggttt cagaagcagg caacaggaac aagatgtgaa 420
ctgtttctct tctgcagaaa aagaggctct tcctcctcct cccgcgacgg caaatgttct 480
gaaaaagact ctgcatggga atggcctgcc ttacgatgac agaaatggag ggaacatcca 540
cctcttctat atatcagaat ggtgatattt ctggaaatgc caattctatg aagcaaatag 600
atccagttct tcaggtgtat ctttaccatt cccttgggaa atctgaggca gattatctga 660
cctttccatc tggggagtat gttgcagaag aaatctgtat tgctgcttct aaagcttgtg 720
gtatcacacc tgtgtatcat aatatgtttg ctttaatgag tgaaacagaa aggatctggt 780
atccacccaa ccatgtcttc catatagatg agtcaaccag gcataatgta ctctacagaa 840
taagatttta ctttcctcgt tggtattgca gtggcagcaa cagagcctat cggcatggaa 900
tatctcgagg tgctgaagct cctcttcttg atgactttgt catgtcttac ctctttgctc 960
```

```
agtggcggca tgattttgtg cacggatgga taaaagtacc tgtgactcat gaaacacagg    1020
aagaatgtct tgggatggca gtgttagata tgatgagaat agccaaagaa aacgatcaaa    1080
ccccactggc catctataac tctatcagct acaagacatt cttaccaaaa tgtattcgag    1140
caaagatcca agactatcat attttgacaa ggaagcgaat aaggtacaga tttcgcagat    1200
ttattcagca attcagccaa tgcaaagcca ctgccagaaa cttgaaactt aagtatctta    1260
taaatctgga aactctgcag tctgccttct acacagagaa atttgaagta aaagaacctg    1320
gaagtggtcc ttcaggtgag gagattttg caaccattat aataactgga aacggtggaa    1380
ttcagtggtc aagagggaaa cataaagaaa gtgagacact gacagaacag gatttacagt    1440
tatattgcga ttttcctaat attattgatg tcagtattaa gcaagcaaac caagagggtt    1500
caaatgaaag ccgagttgta actatccata gcaagatgg taaaaatctg gaaattgaac    1560
ttagctcatt aagggaagct tgtctttcg tgtcattaat tgatggatat tatagattaa    1620
ctgcagatgc acatcattac ctctgtaaag aagtagcacc tccagccgtg cttgaaaata    1680
tacaaagcaa ctgtcatggc ccaatttcga tggattttgc cattagtaaa ctgaagaaag    1740
caggtaatca gactggactg tatgtacttc gatgcagtcc taaggacttt aataaatatt    1800
ttttgacttt tgctgtcgag cgagaaaatg tcattgaata taaacactgt ttgattacaa    1860
aaaatgagaa tgaagagtac aacctcagtg ggacaaagaa gaacttcagc agtcttaaag    1920
atcttttgaa ttgttaccag atggaaactg ttcgctcaga caatataatt ttccagttta    1980
ctaaatgctg tcccccaaag ccaaaagata aatcaaacct tctagtcttc agaacgaatg    2040
gtgtttctga tgtaccaacc tcaccaacat tacagaggcc tactcatatg aaccaaatgg    2100
tgtttcacaa aatcagaaat gaagatttga tatttaatga aagccttggc caaggcactt    2160
ttacaaagat ttttaaaggc gtacgaagag aagtaggaga ctacggtcaa ctgcatgaaa    2220
cagaagttct tttaaaagtt ctggataaag cacacagaaa ctattcagag tctttctttg    2280
aagcagcaag tatgatgagc aagctttctc acaagcattt ggttttaaat tatgtgagtat    2340 gtgtctgtgg agacgagaat attctggttc aggagtttgt aaaatttgga tcactagata    2400
catatctgaa aaagaataaa aattgtataa atatattatg gaaacttgaa gttgctaaac    2460
agttggcatg ggccatgcat tttctagaag aaaacaccct tattcatggg aatgtatgtg    2520
ccaaaaatat tctgcttatc agagaagaag acaggaagac aggaaatcct cctttcatca    2580
aacttagtga tcctggcatt agtattacag ttttgccaaa ggacattctt caggagagaa    2640
taccatgggt accacctgaa tgcattgaaa atcctaaaaa tttaaatttg gcaacagaca    2700
aatggagttt tggtaccact ttgtgggaaa tctgcagtgg aggagataaa cctctaagtg    2760
ctctggattc tcaaagaaag ctacaatttt atgaagatag gcatcagctt cctgcaccaa    2820
agtgggcaga attagcaaac cttataaata attgtatgga ttatgaacca gatttcaggc    2880
cttctttcag agccatcata cgagatctta acagtttgtt tactccagat tatgaactat    2940
taacagaaaa tgacatgtta ccaaatatga ggataggtgc cctggggttt tctggtgcct    3000
ttgaagaccg ggatcctaca cagtttgaag agagacattt gaaatttcta cagcaacttg    3060
gcaagggtaa ttttgggagt gtggagatgt gccggtatga ccctctacag gacaacactg    3120
gggaggtggt cgctgtaaaa aagcttcagc atagtactga agagcaccta agagactttg    3180
aaagggaaat tgaaatcctg aaatccctac agcatgacaa cattgtaaag tacaagggag    3240
tgtgctacag tgctggtcgg cgtaatctaa aattaattat ggaatattta ccatatggaa    3300
gtttacgaga ctatcttcaa aaacataaag aacggataga tcacataaaa cttctgcagt    3360
```

```
acacatctca gatatgcaag ggtatggagt atcttggtac aaaaaggtat atccacaggg    3420
atctggcaac gagaaatata ttggtggaga cgagaacag agttaaaatt ggagattttg      3480
ggttaaccaa agtcttgcca caagacaaag aatactataa agtaaaagaa cctggtgaaa    3540
gtcccatatt ctggtatgct ccagaatcac tgacagagag caagttttct gtggcctcag    3600
atgtttggag ctttggagtg gttctgtatg aacttttcac atacattgag aagagtaaaa    3660
gtccaccagc ggaatttatg cgtatgattg gcaatgacaa acaaggacag atgatcgtgt    3720
tccatttgat agaactttg aagaataatg gaagattacc aagaccagat ggatgcccag      3780
atgagatcta tatgatcatg acagaatgct ggaacaataa tgtaaatcaa cgcccctcct    3840
ttagggatct agctcttcga gtggatcaaa taagggataa catggctgga tgaaagaaat    3900
gaccttcatt ctgagaccaa agtagattta cagaacaaag ttttatattt cacattgctg    3960
tggactatta ttacatatat cattattata taaatcatga tgctagccag caaagatgtg    4020
aaaatatctg ctcaaaactt tcaaagttta gtaagttttt cttcatgagg ccaccagtaa    4080
aagacattaa tgagaattcc ttagcaagga ttttgtaaga agtttcttaa acattgtcag    4140
ttaacatcac tcttgtctgg caaaagaaaa aaaatagact ttttcaactc agcttttga      4200 gacctgaaaa aattattatg taaattttgc aatgttaaag atgcacagaa tatgtatgta    4260
tagtttttac cacagtggat gtataatacc ttggcatctt gtgtgatgtt ttacacacat    4320
gagggctggt gttcattaat actgttttct aattttttcca tagttaatct ataattaatt    4380
acttcactat acaaacaaat taagatgttc agataattga ataagtacct ttgtgtcctt    4440
gttcatttat atcgctggcc agcattataa gcaggtgtat acttttagct tgtagttcca    4500
tgtactgtaa atattttca cataaaggga acaaatgtct agttttattt gtataggaaa      4560
tttccctgac cctaaataat acattttgaa atgaaacaag cttacaaaga tataatctat    4620
tttattatgg tttcccttgt atctatttgt ggtgaatgtg ttttttaaat ggaactatct    4680 ccaaatttt ctaagactac tatgaacagt tttcttttaa aatttgaga ttaagaatgc        4740 caggaatatt gtcatccttt gagctgctga ctgccaataa cattcttcga tctctgggat    4800
ttatgctcat gaactaaatt taagcttaag ccataaaata gattagattg tttttttaaaa    4860 atggatagct cattaagaag tgcagcaggt taagaatttt ttcctaaaga ctgtatattt    4920
gaggggtttc agaattttgc attgcagtca tagaagagat ttatttcctt tttagagggg    4980
aaatgaggta aataagtaaa aaagtatgct tgttaatttt attcaagaat gccagtagaa    5040
aattcataac gtgtatcttt aagaaaaatg agcatacatc ttaaatctttt tcaattaagt    5100 ataaggggtt gttcgttgtt gtcatttgtt atagtgctac tccactttag acaccatagc    5160
taaaataaaa tatggtgggt tttgtgtgtg tgtgtgtgtg tgtgtgtgtg tgtgtgtgtg    5220
tgttatttat acaaaactta aaatacttgc tgttttgatt aaaaagaaaa tagtttctta    5280
cttta                                                                 5285

<210> SEQ ID NO 10
<211> LENGTH: 5386
<212> TYPE: DNA
<213> ORGANISM: Homo sapiens

<400> SEQUENCE: 10
attcggggag actgcaggcc aaccgggagg ctgagttcga agctagcagg gcggcgaagc       60
cagtgtcgcc cgcggcgttg agaagacggt gtggccccgg agagggtgga gacaactgtg     120
acgggcttcc cggctgcccg aagtgggagt ggtgtggggc tgcaggaagg agagaggaag     180
```

-continued

```
aggagcagaa gggggcagca gcggacgccg ctaacggcct ccctcggcgc tgacaggctg    240
ggccggcgcc cggctcgctt gggtgttcgc gtcgccactt cggcttctcg gccggtcggg    300
cccctcggcc cgggcttgcg gcgcgcgtcg gggctgaggg ctgctgcggc gcagggagag    360
gcctggtcct cgctgccgag ggatgtgagt gggagctgag cccacactgg agggcccccg    420
agggcccagc ctggaggtcg ttcagagccg tgcccgtccc ggggcttcgc agaccttgac    480
ccgccgggtt tcagaagcag gcaacaggaa caagatgtga actgtttctc ttctgcagaa    540
aaagaggctc ttcctcctcc tcccgcgacg gcaaatgttc tgaaaagac  tctgcatggg    600 aatggcctgc cttacgatga cagaaatgga gggaacatcc acctcttcta tatatcagaa    660
tggtgatatt tctggaaatg ccaattctat gaagcaaata gatccagttc ttcaggtgta    720
tctttaccat tcccttggga aatctgaggc agattatctg acctttccat ctggggagta    780
tgttgcagaa gaaatctgta ttgctgcttc taaagcttgt ggtatcacac ctgtgtatca    840
taatatgttt gctttaatga gtgaaacaga aaggatctgg tatccaccca accatgtctt    900
ccatatagat gagtcaacca ggcataatgt actctacaga ataagatttt actttcctcg    960
ttggtattgc agtggcagca acagagccta tcggcatgga atatctcgag gtgctgaagc   1020
tcctcttctt gatgactttg tcatgtctta cctctttgct cagtggcggc atgattttgt   1080
gcacggatgg ataaaagtac ctgtgactca tgaaacacag gaagaatgtc ttgggatggc   1140
agtgttagat atgatgagaa tagccaaaga aaacgatcaa accccactgg ccatctataa   1200
ctctatcagc tacaagacat tcttaccaaa atgtattcga gcaaagatcc aagactatca   1260 tatttttgaca aggaagcgaa taaggtacag atttcgcaga tttattcagc aattcagcca   1320
atgcaaagcc actgccagaa acttgaaact taagtatctt ataaatctgg aaactctgca   1380
gtctgccttc tacacagaga aatttgaagt aaaagaaccct ggaagtggtc cttcaggtga   1440
ggagattttt gcaaccatta taataactgg aaacggtgga attcagtggt caagagggaa   1500
acataaagaa agtgagacac tgacagaaca ggatttacag ttatattgcg attttcctaa   1560
tattattgat gtcagtatta agcaagcaaa ccaagagggt tcaaatgaaa gccgagttgt   1620
aactatccat aagcaagatg gtaaaaatct ggaaattgaa cttagctcat taagggaagc   1680
tttgtctttc gtgtcattaa ttgatggata ttatagatta actgcagatg cacatcatta   1740
cctctgtaaa gaagtagcac ctccagccgt gcttgaaaat atacaaagca actgtcatgg   1800
cccaatttcg atggattttg ccattagtaa actgaagaaa gcaggtaatc agactggact   1860
gtatgtactt cgatgcagtc ctaaggactt taataaatat ttttttgactt ttgctgtcga   1920 gcgagaaaat gtcattgaat ataaacactg tttgattaca aaaaatgaga atgaagagta   1980
caacctcagt gggacaaaga agaacttcag cagtcttaaa gatcttttga attgttacca   2040
gatggaaact gttcgctcag acaatataat tttccagttt actaaatgct gtccccccaaa   2100 gccaaaagat aaatcaaacc ttctagtctt cagaacgaat ggtgtttctg atgtaccaac   2160
ctcaccaaca ttacagaggc ctactcatat gaaccaaatg gtgtttcaca aaatcagaaa   2220
tgaagatttg atatttaatg aaagccttgg ccaaggcact tttacaaaga ttttaaagg    2280 cgtacgaaga gaagtaggag actacggtca actgcatgaa acagaagttc ttttaaaagt   2340
tctggataaa gcacacagaa actattcaga gtctttcttt gaagcagcaa gtatgatgag   2400
caagctttct cacaagcatt tggttttaaa ttatggagta tgtgtctgtg gagacgagaa   2460
tattctggtt caggagtttg taaaatttgg atcactagat acatatctga aaagaataa    2520 aaattgtata aatatattat ggaaacttga agttgctaaa cagttggcat gggccatgca   2580
```

-continued

| | |
|---|---|
| ttttctagaa gaaacaccc ttattcatgg gaatgtatgt gccaaaaata ttctgcttat | 2640 |
| cagagaagaa gacaggaaga caggaaatcc tcctttcatc aaacttagtg atcctggcat | 2700 |
| tagtattaca gttttgccaa aggacattct tcaggagaga ataccatggg taccacctga | 2760 |
| atgcattgaa atcctaaaa atttaaattt ggcaacagac aaatggagtt ttggtaccac | 2820 |
| tttgtgggaa atctgcagtg gaggagataa acctctaagt gctctggatt ctcaaagaaa | 2880 |
| gctacaattt tatgaagata ggcatcagct tcctgcacca aagtgggcag aattagcaaa | 2940 |
| ccttataaat aattgtatgg attatgaacc agatttcagg ccttctttca gagccatcat | 3000 |
| acgagatctt aacagtttgt ttactccaga ttatgaacta ttaacagaaa atgacatgtt | 3060 |
| accaaatatg aggataggtg ccctgggggtt ttctggtgcc tttgaagacc gggatcctac | 3120 |
| acagtttgaa gagagacatt tgaaatttct acagcaactt ggcaagggta attttgggag | 3180 |
| tgtggagatg tgccggtatg accctctaca ggacaacact ggggaggtgg tcgctgtaaa | 3240 |
| aaagcttcag catagtactg aagagcacct aagagacttt gaaagggaaa ttgaaatcct | 3300 |
| gaaatcccta cagcatgaca acattgtaaa gtacaaggga gtgtgctaca gtgctggtcg | 3360 |
| gcgtaatcta aaattaatta tggaatattt accatatgga agtttacgag actatcttca | 3420 |
| aaaacataaa gaacggatag atcacataaa acttctgcag tacacatctc agatatgcaa | 3480 |
| gggtatggag tatcttggta caaaaaggta tatccacagg gatctggcaa cgagaaatat | 3540 |
| attggtggag aacgagaaca gagttaaaat tggagatttt gggttaacca aagtcttgcc | 3600 |
| acaagacaaa gaatactata agtaaaaga acctggtgaa agtcccatat tctggtatgc | 3660 |
| tccagaatca ctgacagaga gcaagttttc tgtggcctca gatgtttgga gctttggagt | 3720 |
| ggttctgtat gaacttttca catacattga agagtaaa agtccaccag cggaatttat | 3780 |
| gcgtatgatt ggcaatgaca acaaggaca gatgatcgtg ttccatttga tagaactttt | 3840 |
| gaagaataat ggaagattac aagaccaga tggatgccca gatgagatct atatgatcat | 3900 |
| gacagaatgc tggaacaata atgtaaatca acgcccctcc tttagggatc tagctcttcg | 3960 |
| agtggatcaa ataagggata acatggctgg atgaaagaaa tgaccttcat tctgagacca | 4020 |
| aagtagattt acagaacaaa gttttatatt tcacattgct gtggactatt attacatata | 4080 |
| tcattattat ataaatcatg atgctagcca gcaaagatgt gaaaatatct gctcaaaact | 4140 |
| ttcaaagttt agtaagtttt tcttcatgag gccaccagta aaagacatta atgagaattc | 4200 |
| cttagcaagg attttgtaag aagtttctta acattgtca gttaacatca ctcttgtctg | 4260 |
| gcaaaagaaa aaaatagac ttttcaact cagcttttg agacctgaaa aaattattat | 4320 |
| gtaaattttg caatgttaaa gatgcacaga atatgtatgt atagttttta ccacagtgga | 4380 |
| tgtataatac cttggcatct tgtgtgatgt tttacacaca tgagggctgg tgttcattaa | 4440 |
| tactgttttc taattttcc atagttaatc tataattaat tacttcacta tacaaacaaa | 4500 |
| ttaagatgtt cagataattg aataagtacc tttgtgtcct tgttcattta tatcgctggc | 4560 |
| cagcattata agcaggtgta tacttttagc ttgtagttcc atgtactgta aatatttttc | 4620 |
| acataaaggg aacaaatgtc tagtttatt tgtataggaa atttccctga ccctaaataa | 4680 |
| tacattttga aatgaaacaa gcttacaaag atataatcta ttttattatg gtttcccttg | 4740 |
| tatctatttg tggtgaatgt gttttttaaa tggaactatc tccaattttt tctaagacta | 4800 |
| ctatgaacag ttttctttta aaattttgag attaagaatg ccaggaatat tgtcatcctt | 4860 |
| tgagctgcta actgccaata acattcttcg atctctggga tttatgctca tgaactaaat | 4920 |
| ttaagcttaa gccataaaat agattagatt gttttttaaa aatggatagc tcattaagaa | 4980 |

```
gtgcagcagg ttaagaattt tttcctaaag actgtatatt tgaggggttt cagaattttg    5040
cattgcagtc atagaagaga tttatttcct ttttagaggg gaaatgaggt aaataagtaa    5100
aaaagtatgc ttgttaattt tattcaagaa tgccagtaga aaattcataa cgtgtatctt    5160
taagaaaaat gagcatacat cttaaatctt ttcaattaag tataaggggt tgttcgttgt    5220
tgtcatttgt tatagtgcta ctccactttA gacaccatag ctaaaataaa atatggtggg    5280
ttttgtgtgt gtgtgtgtgt gtgtgtgtgt gtgtgtgtgt gtgttattta tacaaaactt    5340
aaaatacttg ctgttttgat taaaagaaaa atagtttctt acttta                  5386

<210> SEQ ID NO 11
<211> LENGTH: 4904
<212> TYPE: DNA
<213> ORGANISM: Homo sapiens

<400> SEQUENCE: 11
attcggggag actgcaggcc aaccgggagg ctgagttcga agctagcagg gcggcgaagc      60
cagtgtcgcc cgcggcgttg agaagacggc aaatgttctg aaaaagactc tgcatgggaa     120
tggcctgcct tacgatgaca gaaatggagg gaacatccac ctcttctata tatcagaatg     180
gtgatatttc tggaaatgcc aattctatga agcaaataga tccagttctt caggtgtatc     240
tttaccattc ccttgggaaa tctgaggcag attatctgac cttTccatct ggggagtatg     300
ttgcagaaga aatctgtatt gctgcttcta agcttgtgg tatcacacct gtgtatcata     360
atatgtttgc tttaatgagt gaaacagaaa ggatctggta tccacccaac catgtcttcc     420
atatagatga gtcaaccagg cataatgtac tctacagaat aagattttac tttcctcgtt     480
ggtattgcag tggcagcaac agagcctatc ggcatggaat atctcgaggt gctgaagctc     540
ctcttcttga tgactttgtc atgtcttacc tctttgctca gtggcggcat gattttgtgc     600
acggatggat aaaagtacct gtgactcatg aaacacagga agaatgtctt gggatggcag     660
tgttagatat gatgagaata gccaaagaaa acgatcaaac cccactggcc atctataact     720
ctatcagcta caagacattc ttaccaaaat gtattcgagc aaagatccaa gactatcata     780
ttttgacaag gaagcgaata aggtacagat tcgcagatt tattcagcaa ttcagccaat     840
gcaaagccac tgccagaaac ttgaaactta gtatcttat aaatctggaa actctgcagt     900
ctgccttcta cacagagaaa tttgaagtaa agaacctgg aagtggtcct tcaggtgagg     960
agatttttgc aaccattata ataactggaa acggtggaat tcagtggtca agagggaaac    1020
ataaagaaag tgagacactg acagaacagg atttacagtt atattgcgat tttcctaata    1080
ttattgatgt cagtattaag caagcaaacc aagagggttc aaatgaaagc cgagttgtaa    1140
ctatccataa gcaagatggt aaaaatctgg aaattgaact tagctcatta agggaagctt    1200
tgtctttcgt gtcattaatt gatggatatt atagattaac tgcagatgca catcattacc    1260
tctgtaaaga agtagcacct ccagccgtgc ttgaaaatat acaaagcaac tgtcatggcc    1320
caatttcgat ggattttgcc attagtaaac tgaagaaagc aggtaatcag actggactgt    1380
atgtacttcg atgcagtcct aaggacttta ataaatattt tttgactttt gctgtcgagc    1440
gagaaaatgt cattgaatat aaacactgtt tgattacaaa aaatgagaat gaagagtaca    1500
acctcagtgg gacaaagaag aacttcagca gtcttaaaga tcttttgaat tgttaccaga    1560
tggaaactgt tcgctcagac aatataattt tccagtttac taaatgctgt cccccaaagc    1620
caaaagataa atcaaacctt ctagtcttca gaacgaatgg tgtttctgat gtaccaacct    1680
caccaacatt acagaggcct actcatatga accaaatggt gtttcacaaa atcagaaatg    1740
```

```
aagatttgat atttaatgaa agccttggcc aaggcacttt tacaaagatt tttaaaggcg    1800
tacgaagaga agtaggagac tacggtcaac tgcatgaaac agaagttctt ttaaaagttc    1860
tggataaagc acacagaaac tattcagagt cttctttga agcagcaagt atgatgagca     1920
agctttctca caagcatttg gttttaaatt atggagtatg tgtctgtgga gacgagaata    1980
ttctggttca ggagtttgta aaatttggat cactagatac atatctgaaa agaataaaa     2040 attgtataaa tatattatgg aaacttgaag ttgctaaaca gttggcatgg gccatgcatt    2100
ttctagaaga aaacacccct tattcatggga atgtatgtgc caaaaatatt ctgcttatca   2160
gagaagaaga caggaagaca ggaaatcctc ctttcatcaa acttagtgat cctggcatta    2220
gtattacagt tttgccaaag acattcttc aggagagaat accatgggta ccacctgaat     2280
gcattgaaaa tcctaaaaat ttaaatttgg caacagacaa atggagtttt ggtaccactt    2340
tgtgggaaat ctgcagtgga ggagataaac ctctaagtgc tctggattct caaagaaagc    2400
tacaatttta tgaagatagg catcagcttc ctgcaccaaa gtgggcagaa ttagcaaacc    2460
ttataaataa ttgtatggat tatgaaccag atttcaggcc ttctttcaga gccatcatac    2520
gagatcttaa cagtttgttt actccagatt atgaactatt aacagaaaat gacatgttac    2580
caaatatgag gataggtgcc ctggggtttt ctggtgcctt tgaagaccgg gatcctacac    2640
agtttgaaga gagacatttg aaatttctac agcaacttgg caagggtaat tttgggagtg    2700
tggagatgtg ccggtatgac cctctacagg acaacactgg ggaggtggtc gctgtaaaaa    2760
agcttcagca tagtactgaa gagcacctaa gagactttga agggaaatt gaaatcctga     2820 aatccctaca gcatgacaac attgtaaagt acaaggagt gtgctacagt gctggtcggc     2880
gtaatctaaa attaattatg gaatatttac catatggaag tttacgagac tatcttcaaa    2940
aacataaaga acggatagat cacataaaac ttctgcagta cacatctcag atatgcaagg    3000
gtatggagta tcttggtaca aaaaggtata tccacaggga tctggcaacg agaaatatat    3060
tggtggagaa cgagaacaga gttaaaattg agattttgg gttaaccaaa gtcttgccac     3120
aagacaaaga atactataaa gtaaaagaac ctggtgaaag tcccatattc tggtatgctc    3180
cagaatcact gacagagagc aagttttctg tggcctcaga tgtttggagc tttggagtgg    3240
ttctgtatga acttttcaca tacattgaga agagtaaaag tccaccagcg gaatttatgc    3300
gtatgattgg caatgacaaa caaggacaga tgatcgtgtt ccatttgata gaacttttga    3360
agaataatgg aagattacca agaccagatg gatgcccaga tgagatctat atgatcatga    3420
cagaatgctg gaacaataat gtaaatcaac gcccctcctt tagggatcta gctcttcgag    3480
tggatcaaat aagggataac atggctggat gaaagaaatg accttcattc tgagaccaaa    3540
gtagatttac agaacaaagt tttatatttc acattgctgt ggactattat tacatatatc    3600
attattatat aaatcatgat gctagccagc aaagatgtga aaatatctgc tcaaaacttt    3660
caaagtttag taagtttttc ttcatgaggc caccagtaaa agacattaat gagaattcct    3720
tagcaaggat tttgtaagaa gtttcttaaa cattgtcagt taacatcact cttgtctggc    3780
aaaagaaaaa aaatagactt tttcaactca gctttttgag acctgaaaaa attattatgt    3840
aaattttgca atgttaaaga tgcacagaat atgtatgtat agttttttacc acagtggatg    3900 tataataccct tggcatcttg tgtgatgttt tacacacatg agggctggtg ttcattaata    3960
ctgttttcta atttttccat agttaatcta taattaatta cttcactata caaacaaatt    4020
aagatgttca gataattgaa taagtacctt tgtgtccttg ttcatttata tcgctggcca    4080
gcattataag caggtgtata cttttagctt gtagttccat gtactgtaaa tattttcac     4140
```

| | | |
|---|---|---|
| ataaagggaa caaatgtcta gttttatttg tataggaaat ttccctgacc ctaaataata | 4200 | |
| cattttgaaa tgaaacaagc ttacaaagat ataatctatt ttattatggt ttcccttgta | 4260 | |
| tctatttgtg gtgaatgtgt tttttaaatg gaactatctc caaattttc taagactact | 4320 | |
| atgaacagtt ttcttttaaa attttgagat taagaatgcc aggaatattg tcatcctttg | 4380 | |
| agctgctgac tgccaataac attcttcgat ctctgggatt tatgctcatg aactaaattt | 4440 | |
| aagcttaagc cataaaatag attagattgt tttttaaaaa tggatagctc attaagaagt | 4500 | |
| gcagcaggtt aagaattttt tcctaaagac tgtatatttg aggggtttca gaattttgca | 4560 | |
| ttgcagtcat agaagagatt tatttccttt ttagagggga aatgaggtaa ataagtaaaa | 4620 | |
| aagtatgctt gttaatttta ttcaagaatg ccagtagaaa attcataacg tgtatcttta | 4680 | |
| agaaaaatga gcatacatct taaatctttt caattaagta taaggggttg ttcgttgttg | 4740 | |
| tcatttgtta tagtgctact ccactttaga caccatagct aaaataaaat atggtgggtt | 4800 | |
| ttgtgtgtgt gtgtgtgtgt gtgtgtgtgt gtgtgtgtgt gttatttata caaaacttaa | 4860 | |
| aatacttgct gttttgatta aaagaaaat agtttcttac ttta | 4904 | |

<210> SEQ ID NO 12
<211> LENGTH: 5217
<212> TYPE: DNA
<213> ORGANISM: Homo sapiens

<400> SEQUENCE: 12

| | | |
|---|---|---|
| gggagtggtg tggggctgca ggaaggagag aggaagagga gcagaagggg gcagcagcgg | 60 | |
| acgccgctaa cggcctccct cggcgctgac aggctgggcc ggcgcccggc tcgcttgggt | 120 | |
| gttcgcgtcg ccacttcggc ttctcggccg gtcgggcccc tcggcccggg cttgcggcgc | 180 | |
| gcgtcggggc tgagggctgc tgcggcgcag ggagaggcct ggtcctcgct gccgagggat | 240 | |
| gtgagtggga gctgagccca cactggaggg cccccgaggg cccagcctgg aggtcgttca | 300 | |
| gagccgtgcc cgtcccgggg cttcgcagac cttgacccgc cgggtaggag ccgcccctgc | 360 | |
| gggctcgagg gcgcgctctg gtcgcccgat ctgtgtagcc ggcaaatgtt ctgaaaaaga | 420 | |
| ctctgcatgg gaatggcctg ccttacgatg acagaaatgg agggaacatc cacctcttct | 480 | |
| atatatcaga atggtgatat ttctggaaat gccaattcta tgaagcaaat agatccagtt | 540 | |
| cttcaggtgt atctttacca ttcccttggg aaatctgagg cagattatct gacctttcca | 600 | |
| tctggggagt atgttgcaga agaaatctgt attgctgctt ctaaagcttg tggtatcaca | 660 | |
| cctgtgtatc ataatatgtt tgctttaatg agtgaaacag aaaggatctg gtatccaccc | 720 | |
| aaccatgtct tccatataga tgagtcaacc aggcataatg tactctacag aataagattt | 780 | |
| tactttcctc gttggtattg cagtggcagc aacagagcct atcggcatgg aatatctcga | 840 | |
| ggtgctgaag ctcctcttct tgatgacttt gtcatgtctt acctctttgc tcagtggcgg | 900 | |
| catgattttg tgcacggatg gataaaagta cctgtgactc atgaaacaca ggaagaatgt | 960 | |
| cttgggatgg cagtgttaga tatgatgaga atagccaaag aaaacgatca accccactg | 1020 | |
| gccatctata actctatcag ctacaagaca ttcttaccaa aatgtattcg agcaaagatc | 1080 | |
| caagactatc atattttgac aaggaagcga ataaggtaca gatttcgcag atttattcag | 1140 | |
| caattcagcc aatgcaaagc cactgccaga aacttgaaac ttaagtatct tataaatctg | 1200 | |
| gaaactctgc agtctgcctt ctacacagag aaatttgaag taaagaaacc tggaagtggt | 1260 | |
| ccttcaggtg aggagatttt tgcaaccatt ataataactg gaaacggtgg aattcagtgg | 1320 | |
| tcaagaggga acataaaga aagtgagaca ctgacagaac aggatttaca gttatattgc | 1380 | |

```
gattttccta atattattga tgtcagtatt aagcaagcaa accaagaggg ttcaaatgaa    1440
agccgagttg taactatcca taagcaagat ggtaaaaatc tggaaattga acttagctca    1500
ttaagggaag ctttgtcttt cgtgtcatta attgatggat attatagatt aactgcagat    1560
gcacatcatt acctctgtaa agaagtagca cctccagccg tgcttgaaaa tatacaaagc    1620
aactgtcatg gcccaatttc gatggatttt gccattagta aactgaagaa agcaggtaat    1680
cagactggac tgtatgtact tcgatgcagt cctaaggact ttaataaata ttttttgact    1740
tttgctgtcg agcgagaaaa tgtcattgaa tataaacact gtttgattac aaaaaatgag    1800
aatgaagagt acaacctcag tgggacaaag aagaacttca gcagtcttaa agatcttttg    1860
aattgttacc agatggaaac tgttcgctca gacaatataa ttttccagtt tactaaatgc    1920
tgtcccccaa agccaaaaga taaatcaaac cttctagtct tcagaacgaa tggtgtttct    1980
gatgtaccaa cctcaccaac attacagagg cctactcata tgaaccaaat ggtgtttcac    2040
aaaatcagaa atgaagattt gatatttaat gaaagccttg gccaaggcac ttttacaaag    2100 attttttaaag gcgtacgaag agaagtagga gactacggtc aactgcatga aacagaagtt    2160
cttttaaaag ttctggataa agcacacaga aactattcag agtctttctt gaagcagca    2220 agtatgatga gcaagctttc tcacaagcat ttggttttaa attatggagt atgtgtctgt    2280
ggagacgaga atattctggt tcaggagttt gtaaaatttg gatcactaga tacatatctg    2340
aaaaagaata aaaattgtat aaatatatta tggaaacttg aagttgctaa acagttggca    2400
tgggccatgc attttctaga agaaaacacc cttattcatg gaatgtatg tgccaaaaat    2460 attctgctta tcagaagaa agacaggaag acaggaaatc ctcctttcat caaacttagt    2520
gatcctggca ttagtattac agttttgcca aaggacattc ttcaggagag aataccatgg    2580
gtaccacctg aatgcattga aaatcctaaa aatttaaatt tggcaacaga caaatggagt    2640
tttggtacca ctttgtggga aatctgcagt ggaggagata aacctctaag tgctctggat    2700
tctcaaagaa agctacaatt ttatgaagat aggcatcagc ttcctgcacc aaagtgggca    2760
gaattagcaa accttataaa taattgtatg gattatgaac cagatttcag gccttctttc    2820
agagccatca tacgagatct taacagtttg tttactccag attatgaact attaacagaa    2880
aatgacatgt taccaaatat gaggataggt gccctggggt tttctggtgc cttttgaagac    2940 cgggatccta cacagtttga agagagacat ttgaaattttc tacagcaact tggcaagggt    3000
aattttggga gtgtggagat gtgccggtat gaccctctac aggacaacac tggggaggtg    3060
gtcgctgtaa aaaagcttca gcatagtact gaagagcacc taagagactt tgaaagggaa    3120
attgaaatcc tgaaatccct acagcatgac aacattgtaa agtacaaggg agtgtgctac    3180
agtgctggtc ggcgtaatct aaaattaatt atggaatatt taccatatgg aagtttacga    3240
gactatcttc aaaaacataa agaacggata gatcacataa aacttctgca gtacacatct    3300
cagatatgca agggtatgga gtatcttggt acaaaaaggt atatccacag ggatctggca    3360 acgagaaaata tattggtgga gaacgagaac agagttaaaa ttggagattt tgggttaacc    3420
aaagtcttgc cacaagacaa agaatactat aaagtaaaag aacctggtga agtccccata    3480
ttctggtatg ctccagaatc actgacagag agcaagttt ctgtggcctc agatgtttgg    3540
agctttggag tggttctgta tgaacttttc acatacattg agaagagtaa agtccacca    3600 gcggaattta tgcgtatgat tggcaatgac aaacaaggac agatgatcgt gttccattg    3660 atagaacttt tgaagaataa tggaagatta ccaagaccag atggatgccc agatgagatc    3720
tatatgatca tgacagaatg ctggaacaat aatgtaaatc aacgccctc ctttagggat    3780
```

| | |
|---|---:|
| ctagctcttc gagtggatca aataagggat aacatggctg gatgaaagaa atgaccttca | 3840 |
| ttctgagacc aaagtagatt tacagaacaa agttttatat ttcacattgc tgtggactat | 3900 |
| tattacatat atcattatta tataaatcat gatgctagcc agcaaagatg tgaaaatatc | 3960 |
| tgctcaaaac tttcaaagtt tagtaagttt ttcttcatga ggccaccagt aaaagacatt | 4020 |
| aatgagaatt ccttagcaag gattttgtaa gaagtttctt aaacattgtc agttaacatc | 4080 |
| actcttgtct ggcaaaagaa aaaaaataga ctttttcaac tcagcttttt gagacctgaa | 4140 |
| aaaattatta tgtaaatttt gcaatgttaa agatgcacag aatatgtatg tatagttttt | 4200 |
| accacagtgg atgtataata ccttggcatc ttgtgtgatg ttttacacac atgagggctg | 4260 |
| gtgttcatta atactgtttt ctaattttc catagttaat ctataattaa ttacttcact | 4320 |
| atacaaacaa attaagatgt tcagataatt gaataagtac ctttgtgtcc ttgttcattt | 4380 |
| atatcgctgg ccagcattat aagcaggtgt atacttttag cttgtagttc catgtactgt | 4440 |
| aaatattttt cacataaagg gaacaaatgt ctagttttat ttgtatagga aatttccctg | 4500 |
| accctaaata atacatttg aaatgaaaca agcttacaaa gatataatct attttattat | 4560 |
| ggtttccctt gtatctattt gtggtgaatg tgttttttaa atggaactat ctccaaattt | 4620 |
| ttctaagact actatgaaca gttttctttt aaaattttga gattaagaat gccaggaata | 4680 |
| ttgtcatcct ttgagctgct gactgccaat aacattcttc gatctctggg atttatgctc | 4740 |
| atgaactaaa tttaagctta agccataaaa tagattagat tgttttttaa aaatggatag | 4800 |
| ctcattaaga agtgcagcag gttaagaatt ttttcctaaa gactgtatat ttgaggggtt | 4860 |
| tcagaattt gcattgcagt catagaagag atttatttcc tttttagagg ggaaatgagg | 4920 |
| taaataagta aaaagtatg cttgttaatt ttattcaaga atgccagtag aaaattcata | 4980 |
| acgtgtatct ttaagaaaaa tgagcataca tcttaaatct tttcaattaa gtataagggg | 5040 |
| ttgttcgttg ttgtcatttg ttatagtgct actccacttt agacaccata gctaaaataa | 5100 |
| aatatggtgg gttttgtgtg tgtgtgtgtg tgtgtgtgtg tgtgtgtgtg tgtgttattt | 5160 |
| atacaaaact taaaatactt gctgttttga ttaaaaagaa aatagtttct tacttta | 5217 |

<210> SEQ ID NO 13
<211> LENGTH: 5449
<212> TYPE: DNA
<213> ORGANISM: Homo sapiens

<400> SEQUENCE: 13

| | |
|---|---:|
| cacacaggaa ggagccgagt gggactttcc tctcgctgcc tcccggctct gcccgccctt | 60 |
| cgaaagtcca gggtccctgc ccgctaggca agttgcactc atggcacctc caagtgaaga | 120 |
| gacgcccctg atccctcagc gttcatgcag cctcttgtcc acggaggctg gtgccctgca | 180 |
| tgtgctgctg cccgctcggg gccccgggcc cccccagcgc ctatctttct cctttgggga | 240 |
| ccacttggct gaggacctgt gcgtgcaggc tgccaaggcc agcggcatcc tgcctgtgta | 300 |
| ccactcccctc tttgctctgg ccacggagga cctgtcctgc tggttccccc cgagccacat | 360 |
| cttctccgtg gaggatgcca gcacccaagt cctgctgtac aggattcgct tttacttccc | 420 |
| caattggttt gggctggaga agtgccaccg cttcgggcta cgcaaggatt tggccagtgc | 480 |
| tatccttgac ctgccagtcc tggagcacct ctttgcccag caccgcagtg acctggtgag | 540 |
| tgggcgcctc cccgtggggcc tcagtctcaa ggagcagggt gagtgtctca gcctggccgt | 600 |
| gttggacctg gccggatgg cgcgagagca ggccagcgg ccgggagagc tgctgaagac | 660 |
| tgtcagctac aaggcctgcc tacccccaag cctgcgcgac ctgatccagg gcctgagctt | 720 |

```
cgtgacgcgg aggcgtattc ggaggacggt gcgcagagcc ctgcgccgcg tggccgcctg    780
ccaggcagac cggcactcgc tcatggccaa gtacatcatg gacctggagc ggctggatcc    840
agccggggcc gccgagacct tccacgtggg cctccctggg gcccttggtg ccacgacgg     900
gctgggggctc ctccgcgtgg ctggtgacgg cggcatcgcc tggacccagg agaacagga    960
ggtcctccag cccttctgcg actttccaga atcgtagac attagcatca agcaggcccc    1020
gcgcgttggc ccggccggag agcaccgcct ggtcactgtt accaggacag acaaccagat   1080
tttagaggcc gagttcccag ggctgcccga ggctctgtcg ttcgtggcgc tcgtggacgg   1140
ctacttccgg ctgaccacgg actcccagca cttcttctgc aaggaggtgg caccgccgag   1200
gctgctggag gaagtggccg agcagtgcca cggccccatc actctggact tgccatcaa   1260
caagctcaag actgggggct cacgtcctgg ctcctatgtt ctccgccgca gcccccagga   1320
cttttgacagc ttcctcctca ctgtctgtgt ccagaacccc cttggtcctg attataaggg  1380
ctgcctcatc cggcgcagcc ccacaggaac cttccttctg gttggcctca gccgacccca   1440
cagcagtctt cgagagctcc tggcaacctg ctgggatggg gggctgcacg tagatggggt   1500
ggcagtgacc ctcacttcct gctgtatccc cagacccaaa gaaaagtcca acctgatcgt   1560
ggtccagaga ggtcacagcc cacccacatc atccttggtt cagccccaat cccaatacca   1620
gctgagtcag atgacatttc acaagatccc tgctgacagc ctggagtggc atgagaacct   1680
gggccatggg tccttcacca agatttaccg gggctgtcgc catgaggtgg tggatgggga   1740
ggcccgaaag acagaggtgc tgctgaaggt catggatgcc aagcacaaga actgcatgga   1800
gtcattcctg gaagcagcga gcttgatgag ccaagtgtcg taccggcatc tcgtgctgct   1860
ccacggcgtg tgcatggctg agacagcac catggtgcag gaatttgtac acctgggggc   1920
catagacatg tatctgcgaa aacgtggcca cctggtgcca gccagctgga agctgcaggt   1980
ggtcaaacag ctggcctacg ccctcaacta tctggaggac aaaggcctgc ccatggcaa    2040
tgtctctgcc cggaaggtgc tcctggctcg gagggggct gatgggagcc cgcccttcat    2100
caagctgagt gaccctgggg tcagccccgc tgtgttaagc ctggagatgc tcaccgacag   2160
gatcccctgg gtggccccccg agtgtctccg ggaggcgcag acacttagct tggaagctga   2220
caagtggggc ttcggcgcca cggtctggga agtgtttagt ggcgtcacca tgcccatcag   2280
tgccctggat cctgctaaga aactccaatt ttatgaggac cggcagcagc tgccggcccc   2340
caagtggaca gagctggccc tgctgattca acagtgcatg gcctatgagc cggtccagag   2400
gccctccttc cgagccgtca ttcgtgacct caatagcctc atctcttcag actatgagct   2460
cctctcagac cccacacctg gtgccctggc acctcgtgat gggctgtgga atggtgccca   2520
gctctatgcc tgccaagacc ccacgatctt cgaggagaga cacctcaagt acatctcaca   2580
gctgggcaag ggcaactttg gcagcgtgga gctgtgccgc tatgacccgc taggcgacaa   2640
tacaggtgcc ctggtggccg tgaaacagct gcagcacagc gggccagacc agcagaggga   2700
ctttcagcgg gagattcaga tcctcaaagc actgcacagt gatttcattg tcaagtatcg   2760
tggtgtcagc tatggcccgg gccgccagag cctgcggctg gtcatggagt acctgcccag   2820
cggctgcttg cgcgacttcc tgcagcggca ccgcgcgcgc ctcgatgcca gccgcctcct   2880
tctctattcc tcgcagatct gcaagggcat ggagtacctg ggctcccgcc gctgcgtgca   2940
ccgcgacctg gccgcccgaa acatcctcgt ggagagcgag gcacacgtca agatcgctga   3000
cttcggccta gctaagctgc tgccgcttga caaagactac tacgtggtcc gcgagccagg   3060
ccagagccccc attttctggt atgcccccga atccctctcg gacaacatct ctctcgcca   3120
```

```
gtcagacgtc tggagcttcg gggtcgtcct gtacgagctc ttcacctact gcgacaaaag   3180
ctgcagcccc tcggccgagt tcctgcggat gatgggatgt gagcgggatg tccccgccct   3240
ctgccgcctc ttggaactgc tggaggaggg ccagaggctg ccggcgcctc ctgcctgccc   3300
tgctgaggtt cacgagctca tgaagctgtg ctgggcccct agcccacagg accggccatc   3360
attcagcgcc ctgggccccc agctggacat gctgtggagc ggaagccggg ggtgtgagac   3420
tcatgccttc actgctcacc cagagggcaa acaccactcc ctgtccttt catagctcct    3480
gcccgcagac ctctggatta ggtctctgtt gactggctgt gtgaccttag ccccggagct   3540
gcccctctct gggcctcaga ggccttatga gggtcctcta cttcaggaac accccccatga  3600
cattgcattt ggggggggctc ccgtggcctg tagaatagcc tgtggccttt gcaatttgtt  3660
aaggttcaag acagatgggc atatgtgtca gtgggggctct ctgagtcctg gcccaaagaa  3720
gcaaggaacc aaatttaaga ctctcgcatc ttcccaaccc cttaagccct ggccccctga   3780
gtttcctttt ctgtctctct cttttatttt ttttattt tatttttatt tttgagacag    3840
agcctcgctc tgttacccag ggtggagtgc agtggtgcga tctcggctca gtcaacctc   3900
tgcttcccag gttcaagcga ttctcctgcc tcagcctccc gagtagctgg gattacaggt   3960
gtgcaccacc acacccggct aattttttt attttttaata gagatgaggt ttcaccatga   4020
tggccaggct gatctcgaac tcctaacctc aagtgatcct cccacctcag cctcccaaag   4080
tgttggaata ataggcatga gccactgcac ccaggctttt tttttttaa atttattatt    4140
attattttta agagacagga tcttgctacg ttgcccaggc tggtcttgaa ctcctgggct   4200
acagtgatcc tcctgcctta tcctcctaaa tagctgggac tacagcacct agttttgagt   4260
ttcctgtctt atttccaatg gggacattca tgtagctttt ttttttttt ttttttgag    4320
acggagtctc gctctgtcgc ccaggctgga gtacagtggc gcaatctagg ctcactgcaa   4380
gctccgcctc ctgggttcac accattctct cgcctcagcc tcccaagtag ctgggactac   4440
aggcgcccgc caccacaccc ggctaatttt ttgtattttt agtagagacg gggtttcacc   4500
ttgttagcca ggatggtttc catctcctga cctcgtgatc tgcccgtctc ggcctcccaa   4560
agtgctggga ttacaggcat gagccactgc gcccggccct catgtagctt taaatgtatg   4620
atctgacttc tgctccccga tctctgtttc tctggaggaa gccaaggaca agagcagttg   4680
ctgtggctgg gactctgcct tttaggggag cccgtgtatc tctttgggat cctgaaaggg   4740
ggcaggaaag gctgggggtcc cagtccaccc taatggtatc tgagtgtcct agggcttcag   4800
ttttcccacc tgtccaatgg gacccttct gtcctcaccc tacaaggggc acaaagggat    4860
gacaccaaac ctgcaggaa cttttcacgc aatcaaggga aggaaggca ttcctggcag    4920
agggaacagc atgccaagcg tgagaaggct cagagtaagg aggttaagag cccaagtatt   4980
ggagcctaca gttttgcccc ttccatgcag tgtgacagtg ggcaagttcc tttccctctc   5040
tgggtctcag ttcctgtcccc tgcaaaatgg tcagagctta ccccttggct gtgcagggtc   5100
aactttctga ctggtgagag ggattctcat gcaggttaag cttctgctgc tcctcctcac   5160
ctgcaaagct tttctgccac ttttgcctcc ttggaaaact cttatccatc tctcaaaact   5220
ccagctacca catccttgca gccttccctc atataccccc actactactg tagccctgtc   5280
cttccctcca gccccactct ggccctgggg ctggggaagt gtctgtgtcc agctgtctcc   5340
cctgacctca gggttccttg ggggctgggc tgaggcctca gtacagaggg ggctctggaa   5400
atgtttgttg actgaataaa ggaattcagt ggaaaaaaaa aaaaaaaa                5449
```

```
<210> SEQ ID NO 14
<211> LENGTH: 4064
<212> TYPE: DNA
<213> ORGANISM: Homo sapiens

<400> SEQUENCE: 14
ccctctgacc aggactgagg ggcttttttct ctctgtgccc caggcaagtt gcactcatta      60
tggaattccg gcggcccgct aggcaagttg cactcatggc acctccaagt gaagagacgc     120
ccctgatccc tcagcgttca tgcagcctct tgtccacgga ggctggtgcc ctgcatgtgc     180
tgctgcccgc tcgggccccg ggcccccccc agcgcctatc tttctccttt ggggaccact     240
tggctgagga cctgtgcgtg caggctgcca aggccagcgg catcctgcct gtgtaccact     300
ccctctttgc tctggccacg gaggacctgt cctgctggtt ccccccgagc cacatcttct     360
ccgtggagga tgccagcacc caagtcctgc tgtacaggat tcgcttttac ttccccaatt     420
ggtttgggct ggagaagtgc accgcttcg gctacgcaa ggatttggcc agtgctatcc     480
ttgacctgcc agtcctggag cacctctttg cccagcaccg cagtgacctg gtgagtgggc     540
gcctccccgt gggcctcagt ctcaaggagc agggtgagtg tctcagcctg ccgtgttgg      600 acctggcccg gatggcgcga gagcaggccc agcggccggg agagctgctg aagactgtca     660
gctacaaggc ctgcctaccc ccaagcctgc gcgacctgat ccagggcctg agcttcgtga     720
cgcggagggc tattcggagg acggtgcgca gagccctgcc gcgcgtggcc gcctgccagg     780
cagaccggca ctcgctcatg gccaagtaca tcatggacct ggagcggctg gatccagccg     840
gggccgccga gacccttcac gtgggcctcc ctgggggccct tggtggccac gacgggctgg     900 gctgctccg cgtggctggt gacggcggca tcgcctggac ccagggagaa caggaggtcc     960
tccagccctt ctgcgacttt ccagaaatcg tagacattag catcaagcag gccccgcgcg    1020
ttggcccggc cggagagcac cgcctggtca ctgttaccag gacagacaac cagatttttag    1080 aggccgagtt cccagggctg cccgaggctc tgtcgttcgt ggcgctcgtg gacggctact    1140
tccggctgac cacggactcc cagcacttct tctgcaagga ggtggcaccg ccgaggctgc    1200
tggaggaagt ggccgagcag tgccacggcc ccatcactct ggactttgcc atcaacaagc    1260
tcaagactgg gggctcacgt cctggctcct atgttctccg ccgcagcccc caggactttg    1320
acagcttcct cctcactgtc tgtgtccaga accccttgg tcctgattat aagggctgcc    1380
tcatccggcg cagccccaca ggaaccttcc ttctggttgg cctcagccga ccccacagca    1440
gtcttcgaga gctcctggca acctgctggg atgggggggct gcacgtagat ggggtggcag    1500
tgaccctcac ttcctgctgt atccccagac ccaaagaaaa gtccaacctg atcgtggtcc    1560
agagaggtca cagcccaccc acatcatcct tggttcagcc caatcccaa taccagctga    1620 gtcagatgac atttcacaag atccctgctg acagcctgga gtggcatgag aacctgggcc    1680
atgggtcctt caccaagatt taccggggct gtcgccatga ggtggtggat ggggaggccc    1740
gaaagacaga ggtgctgctg aaggtcatgg atgccaagca caagaactgc atggagtcat    1800
tcctggaagc agcgagcttg atgagccaag tgtcgtaccg gcatctcgtg ctgctccacg    1860
gcgtgtgcat ggctggagac agcaccatgg tgcaggaatt tgtacacctg ggggccatag    1920
acatgtatct gcgaaaacgt ggccacctgg tgccagccag ctggaagctg caggtggtca    1980
aacagctggc ctacgccctc aactatctgg aggacaaagg cctgcccat ggcaatgtct    2040 ctgcccggaa ggtgctcctg gctcgggagg gggctgatgg gagcccgccc ttcatcaagc    2100
tgagtgaccc tggggtcagc cccgctgtgt taagcctgga gatgctcacc gacaggatcc    2160
```

| | | | | | |
|---|---|---|---|---|---|
| cctgggtggc | ccccgagtgt | ctccgggagg | cgcagacact | tagcttggaa | gctgacaagt | 2220 |
| ggggcttcgg | cgccacggtc | tgggaagtgt | ttagtggcgt | caccatgccc | atcagtgccc | 2280 |
| tggatcctgc | taagaaactc | caattttatg | aggaccggca | gcagctgccg | gcccccaagt | 2340 |
| ggacagagct | ggccctgctg | attcaacagt | gcatggccta | tgagccggtc | cagaggccct | 2400 |
| ccttccgagc | cgtcattcgt | gacctcaata | gcctcatctc | ttcagactat | gagctcctct | 2460 |
| cagaccccac | acctggtgcc | ctggcacctc | gtgatgggct | gtggaatggt | gcccagctct | 2520 |
| atgcctgcca | agaccccacg | atcttcgagg | agagacacct | caagtacatc | tcacagctgg | 2580 |
| gcaagggcaa | ctttggcagc | gtggagctgt | gccgctatga | cccgctagcc | cacaatacag | 2640 |
| gtgccctggt | ggccgtgaaa | cagctgcagc | acagcgggcc | agaccagcag | agggactttc | 2700 |
| agcgggagat | tcagatcctc | aaagcactgc | acagtgattt | cattgtcaag | tatcgtggtg | 2760 |
| tcagctatgg | cccgggccgg | ccagagctgc | ggctggtcat | ggagtacctg | cccagcggct | 2820 |
| gcttgcgcga | cttcctgcag | cggcaccgcg | cgcgcctcga | tgccagccgc | ctccttctct | 2880 |
| attcctcgca | gatctgcaag | ggcatggagt | acctgggctc | ccgccgctgc | gtgcaccgcg | 2940 |
| acctggccgc | ccgaaacatc | ctcgtggaga | gcgaggcaca | cgtcaagatc | gctgacttcg | 3000 |
| gcctagctaa | gctgctgccg | cttgacaaag | actactacgt | ggtccgcgag | ccaggccaga | 3060 |
| gccccatttt | ctggtatgcc | cccgaatccc | tctcggacaa | catcttctct | cgccagtcag | 3120 |
| acgtctggag | cttcggggtc | gtcctgtacg | agctcttcac | ctactgcgac | aaaagctgca | 3180 |
| gcccctcggc | cgagttcctg | cggatgatgg | gatgtgagcg | ggatgtcccc | gccctctgcc | 3240 |
| gcctcttgga | actgctggag | gagggccaga | ggctgccggc | gcctcctgcc | tgccctgctg | 3300 |
| aggttcacga | gctcatgaag | ctgtgctggg | cccctagccc | acaggaccgg | ccatcattca | 3360 |
| gcgcctggg | ccccagctg | gacatgctgt | ggagcggaag | ccggggggtgt | gagactcatg | 3420 |
| ccttcactgc | tcacccagag | ggcaaacacc | actccctgtc | cttttcatag | ctcctgcccg | 3480 |
| cagacctctg | gattaggtct | ctgttgactg | gctgtgtgac | cttaggcccg | gagctgcccc | 3540 |
| tctctgggcc | tcagaggcct | tatgagggtc | ctctacttca | ggaacacccc | catgacattg | 3600 |
| catttggggg | ggctcccgtg | gcctgtagaa | tagcctgtgg | cctttgcaat | tgttaaggt | 3660 |
| tcaagacaga | tgggcatatg | tgtcagtggg | gctctctgag | tcctggccca | agaagcaag | 3720 |
| gaaccaaatt | taagactctc | gcatcttccc | aaccccttaa | gccctggccc | cctgagtttc | 3780 |
| cttttctcgt | ctctctcttt | ttattttttt | tattttattt | tttattttg | agacagagcc | 3840 |
| tcgctcgtta | cccagggtgg | agtgcagtgg | tagcgatctc | ggctcacagt | gcaacctctg | 3900 |
| cttcccaggt | tcaagcgatt | ctcctgcctc | agcctcccga | gtagctggga | ttacaggtgt | 3960 |
| gcaccaccac | acccggctaa | tttttttttat | ttttaataga | gatgaggttt | caccatgatg | 4020 |
| gccaggctga | tctcgaactc | ctaacctcaa | gtgatcctcc | cacc | | 4064 |

<210> SEQ ID NO 15
<211> LENGTH: 4262
<212> TYPE: DNA
<213> ORGANISM: Homo sapiens

<400> SEQUENCE: 15

| | | | | | |
|---|---|---|---|---|---|
| aagcagtagc | tacccgcggg | agcggggagg | ggtccgggtt | cgagcttgtg | ttcccccgga | 60 |
| agggtgagtc | tggacgcggg | cgcggaagga | gcgcggccgg | aggtcctcag | gaagaagccg | 120 |
| cggggactgc | ctgcgcttga | caggctgcac | ttgatgggga | gcacctggtg | cctcgggact | 180 |
| gctccgatgc | ccgggtctgt | gctgaatgtg | taatatgcgg | aactatattg | aaacattaca | 240 |

```
accatcttttt gatggcaaca ccctgaggac ctccctttc cagatgggga aactgaggcc    300
cagaattgct aagtggcttg cttgagttga cacaggagc tccaggactc accctcagct    360
gagccacctg ccgggagcat gcctctgcgc cactggggga tggccagggg cagtaagccc    420
gttggggatg gagcccagcc catggctgcc atgggaggcc tgaaggtgct tctgcactgg    480
gctggtccag gcggcgggga gccctgggtc actttcagtg agtcatcgct gacagctgag    540
gaagtctgca tccacattgc acataaagtt ggtatcactc ctccttgctt caatctcttt    600
gccctcttcg atgctcaggc ccaagtctgg ttgcccccaa accacatcct agagatcccc    660
agagatgcaa gcctgatgct atatttccgc ataaggtttt atttccggaa ctggcatggc    720
atgaatcctc gggaaccggc tgtgtaccgt tgtgggcccc aggaaccga ggcatcctca    780
gatcagacag cacaggggat gcaactcctg gacccagcct catttgagta cctctttgag    840
cagggcaagc atgagtttgt gaatgacgtg gcatcactgt gggagctgtc gaccgaggag    900
gagatccacc actttaagaa tgagagcctg ggcatggcct ttctgcacct ctgtcacctc    960
gctctccgcc atggcatccc cctggaggag gtggccaaga agaccagctt caaggactgc   1020
atcccgcgct ccttccgccg gcatatccgg cagcacagcg ccctgacccg gctgcgcctt   1080
cggaacgtct tccgcaggtt cctgcgggac ttccagccgg ccgactctc ccagcagatg   1140
gtcatggtca aatacctagc cacactcgag cggctggcac ccgcttcgg cacagagcgt   1200
gtgcccgtgt gccacctgag gctgctggcc caggccgagg gggagccctg ctacatccgg   1260
gacagtgggg tggcccctac agaccctggc cctgagtctg ctgctgggcc cccaacccac   1320
gaggtgctgg tgacaggcac tggtggcatc agtggtggc cagtagagga ggaggtgaac   1380
aaggaggagg gttctagtgg cagcagtggc aggaaccccc aagccagcct gtttgggaag   1440
aaggccaagc tcacaaggc agtcggccag ccggcagaca ggccgcggga gccactgtgg   1500
gcctacttct gtgacttccg ggacatcacc cacgtggtgc tgaaagagca ctgtgtcagc   1560
atccaccggc aggacaacaa gtgcctggag ctgagcttgc cttcccgggc tgcggcgctg   1620
tccttcgtgt cgctggtgga cggctatttc cgcctgacgg ccgactccag ccactacctg   1680
tgccacgagg tggctccccc acggctggtg atgagcatcc gggatgggat ccacggaccc   1740
ctgctggagc catttgtgca ggccaagctg cggcccgagg acggcctgta cctcattcac   1800
tggagcacca gccaccccta ccgcctgatc ctcacagtgg cccagcgtag ccaggcacca   1860
gacggcatgc agagcttgcg gctccgaaag ttccccattg agcagcagga cggggccttc   1920
gtgctggagg gctggggccg gtccttcccc agcgttcggg aacttgggc tgccttgcag   1980
ggctgcttgc tgagggccgg ggatgactgc ttctctctgc gtcgctgttg cctgccccaa   2040
ccaggagaaa cctccaatct catcatcatg cgggggctc gggccagccc caggacactc   2100
aacctcagcc agctcagctt ccaccgggtt gaccagaagg agatcaccca gctgtcccac   2160
ttgggccagg gcacaaggac caacgtgtat gagggccgcc tgcgagtgga gggcagcggg   2220
gaccctgagg agggcaagat ggatgacgag gaccccctcg tgcctggcag ggaccgtggg   2280
caggagctac gagtggtgct caaagtgctg gaccctagtc accatgacat cgccctggcc   2340
ttctacgaga cagccagcct catgagccag gtctcccaca cgcacctggc cttcgtgcat   2400
ggcgtctgtg tgcgcggccc tgaaaatatc atggtgacag agtacgtgga gcacggaccc   2460
ctggatgtgt ggctgcggag ggagcgggc catgtgccca tggcttggaa gatggtggtg   2520
gcccagcagc tggccagcgc cctcagctac ctggagaaca gaacctggt tcatggtaat   2580
gtgtgtggcc ggaacatcct gctggcccgg ctggggttgg cagagggcac cagcccttc    2640
```

-continued

```
atcaagctga gtgatcctgg cgtgggcctg ggcgccctct ccagggagga gcgggtggag    2700
aggatcccct ggctggcccc cgaatgccta ccaggtgggg ccaacagcct aagcaccgcc    2760
atggacaagt gggggtttgg cgccaccctc ctggagatct gctttgacgg agaggcccct    2820
ctgcagagcc gcagtccctc cgagaaggag catttctacc agaggcagca ccggctgccc    2880
gagccctcct gcccacagct ggccacactc accagccagt gtctgaccta tgagccaacc    2940
cagaggccat cattccgcac catcctgcgt gacctcaccc ggctgcagcc ccacaatctt    3000
gctgacgtct tgactgtgaa cccggactca ccggcgtcgg accctacggt tttccacaag    3060
cgctatttga aaaagatccg agatctgggc gagggtcact tcggcaaggt cagcttgtac    3120
tgctacgatc cgaccaacga cggcactggc gagatggtgg cggtgaaagc cctcaaggca    3180
gactgcggcc cccagcaccg ctcgggctgg aagcaggaga ttgacattct gcgcacgctc    3240
taccacgagc acatcatcaa gtacaagggc tgctgcgagg accaaggcga gaagtcgctg    3300
cagctggtca tggagtacgt gcccctgggc agcctccgag actacctgcc ccggcacagc    3360
atcgggctgg cccagctgct gctcttcgcc cagcagatct gcgagggcat ggcctatctg    3420
cacgcgcagc actacatcca ccgagaccta gccgcgcgca acgtgctgct ggacaacgac    3480
aggctggtca agatcgggga ctttggccta gccaaggccg tgcccgaagg ccacgagtac    3540
taccgcgtgc gcgaggatgg ggacagcccc gtgttctggt atgccccaga gtgcctgaag    3600
gagtataagt tctactatgc gtcagatgtc tggtccttcg gggtgaccct gtatgagctg    3660
ctgacgcact gtgactccag ccagagcccc cccacgaaat tccttgagct cataggcatt    3720
gctcagggtc agatgacagt tctgagactc actgagttgc tggaacgagg ggagaggctg    3780
ccacggcccg acaaatgtcc ctgtgaggtc tatcatctca tgaagaactg ctgggagaca    3840
gaggcgtcct ttcgcccaac cttcgagaac ctcataccca ttctgaagac agtccatgag    3900
aagtaccaag gccaggcccc ttcagtgttc agcgtgtgct gaggcacaat ggcagccctg    3960
cctgggagga ctggaccagg cagtggctgc agagggagcc tcctgctccc tgctccagga    4020
tgaaaccaag aggggatgt cagcctcacc cacaccgtgt gccttactcc tgtctagaga    4080
ccccacctct gtgaacttat ttttcttttct tggccgtgag cctaaccatg atcttgaggg    4140
acccaacatt tgtagggggca ctaatccagc ccttaaatcc cccagcttcc aaacttgagg    4200
cccaccatct ccaccatctg gtaataaact catgttttct ctgctggaaa aaaaaaaaa    4260
aa                                                                   4262
```

TREATMENT OF A DISEASE OF THE GASTROINTESTINAL TRACT WITH A JAK INHIBITOR AND DEVICES

CROSS-REFERENCE TO RELATED APPLICATIONS

This application is a National Stage application under 35 U.S.C. § 371 of International Application No. PCT/US2017/066492, filed Dec. 14, 2017, which claims the benefit of the following U.S. Provisional Applications 62/434,374 filed Dec. 14, 2016; 62/478,919 filed Mar. 30, 2017; 62/545,380 filed Aug. 14, 2017; and 62/583,832 filed Nov. 9, 2017, each of which is incorporated by reference in its entirety.

TECHNICAL FIELD

This disclosure features methods and compositions for treating diseases of the gastrointestinal tract with a JAK inhibitor.

BACKGROUND

The Janus kinase (JAK) proteins are a family of non-receptor tyrosine kinases that possess a highly conserved kinase domain responsible for its enzymatic activity. Mammals have four members of this family, JAK1, JAK2, JAK3 and Tyrosine kinase 2 (TYK2). These kinases associate with the intracellular portion of cytokine or hormone receptors, and transduce signals through seven members of the STAT transcription factors—STAT1, STAT2, STAT3, STAT4, STAT5A, STAT5B, and STAT6 in various combinations. JAK1 promotes signaling of multiple cytokines (e.g., certain type I and type II cytokines), including pro-inflammatory cytokines involved in the pathogenesis of autoimmune diseases. Single-nucleotide polymorphisms within the JAK/STAT pathway that confer susceptibility to IBD have been identified (Jostins et al., Host-microbe interactions have shaped the genetic architecture of inflammatory bowel disease, Nature 491:119-124, 2012). Both in vivo and in vitro studies have confirmed the role of JAK/STAT signaling in regulating immune responses (O'Shea and Plenge, JAK and STAT signaling molecules in immunoregulation and immune-mediated disease, Immunity 36:542-550, 2012). Tofacitinib, selective oral JAK inhibitor (including JAK1 and JAK3) has been tested in clinical trials for both ulcerative colitis (Sandborn et al., Tofacitinib, an Oral Janus Kinase Inhibitor, in Active Ulcerative Colitis, New England J. Med 367:616-24, 2012; Panes et al., Randomized trial of tofacitinib in active ulcerative colitis: analysis of efficacy base on patient-reported outcomes, BMC Gastroenterology 15:14, doi: 10.1186/s12876-015-0239-9, 2015) and Crohn's disease.

The gastrointestinal (GI) tract generally provides a therapeutic medium for an individual's body. At times, therapeutic drugs may need to be dispensed to specified locations within the small intestine or large intestine, which is more effective than oral administration of the therapeutic drugs to cure or alleviate the symptoms of some medical conditions. For example, therapeutic drugs dispensed directly within the small intestine would not be contaminated, digested or otherwise compromised in the stomach, and thus allow a higher dose to be delivered at a specific location within the small intestine. However, dispensing therapeutic drugs directly within the small intestine inside a human body (e.g., the cecum, the ascending colon) can be difficult, because a device or mechanism (e.g., special formulation) would be needed to transport a therapeutically effective dose of drug to a desired location within the small intestine and then automatically deliver the therapeutic drug at the desired location. Dispensing therapeutic drugs directly within other locations in the GI tract of the human body can be similarly difficult. Such a device or mechanism also would also need to be operated in a safe manner in that the device or mechanism needs to physically enter the human body.

In sum, there remains a significant unmet medical need for improved treatment regimens for gastrointestinal diseases, such as inflammatory bowel disease (IBD), including a need for regimens which can dispense therapeutics to specific locations within the GI tract, thereby reducing or avoiding the drawbacks of oral or other forms of systemic administration.

SUMMARY

The present disclosure provides novel treatment paradigms for inflammatory conditions of the gastrointestinal tract. The methods and compositions described herein allow for the regio-specific release of therapeutic drugs at or near the site of disease in the gastrointestinal tract. By releasing a therapeutic drug locally instead of systemically, the bioavailability of the drug can be increased at the site of injury and/or decreased in the systemic circulation, thereby resulting in improved overall safety and/or efficacy and fewer adverse side effects. Advantages may include one or more of increased drug engagement at the target, leading to new and more efficacious treatment regimens, and/or lower systemic drug levels, which can translate to reduced toxicity and reduced immunogenicity, e.g., in the case of biologics. In some instances, releasing a therapeutic drug locally also provides for new modes of action that may be unique to local delivery in the GI tract as opposed to systemic administration. For patients, clinicians and payors, this can mean an easier or simpler route of administration, fewer co-medicaments (e.g., immunomodulators), fewer side effects, and/or better outcomes.

Accordingly, described herein are methods for treating disorders of the gastrointestinal (GI) tract. The methods can include one or more of:

diagnosing a GI disease in a subject; and/or
mapping, sampling, and/or assessing the site, severity, pathology, and extent of a GI disease in the GI tract of a subject and/or mapping, sampling, and/or assessing a patient response to a therapeutic agent, e.g., in the patient's GI tract; and/or
identifying, quantifying, and/or monitoring one or more markers of a GI disease in the GI tract of the subject and/or one or more markers of patient response to a therapeutic agent, e.g., in the patient's GI tract; and/or
releasing a therapeutic agent, e.g., proximate to_the site of a GI disease.

The present disclosure accordingly provides patients and physicians more personalized treatment options for GI disorders by facilitating regimens which can release a therapeutic agent according to desired (e.g., customized or optimized) dosage, timing, and/or location parameters. In some cases, the treatment methods can employ one or more ingestible devices to achieve the benefits disclosed herein.

In some embodiments, provided herein is a method of treating a disease of the gastrointestinal tract in a subject, comprising:

administering to the subject a pharmaceutical formulation that comprises an JAK inhibitor, wherein the pharmaceutical formulation is released at a location in the gastrointestinal tract of the subject that is proximate to one or more sites of disease.

In some embodiments, provided herein the pharmaceutical formulation is administered in an ingestible device. In some embodiments, the pharmaceutical formulation is released from an ingestible device. In some embodiments, the ingestible device comprises a housing, a reservoir containing the pharmaceutical formulation, and a release mechanism for releasing the pharmaceutical formulation from the device, wherein the reservoir is releasably or permanently attached to the exterior of the housing or internal to the housing.

In some embodiments, provided herein is a method of treating a disease of the gastrointestinal tract in a subject, comprising:

administering to the subject an ingestible device comprising a housing, a reservoir containing a pharmaceutical formulation, and a release mechanism for releasing the pharmaceutical formulation from the device, wherein the reservoir is releasably or permanently attached to the exterior of the housing or internal to the housing;

wherein the pharmaceutical formulation comprises an JAK inhibitor, and the ingestible device releases the pharmaceutical formulation at a location in the gastrointestinal tract of the subject that is proximate to one or more sites of disease.

In some embodiments, the housing is non-biodegradable in the GI tract. In some embodiments, the release of the formulation is triggered autonomously. In some embodiments, the device is programmed to release the formulation with one or more release profiles that may be the same or different at one or more locations. In some embodiments, the device is programmed to release the formulation at a location proximate to one or more sites of disease. In some embodiments, the location of one or more sites of disease is predetermined.

In some embodiments, the reservoir is made of a material that allows the formulation to leave the reservoir, such as a biodegradable material.

In some embodiments, the release of the formulation is triggered by a pre-programmed algorithm. In some embodiments, the release of the formulation is triggered by data from a sensor or detector to identify the location of the device. In some more particular embodiments, the data is not based solely on a physiological parameter (such as pH, temperature, and/or transit time).

In some embodiments, the device comprises a detector configured to detect light reflectance from an environment external to the housing. In some more particular embodiments, the release is triggered autonomously or based on the detected reflectance.

In some embodiments, the device releases the formulation at substantially the same time as one or more sites of disease are detected. In some embodiments, the one or more sites of disease are detected by the device (e.g., by imaging the GI tract).

In some embodiments, the release mechanism is an actuation system. In some embodiments, the release mechanism is a chemical actuation system. In some embodiments, the release mechanism is a mechanical actuation system. In some embodiments, the release mechanism is an electrical actuation system. In some embodiments, the actuation system comprises a pump and releasing the formulation comprises pumping the formulation out of the reservoir. In some embodiments, the actuation system comprises a gas generating cell. In some embodiments, the device further comprises an anchoring mechanism. In some embodiments, the formulation comprises a therapeutically effective amount of the JAK inhibitor. In some embodiments, the formulation comprises a human equivalent dose (HED) of the JAK inhibitor.

In some embodiments, the device is a device capable of releasing a solid JAK inhibitor or a solid formulation comprising the JAK inhibitor. In some embodiments, the device is a device capable of releasing a liquid JAK inhibitor or a liquid formulation comprising the JAK inhibitor. Accordingly, in some embodiments of the methods herein, the pharmaceutical formulation release from the device is a solid formulation. Accordingly, in some embodiments of the methods herein, the pharmaceutical formulation release from the device is a liquid formulation.

The devices disclosed herein are capable of releasing a JAK inhibitor or a formulation comprising the JAK inhibitor irrespective of the particular type of JAK inhibitor. For example, the JAK inhibitor may be a small molecule, a biological, a nucleic acid, an antibody, a fusion protein, and so on.

In some embodiments, provided herein is a method of releasing an JAK inhibitor into the gastrointestinal tract of a subject for treating one or more sites of disease within the gastrointestinal tract, the method comprising:

administering to the subject a therapeutically effective amount of the JAK inhibitor housed in an ingestible device, wherein the ingestible device comprises a detector configured to detect the presence of the one or more sites of disease, and a controller or processor configured to trigger the release of the JAK inhibitor proximate to the one or more sites of disease in response to the detector detecting the presence of the one or more sites of disease.

In some embodiments, provided herein is a method of releasing an JAK inhibitor into the gastrointestinal tract of a subject for treating one or more pre-determined sites of disease within the gastrointestinal tract, the method comprising:

administering to the subject a therapeutically effective amount of the JAK inhibitor contained in an ingestible device, wherein the ingestible device comprises a detector configured to detect the location of the device within the gastrointestinal tract, and a controller or processor configured to trigger the release of the JAK inhibitor proximate to the one or more predetermined sites of disease in response to the detector detecting a location of the device that corresponds to the location of the one or more pre-determined sites of disease.

In some embodiments, provided herein is a method of releasing an JAK inhibitor into the gastrointestinal tract of a subject for treating one or more sites of disease within the gastrointestinal tract, the method comprising:

administering to the subject a therapeutically effective amount of the JAK inhibitor contained in an ingestible device;

receiving at an external receiver from the device a signal transmitting environmental data;

assessing the environmental data to confirm the presence of the one or more sites of disease; and when the presence of the one or more sites of disease is confirmed, sending from an external transmitter to the device a signal triggering the release of the JAK inhibitor proximate to the one or more sites of disease.

In some embodiments, provided herein is a method of releasing an JAK inhibitor into the gastrointestinal tract of a subject for treating one or more sites of disease within the gastrointestinal tract, the method comprising:
administering to the subject a therapeutically effective amount of the JAK inhibitor contained in an ingestible device;
receiving at an external receiver from the device a signal transmitting environmental or optical data;
assessing the environmental or optical data to confirm the location of the device within the gastrointestinal tract; and
when the location of the device is confirmed, sending from an external transmitter to the device a signal triggering the release of the JAK inhibitor proximate to the one or more sites of disease.

Provided herein in one embodiment is a method of treating a disease of the gastrointestinal tract in a subject, comprising:
delivering a JAK inhibitor at a location in the gastrointestinal tract of the subject,
wherein the method comprises administering to the subject
 a pharmaceutical composition comprising a therapeutically effective amount of the JAK inhibitor.

Provided herein in one embodiment is a method of treating a disease of the large intestine in a subject, comprising:
delivering a JAK inhibitor at a location in the proximal portion of the large intestine of the subject,
wherein the method comprises administering endoscopically to the subject a therapeutically effective amount of the JAK inhibitor.

Provided herein in one embodiment is a method of treating a disease of the gastrointestinal tract in a subject, comprising:
releasing a JAK inhibitor at a location in the gastrointestinal tract of the subject that is proximate to one or more sites of disease,
wherein the method comprises administering to the subject a pharmaceutical composition comprising a therapeutically effective amount of the JAK inhibitor.

Provided herein in one embodiment is a method of treating a disease of the gastrointestinal tract in a subject, comprising:
releasing a JAK inhibitor at a location in the gastrointestinal tract of the subject that is proximate to one or more sites of disease,
wherein the method comprises administering to the subject a pharmaceutical composition comprising a therapeutically effective amount of the JAK inhibitor, wherein the pharmaceutical composition is an ingestible device, and the method comprises administering orally to the subject the pharmaceutical composition.

Provided herein in one embodiment is a method of treating a disease of the gastrointestinal tract in a subject, comprising:
releasing a JAK inhibitor at a location in the gastrointestinal tract of the subject that is proximate to one or more sites of disease, wherein the method comprises administering to the subject a pharmaceutical composition comprising a therapeutically effective amount of the JAK inhibitor, wherein the method provides a concentration of the JAK inhibitor in the plasma of the subject that is less than 3 µg/ml.

Provided herein in one embodiment is a method of treating a disease of the large intestine in a subject, comprising:
releasing a JAK inhibitor at a location in the proximal portion of the large intestine of the subject that is proximate to one or more sites of disease,
wherein the method comprises administering endoscopically to the subject a therapeutically effective amount of the JAK inhibitor.

In another aspect of the present invention, there is provided a JAK inhibitor for use in a method of treating a disease of the gastrointestinal tract in a subject, wherein the method comprises orally administering to the subject an ingestible device loaded with the JAK inhibitor, wherein the JAK inhibitor is released by the device at a location in the gastrointestinal tract of the subject that is proximate to one or more sites of disease.

In another aspect, the present invention provides a composition comprising or consisting of an ingestible device loaded with a therapeutically effective amount of a JAK inhibitor, for use in a method of treatment, wherein the method comprises orally administering the composition to the subject, wherein the JAK inhibitor is released by the device at a location in the gastrointestinal tract of the subject that is proximate to one or more sites of disease.

In another aspect, the present invention provides an ingestible device loaded with a therapeutically effective amount of a JAK inhibitor, wherein the device is controllable to release the JAK inhibitor at a location in the gastrointestinal tract of the subject that is proximate to one or more sites of disease. The device may be for use in a method of treatment of the human or animal body, for example, any method as described herein.

In still another aspect, the present invention provides an ingestible device for use in a method of treating a disease of the gastrointestinal tract in a subject, wherein the method comprises orally administering to the subject the ingestible device loaded with a therapeutically effective amount of a JAK inhibitor, wherein the JAK inhibitor is released by the device at a location in the gastrointestinal tract of the subject that is proximate to one or more sites of disease.

An ingestible device as used in the present invention may comprise one or more mechanical and/or electrical mechanisms which actively control release of the JAK inhibitor. For example, in any of the above aspects and embodiments, the ingestible device as used in the present invention may comprise a release mechanism for release of the JAK inhibitor (e.g., from a reservoir comprising the JAK inhibitor) and an actuator controlling the release mechanism.

In one embodiment, the ingestible device comprises:
an ingestible housing comprising a reservoir having a therapeutically effective amount of the JAK inhibitor stored therein;
a release mechanism having a closed state which retains the JAK inhibitor in the reservoir and an open state which releases the JAK inhibitor from the reservoir to the exterior of the device; and
an actuator which changes the state of the release mechanism from the closed
to the open state.

In one embodiment, the ingestible device comprises:
a housing defined by a first end, a second end substantially opposite from the first end;
a reservoir located within the housing and containing the JAK inhibitor wherein a first end of the reservoir is attached to the first end of the housing;
a mechanism for releasing the JAK inhibitor from the reservoir;
and
an exit valve configured to allow the JAK inhibitor to be released out of the housing from the reservoir.

Here, the exit valve can be considered as the release mechanism having a closed state which retains the JAK inhibitor in the reservoir and an open state which releases the JAK inhibitor from the reservoir to the exterior of the device, and the mechanism for releasing the JAK inhibitor from the reservoir can be considered as the actuator.

In some embodiments of methods of treatment as described herein, the one or more disease sites may have been pre-determined (e.g., determined in a step preceding the administration of the composition of the present invention). The disease site(s) may have been determined by imaging the gastrointestinal tract. For example, the disease site(s) may have been pre-determined by endoscopy (e.g., a step of colonoscopy, enteroscopy, or using a capsule endoscope). Determination that the device is proximate to the disease site may therefore comprise a determining that the device is in a location corresponding to this previously-determined disease site.

In some embodiments, the location of the device in the gut may be detected by tracking the device. For example, the device may comprise a localization mechanism which may be a communication system for transmitting localization data, e.g., by radiofrequency transmission. The device may additionally or alternatively comprise a communication system for receiving a signal remotely triggering the actuator and thus causing release of the JAK inhibitor. The signal may be sent when it is determined that the device is in the correct location in the gut.

Thus, the ingestible device may comprise:
an ingestible housing comprising a reservoir having a therapeutically effective amount of the JAK inhibitor stored therein;
a release mechanism having a closed state which retains the JAK inhibitor in the reservoir and an open state which releases the JAK inhibitor from the reservoir to the exterior of the device;
a communication system for transmitting localization data to an external receiver and for receiving a signal from an external transmitter; and
an actuator which changes the state of the release mechanism from the closed to the open state and which can be triggered by the signal.

In other embodiments, the ingestible device as used in the present invention may comprise an environmental sensor for detecting the location of the device in the gut and/or for detecting the presence of disease in the GI tract. For example, the environment sensor may be an image sensor for obtaining images in vivo.

Detecting the presence of disease may comprise, for example, detecting the presence of inflamed tissue, and/or lesions such as ulceration e.g., aphthoid ulcerations, "punched-out ulcers" and/or superficial ulcers of the mucosa, cobblestoning, stenosis, granulomas, crypt abscesses, fissures, e.g., extensive linear fissures, villous atrophy, fibrosis, and/or bleeding.

Detecting the presence of disease may also comprise molecular sensing, such as detecting the amount of an inflammatory cytokine or other marker of inflammation. Such a marker can be measured locally from a biopsy or systemically in the serum.

Where the ingestible device comprises an environmental sensor, actuation of the release mechanism may be triggered by a processor or controller communicably coupled to the environmental sensor. Thus, in some embodiments, the device may not require any external signal or control in order to release the drug.

In one embodiment, the ingestible device may comprise:
an ingestible housing comprising a reservoir having a therapeutically effective amount of the JAK inhibitor stored therein;
a release mechanism having a closed state which retains the JAK inhibitor in the reservoir and an open state which releases the JAK inhibitor from the reservoir to the exterior of the device;
an actuator which controls the transition of the release mechanism from the closed to the open state;
a detector for detecting the location of the device in the gut and/or the presence of diseased tissue; and
a processor or controller which is coupled to the detector and to the actuator and which triggers the actuator to cause the release mechanism to transition from its closed state to its open state when it is determined that the device is in the presence of diseased tissue and/or in a location in the gut that has been predetermined to be proximal to diseased tissue.

In another embodiment, there is provided:
an ingestible housing comprising a reservoir having a therapeutically effective amount of the JAK inhibitor stored therein;
a detector coupled to the ingestible housing, the detector configured to detect when the ingestible housing is proximate to a respective disease site of the one of the one or more sites of disease;
a valve system in fluid communication with the reservoir system; and
a controller communicably coupled to the valve system and the detector, the controller configured to cause the valve system to open in response to the detector detecting that the ingestible housing is proximate to the respective disease site so as to release the therapeutically effective amount of the JAK inhibitor at the respective disease site.

As above, detection that the ingestible housing is proximate to the respective disease site may be based on environmental data indicating the location of the device in the GI tract (and reference to a pre-determined disease site) or on environmental data directly indicating the presence of diseased tissue.

Additionally, or alternatively, the device may further comprise a communication system adapted to transmit the environment data to an external receiver (e.g., outside of the body). This data may be used, for example, for diagnostic purposes. The external receiver may comprise means for displaying the data.

In some embodiments, this data may be analyzed externally to the device and used to determine when the drug should be released: an external signal may then be sent to the device to trigger release of the drug. Thus, the communication system may further be adapted to receive a signal remotely triggering the actuator and thus causing release of the JAK inhibitor. The signal may be sent from an external transmitter in response to receipt/analysis and/or assessment of the environmental data, e.g., data indicating that the device has reached the desired location of the gut (where the location of the diseased tissue has been pre-determined) and/or data indicating the presence of diseased tissue. "External" may be "outside of the body".

Thus, in another embodiment, the ingestible device may comprise:
an ingestible housing comprising a reservoir having a therapeutically effective amount of the JAK inhibitor stored therein;

a release mechanism having a closed state which retains the JAK inhibitor in the reservoir and an open state which releases the JAK inhibitor from the reservoir to the exterior of the device;

an environmental detector for detecting environmental data indicating the location of the device in the gut and/or the presence of diseased tissue;

a communication system for transmitting the environmental data to an external receiver and for receiving a signal from an external transmitter; and an actuator which controls the transition of the release mechanism from the closed to the open state in response to the signal.

It will be understood from the above that when the device comprises one or more environmental detectors, e.g., comprises an image detector, the compositions may be used both for disease detection and for disease treatment.

Accordingly, in a further embodiment, there is provided a JAK inhibitor for use in a method of detecting and treating a disease of the gastrointestinal tract in a subject, wherein the method comprises orally administering to the subject an ingestible device loaded with the JAK inhibitor, wherein the ingestible device comprises an environmental sensor for determining the presence of diseased tissue in the GI tract, and wherein the JAK inhibitor is released by the device at a location in the gastrointestinal tract of the subject that is proximate to one or more sites of disease, as detected by the environmental sensor. The device may be according to any of the embodiments described herein.

In another embodiment, there is provided a composition for use in a method of detecting and treating a disease of the gastrointestinal tract in a subject, wherein the composition comprises or consists of an ingestible device loaded with a therapeutically effective amount of a JAK inhibitor, wherein the ingestible device comprises an environmental sensor for determining the presence of diseased tissue in the GI tract, and wherein the JAK inhibitor is released by the device at a location in the gastrointestinal tract of the subject that is proximate to one or more sites of disease, as detected by the environmental sensor. Again, the device may be according to any of the embodiments described herein.

In some embodiments, where the ingestible device as used in the present invention comprises an environmental sensor for detecting the presence of disease in the GI tract and a communication system as described above, the method of treatment may comprise:

i) receiving at an external receiver from the ingestible device a signal transmitting the environmental data;

ii) assessing the environmental data to confirm the presence of the disease; and iii) when the presence of the disease is confirmed, sending from an external transmitter to the ingestible device a signal triggering release of the JAK inhibitor.

For example, the presence of disease may be confirmed based on the presence of inflamed tissue and/or lesions associated with any of the disease states referred to herein. For example, the presence of disease may be confirmed based on the presence of inflammation, ulceration e.g., aphthoid ulcerations, "punched-out ulcers" and/or superficial ulcers of the mucosa, cobblestoning, stenosis, granulomas, crypt abscesses, fissures, e.g., extensive linear fissures, villous atrophy, fibrosis, and/or bleeding.

In some embodiments, the present invention may relate to a system comprising:

an ingestible device loaded with a therapeutically effective amount of a JAK inhibitor, a release mechanism for release of the JAK inhibitor (e.g., from a reservoir comprising the JAK inhibitor), an actuator controlling the release mechanism, an environmental sensor for determining the location of the device in the gut and/or for detecting the presence of diseased tissue and a communication system adapted to transmit the environment data and receive a signal triggering the actuator;

a receiver and display module for receiving and displaying outside of the body the environment data from the ingestible device;

a transmitter for sending to the ingestible device a signal triggering the actuator.

In any of the above embodiments, the ingestible device may further comprise an anchoring system for anchoring the device or a portion thereof in a location and an actuator for the anchoring system. This may be triggered in response to a determination that the device is at a location in the gastrointestinal tract of the subject proximate to one or more sites of disease. For instance, this may be detected by the environmental sensor. The triggering may be controlled by a processor in the device, that is, autonomously. A device where the triggering is controlled by a processor in the device is said to be an autonomous device. Alternatively, it may be controlled by a signal sent from outside of the body, as described above.

In any of the above aspects and embodiments, disease of the GI tract may be an inflammatory bowel disease.

In some embodiments, the disease of the GI tract is ulcerative colitis.

In some embodiments, the disease of the GI tract is Crohn's disease.

In general, apparatuses, compositions, and methods disclosed herein are useful in the treatment of diseases of the gastrointestinal tract. Exemplary gastrointestinal tract diseases that can be treated include, without limitation, inflammatory bowel disease (IBD), Crohn's disease (e.g., active Crohn's disease, refractory Crohn's disease, or fistulizing Crohn's disease), ulcerative colitis, indeterminate colitis, microscopic colitis, infectious colitis, drug or chemical-induced colitis, diverticulitis, and ischemic colitis, gastritis, peptic ulcers, stress ulcers, bleeding ulcers, gastric hyperacidity, dyspepsia, gastroparesis, Zollinger-Ellison syndrome, gastroesophageal reflux disease, short-bowel (anastomosis) syndrome, a hypersecretory state associated with systemic mastocytosis or basophilic leukemia or hyperhistaminemia, Celiac disease (e.g., nontropical Sprue), enteropathy associated with seronegative arthropathies, microscopic colitis, collagenous colitis, eosinophilic gastroenteritis, colitis associated with radiotherapy or chemotherapy, colitis associated with disorders of innate immunity as in leukocyte adhesion deficiency-1, chronic granulomatous disease, food allergies, gastritis, infectious gastritis or enterocolitis (e.g., *Helicobacter pylori*-infected chronic active gastritis), other forms of gastrointestinal inflammation caused by an infectious agent, pseudomembranous colitis, hemorrhagic colitis, hemolytic-uremic syndrome colitis, diversion colitis, irritable bowel syndrome, irritable colon syndrome, and pouchitis.

In some embodiments, apparatuses, compositions, and methods disclosed herein are used to treat one gastrointestinal disease. In some embodiments, apparatuses, compositions, and methods disclosed herein are used to treat more than one gastrointestinal disease. In some embodiments, apparatuses, compositions, and methods disclosed herein are used to treat multiple gastrointestinal diseases that occur in the same area of the gastrointestinal tract (e.g., each disease can occur in the small intestine, large intestine, colon, or any sub-region thereof). In some embodiments, apparatuses, compositions, and methods disclosed herein are used to treat multiple gastrointestinal diseases that occur in different areas of the gastrointestinal tract. In some embodiments, administration (e.g., local administration to the gastrointestinal tract) of JAK inhibitor is useful in the treatment of gastrointestinal diseases including, but not limited to, inflammatory bowel disease (IBD), ulcerative colitis, Crohn's disease, or any of the other gastrointestinal diseases described herein.

In some embodiments, administration (e.g., local administration to the gastrointestinal tract) of JAK inhibitor is useful in the treatment of gastrointestinal diseases including, but not limited to, inflammatory bowel disease (IBD), ulcerative colitis, Crohn's disease, or any of the other gastrointestinal diseases described herein.

Aspects and embodiments as described herein are intended to be freely combinable. For example, any details or embodiments described herein for methods of treatment apply equally to a JAK inhibitor, composition or ingestible device for use in said treatment. Any details or embodiments described for a device apply equally to methods of treatment using the device, or to a JAK inhibitor or composition for use in a method of treatment involving the device.

BRIEF DESCRIPTION OF THE DRAWINGS

FIG. 23 illustrates a valve system;

FIGS. 24A and 24B illustrate a portion of a two-stage valve system in its first and second stages, respectively;

FIG. 52 is a representative table of the plasma adalimumab concentrations (μg/mL) as shown in FIG. 4.6.

DETAILED DESCRIPTION

Figure 1:
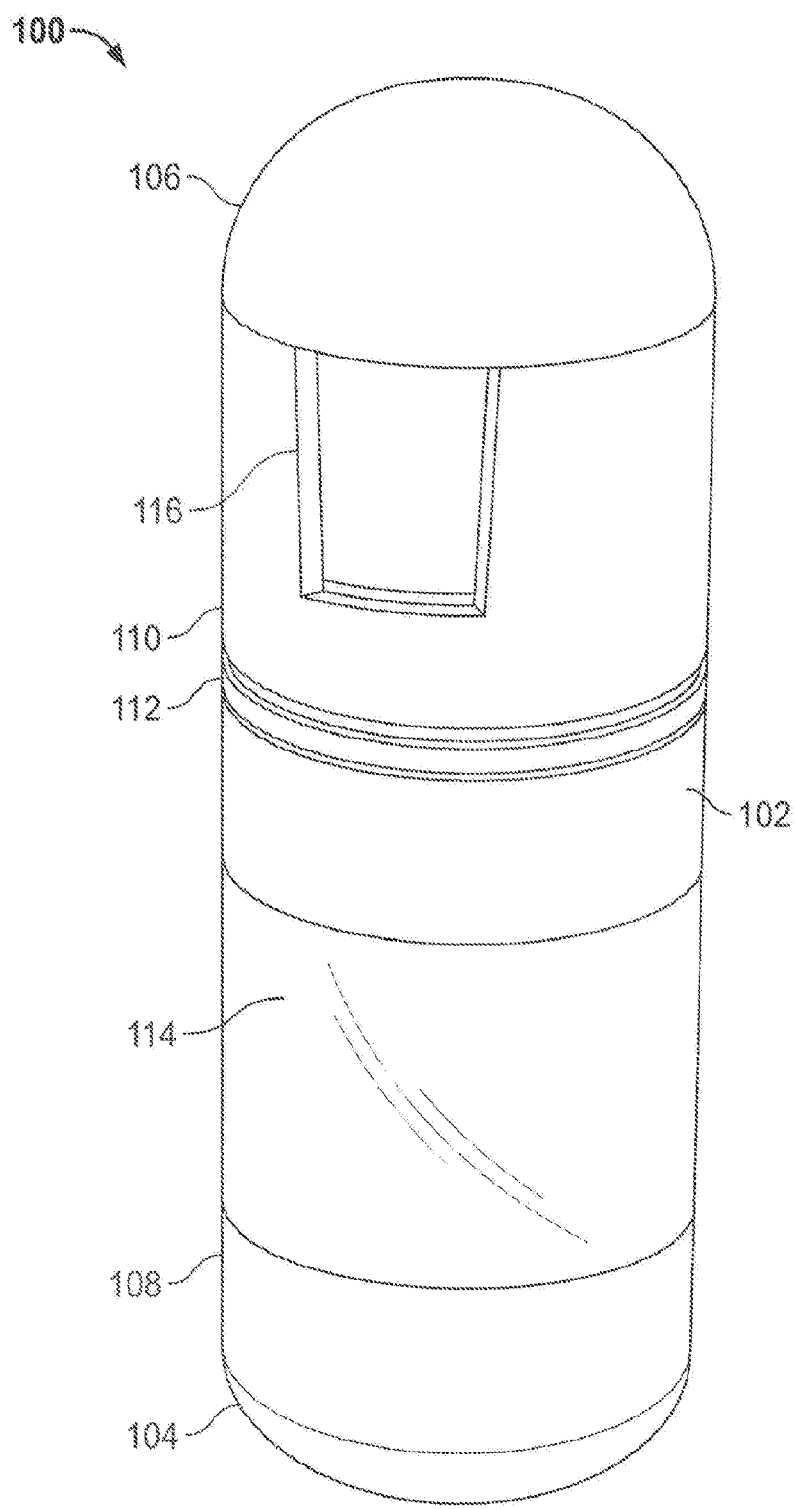
FIG. 1 is a view of an example embodiment of an ingestible device, in accordance with some embodiments of the disclosure.

The present disclosure is directed to various methods and formulations for treating diseases of the gastrointestinal tract with an JAK inhibitor. For example, in an embodiment, a method of treating a disease of the gastrointestinal tract in a subject comprises administering to the subject a pharmaceutical formulation comprising an JAK inhibitor wherein the pharmaceutical formulation is released in the subject's gastrointestinal tract proximate to one or more sites of disease. For example, in an embodiment, the pharmaceutical formulation comprises a therapeutically effective amount of an JAK inhibitor.

In some embodiments, the formulation is contained in an ingestible device, and the device releases the formulation at a location proximate to the site of disease. The location of the site of disease may be predetermined. For example, an ingestible device, the location of which within the GI tract can be accurately determined as disclosed herein, may be used to sample one or more locations in the GI tract and to detect one or more analytes, including markers of the disease, in the GI tract of the subject. A pharmaceutical formulation may be then administered via an ingestible device and released at a location proximate to the predetermined site of disease. The release of the formulation may be triggered autonomously, as further described herein.

The following disclosure illustrates aspects of the formulations and methods embodied in the claims.

Formulations, Including Pharmaceutical Formulations

As used herein, a "formulation" of an JAK inhibitor may refer to either the JAK inhibitor in pure form, such as, for example, a lyophilized JAK inhibitor, or a mixture of the JAK inhibitor with one or more physiologically acceptable carriers, excipients or stabilizers. Thus, therapeutic formulations or medicaments can be prepared by mixing the JAK inhibitor having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) antibody; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX<®>, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases. Exemplary lyophilized formulations are described in U.S. Pat. No. 6,267,958. Aqueous formulations include those described in U.S. Pat. No. 6,171,586 and WO2006/044908, the latter formulations including a histidine-acetate buffer.

A formulation of an JAK inhibitor as disclosed herein, e.g., sustained-release formulations, can further include a mucoadhesive agent, e.g., one or more of polyvinyl pyrolidine, methyl cellulose, sodium carboxyl methyl cellulose, hydroxyl propyl cellulose, carbopol, a polyacrylate, chitosan, a eudragit analogue, a polymer, and a thiomer. Additional examples of mucoadhesive agents that can be included in a formulation with an JAK inhibitor are described in, e.g., Peppas et al., *Biomaterials* 17(16):1553-1561, 1996; Kharenko et al., *Pharmaceutical Chemistry J.* 43(4):200-208, 2009; Salamat-Miller et al., *Adv. Drug Deliv. Reviews* 57(11):1666-1691, 2005; Bernkop-Schnurch, *Adv. Drug Deliv. Rev.* 57(11):1569-1582, 2005; and Harding et al., *Biotechnol. Genet. Eng. News* 16(1):41-86, 1999.

In some embodiments, components of a formulation may include any one of the following components, or any combination thereof:

Acacia, Alginate, Alginic Acid, Aluminum Acetate, an antiseptic, Benzyl Alcohol, Butyl Paraben, Butylated Hydroxy Toluene, an antioxidant. Citric acid, Calcium carbonate, Candelilla wax, a binder, Croscarmellose sodium, Confectioner sugar, Colloidal silicone dioxide, Cellulose, Carnuba wax, Corn starch, Carboxymethylcellulose calcium, Calcium stearate, Calcium disodium EDTA, Chelation agents, Copolyvidone, Castor oil hydrogenated, Calcium hydrogen phosphate dehydrate, Cetylpyridine chloride, Cysteine HCl, Crosspovidone, Dibasic Calcium Phosphate, Disodium hydrogen phosphate, Dimethicone, Erythrosine Sodium, Ethyl Cellulose, Gelatin, Glyceryl monooleate, Glycerin, Glycine, Glyceryl monostearate, Glyceryl behenate, Hydroxy propyl cellulose, Hydroxyl propyl methyl cellulose, Hypromellose, HPMC Pthalate, Iron oxides or ferric oxide, Iron oxide yellow, Iron oxide red or ferric oxide, Lactose (hydrous or anhydrous or monohydrate or spray dried), Magnesium stearate, Microcrystalline cellulose, Mannitol, Methyl cellulose, Magnesium carbonate, Mineral oil, Methacrylic acid copolymer, Magnesium oxide, Methyl paraben, PEG, Polysorbate 80, Propylene glycol, Polyethylene oxide, Propylene paraben, Polaxamer 407 or 188 or plain, Potassium bicarbonate, Potassium sorbate, Potato starch, Phosphoric acid, Polyoxy140 stearate, Sodium starch glycolate, Starch pregelatinized, Sodium crossmellose, Sodium lauryl sulfate, Starch, Silicon dioxide, Sodium benzoate, Stearic acid, Sucrose base for medicated confectionery, a granulating agent, Sorbic acid, Sodium carbonate, Saccharin sodium, Sodium alginate, Silica gel, Sorbiton monooleate, Sodium stearyl fumarate, Sodium chloride, Sodium metabisulfite, Sodium citrate dehydrate, Sodium starch, Sodium carboxy methyl cellulose, Succinic acid, Sodium propionate, Titanium dioxide, Talc, Triacetin, Triethyl citrate.

Accordingly, in some embodiments of the method of treating a disease as disclosed herein, the method comprises administering to the subject a pharmaceutical composition that is a formulation as disclosed herein. In some embodiments the formulation is a dosage form, which may be, as an example, a solid form such as, for example, a capsule, a tablet, a sachet, or a lozenge; or which may be, as an example, a liquid form such as, for example, a solution, a suspension, an emulsion, or a syrup.

In some embodiments, the formulation is not comprised in an ingestible device. In some embodiments wherein the formulation is not comprised in an ingestible device, the formulation may be suitable for oral administration. The formulation may be, for example, a solid dosage form or a liquid dosage form as disclosed herein. In some embodiments wherein the formulation is not comprised in an ingestible device, the formulation may be suitable for rectal administration. The formulation may be, for example, a dosage form such as a suppository or an enema. In embodiments where the formulation is not comprised in an ingestible device, the formulation releases the JAK inhibitor at a location in the gastrointestinal tract of the subject that is proximate to one or more sites of disease. Such localized release may be achieved, for example, with a formulation comprising an enteric coating. Such localized release may be achieved, an another example, with a formulation comprising a core comprising one or more polymers suitable for controlled release of an active substance. A non-limiting list of such polymers includes: poly(2-(diethylamino)ethyl methacrylate, 2-(dimethylamino)ethyl methacrylate, poly (ethylene glycol), poly(2-aminoethyl methacrylate), (2-hydroxypropyl)methacrylamide, poly(β-benzyl-1-aspartate), poly(N-isopropylacrylamide), and cellulose derivatives.

In some embodiments, the formulation is comprised in an ingestible device as disclosed herein. In some embodiments wherein the formulation is comprised in an ingestible device, the formulation may be suitable for oral administration. The formulation may be, for example, a solid dosage form or a liquid dosage form as disclosed herein. In some embodiments the formulation is suitable for introduction and optionally for storage in the device. In some embodiments the formulation is suitable for introduction and optionally for storage in a reservoir comprised in the device. In some embodiments the formulation is suitable for introduction and optionally for storage in a reservoir comprised in the device. Thus, in some embodiments, provided herein is a reservoir comprising a therapeutically effective amount of an JAK inhibitor, wherein the reservoir is configured to fit into an ingestible device. In some embodiments, the reservoir comprising a therapeutically effective amount of an JAK inhibitor is attachable to an ingestible device. In some embodiments, the reservoir comprising a therapeutically effective amount of an JAK inhibitor is capable of anchoring itself to the subject's tissue. As an example, the reservoir capable of anchoring itself to the subject's tissue comprises silicone. As an example, the reservoir capable of anchoring itself to the subject's tissue comprises polyvinyl chloride.

In some embodiments the formulation is suitable for introduction in a spray catheter, as disclosed herein.

The formulation herein may also contain more than one active compound as necessary for the particular indication being treated, for example, those with complementary activities that do not adversely affect each other. For instance, the formulation may further comprise another JAK inhibitor or a chemotherapeutic agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the JAK inhibitor, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated JAK inhibitors remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Pharmaceutical formulations may contain one or more JAK inhibitors. The pharmaceutical formulations may be formulated in any manner known in the art. In some embodiments the formulations include one or more of the following components: a sterile diluent (e.g., sterile water or saline), a fixed oil, polyethylene glycol, glycerin, propylene glycol, or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfite, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811, incorporated by reference herein in its entirety). The formulations can be formulated and enclosed in ampules, disposable syringes, or multiple dose vials. Where required, proper fluidity can be maintained by, for example, the use of a coating, such as lecithin, or a surfactant. Controlled release of the JAK inhibitor can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmacuetical, Inc.).

In some embodiments, the JAK inhibitor is present in a pharmaceutical formulation within the device.

In some embodiments, the JAK inhibitor is present in solution within the device.

In some embodiments, the JAK inhibitor is present in a suspension in a liquid medium within the device.

In some embodiments, the JAK inhibitor is present as a pure, powder (e.g., lyophilized) form of the JAK inhibitor.
Definitions:

By "ingestible", it is meant that the device can be swallowed whole.

"Gastrointestinal inflammatory disorders" are a group of chronic disorders that cause inflammation and/or ulceration in the mucous membrane. These disorders include, for example, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis.

"Inflammatory Bowel Disease" or "IBD" is a chronic inflammatory autoimmune condition of the gastrointestinal (GI) tract. The GI tract can be divided into four main different sections, the oesophagus, stomach, small intestine and large intestine or colon. The small intestine possesses three main subcompartments: the duodenum, jejunum and ileum. Similarly, the large intestine consists of six sections: the cecum, ascending colon, transverse colon, ascending colon, sigmoid colon, and the rectum. The small intestine is about 6 m long, its diameter is 2.5 to 3 cm and the transit time through it is typically 3 hours. The duodenum has a C-shape, and is 30 cm long. Due to its direct connection with the stomach, it is physically more stable than the jejunum and ileum, which are sections that can freely move. The jejunum is 2.4 m in length and the ileum is 3.6 m in length and their surface areas are 180 $m^2$ and 280 $m^2$ respectively. The large intestine is 1.5 m long, its diameter is between 6.3 and 6.5 cm, the transit time though this section is 20 hours and has a reduced surface area of approximately 150 $m^2$. The higher surface area of the small intestine enhances its capacity for systemic drug absorption.

The etiology of IBD is complex, and many aspects of the pathogenesis remain unclear. The treatment of moderate to severe IBD poses significant challenges to treating physicians, because conventional therapy with corticosteroids and immunomodulator therapy (e.g., azathioprine, 6 mercaptopurine, and methotrexate administered via traditional routes such as tablet form, oral suspension, or intravenously) is associated with side effects and intolerance and has not shown proven benefit in maintenance therapy (steroids). Monoclonal antibodies targeting tumor necrosis factor alpha (TNF-a), such as infliximab (a chimeric antibody) and adalimumab (a fully human antibody), are currently used in the management of CD. Infliximab has also shown efficacy and has been approved for use in UC. However, approximately 10%-20% of patients with CD are primary nonresponders to anti TNF therapy, and another ~20%-30% of CD patients lose response over time (Schnitzler et al., Gut 58:492-500 (2009)). Other adverse events (AEs) associated with anti TNFs include elevated rates of bacterial infection, including tuberculosis, and, more rarely, lymphoma and demyelination (Chang et al., Nat Clin Pract Gastroenterol Hepatology 3:220 (2006); Hoentjen et al., World J. Gastroenterol. 15(17):2067 (2009)). No currently available therapy achieves sustained remission in more than 20%-30% of IBD patients with chronic disease (Hanauer et al, Lancet 359: 1541-49 (2002); Sandborn et al, N Engl J Med 353: 1912-25 (2005)). In addition, most patients do not achieve sustained steroid-free remission and mucosal healing, clinical outcomes that correlate with true disease modification.

Although the cause of IBD remains unknown, several factors such as genetic, infectious and immunologic susceptibility have been implicated. IBD is much more common in Caucasians, especially those of Jewish descent. The chronic inflammatory nature of the condition has prompted an intense search for a possible infectious cause. Although agents have been found which stimulate acute inflammation, none has been found to cause the chronic inflammation associated with IBD. The hypothesis that IBD is an autoimmune disease is supported by the previously mentioned extraintestinal manifestation of IBD as joint arthritis, and the known positive response to IBD by treatment with therapeutic agents such as adrenal glucocorticoids, cyclosporine and azathioprine, which are known to suppress immune response. In addition, the GI tract, more than any other organ of the body, is continuously exposed to potential antigenic substances such as proteins from food, bacterial byproducts (LPS), etc.

A chronic inflammatory autoimmune condition of the gastrointestinal (GI) tract presents clinically as either ulcerative colitis (UC) or Crohn's disease (CD). Both IBD conditions are associated with an increased risk for malignancy of the GI tract.

"Crohn's disease" ("CD") is a chronic transmural inflammatory disease with the potential to affect any part of the entire GI tract, and UC is a mucosal inflammation of the colon. Both conditions are characterized clinically by frequent bowel motions, malnutrition, and dehydration, with disruption in the activities of daily living.

CD is frequently complicated by the development of malabsorption, strictures, and fistulae and may require repeated surgery. UC, less frequently, may be complicated by severe bloody diarrhea and toxic megacolon, also requiring surgery. The most prominent feature Crohn's disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual. Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils.

To date, the primary outcome measure in Crohn's Disease clinical trials is the Crohn's Disease Activity Index (CDAI), which has served as the basis for approval of multiple drug treatments, including for example, vedolizumab and natalizumab. The CDAI was developed by regressing clinician global assessment of disease activity on eighteen potential items representing patient reported outcomes (PROs) (i.e. abdominal pain, pain awakening patient from sleep, appetite), physical signs (i.e. average daily temperature, abdominal mass), medication use (i.e. loperamide or opiate use for diarrhea) and a laboratory test (i.e. hematocrit). Backward stepwise regression analysis identified eight independent predictors which are the number of liquid or soft stools, severity of abdominal pain, general well-being, occurrence of extra-intestinal symptoms, need for anti diarrheal drugs, presence of an abdominal mass, hematocrit, and body weight. The final score is a composite of these eight items, adjusted using regression coefficients and standardization to construct an overall CDAI score, ranging from 0 to 600 with higher score indicating greater disease activity. Widely used benchmarks are: CDAI<150 is defined as clinical remission, 150 to 219 is defined as mildly active disease, 220 to 450 is defined as moderately active disease, and above 450 is defined as very severe disease (Best W R, et al., Gastroenterology 77:843-6, 1979). Vedolizumab and natalizumab have been approved on the basis of demonstrated clinical remission, i.e. CDAI<150.

Although the CDAI has been in use for over 40 years, and has served as the basis for drug approval, it has several limitations as an outcome measure for clinical trials. For example, most of the overall score comes from the patient diary card items (pain, number of liquid bowel movements, and general well-being), which are vaguely defined and not standardized terms (Sandler et al., J. Clin. Epidemiol 41:451-8, 1988; Thia et al., Inflamm Bowel Dis 17: 105-11, 2011). In addition, measurement of pain is based on a four-point scale rather than an updated seven-point scale. The remaining 5 index items contribute very little to identifying an efficacy signal and may be a source of measurement noise. Furthermore, concerns have been raised about poor criterion validity for the CDAI, a reported lack of correlation between the CDAI and endoscopic measures of inflammation (which may render the CDAI as a poor discriminator of active CD and irritable bowel syndrome) and high reported placebo rates (Korzenik et al., N Engl J Med. 352:2193-201, 2005; Sandborn W J, et al., N Engl J Med 353: 1912-25, 2005; Sandborn W J, et al., Ann Intern 19; 146:829-38, 2007, Epub 2007 Apr. 30; Kim et al., Gastroenterology 146: (5 supplement 1) S-368, 2014).

It is, thus, generally recognized that additional or alternative measures of CD symptoms are needed, such as new PRO tools or adaptations of the CDAI to derive a new PRO. The PRO2 and PRO3 tools are such adaptations of the CDAI and have been recently described in Khanna et al., Aliment Pharmacol. Ther. 41: 77-86, 2015. The PRO2 evaluates the frequency of loose/liquid stools and abdominal pain {Id). These items are derived and weighted accordingly from the CDAI and are the CDAI diary card items, along with general well-being, that contribute most to the observed clinical benefit measured by CDAI (Sandler et al., J. Clin. Epidemiol 41:451-8, 1988; Thia et al., Inflamm Bowel Dis 17: 105-11, 2011; Kim et al., Gastroenterology 146: (5 supplement 1) S-368, 2014). The remission score of <11 is the CDAI-weighted sum of the average stool frequency and pain scores in a 7-day period, which yielded optimum sensitivity and specificity for identification of CDAI remission (score of <150) in a retrospective data analysis of ustekinumab induction treatment for moderate to severe CD in a Phase II clinical study (Gasink C, et al., abstract, ACG Annual Meeting 2014). The PRO2 was shown to be sensitive and responsive when used as a continuous outcome measure in a retrospective data analysis of MTX treatment in active CD (Khanna R, et al., Inflamm Bowel Dis 20: 1850-61, 2014) measured by CDAI. Additional outcome measures include the Mayo Clinic Score, the Crohn disease endoscopic index of severity (CDEIS), and the Ulcerative colitis endoscopic index of severity (UCEIS). Additional outcome measures include Clinical remission, Mucosal healing, Histological healing (transmural), MRI or ultrasound for measurement or evaluation of bowel wall thickness, abscesses, fistula and histology.

An additional means of assessing the extent and severity of Crohn's Disease is endoscopy. Endoscopic lesions typical of Crohn's disease have been described in numerous studies and include, e.g., aphthoid ulcerations, "punched-out ulcers," cobblestoning and stenosis. Endoscopic evaluation of such lesions was used to develop the first validated endoscopic score, the Crohn's Disease Endoscopic Index of Severity (CDEIS) (Mary et al., Gut 39:983-9, 1989). More recently, because the CDEIS is time-consuming, complicated and impractical for routine use, a Simplified Endoscopic Activity Score for Crohn's Disease (SES-CD) was developed and validated (Daperno et al., Gastrointest. Endosc. 60(4):505-12, 2004). The SES-CD consists of four endoscopic variables (size of ulcers, proportion of surface covered by ulcers, proportion of surface with any other lesions (e.g., inflammation), and presence of narrowings [stenosis]) that are scored in five ileocolonic segments, with each variable, or assessment, rated from 0 to 3.

To date, there is no cure for CD. Accordingly, the current treatment goals for CD are to induce and maintain symptom improvement, induce mucosal healing, avoid surgery, and improve quality of life (Lichtenstein G R, et al., Am J Gastroenterol 104:465-83, 2009; Van Assche G, et al., J Crohns Colitis. 4:63-101, 2010). The current therapy of IBD usually involves the administration of antiinflammatory or immunosuppressive agents, such as sulfasalazine, corticosteroids, 6-mercaptopurine/azathioprine, or cyclosporine, all of which are not typically delivered by localized release of a drug at the site or location of disease. More recently, biologics like TNF-alpha inhibitors and IL-12/IL-23 blockers, are used to treat IBD. If anti-inflammatory/immunosuppressive/biologic therapies fail, colectomies are the last line of defense. The typical operation for CD not involving the rectum is resection (removal of a diseased segment of bowel) and anastomosis (reconnection) without an ostomy. Sections of the small or large intestine may be removed. About 30% of CD patients will need surgery within the first year after diagnosis. In the subsequent years, the rate is about 5% per year. Unfortunately, CD is characterized by a high rate of recurrence; about 5% of patients need a second surgery each year after initial surgery.

Refining a diagnosis of inflammatory bowel disease involves evaluating the progression status of the diseases using standard classification criteria. The classification systems used in IBD include the Truelove and Witts Index (Truelove S. C. and Witts, L. J. Br Med J. 1955; 2: 1041-1048), which classifies colitis as mild, moderate, or severe, as well as Lennard-Jones. (Lennard-Jones J E. Scand J Gastroenterol Suppl 1989; 170:2-6) and the simple clinical colitis activity index (SCCAI). (Walmsley et. al. Gut. 1998; 43:29-32) These systems track such variables as daily bowel movements, rectal bleeding, temperature, heart rate, hemoglobin levels, erythrocyte sedimentation rate, weight, hematocrit score, and the level of serum albumin.

There is sufficient overlap in the diagnostic criteria for UC and CD that it is sometimes impossible to say which a given patient has; however, the type of lesion typically seen is different, as is the localization. UC mostly appears in the colon, proximal to the rectum, and the characteristic lesion is a superficial ulcer of the mucosa; CD can appear anywhere in the bowel, with occasional involvement of stomach, esophagus and duodenum, and the lesions are usually described as extensive linear fissures.

In approximately 10-15% of cases, a definitive diagnosis of ulcerative colitis or Crohn's disease cannot be made and such cases are often referred to as "indeterminate colitis." Two antibody detection tests are available that can help the diagnosis, each of which assays for antibodies in the blood. The antibodies are "perinuclear anti-neutrophil antibody" (pANCA) and "anti-*Saccharomyces cervisiae* antibody" (ASCA). Most patients with ulcerative colitis have the pANCA antibody but not the ASCA antibody, while most patients with Crohn's disease have the ASCA antibody but not the pANCA antibody. However, these two tests have shortcomings as some patients have neither antibody and some Crohn's disease patients may have only the pANCA antibody. A third test, which measures the presence and accumulation of circulating anti-microbial antibodies—particularly flagellin antibodies, has proven to be useful for detecting susceptibility to Crohn's Disease before disease development. See Choung, R. S., et al. "Serologic microbial associated markers can predict Crohn's disease behaviour years before disease diagnosis." Alimentary pharmacology & therapeutics 43.12 (2016): 1300-1310.

"Ulcerative colitis (UC)" afflicts the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis.

The clinical features of UC are highly variable, and the onset may be insidious or abrupt, and may include diarrhea, tenesmus and relapsing rectal bleeding. With fulminant involvement of the entire colon, toxic megacolon, a life-threatening emergency, may occur. Extraintestinal manifestations include arthritis, pyoderma gangrenoum, uveitis, and erythema nodosum.

The terms "antibody" and "immunoglobulin" are used interchangeably in the broadest sense and include monoclonal antibodies (for example, full length or intact monoclonal antibodies), polyclonal antibodies, multivalent antibodies, multispecific antibodies (e.g., bispecific, trispecific etc. antibodies so long as they exhibit the desired biological activity) and may also include certain antibody fragments (as described in greater detail herein). An antibody can be human, humanized and/or affinity matured.

"Antibody fragments" comprise only a portion of an intact antibody, where in certain embodiments, the portion retains at least one, and typically most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, Proc. Natl. Acad. Sci. USA 81:6851-6855 (1984)).

"Treatment regimen" refers to a combination of dosage, frequency of administration, or duration of treatment, with or without addition of a second medication.

"Effective treatment regimen" refers to a treatment regimen that will offer beneficial response to a patient receiving the treatment.

"Effective amount" refers to an amount of drug that offers beneficial response to a patient receiving the treatment. For example, an effective amount may be a Human Equivalent Dose (HED).

"Dispensable", with reference to any substance, refers to any substance that may be released from an ingestible device as disclosed herein, or from a component of the device such as a reservoir. For example, a dispensable substance may be an JAK inhibitor, and/or a formulation comprising an JAK inhibitor.

"Patient response" or "patient responsiveness" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) decrease of auto-immune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment. The term "responsiveness" refers to a measurable response, including complete response (CR) and partial response (PR).

As used herein, "complete response" or "CR" means the disappearance of all signs of inflammation or remission in response to treatment. This does not necessarily mean the disease has been cured.

"Partial response" or "PR" refers to a decrease of at least 50% in the severity of inflammation, in response to treatment.

A "beneficial response" of a patient to treatment with a therapeutic agent and similar wording refers to the clinical or therapeutic benefit imparted to a patient at risk for or suffering from a gastrointestinal inflammatory disorder from or as a result of the treatment with the agent. Such benefit includes cellular or biological responses, a complete response, a partial response, a stable disease (without progression or relapse), or a response with a later relapse of the patient from or as a result of the treatment with the agent.

As used herein, "non-response" or "lack of response" or similar wording means an absence of a complete response, a partial response, or a beneficial response to treatment with a therapeutic agent.

"A patient maintains responsiveness to a treatment" when the patient's responsiveness does not decrease with time during the course of a treatment.

A "symptom" of a disease or disorder (e.g., inflammatory bowel disease, e.g., ulcerative colitis or Crohn's disease) is any morbid phenomenon or departure from the normal in structure, function, or sensation, experienced by a subject and indicative of disease.

Inhibitory Agents of Janus Kinase (JAK) Activity and/or Expression

The term "JAK inhibitor" refers to an agent which decreases the expression of Janus kinase 1 (JAK1), JAK2, JAK3, or non-receptor protein tyrosine kinase 2 (TYK-2) and/or the kinase activity of at least one of JAK1, JAK2, JAK3, and TYK-2. In some embodiments, the JAK inhibitor decreases the expression of JAK1. In some embodiments, the JAK inhibitor decreases the expression of JAK2. In some embodiments, the JAK inhibitor decreases the expression of JAK3. In some embodiments, the JAK inhibitor decreases the expression of TYK-2.

In some embodiments, the JAK inhibitor decreases the kinase activity of JAK1. In some embodiments, the JAK inhibitor decreases the kinase activity of JAK2. In some embodiments, the JAK inhibitor decreases the kinase activity of JAK3. In some embodiments, the JAK inhibitor decreases the kinase activity of TYK-2. In some embodiments, the JAK inhibitor is a decreases the kinase activity of JAK1, JAK2, JAK3, and TYK2. In some embodiments, the JAK inhibitor decreases the kinase activity of two or more (e.g., 3 or 4) of: JAK1, JAK2, JAK3 and TYK2. In some embodiments, the JAK inhibitor decreases the kinase activity of a single JAK isoform (e.g., JAK1, JAK2, JAK3, or TYK2).

In some embodiments, the JAK inhibitor decreases the kinase activity of JAK1 and JAK2. In some embodiments, the JAK inhibitor decreases the kinase activity of JAK1 and JAK3. In some embodiments, the JAK inhibitor decreases the kinase activity of JAK2 and JAK3. In some embodiments, the JAK inhibitor decreases the kinase activity of JAK1, JAK2 and JAK3.

In some embodiments, a JAK inhibitory agent is an inhibitory nucleic acid or a small molecule. In some embodiments, the inhibitory nucleic acid is an antisense nucleic acid, a ribozyme, a small interfering RNA, a small hairpin RNA, or a microRNA. Examples of aspects of these different inhibitory nucleic acids are described below. Any of the examples of inhibitory nucleic acids that can decrease expression of a JAK1, JAK2, JAK3, or TYK2 mRNA in a mammalian cell can be synthesized in vitro.

Inhibitory nucleic acids that can decrease the expression of JAK1, JAK2, JAK3, or TYK2 mRNA expression in a mammalian cell include antisense nucleic acid molecules, i.e., nucleic acid molecules whose nucleotide sequence is complementary to all or part of a JAK1, JAK2, JAK3, or TYK2 mRNA (e.g., complementary to all or a part of any one of SEQ ID NOs: 1-15).

```
Human JAK1 mRNA Variant 1
                                                                (SEQ ID NO: 1)
   1 ggggcgggac gggaggcggt gcgtcgctga gcgcaggccg cggcggccgc ggagtatcct 61 ggagctgcag acagtgcggg cctgcgccca gtcccggctg tcctcgccgc gaccccctcct 121 cagccctggg cgcgcgcacg ctggggcccc gcggggctgg ccgcctagcg agcctgccgg 181 tcgacccag ccagcgcagc gacggggcgc tgcctggccc aggcgcacac ggaagtgcgc 241 ttctctgaag tagctttgga aagtagagaa gaaaatccag tttgcttctt ggagaacact 301 ggacagctga ataaatgcag tatctaaata taaaagagga ctgcaatgcc atggctttct 361 gtgctaaaat gaggagctcc aagaagactg aggtgaacct ggaggcccct gagccagggg 421 tggaagtgat cttctatctg tcggacaggg agcccctccg gctgggcagt ggagagtaca 481 cagcagagga actgtgcatc agggctgcac aggcatgccg tatctctcct ctttgtcaca 541 acctctttgc cctgtatgac gagaacacca agctctggta tgctccaaat cgcaccatca 601 ccgttgatga caagatgtcc ctccggctcc actaccggat gaggttctat ttcaccaatt 661 ggcatggaac caacgacaat gagcagtcag tgtggcgtca ttctccaaag aagcagaaaa 721 atggctacga gaaaaaaaag attccagatg caaccccctct ccttgatgcc agctcactgg 781 agtatctgtt tgctcaggga cagtatgatt tggtgaaatg cctggctcct attcgagacc 841 ccaagaccga gcaggatgga catgatattg agaacgagtg tctagggatg gctgtcctgg 901 ccatctcaca ctatgccatg atgaagaaga tgcagttgcc agaactgccc aaggacatca 961 gctacaagcg atatattcca gaaacattga ataagtccat cagacagagg aaccttctca 1021 ccaggatgcg gataaataat gttttcaagg atttcctaaa ggaatttaac aacaagacca 1081 tttgtgacag cagcgtgtcc acgcatgacc tgaaggtgaa atacttggct acccttggaaa 1141 ctttgacaaa acattacggt gctgaaatat ttgagacttc catgttactg atttcatcag
```

-continued

```
1201  aaaatgagat gaattggttt cattcgaatg acggtggaaa cgttctctac tacgaagtga
1261  tggtgactgg gaatcttgga atccagtgga ggcataaacc aaatgttgtt tctgttgaaa
1321  aggaaaaaaa taaactgaag cggaaaaaac tggaaaataa acacaagaag gatgaggaga
1381  aaaacaagat ccgggaagag tggaacaatt tttcttactt ccctgaaatc actcacattg
1441  taataaagga gtctgtggtc agcattaaca agcaggacaa caagaaaatg gaactgaagc
1501  tctcttccca cgaggaggcc ttgtcctttg tgtccctggt agatggctac ttccggctca
1561  cagcagatgc ccatcattac ctctgcaccg acgtggcccc cccgttgatc gtccacaaca
1621  tacagaatgg ctgtcatggt ccaatctgta cagaatacgc catcaataaa ttgcggcaag
1681  aaggaagcga ggaggggatg tacgtgctga ggtggagctg caccgacttt gacaacatcc
1741  tcatgaccgt cacctgcttt gagaagtctg agcaggtgca gggtgcccag aagcagttca
1801  agaactttca gatcgaggtg cagaagggcc gctacagtct gcacggttcg gaccgcagct
1861  tccccagctt gggagacctc atgagccacc tcaagaagca gatcctgcgc acggataaca
1921  tcagcttcat gctaaaacgc tgctgccagc ccaagccccg agaaatctcc aacctgctgg
1981  tggctactaa gaaagcccag gagtggcagc ccgtctaccc catgagccag ctgagtttcg
2041  atcggatcct caagaaggat ctggtgcagg gcgagcacct gggagaggc acgagaacac
2101  acatctattc tgggaccctg atggattaca aggatgacga aggaacttct gaagagaaga
2161  agataaaagt gatcctcaaa gtcttagacc ccagccacag ggatatttcc ctggccttct
2221  tcgaggcagc cagcatgatg agacaggtct cccacaaaca catcgtgtac ctctatggcg
2281  tctgtgtccg cgacgtggag aatatcatgg tggaagagtt tgtggaaggg ggtcctctgg
2341  atctcttcat gcaccggaaa agcgatgtcc ttaccacacc atggaaattc aaagttgcca
2401  aacagctggc cagtgccctg agctacttgg aggataaaga cctggtccat ggaaatgtgt
2461  gtactaaaaa cctcctcctg gcccgtgagg gcatcgacag tgagtgtggc ccattcatca
2521  agctcagtga ccccggcatc cccattacgg tgctgtctag gcaagaatgc attgaacgaa
2581  tcccatggat tgctcctgag tgtgttgagg actccaagaa cctgagtgtg gctgctgaca
2641  agtggagctt tggaaccacg ctctgggaaa tctgctacaa tggcgagatc cccttgaaag
2701  acaagacgct gattgagaaa gagagattct atgaaagccg gtgcaggcca gtgacaccat
2761  catgtaagga gctggctgac ctcatgaccc gctgcatgaa ctatgacccc aatcagaggc
2821  cttttcttccg agccatcatg agagacatta ataagcttga agagcagaat ccagatattg
2881  tttcagaaaa aaaaccagca actgaagtgg accccacaca tttttgaaaag cgcttcctaa
2941  agaggatccg tgacttggga gagggccact ttgggaaggt tgagctctgc aggtatgacc
3001  ccgaagggga caatacaggg gagcaggtgg ctgttaaatc tctgaagcct gagagtggag
3061  gtaaccacat agctgatctg aaaaaggaaa tcgagatctt aaggaacctc tatcatgaga
3121  acattgtgaa gtacaaagga atctgcacag aagacggagg aaatggtatt aagctcatca
3181  tggaatttct gccttcggga agccttaagg aatatcttcc aaagaataag aacaaaataa
3241  acctcaaaca gcagctaaaa tatgccgttc agatttgtaa ggggatggac tatttgggtt
3301  ctcggcaata cgttcaccgg gacttggcag caagaaatgt ccttgttgag agtgaacacc
3361  aagtgaaaat tggagacttc ggtttaacca agcaattgaa accgataag gagtattaca
3421  ccgtcaagga tgaccgggac agccctgtgt tttggtatgc tccagaatgt ttaatgcaat
3481  ctaaattta tattgcctct gacgtctggt cttttggagt cactctgcat gagctgctga
3541  cttactgtga ttcagattct agtcccatgg ctttgttcct gaaaatgata ggcccaaccc
3601  atggccagat gacagtcaca agacttgtga atacgttaaa agaaggaaaa cgcctgccgt
```

-continued

```
3661  gcccacctaa ctgtccagat gaggtttatc aacttatgag gaaatgctgg gaattccaac
3721  catccaatcg acaagcttt cagaaccta ttgaaggatt tgaagcactt ttaaaataag
3781  aagcatgaat aacatttaaa ttccacagat tatcaagtcc ttctcctgca acaaatgccc
3841  aagtcatttt ttaaaaattt ctaatgaaag aagtttgtgt tctgtccaaa aagtcactga
3901  actcatactt cagtacatat acatgtataa ggcacactgt agtgcttaat atgtgtaagg
3961  acttcctctt taaatttggt accagtaact tagtgacaca taatgacaac caaaatattt
4021  gaaagcactt aagcactcct ccttgtggaa agaatatacc accatttcat ctggctagtt
4081  caccatcaca actgcattac caaaagggga ttttttgaaaa cgaggagttg accaaaataa
4141  tatctgaaga tgattgcttt tccctgctgc cagctgatct gaaatgtttt gctggcacat
4201  taatcataga taaagaaaga ttgatggact tagccctcaa atttcagtat ctatacagta
4261  ctagaccatg cattcttaaa atattagata ccaggtagta tatattgttt ctgtacaaaa
4321  atgactgtat tctctcacca gtaggactta aactttgttt ctccagtggc ttagctcctg
4381  ttcctttggg tgatcactag cacccatttt tgagaaagct ggttctacat gggggatag
4441  ctgtggaata gataatttgc tgcatgttaa ttctcaagaa ctaagcctgt gccagtgctt
4501  tcctaagcag tataccttta atcagaactc attcccagaa cctggatgct attacacatg
4561  cttttaagaa acgtcaatgt atatccttt ataactctac cactttgggg caagctattc
4621  cagcactggt tttgaatgct gtatgcaacc agtctgaata ccacatacg tgcactgttc
4681  ttagagggtt tccatactta ccaccgatct acaagggttg atccctgttt ttaccatcaa
4741  tcatcaccct gtggtgcaac acttgaaaga cccggctaga ggcactatgg acttcaggat
4801  ccactagaca gttttcagtt tgcttggagg tagctgggta atcaaaaatg tttagtcatt
4861  gattcaatgt gaacgattac ggtctttatg accaagagtc tgaaaatctt tttgttatgc
4921  tgtttagtat tcgtttgata ttgttacttt tcacctgttg agcccaaatt caggattggt
4981  tcagtggcag caatgaagtt gccatttaaa tttgttcata gcctacatca ccaaggtctc
5041  tgtgtcaaac ctgtggccac tctatatgca cttgtttac tctttataca aataaatata
5101  ctaaagactt tacatgca
```

Human JAK1 mRNA Variant 2
(SEQ ID NO: 2)
```
  1   agaagcggag cgtatacgga ggaggcggga tgcatttctg catcgagcgc acaaagttat
 61   ctaaaacagt tcatgctgct gaaaacctcc ttcctggcag atgtccctca accctactgg
121   tgcctggctt ctgagacaca cgcttctctg aagtagcttt ggaaagtaga aagaaaatc
181   cagtttgctt cttggagaac actggacagc tgaataaatg cagtatctaa atataaaaga
241   ggactgcaat gccatggctt tctgtgctaa aatgaggagc tccaagaaga ctgaggtgaa
301   cctggaggcc cctgagccag gggtggaagt gatcttctat ctgtcggaca gggagcccct
361   ccggctgggc agtggagagt acacagcaga ggaactgtgc atcagggctg cacaggcatg
421   ccgtatctct cctctttgtc acaacctctt tgccctgtat gacgagaaca ccaagctctg
481   gtatgctcca aatcgcacca tcaccgttga tgacaagatg tccctccggc tccactaccg
541   gatgaggttc tatttcacca attggcatgg aaccaacgac aatgagcagt cagtgtggcg
601   tcattctcca agaagcagaa aaatggcta cgagaaaaaa aagattccag atgcaacccc
661   tctccttgat gccagctcac tggagtatct gtttgctcag ggacagtatg atttggtgaa
721   atgcctggct cctattcgag accccaagac cgagcaggat ggacatgata ttgagaacga
781   gtgtctaggg atggctgtcc tggccatctc acactatgcc atgatgaaga agatgcagtt
841   gccagaactg cccaaggaca tcagctacaa gcgatatatt ccagaaacat gaataagtc
```

-continued

```
 901   catcagacag aggaaccttc tcaccaggat gcggataaat aatgttttca aggatttcct
 961   aaaggaattt aacaacaaga ccatttgtga cagcagcgtg tccacgcatg acctgaaggt
1021   gaaatacttg gctaccttgg aaactttgac aaaacattac ggtgctgaaa tatttgagac
1081   ttccatgtta ctgatttcat cagaaaatga gatgaattgg tttcattcga atgacggtgg
1141   aaacgttctc tactacgaag tgatggtgac tgggaatctt ggaatccagt ggaggcataa
1201   accaaatgtt gtttctgttg aaaaggaaaa aaataaactg aagcggaaaa aactggaaaa
1261   taaacacaag aaggatgagg agaaaaacaa gatccgggaa gagtggaaca attttttctta
1321   cttccctgaa atcactcaca ttgtaataaa ggagtctgtg gtcagcatta caagcagga
1381   caacaagaaa atggaactga agctctcttc ccacgaggag gccttgtcct ttgtgtccct
1441   ggtagatggc tacttccggc tcacagcaga tgcccatcat tacctctgca ccgacgtggc
1501   ccccccgttg atcgtccaca acatacagaa tggctgtcat ggtccaatct gtacagaata
1561   cgccatcaat aaattgcggc aagaaggaag cgaggagggg atgtacgtgc tgaggtggag
1621   ctgcaccgac tttgacaaca tcctcatgac cgtcacctgc tttgagaagt ctgagcaggt
1681   gcagggtgcc cagaagcagt tcaagaactt tcagatcgag gtgcagaagg ccgctacag
1741   tctgcacggt tcggaccgca gcttccccag cttgggagac ctcatgagcc acctcaagaa
1801   gcagatcctg cgcacggata acatcagctt catgctaaaa cgctgctgcc agcccaagcc
1861   ccgagaaatc tccaacctgc tggtggctac taagaaagcc caggagtggc agcccgtcta
1921   ccccatgagc cagctgagtt tcgatcggat cctcaagaag gatctggtgc agggcgagca
1981   ccttgggaga ggcacgagaa cacacatcta ttctgggacc ctgatggatt acaaggatga
2041   cgaaggaact tctgaagaga agaagataaa agtgatcctc aaagtcttag accccagcca
2101   cagggatatt tccctggcct tcttcgaggc agccagcatg atgagacagg tctcccacaa
2161   acacatcgtg tacctctatg gcgtctgtgt ccgcgacgtg gagaatatca tggtggaaga
2221   gtttgtggaa gggggtcctc tggatctctt catgcaccgg aaaagcgatg tccttaccac
2281   accatggaaa ttcaaagttg ccaaacagct ggccagtgcc ctgagctact ggaggataa
2341   agacctggtc catggaaatg tgtgtactaa aaacctcctc ctggcccgtg agggcatcga
2401   cagtgagtgt ggcccattca tcaagctcag tgaccccggc atccccatta cggtgctgtc
2461   taggcaagaa tgcattgaac gaatcccatg gattgctcct gagtgtgttg aggactccaa
2521   gaacctgagt gtggctgctg acaagtggag ctttggaacc acgctctggg aaatctgcta
2581   caatggcgag atcccccttga agacaagac gctgattgag aaagagagat tctatgaaag
2641   ccggtgcagg ccagtgacac catcatgtaa ggagctggct gacctcatga cccgctgcat
2701   gaactatgac cccaatcaga ggccttttctt ccgagccatc atgagagaca ttaataagct
2761   tgaagagcag aatccagata ttgtttcaga aaaaaaacca gcaactgaag tggaccccac
2821   acattttgaa aagcgcttcc taaagaggat ccgtgacttg ggagagggc actttgggaa
2881   ggttgagctc tgcaggtatg accccgaagg ggacaataca ggggagcagg tggctgttaa
2941   atctctgaag cctgagagtg gaggtaacca catagctgat ctgaaaaagg aaatcgagat
3001   cttaaggaac ctctatcatg agaacattgt gaagtacaaa ggaatctgca cagaagacgg
3061   aggaaatggt attaagctca tcatggaatt tctgccttcg ggaagcctta aggaatatct
3121   tccaaagaat aagaacaaaa taaacctcaa acagcagcta aaatatgccg ttcagatttg
3181   taagggggatg gactatttgg gttctcggca atacgttcac cgggacttgg cagcaagaaa
3241   tgtccttgtt gagagtgaac accaagtgaa aattggagac ttcggttaa ccaaagcaat
3301   tgaaaccgat aaggagtatt acaccgtcaa ggatgaccgg gacagccctg tgttttggta
```

```
3361  tgctccagaa tgtttaatgc aatctaaatt ttatattgcc tctgacgtct ggtcttttgg
3421  agtcactctg catgagctgc tgacttactg tgattcagat tctagtccca tggctttgtt
3481  cctgaaaatg ataggcccaa cccatggcca gatgacagtc acaagacttg tgaatacgtt
3541  aaaagaagga aaacgcctgc cgtgcccacc taactgtcca gatgaggttt atcaacttat
3601  gaggaaatgc tgggaattcc aaccatccaa tcggacaagc tttcagaacc ttattgaagg
3661  atttgaagca cttttaaaat aagaagcatg aataacattt aaattccaca gattatcaag
3721  tccttctcct gcaacaaatg cccaagtcat ttttttaaaaa tttctaatga agaagtttg
3781  tgttctgtcc aaaaagtcac tgaactcata cttcagtaca tatacatgta taaggcacac
3841  tgtagtgctt aatatgtgta aggacttcct ctttaaattt ggtaccagta acttagtgac
3901  acataatgac aaccaaaata tttgaaagca cttaagcact cctccttgtg gaaagaatat
3961  accaccattt catctggcta gttcaccatc acaactgcat taccaaaagg ggatttttga
4021  aaacgaggag ttgaccaaaa taatatctga agatgattgc ttttccctgc tgccagctga
4081  tctgaaatgt tttgctggca cattaatcat agataaagaa agattgatgg acttagccct
4141  caaatttcag tatctataca gtactagacc atgcattctt aaaatattag ataccaggta
4201  gtatatattg tttctgtaca aaaatgactg tattctctca ccagtaggac ttaaactttg
4261  tttctccagt ggcttagctc ctgttccttt gggtgatcac tagcacccat ttttgagaaa
4321  gctggttcta catgggggga tagctgtgga atagataatt tgctgcatgt taattctcaa
4381  gaactaagcc tgtgccagtg ctttcctaag cagtatacct ttaatcagaa ctcattccca
4441  gaacctggat gctattacac atgcttttaa gaaacgtcaa tgtatatcct tttataactc
4501  taccactttg gggcaagcta ttccagcact ggttttgaat gctgtatgca accagtctga
4561  ataccacata cgctgcactg ttcttagagg gttccatac ttaccaccga tctacaaggg
4621  ttgatccctg tttttaccat caatcatcac cctgtggtgc aacacttgaa agacccggct
4681  agaggcacta tggacttcag gatccactag acagttttca gtttgcttgg aggtagctgg
4741  gtaatcaaaa atgtttagtc attgattcaa tgtgaacgat tacggtcttt atgaccaaga
4801  gtctgaaaat cttttttgtta tgctgtttag tattcgtttg atattgttac ttttcacctg
4861  ttgagcccaa attcaggatt ggttcagtgg cagcaatgaa gttgccattt aaatttgttc
4921  atagcctaca tcaccaaggt ctctgtgtca aacctgtggc cactctatat gcactttgtt
4981  tactctttat acaaataaat atactaaaga ctttacatgc a
```

Human JAK1 mRNA Variant 3
(SEQ ID NO: 3)
```
   1  atctatcaca tggcagagat agaataaaaa cagaaaaatg cgacggtca cgttgtggcg
  61  agccttgctg cgtcattaga taatcctcat gcaaatagcg ggaagaacaa aggaagggga
 121  gcccgggacc cccggggcg cagcgcttct ctgaagtagc tttggaaagt agagaagaaa
 181  atccagtttg cttcttggag aacactggac agctgaataa atgcagtatc taaatataaa
 241  agaggactgc aatgccatgg ctttctgtgc taaaatgagg agctccaaga agactgaggt
 301  gaacctggag gcccctgagc caggggtgga agtgatcttc tatctgtcgg acagggagcc
 361  cctccggctg ggcagtggag agtacacagc agaggaactg tgcatcaggg ctgcacaggc
 421  atgccgtatc tctcctcttt gtcacaacct ctttgccctg tatgacgaga acaccaagct
 481  ctggtatgct ccaaatcgca ccatcaccgt tgatgacaag atgtccctcc ggctccacta
 541  ccggatgagg ttctatttca ccaattggca tggaaccaac gacaatgagc agtcagtgtg
 601  gcgtcattct ccaaagaagc agaaaaatgg ctacgagaaa aaaaagattc cagatgcaac
 661  ccctctcctt gatgccagct cactggagta tctgtttgct cagggacagt atgatttggt
```

-continued

```
 721   gaaatgcctg gctcctattc gagaccccaa gaccgagcag gatggacatg atattgagaa
 781   cgagtgtcta gggatggctg tcctggccat ctcacactat gccatgatga agaagatgca
 841   gttgccagaa ctgcccaagg acatcagcta caagcgatat attccagaaa cattgaataa
 901   gtccatcaga cagaggaacc ttctcaccag gatgcggata aataatgttt tcaaggattt
 961   cctaaaggaa tttaacaaca agaccatttg tgacagcagc gtgtccacgc atgacctgaa
1021   ggtgaaatac ttggctacct tggaaacttt gacaaaacat tacggtgctg aaatatttga
1081   gacttccatg ttactgattt catcagaaaa tgagatgaat tggtttcatt cgaatgacgg
1141   tggaaacgtt ctctactacg aagtgatggt gactgggaat cttggaatcc agtggaggca
1201   taaaccaaat gttgtttctg ttgaaaagga aaaaaataaa ctgaagcgga aaaaactgga
1261   aaataaacac aagaaggatg aggagaaaaa caagatccgg gaagagtgga caattttttc
1321   ttacttccct gaaatcactc acattgtaat aaaggagtct gtggtcagca ttaacaagca
1381   ggacaacaag aaaatggaac tgaagctctc ttcccacgag gaggccttgt cctttgtgtc
1441   cctggtagat ggctacttcc ggctcacagc agatgcccat cattacctct gcaccgacgt
1501   ggccccccgg ttgatcgtcc acaacataca gaatggctgt catggtccaa tctgtacaga
1561   atacgccatc aataaattgc ggcaagaagg aagcgaggag gggatgtacg tgctgaggtg
1621   gagctgcacc gactttgaca acatcctcat gaccgtcacc tgctttgaga agtctgagca
1681   ggtgcagggt gcccagaagc agttcaagaa ctttcagatc gaggtgcaga agggccgcta
1741   cagtctgcac ggttcggacc gcagcttccc cagcttggga gacctcatga gccacctcaa
1801   gaagcagatc ctgcgcacgg ataacatcag cttcatgcta aaacgctgct gccagcccaa
1861   gccccgagaa atctccaacc tgctggtggc tactaagaaa gcccaggagt ggcagcccgt
1921   ctaccccatg agccagctga gtttcgatcg gatcctcaag aaggatctgg tgcagggcga
1981   gcaccttggg agaggcacga gaacacacat ctattctggg accctgatgg attacaagga
2041   tgacgaagga acttctgaag agaagaagat aaaagtgatc ctcaaagtct tagaccccag
2101   ccacagggat atttccctgg ccttcttcga ggcagccagc atgatgagac aggtctccca
2161   caaacacatc gtgtacctct atggcgtctg tgtccgcgac gtggagaata tcatggtgga
2221   agagtttgtg aagggggtc ctctggatct cttcatgcac cggaaaagcg atgtccttac
2281   cacaccatgg aaattcaaag ttgccaaaca gctggccagt gccctgagct acttggagga
2341   taaagacctg gtccatggaa atgtgtgtac taaaaacctc ctcctggccc gtgagggcat
2401   cgacagtgag tgtggcccat tcatcaagct cagtgacccc ggcatcccca ttacggtgct
2461   gtctaggcaa gaatgcattg aacgaatccc atggattgct cctgagtgtg ttgaggactc
2521   caagaacctg agtgtggctg ctgacaagtg gagctttgga accacgctct gggaaatctg
2581   ctacaatggc gagatcccct tgaaagacaa gacgctgatt gagaaagaga gattctatga
2641   aagccggtgc aggccagtga caccatcatg taaggagctg gctgacctca tgacccgctg
2701   catgaactat gaccccaatc agaggccttt cttccgagcc atcatgagag acattaataa
2761   gcttgaagag cagaatccag atattgtttc agaaaaaaaa ccagcaactg aagtggaccc
2821   cacacatttt gaaaagcgct tcctaaagag gatccgtgac ttgggagagg gccactttgg
2881   gaaggttgag ctctgcaggt atgaccccga aggggacaat acaggggagc aggtggctgt
2941   taaatctctg aagcctgaga gtggaggtaa ccacatagct gatctgaaaa aggaaatcga
3001   gatcttaagg aacctctatc atgagaacat tgtgaagtac aaaggaatct gcacagaaga
3061   cggaggaaat ggtattaagc tcatcatgga atttctgcct tcgggaagcc ttaaggaata
3121   tcttccaaag aataagaaca aaataaacct caaacagcag ctaaaatatg ccgttcagat
```

-continued

```
3181  ttgtaagggg atggactatt tgggttctcg gcaatacgtt caccgggact tggcagcaag
3241  aaatgtcctt gttgagagtg aacaccaagt gaaaattgga gacttcggtt taaccaaagc
3301  aattgaaacc gataaggagt attacaccgt caaggatgac cgggacagcc ctgtgttttg
3361  gtatgctcca gaatgtttaa tgcaatctaa attttatatt gcctctgacg tctggtcttt
3421  tggagtcact ctgcatgagc tgctgactta ctgtgattca gattctagtc ccatggcttt
3481  gttcctgaaa atgataggcc aacccatgg ccagatgaca gtcacaagac ttgtgaatac
3541  gttaaaagaa ggaaaacgcc tgccgtgccc acctaactgt ccagatgagg tttatcaact
3601  tatgaggaaa tgctgggaat tccaaccatc caatcggaca agctttcaga accttattga
3661  aggatttgaa gcacttttaa ataagaagc atgaataaca tttaaattcc acagattatc
3721  aagtccttct cctgcaacaa atgcccaagt cattttttaa aaatttctaa tgaaagaagt
3781  ttgtgttctg tccaaaaagt cactgaactc atacttcagt acatatacat gtataaggca
3841  cactgtagtg cttaatatgt gtaaggactt cctctttaaa tttggtacca gtaacttagt
3901  gacacataat gacaaccaaa atatttgaaa gcacttaagc actcctcctt gtggaaagaa
3961  tataccacca tttcatctgg ctagttcacc atcacaactg cattaccaaa aggggatttt
4021  tgaaaacgag gagttgacca aaataatatc tgaagatgat tgcttttccc tgctgccagc
4081  tgatctgaaa tgttttgctg gcacattaat catagataaa gaaagattga tggacttagc
4141  cctcaaattt cagtatctat acagtactag accatgcatt cttaaaatat tagataccag
4201  gtagtatata ttgtttctgt acaaaaatga ctgtattctc tcaccagtag gacttaaact
4261  ttgtttctcc agtggcttag ctcctgttcc tttgggtgat cactagcacc cattttgag
4321  aaagctggtt ctacatgggg ggatagctgt ggaatagata atttgctgca tgttaattct
4381  caagaactaa gcctgtgcca gtgcttccct aagcagtata cctttaatca gaactcattc
4441  ccagaacctg gatgctatta cacatgcttt taagaaacgt caatgtatat cctttatata
4501  ctctaccact ttggggcaag ctattccagc actggttttg aatgctgtat gcaaccagtc
4561  tgaataccac atacgctgca ctgttcttag agggtttcca tacttaccac cgatctacaa
4621  gggttgatcc ctgttttttac catcaatcat cacctgtgg tgcaacactt gaaagacccg
4681  gctagaggca ctatggactt caggatccac tagacagttt tcagtttgct tggaggtagc
4741  tgggtaatca aaaatgttta gtcattgatt caatgtgaac gattacggtc tttatgacca
4801  agagtctgaa aatctttttg ttatgctgtt tagtattcgt ttgatattgt tacttttcac
4861  ctgttgagcc caaattcagg attggttcag tggcagcaat gaagttgcca tttaaatttg
4921  ttcatagcct acatcaccaa ggtctctgtg tcaaacctgt ggccactcta tatgcacttt
4981  gtttactctt tatacaaata aatatactaa agactttaca tgca
```

Human JAK1 mRNA Variant 4

(SEQ ID NO: 4)
```
  1  atctatcaca tggcagagat agaataaaaa cagaaaaatg gcgacggtca cgttgtggcg
 61  agccttgctg cgtcattaga taatcctcat gcaaatagcg ggaagaacaa aggaagggga
121  gcccgggacc cccgggggcg caggatccgg cgggaggagt ctaagaggag gaggcggcgg
181  tgccggagga ggaggaggag ggagggagaa gagaggaaga ccggagtccc cgcggcggcg
241  gcggtccgga gagagggcga gccccgcgcg gcgccgggga ccgggcgcta ccacgaggcc
301  gggacgctgg agtctgggtt atctaaaaca gttcatgctg ctgaaaaacct ccttcctggc
361  agatgtccct caacccctact ggtgcctggc ttctgagaca cacgcttctc tgaagtagct
421  ttggaaagta gagaagaaaa tccagtttgc cttcttggaga acactggaca gctgaataaa
481  tgcagtatct aaatataaaa gaggactgca atgccatggc tttctgtgct aaaatgagga
```

-continued

```
 541   gctccaagaa gactgaggtg aacctggagg cccctgagcc aggggtggaa gtgatcttct
 601   atctgtcgga cagggagccc ctccggctgg gcagtggaga gtacacagca gaggaactgt
 661   gcatcagggc tgcacaggca tgccgtatct ctcctctttg tcacaacctc tttgccctgt
 721   atgacgagaa caccaagctc tggtatgctc caaatcgcac catcaccgtt gatgacaaga
 781   tgtccctccg gctccactac cggatgaggt tctatttcac caattggcat ggaaccaacg
 841   acaatgagca gtcagtgtgg cgtcattctc caagaagcag aaaaatggc tacgagaaaa
 901   aaaagattcc agatgcaacc cctctccttg atgccagctc actggagtat ctgtttgctc
 961   agggacagta tgatttggtg aaatgcctgg ctcctattcg agaccccaag accgagcagg
1021   atggacatga tattgagaac gagtgtctag ggatggctgt cctggccatc tcacactatg
1081   ccatgatgaa gaagatgcag ttgccagaac tgcccaagga catcagctac aagcgatata
1141   ttccagaaac attgaataag tccatcagac agaggaacct tctcaccagg atgcggataa
1201   ataatgtttt caaggatttc ctaaaggaat ttaacaacaa gaccatttgt gacagcagcg
1261   tgtccacgca tgacctgaag gtgaaatact tggctacctt ggaaactttg acaaaacatt
1321   acggtgctga aatatttgag acttccatgt tactgatttc atcagaaaat gagatgaatt
1381   ggtttcattc gaatgacggt ggaaacgttc tctactacga agtgatggtg actgggaatc
1441   ttggaatcca gtggaggcat aaaccaaatg ttgtttctgt tgaaaaggaa aaaaataaac
1501   tgaagcggaa aaaactggaa aataaacaca agaaggatga ggagaaaaac aagatccggg
1561   aagagtggaa caatttttct tacttccctg aaatcactca cattgtaata aaggagtctg
1621   tggtcagcat taacaagcag gacaacaaga aaatggaact gaagctctct tcccacgagg
1681   aggccttgtc ctttgtgtcc ctggtagatg gctacttccg gctcacagca gatgcccatc
1741   attacctctg caccgacgtg gcccccccgt tgatcgtcca caacatacag aatggctgtc
1801   atggtccaat ctgtacagaa tacgccatca ataaattgcg gcaagaagga agcgaggagg
1861   ggatgtacgt gctgaggtgg agctgcaccg actttgacaa catcctcatg accgtcacct
1921   gctttgagaa gtctgagcag gtgcagggtg cccagaagca gttcaagaac tttcagatcg
1981   aggtgcagaa gggccgctac agtctgcacg gttcggaccg cagcttcccc agcttgggag
2041   acctcatgag ccacctcaag aagcagatcc tgcgcacgga taacatcagc ttcatgctaa
2101   aacgctgctg ccagcccaag ccccgagaaa tctccaacct gctggtggct actaagaaag
2161   cccaggagtg gcagcccgtc taccccatga gccagctgag tttcgatcgg atcctcaaga
2221   aggatctggt gcagggcgag caccttggga gaggcacgag aacacacatc tattctggga
2281   ccctgatgga ttacaaggat gacgaaggaa cttctgaaga gaagaagata aaagtgatcc
2341   tcaaagtctt agaccccagc cacagggata tttcccctggc cttcttcgag gcagccagca
2401   tgatgagaca ggtctcccac aaacacatcg tgtacctcta tggcgtctgt gtccgcgacg
2461   tggagaatat catggtggaa gagtttgtgg aagggggtcc tctggatctc ttcatgcacc
2521   ggaaaagcga tgtccttacc acaccatgga aattcaaagt tgccaaacag ctggccagtg
2581   ccctgagcta cttggaggat aaagacctgg tccatggaaa tgtgtgtact aaaaacctcc
2641   tcctggcccg tgagggcatc gacagtgagt gtggcccatt catcaagctc agtgaccccg
2701   gcatccccat tacggtgctg tctaggcaag aatgcattga acgaatccca tggattgctc
2761   ctgagtgtgt tgaggactcc aagaacctga gtgtggctgc tgacaagtgg agctttggaa
2821   ccacgctctg ggaaatctgc tacaatggcg agatccccct gaaagacaag acgctgattg
2881   agaaagagag attctatgaa gccggtgca ggccagtgac accatcatgt aaggagctgg
2941   ctgacctcat gacccgctgc atgaactatg accccaatca gaggcctttc ttccgagcca
```

-continued

```
3001  tcatgagaga cattaataag cttgaagagc agaatccaga tattgtttca gaaaaaaaac
3061  cagcaactga agtggacccc acacattttg aaaagcgctt cctaaagagg atccgtgact
3121  tgggagaggg ccactttggg aaggttgagc tctgcaggta tgaccccgaa ggggacaata
3181  cagggagca ggtggctgtt aaatctctga agcctgagag tggaggtaac cacatagctg
3241  atctgaaaaa ggaaatcgag atcttaagga acctctatca tgagaacatt gtgaagtaca
3301  aaggaatctg cacagaagac ggaggaaatg gtattaagct catcatggaa tttctgcctt
3361  cgggaagcct taaggaatat cttccaaaga ataagaacaa aataaacctc aaacagcagc
3421  taaaatatgc cgttcagatt tgtaagggga tggactattt gggttctcgg caatacgttc
3481  accgggactt ggcagcaaga aatgtccttg ttgagagtga acaccaagtg aaaattggag
3541  acttcggttt aaccaaagca attgaaaccg ataaggagta ttacaccgtc aaggatgacc
3601  gggacagccc tgtgttttgg tatgctccag aatgtttaat gcaatctaaa ttttatattg
3661  cctctgacgt ctggtctttt ggagtcactc tgcatgagct gctgacttac tgtgattcag
3721  attctagtcc catggctttg ttcctgaaaa tgataggccc aacccatggc cagatgacag
3781  tcacaagact tgtgaatacg ttaaaagaag gaaaacgcct gccgtgccca cctaactgtc
3841  cagatgaggt ttatcaactt atgaggaaat gctgggaatt ccaaccatcc aatcggacaa
3901  gctttcagaa ccttattgaa ggatttgaag cacttttaaa ataagaagca tgaataacat
3961  ttaaattcca cagattatca agtccttctc ctgcaacaaa tgcccaagtc attttttaaa
4021  aatttctaat gaaagaagtt tgtgttctgt ccaaaaagtc actgaactca tacttcagta
4081  catatacatg tataaggcac actgtagtgc ttaatatgtg taaggacttc ctctttaaat
4141  ttggtaccag taacttagtg acacataatg acaaccaaaa tatttgaaag cacttaagca
4201  ctcctccttg tggaaagaat ataccaccat ttcatctggc tagttcacca tcacaactgc
4261  attaccaaaa ggggattttt gaaaacgagg agttgaccaa ataatatct gaagatgatt
4321  gcttttccct gctgccagct gatctgaaat gttttgctgg cacattaatc atagataaag
4381  aaagattgat ggacttagcc ctcaaatttc agtatctata cagtactaga ccatgcattc
4441  ttaaaatatt agataccagg tagtatatat tgtttctgta caaaaatgac tgtattctct
4501  caccagtagg acttaaactt tgtttctcca gtggcttagc tcctgttcct ttgggtgatc
4561  actagcaccc attttgaga aagctggttc tacatggggg gatagctgtg aatagataa
4621  tttgctgcat gttaattctc aagaactaag cctgtgccag tgcttttccta agcagtatac
4681  ctttaatcag aactcattcc cagaacctgg atgctattac acatgctttt aagaaacgtc
4741  aatgtatatc cttttataac tctaccactt tggggcaagc tattccagca ctggttttga
4801  atgctgtatg caaccagtct gaataccaca tacgctgcac tgttcttaga gggtttccat
4861  acttaccacc gatctacaag ggttgatccc tgattttcc atcaatcatc accctgtggt
4921  gcaacacttg aaagacccgg ctagaggcac tatggacttc aggatccact agacagtttt
4981  cagtttgctt ggaggtagct gggtaatcaa aaatgtttag tcattgattc aatgtgaacg
5041  attacggtct ttatgaccaa gagtctgaaa atcttttgt tatgctgttt agtattcgtt
5101  tgatattgtt acttttcacc tgttgagccc aaattcagga ttggttcagt ggcagcaatg
5161  aagttgccat ttaaatttgt tcatagccta catcaccaag gtctctgtgt caaacctgtg
5221  gccactctat atgcactttg tttactcttt atacaaataa atatactaaa gactttacat
5281  gca
```

Human JAK1 mRNA Variant 5

(SEQ ID NO: 5)

```
   1  atctatcaca tggcagagat agaataaaaa cagaaaaatg gcgacggtca cgttgtggcg
  61  agccttgctg cgtcattaga taatcctcat gcaaatagcg ggaagaacaa aggaagggga
 121  gcccgggacc cccgggggcg caggatccgg cgggaggagt ctaagaggag gaggcggcgg
 181  tgccggagga ggaggaggag ggagggagaa gagaggaaga ccggagtccc cgcggcggcg
 241  gcggtccgga gagggggcga gccccgcgcg gcgccgggga ccgggcgcta ccacgaggcc
 301  gggacgctgg agtctgggcg cttctctgaa gtagctttgg aaagtagaga agaaaatcca
 361  gtttgcttct tggagaacac tggacagctg aataaatgca gtatctaaat ataaaagagg
 421  actgcaatgc catggctttc tgtgctaaaa tgaggagctc caagaagact gaggtgaacc
 481  tggaggcccc tgagccaggg gtggaagtga tcttctatct gtcggacagg gagcccctcc
 541  ggctgggcag tggagagtac acagcagagg aactgtgcat cagggctgca caggcatgcc
 601  gtatctctcc tctttgtcac aacctctttg ccctgtatga cgagaacacc aagctctggt
 661  atgctccaaa tcgcaccatc accgttgatg acaagatgtc cctccggctc cactaccgga
 721  tgaggttcta tttcaccaat tggcatggaa ccaacgacaa tgagcagtca gtgtggcgtc
 781  attctccaaa gaagcagaaa atggctacga gaaaaaaaa gattccagat gcaaccccctc
 841  tccttgatgc cagctcactg gagtatctgt ttgctcaggg acagtatgat ttggtgaaat
 901  gcctggctcc tattcgagac cccaagaccg agcaggatgg acatgatatt gagaacgagt
 961  gtctagggat ggctgtcctg gccatctcac actatgccat gatgaagaag atgcagttgc
1021  cagaactgcc caaggacatc agctacaagc gatatattcc agaaacattg aataagtcca
1081  tcagacagag gaaccttctc accaggatgc ggataaataa tgttttcaag gatttcctaa
1141  aggaatttaa caacaagacc atttgtgaca gcagcgtgtc cacgcatgac ctgaaggtga
1201  aatacttggc taccttggaa actttgacaa acattacgg tgctgaaata tttgagactt
1261  ccatgttact gatttcatca gaaaatgaga tgaattggtt tcattcgaat gacggtggaa
1321  acgttctcta ctacgaagtg atggtgactg ggaatcttgg aatccagtgg aggcataaac
1381  caaatgttgt ttctgttgaa aaggaaaaaa ataaactgaa gcggaaaaaa ctggaaaata
1441  aacacaagaa ggatgaggag aaaaacaaga tccgggaaga gtggaacaat tttctttact
1501  tccctgaaat cactcacatt gtaataaagg agtctgtggt cagcattaac aagcaggaca
1561  acaagaaaat ggaactgaag ctctcttccc acgaggaggc cttgtccttt gtgtccctgg
1621  tagatggcta cttccggctc acagcagatg cccatcatta cctctgcacc gacgtggccc
1681  ccccgttgat cgtccacaac atacagaatg gctgtcatgg tccaatctgt acagaatacg
1741  ccatcaataa attgcggcaa gaaggaagcg aggaggggat gtacgtgctg aggtggagct
1801  gcaccgactt tgacaacatc ctcatgaccg tcacctgctt tgagaagtct gagcaggtgc
1861  agggtgccca gaagcagttc aagaactttc agatcgaggt gcagaagggc cgctacagtc
1921  tgcacggttc ggaccgcagc ttccccagct gggagaccct catgagccac ctcaagaagc
1981  agatcctgcg cacggataac atcagcttca tgctaaaacg ctgctgccag cccaagcccc
2041  gagaaatctc caacctgctg gtggctacta gaaagcccca ggagtggcag cccgtctacc
2101  ccatgagcca gctgagtttc gatcggatcc tcaagaagga tctggtgcag ggcgagcacc
2161  ttgggagagg cacgagaaca cacatctatt ctgggaccct gatggattac aaggatgacg
2221  aaggaacttc tgaagagaag aagataaaag tgatcctcaa agtcttagac cccagccaca
2281  gggatattc cctggccttc ttcgaggcag ccagcatgat gagacaggtc tcccacaaac
2341  acatcgtgta cctctatggc gtctgtgtcc gcgacgtgga gaatatcatg gtggaagagt
```

-continued

```
2401  ttgtggaagg gggtcctctg gatctcttca tgcaccggaa aagcgatgtc cttaccacac
2461  catggaaatt caaagttgcc aaacagctgg ccagtgccct gagctacttg gaggataaag
2521  acctggtcca tggaaatgtg tgtactaaaa acctcctcct ggcccgtgag ggcatcgaca
2581  gtgagtgtgg cccattcatc aagctcagtg accccggcat ccccattacg gtgctgtcta
2641  ggcaagaatg cattgaacga atcccatgga ttgctcctga gtgtgttgag gactccaaga
2701  acctgagtgt ggctgctgac aagtggagct tggaaccac gctctgggaa atctgctaca
2761  atggcgagat cccccttgaaa gacaagacgc tgattgagaa agagagattc tatgaaagcc
2821  ggtgcaggcc agtgacacca tcatgtaagg agctggctga cctcatgacc cgctgcatga
2881  actatgaccc caatcagagg cctttcttcc gagccatcat gagagacatt aataagcttg
2941  aagagcagaa tccagatatt gtttcagaaa aaaaaccagc aactgaagtg gaccccacac
3001  attttgaaaa gcgcttccta aagaggatcc gtgacttggg agagggccac tttgggaagg
3061  ttgagctctg caggtatgac cccgaagggg acaatacagg ggagcaggtg gctgttaaat
3121  ctctgaagcc tgagagtgga ggtaaccaca tagctgatct gaaaaaggaa atcgagatct
3181  taaggaacct ctatcatgag aacattgtga agtacaaagg aatctgcaca gaagacggag
3241  gaaatggtat taagctcatc atggaatttc tgccttcggg aagccttaag gaatatcttc
3301  caaagaataa gaacaaaata aacctcaaac agcagctaaa atatgccgtt cagatttgta
3361  aggggatgga ctatttgggt tctcggcaat acgttcaccg ggacttggca gcaagaaatg
3421  tccttgttga gagtgaacac caagtgaaaa ttggagactt cggtttaacc aaagcaattg
3481  aaaccgataa ggagtattac accgtcaagg atgaccggga cagccctgtg ttttggtatg
3541  ctccagaatg tttaatgcaa tctaaatttt atattgcctc tgacgtctgg tcttttggag
3601  tcactctgca tgagctgctg acttactgtg attcagattc tagtcccatg gctttgttcc
3661  tgaaaatgat aggcccaacc catggccaga tgacagtcac aagacttgtg aatacgttaa
3721  aagaaggaaa acgcctgccg tgcccaccta actgtccaga tgaggtttat caacttatga
3781  ggaaatgctg ggaattccaa ccatccaatc ggacaagctt tcagaacctt attgaaggat
3841  ttgaagcact tttaaaataa gaagcatgaa taacatttaa attccacaga ttatcaagtc
3901  cttctcctgc aacaaatgcc caagtcattt tttaaaaatt tctaatgaaa gaagtttgtg
3961  ttctgtccaa aaagtcactg aactcatact tcagtacata tacatgtata aggcacactg
4021  tagtgcttaa tatgtgtaag gacttcctct ttaaatttgg taccagtaac ttagtgacac
4081  ataatgacaa ccaaaatatt tgaaagcact taagcactcc tccttgtgga agaatatac
4141  caccatttca tctggctagt tcaccatcac aactgcatta ccaaaagggg attttttgaaa
4201  acgaggagtt gaccaaaata atatctgaag atgattgctt ttccctgctg ccagctgatc
4261  tgaaatgttt tgctggcaca ttaatcatag ataaagaaag attgatggac ttagccctca
4321  aatttcagta tctatacagt actagaccat gcattcttaa aatattagat accaggtagt
4381  atatattgtt tctgtacaaa aatgactgta ttctctcacc agtaggactt aaactttgtt
4441  tctccagtgg cttagctcct gttcctttgg gtgatcacta gcacccattt tgagaaagc
4501  tggttctaca tgggggggata gctgtggaat agataatttg ctgcatgtta attctcaaga
4561  actaagcctg tgccagtgct ttcctaagca gtatacccttt aatcagaact cattcccaga
4621  acctggatgc tattacacat gcttttaaga aacgtcaatg tatatccttt tataactcta
4681  ccactttggg gcaagctatt ccagcactgg ttttgaatgc tgtatgcaac cagtctgaat
4741  accacatacg ctgcactgtt cttagagggt ttccatactt accaccgatc tacaagggtt
4801  gatccctgtt tttaccatca atcatcaccc tgtggtgcaa cacttgaaag acccggctag
```

```
                              -continued
4861  aggcactatg gacttcagga tccactagac agtttcagt ttgcttggag gtagctgggt 4921  aatcaaaaat gtttagtcat tgattcaatg tgaacgatta cggtctttat gaccaagagt 4981  ctgaaaatct ttttgttatg ctgtttagta ttcgtttgat attgttactt ttcacctgtt 5041  gagcccaaat tcaggattgg ttcagtggca gcaatgaagt tgccatttaa atttgttcat 5101  agcctacatc accaaggtct ctgtgtcaaa cctgtggcca ctctatatgc actttgttta 5161  ctctttatac aaataaatat actaaagact ttacatgca
```

Human JAK1 mRNA Variant 6

(SEQ ID NO: 6)
```
  1  ggggcgggac gggaggcggt gcgtcgctga gcgcaggccg cggcggccgc ggagtatcct 61  ggagctgcag acagtgcggg cctgcgccca gtcccggctg tcctcgccgc gaccccctcct 121  cagccctggg cgcgcgcacg ctggggcccc gcggggctgg ccgcctagcg agcctgccgg 181  tcgaccccag ccagcgcagc gacggggcgc tgcctggccc aggcgcacac ggaagtgtta 241  tctaaaacag ttcatgctgc tgaaaacctc cttcctggca gatgtccctc aaccctactg 301  gtgcctggct tctgagacac acgcttctct gaagtagctt tggaaagtag agaagaaaat 361  ccagtttgct tcttggagaa cactggacag ctgaataaat gcagtatcta aatataaaag 421  aggactgcaa tgccatggct ttctgtgcta aaatgaggag ctccaagaag actgaggtga 481  acctggaggc ccctgagcca ggggtggaag tgatcttcta tctgtcggac agggagcccc 541  tccggctggg cagtggagag tacacagcag aggaactgtg catcagggct gcacaggcat 601  gccgtatctc tcctctttgt cacaacctct tgccctgta tgacgagaac accaagctct 661  ggtatgctcc aaatcgcacc atcaccgttg atgacaagat gtccctccgc tcccactacc 721  ggatgaggtt ctatttcacc aattggcatg gaaccaacga caatgagcag tcagtgtggc 781  gtcattctcc aaagaagcag aaaaatggct acgagaaaaa aaagattcca gatgcaaccc 841  ctctccttga tgccagctca ctggagtatc tgtttgctca gggacagtat gatttggtga 901  aatgcctggc tcctattcga gaccccaaga ccgagcagga tggacatgat attgagaacg 961  agtgtctagg gatggctgtc ctggccatct cacactatgc catgatgaag aagatgcagt 1021 tgccagaact gcccaaggac atcagctaca gcgatatat tccagaaaca ttgaataagt 1081 ccatcagaca gaggaacctt ctcaccagga tgcggataaa taatgttttc aaggatttcc 1141 taaaggaatt taacaacaag accatttgtg acagcagcgt gtccacgcat gacctgaagg 1201 tgaaatactt ggctaccttg gaaactttga caaaacatta cggtgctgaa atatttgaga 1261 cttccatgtt actgattca tcagaaaatg agatgaattg gtttcattcg aatgacggtg 1321 gaaacgttct ctactacgaa gtgatggtga ctgggaatct tggaatccag tggaggcata 1381 aaccaaatgt tgtttctgtt gaaaaggaaa aaaataaact gaagcggaaa aaactggaaa 1441 ataaacacaa gaaggatgag gagaaaaaca agatccggga agagtggaac aattttttctt 1501 acttccctga aatcactcac attgtaataa aggagtctgt ggtcagcatt aacaagcagg 1561 acaacaagaa aatggaactg aagctctctt cccacgagga ggccttgtcc tttgtgtccc 1621 tggtagatgg ctacttccgg ctcacagcag atgcccatca ttacctctgc accgacgtgg 1681 ccccccccgtt gatcgtccac aacatacaga atggctgtca tggtccaatc tgtacagaat 1741 acgccatcaa taaattgcgg caagaaggaa gcgaggaggg gatgtacgtg ctgaggtgga 1801 gctgcaccga ctttgacaac atcctcatga ccgtcacctg ctttgagaag tctgagcagg 1861 tgcagggtgc ccagaagcag ttcaagaact ttcagatcga ggtgcagaag ggccgctaca 1921 gtctgcacgg ttcggaccgc agcttcccca gcttgggaga cctcatgagc cacctcaaga 1981 agcagatcct gcgcacggat aacatcagct tcatgctaaa acgctgctgc cagcccaagc
```

```
2041  cccgagaaat ctccaacctg ctggtggcta ctaagaaagc ccaggagtgg cagcccgtct
2101  accccatgag ccagctgagt ttcgatcgga tcctcaagaa ggatctggtg cagggcgagc
2161  accttgggag aggcacgaga acacacatct attctgggac cctgatggat tacaaggatg
2221  acgaaggaac ttctgaagag aagaagataa aagtgatcct caaagtctta accccagcc
2281  acagggatat ttccctggcc ttcttcgagg cagccagcat gatgagacag gtctcccaca
2341  aacacatcgt gtacctctat ggcgtctgtg tccgcgacgt ggagaatatc atggtggaag
2401  agtttgtgga agggggtcct ctggatctct tcatgcaccg gaaaagcgat gtccttacca
2461  caccatggaa attcaaagtt gccaaacagc tggccagtgc cctgagctac ttggaggata
2521  aagacctggt ccatggaaat gtgtgtacta aaaacctcct cctggcccgt gagggcatcg
2581  acagtgagtg tggcccattc atcaagctca gtgaccccgg catccccatt acggtgctgt
2641  ctaggcaaga atgcattgaa cgaatcccat ggattgctcc tgagtgtgtt gaggactcca
2701  agaacctgag tgtggctgct gacaagtgga gctttggaac cacgctctgg gaaatctgct
2761  acaatggcga gatccccttg aaagacaaga cgctgattga gaaagagaga ttctatgaaa
2821  gccggtgcag gccagtgaca ccatcatgta aggagctggc tgacctcatg acccgctgca
2881  tgaactatga ccccaatcag aggcctttct tccgagccat catgagagac attaataagc
2941  ttgaagagca gaatccagat attgtttcag aaaaaaaacc agcaactgaa gtggaccccca
3001  cacattttga aaagcgcttc ctaagagga tccgtgactt gggagagggc cactttggga
3061  aggttgagct ctgcaggtat gaccccgaag gggacaatac aggggagcag gtggctgtta
3121  aatctctgaa gcctgagagt ggaggtaacc acatagctga tctgaaaaag gaaatcgaga
3181  tcttaaggaa cctctatcat gagaacattg tgaagtacaa aggaatctgc acagaagacg
3241  gaggaaatgg tattaagctc atcatggaat ttctgccttc gggaagcctt aaggaatatc
3301  ttccaaagaa taagaacaaa ataaacctca acagcagct aaaatatgcc gttcagattt
3361  gtaaggggat ggactatttg ggttctcggc aatacgttca ccgggacttg cagcaagaa
3421  atgtccttgt tgagagtgaa caccaagtga aaattggaga cttcggttta accaaagcaa
3481  ttgaaaccga taaggagtat tacaccgtca aggatgaccg ggacagccct gtgttttggt
3541  atgctccaga atgtttaatg caatctaaat tttatattgc ctctgacgtc tggtcttttg
3601  gagtcactct gcatgagctg ctgacttact gtgattcaga ttctagtccc atggctttgt
3661  tcctgaaaat gataggccca acccatggcc agatgacagt cacaagactt gtgaatacgt
3721  taaaagaagg aaaacgcctg ccgtgcccac ctaactgtcc agatgaggtt tatcaactta
3781  tgaggaaatg ctgggaattc caaccatcca atcggacaag ctttcagaac cttattgaag
3841  gatttgaagc actttttaaaa taagaagcat gaataacatt taaattccac agattatcaa
3901  gtccttctcc tgcaacaaat gcccaagtca ttttttaaaa atttctaatg aaagaagttt
3961  gtgttctgtc caaaaagtca ctgaactcat acttcagtac atatacatgt ataaggcaca
4021  ctgtagtgct taatatgtgt aaggacttcc tctttaaatt tggtaccagt aacttagtga
4081  cacataatga caccaaaat atttgaaagc acttaagcac tcctccttgt ggaaagaata
4141  taccaccatt tcatctggct agttcaccat cacaactgca ttaccaaaag gggattttttg
4201  aaaacgagga gttgaccaaa ataatatctg aagatgattg cttttccctg ctgccagctg
4261  atctgaaatg ttttgctggc acattaatca tagataaaga aagattgatg gacttagccc
4321  tcaaatttca gtatctatac agtactagac catgcattct taaaatatta gataccaggt
4381  agtatatatt gtttctgtac aaaaatgact gtattctctc accagtagga cttaaacttt
4441  gtttctccag tggcttagct cctgttcctt tgggtgatca ctagcaccca ttttgagaa
```

```
                                    -continued
4501  agctggttct acatgggggg atagctgtgg aatagataat ttgctgcatg ttaattctca 4561  agaactaagc ctgtgccagt gctttcctaa gcagtatacc tttaatcaga actcattccc 4621  agaacctgga tgctattaca catgctttta agaaacgtca atgtatatcc ttttataact 4681  ctaccacttt ggggcaagct attccagcac tggttttgaa tgctgtatgc aaccagtctg 4741  aataccacat acgctgcact gttcttagag ggtttccata cttaccaccg atctacaagg 4801  gttgatccct gttttttacca tcaatcatca ccctgtggtg caacacttga aagacccggc 4861  tagaggcact atggacttca ggatccacta gacagttttc agtttgcttg gaggtagctg 4921  ggtaatcaaa aatgtttagt cattgattca atgtgaacga ttacggtctt tatgaccaag 4981  agtctgaaaa tcttttttgtt atgctgttta gtattcgttt gatattgtta cttttcacct 5041  gttgagccca aattcaggat tggttcagtg gcagcaatga agttgccatt taaatttgtt 5101  catagcctac atcaccaagg tctctgtgtc aaacctgtgg ccactctata tgcactttgt 5161  ttactcttta tacaaataaa tatactaaag actttacatg ca
```

Human JAK1 mRNA Variant 7
(SEQ ID NO: 7)

```
   1  agaagcggag cgtatacgga ggaggcggga tgcatttctg catcgagcgc acaaagcgct 61  tctctgaagt agctttggaa agtagagaag aaaatccagt ttgcttcttg gagaacactg 121  gacagctgaa taaatgcagt atctaaatat aaaagaggac tgcaatgcca tggctttctg 181  tgctaaaatg aggagctcca agaagactga ggtgaacctg gaggcccctg agccagggggt 241  ggaagtgatc ttctatctgt cggacaggga gcccctccgg ctgggcagtg agagtacac 301  agcagaggaa ctgtgcatca gggctgcaca gcatgccgt atctctcctc tttgtcacaa 361  cctctttgcc ctgtatgacg agaacaccaa gctctggtat gctccaaatc gcaccatcac 421  cgttgatgac aagatgtccc tccggctcca ctaccggatg aggttctatt tcaccaattg 481  gcatggaacc aacgacaatg agcagtcagt gtggcgtcat tctccaaaga agcagaaaaa 541  tggctacgag aaaaaaaaga ttccagatgc aaccctctc cttgatgcca gctcactgga 601  gtatctgttt gctcagggac agtatgattt ggtgaaatgc tggctcctta ttcgagaccc 661  caagaccgag caggatggac atgatattga aacgagtgt ctagggatgg ctgtcctggc 721  catctcacac tatgccatga tgaagaagat gcagttgcca gaactgccca aggacatcag 781  ctacaagcga tatattccag aaacattgaa taagtccatc agacagagga accttctcac 841  caggatgcgg ataaataatg ttttcaagga tttcctaaag gaatttaaca caagaccat 901  ttgtgacagc agcgtgtcca cgcatgacct gaaggtgaaa tacttggcta ccttggaaac 961  tttgacaaaa cattacggtg ctgaaatatt tgagacttcc atgttactga tttcatcaga 1021  aaatgagatg aattggtttc attcgaatga cggtggaaac gttctctact acgaagtgat 1081  ggtgactggg aatcttggaa tccagtggag gcataaacca aatgttgttt ctgttgaaaa 1141  ggaaaaaaat aaactgaagc ggaaaaaact ggaaaataaa acaagaagg atgaggagaa 1201  aaacaagatc cgggaagagt ggaacaattt ttcttacttc cctgaaatca ctcacattgt 1261  aataaaggag tctgtggtca gcattaacaa gcaggacaac aagaaaatga aactgaagct 1321  ctcttcccac gaggaggcct tgtcctttgt gtccctggta gatggctact tccggctcac 1381  agcagatgcc catcattacc tctgcaccga cgtggccccc cgttgatcg tccacaacat 1441  acagaatggc tgtcatggtc caatctgtac agaatacgcc atcaataaat gcggcaagaa 1501  aggaagcgag gaggggatgt acgtgctgag gtggagctgc accgactttg acaacatcct 1561  catgaccgtc acctgctttg agaagtctga gcaggtgcag ggtgcccaga gcagttcaa 1621  gaactttcag atcgaggtgc agaagggccg ctacagtctg cacggttcgg accgcagctt
```

-continued

```
1681   ccccagcttg ggagacctca tgagccacct caagaagcag atcctgcgca cggataacat
1741   cagcttcatg ctaaaacgct gctgccagcc caagcccga gaaatctcca acctgctggt
1801   ggctactaag aaagcccagg agtggcagcc cgtctacccc atgagccagc tgagtttcga
1861   tcggatcctc aagaaggatc tggtgcaggg cgagcacctt gggagaggca cgagaacaca
1921   catctattct gggaccctga tggattacaa ggatgacgaa ggaacttctg aagagaagaa
1981   gataaaagtg atcctcaaag tcttagaccc cagccacagg gatatttccc tggccttctt
2041   cgaggcagcc agcatgatga gacaggtctc ccacaaacac atcgtgtacc tctatggcgt
2101   ctgtgtccgc gacgtggaga atatcatggt ggaagagttt gtggaagggg gtcctctgga
2161   tctcttcatg caccggaaaa gcgatgtcct taccacacca tggaaattca agttgccaa
2221   acagctggcc agtgccctga gctacttgga ggataaagac ctggtccatg gaaatgtgtg
2281   tactaaaaac ctcctcctgg cccgtgaggg catcgacagt gagtgtggcc cattcatcaa
2341   gctcagtgac cccggcatcc ccattacggt gctgtctagg caagaatgca ttgaacgaat
2401   cccatggatt gctcctgagt gtgttgagga ctccaagaac ctgagtgtgg ctgctgacaa
2461   gtggagcttt ggaaccacgc tctgggaaat ctgctacaat ggcgagatcc ccttgaaaga
2521   caagacgctg attgagaaag agagattcta tgaaagccgg tgcaggccag tgacaccatc
2581   atgtaaggag ctggctgacc tcatgacccg ctgcatgaac tatgacccca atcagaggcc
2641   tttcttccga gccatcatga gagacattaa taagcttgaa gagcagaatc cagatattgt
2701   ttcagaaaaa aaaccagcaa ctgaagtgga ccccacacat tttgaaaagc gcttcctaaa
2761   gaggatccgt gacttgggag agggccactt tgggaaggtt gagctctgca ggtatgaccc
2821   cgaaggggac aatacagggg agcaggtggc tgttaaatct ctgaagcctg agagtggagg
2881   taaccacata gctgatctga aaaggaaat cgagatctta aggaacctct atcatgagaa
2941   cattgtgaag tacaaaggaa tctgcacaga agacggagga aatggtatta agctcatcat
3001   ggaatttctg ccttcggaa gccttaagga atatcttcca agaataaga acaaaataaa
3061   cctcaaacag cagctaaaat atgccgttca gatttgtaag gggatggact atttgggttc
3121   tcggcaatac gttcaccggg acttggcagc aagaaatgtc cttgttgaga gtgaacacca
3181   agtgaaaatt ggagacttcg gtttaaccaa agcaattgaa accgataagg agtattacac
3241   cgtcaaggat gaccgggaca gccctgtgtt ttggtatgct ccagaatgtt aatgcaatc
3301   taaattttat attgcctctg acgtctggtc ttttggagtc actctgcatg agctgctgac
3361   ttactgtgat tcagattcta gtcccatggc tttgttcctg aaaatgatag gcccaaccca
3421   tggccagatg acagtcacaa gacttgtgaa tacgttaaaa gaaggaaaac gcctgccgtg
3481   cccacctaac tgtccagatg aggtttatca acttatgagg aaatgctggg aattccaacc
3541   atccaatcgg acaagctttc agaaccttat tgaaggattt gaagcacttt taaaataaga
3601   agcatgaata acatttaaat tccacagatt atcaagtcct tctcctgcaa caaatgccca
3661   agtcattttt taaaaatttc taatgaaaga agtttgtgtt ctgtccaaaa agtcactgaa
3721   ctcatacttc agtacatata catgtataag gcacactgta gtgcttaata tgtgtaagga
3781   cttcctcttt aaatttggta ccagtaactt agtgacacat aatgacaacc aaaatatttg
3841   aaagcactta agcactcctc cttgtggaaa gaatatacca ccatttcatc tggctagttc
3901   accatcacaa ctgcattacc aaaagggat ttttgaaaac gaggagttga ccaaaataat
3961   atctgaagat gattgctttt ccctgctgcc agctgatctg aaatgttttg ctggcacatt
4021   aatcatagat aaagaaagat tgatggactt agccctcaaa tttcagtatc tatacagtac
4081   tagaccatgc attcttaaaa tattagatac caggtagtat atattgtttc tgtacaaaaa
```

-continued

```
4141  tgactgtatt ctctcaccag taggacttaa actttgtttc tccagtggct tagctcctgt 4201  tcctttgggt gatcactagc acccattttt gagaaagctg gttctacatg ggggatagc 4261  tgtggaatag ataatttgct gcatgttaat tctcaagaac taagcctgtg ccagtgcttt 4321  cctaagcagt atacctttaa tcagaactca ttcccagaac ctggatgcta ttacacatgc 4381  ttttaagaaa cgtcaatgta tatccttta taactctacc actttggggc aagctattcc 4441  agcactggtt ttgaatgctg tatgcaacca gtctgaatac cacatacgct gcactgttct 4501  tagagggttt ccatacttac caccgatcta caaggggttga tccctgtttt taccatcaat 4561  catcaccctg tggtgcaaca cttgaaagac ccggctagag gcactatgga cttcaggatc 4621  cactagacag ttttcagttt gcttggaggt agctgggtaa tcaaaaatgt ttagtcattg 4681  attcaatgtg aacgattacg gtctttatga ccaagagtct gaaaatcttt ttgttatgct 4741  gtttagtatt cgtttgatat tgttactttt cacctgttga gcccaaattc aggattggtt 4801  cagtggcagc aatgaagttg ccatttaaat ttgttcatag cctacatcac caaggtctct 4861  gtgtcaaacc tgtggccact ctatatgcac tttgtttact ctttatacaa ataaatatac 4921  taaagacttt acatgca
```

Human JAK1 mRNA Variant 8
(SEQ ID NO: 8)

```
   1  ggggcgggac gggaggcggt gcgtcgctga gcgcaggccg cggcggccgc ggagtatcct 61  ggagctgcag acagtgcggg cctgcgccca gtcccggctg tcctcgccgc gaccoctcct 121  cagccctggg cgcgcgcacg ctggggcccc gcggggctgg ccgcctagcg agcctgccgg 181  tcgaccccag ccagcgcagc gacggggcgc tgcctggccc aggcgcacac ggaagtgcgc 241  ttctctgaag tagctttgga aagtagagaa gaaaatccag tttgcttctt ggagaacact 301  ggacagctga ataaatgcag tatctaaata taaagagga ctgcaatgcc atggctttct 361  gtgctaaaat gaggagctcc aagaagactg aggtgaacct ggaggcccct gagccagggg 421  tggaagtgat cttctatctg tcggacaggg agccctccg gctgggcagt ggagagtaca 481  cagcagagga actgtgcatc agggctgcac aggcatgccg tatctctcct ctttgtcaca 541  acctctttgc cctgtatgac gagaacacca agctctggta tgctccaaat cgcaccatca 601  ccgttgatga caagatgtcc ctccggctcc actaccggat gaggttctat ttcaccaatt 661  ggcatggaac caacgacaat gagcagtcag tgtggcgtca ttctccaaag aagcagaaaa 721  atggctacga gaaaaaaag attccagatg caaccccctct ccttgatgcc agctcactgg 781  agtatctgtt tgctcaggga cagtatgatt tggtgaaatg cctggctcct attcgagacc 841  ccaagaccga gcaggatgga catgatattg agaacgagtg tctagggatg gctgtcctgg 901  ccatctcaca ctatgccatg atgaagaaga tgcagttgcc agaactgccc aaggacatca 961  gctacaagcg atatattcca gaaacattga ataagtccat cagacagagg aaccttctca 1021  ccaggatgcg gataaataat gttttcaagg atttcctaaa ggaatttaac aacaagacca 1081  tttgtgacag cagcgtgtcc acgcatgacc tgaaggtgaa atacttggct accttggaaa 1141  ctttgacaaa acattaccgt gctgaaatat ttgagacttc catgttactg atttcatcag 1201  aaaatgagat gaattggttt cattcgaatg acgtggaaa cgttctctac tacgaagtga 1261  tggtgactgg gaatcttgga atccagtgga ggcataaacc aaatgttgtt tctgttgaaa 1321  aggaaaaaaa taaactgaag cggaaaaaac tggaaaataa acacaagaag gatgaggaga 1381  aaaacaagat ccgggaagag tggaacaatt tttcttactt ccctgaaatc actcacattg 1441  taataaagga gtctgtggtc agcattaaca gcaggacaa caagaaaatg gaactgaagc 1501  tctcttccca cgaggaggcc ttgtccttg tgtccctggt agatggctac ttccggctca
```

-continued

```
1561  cagcagatgc ccatcattac ctctgcaccg acgtggcccc cccgttgatc gtccacaaca
1621  tacagaatgg ctgtcatggt ccaatctgta cagaatacgc catcaataaa ttgcggcaag
1681  aaggaagcga ggaggggatg tacgtgctga ggtggagctg caccgacttt gacaacatcc
1741  tcatgaccgt cacctgcttt gagaagtctg aggtgcaggg tgcccagaag cagttcaaga
1801  actttcagat cgaggtgcag aagggccgct acagtctgca cggttcggac cgcagcttcc
1861  ccagcttggg agacctcatg agccacctca agaagcagat cctgcgcacg gataacatca
1921  gcttcatgct aaaacgctgc tgccagccca gccccgaga atctccaac ctgctggtgg
1981  ctactaagaa agcccaggag tggcagcccg tctacccat gagccagctg agtttcgatc
2041  ggatcctcaa gaaggatctg gtgcagggcg agcaccttgg gagaggcacg agaacacaca
2101  tctattctgg gaccctgatg gattacaagg atgacgaagg aacttctgaa gagaagaaga
2161  taaaagtgat cctcaaagtc ttagacccca gccacaggga tatttccctg gccttcttcg
2221  aggcagccag catgatgaga caggtctccc acaaacacat cgtgtacctc tatggcgtct
2281  gtgtccgcga cgtggagaat atcatggtgg aagagtttgt ggaaggggt cctctggatc
2341  tcttcatgca ccggaaaagc gatgtcctta ccacaccatg gaaattcaaa gttgccaaac
2401  agctggccag tgccctgagc tacttggagg ataaagacct ggtccatgga atgtgtgta
2461  ctaaaaacct cctcctggcc cgtgagggca tcgacagtga gtgtggccca ttcatcaagc
2521  tcagtgaccc cggcatcccc attacggtgc tgtctaggca agaatgcatt gaacgaatcc
2581  catggattgc tcctgagtgt gttgaggact ccaagaacct gagtgtggct gctgacaagt
2641  ggagctttgg aaccacgctc tgggaaatct gctacaatgg cgagatcccc ttgaaagaca
2701  agacgctgat tgagaaagag agattctatg aaagccggtg caggccagtg acaccatcat
2761  gtaaggagct ggctgacctc atgacccgct gcatgaacta tgaccccaat cagaggcctt
2821  tcttccgagc catcatgaga gacattaata agcttgaaga gcagaatcca gatattgttt
2881  cagaaaaaaa accagcaact gaagtggacc ccacacattt tgaaaagcgc ttcctaaaga
2941  ggatccgtga cttgggagag ggccactttg ggaaggttga gctctgcagg tatgaccccg
3001  aaggggacaa tacaggggag caggtggctg ttaaatctct gaagcctgag agtggaggta
3061  accacatagc tgatctgaaa aaggaaatcg agatcttaag gaacctctat catgagaaca
3121  ttgtgaagta caaaggaatc tgcacagaag acggaggaaa tggtattaag ctcatcatgg
3181  aatttctgcc ttcgggaagc cttaaggaat atcttccaaa gaataagaac aaaataaacc
3241  tcaaacagca gctaaaatat gccgttcaga tttgtaaggg gatggactat ttgggttctc
3301  ggcaatacgt tcaccgggac ttggcagcaa gaaatgtcct tgttgagagt gaacaccaag
3361  tgaaaattgg agacttcggt ttaaccaaag caattgaaac cgataaggag tattacaccg
3421  tcaaggatga ccgggacagc cctgtgtttt ggtatgctcc agaatgttta atgcaatcta
3481  aatttatat tgcctctgac gtctggtctt ttggagtcac tctgcatgag ctgctgactt
3541  actgtgattc agattctagt cccatggctt tgttcctgaa aatgataggc ccaacccatg
3601  gccagatgac agtcacaaga cttgtgaata cgttaaaaga aggaaaacgc ctgccgtgcc
3661  cacctaactg tccagatgag gtttatcaac ttatgaggaa atgctgggaa ttccaaccat
3721  ccaatcggac aagctttcag aaccttattg aaggatttga agcactttta aaataagaag
3781  catgaataac atttaaattc cacagattat caagtccttc tcctgcaaca aatgcccaag
3841  tcatttttta aaaatttcta atgaaagaag tttgtgttct gtccaaaaag tcactgaact
3901  catacttcag tacatataca tgtataaggc acactgtagt gcttaatatg tgtaaggact
3961  tcctctttaa atttggtacc agtaacttag tgacacataa tgacaaccaa aatatttgaa
```

-continued

```
4021 agcacttaag cactcctcct tgtggaaaga atataccacc atttcatctg gctagttcac 4081 catcacaact gcattaccaa aagggga ttt ttgaaaacga ggagttgacc aaaataatat 4141 ctgaagatga ttgcttttcc ctgctgccag ctgatctgaa atgttttgct ggcacattaa 4201 tcatagataa agaaagattg atggacttag ccctcaaatt tcagtatcta tacagtacta 4261 gaccatgcat tcttaaaata ttagatacca ggtagtatat attgtttctg tacaaaaatg 4321 actgtattct ctcaccagta ggacttaaac tttgtttctc cagtggctta gctcctgttc 4381 ctttgggtga tcactagcac ccattttga gaaagctggt tctacatggg gggatagctg 4441 tggaatagat aatttgctgc atgttaattc tcaagaacta agcctgtgcc agtgctttcc 4501 taagcagtat acctttaatc agaactcatt cccagaacct ggatgctatt acacatgctt 4561 ttaagaaacg tcaatgtata tccttttata actctaccac tttggggcaa gctattccag 4621 cactggtttt gaatgctgta tgcaaccagt ctgaatacca catacgctgc actgttctta 4681 gagggtttcc atacttacca ccgatctaca agggttgatc cctgttttta ccatcaatca 4741 tcaccctgtg gtgcaacact tgaaagaccc ggctagaggc actatggact tcaggatcca 4801 ctagacagtt ttcagtttgc ttggaggtag ctgggtaatc aaaaatgttt agtcattgat 4861 tcaatgtgaa cgattacggt ctttatgacc aagagtctga aaatctttt gttatgctgt 4921 ttagtattcg tttgatattg ttacttttca cctgttgagc ccaaattcag gattggttca 4981 gtggcagcaa tgaagttgcc atttaaattt gttcatagcc tacatcacca aggtctctgt 5041 gtcaaacctg tggccactct atatgcactt tgtttactct ttatacaaat aaatatacta 5101 aagactttac atgca
```

Human JAK2 mRNA Variant 1

(SEQ ID NO: 9)

```
   1 ctgcaggaag gagagaggaa gaggagcaga aggggggcagc agcggacgcc gctaacggcc 61 tccctcggcg ctgacaggct gggccggcgc ccggctcgct tgggtgttcg cgtcgccact 121 tcggcttctc ggccggtcgg gcccctcggc ccgggcttgc ggcgcgcgt  ggggctgagg 181 gctgctgcgg cgcagggaga ggcctggtcc tcgctgccga gggatgtgag tgggagctga 241 gcccacactg gagggccccc gagggcccag cctggaggtc gttcagagcc gtgcccgtcc 301 cggggcttcg cagaccttga cccgccgggt aggagccgcc cctgcgggct cgagggcgcg 361 ctctggtcgc ccgatctgtg tagccggttt cagaagcagg caacaggaac aagatgtgaa 421 ctgtttctct tctgcagaaa aagaggctct tcctcctcct cccgcgacgg caaatgttct 481 gaaaaagact ctgcatggga atggcctgcc ttacgatgac agaaatggag ggaacatcca 541 cctcttctat atatcagaat ggtgatattt ctggaaatgc caattctatg aagcaaatag 601 atccagttct tcaggtgtat ctttaccatt cccttgggaa atctgaggca gattatctga 661 cctttccatc tggggagtat gttgcagaag aaatctgtat tgctgcttct aaagcttgtg 721 gtatcacacc tgtgtatcat aatatgtttg ctttaatgag tgaaacagaa aggatctggt 781 atccacccaa ccatgtcttc catatagatg agtcaaccag gcataatgta ctctacagaa 841 taagatttta ctttcctcgt tggtattgca gtggcagcaa cagagcctat cggcatggaa 901 tatctcgagg tgctgaagct cctcttcttg atgactttgt catgtcttac ctctttgctc 961 agtggcggca tgattttgtg cacggatgga taaaagtacc tgtgactcat gaaacacagg 1021 aagaatgtct tgggatggca gtgttagata tgatgagaat agccaaagaa acgatcaaa 1081 ccccactggc catctataac tctatcagct acaagacatt cttaccaaaa tgtattcgag 1141 caaagatcca agactatcat attttgacaa ggaagcgaat aaggtacaga tttcgcagat 1201 ttattcagca attcagccaa tgcaaagcca ctgccagaaa cttgaaactt aagtatctta
```

-continued

```
1261  taaatctgga aactctgcag tctgccttct acacagagaa atttgaagta aaagaacctg
1321  gaagtggtcc ttcaggtgag gagattttg caaccattat aataactgga aacggtggaa
1381  ttcagtggtc aagagggaaa cataaagaaa gtgagacact gacagaacag gatttacagt
1441  tatattgcga ttttcctaat attattgatg tcagtattaa gcaagcaaac caagagggtt
1501  caaatgaaag ccgagttgta actatccata agcaagatgg taaaaatctg gaaattgaac
1561  ttagctcatt aagggaagct ttgtctttcg tgtcattaat tgatggatat tatagattaa
1621  ctgcagatgc acatcattac ctctgtaaag aagtagcacc tccagccgtg cttgaaaata
1681  tacaaagcaa ctgtcatggc ccaatttcga tggattttgc cattagtaaa ctgaagaaag
1741  caggtaatca gactggactg tatgtacttc gatgcagtcc taaggacttt aataaatatt
1801  ttttgacttt tgctgtcgag cgagaaaatg tcattgaata taaacactgt tgattacaa
1861  aaaatgagaa tgaagagtac aacctcagtg ggacaaagaa gaacttcagc agtcttaaag
1921  atcttttgaa ttgttaccag atggaaactg ttcgctcaga caatataatt ttccagttta
1981  ctaaatgctg tcccccaaag ccaaaagata aatcaaacct tctagtcttc agaacgaatg
2041  gtgtttctga tgtaccaacc tcaccaacat tacagaggcc tactcatatg aaccaaatgg
2101  tgtttcacaa aatcagaaat gaagatttga tatttaatga aagccttggc caaggcactt
2161  ttacaaagat ttttaaaggc gtacgaagag aagtaggaga ctacggtcaa ctgcatgaaa
2221  cagaagttct ttttaaagtt ctggataaag cacacagaaa ctattcagag tctttctttg
2281  aagcagcaag tatgatgagc aagctttctc acaagcattt ggttttaaat tatggagtat
2341  gtgtctgtgg agacgagaat attctggttc aggagtttgt aaaatttgga tcactagata
2401  catatctgaa aaagaataaa aattgtataa atatattatg gaaacttgaa gttgctaaac
2461  agttggcatg ggccatgcat tttctagaag aaaacacccct tattcatggg aatgtatgtg
2521  ccaaaaatat tctgcttatc agagaagaag acaggaagac aggaaatcct cctttcatca
2581  aacttagtga tcctggcatt agtattacag ttttgccaaa ggacattctt caggagagaa
2641  taccatgggt accacctgaa tgcattgaaa atcctaaaaa tttaaatttg gcaacagaca
2701  aatggagttt tggtaccact ttgtgggaaa tctgcagtgg aggagataaa cctctaagtg
2761  ctctggattc tcaaagaaag ctacaatttt atgaagatag gcatcagctt cctgcaccaa
2821  agtgggcaga attagcaaac cttataaata attgtatgga ttatgaacca gatttcaggc
2881  cttctttcag agccatcata cgagatctta acagtttgtt tactccagat tatgaactat
2941  taacagaaaa tgacatgtta ccaaatatga ggataggtgc cctggggttt tctggtgcct
3001  ttgaagaccg ggatcctaca cagtttgaag agagacattt gaaatttcta cagcaacttg
3061  gcaagggtaa ttttgggagt gtggagatgt gccggtatga ccctctacag gacaacactg
3121  gggaggtggt cgctgtaaaa aagcttcagc atagtactga agagcaccta agagactttg
3181  aaagggaaat tgaaatcctg aaatccctac agcatgacaa cattgtaaag tacaagggag
3241  tgtgctacag tgctggtcgg cgtaatctaa aattaattat ggaatattta ccatatggaa
3301  gtttacgaga ctatcttcaa aaacataaag aacggataga tcacataaaa cttctgcagt
3361  acacatctca gatatgcaag ggtatggagt atcttggtac aaaaaggtat atccacaggg
3421  atctggcaac gagaaatata ttggtggaga acgagaacag agttaaaatt ggagattttg
3481  ggttaaccaa agtccttgcca caagacaaag aatactataa agtaaaagaa cctggtgaaa
3541  gtcccatatt ctggtatgct ccagaatcac tgacagagag caagttttct gtggcctcag
3601  atgtttggag ctttggagtg gttctgtatg aacttttcac atacattgag aagagtaaaa
3661  gtccaccagc ggaatttatg cgtatgattg gcaatgacaa acaaggacag atgatcgtgt
```

-continued

```
3721  tccatttgat agaacttttg aagaataatg gaagattacc aagaccagat ggatgcccag 3781  atgagatcta tatgatcatg acagaatgct ggaacaataa tgtaaatcaa cgcccctcct 3841  ttagggatct agctcttcga gtggatcaaa taagggataa catggctgga tgaaagaaat 3901  gaccttcatt ctgagaccaa agtagattta cagaacaaag ttttatattt cacattgctg 3961  tggactatta ttacatatat cattattata taaatcatga tgctagccag caaagatgtg 4021  aaaatatctg ctcaaaactt tcaaagttta gtaagttttt cttcatgagg ccaccagtaa 4081  aagacattaa tgagaattcc ttagcaagga ttttgtaaga gtttcttaa acattgtcag 4141  ttaacatcac tcttgtctgg caaaagaaaa aaaatagact ttttcaactc agcttttga 4201  gacctgaaaa aattattatg taaattttgc aatgttaaag atgcacagaa tatgtatgta 4261  tagtttttac cacagtggat gtataatacc ttggcatctt gtgtgatgtt ttacacacat 4321  gagggctggt gttcattaat actgttttct aattttttcca tagttaatct ataattaatt 4381  acttcactat acaaacaaat taagatgttc agataattga ataagtaccct ttgtgtcctt 4441  gttcatttat atcgctggcc agcattataa gcaggtgtat acttttagct tgtagttcca 4501  tgtactgtaa atatttttca cataaaggga acaaatgtct agttttattt gtataggaaa 4561  tttccctgac cctaaataat acattttgaa atgaaacaag cttacaaaga tataatctat 4621  tttattatgg tttcccttgt atctatttgt ggtgaatgtg ttttttaaat ggaactatct 4681  ccaaattttt ctaagactac tatgaacagt tttcttttaa aattttgaga ttaagaatgc 4741  caggaatatt gtcatccttt gagctgctga ctgccaataa cattcttcga tctctgggat 4801  ttatgctcat gaactaaatt taagcttaag ccataaaata gattagattg tttttaaaa 4861  atggatagct cattaagaag tgcagcaggt taagaatttt ttcctaaaga ctgtatattt 4921  gagggtttc agaatttgc attgcagtca tagaagagat ttatttcctt tttagagggg 4981  aaatgaggta aataagtaaa aaagtatgct tgttaatttt attcaagaat gccagtagaa 5041  aattcataac gtgtatcttt aagaaaaatg agcatacatc ttaaatcttt tcaattaagt 5101  ataagggggtt gttcgttgtt gtcatttgtt atagtgctac tccactttag acaccatagc 5161  taaaataaaa tatggtgggt tttgtgtgtg tgtgtgtgtg tgtgtgtgtg tgtgtgtgtg 5221  tgttatttat acaaaactta aaatacttgc tgttttgatt aaaaagaaaa tagtttctta 5281  cttta
```

Human JAK2 mRNA Variant 2

(SEQ ID NO: 10)

```
  1  attcggggag actgcaggcc aaccgggagg ctgagttcga agctagcagg gcggcgaagc 61  cagtgtcgcc cgcggcgttg agaagacggt gtggccccgg agagggtgga gacaactgtg 121  acgggcttcc cggctgcccg aagtgggagt ggtgtgggc tgcaggaagg agagaggaag 181  aggagcagaa gggggcagca gcggacgccg ctaacggcct ccctcggcgc tgacaggctg 241  ggccggcgcc cggctcgctt gggtgttcgc gtcgccactt cggcttctcg gccggtcggg 301  ccctcggcc cgggcttgcg gcgcgcgtcg gggctgaggg ctgctgcggc cagggagag 361  gcctggtcct cgctgccgag ggatgtgagt gggagctgag cccacactgg agggcccccg 421  agggcccagc ctggaggtcg ttcagagccg tgcccgtccc ggggcttcgc agaccttgac 481  ccgccgggtt tcagaagcag gcaacaggaa caagatgtga actgtttctc ttctgcagaa 541  aaagaggctc ttcctcctcc tcccgcgacg gcaaatgttc tgaaaaagac tctgcatggg 601  aatggcctgc cttacgatga cagaaatgga gggaacatcc acctcttcta tatatcagaa 661  tggtgatatt tctggaaatg ccaattctat gaagcaaata gatccagttc ttcaggtgta 721  tctttaccat tcccttggga aatctgaggc agattatctg acctttccat ctggggagta
```

-continued

```
 781   tgttgcagaa gaaatctgta ttgctgcttc taaagcttgt ggtatcacac ctgtgtatca
 841   taatatgttt gctttaatga gtgaaacaga aaggatctgg tatccaccca accatgtctt
 901   ccatatagat gagtcaacca ggcataatgt actctacaga ataagatttt actttcctcg
 961   ttggtattgc agtggcagca acagagccta tcggcatgga atatctcgag gtgctgaagc
1021   tcctcttctt gatgactttg tcatgtctta cctctttgct cagtggcggc atgattttgt
1081   gcacggatgg ataaaagtac ctgtgactca tgaaacacag gaagaatgtc ttgggatggc
1141   agtgttagat atgatgagaa tagccaaaga aaacgatcaa accccactgg ccatctataa
1201   ctctatcagc tacaagacat tcttaccaaa atgtattcga gcaaagatcc aagactatca
1261   tattttgaca aggaagcgaa taaggtacag atttcgcaga tttattcagc aattcagcca
1321   atgcaaagcc actgccagaa acttgaaact taagtatctt ataaatctgg aaactctgca
1381   gtctgccttc tacacagaga aatttgaagt aaaagaacct ggaagtggtc cttcaggtga
1441   ggagatttt gcaaccatta taataactgg aaacggtgga attcagtggt caagagggaa
1501   acataaagaa agtgagacac tgacagaaca ggatttacag ttatattgcg attttcctaa
1561   tattattgat gtcagtatta agcaagcaaa ccaagagggt tcaaatgaaa gccgagttgt
1621   aactatccat aagcaagatg gtaaaaatct ggaaattgaa cttagctcat taagggaagc
1681   tttgtctttc gtgtcattaa ttgatggata ttatagatta actgcagatg cacatcatta
1741   cctctgtaaa gaagtagcac ctccagccgt gcttgaaaat atacaaagca actgtcatgg
1801   cccaatttcg atggattttg ccattagtaa actgaagaaa gcaggtaatc agactggact
1861   gtatgtactt cgatgcagtc ctaaggactt aataaatat tttttgactt tgctgtcga
1921   gcgagaaaat gtcattgaat ataaacactg tttgattaca aaaaatgaga atgaagagta
1981   caacctcagt gggacaaaga agaacttcag cagtcttaaa gatcttttga attgttacca
2041   gatggaaact gttcgctcag acaatataat tttccagttt actaaatgct gtcccccaaa
2101   gccaaaagat aaatcaaacc ttctagtctt cagaacgaat ggtgtttctg atgtaccaac
2161   ctcaccaaca ttacagaggc ctactcatat gaaccaaatg gtgtttcaca aaatcagaaa
2221   tgaagatttg atatttaatg aaagccttgg ccaaggcact tttcaaaga ttttaaagg
2281   cgtacgaaga gaagtaggag actacggtca actgcatgaa acagaagttc ttttaaaagt
2341   tctggataaa gcacacagaa actattcaga gtcttccttt gaagcagcaa gtatgatgag
2401   caagctttct cacaagcatt tggttttaaa ttatggagta tgtgtctgtg gagacgagaa
2461   tattctggtt caggagtttg taaaatttgg atcactagat acatatctga aaaagaataa
2521   aaattgtata aatatattat ggaaacttga agttgctaaa cagttggcat gggccatgca
2581   ttttctagaa gaaacaccc ttattcatgg gaatgtatgt gccaaaaata ttctgcttat
2641   cagagaagaa gacaggaaga caggaaatcc tcctttcatc aaacttagtg atcctggcat
2701   tagtattaca gttttgccaa aggacattct tcaggagaga ataccatggg taccacctga
2761   atgcattgaa aatcctaaaa atttaaattt ggcaacagac aaatggagtt ttggtaccac
2821   tttgtgggaa atctgcagtg gaggagataa aacctctaagt gctctggatt ctcaaagaaa
2881   gctacaattt tatgaagata ggcatcagct tcctgcacca aagtgggcag aattagcaaa
2941   cctttataaat aattgtatgg attatgaacc agattcagg ccttctttca gagccatcat
3001   acgagatctt aacagtttgt ttactccaga ttatgaacta ttaacagaaa atgacatgtt
3061   accaaatatg aggataggtg ccctgggtt ttctggtgcc tttgaagacc gggatcctac
3121   acagtttgaa gagagacatt tgaaatttct acagcaactt ggcaaggta attttgggag
3181   tgtggagatg tgccggtatg accctctaca ggacaacact ggggaggtgg tcgctgtaaa
```

-continued

```
3241  aaagcttcag catagtactg aagagcacct aagagacttt gaaagggaaa ttgaaatcct 3301  gaaatcccta cagcatgaca acattgtaaa gtacaaggga gtgtgctaca gtgctggtcg 3361  gcgtaatcta aaattaatta tggaatattt accatatgga agtttacgag actatcttca 3421  aaaacataaa gaacggatag atcacataaa acttctgcag tacacatctc agatatgcaa 3481  gggtatggag tatcttggta caaaaaggta tatccacagg gatctggcaa cgagaaatat 3541  attggtggag aacgagaaca gagttaaaat tggagatttt gggttaacca aagtcttgcc 3601  acaagacaaa gaatactata agtaaaaga acctggtgaa agtcccatat tctggtatgc 3661  tccagaatca ctgacagaga gcaagttttc tgtggcctca gatgtttgga gctttggagt 3721  ggttctgtat gaacttttca catacattga aagagtaaaa agtccaccag cggaatttat 3781  gcgtatgatt ggcaatgaca acaaggaca gatgatcgtg ttccatttga tagaactttt 3841  gaagaataat ggaagattac caagaccaga tggatgccca gatgagatct atatgatcat 3901  gacagaatgc tggaacaata atgtaaatca acgcccctcc tttagggatc tagctcttcg 3961  agtggatcaa ataagggata acatggctgg atgaaagaaa tgaccttcat tctgagacca 4021  aagtagattt acagaacaaa gttttatatt tcacattgct gtggactatt attacatata 4081  tcattattat ataaatcatg atgctagcca gcaaagatgt gaaaatatct gctcaaaact 4141  ttcaaagttt agtaagtttt tcttcatgag gccaccagta aaagacatta atgagaattc 4201  cttagcaagg attttgtaag aagtttctta acattgtca gttaacatca ctcttgtctg 4261  gcaaaagaaa aaaatagac tttttcaact cagcttttttg agacctgaaa aaattattat 4321  gtaaattttg caatgttaaa gatgcacaga atatgtatgt atagtttttta ccacagtgga 4381  tgtataatac cttggcatct tgtgtgatgt tttacacaca tgagggctgg tgttcattaa 4441  tactgttttc taattttttcc atagttaatc tataattaat tacttcacta tacaaacaaa 4501  ttaagatgtt cagataattg aataagtacc tttgtgtcct tgttcattta tatcgctggc 4561  cagcattata agcaggtgta tacttttagc ttgtagttcc atgtactgta aatatttttc 4621  acataaaggg aacaaatgtc tagttttatt tgtataggaa atttccctga ccctaaataa 4681  tacattttga aatgaaacaa gcttacaaag atataatcta tttttattatg gtttcccttg 4741  tatctatttg tggtgaatgt gttttttaaa tggaactatc tccaaatttt tctaagacta 4801  ctatgaacag ttttctttta aaatttttgag attaagaatg ccaggaatat tgtcatcctt 4861  tgagctgctg actgccaata acattcttcg atctctggga tttatgctca tgaactaaat 4921  ttaagcttaa gccataaaat agattagatt gtttttttaaa aatggatagc tcattaagaa 4981  gtgcagcagg ttaagaattt tttcctaaag actgtatatt tgagggggttt cagaattttg 5041  cattgcagtc atagaagaga tttatttcct ttttagaggg gaatgaggt aaataagtaa 5101  aaaagtatgc ttgttaattt tattcaagaa tgccagtaga aaattcataa cgtgtatctt 5161  taagaaaaat gagcatacat cttaaatctt ttcaattaag tataaggggt tgttcgttgt 5221  tgtcatttgt tatagtgcta ctccactttta gacaccatag ctaaaataaa atatggtggg 5281  ttttgtgtgt gtgtgtgtgt gtgtgtgtgt gtgtgtgtgt gtgttatttta tacaaaactt 5341  aaaatacttg ctgttttgat taaaagaaa atagtttctt acttta
```

Human JAK2 mRNA Variant 3
(SEQ ID NO: 11)

```
  1  attcggggag actgcaggcc aaccgggagg ctgagttcga agctagcagg gcggcgaagc 61  cagtgtcgcc cgcggcgttg agaagacggc aaatgttctg aaaaagactc tgcatgggaa 121  tggcctgcct tacgatgaca gaaatggagg gaacatccac ctcttctata tatcagaatg 181  gtgatatttc tggaaatgcc aattctatga agcaaataga tccagttctt caggtgtatc
```

-continued

```
 241  tttaccattc ccttgggaaa tctgaggcag attatctgac ctttccatct ggggagtatg
 301  ttgcagaaga aatctgtatt gctgcttcta aagcttgtgg tatcacacct gtgtatcata
 361  atatgtttgc tttaatgagt gaaacagaaa ggatctggta tccacccaac catgtcttcc
 421  atatagatga gtcaaccagg cataatgtac tctacagaat aagattttac tttcctcgtt
 481  ggtattgcag tggcagcaac agagcctatc ggcatggaat atctcgaggt gctgaagctc
 541  ctcttcttga tgactttgtc atgtcttacc tctttgctca gtggcggcat gattttgtgc
 601  acggatggat aaaagtacct gtgactcatg aaacacagga agaatgtctt gggatggcag
 661  tgttagatat gatgagaata gccaaagaaa cgatcaaac cccactggcc atctataact
 721  ctatcagcta caagacattc ttaccaaaat gtattcgagc aaagatccaa gactatcata
 781  ttttgacaag gaagcgaata aggtacagat tcgcagatt tattcagcaa ttcagccaat
 841  gcaaagccac tgccagaaac ttgaaactta gtatcttat aaatctggaa actctgcagt
 901  ctgccttcta cacagagaaa tttgaagtaa aagaacctgg aagtggtcct tcaggtgagg
 961  agatttttgc aaccattata ataactggaa acggtggaat tcagtggtca agagggaaac
1021  ataaagaaag tgagacactg acagaacagg atttacagtt atattgcgat tttcctaata
1081  ttattgatgt cagtattaag caagcaaacc aagagggttc aaatgaaagc cgagttgtaa
1141  ctatccataa gcaagatggt aaaaatctgg aaattgaact tagctcatta agggaagctt
1201  tgtctttcgt gtcattaatt gatggatatt atagattaac tgcagatgca catcattacc
1261  tctgtaaaga agtagcacct ccagccgtgc ttgaaaatat acaaagcaac tgtcatggcc
1321  caatttcgat ggattttgcc attagtaaac tgaagaaagc aggtaatcag actggactgt
1381  atgtacttcg atgcagtcct aaggacttta ataaatattt tttgactttt gctgtcgagc
1441  gagaaaatgt cattgaatat aaacactgtt tgattacaaa aaatgagaat aagagtaca
1501  acctcagtgg gacaaagaag aacttcagca gtcttaaaga tcttttgaat tgttaccaga
1561  tggaaactgt tcgctcagac aatataaattt tccagtttac taaatgctgt cccccaaagc
1621  caaaagataa atcaaacctt ctagtcttca gaacgaatgg tgtttctgat gtaccaacct
1681  caccaacatt acagaggcct actcatatga accaaatggt gtttcacaaa atcagaaatg
1741  aagatttgat atttaatgaa agccttggcc aaggcacttt tacaaagatt tttaaaggcg
1801  tacgaagaga gtaggagac tacggtcaac tgcatgaaac agaagttctt taaaagttc
1861  tggataaagc acacagaaac tattcagagt ctttctttga agcagcaagt atgatgagca
1921  agctttctca caagcatttg gttttaaatt atggagtatg tgtctgtgga gacgagaata
1981  ttctggttca ggagtttgta aaatttggat cactagatac atatctgaaa agaataaaa
2041  attgtataaa tatattatgg aaacttgaag ttgctaaaca gttggcatgg ccatgcatt
2101  ttctagaaga aaacacccctt attcatggga atgtatgtgc caaaaatatt ctgcttatca
2161  gagaagaaga caggaagaca ggaaatcctc ctttcatcaa acttagtgat cctggcatta
2221  gtattacagt tttgccaaag gacattcttc aggagagaat accatgggta ccacctgaat
2281  gcattgaaaa tcctaaaaat ttaaatttgg caacagacaa atggagtttt ggtaccactt
2341  tgtgggaaat ctgcagtgga ggagataaac ctctaagtgc tctggattct caaagaaagc
2401  tacaatttta tgaagatagg catcagcttc ctgcaccaaa gtgggcagaa ttagcaaacc
2461  ttataaataa ttgtatggat tatgaaccag atttcaggcc ttcttttcaga gccatcatac
2521  gagatcttaa cagtttgttt actccagatt atgaactatt aacagaaaat gacatgttac
2581  caaatatgag gataggtgcc ctggggtttt ctggtgcctt tgaagaccgg gatcctacac
2641  agtttgaaga gagacatttg aaatttctac agcaacttgg caagggtaat tttgggagtg
```

-continued

```
2701  tggagatgtg ccggtatgac cctctacagg acaacactgg ggaggtggtc gctgtaaaaa 2761  agcttcagca tagtactgaa gagcacctaa gagactttga aagggaaatt gaaatcctga 2821  aatccctaca gcatgacaac attgtaaagt acaagggagt gtgctacagt gctggtcggc 2881  gtaatctaaa attaattatg gaatatttac catatggaag tttacgagac tatcttcaaa 2941  aacataaaga acggatagat cacataaaac ttctgcagta cacatctcag atatgcaagg 3001  gtatggagta tcttggtaca aaaaggtata tccacaggga tctggcaacg agaaatatat 3061  tggtggagaa cgagaacaga gttaaaattg gagattttgg gttaaccaaa gtcttgccac 3121  aagacaaaga atactataaa gtaaaagaac ctggtgaaag tcccatattc tggtatgctc 3181  cagaatcact gacagagagc aagttttctg tggcctcaga tgtttggagc tttggagtgg 3241  ttctgtatga acttttcaca tacattgaga agagtaaaag tccaccagcg gaatttatgc 3301  gtatgattgg caatgacaaa caaggacaga tgatcgtgtt ccatttgata gaacttttga 3361  agaataatgg aagattacca agaccagatg gatgcccaga tgagatctat atgatcatga 3421  cagaatgctg gaacaataat gtaaatcaac gcccctcctt tagggatcta gctcttcgag 3481  tggatcaaat aagggataac atggctggat gaaagaaatg accttcattc tgagaccaaa 3541  gtagatttac agaacaaagt tttatatttc acattgctgt ggactattat tacatatatc 3601  attattatat aaatcatgat gctagccagc aaagatgtga aaatatctgc tcaaaacttt 3661  caaagtttag taagtttttc ttcatgaggc caccagtaaa agacattaat gagaattcct 3721  tagcaaggat tttgtaagaa gtttcttaaa cattgtcagt taacatcact cttgtctggc 3781  aaaagaaaaa aaatagactt tttcaactca gcttttttgag acctgaaaaa attattatgt 3841  aaattttgca atgttaaaga tgcacagaat atgtatgtat agatttttcc acagtggatg 3901  tataatacct tggcatcttg tgtgatgttt tacacacatg agggctggtg ttcattaata 3961  ctgttttcta atttttccat agttaatcta taattaatta cttcactata caaacaaatt 4021  aagatgttca gataattgaa taagtacctt tgtgtccttg ttcatttata tcgctggcca 4081  gcattataag caggtgtata cttttagctt gtagttccat gtactgtaaa tattttttcac 4141  ataaagggaa caaatgtcta gttttatttg tataggaaat ttccctgacc ctaaataata 4201  cattttgaaa tgaaacaagc ttacaaagat ataatctatt ttattatggt ttcccttgta 4261  tctatttgtg gtgaatgtgt tttttaaatg gaactatctc caaatttttc taagactact 4321  atgaacagtt ttcttttaaa attttgagat taagaatgcc aggaatattg tcatcctttg 4381  agctgctgac tgccaataac attcttcgat ctctgggatt tatgctcatg aactaaattt 4441  aagcttaagc cataaaatag attagattgt ttttttaaaaa tggatagctc attaagaagt 4501  gcagcaggtt aagaatttt tcctaaagac tgtatatttg aggggttttca gaattttgca 4561  ttgcagtcat agaagagatt tatttccttt ttagagggga aatgaggtaa ataagtaaaa 4621  aagtatgctt gttaattta ttcaagaatg ccagtagaaa attcataacg tgtatcttta 4681  agaaaaatga gcatacatct taaatctttt caattaagta taagggggttg ttcgttgttg 4741  tcatttgtta tagtgctact ccactttaga caccatagct aaaataaaat atggtgggtt 4801  ttgtgtgtgt gtgtgtgtgt gtgtgtgtgt gtgtgtgtgt gttatttata caaaacttaa 4861  aatacttgct gttttgatta aaaagaaaat agtttcttac ttta
```

Human JAK2 mRNA Variant 4

(SEQ ID NO: 12)

```
   1  gggagtggtg tggggctgca ggaaggagag aggaagagga gcagaagggg gcagcagcgg 61  acgccgctaa cggcctccct cggcgctgac aggctgggcc ggcgcccggc tcgcttgggt 121  gttcgcgtcg ccacttcggc ttctcggccg gtcgggcccc tcggcccggg cttgcggcgc
```

-continued

```
 181  gcgtcggggc tgagggctgc tgcggcgcag ggagaggcct ggtcctcgct gccgagggat
 241  gtgagtggga gctgagccca cactggaggg cccccgaggg cccagcctgg aggtcgttca
 301  gagccgtgcc cgtcccgggg cttcgcagac cttgacccgc cgggtaggag ccgcccctgc
 361  gggctcgagg gcgcgctctg gtcgcccgat ctgtgtagcc ggcaaatgtt ctgaaaaaga
 421  ctctgcatgg gaatggcctg ccttacgatg acagaaatgg agggaacatc cacctcttct
 481  atatatcaga atggtgatat ttctggaaat gccaattcta tgaagcaaat agatccagtt
 541  cttcaggtgt atctttacca ttcccttggg aaatctgagg cagattatct gacctttcca
 601  tctggggagt atgttgcaga agaaatctgt attgctgctt ctaaagcttg tggtatcaca
 661  cctgtgtatc ataatatgtt tgctttaatg agtgaaacag aaaggatctg gtatccaccc
 721  aaccatgtct tccatataga tgagtcaacc aggcataatg tactctacag aataagattt
 781  tactttcctc gttggtattg cagtggcagc aacagagcct atcggcatgg aatatctcga
 841  ggtgctgaag ctcctcttct tgatgacttt gtcatgtctt acctctttgc tcagtggcgg
 901  catgattttg tgcacggatg gataaaagta cctgtgactc atgaaacaca ggaagaatgt
 961  cttgggatgg cagtgttaga tatgatgaga atagccaaag aaaacgatca accccactg
1021  gccatctata actctatcag ctacaagaca ttcttaccaa atgtattcg agcaaagatc
1081  caagactatc atattttgac aaggaagcga ataaggtaca gatttcgcag atttattcag
1141  caattcagcc aatgcaaagc cactgccaga aacttgaaac ttaagtatct tataaatctg
1201  gaaactctgc agtctgcctt ctacacagag aaatttgaag taaagaacc tggaagtggt
1261  ccttcaggtg aggagatttt tgcaaccatt ataataactg aaacggtgg aattcagtgg
1321  tcaagaggga acataaaga aagtgagaca ctgacagaac aggatttaca gttatattgc
1381  gattttccta atattattga tgtcagtatt aagcaagcaa accaagaggg ttcaaatgaa
1441  agccgagttg taactatcca taagcaagat ggtaaaaatc tggaaattga acttagctca
1501  ttaagggaag ctttgtcttt cgtgtcatta attgatggat attatagatt aactgcagat
1561  gcacatcatt acctctgtaa agaagtagca cctccagccg tgcttgaaaa tatacaaagc
1621  aactgtcatg gcccaatttc gatggatttt gccattagta aactgaagaa agcaggtaat
1681  cagactggac tgtatgtact tcgatgcagt cctaaggact ttaataaata tttttttgact
1741  tttgctgtcg agcgagaaaa tgtcattgaa tataaacact gtttgattac aaaaaatgag
1801  aatgaagagt acaacctcag tgggacaaag aagaacttca gcagtcttaa agatctttg
1861  aattgttacc agatggaaac tgttcgctca gacaatataa ttttccagtt tactaaatgc
1921  tgtcccccaa agccaaaaga taaatcaaac cttctagtct tcagaacgaa tggtgtttct
1981  gatgtaccaa cctcaccaac attacagagg cctactcata tgaaccaaat ggtgtttcac
2041  aaaatcagaa atgaagattt gatatttaat gaaagccttg ccaaggcac ttttacaaag
2101  atttttaaag gcgtacgaag agaagtagga gactacggtc aactgcatga acagaagtt
2161  cattttaaag ttctggataa agcacacaga aactattcag agtctttctt tgaagcagca
2221  agtatgatga gcaagctttc tcacaagcat ttggttttaa attatggagt atgtgtctgt
2281  ggagacgaga atattctggt tcaggagttt gtaaaatttg gatcactaga tacatatctg
2341  aaaaagaata aaaattgtat aaatatatta tggaaacttg aagttgctaa acagttggca
2401  tgggccatgc attttctaga agaaacacc ttattcatg gaatgtatg tgccaaaaat
2461  attctgctta tcagagaaga agacaggaag acaggaaatc ctcctttcat caaacttagt
2521  gatcctggca ttagtattac agttttgcca aaggacattc ttcaggagag aataccatgg
2581  gtaccacctg aatgcattga aaatcctaaa aatttaaatt tggcaacaga caaatggagt
```

-continued

```
2641   tttggtacca ctttgtggga aatctgcagt ggaggagata aacctctaag tgctctggat
2701   tctcaaagaa agctacaatt ttatgaagat aggcatcagc ttcctgcacc aaagtgggca
2761   gaattagcaa accttataaa taattgtatg gattatgaac cagatttcag gccttctttc
2821   agagccatca tacgagatct taacagtttg tttactccag attatgaact attaacagaa
2881   aatgacatgt taccaaatat gaggataggt gccctggggt tttctggtgc ctttgaagac
2941   cggatccta cacagtttga agagagacat ttgaaatttc tacagcaact tggcaagggt
3001   aattttggga gtgtggagat gtgccggtat gaccctctac aggacaacac tggggaggtg
3061   gtcgctgtaa aaagcttca gcatagtact gaagagcacc taagagactt gaaagggaa
3121   attgaaatcc tgaaatccct acagcatgac aacattgtaa agtacaaggg agtgtgctac
3181   agtgctggtc ggcgtaatct aaaattaatt atggaatatt taccatatg aagtttacga
3241   gactatcttc aaaaacataa agaacggata gatcacataa aacttctgca gtacacatct
3301   cagatatgca agggtatgga gtatcttggt acaaaaaggt atatccacag ggatctggca
3361   acgagaaata tattggtgga gaacgagaac agagttaaaa ttggagattt tgggttaacc
3421   aaagtcttgc cacaagacaa agaatactat aaagtaaaag aacctggtga agtcccata
3481   ttctggtatg ctccagaatc actgacagag agcaagtttt ctgtggcctc agatgtttgg
3541   agctttggag tggttctgta tgaactttttc acatacattg agaagagtaa aagtccacca
3601   gcggaattta tgcgtatgat tggcaatgca aaacaaggac agatgatcgt gttccatttg
3661   atagaacttt tgaagaataa tggaagatta ccaagaccag atggatgccc agatgagatc
3721   tatatgatca tgacagaatg ctggaacaat aatgtaaatc aacgcccctc ctttagggat
3781   ctagctcttc gagtggatca aataagggat aacatggctg gatgaaagaa atgaccttca
3841   ttctgagacc aaagtagatt tacagaacaa agttttatat ttcacattgc tgtggactat
3901   tattacatat atcattatta tataaatcat gatgctagcc agcaaagatg tgaaaatatc
3961   tgctcaaaac tttcaaagtt tagtaagttt ttcttcatga ggccaccagt aaaagacatt
4021   aatgagaatt ccttagcaag gatttttgtaa gaagtttctt aaacattgtc agttaacatc
4081   actcttgtct ggcaaaagaa aaaaaataga cttttttcaac tcagcttttt gagacctgaa
4141   aaaattatta tgtaaatttt gcaatgttaa agatgcacag aatatgtatg tatagttttt
4201   accacagtgg atgtataata ccttggcatc ttgtgtgatg ttttacacac atgagggctg
4261   gtgttcatta atactgttttt ctaattttttc catagttaat ctataattaa ttacttcact
4321   atacaaacaa attaagatgt tcagataatt gaataagtac ctttgtgtcc ttgttcattt
4381   atatcgctgg ccagcattat aagcaggtgt atacttttag cttgtagttc catgtactgt
4441   aaatatttttt cacataaagg gaacaaatgt ctagtttttat ttgtatagga aatttccctg
4501   accctaaata atacattttg aaatgaaaca agcttacaaa gatataatct attttattat
4561   ggtttccctt gtatctattt gtggtgaatg tgttttttaa atggaactat ctccaaattt
4621   ttctaagact actatgaaca gttttctttt aaaattttga gattaagaat gccaggaata
4681   ttgtcatcct ttgagctgct gactgccaat aacattcttc gatctctggg atttatgctc
4741   atgaactaaa tttaagctta agccataaaa tagattagat tgttttttaa aaatggatag
4801   ctcattaaga agtgcagcag gttaagaatt ttttcctaaa gactgtatat ttgaggggtt
4861   tcagaatttt gcattgcagt catagaagag atttatttcc tttttagagg ggaaatgagg
4921   taaataagta aaaagtatg cttgttaatt ttattcaaga atgccagtag aaaattcata
4981   acgtgtatct ttaagaaaaa tgagcataca tcttaaatct tttcaattaa gtataagggg
5041   ttgttcgttg ttgtcatttg ttatagtgct actccacttt agacaccata gctaaaataa
```

```
5101  aatatggtgg gttttgtgtg tgtgtgtgtg tgtgtgtgtg tgtgtgtgtg tgtgttattt
5161  atacaaaact taaaatactt gctgttttga ttaaaaagaa aatagtttct tacttta
```

Human JAK3 mRNA (SEQ ID NO: 13)

```
   1  cacacaggaa ggagccgagt gggactttcc tctcgctgcc tcccggctct gcccgccctt
  61  cgaaagtcca gggtccctgc ccgctaggca agttgcactc atggcacctc caagtgaaga
 121  gacgcccctg atccctcagc gttcatgcag cctcttgtcc acggaggctg gtgccctgca
 181  tgtgctgctg cccgctcggg gccccgggcc cccccagcgc ctatctttct cctttgggga
 241  ccacttggct gaggacctgt gcgtgcaggc tgccaaggcc agcggcatcc tgcctgtgta
 301  ccactccctc tttgctctgg ccacggagga cctgtcctgc tggttccccc cgagccacat
 361  cttctccgtg gaggatgcca gcacccaagt cctgctgtac aggattcgct tttacttccc
 421  caattggttt gggctggaga agtgccaccg cttcgggcta cgcaaggatt tggccagtgc
 481  tatccttgac ctgccagtcc tggagcacct ctttgcccag caccgcagtg acctggtgag
 541  tgggcgcctc cccgtgggcc tcagtctcaa ggagcagggt gagtgtctca gcctggccgt
 601  gttggacctg gcccggatgg cgcgagagca gcccagcgg ccgggagagc tgctgaagac
 661  tgtcagctac aaggcctgcc tacccccaag cctgcgcgac ctgatccagg gcctgagctt
 721  cgtgacgcgg aggcgtattc ggaggacggt gcgcagagcc tgcgccgcg tggccgcctg
 781  ccaggcagac cggcactcgc tcatggccaa gtacatcatg gacctggagc ggctggatcc
 841  agccggggcc gccgagacct tccacgtggg cctccctggg gccttggtg ccacgacgg
 901  gctggggctg ctccgcgtgg ctggtgacgg cggcatcgcc tggacccagg agaacagga
 961  ggtcctccag cccttctgcg actttccaga aatcgtagac attagcatca agcaggcccc
1021  gcgcgttggc ccggccgag agcaccgcct ggtcactgtt accaggacag acaaccagat
1081  tttagaggcc gagttcccag ggctgccga ggctctgtcg ttcgtggcgc tcgtggacgg
1141  ctacttccgg ctgaccacgg actcccagca cttcttctgc aaggaggtgg caccgccgag
1201  gctgctggag gaagtggccg agcagtgcca cggccccatc actctggact tgccatcaa
1261  caagctcaag actgggggct cacgtcctgg ctcctatgtt ctccgccgca gccccagga
1321  cttttgacagc ttcctcctca ctgtctgtgt ccagaacccc cttggtcctg attataaggg
1381  ctgcctcatc cggcgcagcc ccacaggaac cttccttctg gttggcctca gccgaccca
1441  cagcagtctt cgagagctcc tggcaacctg ctgggatggg gggctgcacg tagatggggt
1501  ggcagtgacc ctcacttcct gctgtatccc cagacccaaa gaaaagtcca acctgatcgt
1561  ggtccagaga ggtcacagcc cacccacatc atccttggtt cagccccaat cccaatacca
1621  gctgagtcag atgacatttc acaagatccc tgctgacagc ctggagtggc atgagaacct
1681  gggccatggg tccttcacca agatttaccg gggctgtcgc catgaggtgg tggatgggga
1741  ggcccgaaag acagaggtgc tgctgaaggt catggatgcc aagcacaaga actgcatgga
1801  gtcattcctg gaagcagcga gcttgatgag ccaagtgtcg taccggcatc tcgtgctgct
1861  ccacgcgtg tgcatggctg gagacagcac catggtgcag gaatttgtac acctggggc
1921  catagacatg tatctgcgaa aacgtggcca cctggtgcca gccagctgga agctgcaggt
1981  ggtcaaacag ctggcctacg ccctcaacta tctggaggac aaaggcctgc cccatggcaa
2041  tgtctctgcc cggaaggtgc tcctggctcg ggaggggct gatgggagcc cgcccttcat
2101  caagctgagt gaccctgggg tcagccccgc tgtgttaagc ctggagatgc tcaccgacag
2161  gatcccctgg gtgggccccg agtgtctccg ggaggcgcag acacttagct tggaagctga
2221  caagtgggc ttcggcgcca cggtctggga agtgtttagt ggcgtcacca tgcccatcag
```

-continued

```
2281  tgccctggat cctgctaaga aactccaatt ttatgaggac cggcagcagc tgccggcccc
2341  caagtggaca gagctggccc tgctgattca acagtgcatg gcctatgagc cggtccagag
2401  gccctccttc cgagccgtca ttcgtgacct caatagcctc atctcttcag actatgagct
2461  cctctcagac cccacacctg gtgccctggc acctcgtgat gggctgtgga atggtgccca
2521  gctctatgcc tgccaagacc ccacgatctt cgaggagaga cacctcaagt acatctcaca
2581  gctgggcaag gcaactttg gcagcgtgga gctgtgccgc tatgacccgc taggcgacaa
2641  tacaggtgcc ctggtggccg tgaaacagct gcagcacagc gggccagacc agcagaggga
2701  ctttcagcgg gagattcaga tcctcaaagc actgcacagt gatttcattg tcaagtatcg
2761  tggtgtcagc tatggcccgg gccgccagag cctgcggctg gtcatggagt acctgcccag
2821  cggctgcttg cgcgacttcc tgcagcggca ccgcgcgcgc ctcgatgcca gccgcctcct
2881  tctctattcc tcgcagatct gcaagggcat ggagtacctg ggctcccgcc gctgcgtgca
2941  ccgcgacctg gccgcccgaa acatcctcgt ggagagcgag gcacacgtca agatcgctga
3001  cttcggccta gctaagctgc tgccgcttga caaagactac tacgtggtcc gcgagccagg
3061  ccagagcccc attttctggt atgcccccga atccctctcg acaacatct tctctcgcca
3121  gtcagacgtc tggagcttcg gggtcgtcct gtacgagctc ttcacctact gcgacaaaag
3181  ctgcagcccc tcggccgagt tcctgcggat gatgggatgt gagcgggatg tccccgccct
3241  ctgccgcctc ttggaactgc tggaggaggg ccagaggctg ccggcgcctc ctgcctgccc
3301  tgctgaggtt cacgagctca tgaagctgtg ctgggcccct agcccacagg accggccatc
3361  attcagcgcc ctgggccccc agctggacat gctgtggagc ggaagccggg ggtgtgagac
3421  tcatgccttc actgctcacc cagagggcaa acaccactcc ctgtccttt catagctcct
3481  gcccgcagac ctctggatta ggtctctgtt gactggctgt gtgacttag gccggagct
3541  gccctctct gggcctcaga ggccttatga gggtcctcta cttcaggaac acccccatga
3601  cattgcattt gggggggctc ccgtggcctg tagaatagcc tgtgccttt gcaatttgtt
3661  aaggttcaag acagatgggc atatgtgtca gtgggctct ctgagtcctg gcccaaagaa
3721  gcaaggaacc aaattaaga ctctcgcatc ttcccaaccc cttaagccct ggcccctga
3781  gtttccttt ctgtctctct cttttatt tttttattt tatttttatt tttgagacag
3841  agcctcgctc tgttacccag ggtggagtgc agtggtgcga tctcggctca gtgcaacctc
3901  tgcttcccag gttcaagcga ttctcctgcc tcagcctccc gagtagctgg gattacaggt
3961  gtgcaccacc acacccggct aattttttt atttttaata gagatgaggt ttcaccatga
4021  tggccaggct gatctcgaac tcctaaccct aagtgatcct cccacctcag cctcccaaag
4081  tgttggaata ataggcatga gccactgcac ccaggctttt ttttttaa atttattat
4141  attatttta agagacagga tcttgctacg ttgcccaggc tggtcttgaa ctcctgggct
4201  acagtgatcc tcctgcctta tcctcctaaa tagctgggac tacagcacct agttttgagt
4261  ttcctgtctt atttccaatg gggacattca tgtagctttt tttttttt tttttttgag
4321  acggagtctc gctctgtcgc ccaggctgga gtacagtggc gcaatctagg ctcactgcaa
4381  gctccgcctc ctgggttcac accattctct cgcctcagcc tcccaagtag ctgggactac
4441  aggcgcccgc caccacaccc ggctaatttt ttgtatttt agtagagacg gggtttcacc
4501  ttgttagcca ggatggtttc catctcctga cctcgtgatc tgcccgtctc ggcctcccaa
4561  agtgctggga ttacaggcat gagccactgc gcccggccct catgtagctt taaatgtatg
4621  atctgacttc tgctccccga tctctgtttc tctggaggaa gccaaggaca agagcagttg
4681  ctgtggctgg gactctgcct tttaggggag cccgtgtatc tctttgggat cctgaaaggg
```

-continued

```
4741  ggcaggaaag gctggggtcc cagtccaccc taatggtatc tgagtgtcct agggcttcag
4801  tttccccacc tgtccaatgg gacccttct gtcctcaccc tacaaggggc acaaagggat
4861  gacaccaaac ctggcaggaa cttttcacgc aatcaaggga aggaaaggca ttcctggcag
4921  agggaacagc atgccaagcg tgagaaggct cagagtaagg aggttaagag cccaagtatt
4981  ggagcctaca gttttgcccc ttccatgcag tgtgacagtg ggcaagttcc tttccctctc
5041  tgggtctcag ttctgtcccc tgcaaaatgg tcagagctta ccccttggct gtgcagggtc
5101  aactttctga ctggtgagag ggattctcat gcaggttaag cttctgctgc tcctcctcac
5161  ctgcaaagct tttctgccac ttttgcctcc ttggaaaact cttatccatc tctcaaaact
5221  ccagctacca catccttgca gccttccctc atataccccc actactactg tagccctgtc
5281  cttccctcca gccccactct ggccctgggg ctggggaagt gtctgtgtcc agctgtctcc
5341  cctgacctca gggttccttg ggggctgggc tgaggcctca gtacagaggg ggctctggaa
5401  atgtttgttg actgaataaa ggaattcagt ggaaaaaaaa aaaaaaaaa
```

Human JAK3 mRNA
(SEQ ID NO: 14)
```
   1  ccctctgacc aggactgagg ggcttttct ctctgtgccc caggcaagtt gcactcatta
  61  tggaattccg gcggcccgct aggcaagttg cactcatggc acctccaagt gaagagacgc
 121  ccctgatccc tcagcgttca tgcagcctct gtccacggag ggctggtgcc ctgcatgtgc
 181  tgctgcccgc tcgggccccg ggcccccccc agcgcctatc tttctccttt ggggaccact
 241  tggctgagga cctgtgcgtg caggctgcca aggccagcgg catcctgcct gtgtaccact
 301  ccctctttgc tctggccacg gaggacctgt cctgctggtt cccccccgagc acatcttct
 361  ccgtggagga tgccagcacc caagtcctgc tgtacaggat tcgcttttac ttccccaatt
 421  ggtttgggct ggagaagtgc accgcttcg ggctacgcaa ggatttggcc agtgctatcc
 481  ttgacctgcc agtcctggag cacctctttg cccagcaccg cagtgacctg gtgagtgggc
 541  gcctccccgt gggcctcagt ctcaaggagc agggtgagtg tctcagcctg ccgtgttgg
 601  acctggcccg gatggcgcga gagcaggccc agcggccggg agagctgctg aagactgtca
 661  gctacaaggc ctgcctaccc ccaagcctgc gcgacctgat ccagggcctg agcttcgtga
 721  cgcggagggc tattcggagg acggtgcgca gagccctgcc gcgcgtggcc gcctgccagg
 781  cagaccggca ctcgctcatg gccaagtaca tcatggacct ggagcggctg gatccagccg
 841  gggccgccga gaccttccac gtgggcctcc ctgggccct tggtggccac gacgggctgg
 901  ggctgctccg cgtggctggt gacggcggca tcgcctggac ccagggagaa caggaggtcc
 961  tccagcccct ctgcgacttt ccagaaatcg tagacattag catcaagcag gccccgcgcg
1021  ttggccccgc cggagagcac cgcctggtca ctgttaccag acagacaac cagattttag
1081  aggccgagtt cccagggctg cccgaggctc tgtcgttcgt ggcgctcgtg gacggctact
1141  tccggctgac cacggactcc cagcacttct ctgcaagga ggtggcaccc ccgaggctgc
1201  tggaggaagt ggccgagcag tgccacggcc ccatcactct ggactttgcc atcaacaagc
1261  tcaagactgg gggctcacgt cctggctcct atgttctccg ccgcagcccc caggactttg
1321  acagcttcct cctcactgtc tgtgtccaga cccccttgg tcctgattat aagggctgcc
1381  tcatccggcg cagccccaca ggaaccttcc ttctggttgg cctcagccga ccccacagca
1441  gtcttcgaga gctcctgca acctgctggg atgggggct gcacgtagat ggggtggcag
1501  tgaccctcac ttcctgctgt atccccagac ccaaagaaaa gtccaacctg atcgtggtcc
1561  agagaggtca cagcccaccc acatcatcct tggttcagcc ccaatcccaa taccagctga
1621  gtcagatgac atttcacaag atccctgctg acagcctgga gtggcatgag aacctgggcc
```

-continued

```
1681  atgggtcctt caccaagatt taccggggct gtcgccatga ggtggtggat ggggaggccc
1741  gaaagacaga ggtgctgctg aaggtcatgg atgccaagca caagaactgc atggagtcat
1801  tcctggaagc agcgagcttg atgagccaag tgtcgtaccg gcatctcgtg ctgctccacg
1861  gcgtgtgcat ggctggagac agcaccatgg tgcaggaatt tgtacacctg ggggccatag
1921  acatgtatct gcgaaaacgt ggccacctgg tgccagccag ctggaagctg caggtggtca
1981  aacagctggc ctacgccctc aactatctgg aggacaaagg cctgccccat ggcaatgtct
2041  ctgcccggaa ggtgctcctg gctcgggagg gggctgatgg gagcccgccc ttcatcaagc
2101  tgagtgaccc tggggtcagc cccgctgtgt taagcctgga gatgctcacc gacaggatcc
2161  cctgggtggc ccccgagtgt ctccggagg cgcagacact tagcttggaa gctgacaagt
2221  ggggcttcgg cgccacggtc tgggaagtgt ttagtggcgt caccatgccc atcagtgccc
2281  tggatcctgc taagaaactc caattttatg aggaccggca gcagctgccg gcccccaagt
2341  ggacagagct ggccctgctg attcaacagt gcatggccta tgagccggtc cagaggccct
2401  ccttccgagc cgtcattcgt gacctcaata gcctcatctc ttcagactat gagctcctct
2461  cagaccccac acctggtgcc ctggcacctc gtgatgggct gtggaatggt gcccagctct
2521  atgcctgcca agaccccacg atcttcgagg agacacct caagtacatc tcacagctgg
2581  gcaagggcaa ctttggcagc gtggagctgt gccgctatga cccgctagcc cacaatacag
2641  gtgccctggt ggccgtgaaa cagctgcagc acagcgggcc agaccagcag agggactttc
2701  agcgggagat tcagatcctc aaagcactgc acagtgattt cattgtcaag tatcgtggtg
2761  tcagctatgg cccgggccgg ccagagctgc ggctggtcat ggagtacctg cccagcggct
2821  gcttgcgcga cttcctgcag cggcaccgcg cgcgcctcga tgccagccgc ctccttctct
2881  attcctcgca gatctgcaag ggcatggagt acctgggctc ccgccgctgc gtgcaccgcg
2941  acctggccgc ccgaaacatc ctcgtggaga gcgaggcaca cgtcaagatc gctgacttcg
3001  gcctagctaa gctgctgccg cttgacaaag actactacgt ggtccgcgag ccaggccaga
3061  gccccatttt ctggtatgcc cccgaatccc tctcggacaa catcttctct cgccagtcag
3121  acgtctggag cttcggggtc gtcctgtacg agctcttcac ctactgcgac aaaagctgca
3181  gccctcggc cgagttcctg cggatgatgg gatgtgagcg ggatgtcccc gccctctgcc
3241  gcctcttgga actgctggag gagggccaga ggctgccggc gcctcctgcc tgccctgctg
3301  aggttcacga gctcatgaag ctgtgctggg cccctagccc acaggaccgg ccatcattca
3361  gcgccctggg cccccagctg gacatgctgt ggagcggaag ccgggggtgt gagactcatg
3421  ccttcactgc tcacccagag ggcaaacacc actccctgtc cttttcatag ctcctgcccg
3481  cagacctctg gattaggtct ctgttgactg gctgtgtgac cttaggcccg gagctgcccc
3541  tctctgggcc tcagaggcct tatgagggtc ctctacttca ggaacacccc catgacattg
3601  catttggggg ggctcccgtg gcctgtagaa tagcctgtgg cctttgcaat ttgttaaggt
3661  tcaagacaga tgggcatatg tgtcagtggg gctctctgag tcctggccca aagaagcaag
3721  gaaccaaatt taagactctc gcatcttccc aaccccttaa gccctggccc cctgagtttc
3781  cttttctcgt ctctctcttt ttattttttt tattttttatt tttatttttg agacagagcc
3841  tcgctcgtta cccagggtgg agtgcagtgg tagcgatctc ggctcacagt gcaacctctg
3901  cttcccaggt tcaagcgatt tcctgcctc agcctcccga gtagctggga ttacaggtgt
3961  gcaccaccac acccggctaa ttttttttat ttttaataga gatgaggttt caccatgatg
4021  gccaggctga tctcgaactc ctaacctcaa gtgatcctcc cacc
```

Human TYK2 mRNA (SEQ ID NO: 15)

```
   1  aagcagtagc tacccgcggg agcggggagg ggtccgggtt cgagcttgtg ttccccggga
  61  agggtgagtc tggacgcggg cgcggaagga gcgcggccgg aggtcctcag gaagaagccg
 121  cggggactgg ctgcgcttga caggctgcac ttggatggga gcacctggtg cctcgggact
 181  gctccgatgc ccgggtctgt gctgaatgtg taatatgcgg aactatattg aaacattaca
 241  accatctttt gatggcaaca ccctgaggac ctccctttc cagatgggga aactgaggcc
 301  cagaattgct aagtggcttg cttgagttga cacagggagc tccaggactc accctcagct
 361  gagccacctg ccgggagcat gcctctgcgc cactggggga tggcaggggc cagtaagccc
 421  gttggggatg gagcccagcc catggctgcc atgggaggcc tgaaggtgct tctgcactgg
 481  gctggtccag gcggcgggga gccctgggtc actttcagtg agtcatcgct gacagctgag
 541  gaagtctgca tccacattgc acataaagtt ggtatcactc ctccttgctt caatctcttt
 601  gccctcttcg atgctcaggc ccaagtctgg ttgcccccaa accacatcct agagatcccc
 661  agagatgcaa gcctgatgct atatttccgc ataaggtttt atttccggaa ctggcatggc
 721  atgaatcctc gggaaccggc tgtgtaccgt tgtgggcccc aggaaccga ggcatcctca
 781  gatcagacag cacaggggat gcaactcctg acccagcct catttgagta cctctttgag
 841  cagggcaagc atgagtttgt gaatgacgtg gcatcactgt gggagctgtc gaccgaggag
 901  gagatccacc actttaagaa tgagagcctg gcatggcct ttctgcacct ctgtcacctc
 961  gctctccgcc atggcatccc cctggaggag gtggccaaga gaccagctt caaggactgc
1021  atcccgcgct ccttccgccg gcatatccgg cagcacagcg ccctgacccg gctgcgcctt
1081  cggaacgtct tccgcaggtt cctgcgggac ttccagccgg ccgactctc ccagcagatg
1141  gtcatggtca aatacctagc cacactcgag cggctggcac cccgcttcgg cacagagcgt
1201  gtgccggtgt gccacctgag gctgctggcc caggccgagg gggagccctg ctacatccgg
1261  gacagtgggg tggcccctac agaccctggc cctgagtctg ctgctgggc cccaacccac
1321  gaggtgctgg tgacaggcac tggtggcatc cagtggtggc cagtagagga ggaggtgaac
1381  aaggaggagg gttctagtgg cagcagtggc aggaaccccc aagccagcct gtttgggaag
1441  aaggccaagg ctcacaaggc agtcggccag ccggcagaca ggccgcggga gccactgtgg
1501  gcctacttct gtgacttccg ggacatcacc cacgtggtgc tgaaagagca ctgtgtcagc
1561  atccaccggc aggacaacaa gtgcctggag ctgagcttgc cttccgggc tgcggcgctg
1621  tccttcgtgt cgctggtgga cggctatttc cgcctgacgg ccgactccag ccactacctg
1681  tgccacgagg tggctccccc acggctggtg atgagcatcc gggatgggat ccacggaccc
1741  ctgctggagc catttgtgca ggccaagctg cggcccgagg acggcctgta cctcattcac
1801  tggagcacca gccacccta ccgcctgatc ctcacagtgg cccagcgtag ccaggcacca
1861  gacggcatgc agagcttgcg gctccgaaag ttccccattg agcagcagga cggggccttc
1921  gtgctggagg gctggggccg gtccttcccc agcgttcggg aacttgggc tgccttgcag
1981  ggctgcttgc tgagggccgg ggatgactgc ttctctctgc gtcgctgttg cctgccccaa
2041  ccaggagaaa cctccaatct catcatcatg cggggggctc gggccagccc caggacactc
2101  aacctcagcc agctcagctt ccaccgggtt gaccagaagg agatcaccca gctgtcccac
2161  ttgggccagg gcacaaggac caacgtgtat gagggcgcc tgcgagtgga gggcagcggg
2221  gaccctgagg agggcaagat ggatgacgag gaccccctcg tgcctggcag ggaccgtggg
2281  caggagctac gagtggtgct caaagtgctg gaccctagtc accatgacat cgccctggcc
2341  ttctacgaga cagccagcct catgagccag gtctcccaca cgcacctggc cttcgtgcat
```

```
-continued
2401  ggcgtctgtg tgcgcggccc tgaaaatatc atggtgacag agtacgtgga gcacggaccc 2461  ctggatgtgt ggctgcggag ggagcggggc catgtgccca tggcttggaa gatggtggtg 2521  gcccagcagc tggccagcgc cctcagctac ctggagaaca agaacctggt tcatggtaat 2581  gtgtgtggcc ggaacatcct gctggcccgg ctggggttgg cagagggcac cagccccttc 2641  atcaagctga gtgatcctgg cgtgggcctg ggcgccctct ccagggagga gcgggtggag 2701  aggatccct  ggctggcccc cgaatgccta ccaggtgggg ccaacagcct aagcaccgcc 2761  atggacaagt gggggtttgg cgccaccctc ctggagatct gctttgacgg agaggcccct 2821  ctgcagagcc gcagtccctc cgagaaggag catttctacc agaggcagca ccggctgccc 2881  gagccctcct gcccacagct ggccacactc accagccagt gtctgaccta tgagccaacc 2941  cagaggccat cattccgcac catcctgcgt gacctcaccc ggctgcagcc ccacaatctt 3001  gctgacgtct tgactgtgaa cccggactca ccggcgtcgg accctacggt tttccacaag 3061  cgctatttga aaaagatccg agatctgggc gagggtcact tcggcaaggt cagcttgtac 3121  tgctacgatc cgaccaacga cggcactggc gagatggtgg cggtgaaagc cctcaaggca 3181  gactgcggcc cccagcaccg ctcgggctgg aagcaggaga ttgacattct gcgcacgctc 3241  taccacgagc acatcatcaa gtacaagggc tgctgcgagg accaaggcga gaagtcgctg 3301  cagctggtca tggagtacgt gccctgggc agcctccgag actacctgcc ccggcacagc 3361  atcgggctgg cccagctgct gctcttcgcc cagcagatct gcgagggcat ggcctatctg 3421  cacgcgcagc actacatcca ccgagaccta gccgcgcgca acgtgctgct ggacaacgac 3481  aggctggtca agatcggga ctttggccta gccaaggccg tgcccgaagg ccacgagtac 3541  taccgcgtgc gcgaggatgg ggacagcccc gtgttctggt atgcccaga gtgcctgaag 3601  gagtataagt tctactatgc gtcagatgtc tggtccttcg gggtgaccct gtatgagctg 3661  ctgacgcact gtgactccag ccagagcccc cccacgaaat tccttgagct cataggcatt 3721  gctcagggtc agatgacagt tctgagactc actgagttgc tggaacgagg ggagaggctg 3781  ccacggcccg acaaatgtcc ctgtgaggtc tatcatctca tgaagaactg ctgggagaca 3841  gaggcgtcct ttcgcccaac cttcgagaac ctcataccca ttctgaagac agtccatgag 3901  aagtaccaag gccaggcccc ttcagtgttc agcgtgtgct gaggcacaat ggcagccctg 3961  cctgggagga ctggaccagg cagtggctgc agagggagcc tcctgctccc tgctccagga 4021  tgaaaccaag aggggatgt cagcctcacc cacaccgtgt gccttactcc tgtctagaga 4081  ccccacctct gtgaacttat ttttctttct tggccgtgag cctaaccatg atcttgaggg 4141  acccaacatt tgtagggca ctaatccagc ccttaaatcc cccagcttcc aaacttgagg 4201  cccaccatct ccaccatctg gtaataaact catgttttct ctgctggaaa aaaaaaaaaa 4261  aa
```

Inhibitory Nucleic Acids

An antisense nucleic acid molecule can be complementary to all or part of a non-coding region of the coding strand of a nucleotide sequence encoding a JAK1, JAK2, JAK3, or TYK2 protein. Non-coding regions (5' and 3' untranslated regions) are the 5' and 3' sequences that flank the coding region in a gene and are not translated into amino acids.

Based upon the sequences disclosed herein, one of skill in the art can easily choose and synthesize any of a number of appropriate antisense nucleic acids to target a nucleic acid encoding a JAK1, JAK2, JAK3, or TYK2 protein described herein. Antisense nucleic acids targeting a nucleic acid encoding a JAK1, JAK2, JAK3, or TYK2 protein can be designed using the software available at the Integrated DNA Technologies website.

An antisense nucleic acid can be, for example, about 5, 10, 15, 20, 25, 30, 35, 40, 45, or 50 nucleotides or more in length. An antisense oligonucleotide can be constructed using chemical synthesis and enzymatic ligation reactions using procedures known in the art. For example, an antisense nucleic acid can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides which can be used to generate an antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules described herein can be prepared in vitro and administered to a mammal, e.g., a human. Alternatively, they can be generated in situ such that they hybridize with or bind to cellular mRNA and/or genomic DNA encoding a JAK1, JAK2, JAK3, or TYK2 protein to thereby inhibit expression, e.g., by inhibiting transcription and/or translation. The hybridization can be by conventional nucleotide complementarities to form a stable duplex, or, for example, in the case of an antisense nucleic acid molecule that binds to DNA duplexes, through specific interactions in the major groove of the double helix. The antisense nucleic acid molecules can be delivered to a mammalian cell using a vector (e.g., a lentivirus, a retrovirus, or an adenovirus vector).

An antisense nucleic acid can be an α-anomeric nucleic acid molecule. An α-anomeric nucleic acid molecule forms specific double-stranded hybrids with complementary RNA in which, contrary to the usual, β-units, the strands run parallel to each other (Gaultier et al., *Nucleic Acids Res.* 15:6625-6641, 1987). The antisense nucleic acid can also comprise a 2'-O-methylribonucleotide (Inoue et al., *Nucleic Acids Res.* 15:6131-6148, 1987) or a chimeric RNA-DNA analog (Inoue et al., *FEBS Lett* 215:327-330, 1987).

Another example of an inhibitory nucleic acid is a ribozyme that has specificity for a nucleic acid encoding a JAK1, JAK2, JAK3, or TYK2 protein (e.g., specificity for a JAK1, JAK2, JAK3, or TYK2 mRNA, e.g., specificity for any one of SEQ ID NOs: 1-15). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, *Nature* 334:585-591, 1988)) can be used to catalytically cleave mRNA transcripts to thereby inhibit translation of the protein encoded by the mRNA. A ribozyme having specificity for a JAK1, JAK2, JAK3, or TYK2 mRNA can be designed based upon the nucleotide sequence of any of the JAK1, JAK2, JAK3, or TYK2 mRNA sequences disclosed herein. For example, a derivative of a Tetrahymena L-19 IVS RNA can be constructed in which the nucleotide sequence of the active site is complementary to the nucleotide sequence to be cleaved in a JAK1, JAK2, JAK3, or TYK2 mRNA (see, e.g., U.S. Pat. Nos. 4,987,071 and 5,116,742). Alternatively, a JAK1, JAK2, JAK3, or TYK2 mRNA can be used to select a catalytic RNA having a specific ribonuclease activity from a pool of RNA molecules. See, e.g., Bartel et al., *Science* 261:1411-1418, 1993.

An inhibitory nucleic acid can also be a nucleic acid molecule that forms triple helical structures. For example, expression of a JAK1, JAK2, JAK3, or JAK4 polypeptide can be inhibited by targeting nucleotide sequences complementary to the regulatory region of the gene encoding the JAK1, JAK2, JAK3, or TYK2 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells. See generally Helene, *Anticancer Drug Des.* 6(6):569-84, 1991; Helene, *Ann. N.Y. Acad. Sci.* 660:27-36, 1992; and Maher, *Bioassays* 14(12):807-15, 1992.

In various embodiments, inhibitory nucleic acids can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see, e.g., Hyrup et al., *Bioorganic Medicinal Chem.* 4(1):5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to DNA and RNA under conditions of low ionic strength. The synthesis of PNA oligomers can be performed using standard solid phase peptide synthesis protocols (see, e.g., Perry-O'Keefe et al., *Proc. Natl. Acad. Sci. U.S.A.* 93:14670-675, 1996). PNAs can be used as antisense or antigene agents for sequence-specific modulation of gene expression by, e.g., inducing transcription or translation arrest or inhibiting replication.

PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation.

The synthesis of PNA-DNA chimeras can be performed as described in Finn et al., *Nucleic Acids Res.* 24:3357-63, 1996. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., *Nucleic Acids Res.* 17:5973-88, 1989). PNA monomers are then coupled in a stepwise manner to produce a chimeric molecule with a 5' PNA segment and a 3' DNA segment (Finn et al., *Nucleic Acids Res.* 24:3357-63, 1996). Alternatively, chimeric molecules can be synthesized with a 5' DNA segment and a 3' PNA segment (Peterser et al., *Bioorganic Med. Chem. Lett.* 5:1119-11124, 1975).

In some embodiments, the inhibitory nucleic acids can include other appended groups such as peptides, or agents facilitating transport across the cell membrane (see, Letsinger et al., *Proc. Natl. Acad. Sci. U.S.A.* 86:6553-6556, 1989; Lemaitre et al., *Proc. Natl. Acad. Sci. U.S.A.* 84:648-

652, 1989; and WO 88/09810). In addition, the inhibitory nucleic acids can be modified with hybridization-triggered cleavage agents (see, e.g., Krol et al., *Bio/Techniques* 6:958-976, 1988) or intercalating agents (see, e.g., Zon, *Pharm. Res.*, 5:539-549, 1988). To this end, the oligonucleotide may be conjugated to another molecule, e.g., a peptide, hybridization triggered cross-linking agent, transport agent, hybridization-triggered cleavage agent, etc.

Another means by which expression of a JAK1, JAK2, JAK3, or TYK2 mRNA can be decreased in a mammalian cell is by RNA interference (RNAi). RNAi is a process in which mRNA is degraded in host cells. To inhibit an mRNA, double-stranded RNA (dsRNA) corresponding to a portion of the gene to be silenced (e.g., a gene encoding a JAK1, JAK2, JAK3, or TYK2 polypeptide) is introduced into a mammalian cell. The dsRNA is digested into 21-23 nucleotide-long duplexes called short interfering RNAs (or siRNAs), which bind to a nuclease complex to form what is known as the RNA-induced silencing complex (or RISC). The RISC targets the homologous transcript by base pairing interactions between one of the siRNA strands and the endogenous mRNA. It then cleaves the mRNA about 12 nucleotides from the 3' terminus of the siRNA (see Sharp et al., *Genes Dev.* 15:485-490, 2001, and Hammond et al., *Nature Rev. Gen.* 2:110-119, 2001).

RNA-mediated gene silencing can be induced in a mammalian cell in many ways, e.g., by enforcing endogenous expression of RNA hairpins (see, Paddison et al., *Proc. Natl. Acad. Sci. U.S.A.* 99:1443-1448, 2002) or, as noted above, by transfection of small (21-23 nt) dsRNA (reviewed in Caplen, *Trends Biotech.* 20:49-51, 2002). Methods for modulating gene expression with RNAi are described, e.g., in U.S. Pat. No. 6,506,559 and US 2003/0056235, which are hereby incorporated by reference.

Standard molecular biology techniques can be used to generate siRNAs. Short interfering RNAs can be chemically synthesized, recombinantly produced, e.g., by expressing RNA from a template DNA, such as a plasmid, or obtained from commercial vendors, such as Dharmacon. The RNA used to mediate RNAi can include synthetic or modified nucleotides, such as phosphorothioate nucleotides. Methods of transfecting cells with siRNA or with plasmids engineered to make siRNA are routine in the art.

The siRNA molecules used to decrease expression of a JAK1, JAK2, JAK3, or TYK2 mRNA can vary in a number of ways. For example, they can include a 3' hydroxyl group and strands of 21, 22, or 23 consecutive nucleotides. They can be blunt ended or include an overhanging end at either the 3' end, the 5' end, or both ends. For example, at least one strand of the RNA molecule can have a 3' overhang from about 1 to about 6 nucleotides (e.g., 1-5, 1-3, 2-4, or 3-5 nucleotides (whether pyrimidine or purine nucleotides) in length. Where both strands include an overhang, the length of the overhangs may be the same or different for each strand.

To further enhance the stability of the RNA duplexes, the 3' overhangs can be stabilized against degradation (by, e.g., including purine nucleotides, such as adenosine or guanosine nucleotides or replacing pyrimidine nucleotides by modified analogues (e.g., substitution of uridine 2-nucleotide 3' overhangs by 2'-deoxythymidine is tolerated and does not affect the efficiency of RNAi). Any siRNA can be used in the methods of decreasing a JAK1, JAK2, JAK3, or TYK2 mRNA, provided it has sufficient homology to the target of interest (e.g., a sequence present in any one of SEQ ID NOs: 1-15, e.g., a target sequence encompassing the translation start site or the first exon of the mRNA). There is no upper limit on the length of the siRNA that can be used (e.g., the siRNA can range from about 21 base pairs of the gene to the full length of the gene or more (e.g., about 20 to about 30 base pairs, about 50 to about 60 base pairs, about 60 to about 70 base pairs, about 70 to about 80 base pairs, about 80 to about 90 base pairs, or about 90 to about 100 base pairs).

Non-limiting examples of JAK inhibitors that are short interfering RNAs (siRNAs) are described in Cook et al., *Blood* 123:2826-2837, 2014. Non-limiting examples of JAK inhibitors that are short hairpin RNAs (shRNAs) are described in Koppikar et al., *Nature* 489(7414):155-159, 2012).

In certain embodiments, a therapeutically effective amount of an inhibitory nucleic acid targeting a nucleic acid encoding a JAK1, JAK2, JAK3, or TYK2 protein can be administered to a subject (e.g., a human subject) in need thereof.

In some embodiments, the inhibitory nucleic acid can be about 10 nucleotides to about 40 nucleotides (e.g., about 10 to about 30 nucleotides, about 10 to about 25 nucleotides, about 10 to about 20 nucleotides, about 10 to about 15 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, or 40 nucleotides) in length. One skilled in the art will appreciate that inhibitory nucleic acids may comprise at least one modified nucleic acid at either the 5' or 3'end of DNA or RNA.

As is known in the art, the term "thermal melting point (Tm)" refers to the temperature, under defined ionic strength, pH, and inhibitory nucleic acid concentration, at which 50% of the inhibitory nucleic acids complementary to the target sequence hybridize to the target sequence at equilibrium. In some embodiments, an inhibitory nucleic acid can bind specifically to a target nucleic acid under stingent conditions, e.g., those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions can also be achieved with the addition of destabilizing agents such as formamide.

In some embodiments of any of the inhibitory nucleic acids described herein, the inhibitory nucleic acid binds to a target nucleic acid (e.g., a nucleic acid encoding JAK1, JAK2, JAK3, or TYK2) with a $T_m$ of greater than 20° C., greater than 22° C., greater than 24° C., greater than 26° C., greater than 28° C., greater than 30° C., greater than 32° C., greater than 34° C., greater than 36° C., greater than 38° C., greater than 40° C., greater than 42° C., greater than 44° C., greater than 46° C., greater than 48° C., greater than 50° C., greater than 52° C., greater than 54° C., greater than 56° C., greater than 58° C., greater than 60° C., greater than 62° C., greater than 64° C., greater than 66° C., greater than 68° C., greater than 70° C., greater than 72° C., greater than 74° C., greater than 76° C., greater than 78° C., or greater than 80° C., e.g., as measured in phosphate buffered saline using a UV spectrophotometer.

In some embodiments of any of the inhibitor nucleic acids described herein, the inhibitory nucleic acid binds to a target nucleic acid (e.g., a nucleic acid encoding a JAK1, JAK2, JAK3, or TYK2) with a $T_m$ of about 20° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., about 34° C., about 32° C., about 30° C., about 28° C., about 26° C., about 24° C., or about 22° C. (inclusive); about 22° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., about 34° C., about 32° C., about 30° C., about 28° C., about 26° C., or about 24° C. (inclusive); about 24° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., about 34° C., about 32° C., about 30° C., about 28° C., or about 26° C. (inclusive); about 26° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., about 34° C., about 32° C., about 30° C., or about 28° C. (inclusive); about 28° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., about 34° C., about 32° C., or about 30° C. (inclusive); about 30° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., about 34° C., or about 32° C. (inclusive); about 32° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., or about 34° C. (inclusive); about 34° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., or about 36° C. (inclusive); about 36° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., or about 38° C. (inclusive); about 38° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., or about 42° C. (inclusive); about 40° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., or about 42° C. (inclusive); about 42° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., or about 44° C. (inclusive); about 44° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., or about 46° C. (inclusive); about 46° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., or about 48° C. (inclusive); about 48° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., or about 50° C. (inclusive); about 50° C. to about 80° C., about 78° C., about 76° C., about 74° C., about 72° C., about 70° C., about 68° C., about 66° C., about 64° C., about 62° C., about 60° C., about 58° C., about 56° C., about 54° C., or about 52° C. (inclusive); about 52° C. to about 80° C., about 78° C., about 76° C., about 74° C., about 72° C., about 70° C., about 68° C., about 66° C., about 64° C., about 62° C., about 60° C., about 58° C., about 56° C., or about 54° C. (inclusive); about 54° C. to about 80° C., about 78° C., about 76° C., about 74° C., about 72° C., about 70° C., about 68° C., about 66° C., about 64° C., about 62° C., about 60° C., about 58° C., or about 56° C. (inclusive); about 56° C. to about 80° C., about 78° C., about 76° C., about 74° C., about 72° C., about 70° C., about 68° C., about 66° C., about 64° C., about 62° C., about 60° C., or about 58° C. (inclusive); about 58° C. to about 80° C., about 78° C., about 76° C., about 74° C., about 72° C., about 70° C., about 68° C., about 66° C., about 64° C., about 62° C., or about 60° C. (inclusive); about 60° C. to about 80° C., about 78° C., about 76° C., about 74° C., about 72° C., about 70° C., about 68° C., about 66° C., about 64° C., or about 62° C. (inclusive); about 62° C. to about 80° C., about 78° C., about 76° C., about 74° C., about 72° C., about 70° C., about 68° C., about 66° C., or about 64° C. (inclusive); about 64° C. to about 80° C., about 78° C., about 76° C., about 74° C., about 72° C., about 70° C., about 68° C., or about 66° C. (inclusive); about 66° C. to about 80° C., about 78° C., about 76° C., about 74° C., about 72° C., about 70° C., or about 68° C. (inclusive); about 68° C. to about 80° C., about 78° C., about 76° C., about 74° C., about 72° C., or about 70° C. (inclusive); about 70° C. to about 80° C., about 78° C., about 76° C., about 74° C., or about 72° C. (inclusive); about 72° C. to about 80° C., about 78° C., about 76° C., or about 74° C. (inclusive); about 74° C. to about 80° C., about 78° C., or about 76° C. (inclusive); about 76° C. to about 80° C. or about 78° C. (inclusive); or about 78° C. to about 80° C. (inclusive), In some embodiments, the inhibitory nucleic acid can be formulated in a nanoparticle (e.g., a nanoparticle including one or more synthetic polymers, e.g., Patil et al., *Pharmaceutical Nanotechnol.* 367:195-203, 2009; Yang et al., *ACS Appl. Mater. Interfaces*, doi: 10.1021/acsami.6b16556, 2017; Perepelyuk et al., *Mol. Ther. Nucleic Acids* 6:259-268, 2017). In some embodiments, the nanoparticle can be a mucoadhesive particle (e.g., nanoparticles having a positively-charged exterior surface) (Andersen et al., *Methods Mol. Biol.* 555:77-86, 2009). In some embodiments, the nanoparticle can have a neutrally-charged exterior surface.

In some embodiments, the inhibitory nucleic acid can be formulated, e.g., as a liposome (Buyens et al., *J. Control Release* 158(3): 362-370, 2012; Scarabel et al., *Expert Opin. Drug Deliv.* 17:1-14, 2017), a micelle (e.g., a mixed micelle) (Tangsangasaksri et al., *BioMacromolecules* 17:246-255, 2016; Wu et al., *Nanotechnology*, doi: 10.1088/1361-6528/aa6519, 2017), a microemulsion (WO 11/004395), a nanoemulsion, or a solid lipid nanoparticle (Sahay et al., *Nature Biotechnol.* 31:653-658, 2013; and Lin et al., *Nanomedicine* 9(1):105-120, 2014). Additional exemplary structural features of inhibitory nucleic acids and formulations of inhibitory nucleic acids are described in US 2016/0090598.

In some embodiments, a pharmaceutical composition can include a sterile saline solution and one or more inhibitory nucleic acid (e.g., any of the inhibitory nucleic acids described herein). In some examples, a pharmaceutical composition consists of a sterile saline solution and one or more inhibitory nucleic acid (e.g., any of the inhibitory nucleic acids described herein). In certain embodiments, the sterile saline is a pharmaceutical grade saline. In certain embodiments, a pharmaceutical composition can include one or more inhibitory nucleic acid (e.g., any of the inhibitory nucleic acids described herein) and sterile water. In certain embodiments, a pharmaceutical composition consists of one or more inhibitory nucleic acid (e.g., any of the inhibitory nucleic acids described herein) and sterile water. In certain embodiments, a pharmaceutical composition includes one or more inhibitory nucleic acid (e.g., any of the inhibitory nucleic acids described herein) and phosphate-buffered saline (PBS). In certain embodiments, a pharmaceutical composition consists of one or more inhibitory nucleic acids (e.g., any of the inhibitory nucleic acids described herein) and sterile phosphate-buffered saline (PBS). In some examples, the sterile saline is a pharmaceutical grade PBS.

In certain embodiments, one or more inhibitory nucleic acids (e.g., any of the inhibitory nucleic acids described herein) may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions including one or more inhibitory nucleic acids encompass any pharmaceutically acceptable salts, esters, or salts of such esters. Non-limiting examples of pharmaceutical compositions include pharmaceutically acceptable salts of inhibitory nucleic acids. Suitable pharmaceutically acceptable salts include, but are not limited to, sodium and potassium salts.

Also provided herein are prodrugs that can include additional nucleosides at one or both ends of an inhibitory nucleic acid which are cleaved by endogenous nucleases within the body, to form the active inhibitory nucleic acid.

Lipid moieties can be used to formulate an inhibitory nucleic acid. In certain such methods, the inhibitory nucleic acid is introduced into preformed liposomes or lipoplexes made of mixtures of cationic lipids and neutral lipids. In certain methods, inhibitory nucleic acid complexes with mono- or poly-cationic lipids are formed without the presence of a neutral lipid. In certain embodiments, a lipid moiety is selected to increase distribution of an inhibitory nucleic acid to a particular cell or tissue in a mammal. In some examples, a lipid moiety is selected to increase distribution of an inhibitory nucleic acid to fat tissue in a mammal. In certain embodiments, a lipid moiety is selected to increase distribution of an inhibitory nucleic acid to muscle tissue.

In certain embodiments, pharmaceutical compositions provided herein comprise one or more inhibitory nucleic acid and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In some examples, a pharmaceutical composition provided herein includes liposomes and emulsions. Liposomes and emulsions can be used to formulate hydrophobic compounds. In some examples, certain organic solvents such as dimethylsulfoxide are used.

In some examples, a pharmaceutical composition provided herein includes one or more tissue-specific delivery molecules designed to deliver one or more inhibitory nucleic acids to specific tissues or cell types in a mammal. For example, a pharmaceutical composition can include liposomes coated with a tissue-specific antibody.

In some embodiments, a pharmaceutical composition provided herein can include a co-solvent system. Examples of such co-solvent systems include benzyl alcohol, a non-polar surfactant, a water-miscible organic polymer, and an aqueous phase. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. As can be appreciated, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In some examples, a pharmaceutical composition can be formulated for oral administration. In some examples, pharmaceutical compositions are formulated for buccal administration.

In some examples, a pharmaceutical composition is formulated for administration by injection (e.g., intravenous, subcutaneous, intramuscular, etc.). In some of these embodiments, a pharmaceutical composition includes a carrier and is formulated in aqueous solution, such as water or physiologically compatible buffers such as Hanks's solution, Ringer's solution, or physiological saline buffer. In some examples, other ingredients are included (e.g., ingredients that aid in solubility or serve as preservatives). In some examples, injectable suspensions are prepared using appropriate liquid carriers, suspending agents, and the like. Some pharmaceutical compositions for injection are formulated in unit dosage form, e.g., in ampoules or in multi-dose containers. Some pharmaceutical compositions for injection are suspensions, solutions, or emulsions in oily or aqueous vehicles, and may contain formulatory agents such as suspending, stabilizing, and/or dispersing agents. Solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Small Molecules

In some embodiments, the JAK inhibitor is a small molecule. In some embodiments, the JAK inhibitory agent is a pan-JAK inhibitor (e.g., 3-O-methylthespesilactam (Li et al., *Biochem. Pharmacol.* 86(10):1411-8, 2013)).

In some embodiments, the JAK inhibitor is a JAK1 and JAK2 inhibitor. In some embodiments, the JAK1 and JAK2 inhibitor is ruxolitinib (Jakafi®, Jakavi®, INCB018424) (Harrison et al., *N. Engl. J. Med.* 366:787-798, 2012; Pieri et al., *Am. J. Hematol.* 92(2):187-195, 2017; Mackay-Wiggan et al., *JCI Insight* 1(15):e89790, 2016; Rudolph et al., *Leukemia* 30(10):2119-2123, 2016; Furqan et al., *Biomark Res.* 1(1):5, 2013), baricitinib (INCB028050, LY3009104) (Gras, *Drugs Today (Barc)* 52(10):543-550, 2016; Smolen et al., *Ann. Rheum. Dis.* 76(4):694-700, 2016; Kubo et al., *Expert. Rev. Clin. Immunol.* 12(9):911-919, 2016; Fridman et al., *J. Immunol.* 84(9):5298-5307, 2010), AZD1480 (Guschin et al., *EMBO J.* 14:1421-1429, 1995; Ioannidis et al., *J. Med. Chem.* 54: 262-276, 2011; Moisan et al., *Nat. Cell Biol.* 17(1):57-67, 2015; Qin et al., *J. Neurosci.* 36(18):5144059, 2016; Jiang et al., *Biochem. Biophys. Res. Commun.* 458(4): 908-912, 2015; Verstovsek et al., *Leuk. Res.* 39(2):157-163, 2015; Plimack et al., *Oncologist* 18(7): 819-820, 2013; Yan et al., *Oncotarget* 4(3):433-445, 2013), filgotinib (GLPG0634, G146034) (Vermeire et al., *Lancet* 389 (10066):266-275, 2017; Menet et al., *J. Med. Chem.* 57(22): 9323-9342, 2014; Van Rompaey et al., *J. Immunol.* 191(7): 3568-3577, 2013; Namour et al., *Clin. Pharmacokinet.* 54(8):859-874, 2015), momelotinib (GS-0387, CYT387) (Pardanani et al., *Leukemia* 23: 1441-1445, 2009; Gupta et al., *Haematologica* 102(1):94-102, 2017; Hu et al., *Mol. Pharm.* 13(2):689-697, 2016; Abubaker et al., *BMC Cancer* 14: 317, 2014; Durmus et al., *Pharmacol. Res.* 76:9-16, 2013; Pardanani et al., *Leukemia* 27(6): 1322-1327, 2013; Monaghan et al., *Leukemia* 25(12):1891-1899, 2011; Tyner et al., *Blood* 115(25):5232-5240, 2010).

In some embodiments, the JAK inhibitory agent is a JAK1 inhibitor (e.g., GSK2586184 (Kahl et al., *Lupus* 25(13): 1420-1430, 2016; Ludbrook et al., *Br. J. Dermatol.* 174(5): 985-995, 2016; van Vollenhoven et al., *Lupus* 24(6): 648-649, 2015), oclacitinib (PF03394197, Apoquel®) (Gonzales et al., *J. Vet. Pharmacol. Ther.* 37(4):317-324, 2014; Collard et al., *J. Vet. Pharmacol. Ther.* 37(3):279-285, 2014; Cosgrove et al., *Vet. Dermatol.* 24(6):587-597, 2013), upadacitinib (ABT494) (Kremer et al., *Arthritis Rheumatol.* 68(12): 2867-2877, 2016; Mohamed et al., *Clin. Pharmaco.* 55(12): 1547-1558, 2016), GLG0778 (O'Shea et al., *Ann. Rev. Med.* 66(1):311-28, 2015; Schwartz et al., *Nat. Rev. Rheum.* 12: 25-36, 2016), INCB039110 (Mascarenhas et al., *Haematologica* 102(2):327-335, 2017; Bissonnette et al., *J. Dermatolog. Treat.* 27(4):332-338, 2016; Rosenthal et al., *Exp. Opin. Pharmacother.* 15(9):1265-1276, 2014), PF04965842 (Gadina et al., *Curr. Opin. Rheumatol.* 26(2):237-243, 2014; Degryset et al., *J. Hematol. Oncol.* 8:91, 2015); SAR-20347 (Works et al., *J. Immunol.* 193(7):3278-3287, 2014)).

In some embodiments, the JAK inhibitory agent is a JAK2 inhibitor (e.g., CEP-33779 (Dugan et al., *J. Med. Chem.* 55(11):5243-5254, 2012; Seavey et al., *Mol. Cancer Ther.* 11(4):984-993, 2012; Stump et al., *Arthritis Res. Ther.* 13(2):R68, 2011), fedratinib (TG101348, SAR302503) (Pardanani et al., *J. Clin. Oncol.* 29:789-796, 2011; Jamieson et al., *J. Transl. Med.* 13:294, 2015; Zhang et al., *Oncotarget* 6(16):14329-14343, 2015; Wernig et al., *Blood* 105:4508-4515, 2008); lestaurtinib (CEP-701) (Hexnet et al., *Blood* 111:5663-5671, 2008; Santos et al., *Blood* 115: 1131-1136, 2010; Smith et al., *Blood* 103: 3669-3676, 2004; Hexner et al., *Leuk. Lymphoma.* 56(9):2543, 2015; Geyer et al., *Hematology* 17(Suppl1):S129-132, 2012; Diaz et al., *PLoS One* 6(4):e18856, 2011; Minturn et al., *Cancer Chemother. Pharmacol.* 68(4):1057-1065, 2011), AC-430 (O'Shea et al., *Immunity* 36(4):542-550, 2012; Patterson et al., *Clin. Exp. Immunol.* 176:1-10, 2014), pacritinib (SB1518) (Deeg et al., *J. Clin. Oncol.* 29: Abstract 6515, 2011; Verstovsek et al., *J. Hematol. Oncol.* 9(1):137, 2016; Chow et al., *Onco Targets. Ther.* 9:2655-2665, 2016; Komrokji et al., *Blood* 125(17): 2649-2655, 2015; Jayaraman et al., *Drug Metab. Lett.* 9(1): 28-47, 2015), BMS-911543 (Mace et al., *Oncotarget* 6(42): 44509-44522, 2015; Wan et al., *ACS Med. Chem. Lett.* 6(8):850-855, 2015; Purandare et al., *Leukemia* 26(2):280-288, 2012), XL019 (Verstovsek et al., *Leuk. Res.* 38(3):316-322, 2014; Forsyth et al., *Bioorg. Med. Chem. Lett.* 22(24): 7653-7658, 2012), INCB039110 (Mascarenhas et al., *Haematologica* 102(2):327-335, 2017; Bissonnette et al., *J. Dermatol. Treat.* 27(4):332-338, 2016), Gandotinib® (LY-2784544) (Ma et al., *Blood Cancer J.* 3:e109, 2013; Verstovsek et al., *Blood* 122: 665, 2013; Mitchell et al., *Org. Process Res. Dev.* 16(1):70-81. 2012); R723 (Shide et al., *Blood* 117(25): 6866-6875, 2011)); Z3 (Sayyah et al., *Mol. Cancer. Ther.* 7(8):2308-2318, 2008)) or a variant thereof.

In some embodiments, the JAK inhibitory agent is a JAK3 inhibitor (e.g., decernotinib (VX-509) (Elwood et al., *J. Pharmacol. Exp. Ther.* 2017; Genovese et al., *Ann Rheum Dis.* 75(11):1979-1983, 2016; Gadina et al., *Arthritis Rheumatol.* 68(1):31-34, 2016; Farmer et al., *J. Med. Chem.* 58(18):7195-7216, 2015; Fleischmann et al., *Arthritis Rheumatol.* 67(2):334-343, 2015; Mahajan et al., *J. Pharmacol.* 353(2):405-414, 2015), R348 or a variant thereof (Velotta et al., *Transplantation* 87(5):653-659, 2009; Deuse et al., *Transplantation* 85(6):885-892, 2008)). In some embodiments, the small molecule is R256 or a variant thereof (Ashino et al., *J. Allergy Clin. Immunol.* 133(4):1162-1174, 2014). In some embodiments, the small molecule is R333 or a variant thereof. In some embodiments, the small molecule is INCB047986 or a variant thereof (Norman, *Exp. Opin. Investig. Drugs* 23(8):1067-1077, 2014). In some embodiments, the small molecule is INCB16562 or a variant thereof (Koppikar et al., *Blood* 115(4):2919-2927, 2010; Li et al., *Neoplasia* 12(1):28-38, 2010). In some embodiments, the small molecule is NVP-BSK805 or a variant thereof (Ringel et al., *Acta Haematol.* 132(1):75-86, 2014; Baffert et al., *Mol. Cancer. Ther.* 9(7):1945-1955, 2010). In some embodiments, the small molecule is peficitinib (ASP015K, JNJ-54781532) or a variant thereof (Genovese et al., *Arthritis Rheumatol.*, 2017; Ito et al., *J. Pharmacol. Sci.* 133(1):25-33, 2017; Cao et al. (2016) *Clin. Pharmacol. Drug Dev.* 5(6):435-449, 2016; Takeuchi et al., *Ann. Rheum. Dis.* 75(6):1057-1064, 2016). In some embodiments, the small molecule is tofacitinib (Xeljanz®, Jakvinus®, CP-690, 500) or a variant thereof (Ghoreschi et al., *J. Immunol.* 186(7): 4234-4243, 2011; Yoshida et al., *Biochem. Biophys. Res. Commun* 418(2):234-240, 2012; Calama et al., *Pulm. Pharmacol. Ther.* S1094-5539(16):30060-30068, 2017; Cutolo et al., *J. Inflamm. Res.* 6:129-137, 2013). In some embodiments, the small molecule is cucurbitacin I (JSI-124) or a variant thereof (Oi et al., *Int. J. Oncol.* 49(6):2275-2284, 2016; Qi et al., *Am. J. Chin. Med.* 43(2):337-347, 2015; Seo et al., *Food Chem. Toxicol.* 64:217-224, 2014). In some embodiments, the small molecule is CHZ868 or a variant thereof (Wu et al., *Cancer Cell* 28(1):29-41, 2015; Meyer et al., *Cancer Cell* 28(1):15-28, 2015).

In some embodiments, the small molecule is a TYK2 inhibitor (e.g., Masse et al., *J. Immunol.* 194(1):67, 2015; Menet, *Pharm. Pat. Anal.* 3(4):449-466, 2014; Liang et al., *Euro. J. Med. Chem.* 67: 175-187, 2013; Jang et al., *Bioorg. Med. Chem. Lett.* 25(18):3947-3952, 2015); U.S. Pat. Nos. 9,296,725 and 9,309,240; US 2013/0231340; and US 2016/0251376). In some embodiments, the TYK2 inhibitor is Ndi-031301 (Akahane et al., *Blood* 128:1596, 2016); BMS-986165 (Gillooly et al., 2016 *ACR/ARHP Annual Meeting*, Abstract 11L, 2016); SAR-20347 (Works et al., *J. Immunol.* 193(7):3278-3287, 2014); tyrphostin A1 (Ishizaki et al., *Int. Immunol.* 26(5):257-267, 2014); a triazolopyridine (US 2013/0143915); or a variant thereof.

Additional examples of JAK inhibitors that are small molecules are described in, e.g., Furomoto et al., *BioDrugs* 27(5):431-438, 2013; O'Shea et al., *Ann. Rheum. Dis.* 72(2): ii111-ii-115, 2013; Sonbol et al., *Ther. Adv. Hematol.* 4(1): 15-35, 2013; and Tanaka et al. (2015) *J. Biochem.* 158(3): 173-179, 2015.

In some embodiments, the JAK inhibitor is a pan-JAK inhibitor. As used herein, the term "pan-JAK inhibitor" is an agent that has an $IC_{50}$ of about 500 nM to 4 µM (e.g., about 500 nM to about 2 µM) for each of human JAK1, human JAK2, and human JAK3 isoforms, when the $IC_{50}$ is determined for each of wildtype human JAK1, wildtype human JAK2, and wildtype human JAK3 using similar assay conditions (e.g., the same assay conditions). In some embodiments, a pan-JAK inhibitor can be an agent that has an $IC_{50}$ for wildtype human JAK1, wildtype human JAK2, and wildtype human JAK3 that are within ±10% of each other, when each of the $IC_{50}$ values is assays under similar assay conditions (e.g., the same assay, e.g., the human wildtype JAK1, wildtype human JAK2, and wildtype human JAK3 assay described in Kim et al., *J. Med. Chem.* 58(18):7596-5602, 2015).

In some embodiments, the pan-JAK inhibitor is tofacitinib (Xeljanz®, Jakvinus®, tasocitinib, CP-690550; Yokoyama et al., *J. Clin. Immunol.* 33(3):586-594, 2013; and Thoma et al., *J. Med. Chem.* 54(1):284-288, 2011); cerdulatinib (PRT2070; Coffey et al. (2014) *J. Pharmacol. Exp. Ther.* 351(3):538-548, 2014; and Ma et al., *Oncotarget* 6(41):43881-43896, 2015); Pyridone 6 (P6; Nakagawa et al., *J. Immunol.* 187(9): 4611-4620, 2011; and Pedranzini et al., *Cancer Res.* 66(19):9714-9721, 2006); PF-06263276 (Jones et al. "Design and Synthesis of a Pan-Janus Kinase Inhibitor Clinical Candidate (PF-06263276) Suitable for Inhaled and Topical Delivery for the Treatment of Inflammatory Diseases of the Lungs and Skin" J. Med. Chem., 2017, 60 (2), pp 767-786); JAK inhibitor 1 (CAS 457081-03-07; JAKi; Wang et al., *Antimicrob. Agents Chemother.* 60(5):2834-48, 2016; Bordonaro et al., *PLoS One* 9:e115068, 2014; and Osorio et al., *PLoS Pathogens* 10(6):e1004165, 2014); or baricitinib (Olumiant; LY3009104; INCB-28050; and Hsu and Armstrong, *J. Immunol. Res.* Article ID 283617, 2014).

In some embodiments, the JAK inhibitor is a selective JAK1/JAK3 inhibitor. As used herein, the term "selective JAK1/JAK3 inhibitor" means an agent that has an $IC_{50}$ for wildtype human JAK1 and wildtype human JAK3, that are each at least 5-fold (e.g., at least 10-fold or at least 20-fold) lower than the $IC_{50}$ for wildtype human JAK2, when the $IC_{50}$ is determined for each of wildtype human JAK1, wildtype human JAK2, and wildtype human JAK3 using similar assay conditions (e.g., the same assay, e.g., the human wildtype JAK1, wildtype human JAK2, and wildtype human JAK3 assay described in Kim et al., *J. Med. Chem.* 58(18):7596-5602, 2015).

In some embodiments, the JAK inhibitor is a selective JAK1 inhibitor. As used herein, the term "selective JAK1 inhibitor" means an agent that has an $IC_{50}$ for wildtype human JAK1 that is at least 10-fold (e.g., at least 20-fold) lower than each of the $IC_{50}$ for wildtype human JAK2 and the $IC_{50}$ for wildtype human JAK3 when measured using similar assay conditions (e.g., the same assay, e.g., the human wildtype JAK1, wildtype human JAK2, and wildtype human JAK3 assay described in Kim et al., *J. Med. Chem.* 58(18):7596-5602, 2015). In some embodiments, the JAK1 inhibitor is (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide as disclosed in international patent application PCT/US2014/062145, incorporated by reference herein in its entirety.

In some embodiments, the JAK inhibitor is a selective JAK3 inhibitor. As used herein, the term "selective JAK3 inhibitor" means an agent that has an $IC_{50}$ for wildtype human JAK3 that is at least 10-fold (e.g., at least 20-fold) lower than each of the $IC_{50}$ for wildtype human JAK2 and the $IC_{50}$ for wildtype human JAK1 when measured using similar assay conditions (e.g., the same assay, e.g., the human wildtype JAK1, wildtype human JAK2, and wildtype human JAK3 assay described in Kim et al., *J. Med. Chem.* 58(18):7596-5602, 2015).

In some embodiments, the JAK inhibitor is a JAK1 and JAK 3 inhibitor (e.g., a selective JAK1/JAK3 inhibitor). In some embodiments, the selective JAK1/JAK3 inhibitor is ZM 39923 (Brown et al., *Bioorg. Med. Chem. Lett.* 10(6): 575-579, 2000; and Lai et al., *Chem. Biol.* 15(9):969-978, 2008); or peficitinib (ASP015K; JNJ-54781532; Ito et al., *J. Pharmacol. Sci.* 133(1):25-33, 2017; Cao et al., *Clin. Pharmacol. Drug Dev.* 5(6):435-449, 2016; Takeuchi et al., *Ann. Rheum. Dis.* 75(6):1057-1064, 2016); and Papp et al., *Br. J. Dermatol.* 173(3):767-776, 2015).

In some embodiments, the JAK inhibitor is PF-06700841. In some embodiments, the JAK inhibitor is PF-06651600.

In some embodiments, the inhibitor is one of the following:

| Common Name | Brand name | Company |
| --- | --- | --- |
| Tofacitinib | Xeljanz | Pfizer |
| peficitinib (ASP015K or JNJ-54781532) | | JNJ |
| TD-1473 | | Theravance Biopharma |
| PF-06263276 | | Pfizer |
| Cerdulatinib (PRT-062070) | | |
| upadacitinib (ABT494) | | Abbvie |
| Baricitinib (INCB028050, LY3009104) | Olumiant | Incyte & Eli Lilly |
| Filgotinib (GLPG0634) | TBD | Gilead, Galapagos NV |
| Jakafi®, Jakavi® | ruxolitinib (INCB018424) | |
| AZD1480 | | AstraZeneca |
| momelotinib (GS-0387) | | |
| GSK2586184 | | GSK |
| oclacitinib (PF03394197) | Apoquel® | Pfizer |
| oclacitinib (PF03394197) | | Abbvie |
| GLG0778 | | |
| GLG0778 | | |
| fedratinib (TG101348, SAR302503) | | |
| lestaurtinib (CEP-701) | | |
| AC-430 | | |
| pacritinib (SB1518) | | |
| XL019 | | |
| gandotinib® (LY-2784544) | | |
| BMS-911543 | | BMS |
| NVP-BSK805 | | |
| INCB16562 | | |
| Decernotinib (VX509) | | |
| cucurbitacin I (JSI-124) | | |
| R333 | | |
| Ndi-031301 | | |
| SAR-20347 | | |
| tyrphostin A1 | | |
| triazolopyridine | | |
| BMS-986165 | | |
| TOP-1288 | | Topivert Pharma Ltd |
| PF-06700841 | | Pfizer |
| PF-06651600 | | Pfizer |
| Inhibitory Nucleic Acids | | |

In some embodiments, the kinase inhibitor is TOP-1288 from TopiVert Pharma Ltd., which is described in "The Pharmacological Profile of TOP1288, a Narrow Spectrum Kinase Inhibitor (NSKI) in Clinical Development as an Anti-Inflammatory Treatment for Ulcerative Colitis" Foster, Martyn et al. Gastroenterology, Volume 152, Issue 5, S766.

Endoscopes, Ingestible Devices, and Reservoirs

As discussed herein, in some embodiments, a method of treating a disease of the gastrointestinal tract comprises administering to the subject a pharmaceutical formulation wherein the pharmaceutical formulation is delivered proximate to one or more sites of disease by one of various methods. For example, the pharmaceutical formulation may be delivered via a medical device such as an endoscope, ingestible device, or reservoir; the pharmaceutical formulation may be a solid dosage form, a liquid dosage form, a suppository or an enema for rectal administration with different types of release such as sustained or delayed release.

In one embodiment, the pharmaceutical formulation is delivered proximate to one or more sites of disease by an endoscope, ingestible device, or reservoir containing the pharmaceutical formulation.

The GI tract can be imaged using endoscopes, or more recently, by ingestible devices that are swallowed. Direct visualization of the GI mucosa is useful to detect subtle mucosal alterations, as in inflammatory bowel diseases, as well as any flat or sessile lesions.

As discussed herein, in some embodiments, the method of treating a disease of the gastrointestinal tract comprises administering to the subject a pharmaceutical formulation. In some embodiments, the pharmaceutical formulation is delivered proximate to one or more sites of disease by one of various methods. For example, the pharmaceutical formulation may be delivered via a medical device such as an endoscope, ingestible device, or reservoir; the pharmaceutical formulation may be a solid dosage form, a liquid dosage form, a suppository or an enema for rectal administration with different types of release such as sustained or delayed release.

In one embodiment, the pharmaceutical formulation is delivered proximate to one or more sites of disease by an endoscope, ingestible device, or reservoir containing the pharmaceutical formulation.

The technology behind standard colonoscopy consists of a long, semi-rigid insertion tube with a steerable tip (stiff if compared to the colon), which is pushed by the physician from the outside. However, invasiveness, patient discomfort, fear of pain, and—more often than not—the need for conscious sedation limit the take-up of screening colonoscopy. Diagnosis and treatment in the GI tract are dominated by the use of flexible endoscopes. A few large companies, namely Olympus Medical Systems Co. (Tokyo, Japan), Pentax Medical Co. (Montvale, N.J., USA), Fujinon, Inc. (Wayne, N.J., USA) and Karl Storz GmbH & Co. KG (Tuttlingen, Germany), cover the majority of the market in flexible GI endoscopy.

Endoscopes may comprise a catheter. As an example, the catheter may be a spray catheter. As an example, a spray catheter may be used to deliver dyes for diagnostic purposes. As an example, a spray catheter may be used to deliver a therapeutic agent at the site of disease in the GI tract. For example, the Olympus PW-205V is a ready-to-use spray catheter that enables efficient spraying for maximal differentiation of tissue structures during endoscopy, but may also be used to deliver drugs diseased tissue.

In a review of robotic endoscopic capsules, Journal of Micro-Bio Robotics 11.1-4 (2016): 1-18, Ciuti et al. state that progress in micro-electromechanical systems (MEMS) technologies have led to the development of new endoscopic capsules with enhanced diagnostic capabilities, in addition to traditional visualization of mucosa (embedding, e.g. pressure, pH, blood detection and temperature sensors).

Endoscopic capsules, however, do not have the capability of accurately locating a site autonomously. They require doctor oversight over a period of hours in order to manually determine the location. Autonomous ingestible devices are advantageous in that regard.

Ingestible devices are also advantageous over spray catheters in that they are less invasive, thereby allowing for regular dosing more frequently than spray catheters. Another advantage of ingestible devices is the greater ease with which they can access, relative to a catheter, certain sections of the GI tract such as the ascending colon, the cecum, and all portions of the small intestine.

Methods and Mechanisms for Localization

In addition to, or as an alternative, to directly visualizing the GI tract, one or more different mechanisms can be used to determine the location of an ingestible device within the GI tract. Various implementations may be used for localization of ingestible devices within the GI tract.

For example, certain implementations can include one or more electromagnetic sensor coils, magnetic fields, electromagnetic waves, electric potential values, ultrasound positioning systems, gamma scintigraphy techniques or other radio-tracker technology have been described by others. Alternatively, imaging can be used to localize, for example, using anatomical landmarks or more complex algorithms for 3D reconstruction based on multiple images. Other technologies rely on radio frequency, which relies on sensors placed externally on the body to receive the strength of signals emitted by the capsule. Ingestible devices may also be localized based on reflected light in the medium surrounding the device; pH; temperature; time following ingestion; and/or acoustic signals.

The disclosure provides an ingestible device, as well as related systems and methods that provide for determining the position of the ingestible device within the GI tract of a subject with very high accuracy. In some embodiments, the ingestible device can autonomously determine its position within the GI tract of the subject.

Typically, the ingestible device includes one or more processing devices, and one more machine readable hardware storage devices. In some embodiments, the one or more machine readable hardware storage devices store instructions that are executable by the one or more processing devices to determine the location of the ingestible device in a portion of a GI tract of the subject. In certain embodiments, the one or more machine readable hardware storage devices store instructions that are executable by the one or more processing devices to transmit data to an external device (e.g., a base station external to the subject, such as a base station carried on an article worn by the subject) capable of implementing the data to determine the location of the device within the GI tract of the subject.

In some embodiments, the location of the ingestible device within the GI tract of the subject can be determined to an accuracy of at least 85%, e.g., at least 90%, at least 95%, at least 97%, at least 98%, at least 99%, 100%. In some embodiments, the location of the ingestible device within the GI tract of the subject can be determined to an accuracy of at least 85%, e.g., at least 90%, at least 95%, at least 97%, at least 98%, at least 99%, 100%. In such embodiments, the portion of the GI tract of the subject can include, for example, the esophagus, the stomach, duodenum, the jejunum, and/or the terminal ileum, cecum and colon. An exemplary and non-limiting embodiment is provided below in Example 13.

In certain embodiments, the location of the ingestible device within the esophagus of the subject can be determined to an accuracy of at least 85%, e.g., at least 90%, at least 95%, at least 97%, at least 98%, at least 99%, 100%. An exemplary and non-limiting embodiment is provided below in Example 13.

In some embodiments, the location of the ingestible device within the stomach of the subject can be determined to an accuracy of at least 85%, e.g., at least 90%, at least 95%, at least 97%, at least 98%, at least 99%, 100%. An exemplary and non-limiting embodiment is provided below in Example 13.

In certain embodiments, the location of the ingestible device within the duodenum of the subject can be determined to an accuracy of at least 85%, e.g., at least 90%, at least 95%, at least 97%, at least 98%, at least 99%, 100%. An exemplary and non-limiting embodiment is provided below in Example 13.

In some embodiments, the location of the ingestible device within the jejunum of the subject can be determined to an accuracy of at least 85%, e.g., at least 90%, at least 95%, at least 97%, at least 98%, at least 99%, 100%. An exemplary and non-limiting embodiment is provided below in Example 13.

In certain embodiments, the location of the ingestible device within the terminal ileum, cecum and colon of the subject can be determined to an accuracy of at least 85%, e.g., at least 90%, at least 95%, at least 97%, at least 98%, at least 99%, 100%.

In some embodiments, the location of the ingestible device
within the cecum of the subject can be determined to an accuracy of at least 85%, e.g., at least 90%, at least 95%, at least 97%, at least 98%, at least 99%, 100%. An exemplary and non-limiting embodiment is provided below in Example 13. In such embodiments, the portion of the portion of the GI tract of the subject can include, for example, the esophagus, the stomach, duodenum, the jejunum, and/or the terminal ileum, cecum and colon.

In certain embodiments, the location of the ingestible device within the esophagus of the subject can be determined to an accuracy of at least 85%, e.g., at least 90%, at least 95%, at least 97%, at least 98%, at least 99%, 100%.

In some embodiments, the location of the ingestible device within the stomach of the subject can be determined to an accuracy of at least 85%, e.g., at least 90%, at least 95%, at least 97%, at least 98%, at least 99%, 100%.

In certain embodiments, the location of the ingestible device within the duodenum of the subject can be determined to an accuracy of at least 85%, e.g., at least 90%, at least 95%, at least 97%, at least 98%, at least 99%, 100%.

In some embodiments, the location of the ingestible device within the jejunum of the subject can be determined to an accuracy of at least 85%, e.g., at least 90%, at least 95%, at least 97%, at least 98%, at least 99%, 100%.

In certain embodiments, the location of the ingestible device within the terminal ileum, cecum and colon of the subject can be determined to an accuracy of at least 85%, e.g., at least 90%, at least 95%, at least 97%, at least 98%, at least 99%, 100%.

In some embodiments, the location of the ingestible device within the cecum of the subject can be determined to an accuracy of at least 85%, e.g., at least 90%, at least 95%, at least 97%, at least 98%, at least 99%, 100%.

As used herein, the term "reflectance" refers to a value derived from light emitted by the device, reflected back to the device, and received by a detector in or on the device. For example, in some embodiments this refers to light emitted by the device, wherein a portion of the light is reflected by a surface external to the device, and the light is received by a detector located in or on the device.

As used herein, the term "illumination" refers to any electromagnetic emission. In some embodiments, an illumination may be within the range of Infrared Light (IR), the visible spectrum and ultraviolet light (UV), and an illumination may have a majority of its power centered at a particular wavelength in the range of 100 nm to 1000 nm. In some embodiments, it may be advantageous to use an illumination with a majority of its power limited to one of the infrared (750 nm-1000 nm), red (600 nm-750 nm), green (495 nm-600 nm), blue (400 nm-495 nm), or ultraviolet (100 nm-400 nm) spectrums. In some embodiments a plurality of illuminations with different wavelengths may be used. For illustrative purposes, the embodiments described herein may refer to the use of green or blue spectrums of light. However, it is understood that these embodiments may use any suitable light having a wavelength that is substantially or approximately within the green or blue spectra defined above, and the localization systems and methods described herein may use any suitable spectra of light.

Referring now to FIG. 1, shown therein is a view of an example embodiment of an ingestible device 100, which may be used to identify a location within a gastrointestinal (GI) tract. In some embodiments, ingestible device 100 may be configured to autonomously determine whether it is located in the stomach, a particular portion of the small intestine such as a duodenum, jejunum, or ileum, or the large intestine by utilizing sensors operating with different wavelengths of light. Additionally, ingestible device 100 may be configured to autonomously determine whether it is located within certain portions of the small intestine or large intestine, such as the duodenum, the jejunum, the cecum, or the colon.

Ingestible device 100 may have a housing 102 shaped similar to a pill or capsule. The housing 102 of ingestible device 100 may have a first end portion 104, and a second end portion 106. The first end portion 104 may include a first wall portion 108, and second end portion 106 may include a second wall portion 110. In some embodiments, first end portion 104 and second end portion 106 of ingestible device 100 may be manufactured separately, and may be affixed together by a connecting portion 112.

In some embodiments, ingestible device 100 may include an optically transparent window 114. Optically transparent window 114 may be transparent to various types of illumination in the visible spectrum, infrared spectrum, or ultraviolet light spectrum, and ingestible device 100 may have various sensors and illuminators located within the housing 102, and behind the transparent window 114. This may allow ingestible device 100 to be configured to transmit illumination at different wavelengths through transparent window 114 to an environment external to housing 102 of ingestible device 100, and to detect a reflectance from a portion of the illumination that is reflected back through transparent window 114 from the environment external to housing 102. Ingestible device 100 may then use the detected level of reflectance in order to determine a location of ingestible device 100 within a GI tract. In some embodiments, optically transparent window 114 may be of any shape and size, and may wrap around the circumference of ingestible device 100. In this case, ingestible device 100 may have multiple sets of sensors and illuminators positioned at different locations azimuthally behind window 114.

In some embodiments, ingestible device 100 may optionally include an opening 116 in the second wall portion 110. In some embodiments, the second wall portion 110 may be configured to rotate around the longitudinal axis of ingestible device 100 (e.g., by means of a suitable motor or other actuator housed within ingestible device 100). This may allow ingestible device 100 to obtain a fluid sample from the GI tract, or release a substance into the GI tract, through opening 116.

Figure 2:
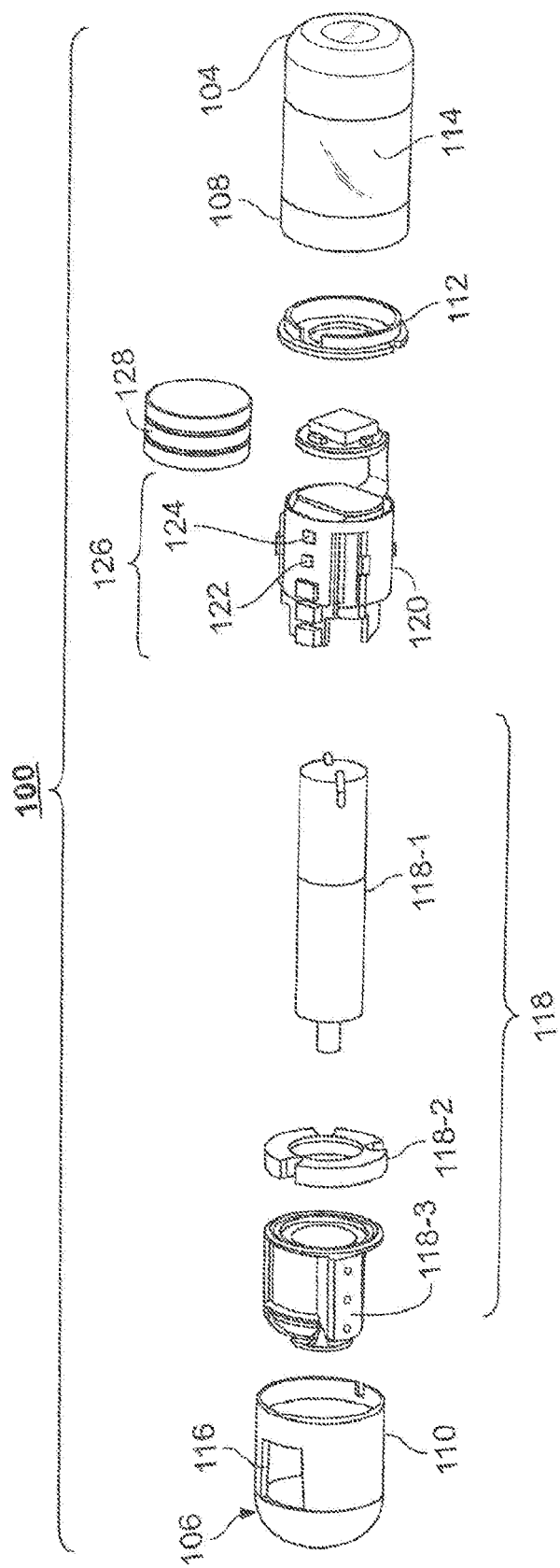
FIG. 2 is an exploded view of the ingestible device of FIG. 1, in accordance with some embodiments of the disclosure.

FIG. 2 shows an exploded view of ingestible device 100. In some embodiments, ingestible device 100 may optionally include a rotation assembly 118. Optional rotation assembly 118 may include a motor 118-1 driven by a microcontroller (e.g., a microcontroller coupled to printed circuit board 120), a rotation position sensing ring 118-2, and a storage sub-unit 118-3 configured to fit snugly within the second end portion 104. In some embodiments, rotation assembly 118 may cause second end portion 104, and opening 116, to rotate relative to the storage sub-unit 118-3. In some embodiments, there may be cavities on the side of storage sub-unit 118-3 that function as storage chambers. When the opening 116 is aligned with a cavity on the side of the storage sub-unit 118-3, the cavity on the side of the storage sub-unit 118-3 may be exposed to the environment external to the housing 102 of ingestible device 100. In some embodiments, the storage sub-unit 118-3 may be loaded with a medicament or other substance prior to the ingestible device 100 being administered to a subject. In this case, the medicament or other substance may be released from the ingestible device 100 by aligning opening 116 with the cavity within storage sub-unit 118-3. In some embodiments, the storage sub-unit 118-3 may be configured to hold a fluid sample obtained from the GI tract. For example, ingestible device 100 may be configured to align opening 116 with the cavity within storage sub-unit 118-3, thus allowing a fluid sample from the GI tract to enter the cavity within storage sub-unit 118-3. Afterwards, ingestible device 100 may be configured to seal the fluid sample within storage sub-unit 118-3 by further rotating the second end portion 106 relative to storage sub-unit 118-3. In some embodiments, storage sub-unit 118-3 may also contain a hydrophilic sponge, which may enable ingestible device 100 to better draw certain types of fluid samples into ingestible device 100. In some embodiments, ingestible device 100 may be configured to either obtain a sample from within the GI tract, or to release a substance into the GI tract, in response to determining that ingestible device 100 has reached a predetermined location within the GI tract. For example, ingestible device 100 may be configured to obtain a fluid sample from the GI tract in response to determining that the ingestible device has entered the jejunum portion of the small intestine (e.g., as determined by process 900 discussed in relation to FIG. 9). Other ingestible devices capable of obtaining samples or releasing substances are discussed in commonly-assigned PCT Application No. PCT/CA2013/000133 filed Feb. 15, 2013, commonly-assigned U.S. Provisional Application No. 62/385,553, and commonly-assigned U.S. Provisional Application No. 62/376,688, which each are hereby incorporated by reference herein in their entirety. It is understood that any suitable method of obtaining samples or releasing substances may be incorporated into some of the embodiments of the ingestible devices disclosed herein, and that the systems and methods for determining a location of an ingestible device may be incorporated into any suitable type of ingestible device.

Ingestible device 100 may include a printed circuit board (PCB) 120, and a battery 128 configured to power PCB 120. PCB 120 may include a programmable microcontroller, and control and memory circuitry for holding and executing firmware or software for coordinating the operation of ingestible device 100, and the various components of ingestible device 100. For example, PCB 120 may include memory circuitry for storing data, such as data sets of measurements collected by sensing sub-unit 126, or instructions to be executed by control circuitry to implement a localization process, such as, for example, one or more of the processes, discussed herein, including those discussed below in connection with one or more of the associated flow charts. PCB 120 may include a detector 122 and an illuminator 124, which together form sensing sub-unit 126. In some embodiments, control circuitry within PCB 120 may include processing units, communication circuitry, or any other suitable type of circuitry for operating ingestible device 100. For illustrative purposes, only a single detector 122 and a single illuminator 124 forming a single sensing sub-unit 126 are shown. However, it is understood that in some embodiments there may be multiple sensing sub-units, each with a separate illuminator and detector, within ingestible device 100. For example, there may be several sensing sub-units spaced azimuthally around the circumference of the PCB 120, which may enable ingestible device 100 to transmit illumination and detect reflectances or ambient light in all directions around the circumference of the device. In some embodiments, sensing sub-unit 126 may be configured to generate an illumination using illuminator 124, which is directed through the window 114 in a radial direction away from ingestible device 100. This illumination may reflect off of the environment external to ingestible device 100, and the reflected light coming back into ingestible device 100 through window 114 may be detected as a reflectance by detector 122.

In some embodiments, window 114 may be of any suitable shape and size. For example, window 114 may extend around a full circumference of ingestible device 100. In some embodiments there may be a plurality of sensing sub-units (e.g., similar to sensing sub-unit 126) located at different positions behind the window. For example, three sensing sub-units may be positioned behind the window at the same longitudinal location, but spaced 120 degrees apart azimuthally. This may enable ingestible device 100 to transmit illuminations in all directions radially around ingestible device 100, and to measure each of the corresponding reflectances.

In some embodiments, illuminator 124 may be capable of producing illumination at a variety of different wavelengths in the ultraviolet, infrared, or visible spectrum. For example, illuminator 124 may be implemented by using Red-Green-Blue Light-Emitting diode packages (RGB-LED). These types of RGB-LED packages are able to transmit red, blue, or green illumination, or combinations of red, blue, or green illumination. Similarly, detector 122 may be configured to sense reflected light of the same wavelengths as the illumination produced by illuminator 124. For example, if illuminator 124 is configured to produce red, blue, or green illumination, detector 122 may be configured to detect different reflectances produced by red, blue, or green illumination (e.g., through the use of an appropriately configured photodiode). These detected reflectances may be stored by ingestible device 100 (e.g., within memory circuitry of PCB 120), and may then be used by ingestible device 100 in determining a location of ingestible device 100 within the GI tract (e.g., through the use of process 500 (FIG. 5), process 600 (FIG. 6), or process 900 (FIG. 9)).

It is understood that ingestible device 100 is intended to be illustrative, and not limiting. It will be understood that modifications to the general shape and structure of the various devices and mechanisms described in relation to FIG. 1 and FIG. 2 may be made without significantly changing the functions and operations of the devices and mechanisms. For example, ingestible device 100 may have a housing formed from a single piece of molded plastic, rather than being divided into a first end portion 104 and a second end portion 106. As an alternate example, the location of window 114 within ingestible device 100 may be moved to some other location, such as the center of ingestible device 100, or to one of the ends of ingestible device 100. Moreover, the systems and methods discussed in relation to FIGS. 1-10 may be implemented on any suitable type of ingestible device, provided that the ingestible device is capable of detecting reflectances or levels of illumination in some capacity. For example, in some embodiments ingestible device 100 may be modified to replace detector 122 with an image sensor, and the ingestible device may be configured to measure relative levels of red, blue, or green light by decomposing a recorded image into its individual spectral components. Other examples of ingestible devices with localization capabilities, which may be utilized in order to implement the systems and methods discussed in relation to FIG. 1-11, are discussed in co-owned PCT Application No. PCT/US2015/052500 filed on Sep. 25, 2015, which is hereby incorporated by reference herein in its entirety. Furthermore, it should be noted that the features and limitations described in any one embodiment may be applied to any other embodiment herein, and the descriptions and examples relating to one embodiment may be combined with any other embodiment in a suitable manner.

Figure 3:
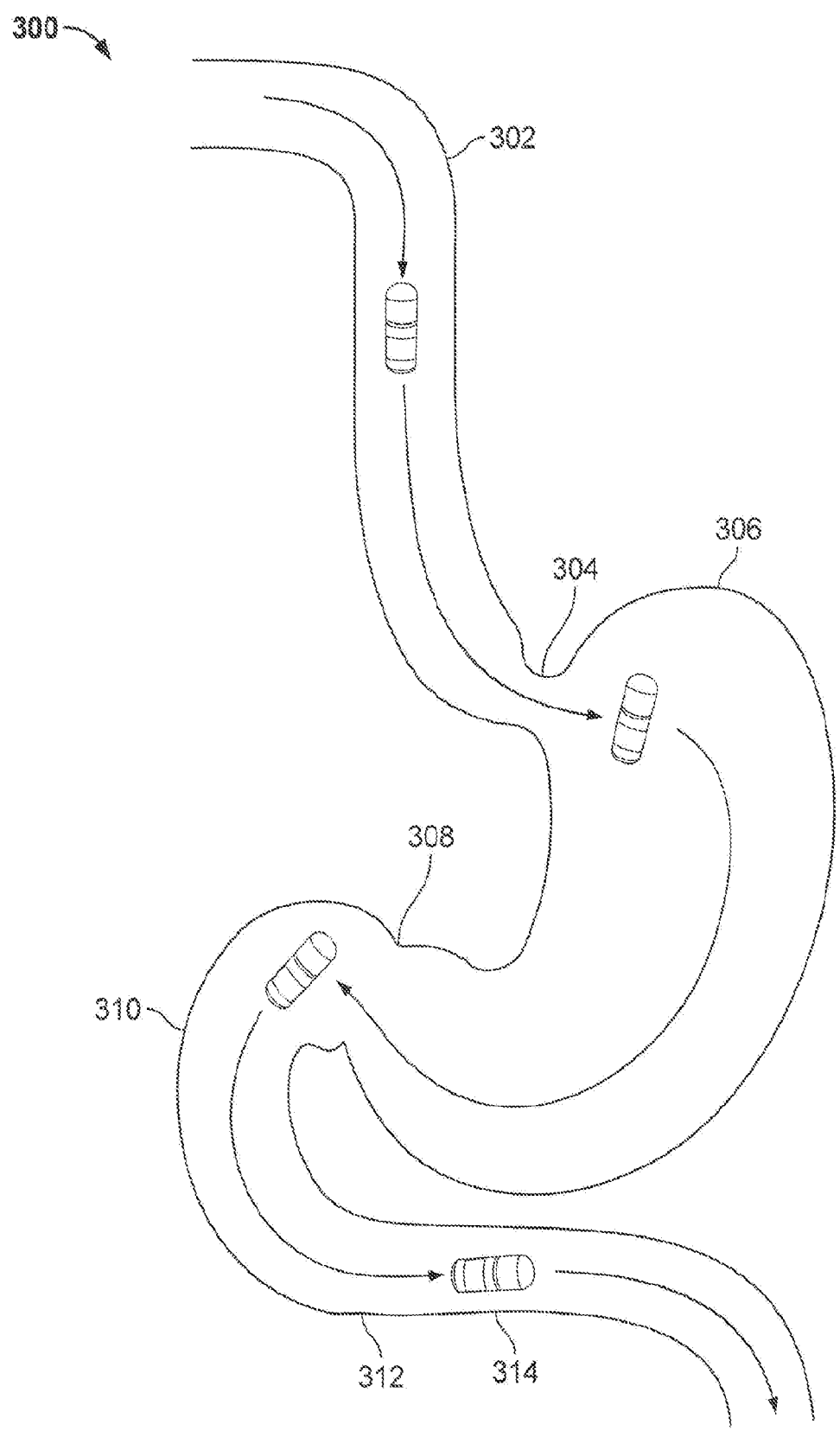
FIG. 3 is a diagram of an ingestible device during an example transit through a GI tract, in accordance with some embodiments of the disclosure.

FIG. 3 is a diagram of an ingestible device during an example transit through a gastrointestinal (GI) tract, in accordance with some embodiments of the disclosure. Ingestible device 300 may include any portion of any other ingestible device discussed in this disclosure (e.g., ingestible device 100 (FIG. 1)), and may be any suitable type of ingestible device with localization capabilities. For example, ingestible device 300 may be one embodiment of ingestible device 100 without the optional opening 116 (FIG. 1) or optional rotation assembly 118 (FIG. 2)). In some embodiments, ingestible device 300 may be ingested by a subject, and as ingestible device 300 traverses the GI tract, ingestible device 300 may be configured to determine its location within the GI tract. For example, the movement of ingestible device 300 and the amount of light detected by ingestible device 300 (e.g., via detector 122 (FIG. 2)) may vary substantially depending on the location of ingestible device 300 within the GI tract, and ingestible device 300 may be configured to use this information to determine a location of ingestible device 300 within the GI tract. For instance, ingestible device 300 may detect ambient light from the surrounding environment, or reflectances based on illumination generated by ingestible device 300 (e.g., generated by illuminator 124 (FIG. 1)), and use this information to determine a location of ingestible device 300 through processes, such as described herein. The current location of ingestible device 300, and the time that ingestible device 300 detected each transition between the various portions of the GI tract, may then be stored by ingestible device 300 (e.g., in memory circuitry of PCB 120 (FIG. 2)), and may be used for any suitable purpose.

Shortly after ingestible device 300 is ingested, ingestible device will traverse the esophagus 302, which may connect the subject's mouth to a stomach 306. In some embodiments, ingestible device 300 may be configured to determine that it has entered the esophagus portion GI tract by measuring the amount and type of light (e.g., via detector 122 (FIG. 2)) in the environment surrounding the ingestible device 300. For instance, ingestible device 300 may detect higher levels of light in the visible spectrum (e.g., via detector 122 (FIG. 2)) while outside the subject's body, as compared to the levels of light detected while within the GI tract. In some embodiments, ingestible device 300 may have previously stored data (e.g., on memory circuitry of PCB 120 (FIG. 2)) indicating a typical level of light detected when outside of the body, and the ingestible device 300 may be configured to determine that entry to the body has occurred when a detected level of light (e.g., detected via detector 122 (FIG. 2)) has been reduced beyond a threshold level (e.g., at least a 20-30% reduction) for a sufficient period of time (e.g., 5.0 seconds).

In some embodiments, ingestible device 300 may be configured to detect a transition from esophagus 302 to stomach 306 by passing through sphincter 304. In some embodiments, ingestible device 300 may be configured to determine whether it has entered stomach 306 based at least in part on a plurality of parameters, such as but not limited to the use of light or temperature measurements (e.g., via detector 122 (FIG. 2) or via a thermometer within ingestible device 300), pH measurements (e.g., via a pH meter within ingestible device 300), time measurements (e.g., as detected through the use of clock circuitry included within PCB 120 (FIG. 2)), or any other suitable information. For instance, ingestible device 300 may be configured to determine that ingestible device 300 has entered stomach 306 after detecting that a measured temperature of ingestible device 300 exceeds 31 degrees Celsius. Additionally, or alternately, ingestible device 300 may be configured to automatically determine it has entered stomach 306 after one minute (or another pre-set time duration parameter, 80 seconds, 90 seconds, etc.) has elapsed from the time that ingestible device 300 was ingested, or one minute (or another pre-set time duration parameter, 80 seconds, 90 seconds, etc.) from the time that ingestible device 300 detected that it has entered the GI tract.

Stomach 306 is a relatively large, open, and cavernous organ, and therefore ingestible device 300 may have a relatively large range of motion. By comparison, the motion of ingestible device 300 is relatively restricted within the tube-like structure of the duodenum 310, the jejunum 314, and the ileum (not shown), all of which collectively form the small intestine. Additionally, the interior of stomach 306 has distinct optical properties from duodenum 310 and jejunum 314, which may enable ingestible device 300 to detect a transition from stomach 306 to duodenum 310 through the appropriate use of measured reflectances (e.g., through the use of reflectances measured by detector 122 (FIG. 2)), as used in conjunction with process 600 (FIG. 6)).

In some embodiments, ingestible device 300 may be configured to detect a pyloric transition from stomach 306 to duodenum 310 through the pylorus 308. For instance, in some embodiments, ingestible device 300 may be configured to periodically generate illumination in the green and blue wavelengths (e.g., via illuminator 124 (FIG. 2)), and measure the resulting reflectances (e.g., via detector 122

(FIG. 2)). Ingestible device 300 may be configured to then use a ratio of the detected green reflectance to the detected blue reflectance to determine whether ingestible device 300 is located within the stomach 306, or duodenum 310 (e.g., via process 600 (FIG. 6)). In turn, this may enable ingestible device 300 to detect a pyloric transition from stomach 306 to duodenum 310, an example of which is discussed in relation to FIG. 6.

Similarly, in some embodiments, ingestible device 300 may be configured to detect a reverse pyloric transition from duodenum 310 to stomach 306. Ingestible device 300 will typically transition naturally from stomach 306 to duodenum 310, and onward to jejunum 314 and the remainder of the GI tract. However, similar to other ingested substances, ingestible device 300 may occasionally transition from duodenum 310 back to stomach 306 as a result of motion of the subject, or due to the natural behavior of the organs with the GI tract. To accommodate this possibility, ingestible device 300 may be configured to continue to periodically generate illumination in the green and blue wavelengths (e.g., via illuminator 124 (FIG. 2)), and measure the resulting reflectances (e.g., via detector 122 (FIG. 2)) to detect whether or not ingestible device 300 has returned to stomach 306. An exemplary detection process is described in additional detail in relation to FIG. 6.

After entering duodenum 310, ingestible device 300 may be configured to detect a transition to the jejunum 314 through the duodenojejunal flexure 312. For example, ingestible device 300 may be configured to use reflectances to detect peristaltic waves within the jejunum 314, caused by the contraction of the smooth muscle tissue lining the walls of the jejunum 314. In particular, ingestible device 300 may be configured to begin periodically transmitting illumination (and measuring the resulting reflectances (e.g., via detector 122 and illuminator 124 of sensing sub-unit 126 (FIG. 2)) at a sufficiently high frequency in order to detect muscle contractions within the jejunum 314. Ingestible device 300 may then determine that it has entered the jejunum 314 in response to having detected either a first muscle contraction, or a predetermined number of muscle contractions (e.g., after having detected three muscle contractions in sequence). The interaction of ingestible device 300 with the walls of jejunum 314 is also discussed in relation to FIG. 4, and an example of this detection process is described in additional detail in relation to FIG. 9.

Figure 4:
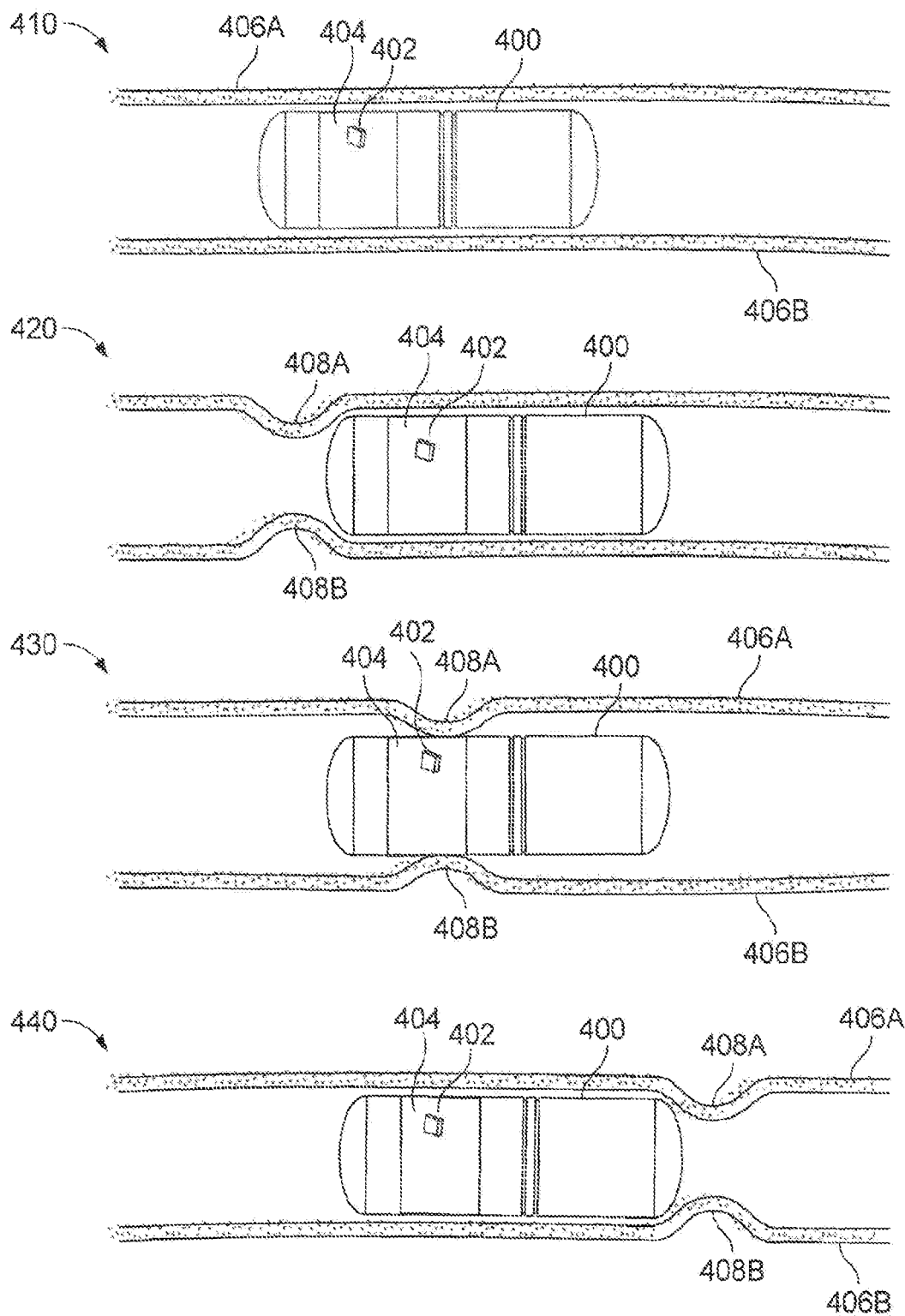
FIG. 4 is a diagram of an ingestible device during an example transit through a jejunum, in accordance with some embodiments of the disclosure.

FIG. 4 is a diagram of an ingestible device during an example transit through a jejunum, in accordance with some embodiments of the disclosure. Diagrams 410, 420, 430, and 440 depict ingestible device 400 as it traverses through a jejunum (e.g., jejunum 314), and how ingestible device 400 interacts with peristaltic waves formed by walls 406A and 406B (collectively, walls 406) of the jejunum. In some implementations, ingestible device 400 may include any portion of any other ingestible device discussed in this disclosure (e.g., ingestible device 100 (FIG. 1) or ingestible device 300 (FIG. 3)), and may be any suitable type of ingestible device with localization capabilities. For example, ingestible device 400 may be substantially similar to the ingestible device 300 (FIG. 3) or ingestible device 100 (FIG. 1), with window 404 being the same as window 114 (FIG. 1), and sensing sub-unit 402 being the same as sensing sub-unit 126 (FIG. 2).

Diagram 410 depicts ingestible device 400 within the jejunum, when the walls 406 of the jejunum are relaxed. In some embodiments, the confined tube-like structure of the jejunum naturally causes ingestible device 400 to be oriented longitudinally along the length of the jejunum, with window 404 facing walls 406. In this orientation, ingestible device 400 may use sensing sub-unit 402 to generate illumination (e.g., via illuminator 124 (FIG. 2)) oriented towards walls 406, and to detect the resulting reflectances (e.g., via detector 122 (FIG. 2)) from the portion of the illumination reflected off of walls 406 and back through window 404. In some embodiments, ingestible device 400 may be configured to use sensing sub-unit 402 to generate illumination and measure the resulting reflectance with sufficient frequency to detect peristaltic waves within the jejunum. For instance, in a healthy human subject, peristaltic waves may occur at a rate of approximately 0.1 Hz to 0.2 Hz. Therefore, the ingestible device 400 may be configured to generate illumination and measure the resulting reflectance at least once every 2.5 seconds (i.e., the minimum rate necessary to detect a 0.2 Hz signal), and preferably at a higher rate, such as once every 0.5 seconds, which may improve the overall reliability of the detection process due to more data points being available. It is understood that the ingestible device 400 need not gather measurements at precise intervals, and in some embodiments the ingestible device 400 may be adapted to analyze data gathered at more irregular intervals, provided that there are still a sufficient number of appropriately spaced data points to detect 0.1 Hz to 0.2 Hz signals.

Diagram 420 depicts ingestible device 400 within the jejunum, when the walls 406 of the jejunum begin to contract and form a peristaltic wave. Diagram 420 depicts contracting portion 408A of wall 406A and contracting portion 408B of wall 406B (collectively, contracting portion 408 of wall 406) that form a peristaltic wave within the jejunum. The peristaltic wave proceeds along the length of the jejunum as different portions of wall 406 contract and relax, causing it to appear as if contracting portions 408 of wall 406 proceed along the length of the jejunum (i.e., as depicted by contracting portions 408 proceeding from left to right in diagrams 410-430). While in this position, ingestible device 400 may detect a similar level of reflectance (e.g., through the use of illuminator 124 and detector 122 of sensing sub-unit 126 (FIG. 2)) as detected when there is no peristaltic wave occurring (e.g., as detected when ingestible device 400 is in the position indicated in diagram 410).

Diagram 430 depicts ingestible device 400 within the jejunum, when the walls 406 of the jejunum continue to contract, squeezing around ingestible device 400. As the peristaltic wave proceeds along the length of the jejunum, contracting portions 408 of wall 406 may squeeze tightly around ingestible device 400, bringing the inner surface of wall 406 into contact with window 404. While in this position, ingestible device 400 may detect a change in a reflectance detected as a result of illumination produced by sensing sub-unit 402. The absolute value of the change in the measured reflectance may depend on several factors, such as the optical properties of the window 404, the spectral components of the illumination, and the optical properties of the walls 406. However, ingestible device 400 may be configured to store a data set with the reflectance values over time, and search for periodic changes in the data set consistent with the frequency of the peristaltic waves (e.g., by analyzing the data set in the frequency domain, and searching for peaks between 0.1 Hz to 0.2 Hz). This may enable ingestible device 400 to detect muscle contractions due to peristaltic waves without foreknowledge of the exact changes in reflectance signal amplitude that may occur as a result of detecting the muscle contractions of the peristaltic wave. An example procedure for detecting muscle contractions is discussed further in relation to FIG. 9, and an example of a reflectance data set gathered while ingestible device 400 is located within the jejunum is discussed in relation to FIG. 10.

Diagram 440 depicts ingestible device 400 within the jejunum, when the peristaltic wave has moved past ingestible device 400. Diagram 440 depicts contracting portions 408 that form the peristaltic wave within the jejunum having moved past the end of ingestible device 400. The peristaltic wave proceeds along the length of the jejunum as different portions of wall 406 contract and relax, causing it to appear as if contracting portions 408 of wall 406 proceed along the length of the jejunum (i.e., as depicted by contracting portions 408 proceeding from left to right in diagrams 410-430). While in this position, ingestible device 400 may detect a similar level of reflectance (e.g., through the use of illuminator 124 and detector 122 of sensing sub-unit 126 (FIG. 2)) as detected when there is no peristaltic wave occurring (e.g., as detected when ingestible device 400 is in the position indicated in diagram 410, or diagram 420).

Depending on the species of the subject, peristaltic waves may occur with relatively predictable regularity. After the peristaltic wave has passed over ingestible device 400 (e.g., as depicted in diagram 440), the walls 406 of the jejunum may relax again (e.g., as depicted in diagram 410), until the next peristaltic wave begins to form. In some embodiments, ingestible device 400 may be configured to continue to gather reflectance value data while it is within the GI tract, and may store a data set with the reflectance values over time. This may allow ingestible device 400 to detect each of the muscle contractions as the peristaltic wave passes over ingestible device 400 (e.g., as depicted in diagram 430), and may enable ingestible device 400 to both count the number of muscle contractions that occur, and to determine that a current location of the ingestible device 400 is within the jejunum. For example, ingestible device 400 may be configured to monitor for possible muscle contractions while is inside either the stomach or the duodenum, and may determine that ingestible device 400 has moved to the jejunum in response to detecting a muscle contraction consistent with a peristaltic wave.

Figure 5:
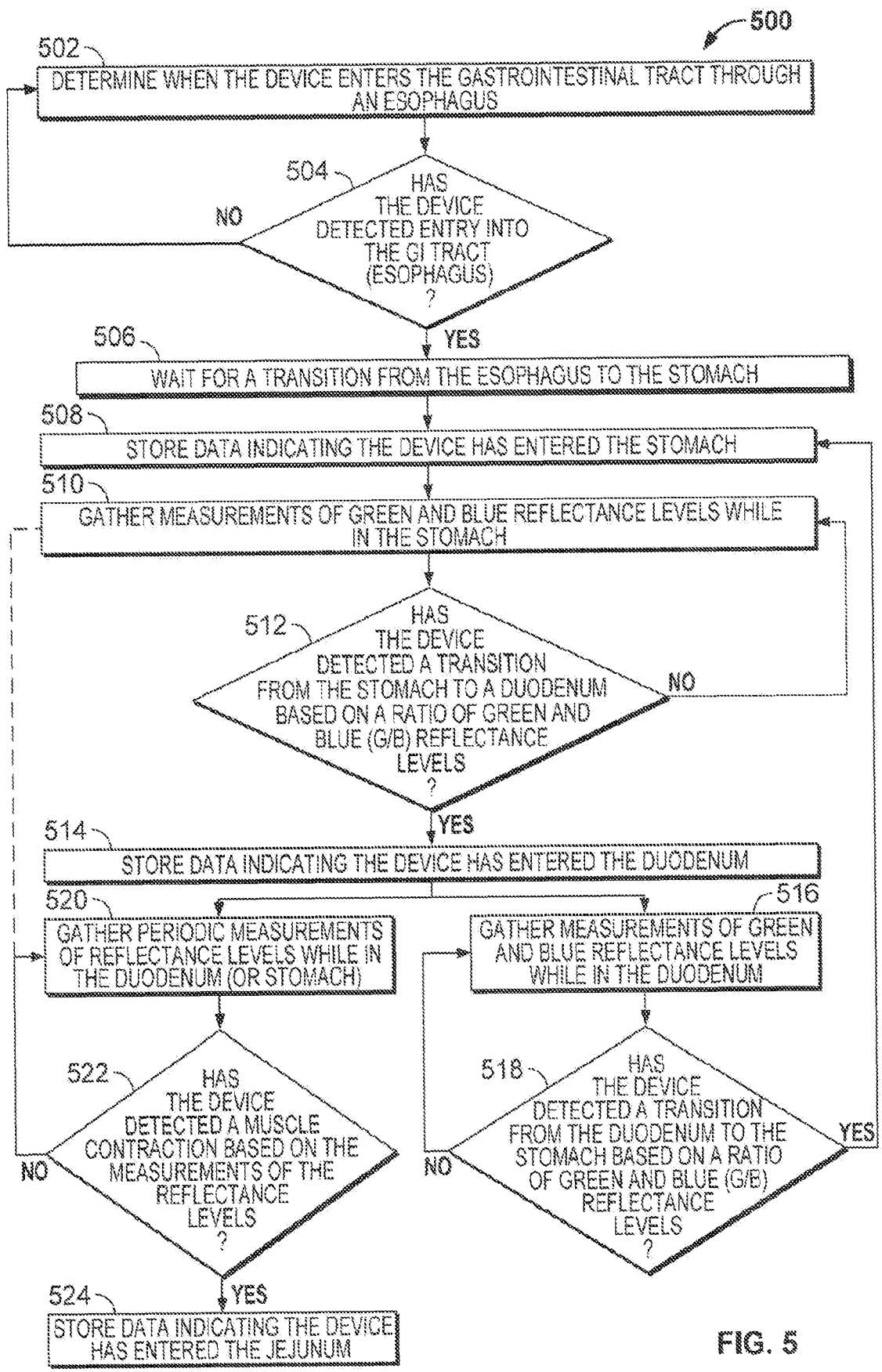
FIG. 5 is a flowchart of illustrative steps for determining a location of an ingestible device as it transits through a GI tract, in accordance with some embodiments of the disclosure.

FIG. 5 is a flowchart illustrating some aspects of a localization process used by the ingestible device. Although FIG. 5 may be described in connection with the ingestible device 100 for illustrative purposes, this is not intended to be limiting, and either portions or the entirety of the localization procedure 500 described in FIG. 5 may be applied to any device discussed in this application (e.g., the ingestible devices 100, 300, and 400), and any of the ingestible devices may be used to perform one or more parts of the process described in FIG. 5. Furthermore, the features of FIG. 5 may be combined with any other systems, methods or processes described in this application. For example, portions of the process in FIG. 5 may be integrated into or combined with the pyloric transition detection procedure described by FIG. 6, or the jejunum detection process described by FIG. 9.

At 502, the ingestible device (e.g., ingestible device 100, 300, or 400) gathers measurements (e.g., through detector 122 (FIG. 2)) of ambient light. For example, ingestible device 100 may be configured to periodically measure (e.g., through detector 122 (FIG. 2)) the level of ambient light in the environment surrounding ingestible device 100. In some embodiments, the type of ambient light being measured may depend on the configuration of detector 122 within ingestible device 100. For example, if detector 122 is configured to measure red, green, and blue wavelengths of light, ingestible device 100 may be configured to measure the ambient amount of red, green, and blue light from the surrounding environment. In some embodiments, the amount of ambient light measured by ingestible device 100 will be larger in the area external to the body (e.g., a well-lit room where ingestible device 100 is being administered to a subject) and in the oral cavity of the subject, as compared to the ambient level of light measured by ingestible device 100 when inside of an esophagus, stomach, or other portion of the GI tract (e.g., esophagus 302, stomach 306, duodenum 310, or jejunum 314 (FIG. 3)).

At 504, the ingestible device (e.g., ingestible device 100, 300, or 400) determines (e.g., via control circuitry within PCB 120 (FIG. 2)) whether the ingestible device has detected entry into the GI tract. For example, ingestible device 100 may be configured to determine when the most recent measurement of ambient light (e.g., the measurement gathered at 502) indicates that the ingestible device has entered the GI tract. For instance, the first time that ingestible device 100 gatherers a measurement of ambient light at 502, ingestible device 100 may store that measurement (e.g., via storage circuitry within PCB 120 (FIG. 2)) as a typical level of ambient light external to the body. Ingestible device 100 may be configured to then compare the most recent measurement of ambient light to the typical level of ambient light external to the body (e.g., via control circuitry within PCB 120 (FIG. 2)), and determine that ingestible device 100 has entered the GI tract when the most recent measurement of ambient light is substantially smaller than the typical level of ambient light external to the body. For example, ingestible device 100 may be configured to detect that it has entered the GI tract in response to determining that the most recent measurement of ambient light is less than or equal to 20% of the typical level of ambient light external to the body. If ingestible device 100 determines that it has detected entry into the GI tract (e.g., that ingestible device 100 has entered at least the esophagus 302 (FIG. 3)), process 500 proceeds to 506. Alternately, if ingestible device 100 determines that it has not detected entry into the GI tract (e.g., as a result of the most recent measurement being similar to the typical level of ambient light external to the body), process 500 proceeds back to 502 where the ingestible device 100 gathers further measurements. For instance, ingestible device 100 may be configured to wait a predetermined amount of time (e.g., five seconds, ten seconds, etc.), and then gather another measurement of the level of ambient light from the environment surrounding ingestible device 100.

At 506, the ingestible device (e.g., ingestible device 100, 300, or 400) waits for a transition from the esophagus to the stomach (e.g., from esophagus 302 to stomach 306 (FIG. 3)). For example, ingestible device 100 may be configured to determine that it has entered the stomach (e.g., stomach 306 (FIG. 3)) after waiting a predetermined period of time after having entered the GI tract. For instance, a typical esophageal transit time in a human patient may be on the order of 15-30 seconds. In this case, after having detected that ingestible device 100 has entered the GI tract at 504 (i.e., after detecting that ingestible device 100 has reached at least esophagus 302 (FIG. 3)), ingestible device 100 may be configured to wait one minute, or a similar amount of time longer than the typical esophageal transmit time (e.g., ninety-seconds), before automatically determining that ingestible device 100 has entered at least the stomach (e.g., stomach 306 (FIG. 3)).

In some embodiments, the ingestible device (e.g., ingestible device 100, 300, or 400) may also determine it has entered the stomach based on measurements of pH or temperature. For example, ingestible device 100 may be configured to determine that it has entered the stomach if a temperature of ingestible device has increased to at least 31 degrees Celsius (i.e., consistent with the temperature inside the stomach), or if a measured pH of the environment surrounding ingestible device 100 is sufficiently acidic (i.e., consistent with the acidic nature of gastric juices that may be found inside the stomach).

At 508, the ingestible device (e.g., ingestible device 100, 300, or 400) stores data indicating the ingestible device has entered the stomach (e.g., stomach 306 (FIG. 3)). For example, after having waited a sufficient amount of time at 506, ingestible device 100 may store data (e.g., within storage circuitry of PCB 120 (FIG. 2)) indicative of ingestible device 100 having entered at least the stomach. Once ingestible device 100 reaches at least the stomach, process 500 proceeds to 510 where ingestible device 100 may be configured to gather data to detect entry into the duodenum (e.g., duodenum 310 (FIG. 3)).

In some embodiments, process 500 may also simultaneously proceed from 508 to 520, where ingestible device 100 may be configured to gather data in order to detect muscle contractions and detect entry into the jejunum (e.g., jejunum 314 (FIG. 3)). In some embodiments, ingestible device 100 may be configured to simultaneously monitor for entry into the duodenum at 516-518, as well as detect for entry into the jejunum at 520-524. This may allow ingestible device 100 to determine when it has entered the jejunum (e.g., as a result of detecting muscle contractions), even when it fails to first detect entry into the duodenum (e.g., as a result of very quick transit times of the ingestible device through the duodenum).

At 510, the ingestible device (e.g., ingestible device 100, 300, or 400) gathers measurements of green and blue reflectance levels (e.g., through the use of illuminator 124 and detector 122 of sensing sub-unit 126 (FIG. 2)) while in the stomach (e.g., stomach 306 (FIG. 3)). For example, ingestible device 100 may be configured to periodically gather measurements of green and blue reflectance levels while in the stomach. For instance, ingestible device 100 may be configured to transmit a green illumination and a blue illumination (e.g., via illuminator 124 (FIG. 2)) every five to fifteen seconds, and measure the resulting reflectance (e.g., via detector 122 (FIG. 2)). Every time that ingestible device 100 gathers a new set of measurements, the measurements may be added to a stored data set (e.g., stored within memory circuitry of PCB 120 (FIG. 2)). The ingestible device 100 may then use this data set to determine whether or not ingestible device 100 is still within a stomach (e.g., stomach 306 (FIG. 3)), or a duodenum (e.g., duodenum 310 (FIG. 3)).

In some embodiments, the ingestible device (e.g., ingestible device 100, 300, or 400) may be configured to detect a first reflectance based on generating an illumination of a first wavelength in approximately the green spectrum of light (between 495-600 nm), and detecting a second reflectance based on generating an illumination of the second wavelength in approximately the blue spectrum of light (between 400-495 nm). In some embodiments, the ingestible device may ensure that the illumination in the green spectrum and the illumination in the blue spectrum have wavelengths separated by at least 50 nm. This may enable ingestible device 100 to sufficiently distinguish between the two wavelengths when detecting the reflectances (e.g., via detector 122 (FIG. 2)). It is understood that the separation of 50 nm is intended to be illustrative, and not limiting, and depending on the accuracy of the detectors within ingestible device 100, smaller separations may be possible to be used.

At 512, the ingestible device (e.g., ingestible device 100, 300, or 400) determines (e.g., using control circuitry within PCB 120 (FIG. 2)) whether the ingestible device has detected a transition from the stomach (e.g., stomach 306 (FIG. 3)) to a duodenum (e.g., duodenum 310 (FIG. 3)) based on a ratio of green and blue (G/B) reflectance levels. For example, ingestible device 100 may obtain (e.g., from memory circuitry of PCB 120 (FIG. 2)) a data set containing historical data for the respective ratio of the green reflectance to the blue reflectance as measured at a respective time. Generally speaking, a duodenum (e.g., duodenum 310 (FIG. 3)) of a human subject reflects a higher ratio of green light to blue light, as compared to the ratio of green light to blue light that is reflected by a stomach (e.g., stomach 306 (FIG. 3)). Based on this, ingestible device 100 may be configured to take a first set of ratios from the data set, representing the result of recent measurements, and compare them to a second set of ratios from the data set, representing the results of past measurements. When the ingestible device 100 determines that the mean value of the first set of ratios is substantially larger than the mean value of the second set of ratios (i.e., that the ratio of reflected green light to reflected blue light has increased), the ingestible device 100 may determine that it has entered the duodenum (e.g., duodenum 310 (FIG. 3)) from the stomach (e.g., stomach 306 (FIG. 3)). If the ingestible device 100 detects a transition from the stomach (e.g., stomach 306 (FIG. 3)) to a duodenum (e.g., duodenum 310 (FIG. 3)), process 500 proceeds to 514, where ingestible device 100 stores data indicating that the ingestible device 100 has entered the duodenum (e.g., duodenum 310 (FIG. 3)). Alternatively, if the ingestible device determines that the ingestible device has not transitioned from the stomach (e.g., stomach 306 (FIG. 3)) to the duodenum (e.g., duodenum 310 (FIG. 3)), process 500 proceeds back to 510 to gather more measurements of green and blue reflectance levels while still in the stomach (e.g., stomach 306 (FIG. 3)). An example procedure for using measurements of green and blue reflectances to monitor for transitions between the stomach and the duodenum is discussed in greater detail in relation to FIG. 6.

In some embodiments, the first time that ingestible device 100 detects a transition from the stomach (e.g., stomach 306 (FIG. 3)) to the duodenum (e.g., duodenum 310 (FIG. 3)), ingestible device 100 may be configured to take a mean of the second set of data, (e.g., the set of data previously recorded while in stomach 306 (FIG. 3)) and store this as a typical ratio of green light to blue light detected within the stomach (e.g., stomach 306 (FIG. 3)) (e.g., within memory circuitry of PCB 120 (FIG. 2)). This stored information may later be used by ingestible device 100 to determine when ingestible device 100 re-enters the stomach (e.g., stomach 306 (FIG. 3)) from the duodenum (e.g., duodenum 310 (FIG. 3)) as a result of a reverse pyloric transition.

At 514, the ingestible device (e.g., ingestible device 100, 300, or 400) stores data indicating that the ingestible device has entered the duodenum (e.g., duodenum 310 (FIG. 3)). For example, ingestible device 100 may store a flag within local memory (e.g., memory circuitry of PCB 120) indicating that the ingestible device 100 is currently in the duodenum. In some embodiments, the ingestible device 100 may also store a timestamp indicating the time when ingestible device 100 entered the duodenum. Once ingestible device 100 reaches the duodenum, process 500 proceeds to 520 where ingestible device 100 may be configured to gather data in order to detect muscle contractions and detect entry into the jejunum (e.g., jejunum 314 (FIG. 3)). Process 500 also proceeds from 514 to 516, where ingestible device 100 may be configured to gather data additional data in order to detect re-entry into the stomach (e.g., stomach 306 (FIG. 3)) from the duodenum (e.g., duodenum 310 (FIG. 3)).

At 516, the ingestible device (e.g., ingestible device 100, 300, or 400) gathers measurements (e.g., via sensing sub-unit 126 (FIG. 2)) of green and blue reflectance levels while in the duodenum (e.g., duodenum 310 (FIG. 3)). For example, ingestible device 100 may be configured to periodically gather measurements (e.g., via sensing sub-unit 126 (FIG. 2)) of green and blue reflectance levels while in the duodenum, similar to the measurements made at 510 while in the stomach. For instance, ingestible device 100 may be configured to transmit a green illumination and a blue illumination (e.g., via illuminator 124 (FIG. 2)) every five to fifteen seconds, and measure the resulting reflectance (e.g., via detector 122 (FIG. 2)). Every time that ingestible device 100 gathers a new set of measurements, the measurements may be added to a stored data set (e.g., stored within memory circuitry of PCB 120 (FIG. 2)). The ingestible device 100 may then use this data set to determine whether or not ingestible device 100 is still within the duodenum (e.g., duodenum 310 (FIG. 3)), or if the ingestible device 100 has transitioned back into the stomach (e.g., stomach 306 (FIG. 3)).

At 518, the ingestible device (e.g., ingestible device 100, 300, or 400) determines a transition from the duodenum (e.g., duodenum 310 (FIG. 3)) to the stomach (e.g., stomach 306 (FIG. 3)) based on a ratio of the measured green reflectance levels to the measured blue reflectance levels. In some embodiments, ingestible device 100 may compare the ratio of the measured green reflectance levels to the measured blue reflectance levels recently gathered by ingestible device 100 (e.g., measurements gathered at 516), and determine whether or not the ratio of the measured green reflectance levels to the measured blue reflectance levels is similar to the average ratio of the measured green reflectance levels to the measured blue reflectance levels seen in the stomach (e.g., stomach 306 (FIG. 3)). For instance, ingestible device 100 may retrieve data (e.g., from memory circuitry of PCB 120 (FIG. 2)) indicative of the average ratio of the measured green reflectance levels to the measured blue reflectance levels seen in the stomach, and determine that ingestible device 100 has transitioned back to the stomach if the recently measured ratio of the measured green reflectance levels to the measured blue reflectance levels is sufficiently similar to the average level in the stomach (e.g., within 20% of the average ratio of the measured green reflectance levels to the measured blue reflectance levels seen in the stomach, or within any other suitable threshold level). If the ingestible device detects a transition from the duodenum (e.g., duodenum 310 (FIG. 3)) to the stomach (e.g., stomach 306 (FIG. 3)), process 500 proceeds to 508 to store data indicating the ingestible device has entered the stomach (e.g., stomach 306 (FIG. 3)), and continues to monitor for further transitions. Alternatively, if the ingestible device does not detect a transition from the duodenum (e.g., duodenum 310 (FIG. 3)) to the stomach (e.g., stomach 306 (FIG. 3)), process 500 proceeds to 516 to gather additional measurements of green and blue reflectance levels while in the duodenum (e.g., duodenum 310 (FIG. 3)), which may be used to continuously monitor for possible transitions back into the stomach. An example procedure for using measurements of green and blue reflectances to monitor for transitions between the stomach and the duodenum is discussed in greater detail in relation to FIG. 6.

At 520, the ingestible device (e.g., ingestible device 100, 300, or 400) gathers periodic measurements of the reflectance levels (e.g., via sensing sub-unit 126 (FIG. 2)) while in the duodenum (e.g., duodenum 310 (FIG. 3)). In some embodiments, the ingestible device (e.g., ingestible device 100, 300, or 400) may gather similar periodic measurements while in the stomach as well. In some embodiments, these periodic measurements may enable ingestible device 100 to detect muscle contractions (e.g., muscle contractions due to a peristaltic wave as discussed in relation to FIG. 4), which may be indicative of entry into a jejunum (e.g., jejunum 314 (FIG. 3)). Ingestible device 100 may be configured to gather periodic measurements using any suitable wavelength of illumination (e.g., by generating illumination using illuminator 124, and detecting the resulting reflectance using detector 122 (FIG. 2)), or combinations of wavelengths of illumination. For example, in some embodiments, ingestible device 100 may be configured to generate red, green, and blue illumination, store separate data sets indicative of red, green, and blue illumination, and analyze each of the data sets separately to search for frequency components in the recorded data indicative of detected muscle contractions. In some embodiments, the measurements gathered by ingestible device 100 at 520 may be sufficiently fast as to detect peristaltic waves in a subject. For instance, in a healthy human subject, peristaltic waves may occur at a rate of approximately 0.1 Hz to 0.2 Hz. Therefore, the ingestible device 400 may be configured to generate illumination and measure the resulting reflectance at least once every 2.5 seconds (i.e., the minimum rate necessary to detect a 0.2 Hz signal), and preferably at a higher rate, such as once every 0.5 seconds or faster, and store values indicative of the resulting reflectances in a data set (e.g., within memory circuitry of PCB 120 (FIG. 2)). After gathering additional data (e.g., after gathering one new data point, or a predetermined number of new data points), process 500 proceeds to 522, where ingestible device 100 determines whether or not a muscle contraction has been detected.

At 522, the ingestible device (e.g., ingestible device 100, 300, or 400) determines (e.g., via control circuitry within PCB 120 (FIG. 2)) whether the ingestible device detects a muscle contraction based on the measurements of reflectance levels (e.g., as gathered by sensing sub-unit 126 (FIG. 2)). For example, ingestible device 100 may obtain a fixed amount of data stored as a result of measurements made at 520 (e.g., retrieve the past minute of data from memory circuitry within PCB 120 (FIG. 2)). Ingestible device 100 may then convert the obtained data into the frequency domain, and search for peaks in a frequency range that would be consistent with peristaltic waves. For example, in a healthy human subject, peristaltic waves may occur at a rate of approximately 0.1 Hz to 0.2 Hz, and an ingestible device 100 may be configured to search for peaks in the frequency domain representation of the data between 0.1 Hz and 0.2 Hz above a threshold value. If the ingestible device 100 detects a contraction based on the reflectance levels (e.g., based on detecting peaks in the frequency domain representation of the data between 0.1 Hz and 0.2 Hz), process 500 proceeds to 524 to store data indicating that the device has entered the jejunum. Alternatively, if the ingestible device 100 does not detect a muscle contraction, process 500 proceeds to 520 to gather periodic measurements of the reflectance levels while in the duodenum (e.g., duodenum 310 (FIG. 3)). In some embodiments, the ingestible device (e.g., ingestible device 100, 300, or 400) may store data (e.g., within memory circuitry of PCB 120 (FIG. 2)) indicating that a muscle contraction was detected, and process 500 will not proceed from 522 to 524 until a sufficient number of muscle contractions have been detected.

At 524, the ingestible device (e.g., ingestible device 100, 300, or 400) stores data (e.g., within memory circuitry of PCB 120 (FIG. 2)) indicating that the device has entered the jejunum (e.g., jejunum 314 (FIG. 3)). For example, in response to detecting that muscle contraction has occurred at 522, ingestible device 100 may determine that it has entered the jejunum 314, and is no longer inside of the duodenum (e.g., duodenum 310 (FIG. 3)) or the stomach (e.g., stomach 306 (FIG. 3)). In some embodiments, the ingestible device 100 may continue to measure muscle contractions while in the jejunum, and may store data indicative of the frequency, number, or strength of the muscle contractions over time (e.g., within memory circuitry of PCB 120 (FIG. 2)). In some embodiments, the ingestible device 100 may also be configured to monitor for one or more transitions. Such transitions can include a transition from the jejunum to the ileum, an ileoceacal transition from the ileum to the cecum, a transition from the cecum to the colon, or detect exit from the body (e.g., by measuring reflectances, temperature, or levels of ambient light).

In some embodiments, the ingestible device (e.g., ingestible device 100, 300, or 400) may also determine that it has entered the jejunum (e.g., jejunum 314 (FIG. 3)) after a pre-determined amount of time has passed after having detected entry into the duodenum (e.g., duodenum 310 (FIG. 3)). For example, barring a reverse pyloric transition from the duodenum (e.g., duodenum 310 (FIG. 3)) back to the stomach (e.g., stomach 306 (FIG. 3)), the typical transit time for an ingestible device to reach the jejunum from the duodenum in a healthy human subject is less than three minutes. In some embodiments, the ingestible device (e.g., ingestible device 100, 300, or 400) may therefore be configured to automatically determine that it has entered the jejunum after spending at least three minutes within the duodenum. This determination may be made separately from the determination made based on measured muscle contractions (e.g., the determination made at 522), and in some embodiments, ingestible device 100 may determine that it has entered the jejunum in response to either detecting muscle contractions, or after three minutes has elapsed from having entered the duodenum (e.g., as determined by storing data at 514 indicative of the time that ingestible device entered the duodenum).

For illustrative purposes, 512-518 of process 500 describe the ingestible device (e.g., ingestible device 100, 300, or 400) measuring green reflectances and blue reflectances, calculating a ratio of the two reflectances, and using this information to determine when the ingestible device has transitioned between the duodenum and stomach. However, in some embodiments, other wavelengths of light may be used other than green and blue, provided that the wavelengths of light chosen have different reflective properties within the stomach and the duodenum (e.g., as a result of different reflection coefficients of the stomach tissue and the tissue of the duodenum).

It will be understood that the steps and descriptions of the flowcharts of this disclosure, including FIG. 5, are merely illustrative. Any of the steps and descriptions of the flowcharts, including FIG. 5, may be modified, omitted, rearranged, and performed in alternate orders or in parallel, two or more of the steps may be combined, or any additional steps may be added, without departing from the scope of the present disclosure. For example, the ingestible device 100 may calculate the mean and the standard deviation of multiple data sets in parallel in order to speed up the overall computation time. As another example, ingestible device 100 may gather data periodic measurements and detect possible muscle contractions (e.g., at 520-522) while simultaneously gathering green and blue reflectance levels to determine transitions to and from the stomach and duodenum (e.g., at 510-518). Furthermore, it should be noted that the steps and descriptions of FIG. 5 may be combined with any other system, device, or method described in this application, including processes 600 (FIG. 6) and 900 (FIG. 9), and any of the ingestible devices or systems discussed in this application (e.g., ingestible devices 100, 300, or 400) could be used to perform one or more of the steps in FIG. 5.

Figure 6:
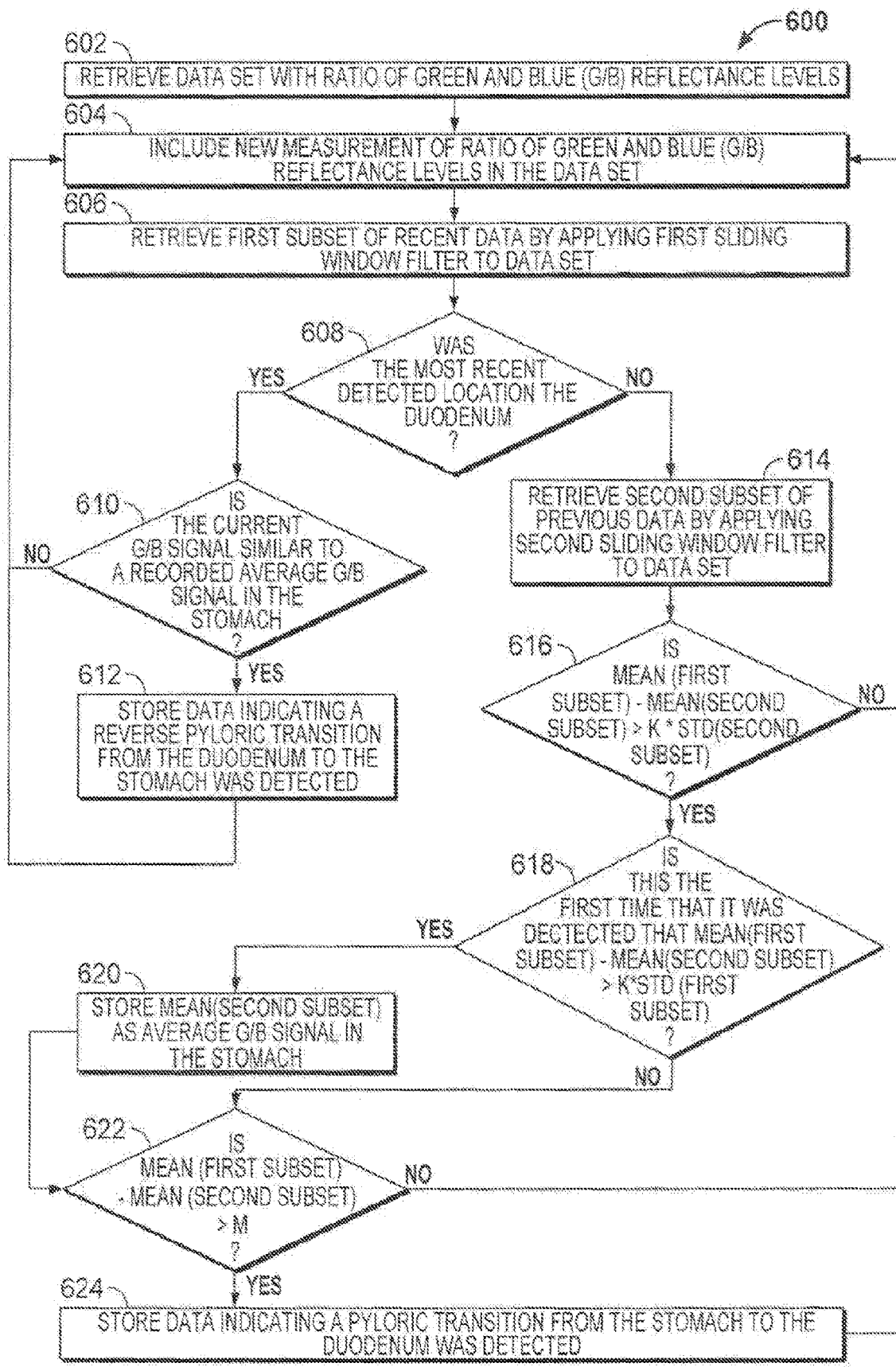
FIG. 6 is a flowchart of illustrative steps for detecting transitions from a stomach to a duodenum and from a duodenum back to a stomach, which may be used when determining a location of an ingestible device as it transits through a GI tract, in accordance with some embodiments of the disclosure.

FIG. 6 is a flowchart illustrating some aspects of a process for detecting transitions from a stomach to a duodenum and from a duodenum back to a stomach, which may be used when determining a location of an ingestible device as it transits through a gastrointestinal (GI) tract, in accordance with some embodiments of the disclosure. In some embodiments, process 600 may begin when an ingestible device first detects that it has entered the stomach, and will continue as long as the ingestible device determines that it is within the stomach or the duodenum. In some embodiments, process 600 may only be terminated when an ingestible device determines that it has entered the jejunum, or otherwise progressed past the duodenum and the stomach. Although FIG. 6 may be described in connection with the ingestible device 100 for illustrative purposes, this is not intended to be limiting, and either portions or the entirety of the duodenum detection process 600 described in FIG. 6 may be applied to any device discussed in this application (e.g., the ingestible devices 100, 300, or 400), and any of the ingestible devices may be used to perform one or more parts of the process described in FIG. 6. Furthermore, the features of FIG. 6 may be combined with any other systems, methods or processes described in this application. For example, portions of the process described by the process in FIG. 6 may be integrated into process 500 discussed in relation to FIG. 5.

At 602, the ingestible device (e.g., ingestible device 100, 300, or 400) retrieves a data set (e.g., from memory circuitry within PCB 120 (FIG. 2)) with ratios of the measured green reflectance levels to the measured blue reflectance levels over time. For example, ingestible device 100 may retrieve a data set from PCB 120 containing recently recorded ratios of the measured green reflectance levels to the measured blue reflectance levels (e.g., as recorded at 510 or 516 of process 500 (FIG. 5)). In some embodiments, the retrieved data set may include the ratios of the measured green reflectance levels to the measured blue reflectance levels over time. Example plots of data sets of ratios of the measured green reflectance levels to the measured blue reflectance levels are discussed further in relation to FIG. 7 and FIG. 8.

At 604, the ingestible device (e.g., ingestible device 100, 300, or 400) includes a new measurement (e.g., as made with sensing sub-unit 126 (FIG. 2)) of a ratio of the measured green reflectance level to the measured blue reflectance level in the data set. For example, ingestible device 100 may be configured to occasionally record new data by transmitting green and blue illumination (e.g., via illuminator 124 (FIG. 2)), detecting the amount of reflectance received due to the green and blue illumination (e.g., via detector 122 (FIG. 2)), and storing data indicative of the amount of the received reflectance (e.g., in memory circuitry of PCB 120 (FIG. 2)). The ingestible device 100 may be configured to record new data every five to fifteen seconds, or at any other convenient interval of time. For illustrative purposes, ingestible device 100 is described as storing and retrieving the ratio of the measured green reflectance levels to the measured blue reflectance levels (e.g., if the amount of detected green reflectance was identical to the amount of detected blue reflectance at a given time, the ratio of the green and blue reflectances would be "1.0" at that given time); however, it is understood that the green reflectance data and the blue reflectance data may be stored separately within the memory of ingestible device 100 (e.g., stored as two separate data sets within memory circuitry of PCB 120 (FIG. 2)).

At 606, the ingestible device (e.g., ingestible device 100, 300, or 400) retrieves a first subset of recent data by applying a first sliding window filter to the data set. For example, ingestible device 100 may use a sliding window filter to obtain a predetermined amount of the most recent data within the data set, which may include any new values of the ratio of the measured green reflectance level to the measured blue reflectance level obtained at 604. For instance, the ingestible device may be configured to select between ten and forty data points from the data set, or ingestible device 100 may be configured to select a predetermined range of data values between fifteen seconds of data and five minutes of data. In some embodiments, other ranges of data may be selected, depending on how frequently measurements are recorded, and the particular application at hand. For instance, any suitable amount of data may be selected in the sliding window, provided that it is sufficient to detect statistically significant differences between the data selected in a second sliding window (e.g., the second subset of data selected at 614).

In some embodiments, the ingestible device (e.g., ingestible device 100, 300, or 400) may also be configured to remove outliers from the data set, or to smooth out unwanted noise in the data set. For example, ingestible device 100 may select the first subset of data, or any other subset of data, by first obtaining a raw set of values by applying a window filter to the data set (e.g., selecting a particular range of data to be included). Ingestible device 100 may then be configured to identify outliers in the raw set of values; for instance, by identifying data points that are over three standard deviations away from the mean value of the raw set of values, or any other suitable threshold. Ingestible device 100 may then determine the subset of data by removing outliers from the raw set of values. This may enable ingestible device 100 to avoid spurious information when determining whether or not it is located within the stomach or the duodenum.

At 608, the ingestible device (e.g., ingestible device 100, 300, or 400) determines whether the most recently detected location was the duodenum (e.g., duodenum 310 (FIG. 3)). In some embodiments, ingestible device 100 may store a data flag (e.g., within memory circuitry of PCB 120 (FIG. 2)) indicating the most recent portion of the GI tract that the ingestible device 100 detected itself to be within. For instance, every time ingestible device 100 detects entry to the stomach (e.g., detects entry into stomach 306 (FIG. 3) as a result of the decision made at 610), a flag is stored in memory indicating the ingestible device 100 is in the stomach (e.g., as part of storing data at 612). If ingestible device 100 subsequently detects entry into the duodenum (e.g., detects entry into duodenum 310 (FIG. 3) as a result of a decision made at 624), another different flag is stored in memory indicating that the ingestible device 100 is in the duodenum (e.g., as part of storing data at 624). In this case, ingestible device 100 may retrieve the most recently stored flag at 608, and determine whether or not the flag indicates that the ingestible device 100 was most recently within the duodenum. If ingestible device 100 detects that it was most recently in the duodenum, process 600 proceeds to 610 where the ingestible device compares the recent measurements of the ratios of the measured green reflectance levels to the measured blue reflectance levels (e.g., measurements that include the recent measurement made at 606) to the typical ratios measured within the stomach, and uses this information to determine whether a reverse pyloric transition from the duodenum back to the stomach has occurred. Alternately, if ingestible device 100 detects that it was not most recently in the duodenum (e.g., because it was in the stomach instead), process 600 proceeds to 614 where the ingestible device compares the recent measurements of the ratios of the measured green reflectance levels to the measured blue reflectance levels (e.g., measurements that include the recent measurement made at 606) to past measurements, and uses this information to determine whether a pyloric transition from the stomach to the duodenum has occurred.

Process 600 proceeds from 608 to 610 when the ingestible device determined that it was most recently in the duodenum. At 610, the ingestible device (e.g., ingestible device 100, 300, or 400) determines (e.g., via control circuitry within PCB 120 (FIG. 2)) whether the current G/B signal is similar to a recorded average G/B signal in the stomach. For example, ingestible device 100 may be configured to have previously stored data (e.g., within memory circuitry of PCB 120 (FIG. 2)) indicative of the average ratio of the measured green reflectance levels to the measured blue reflectance levels measured in the stomach. Ingestible device 100 may then retrieve this stored data indicative of the average ratio of the measured green reflectance levels to the measured blue reflectance levels in the stomach, and compare this against the recent measurements in order to determine whether or not ingestible device 100 has returned back to the stomach from the duodenum. For instance, ingestible device 100 may determine if the mean value of the first subset of recent data (i.e., the average value of the recently measured ratios of the measured green reflectance levels to the measured blue reflectance levels) is less than the average ratio of the measured green reflectance levels to the measured blue reflectance levels within the stomach, or less that the average ratio measured within the stomach plus a predetermined number times the standard deviation of the ratios measured within the stomach. For instance, if the average ratio of the measured green reflectance levels to the measured blue reflectance levels in the stomach was "1," with a standard deviation of "0.2," ingestible device 100 may determine whether or not the mean value of the first subset of data is less than "1.0+k*0.2," where "k" is a number between zero and five. It is understood that, in some embodiments, the ingestible device 100 may be configured to use a different threshold level to determine whether or not the mean value of the first subset of recent data is sufficiently similar to the average ratio of the measured green reflectance levels to the measured blue reflectance levels within the stomach. In response to determining that the recent ratio of the measured green reflectance levels to the measured blue reflectance levels is similar to the average ratio of measured green and blue reflectance levels seen in the stomach, process 600 proceeds to 612 where ingestible device 100 stores data indicating that it has re-entered the stomach from the duodenum. Alternately, in response to determining that the recent ratio of measured green and blue reflectance levels is sufficiently different from the average ratio of measured green and blue reflectance levels seen in the stomach, ingestible device 100 proceeds directly to 604, and continues to obtain new data on an ongoing basis.

At 612, the ingestible device (e.g., ingestible device 100, 300, or 400) stores data indicating a reverse pyloric transition from the duodenum to the stomach was detected. For example ingestible device 100 may store a data flag (e.g., within memory circuitry of PCB 120 (FIG. 2)) indicating that the ingestible device 100 most recently detected itself to be within the stomach portion of the GI tract (e.g., stomach 306 (FIG. 3)). In some embodiments, ingestible device 100 may also store data (e.g., within memory circuitry of PCB 120 (FIG. 2)) indicating a time that ingestible device 100 detected the reverse pyloric transition from the duodenum to the stomach. This information may be used by ingestible device 100 at 608, and as a result process 600 may proceed from 608 to 614, rather than proceeding from 618 to 610. After ingestible device 100 stores the data indicating a reverse pyloric transition from the duodenum to the stomach was detected, process 600 proceeds to 604 where ingestible device 100 continues to gather additional measurements, and continues to monitor for further transitions between the stomach and the duodenum.

Process 600 proceeds from 608 to 614 when the ingestible device determined that it was not most recently in the duodenum (e.g., as a result of having most recently been in the stomach instead). At 614, the ingestible device (e.g., ingestible device 100, 300, or 400) retrieves a second subset of previous data by applying a second sliding window filter to the data set. For example, ingestible device 100 may use a sliding window filter to obtain a predetermined amount of older data from a past time range, which may be separated from recent time range used to select the first subset of data gathered at 606 by a predetermined period of time. In some embodiments, any suitable amount of data may be selected by the first and second window filters, and the first and second window filters may be separated by any appropriate predetermined amount of time. For example, in some embodiments, the first window filter and the second window filter may each be configured to select a predetermined range of data values from the data set, the predetermined range being between fifteen seconds of data and five minutes of data. In some embodiments, the recent measurements and the past measurements may then be separated by a predetermined period of time that is between one to five times the predetermined range of data values. For instance, ingestible device 100 may select the first subset of data and the second subset of data to each be one minute of data selected from the dataset (i.e., selected to have a predetermined range of one minute), and the first subset of data and the second subset of data are selected from recorded measurements that are at least two minutes apart (i.e., the predetermined period of time is two minutes, which is twice the range used to select the subsets of data using the window filters). As another example, ingestible device 100 may select the first subset of data and the second subset of data to each be five minutes of data selected from the dataset (i.e., selected to have a predetermined range of five minutes), and the first subset of data and the second subset of data are selected from recorded measurements that are at least 10 minutes apart (i.e., the predetermined period of time is two minutes, which is twice the range used to select the subsets of data using the window filters).

In some embodiments, if ingestible device 100 recently transitioned to the stomach from the duodenum (e.g., as determined by checking for recent data stored within ingestible device 100 at 612), ingestible device 100 may select the second subset of data at 614 from a time frame when ingestible device 100 is known to be within the stomach. In some embodiments, ingestible device 100 may alternately select a previously recorded average and standard deviation for ratios of green reflectances and blue reflectances within the stomach (e.g., an average and standard deviation typical of data recorded within the stomach, as previously recorded within memory circuitry of PCB 120 at 620) in place of the second subset of data. In this case, ingestible device 100 may simply use the previously recorded average and previously recorded standard deviation when making a determination at 616, rather than expending resources to calculate the mean and standard deviation of the second subset.

At 616, the ingestible device (e.g., ingestible device 100, 300, or 400) determines whether the difference between the mean of the second subset and the mean of the first subset is greater than a predetermined multiple of the standard deviation of the first subset. For example, ingestible device 100 may compute a difference between a mean of the first subset of recent data and a mean of a second subset of past data, and determine whether this difference is greater than three times the standard deviation of the second subset of past data. In some embodiments, it is understood that any convenient threshold level may be used other than three times the standard deviation, such as any value between one and five times the standard deviation. Also, in some embodiments, the ingestible device may instead set the threshold level based on the standard deviation of the second subset instead of the first subset. In response to determining that the difference between the mean of the first subset and the mean of the second subset is greater than a predetermined multiple of the standard deviation of the second subset, process 600 proceeds to 618. Otherwise, process 600 proceeds back to 604, where the ingestible device 604 continues to gather new data to be used in monitoring for transitions between the stomach (e.g., stomach 306 (FIG. 3)) and the duodenum (e.g., duodenum 310 (FIG. 3)).

At 618, the ingestible device (e.g., ingestible device 100, 300, or 400) determines (e.g., via control circuitry within PCB 120 (FIG. 2)) whether the determination made at 616 is the first time that the difference between the mean of the first subset of recent data and the mean of the second subset of past data is calculated to be greater than the standard deviation of the second subset. If the ingestible device determines that this is the first time that the difference between the mean of the first subset and the mean of the second subset is calculated to be greater than the standard deviation of the second subset, process 600 proceeds to 620 to store the mean of the second subset of past data as an average G/B signal in the stomach. Alternatively, if the ingestible device determines that the immediately preceding determination made at 616 is not the first time that the difference between the mean of the first subset of recent data and the mean of the second subset of past data is calculated to be greater than the standard deviation of the second subset, process 600 proceeds directly to 622.

At 620, the ingestible device (e.g., ingestible device 100, 300, or 400) stores the mean of the second subset as an average G/B signal in the stomach. For example, ingestible device 100 may be configured to store the mean of the second subset of past data (e.g., store within memory circuitry of PCB 120 (FIG. 2)) as the average ratio of the measured green reflectance levels to the measured blue reflectance levels measured in the stomach. In some embodiments, ingestible device 100 may also store the standard deviation of the second subset of past data as a typical standard deviation of the ratios of the measured green reflectance levels to the measured blue reflectance levels detected within the stomach. This stored information may be used by the ingestible device later on (e.g., at 610) to compare against future data, which may enable the ingestible device to detect reverse pyloric transitions from the duodenum (e.g., duodenum 310 (FIG. 3)) back to the stomach (e.g., stomach 306 (FIG. 3)), and may generally be used in place of other experimental data gathered from the stomach (e.g., in place of the second subset of data at 616). After storing the mean of the second subset as an average G/B signal in the stomach, process 600 proceeds to 622.

At 622, the ingestible device (e.g., ingestible device 100, 300, or 400) determines whether a difference of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable ingestible device 100 to ensure that it detected an actual transition to the duodenum. This may be particularly advantageous when the determination made at 616 is potentially unreliable due to the standard deviation of the second subset of past data being abnormally small. For example, a typical value of the predetermined threshold "M," may be on the order of 0.1 to 0.5. If ingestible device 100 determines that the difference of the mean of the first subset of recent data to the second subset of past data is greater than a predetermined threshold, process 600 proceeds to 624 to store data indicating that a pyloric transition from the stomach to the duodenum (e.g., from stomach 306 to duodenum 310 (FIG. 3)) was detected. Alternatively, if the ingestible device determines that the ratio of the mean of the first subset to the second subset is less than or equal to the predetermined threshold, "M" (i.e., determines that a transition to the duodenum has not occurred), process 600 proceeds directly to 604 where ingestible device 100 continues to make new measurements and monitor for possible transitions between the stomach and the duodenum.

In some embodiments, instead of using a difference of the mean of the first subset of recent data to the mean of the second subset of past data, the ingestible device (e.g., ingestible device 100, 300, or 400) determines whether the ratio of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable ingestible device 100 to ensure that it detected an actual transition to the duodenum. This may be particularly advantageous when the determination made at 616 is potentially unreliable due to the standard deviation of the second subset of past data being abnormally small. For example, a typical value of the predetermined threshold "M," may be on the order of 1.2 to 2.0. It is understood any convenient type of threshold or calculation may be used to determine whether or not the first subset of data and the second subset of data are both statistically distinct from one another, and also substantially different from one another in terms of overall average value.

At 624, the ingestible device (e.g., ingestible device 100, 300, or 400) stores data indicating a pyloric transition from the stomach to the duodenum was detected. For example ingestible device 100 may store a data flag (e.g., within memory circuitry of PCB 120 (FIG. 2)) indicating that the ingestible device 100 most recently detected itself to be within the duodenum portion of the GI tract (e.g., duodenum 310 (FIG. 3)). In some embodiments, ingestible device 100 may also store data (e.g., within memory circuitry of PCB 120 (FIG. 2)) indicating a time that ingestible device 100 detected the pyloric transition from the stomach to the duodenum. This information may be used by ingestible device 100 at 608, and as a result process 600 may proceed from 608 to 610, rather than proceeding from 618 to 614. After ingestible device 100 stores the data indicating a pyloric transition from the stomach to the duodenum was detected, process 600 proceeds to 604 where ingestible device 100 continues to gather additional measurements, and continues to monitor for further transitions between the stomach and the duodenum.

It will be understood that the steps and descriptions of the flowcharts of this disclosure, including FIG. 6, are merely illustrative. Any of the steps and descriptions of the flowcharts, including FIG. 6, may be modified, omitted, rearranged, and performed in alternate orders or in parallel, two or more of the steps may be combined, or any additional steps may be added, without departing from the scope of the present disclosure. For example, the ingestible device 100 may calculate the mean and the standard deviation of multiple data sets in parallel in order to speed up the overall computation time. Furthermore, it should be noted that the steps and descriptions of FIG. 6 may be combined with any other system, device, or method described in this application, and any of the ingestible devices or systems discussed in this application could be used to perform one or more of the steps in FIG. 6. For example, portions of process 600 may be incorporated into 508-516 of process 500 (FIG. 5), and may be part of a more general process for determining a location of the ingestible device. As another example, the ratio of detected blue and green light (e.g., as measured and added to the data set at 604) may continue even outside of the stomach or duodenum, and similar information may be recorded by the ingestible device throughout its transit in the GI tract. Example plots of data sets of ratios of measured green and blue reflectance levels, which may be gathered throughout the GI tract, are discussed further in relation to FIG. 7 and FIG. 8 below.

Figure 7:
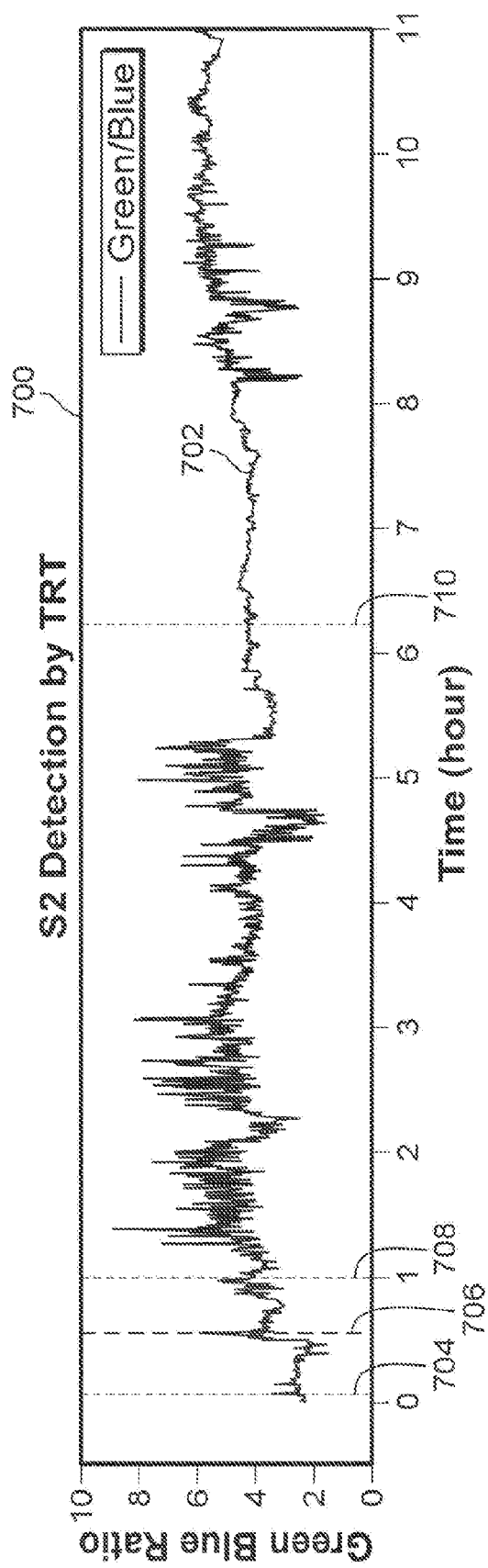
FIG. 7 is a plot illustrating data collected during an example operation of an ingestible device, which may be used when determining a location of an ingestible device as it transits through a GI tract, in accordance with some embodiments of the disclosure.

FIG. 7 is a plot illustrating data collected during an example operation of an ingestible device (e.g., ingestible device 100, 300, or 400), which may be used when determining a location of an ingestible device as it transits through a gastrointestinal (GI) tract, in accordance with some embodiments of the disclosure.

Although FIG. 7 may be described in connection with ingestible device 100 for illustrative purposes, this is not intended to be limiting, and plot 700 and data set 702 may be typical of data gathered by any device discussed in this application. Plot 700 depicts the ratios of the measured green reflectance levels to the measured blue reflectance levels over time. For example, ingestible device 100 may have computed the value for each point in the data set 702 by transmitting green and blue illumination at a given time (e.g., via illuminator 124 (FIG. 2)), measuring the resulting green and blue reflectances (e.g., via detector 122 (FIG. 2)), calculating the ratio of the resulting reflectances, and storing the ratio in the data set along with a timestamp indicating the time that the reflectances were gathered.

At 704, shortly after ingestible device 100 begins operation, ingestible device 100 determines that it has reached at least the stomach (e.g., as a result of making a determination similar to the determination discussed in relation to 506 in process 500 (FIG. 5)). Ingestible device 100 continues to gather additional measurements of green and blue reflectance levels, and at 706 ingestible device 100 determines that a pyloric transition has occurred from the stomach to the duodenum (e.g., as a result of making a determination similar to the determinations discussed in relation to 616-624 of process 600 (FIG. 6)). Notably, the values in data set 702 around 706 jump up precipitously, which is indicative of the higher ratios of measured green reflectance levels to measured blue reflectance levels typical of the duodenum.

The remainder of the data set 702 depicts the ratios of the measured green reflectance levels to the measured blue reflectance levels throughout the remainder of the GI tract. At 708, ingestible device 100 has reached the jejunum (e.g., as determined through measurements of muscle contractions, as discussed in relation to FIG. 9), and by 710, ingestible device 100 has reached the cecum. It is understood that, in some embodiments, the overall character and appearance of data set 702 changes within the small intestine (i.e., the duodenum, jejunum, and ileum) versus the cecum. Within the jejunum and ileum, there may typically be a wide variation in the ratios of the measured green reflectance levels to the measured blue reflectance levels, resulting in relatively noisy data with a high standard deviation. By comparison, within the cecum ingestible device 100 may measure a relatively stable ratio of the measured green reflectance levels to the measured blue reflectance levels. In some embodiments, ingestible device 100 may be configured to determine transitions from the small intestine to the cecum based on these differences. For example, ingestible device 100 may compare recent windows of data to past windows of data, and detect a transition to the cecum in response to determining that the standard deviation of the ratios in the recent window of data is substantially less than the standard deviation of the ratios in the past window of data.

Figure 8:
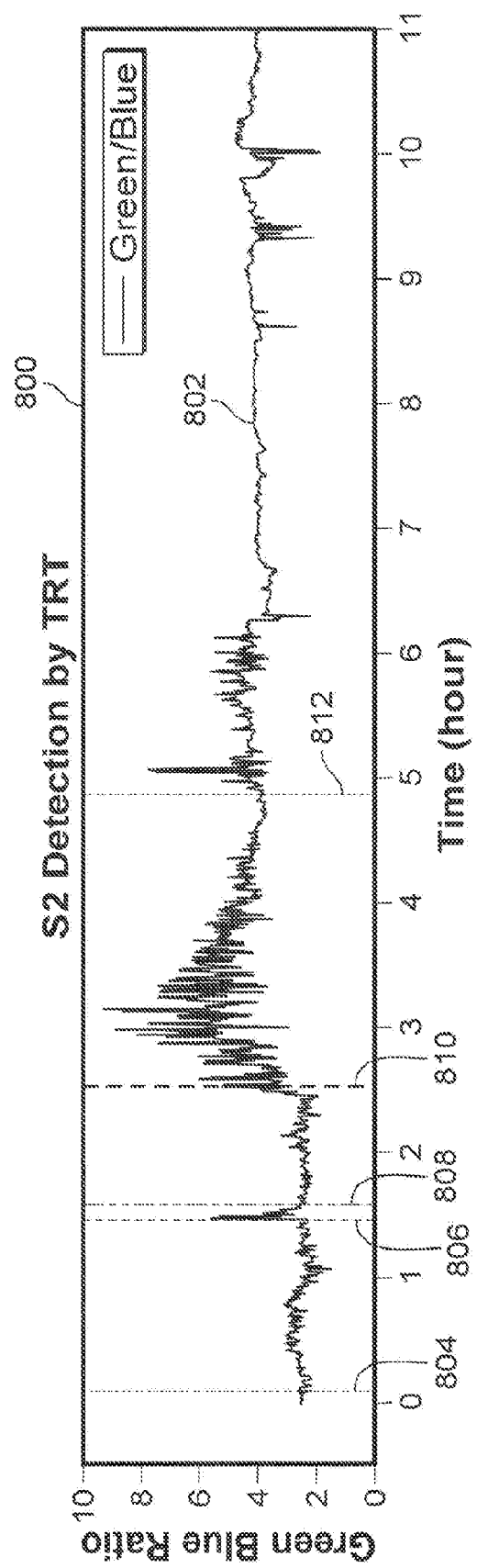
FIG. 8 is another plot illustrating data collected during an example operation of an ingestible device, which may be used when determining a location of an ingestible device as it transits through a GI tract, in accordance with some embodiments of the disclosure.

FIG. 8 is another plot illustrating data collected during an example operation of an ingestible device, which may be used when determining a location of an ingestible device as it transits through a gastrointestinal (GI) tract, in accordance with some embodiments of the disclosure. Similar to FIG. 7, FIG. 8 may be described in connection with the ingestible device 100 for illustrative purposes. However, this is not intended to be limiting, and plot 800 and data set 802 may be typical of data gathered by any device discussed in this application.

At 804, shortly after ingestible device 100 begins operation, ingestible device 100 determines that it has reached at least the stomach (e.g., as a result of making a determination similar to the determination discussed in relation to 506 in process 500 (FIG. 5)). Ingestible device 100 continues to gather additional measurements of green and blue reflectance levels (e.g., via sensing sub-unit 126 (FIG. 2)), and at 806 ingestible device 100 determines that a pyloric transition has occurred from the stomach to the duodenum (e.g., as a result of making a determination similar to the determinations discussed in relation to 616-624 of process 600 (FIG. 6)). Notably, the values in data set 802 around 806 jump up precipitously, which is indicative of the higher ratios of measured green reflectance levels to measured blue reflectance levels typical of the duodenum, before falling shortly thereafter. As a result of the reduced values in data set 802, ingestible device 100 determines that a reverse pyloric transition has occurred from the duodenum back to the stomach at 808 (e.g., as a result of making a determination similar to the determinations discussed in relation to 610-612 of process 600 (FIG. 6)). At 810, as a result of the values in data set 802 increasing again, ingestible device 100 determines that another pyloric transition has occurred from the stomach to the duodenum, and shortly thereafter ingestible device 100 proceeds onwards to the jejunum, ileum, and cecum.

The remainder of the data set 802 depicts the ratios of the measured green reflectance levels to the measured blue reflectance levels throughout the remainder of the GI tract. Notably, at 812, ingestible device reaches the transition point between the ileum and the cecum. As discussed above in relation to FIG. 7, the transition to the cecum is marked by a reduced standard deviation in the ratios of measured green reflectances and measured blue reflectances over time, and ingestible device 100 may be configured to detect a transition to the cecum based on determining that the standard deviation of a recent set of measurements is substantially smaller than the standard deviation of past measurements taken from the jejunum or ileum.

Figure 9:
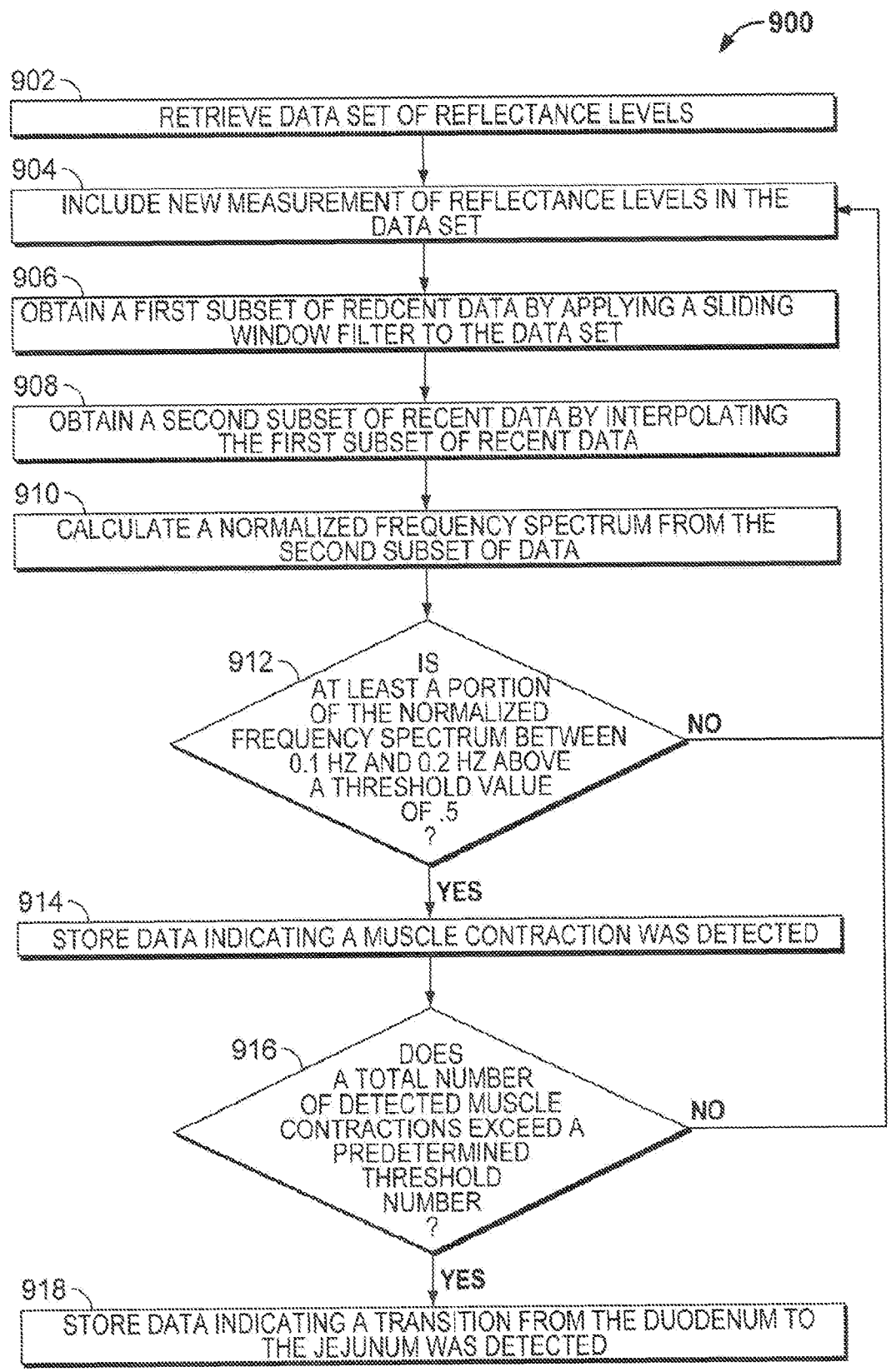
FIG. 9 is a flowchart of illustrative steps for detecting a transition from a duodenum to a jejunum, which may be used when determining a location of an ingestible device as it transits through a GI tract, in accordance with some embodiments of the disclosure.

FIG. 9 is a flowchart of illustrative steps for detecting a transition from a duodenum to a jejunum, which may be used when determining a location of an ingestible device as it transits through a gastrointestinal (GI) tract, in accordance with some embodiments of the disclosure. Although FIG. 9 may be described in connection with the ingestible device 100 for illustrative purposes, this is not intended to be limiting, and either portions or the entirety of process 900 described in FIG. 9 may be applied to any device discussed in this application (e.g., the ingestible devices 100, 300, and 400), and any of these ingestible devices may be used to perform one or more parts of the process described in FIG. 9. Furthermore, the features of FIG. 9 may be combined with any other systems, methods or processes described in this application. For example, portions of the process described by the process in FIG. 9 may be integrated into the localization process described by FIG. 5 (e.g., as part of 520-524 of process 500 (FIG. 5)). In some embodiments, an ingestible device 100 may perform process 900 while in the duodenum, or in response to detecting entry to the duodenum. In other embodiments, an ingestible device 100 may perform process 900 while in the stomach, or in response to detecting entry into the GI tract. It is also understood that process 900 may be performed in parallel with any other process described in this disclosure (e.g., process 600 (FIG. 6)), which may enable ingestible device 100 to detect entry into various portions of the GI tract, without necessarily detecting entry into a preceding portion of the GI tract.

For illustrative purposes, FIG. 9 may be discussed in terms of ingestible device 100 generating and making determinations based on a single set of reflectance levels generated at a single wavelength by a single sensing sub-unit (e.g., sensing sub-unit 126 (FIG. 2)). However, it is understood that ingestible device 100 may generate multiple wavelengths of illumination from multiple different sensing sub-units positioned around the circumference of ingestible device (e.g., multiple sensing sub-units positioned at different locations behind window 114 of ingestible device 100 (FIG. 1), and each of the resulting reflectances may be stored as a separate data set. Moreover, each of these sets of reflectance levels may be used to detect muscle contractions by running multiple versions of process 900, each one of which processes data for a different set of reflectances corresponding to data sets obtained from measurements of different wavelengths or measurements made by different sensing sub-units.

At 902, the ingestible device (e.g., ingestible device 100, 300, or 400) retrieves a set of reflectance levels. For example, ingestible device 100 may retrieve a data set of previously recorded reflectance levels from memory (e.g., from memory circuitry of PCB 120 (FIG. 2)). Each of the reflectance levels may correspond to reflectances previously detected by ingestible device 100 (e.g., via detector 122 (FIG. 2)) from illumination generated by ingestible device 100 (e.g., via illuminator 124 (FIG. 2)), and may represent a value indicative of an amount of light detected in a given reflectance. However, it is understood that any suitable frequency of light may be used, such as light in the infrared, visible, or ultraviolet spectrums. In some embodiments, the reflectance levels may correspond to reflectances previously detected by ingestible device 100 at periodic intervals.

At 904, the ingestible device (e.g., ingestible device 100, 300, or 400) includes new measurements of reflectance levels in the data set. For example, ingestible device 100 may be configured to detect a new reflectance (e.g., transmit illumination and detect the resulting reflectance using sensing sub-unit 126 (FIG. 2)) at regular intervals, or with sufficient speed as to detect peristaltic waves. For example, ingestible device 100 may be configured to generate illumination and measure the resulting reflectance once every three seconds (i.e., the minimum rate necessary to detect a 0.17 Hz signal), and preferably at a higher rate, as fast at 0.1 second or even faster. It is understood that the periodic interval between measurements may be adapted as needed based on the species of the subject, and the expected frequency of the peristaltic waves to be measured. Every time ingestible device 100 makes a new reflectance level measurement at 904, the new data is included to the data set (e.g., a data set stored within memory circuitry of PCB 120 (FIG. 2)).

At 906, the ingestible device (e.g., ingestible device 100, 300, or 400) obtains a first subset of recent data by applying a sliding window filter to the data set. For example, ingestible device 100 may retrieve a one-minute worth of data from the data set. If the data set includes values for reflectances measured every second, this would be approximately 60 data points worth of data. Any suitable type of window size may be used, provided that the size of the window is sufficiently large to detect peristaltic waves (e.g., fluctuations on the order of 0.1 Hz to 0.2 Hz for healthy human subjects). In some embodiments, ingestible device 100 may also clean the data, for example, by removing outliers from the first subset of data obtained through the use of the sliding window filter.

At 908, the ingestible device (e.g., ingestible device 100, 300, or 400) obtains a second subset of recent data by interpolating the first subset of recent data. For example, ingestible device 100 may interpolate the first subset of data in order to generate a second subset of data with a sufficient number of data points (e.g., data points spaced every 0.5 seconds or greater). In some embodiments, this may enable ingestible device 100 to also replace any outlier data points that may have been removed as part of applying the window filter at 906.

At 910, the ingestible device (e.g., ingestible device 100, 300, or 400) calculates a normalized frequency spectrum from the second subset of data. For example, ingestible device 100 may be configured to perform a fast Fourier transform to convert the second subset of data from a time domain representation into a frequency domain representation. It is understood that depending on the application being used, and the nature of the subset of data, any number of suitable procedures (e.g., Fourier transform procedures) may be used to determine a frequency spectrum for the second subset of data. For example, the sampling frequency and size of the second subset of data may be known in advance, and ingestible device 100 may be configured to have pre-stored values of a normalized discreet Fourier transform (DFT) matrix, or the rows of the DFT matrix corresponding to the 0.1 Hz to 0.2 Hz frequency components of interest, within memory (e.g., memory circuitry of PCB 120 (FIG. 2)). In this case, the ingestible device may use matrix multiplication between the DFT matrix and the data set to generate an appropriate frequency spectrum. An example data set and corresponding frequency spectrum that may be obtained by the ingestible device is discussed in greater detail in relation to FIG. 10.

At 912, the ingestible device (e.g., ingestible device 100, 300, or 400) determines whether at least a portion of the normalized frequency spectrum is between 0.1 Hz and 0.2 Hz above a threshold value of 0.5 Hz. Peristaltic waves in a healthy human subject occur at a rate between 0.1 Hz and 0.2 Hz, and an ingestible device experiencing peristaltic waves (e.g., ingestible device 400 detecting contractions in walls 406 of the jejunum (FIG. 4)) may detect sinusoidal variations in the amplitude of detected reflectances levels that follow a similar 0.1 Hz to 0.2 Hz frequency. If the ingestible device determines that a portion of the normalized frequency spectrum between 0.1 Hz and 0.2 Hz is above a threshold value of 0.5, this measurement may be consistent with peristaltic waves in a healthy human subject, and process 900 proceeds to 914 where ingestible device 100 stores data indicating a muscle contraction was detected. Alternatively, if the ingestible device determines that no portion of the normalized frequency spectrum between 0.1 Hz and 0.2 Hz above a threshold value of 0.5, process 900 proceeds directly to 904 to make new measurements and to continue to monitor for new muscle contractions. It is understood that a threshold value other than 0.5 may be used, and that the exact threshold may depend on the sampling frequency and type of frequency spectrum used by ingestible device 100.

At 914, the ingestible device (e.g., ingestible device 100, 300, or 400) stores data indicating a muscle contraction was detected. For example, ingestible device 100 may store data in memory (e.g., memory circuitry of PCB 120 (FIG. 2)) indicating that a muscle contraction was detected, and indicating the time that the muscle contraction was detected. In some embodiments, ingestible device 100 may also monitor the total number of muscle contractions detected, or the number of muscle contractions detected in a given time frame. In some embodiments, detecting a particular number of muscle contractions may be consistent with ingestible device 100 being within the jejunum (e.g., jejunum 314 (FIG. 3)) of a healthy human subject. After detecting a muscle contraction, process 900 proceeds to 916.

At 916, the ingestible device (e.g., ingestible device 100, 300, or 400) determines whether a total number of muscle contractions exceeds a predetermined threshold number. For example, ingestible device 100 may retrieve the total number of muscle contractions detected from memory (e.g., from memory circuitry of PCB 120 (FIG. 2)), and compare the total number to a threshold value. In some embodiments, the threshold value may be one, or any number larger than one. The larger the threshold value, the more muscle contractions need to be detected before ingestible device 100 stores data indicating that it has entered the jejunum. In practice, setting the threshold value as three or higher may prevent the ingestible device from detecting false positives (e.g., due to natural movement of the GI tract organs, or due to movement of the subject). If the total number of contractions exceeds the predetermined threshold number, process 900 proceeds to 918 to store data indicating detection of a transition from the duodenum to the jejunum. Alternatively, if the total number of contractions does not exceed a predetermined threshold number, process 900 proceeds to 904 to include new measurements of reflectance levels in the data set. An example plot of the muscle contractions detected over time is discussed in greater detail in relation to FIG. 11.

At 918, the ingestible device (e.g., ingestible device 100, 300, or 400) stores data indicating detection of a transition from the duodenum to the jejunum. For example, ingestible device 100 may store data in memory (e.g., from memory circuitry of PCB 120 (FIG. 2)) indicating that the jejunum has been reached. In some embodiments, if ingestible device 100 is configured to perform all or part of process 900 while in the stomach, ingestible device 100 may store data at 918 indicating detection of a transition from the stomach directly to the jejunum (e.g., as a result of transitioning too quickly through the duodenum for the pyloric transition to be detected using process 600 (FIG. 6)).

In some embodiments, the ingestible device (e.g., ingestible device 100, 300, or 400) may be configured to obtain a fluid sample from the environment external to a housing of the ingestible device in response to identifying a change in the location of the ingestible device. For example, ingestible device 100 may be configured to obtain a fluid sample from the environment external to the housing of ingestible device 100 (e.g., through the use of optional opening 116 and optional rotating assembly 118 (FIG. 2)) in response to determining that the ingestible device is located within the jejunum (e.g., jejunum 314 (FIG. 3)). In some embodiments, ingestible device 100 may also be equipped with appropriate diagnostics to detect certain medical conditions based on the retrieved fluid sample, such as small intestinal bacterial overgrowth (SIBO).

In some embodiments, the ingestible device (e.g., ingestible device 100, 300, or 400) may be configured to deliver a dispensable substance that is pre-stored within the ingestible device from the ingestible device into the gastrointestinal tract in response to identifying the change in the location of the ingestible device. For example, ingestible device 100 may have a dispensable substance pre-stored within the ingestible device 100 (e.g., within a storage chamber or cavity on optional storage sub-unit 118-3 (FIG. 2)), and ingestible device 100 may be configured to dispense the substance into the gastrointestinal tract (e.g., through the use of optional opening 116 and optional rotating assembly 118 (FIG. 2)) when the ingestible device 100 detects that the ingestible device 100 is located within the jejunum (e.g., jejunum 314 (FIG. 3)). In some embodiments, this may enable ingestible device 100 to deliver substances (e.g., therapeutics and medicaments) at targeted locations within the GI tract.

In some embodiments, the ingestible device (e.g., ingestible device 100, 300, or 400) may be configured to perform an action based on the total number of detected muscle contractions. For example, ingestible device 100 may be configured to retrieve data indicative of the total number of muscle contractions (e.g., from memory circuitry of PCB 120 (FIG. 2)), and compare that to an expected number muscle contractions in a healthy individual. In response, the ingestible device may either dispense a substance into the gastrointestinal tract (e.g., through the use of optional opening 116 and optional rotating assembly 118 (FIG. 2)), or may obtain a fluid sample from the environment external to the housing of ingestible device 100 (e.g., through the use of optional opening 116 and optional rotating assembly 118 (FIG. 2)). For instance, ingestible device 100 may be configured to obtain a sample in response to determining that a number of detected muscle contractions is abnormal, and differs greatly from the expected number. As another example, ingestible device 100 may be configured to deliver a substance into the GI tract (such as a medicament), in response to determining that the detected muscle contractions are consistent with a functioning GI tract in a healthy individual.

It will be understood that the steps and descriptions of the flowcharts of this disclosure, including FIG. 9, are merely illustrative. Any of the steps and descriptions of the flowcharts, including FIG. 9, may be modified, omitted, rearranged, performed in alternate orders or in parallel, two or more of the steps may be combined, or any additional steps may be added, without departing from the scope of the present disclosure. For example, the ingestible device 100 may calculate the mean and the standard deviation of multiple data sets in parallel (e.g., multiple data sets, each one corresponding to a different wavelength of reflectance or different sensing sub-unit used to detect the reflectance) in order to speed up the overall computation time. Furthermore, it should be noted that the steps and descriptions of FIG. 9 may be combined with any other system, device, or method described in this application, and any of the ingestible devices or systems discussed in this application could be used to perform one or more of the steps in FIG. 9.

Figure 10:
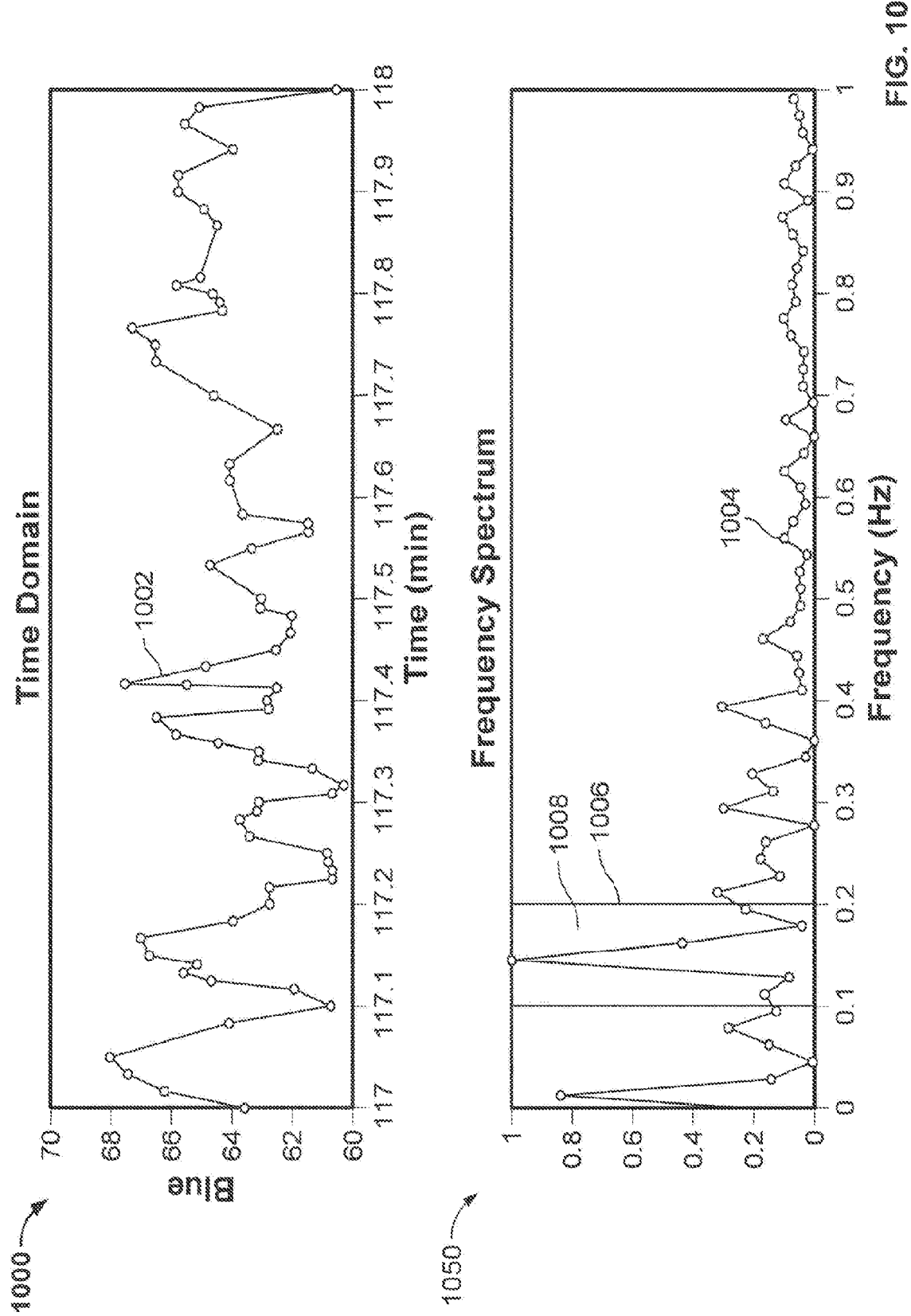
FIG. 10 is a plot illustrating data collected during an example operation of an ingestible device, which may be used when detecting a transition from a duodenum to a jejunum, in accordance with some embodiments of the disclosure.

FIG. 10 is a plot illustrating data collected during an example operation of an ingestible device, which may be used when detecting a transition from a duodenum to a jejunum, in accordance with some embodiments of the disclosure. Diagram 1000 depicts a time domain plot 1002 of a data set of reflectance levels measured by an ingestible device (e.g., the second subset of data discussed in relation to 908 of FIG. 9). In some embodiments, ingestible device 100 may be configured to gather data points at semi-regular intervals approximately 0.5 seconds apart. By comparison, diagram 1050 depicts a frequency domain plot 1004 of the same data set of reflectance levels measured by an ingestible device (e.g., as a result of ingestible device 100 calculating a frequency spectrum at 910 of FIG. 9). In some embodiments, ingestible device 100 may be configured to calculate the frequency spectrum through any convenient means.

In diagram 1050, the range of frequencies 1006 between 0.1 Hz and 0.2 Hz may be the range of frequencies that ingestible device 100 searches in order to detect muscle contractions. As shown in diagram 1050, there is a strong peak in the frequency domain plot 1004 around 0.14 Hz, which is consistent with the frequency of peristaltic motion in a healthy human individual. In this case, an ingestible device 100 analyzing frequency domain plot 1004 may be configured to determine that the data is consistent with a detected muscle contraction (e.g., using a process similar to 912 of process 900 (FIG. 9)), and may store data (e.g., in memory circuitry of PCB 120 (FIG. 2)) indicating that a muscle contraction has been detected. Because the muscle contraction was detected from the one-minute window of data ending at 118 minutes, ingestible device 100 may also store data indicating that the muscle contraction was detected at the 118-minute mark (i.e., which may indicate that the ingestible device 100 was turned on and ingested by the subject 118 minutes ago).

Figure 11:
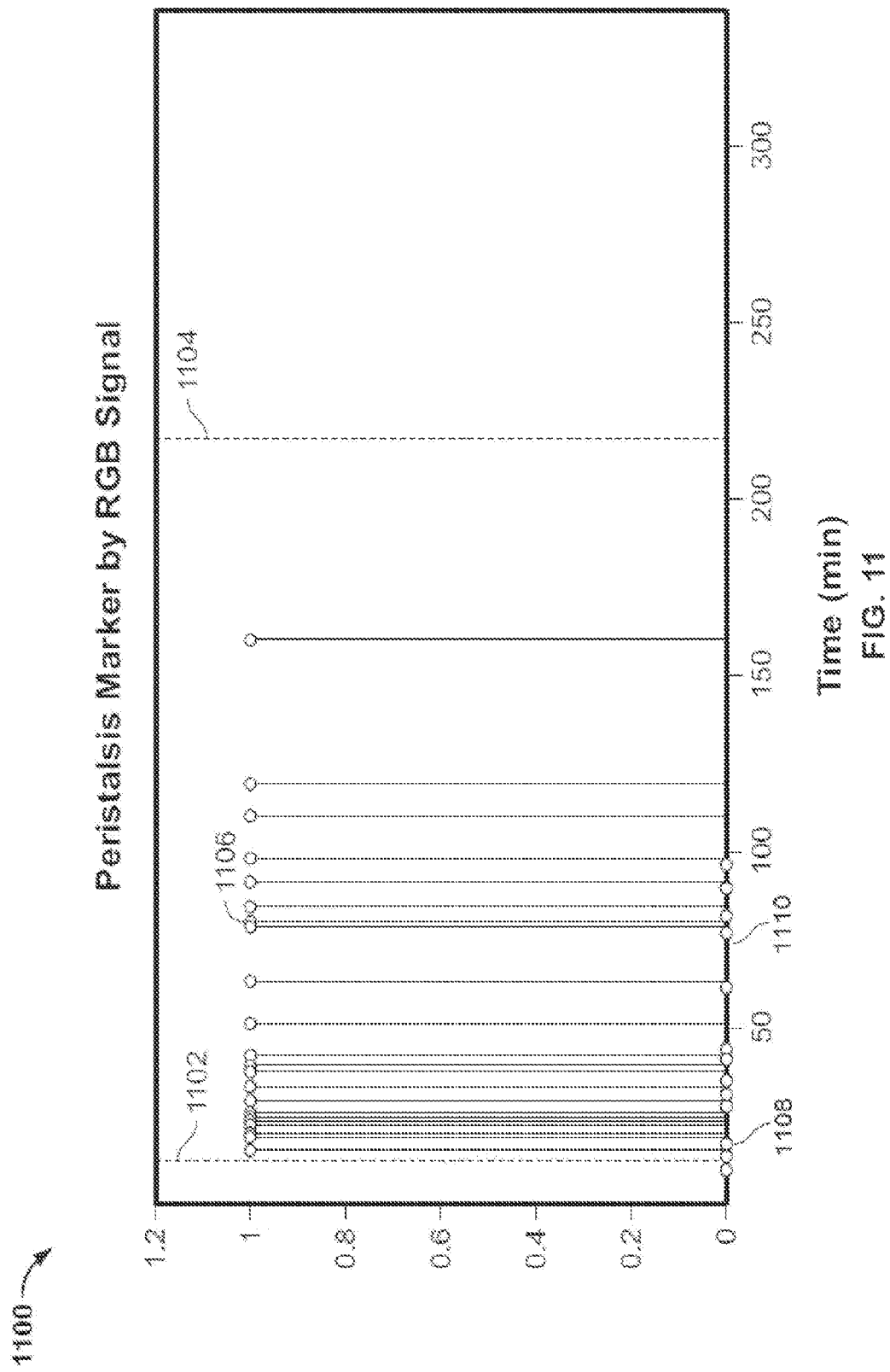
FIG. 11 is a plot illustrating muscle contractions detected by an ingestible device over time, which may be used when determining a location of an ingestible device as it transits through a GI tract, in accordance with some embodiments of the disclosure.

FIG. 11 is a plot illustrating muscle contractions detected by an ingestible device over time, which may be used when determining a location of an ingestible device as it transits through a gastrointestinal (GI) tract, in accordance with some embodiments of the disclosure. In some embodiments, ingestible device 100 may be configured to detect muscle contractions, and store data indicative of when each muscle contraction is detected (e.g., as part of 914 of process 900 (FIG. 9)). Plot 1100 depicts the detected muscle contractions 1106 over time, with each muscle contraction being represented by a vertical line reaching from "0" to "1" on the y-axis.

At 1102, around the 10-minute mark, ingestible device 100 first enters the duodenum (e.g., as determined by ingestible device 100 performing process 600 (FIG. 6)). Shortly thereafter, at 1108, ingestible device 100 begins to detect several muscle contractions 1106 in quick succession, which may be indicative of the strong peristaltic waves that form in the jejunum (e.g., jejunum 314 (FIG. 3)). Later, around 1110, ingestible device 100 continues to detect intermittent muscle contractions, which may be consistent with an ingestible device 100 within the ileum. Finally at 1104, ingestible device 100 transitions out of the small intestine, and into the cecum. Notably, ingestible device 100 detects more frequent muscle contractions in the jejunum portion of the small intestine as compared to the ileum portion of the small intestine, and ingestible device 100 does not measure any muscle contractions after having exited the small intestine. In some embodiments, ingestible device 100 may incorporate this information into a localization process. For example, ingestible device 100 may be configured to detect a transition from a jejunum to an ileum in response to determining that a frequency of detected muscle contractions (e.g., the number of muscle contractions measured in a given 10-minute window) has fallen below a threshold number. As another example, ingestible device 100 may be configured to detect a transition from an ileum to a cecum in response to determining that no muscle contractions have been detected for a threshold period of time. It is understood that these examples are intended to be illustrative, and not limiting, and that measurements of muscle contractions may be combined with any of the other processes, systems, or methods discussed in this disclosure.

Figure 12:
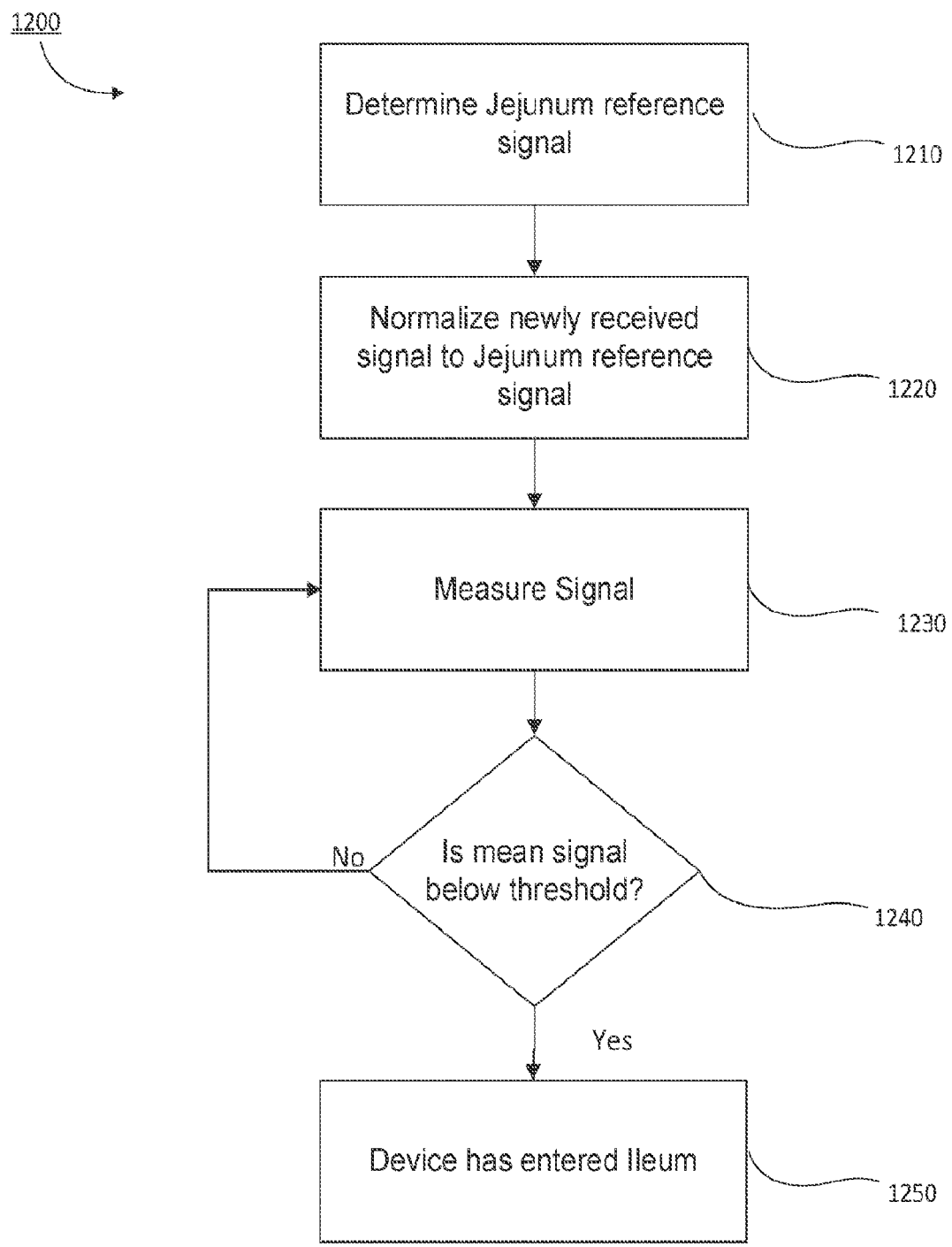
FIG. 12 is a flowchart of illustrative steps for detecting a transition from a jejunum to an ileum, which may be used when determining a location of an ingestible device as it transits through a GI tract, in accordance with some embodiments of the disclosure.

FIG. 12 is a flowchart 1200 for certain embodiments for determining a transition of the device from the jejunum to the ileum. It is to be noted that, in general, the jejunum is redder and more vascular than the ileum. Moreover, generally, in comparison to the ileum, the jejunum has a thicker intestine wall with more messentary fat. These differences between the jejunum and the ileum are expected to result in differences in optical responses in the jejunum relative to the ileum. Optionally, one or more optical signals may be used to investigate the differences in optical responses. For example, the process can include monitoring a change in optical response in reflected red light, blue light, green light, ratio of red light to green light, ratio of red light to blue light, and/or ratio of green light to blue light. In some embodiments, reflected red light is detected in the process.

Flowchart 1200 represents a single sliding window process. In step 1210, the jejunum reference signal is determined based on optical reflection. Typically, this signal is as the average signal (e.g., reflected red light) over a period of time since the device was determined to enter the jejunum. The period of time can be, for example, from five minutes to 40 minutes (e.g., from 10 minutes to 30 minutes, from 15 minutes to 25 minutes). In step 1220, the detected signal (e.g., reflected red light) just after the period of time used in step 1210 is normalized to the reference signal determined in step 1210. In step 1230, the signal (e.g., reflected red light) is detected. In step 1240, the mean signal detected based on the single sliding window is compared to a signal threshold. The signal threshold in step 1240 is generally a fraction of the reference signal of the jejunum reference signal determined in step 1210. For example, the signal threshold can be from 60% to 90% (e.g., from 70% to 80%) of the jejunum reference signal. If the mean signal exceeds the signal threshold, then the process determines that the device has entered the ileum at step 1250. If the mean signal does not exceed the signal threshold, then the process returns to step 1230.

Figure 13:
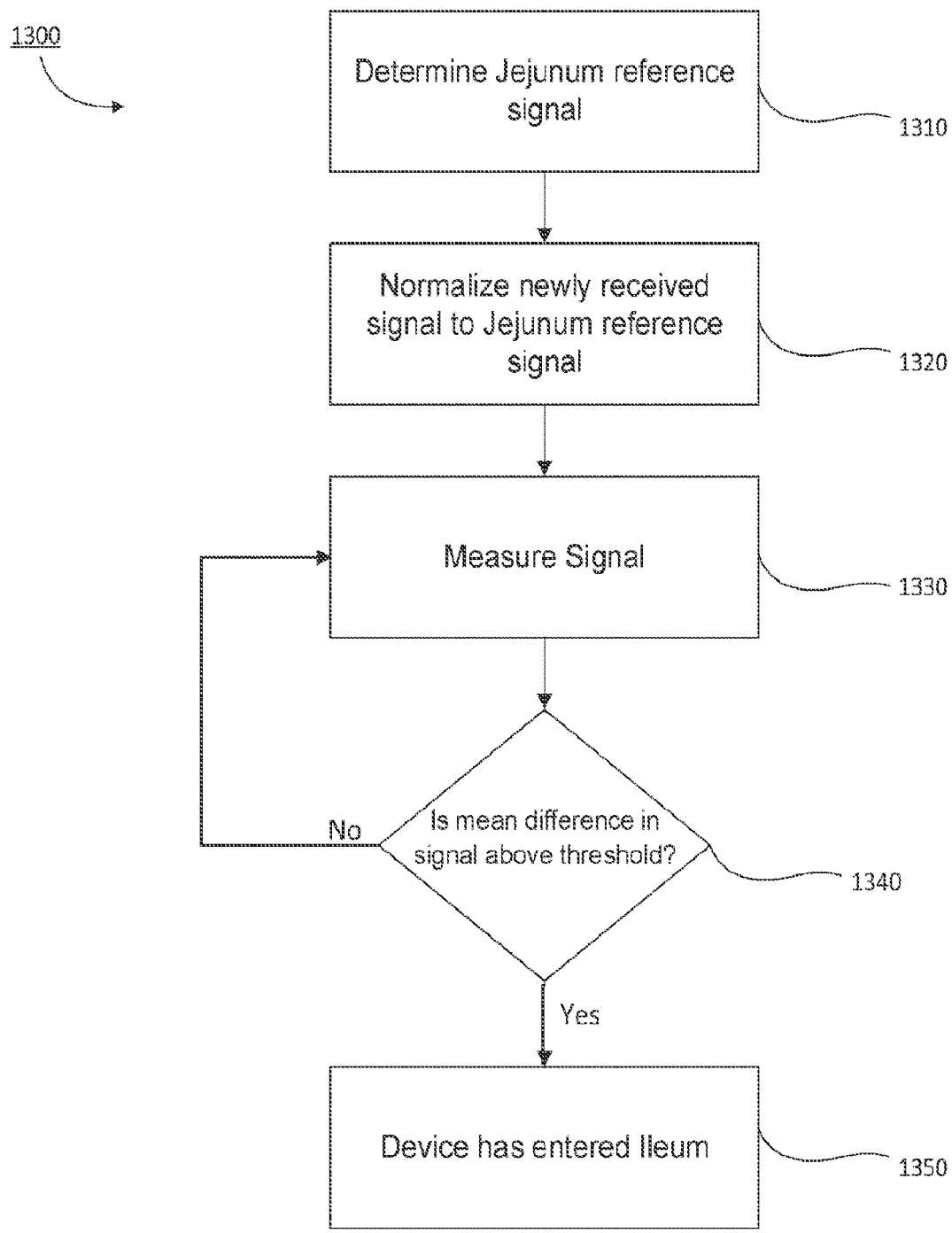
FIG. 13 is a flowchart of illustrative steps for detecting a transition from a jejunum to an ileum, which may be used when determining a location of an ingestible device as it transits through a GI tract, in accordance with some embodiments of the disclosure.

FIG. 13 is a flowchart 1200 for certain embodiments for determining a transition of the device from the jejunum to the ileum using a two sliding window process. In step 1310, the jejunum reference signal is determined based on optical reflection. Typically, this signal is as the average signal (e.g., reflected red light) over a period of time since the device was determined to enter the jejunum. The period of time can be, for example, from five minutes to 40 minutes (e.g., from 10 minutes to 30 minutes, from 15 minutes to 25 minutes). In step 1320, the detected signal (e.g., reflected red light) just after the period of time used in step 1310 is normalized to the reference signal determined in step 1310. In step 1330, the signal (e.g., reflected red light) is detected. In step 1340, the mean difference in the signal detected based on the two sliding windows is compared to a signal threshold. The signal threshold in step 1340 is based on whether the mean difference in the detected signal exceeds a multiple (e.g., from 1.5 times to five times, from two times to four times) of the detected signal of the first window. If signal threshold is exceeded, then the process determines that the device has entered the ileum at step 1350. If the signal threshold is not exceeded, then the process returns to step 1330.

Figure 14:
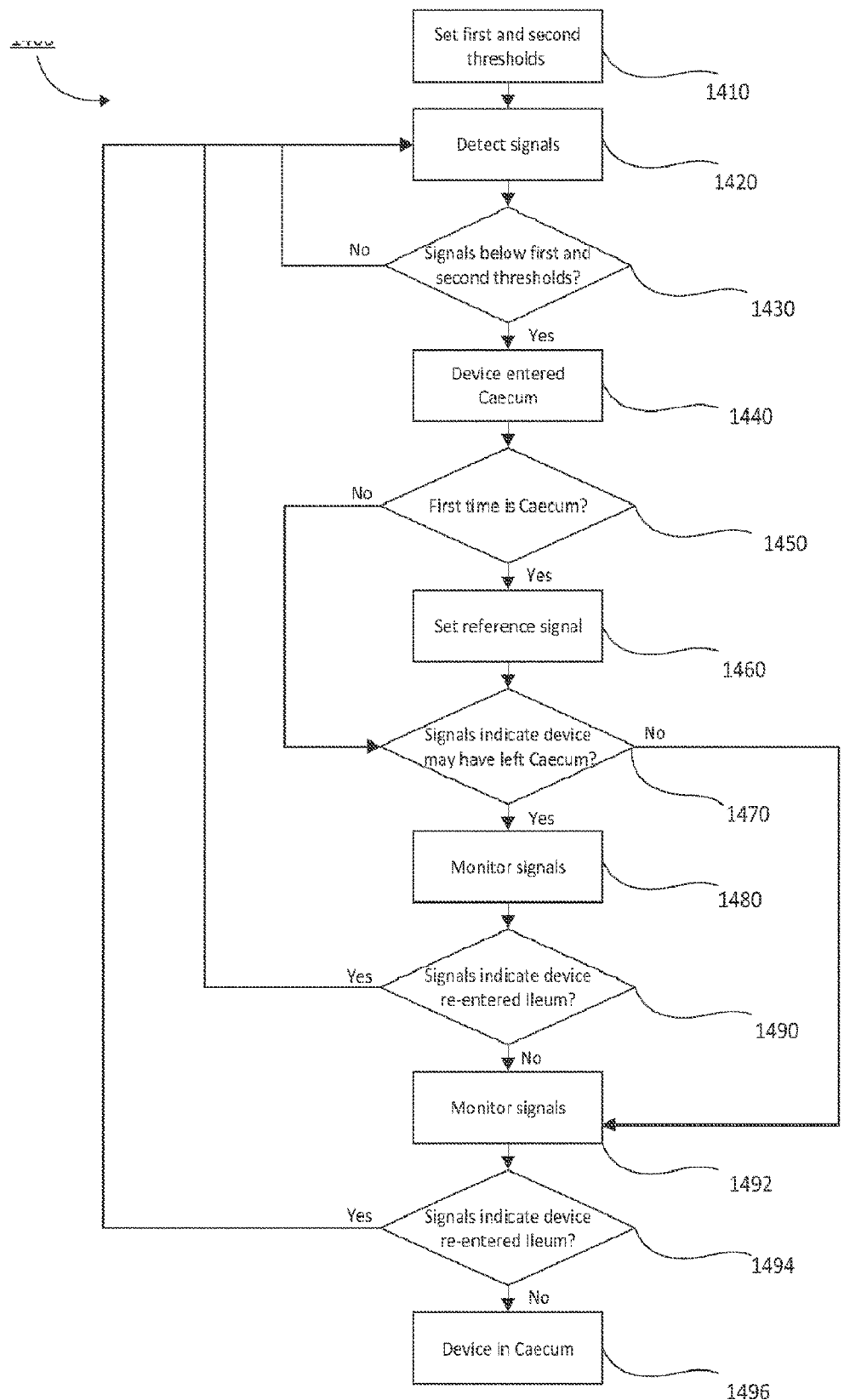
FIG. 14 is a flowchart of illustrative steps for detecting a transition from an ileum to a cecum, which may be used when determining a location of an ingestible device as it transits through a GI tract, in accordance with some embodiments of the disclosure.

FIG. 14 is a flowchart 1400 for a process for certain embodiments for determining a transition of the device from the ileum to the cecum. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected green light to reflected blue light. Generally, in the process 1400, the sliding window analysis (first and second windows) discussed with respect to process 600 is continued.

Step 1410 includes setting a first threshold in a detected signal, e.g., ratio of detected red light to detected green light, and setting a second threshold for the coefficient of variation for a detected signal, e.g., the coefficient of variation for the ratio of detected green light to detected blue light. The first threshold can be set to a fraction (e.g., from 0.5 to 0.9, from 0.6 to 0.8) of the average signal (e.g., ratio of detected red light to detected green light) in the first window, or a fraction (e.g., from 0.4 to 0.8, from 0.5 to 0.7) of the mean difference between the detected signal (e.g., ratio of detected red light to detected green light) in the two windows. The second threshold can be set to 0.1 (e.g., 0.05, 0.02).

Step 1420 includes detecting the signals in the first and second windows that are to be used for comparing to the first and second thresholds.

Step 1430 includes comparing the detected signals to the first and second thresholds. If the corresponding value is not below the first threshold or the corresponding value is not below the second threshold, then it is determined that the device has not left the ileum and entered the cecum, and the process returns to step 1420. If the corresponding value is below the first threshold and the corresponding value is below the second threshold, then it is determined that the device has left the ileum and entered the cecum, and the proceeds to step 1440.

Step 1450 includes determining whether it is the first time that that the device was determined to leave the ileum and enter the cecum. If it is the first time that the device was determined to leave the ileum and enter the cecum, then the process proceeds to step 1460. If it is not the first time that the device has left the ileum and entered the cecum, then the process proceeds to step 1470.

Step 1460 includes setting a reference signal. In this step the optical signal (e.g., ratio of detected red light to detected green light) as a reference signal.

Step 1470 includes determining whether the device may have left the cecum and returned to the ileum. The device is determined to have left the cecum and returned to the ileum if the corresponding detected signal (e.g., ratio of detected red light to detected green light) is statistically comparable to the reference signal (determined in step 1460) and the coefficient of variation for the corresponding detected signal (e.g., ratio of detected green light to detected blue light) exceeds the second threshold. If it is determined that the device may have left the cecum and returned to the ileum, the process proceeds to step 1480.

Step 1480 includes continuing to detect the relevant optical signals for a period of time (e.g., at least one minute, from five minutes to 15 minutes).

Step 1490 includes determining whether the signals determined in step 1480 indicate (using the methodology discussed in step 1470) that the device re-entered the ileum. If the signals indicate that the device re-entered the ileum, the process proceeds to step 1420. If the signals indicate that the device is in the cecum, the process proceeds to step 1492.

Step 1492 includes continuing to monitor the relevant optical signals for a period of time (e.g., at least 30 minutes, at least one hour, at least two hours).

Step 1494 includes determining whether the signals determined in step 1492 indicate (using the methodology discussed in step 1470) that the device re-entered the ileum. If the signals indicate that the device re-entered the ileum, the process proceeds to step 1420. If the signals indicate that the device is in the cecum, the process proceeds to step 1496.

At step 1496, the process determines that the device is in the cecum.

Figure 15:
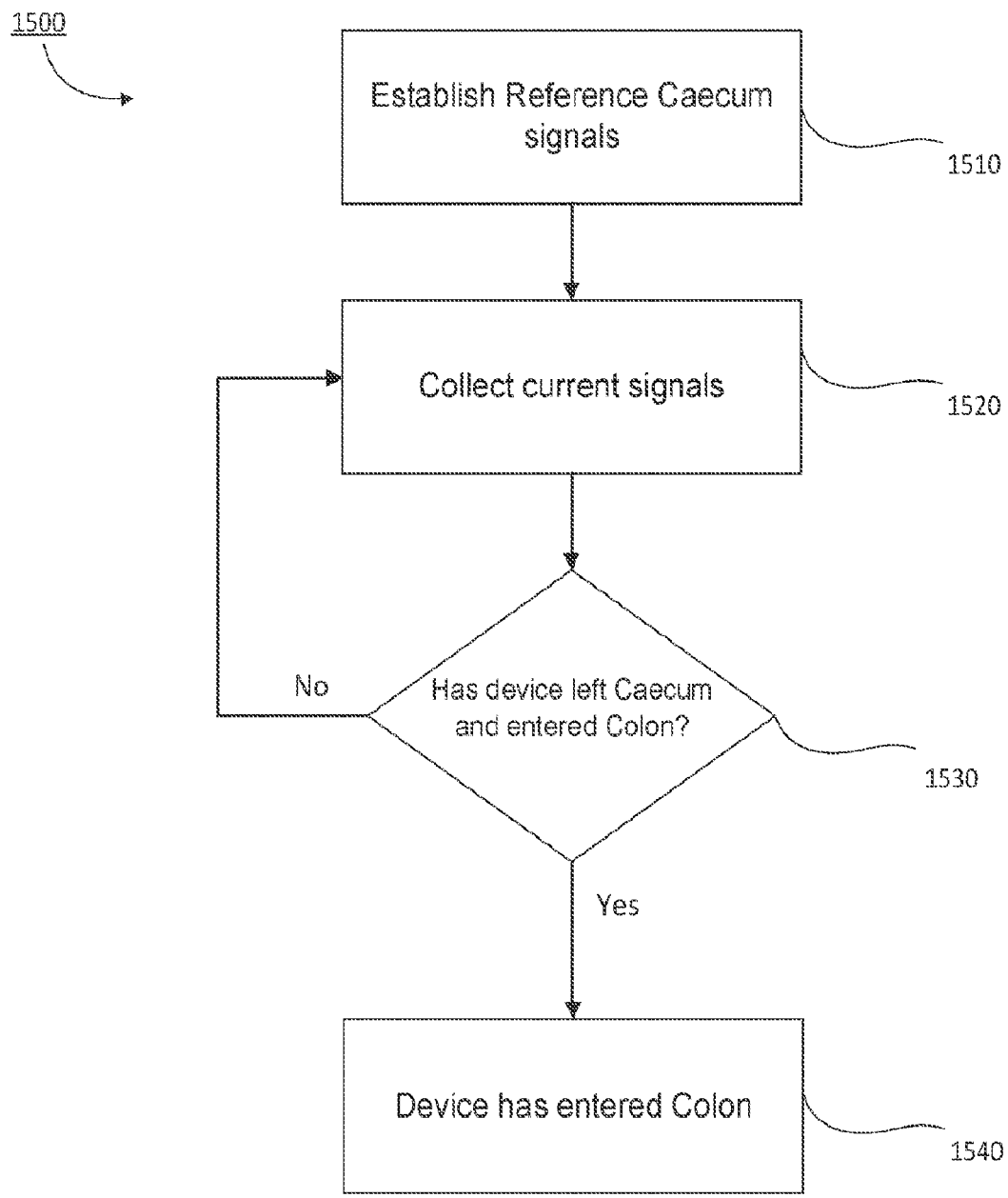
FIG. 15 is a flowchart of illustrative steps for detecting a transition from a cecum to a colon, which may be used when determining a location of an ingestible device as it transits through a GI tract, in accordance with some embodiments of the disclosure.

FIG. 15 is a flowchart 1500 for a process for certain embodiments for determining a transition of the device from the cecum to the colon. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected blue light. Generally, in the process 1500, the sliding window analysis (first and second windows) discussed with respect to process 1400 is continued.

In step 1510, optical signals (e.g., the ratio of reflected red signal to reflected green signal, and reflected blue signal) are collected for a period of time (e.g., at least one minute, at least five minutes, at least 10 minutes) while the device is in the cecum (e.g., during step 1480). The average values for the recorded optical signals (e.g., the ratio of reflected red signal to reflected green signal, and reflected blue signal) establish the cecum reference signals.

In step 1520, the optical signals are detected after it has been determined that the device entered the cecum (e.g., at step 1440). The optical signals are normalized to the cecum reference signals.

Step 1530 involves determining whether the device has entered the colon. This includes determining whether any of three different criteria are satisfied. The first criterion is satisfied if the mean difference in the ratio of a detected optical signal (e.g., ratio of detected red signal to the detected green) is a multiple greater than one (e.g., 2×, 3×, 4×) the standard deviation of the corresponding signal (e.g., ratio of detected red signal to the detected green) in the second window. The second criterion is satisfied if the mean of a detected optical signal (e.g., a ratio of detected red light to detected green light) exceeds a given value (e.g., exceeds one). The third criterion is satisfied if the coefficient of variation of an optical signal (e.g., detected blue light) in the first window exceeds a given value (e.g., exceeds 0.2). If any of the three criteria are satisfied, then the process proceeds to step 1540. Otherwise, none of the three criteria are satisfied, the process returns to step 1520.

For illustrative purposes the disclosure focuses primarily on a number of different example embodiments of an ingestible device, and example embodiments of methods for determining a location of an ingestible device within a GI tract. However, the possible ingestible devices that may be constructed are not limited to these embodiments, and variations in the shape and design may be made without significantly changing the functions and operations of the device. Similarly, the possible procedures for determining a location of the ingestible device within the GI tract are not limited to the specific procedures and embodiments discussed (e.g., process 500 (FIG. 5), process 600 (FIG. 6), process 900 (FIG. 9), process 1200 (FIG. 12), process 1300 (FIG. 13), process 1400 (FIG. 14) and process 1500 (FIG. 15)). Also, the applications of the ingestible devices described herein are not limited merely to gathering data, sampling and testing portions of the gastrointestinal tract, or delivering medicament. For example, in some embodiments the ingestible device may be adapted to include a number of chemical, electrical, or optical diagnostics for diagnosing a number of diseases. Similarly, a number of different sensors for measuring bodily phenomenon or other physiological qualities may be included on the ingestible device. For example, the ingestible device may be adapted to measure elevated levels of certain chemical compounds or impurities in the gastrointestinal tract, or the combination of localization, sampling, and appropriate diagnostic and assay techniques incorporated into a sampling chamber may be particularly well suited to determine the presence of small intestinal bacterial overgrowth (SIBO).

At least some of the elements of the various embodiments of the ingestible device described herein that are implemented via software (e.g., software executed by control circuitry within PCB 120 (FIG. 2)) may be written in a high-level procedural language such as object oriented programming, a scripting language or both. Accordingly, the program code may be written in C, C$^{++}$ or any other suitable programming language and may comprise modules or classes, as is known to those skilled in object oriented programming. Alternatively, or in addition, at least some of the elements of the embodiments of the ingestible device described herein that are implemented via software may be written in assembly language, machine language or firmware as needed. In either case, the language may be a compiled or an interpreted language.

At least some of the program code used to implement the ingestible device can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Furthermore, at least some of the programs associated with the systems, devices, and methods of the example embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In some embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The techniques described above can be implemented using software for execution on a computer. For instance, the software forms procedures in one or more computer programs that execute on one or more programmed or programmable computer systems (which may be of various architectures such as distributed, client/server, or grid) each including at least one processor, at least one data storage system (including volatile and non-volatile memory and/or storage elements), at least one input device or port, and at least one output device or port.

The software may be provided on a storage medium, such as a CD-ROM, readable by a general or special purpose programmable computer or delivered (encoded in a propagated signal) over a communication medium of a network to the computer where it is executed. All of the functions may be performed on a special purpose computer, or using special-purpose hardware, such as coprocessors. The software may be implemented in a distributed manner in which different parts of the computation specified by the software are performed by different computers. Each such computer program is preferably stored on or downloaded to a storage media or device (e.g., solid state memory or media, or magnetic or optical media) readable by a general or special purpose programmable computer, for configuring and operating the computer when the storage media or device is read by the computer system to perform the procedures described herein. The inventive system may also be considered to be implemented as a computer-readable storage medium, configured with a computer program, where the storage medium so configured causes a computer system to operate in a specific and predefined manner to perform the functions described herein.

Methods and Mechanisms of Delivery

Figure 16:
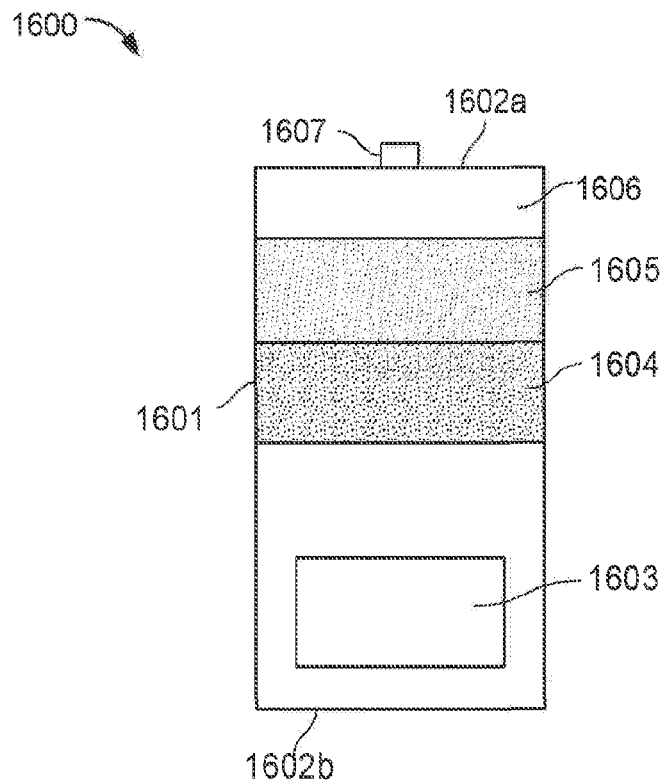
FIG. 16 illustrates an ingestible device for delivering a substance in the GI tract.

FIG. 16 provides an example mock-up diagram illustrating aspects of a structure of an ingestible device 1600 for delivering a dispensable substance, such as a formulation of a therapeutic agent described herein, according to some embodiments described herein. In some embodiments, the ingestible device 1600 may generally be in the shape of a capsule, a pill or any swallowable form that may be orally consumed by an individual. In this way, the ingestible device 1600 may be ingested by a patient and may be prescribed by healthcare practitioners and patients.

The ingestible device 1600 includes a housing 1601 that may take a shape similar to a capsule, a pill, and/or the like, which may include two ends 1602a-b. The housing 1601 may be designed to withstand the chemical and mechanical environment of the GI tract (e.g., effects of muscle contractile forces and concentrated hydrochloric acid in the stomach). A broad range of materials that may be used for the housing 1601. Examples of these materials include, but are not limited to, thermoplastics, fluoropolymers, elastomers, stainless steel and glass complying with ISO 10993 and USP Class VI specifications for biocompatibility; and any other suitable materials and combinations thereof.

In some embodiment, the wall of the housing 1601 may have a thickness of 0.5 mm-1 mm, which is sufficient to sustain an internal explosion (e.g., caused by hydrogen ignition or over pressure inside the housing).

The housing 1601 may or may not have a pH-sensitive enteric coating to detect or otherwise be sensitive to a pH level of the environment external to the ingestible device. As discussed elsewhere in the application in more detail, the ingestible device 1600 may additionally or alternatively include one more sensors, e.g., temperature sensor, optical sense.

The housing 1601 may be formed by coupling two enclosure portions together. The ingestible device 1600 may include an electronic component within the housing 1600. The electronic component may be placed proximally to an end 1602b of the housing, and includes a printed circuit board (PCB), a battery, an optical sensing unit, and/or the like.

The ingestible device 1600 further includes a gas generating cell 1603 that is configured to generate gas and thus cause an internal pressure within the housing 1601. In some embodiments, the gas generating cell may include or be connected to a separate channel or valve of the ingestible device such that gas may be release through the channel or valve to create a motion to alter the position of the ingestible device within the GI tract. Such gas release can also be used to position the ingestible device relative to the intestinal lining. In another embodiment, gas may be released through the separate channel or valve to alter the surface orientation of the intestinal tissue prior to delivery of the dispensable substance.

A traveling plunger 1604 may be placed on top of the gas generating cell 1603 within the housing 1601. The traveling plunger 1604 is a membrane that separates the gas generating cell 1603 and a storage reservoir that stores the dispensable substance 1605. In some embodiments, the traveling plunger 1604 may be a movable piston. In some embodiments, the traveling plunger 1604 may instead be a flexible membrane such as but not limited to a diaphragm. In some embodiments, the traveling plunger 1604, which may have the form of a flexible diaphragm, may be placed along an axial direction of the housing 1601, instead of being placed on top of the gas generating cell 1603. The traveling plunger or the membrane 1604 may move (when the membrane 1604 is a piston) or deform (when the membrane 1604 is a diaphragm) towards a direction of the end 1602a of the housing, when the gas generating cell 1603 generates gas to create an internal pressure that pushes the membrane 1604. In this way, the membrane or traveling plunger 1604 may push the dispensable substance 1605 out of the housing via a dispensing outlet 1607.

The housing 1601 may include a storage reservoir storing one or more dispensable substances 1605 adjacent to the traveling plunger 1604. The dispensable substance 1605 may be a therapeutic or medical agent that may take a form of a powder, a compressed powder, a fluid, a semi-liquid gel, or any other dispensable or deliverable form. The delivery of the dispensable substance 1605 may take a form such as but not limited to bolus, semi-bolus, continuous, burst drug delivery, and/or the like. In some embodiments, a single bolus is delivered proximate to the disease location. In some embodiments, more than one bolus is released at one location or more than one location. In some embodiments the release of more than one bolus is triggered according to a pre-programmed algorithm. In some embodiments the release profile is continuous. In some embodiments the release profile is time-based. In some embodiments the release profile is location-based. In some embodiments, the amount delivered is based on the severity and/or extent of the disease in the following manner. In some embodiments, the bolus is delivered in one or more of the following locations: stomach; duodenum; proximal jejunum; ileum; cecum; ascending colon; transverse colon; descending colon. In some embodiments, the JAK inhibitor is ustekinumab. In some embodiments, the JAK inhibitor is briakinumab. In some embodiments, the JAK inhibitor is guselkumab. In some embodiments, the JAK inhibitor is tildrakizumab. In some embodiments, the JAK inhibitor is brazikumab. In some embodiments, the JAK inhibitor is ustekinumab.

In some embodiments the dispensable substance is a small molecule therapeutic that is released in the cecum and/or other parts of the large intestine. Small molecules that are administered by typical oral routes are primarily absorbed in the small intestine, with much lower absorption taking place in the large intestine (outside of the rectum). Accordingly, an ingestible device that is capable of releasing a small molecule selectively in the large intestine (e.g., the cecum) with resulting low systemic levels (even when high doses are used) is attractive for subjects with inflammatory bowel disease in the large intestine.

In some embodiments, the storage reservoir may include multiple chambers, and each chamber stores a different dispensable substance. For example, the different dispensable substances can be released at the same time via the dispensing outlet 1607. Alternatively, the multiple chambers may take a form of different layers within the storage reservoir such that the different dispensable substance from each chamber is delivered sequentially in an order. In one example, each of the multiple chambers is controlled by a separate traveling plunger, which may be propelled by gas generation. The electronic component may control the gas generating cell 1603 to generate gas to propel a specific traveling plunger, e.g., via a separate gas generation chamber, etc., to delivery the respective substance. In some embodiments, the content of the multiple chambers may be mixed or combined prior to release, for example, to activate the drug.

The ingestible device 1600 may include a dispensing outlet 1607 at one end 1602*a* of the housing 1601 to direct the dispensable substance 105 out of the housing. The dispensing outlet 1607 may include an exit valve, a slit or a hole, a jet injection nozzle with a syringe, and/or the like. When the traveling plunger 1604 moves towards the end 1602*a* of the housing 1601, an internal pressure within the storage reservoir may increase and push the dispensing outlet to be open to let the dispensable substance 1605 be released out of the housing 1601.

In an embodiment, a pressure relief device 1606 may be placed within the housing 1601, e.g., at the end 1602*a* of the housing 1601.

In some embodiments, the housing 1601 may include small holes (e.g., with a diameter smaller than 2 mm), e.g., on the side of the housing 1601, or at the end 1602*a* to facilitate loading the dispensable substance into the storage reservoir.

In some embodiments, a feedback control circuit (e.g., a feedback resistor, etc.) may be added to send feedback from the gas generating cell 1603 to the electronic component such that when the internal pressure reaches a threshold level, the electronic component may control the gas generating cell 1603 to turn off gas generation, or to activate other safety mechanism (e.g., feedback-controlled release valve, etc.). For example, an internal pressure sensor may be used to measure the internal pressure within the ingestible device and generate feedback to the feedback control circuit.

Figure 17:
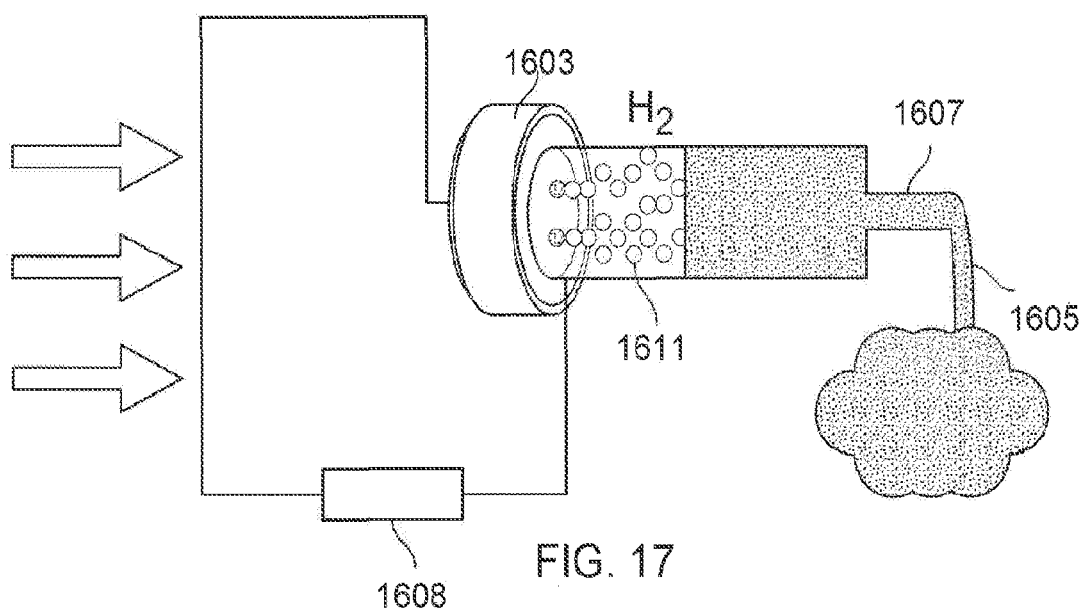
FIG. 17 illustrates aspects of a mechanism for an ingestible device with a gas generating cell configured to generate a gas to dispense a substance.

FIG. 17 provides an example diagram illustrating aspects of a mechanism for a gas generating cell 1603 configured to generate a gas to dispense a substance, according to some embodiments described herein. As shown in FIG. 17, the gas generating cell 1603 generates a gas 1611 which can propel the dispensable substance 1605 out of the dispensing outlet 1607. A variable resistor 1608 may be connected to a circuit with the gas generating cell 1603 such that the variable resistor 1608 may be used to control an intensity and/or an amount of gas 1611 (e.g., hydrogen) generated by the cell 1603. Specifically, the gas generating cell 1603 may be a battery form factor cell that is capable of generating hydrogen when a resistor is applied. In this way, as the gas generating cell 1603 only needs the use of a resistor only without any active power requirements, the gas generating cell 1603 may be integrated into an ingestible device such as a capsule with limited energy/power available. For example, the gas generating cell 1603 may be compatible with a capsule at a size of 26 mm×13 mm or smaller.

In some embodiments, based on the elution rate of gas from the cell, and an internal volume of the ingestible device, it may take time to generate sufficient gas 1611 to deliver the substance 1605, and the time required may be 30 seconds or longer. For example, the time to generate a volume of hydrogen equivalent to 500 µL of fluid would be approximately 5 minutes. A longer period of time may be needed based upon non-ideal conditions within the ingestible device, such as friction, etc. Thus, given that the production of gas (e.g., hydrogen) may take time, gas generation may need to start prior to the ingestible device arriving at the site of delivery to build pressure up within the device. The ingestible device may then need to know when it is approaching the site of delivery. For example, the device may start producing gas on an "entry transition," which is determined by temperature, so as to produce enough gas to be close to the pressure high enough to deliver the dispensable substance. The ingestible device may then only start producing gas again when it arrives at the site of delivery, which will cause the internal pressure within the ingestible device to reach a level required by the dispensing outlet to release the dispensable substance. Also, for regio-specific delivery, the ingestible device may estimate the time it takes to build up enough pressure to deliver the dispensable substance before the ingestible device arrives at a specific location, to activate gas generation.

For example, for systemic delivery, when an internal volume of the ingestible device is around 500 µL, a gas generation time of 2 hours, an initial pressure of approximately 300 pound per square inch absolute (psia) may be generated, with higher and lower pressures possible. The generated pressure may drop when air enters the storage reservoir which was previously occupied by the dispensable substance during the dispensing process. For systemic drug delivery, a force with a generated pressure of approximately 100 to 360 pound per square inch (psi) may be required for dermal penetration, e.g., to penetrate the mucosa or epithelial layer. The pressure may also vary depending on the nozzle design at the dispensing outlet, fluid viscosity, and surrounding tissue proximity and properties.

The gas 1611 that may be generated for a continuous delivery of drug (e.g., 1 cc $H_2$ in 4 hours, 16 breaths per minute at 0.5 L tidal volume) may equate to 1 cc hydrogen in approximately 2000 L of exhaled air, or approximately 0.5 ppm H2, which is below physiologic values of exhaled hydrogen. Reducing this time to 10 minutes equates to approximately 13 ppm hydrogen. Thus, due to the length of intestine that may be covered during this time period, the ingestible device may possess a higher localized value than physiologic.

Figure 18:
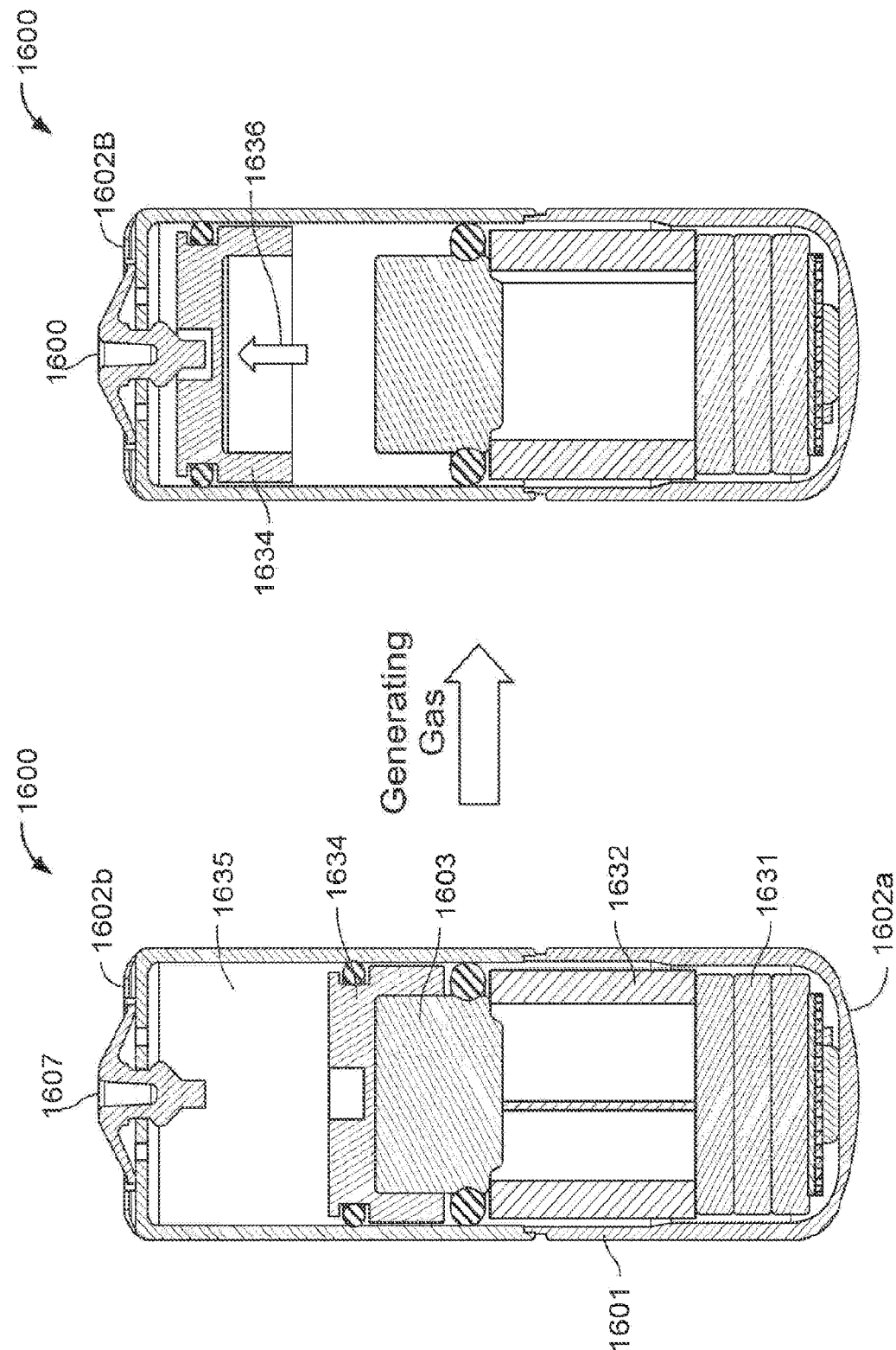
FIG. 18 illustrates an ingestible device having a piston to push for drug delivery.
Figure 19:
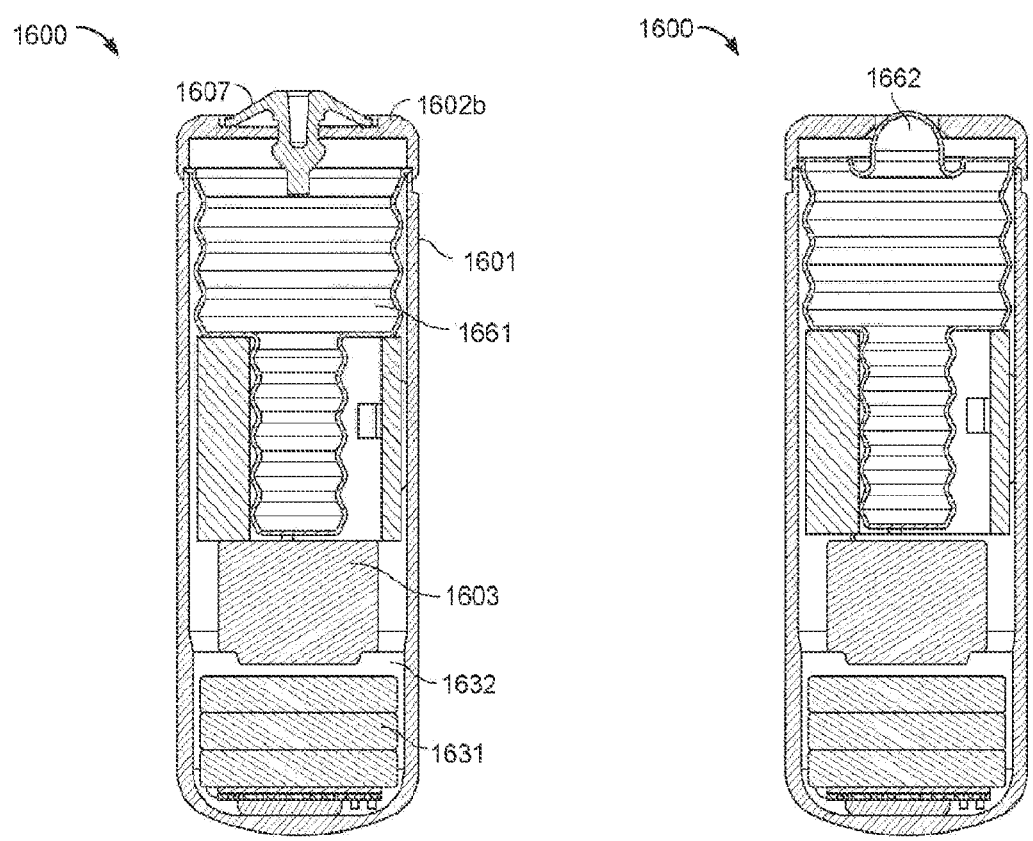
FIG. 19 illustrates an ingestible device having a bellow structure for a storage reservoir of dispensable substances.

FIGS. 18 and 19, disclosed in U.S. Provisional Application No. 62/385,553, incorporated by reference herein in its entirety, illustrates an example of an ingestible device for localized delivery of pharmaceutical compositions disclosed herein, in accordance with particular implementations. The ingestible device 1600 includes a piston or drive element 1634 to push for drug delivery, in accordance with particular implementations described herein. The ingestible device 1600 may have one or more batteries 1631 placed at one end 1602*a* of a housing 1601 to provide power for the ingestible device 1600. A printed circuit board (PCB) 1632 may be placed adjacent to a battery or other power source 1631, and a gas generating cell 1603 may be mounted on or above the PCB 1632. The gas generating cell 1603 may be sealed from the bottom chamber (e.g., space including 1631 and 1632) of the ingestible device 1600. A movable piston 1634 may be placed adjacent to the gas generating cell 1603. In this way, gas generation from the gas generating cell 1603 may propel a piston 1634 to move towards another end 1602*b* of the housing 1601 such that the dispensable substance in a reservoir compartment 1635 can be pushed out of the housing through a dispensing outlet 1607, e.g., the movement is shown at 1636, with the piston 1634 at a position after dispensing the substance. The dispensing outlet 1607 may comprise a plug. The reservoir compartment 1635 can store the dispensable substance (e.g., drug substance), or alternatively the reservoir compartment can house a storage reservoir 1661 which comprises the dispensable substance. The reservoir compartment 1635 or storage reservoir 1661 may have a volume of approximately 600 μL or even more dispensable substance, which may be dispensed in a single bolus, or gradually over a period of time.

The battery cells 1631 may have a height of 1.65 mm each, and one to three batteries may be used. The height of the piston may be reduced with custom molded part for around 1.5 mm to save space. If the gas generating cell 1603 is integrated with the piston 1634, the overall height of the PCB, batteries and gas generating cell in total can be reduced to around 5 mm, thus providing more space for drug storage. For example, for an ingestible device of 7.8 mm in length (e.g., from end 1602*a* to the other end 1602*b*), a reservoir compartment 1635 or a storage reservoir 1661 of approximately 600 μL may be used for drug delivery. For another example, for an ingestible device of 17.5 mm in length, a reservoir compartment 1635 or a storage reservoir 1661 of approximately 1300 μL may be used for drug release.

In some implementations, at the reservoir 1635 or 1661 for storing a therapeutically effective amount of the JAK inhibitor forms at least a portion of the device housing 1601. The therapeutically effective amount of the JAK inhibitor can be stored in the reservoir 1635 or 1661 at a particular pressure, for example, determined to be higher than a pressure inside the GI tract so that once the reservoir 1635 or 1661 is in fluid communication with the GI tract, the JAK inhibitor is automatically released. In certain implementations, the reservoir compartment 1635 includes a plurality of chambers, and each of the plurality of the chambers stores a different dispensable substance or a different storage reservoir 1661.

In certain embodiments, the storage reservoir 1661 is a compressible component or has compressible side walls. In particular embodiments, the compressible component can be composed, at least in part, or coated (e.g., internally) with polyvinyl chloride (PVC), silicone, DEHP (di-2-ethylhexyl phthalate), Tyvek, polyester film, polyolefin, polyethylene, polyurethane, or other materials that inhibit the JAK inhibitor from sticking to the reservoir and provide a sterile reservoir environment for the JAK inhibitor. The storage reservoir 1661 can be hermetically sealed. The reservoir compartment 1635 or storage reservoir 1661 can be configured to store JAK inhibitor in quantities in the range of 0.01 mL-2 mL, such as 0.05 mL-2 mL, such as 0.05 mL-2 mL, such as 0.6 mL-2 mL. In some embodiments, the storage reservoir 1661 is attachable to the device housing 1601, for example, in the reservoir compartment. Accordingly, the storage reservoir 1635 can be loaded with the JAK inhibitor prior to being positioned in and/or coupled to the ingestible device housing 1601. The ingestible device housing 1601 includes one or more openings configured as a loading port to load the dispensable substance into the reservoir compartment. In another embodiment, the ingestible device housing 1601 includes one or more openings configured as a vent.

As noted above, in some embodiments, a storage reservoir (optionally, containing a JAK inhibitor, such as a therapeutically effective amount of JAK inhibitor) is attachable to an ingestible device. In general, in such embodiments the storage reservoir and ingestible device can be designed in any appropriate fashion so that the storage reservoir can attach to the ingestible device when desired. Examples of designs include a storage reservoir that fits entirely within the ingestible device (e.g., in the ingestible device so that the storage reservoir is sealed within the device at the time the device is ingested by a subject), a storage reservoir that fits partially within the ingestible device, and a storage reservoir that is carried by the housing of the device. In some embodiments, the storage reservoir snap fits with the ingestible device. In certain embodiments, the storage reservoir is friction fit with the ingestible device. In some embodiments, the storage reservoir is held together with the ingestible device via a biasing mechanism, such as one or more springs, one or more latches, one or more hooks, one or more magnets, and/or electromagnetic radiation. In certain embodiments, the storage reservoir can be a piercable member. In some embodiments, the ingestible device has a sleeve into which the storage reservoir securely fits. In some embodiments, the storage reservoir is disposed in/on a slidable track/groove so that it can move onto a piercing needle when delivery of the therapeutic agent is desired. In certain embodiments, the storage reservoir is made of a soft plastic coating, which is contacted with a needle at any orientation to deliver the therapeutic agent when desired. Generally, the storage reservoir can be made of one or more appropriate materials, such as, for example, one or more plastics and/or one or more metals or alloys. Exemplary materials include silicone, polyvinyl chloride, polycarbonate and stainless steel. Optionally, the design may be such that the storage reservoir carries some or all of the electrical componentry to be used by the ingestible device. Although the foregoing discussion relates to one storage reservoir, it is to be understood that an ingestible device can be designed to carry any desired number (e.g., two, three, four, five) storage reservoirs. Different storage reservoirs can have the same or different designs. In some embodiments, the ingestible device (when fully assembled and packaged) satisfies the regulatory requirements for marketing a medical device in one or more jurisdictions selected from the United States of America, the European Union or any member state thereof, Japan, China, Brazil, Canada, Mexico, Colombia, Argentina, Chile, Peru, Russia, the UK, Switzerland, Norway, Turkey, Israel, any member state of the Gulf Cooperative Council, South Africa, India, Australia, New Zealand, South Korea, Singapore, Thailand, the Philippines, Malaysia, Viet Nam, Indonesia, Taiwan and Hong Kong.

In certain embodiments, the ingestible device housing 1601 includes one or more actuation systems (e.g., gas generating cell 1603) for pumping the JAK inhibitor from the reservoir 1635. In some embodiments, the actuation system can include a mechanical, electrical, electromechanical, hydraulic, and/or fluid actuation system. For example, a chemical actuation means may use chemical reaction of mixing one or more reagents to generate a sufficient volume of gas to propel the piston or drive element 1634 for drug release. The actuation system can be integrated into the reservoir compartment 1635 or can be an auxiliary system acting on or outside of the reservoir compartment 1635. For example, the actuation system can include pumping system for pushing/pulling the JAK inhibitor out of the reservoir compartment 1635 or the actuation system can be configured to cause the reservoir compartment 1635 to change structurally so that the volume inside of the reservoir compartment 1635 changes, thereby dispensing the JAK inhibitor from the reservoir compartment 1635. The actuation system can include an energy storage component such as a battery or a capacitor for powering the actuation system. The actuation system can be actuated via gas pressure or a system storing potential energy, such as energy from an elastic reservoir component being expanded during loading of the reservoir and after being positioned in the ingestible device housing 1601 being subsequently released from the expanded state when the ingestible device housing is at the location for release within the GI tract. In certain embodiments, the reservoir compartment 1635 can include a membrane portion, whereby the JAK inhibitor is dispensed from the reservoir compartment 1635 or storage reservoir 1661 via osmotic pressure.

In particular embodiments the storage reservoir 1661 is in a form of a bellow that is configured to be compressed via a pressure from the gas generating cell. The JAK inhibitor may be loaded into the bellow, which may be compressed by gas generation from the gas generating cell or other actuation means to dispense the dispensable substance through the dispensing outlet 1607 and out of the housing 1601. In some embodiments, the ingestible device includes a capillary plate placed between the gas generating cell and the first end of the housing, and a wax seal between the gas generating cell and the reservoir, wherein the wax seal is configured to melt and the dispensable substance is pushed through the capillary plate by a pressure from the gas generating cell. The shape of the bellow may aid in controlled delivery. The reservoir compartment 1635 includes a dispensing outlet, such as a valve or dome slit 1662 extending out of an end of the housing 1601, in accordance with particular implementations. Thus when the bellow is being compressed, the dispensable substance may be propelled out of the bellow through the valve or the dome slit.

In certain embodiments, the reservoir compartment 1635 includes one or more valves (e.g. a valve in the dispensing outlet 1607) that are configured to move or open to fluidly couple the reservoir compartment 1635 to the GI tract. In certain embodiments, a housing wall of the housing 1601 can form a portion of the reservoir compartment 1635. In certain embodiments, the housing walls of the reservoir serve as a gasket. One or more of the one or more valves are positioned in the housing wall of the device housing 1601, in accordance with particular implementations. One or more conduits may extend from the reservoir 1635 to the one or more valves, in certain implementations.

In certain embodiments, a housing wall of the housing 1601 can be formed of a material that is configured to dissolve, for example, in response to contact at the disease site. In certain embodiments, a housing wall of the housing 1601 can be configured to dissolve in response to a chemical reaction or an electrical signal. The one or more valves and/or the signals for causing the housing wall of the housing 1601 to dissolve or dissipate can be controlled by one or more processors or controllers positioned on PCB 1632 in the device housing 1601. The controller is communicably coupled to one or more sensors or detectors configured to determine when the device housing 1601 is proximate to a disease site. The sensors or detectors comprise a plurality of electrodes comprising a coating, in certain implementations. Releasing of the JAK inhibitor from the reservoir compartment 1635 is triggered by an electric signal from the electrodes resulting from the interaction of the coating with the one or more sites of disease site. The one or more sensors can include a chemical sensor, an electrical sensor, an optical sensor, an electromagnetic sensor, a light sensor, and/or a radiofrequency sensor.

In particular embodiments, the device housing 1601 can include one or more pumps configured to pump the therapeutically effective amount of the JAK inhibitor from the reservoir compartment 1635. The pump is communicably coupled to the one or more controllers. The controller is configured to activate the pump in response to detection by the one or more detectors of the disease site and activation of the valves to allow the reservoir 1635 to be in fluid communication with the GI tract. The pump can include a fluid actuated pump, an electrical pump, or a mechanical pump.

In certain embodiments, the device housing 1601 comprises one or more anchor systems for anchoring the device housing 1601 or a portion thereof at a particular location in the GI tract adjacent the disease site. In some embodiments, a storage reservoir comprises an anchor system, and the storage reservoir comprising a releasable substance is anchored to the GI tract. The anchor system can be activated by the controller in response to detection by the one or more detectors of the disease site. In certain implementations, the anchor system includes legs or spikes configured to extend from the housing wall(s) of the device housing 1601. The spikes can be configured to retract and/or can be configured to dissolve over time. An example of an attachable device that becomes fixed to the interior surface of the GI tract is described in PCT Patent Application PCT/US2015/012209, "Gastrointestinal Sensor Implantation System", filed Jan. 21, 2015, which is hereby incorporated by reference herein in its entirety.

Figure 20:
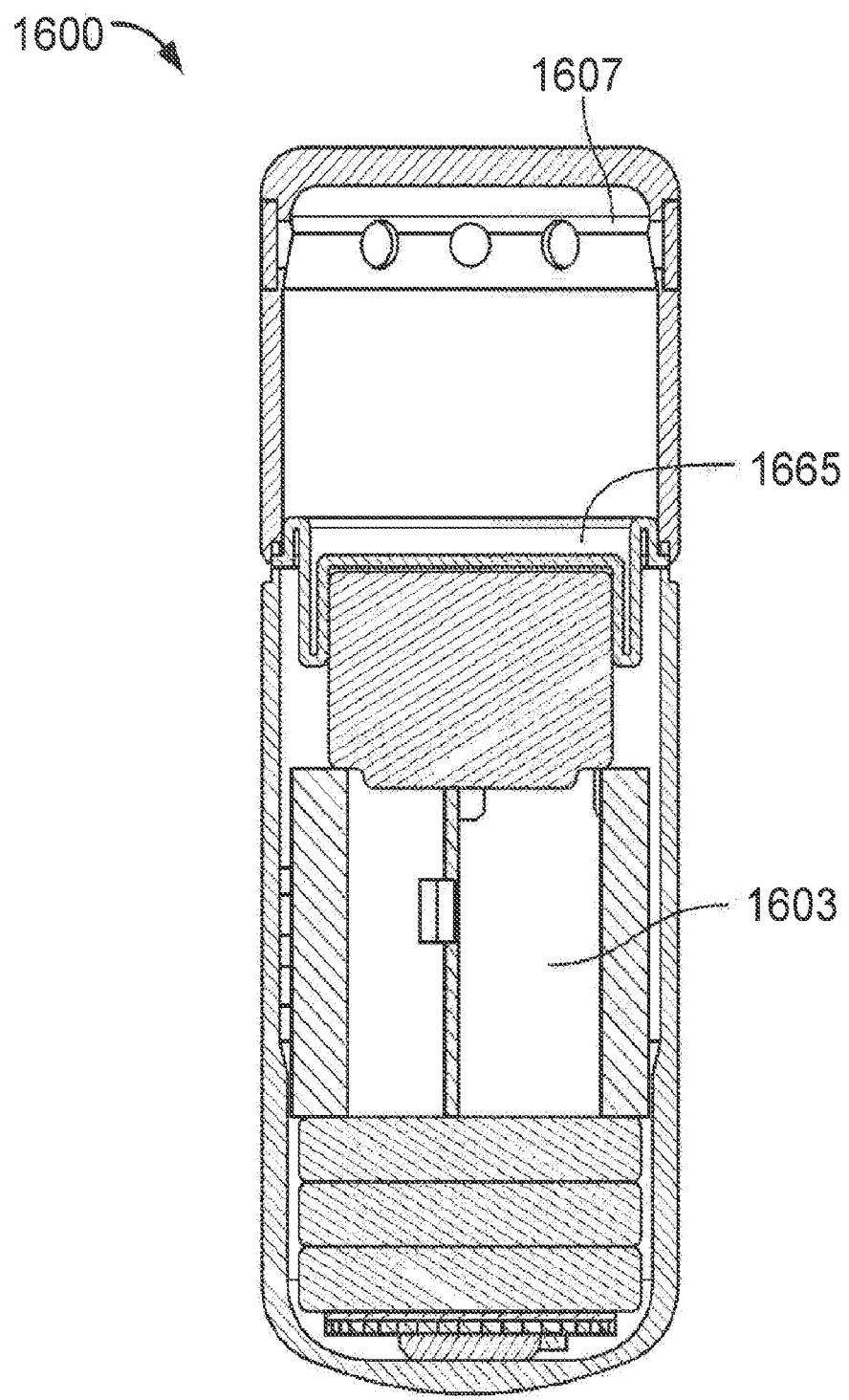
FIG. 20 illustrates an ingestible device having a flexible diaphragm to deform for drug delivery.

FIG. 20 provides an example structural diagram having a flexible diaphragm 1665 that may deform towards the dispensing outlet 1607 when the gas generating cell 1603 generates gas. The dispensable substance may then be propelled by the deformed diaphragm out of the housing through the dispensing outlet 1607. The dispensing outlet 1607 shown at FIG. 20 is in the form of a ring valve, however, any outlet design can be applied.

In some embodiments, an ingestible device can have an umbrella-shaped exit valve structure as a dispensing outlet of the ingestible device. Optionally, an ingestible device can have a flexible diaphragm to deform for drug delivery, and/or an integrated piston and gas generating cell such that the gas generating cell is movable with the piston to push for drug delivery.

In certain embodiments, an ingestible device can be anchored within the intestine by extending hooks from the ingestible device after it has entered the region of interest. For example, when the ingestible device determines it has arrived at a location within the GI tract, the hooks can be actuated to extend outside of the ingestible device to catch in the intestinal wall and hold the ingestible device in the respective location. In some embodiments, the hook can pierce into the intestinal wall to hold the ingestible device 100 in place. The hooks can be hollow. A hollow hook can be used to anchor the ingestible device and/or to dispense a substance from the dispensable substance, e.g., into the intestinal wall.

In some embodiments an ingestible device includes an intestinal gripper to grip a portion of the intestinal wall for delivering the dispensable substance. Such a gripper can include two or more arms configured to out of the device and close to grip a portion of the intestinal wall.

An injecting needle can be used with the anchoring arms to inject dispensable substance into the intestinal wall after a portion of the intestinal wall is gripped.

In some embodiments, when the gas generating cell generates gas to propel the piston to move towards the nozzle such that the dispensable substance can be pushed under the pressure to break a burst disc to be injected via the nozzle.

In some embodiments, an ingestible device has a jet delivery mechanism with enhanced usable volume of dispensable substance. For example, the nozzle may be placed at the center of the ingestible device, and gas channels may be placed longitudinally along the wall of the ingestible device to transport gas from the gas generating cell to propel the piston, which is placed at an end of the ingestible device.

In some embodiments, the ingestible device can use osmotic pressure to adhere a suction device of the ingestible device to the intestinal wall. For example, the ingestible device may have an osmotic mechanism that has a chamber storing salt crystals. The chamber can include a mesh placed in proximate to a burst valve at one end of the chamber, and a reverse osmosis (RO) membrane placed in proximate to a valve on the other end of the chamber. A suction device, e.g., two or more suction fingers, is placed outside of the chamber with an open outlet exposed to luminal fluid in the GI tract. When the osmotic mechanism is inactivated, e.g., the valve is closed so that no luminal fluid is drawn into the osmotic chamber. When the osmotic mechanism is activated by opening the valve, luminal fluid enters the ingestible device through an outlet of the suction device and enters the osmotic chamber through the valve. The salt in the chamber is then dissolved into the fluid. The RO membrane prevents any fluid to flow in the reverse direction, e.g., from inside the chamber to the valve. The fluid continues to flow until all the salt contained in the chamber is dissolved or until intestinal tissue is drawn into the suction device. As luminal fluid keeps flowing into the chamber, the solution of the luminal fluid with dissolved salt in the chamber may reduce osmotic pressure such that the suction force at may also be reduced. In this way, suction of the intestinal tissue may stall before the tissue is in contact with the valve to avoid damage to the intestinal tissue.

An ingestible device employing an osmotic mechanism can also include a suction device as illustrated. The suction device can be two or more suction fingers 347*a-b* disposed proximate to the outlet. The outlet can be connected to a storage reservoir storing the dispensable substance (e.g., therapeutic agent). The storage reservoir can contact a piston (similar to 104 in FIG. 16), which can be propelled by pressure generated from the osmotic pump to move towards the outlet. The osmotic pump can be similar to the osmotic mechanism described in the preceding paragraph. A breakaway section can be placed in proximate to the other end (opposite to the end where the outlet 107 is disposed) of the ingestible device.

In some embodiments, tumbling suction by an ingestible device is used. Such an ingestible device does not require any electronics or other actuation elements. Such an ingestible device may constantly, intermittently, or periodically tumble when travelling through the intestine. When the ingestible device tumbles to a position that the outlet is in direct contact with the intestinal wall, a suction process similar to that described in the preceding paragraph may occur. Additional structural elements such as fins, flutes or the like may be added to the outer wall of the ingestible device 100 to promote the tumbling motion.

In certain embodiments, the reservoir is an anchorable reservoir, which is a reservoir comprising one or more anchor systems for anchoring the reservoir at a particular location in the GI tract adjacent the disease site. In certain embodiments, the anchor system includes legs or spikes or other securing means such as a piercing element, a gripping element, a magnetic-flux-guiding element, or an adhesive material, configured to extend from the anchorable reservoir of the device housing. The spikes can be configured to retract and/or can be configured to dissolve over time. In some embodiments, the anchorable reservoir is suitable for localizing, positioning and/or anchoring. In some embodiments, the anchorable reservoir is suitable for localizing, and positioning and/or anchoring by an endoscope. In some embodiments, the anchorable reservoir is connected to the endoscope. In some embodiments, the anchorable reservoir is connected to the endoscope in a manner suitable for oral administration. In some embodiments, the anchorable reservoir is connected to the endoscope in a manner suitable for rectal administration. Accordingly, provided herein in some embodiments is an anchorable reservoir is connected to an endoscope wherein the anchorable reservoir comprises a therapeutically effective amount of the JAK inhibitor. In some embodiments the endoscope is fitted with a spray catheter.

Exemplary embodiments of anchorable reservoirs are as follows. In more particular examples of the following exemplary embodiments the reservoir is connected to an endoscope.

In one embodiment, the anchorable reservoir comprises an implant capsule for insertion into a body canal to apply radiation treatment to a selected portion of the body canal. The reservoir includes a body member defining at least one therapeutic treatment material receiving chamber and at least one resilient arm member associated with the body member for removably engaging the body canal when the device is positioned therein.

In one embodiment the anchorable reservoir has multiple suction ports and permits multiple folds of tissue to be captured in the suction ports with a single positioning of the device and attached together by a tissue securement mechanism such as a suture, staple or other form of tissue bonding.

The suction ports may be arranged in a variety of configurations on the reservoir to best suit the desired resulting tissue orientation.

In some embodiments an anchorable reservoir comprises a tract stimulator and/or monitor IMD comprising a housing enclosing electrical stimulation and/or monitoring circuitry and a power source and an elongated flexible member extending from the housing to an active fixation mechanism adapted to be fixed into the GI tract wall is disclosed. After fixation is effected, the elongated flexible member bends into a preformed shape that presses the housing against the mucosa so that forces that would tend to dislodge the fixation mechanism are minimized. The IMD is fitted into an esophageal catheter lumen with the fixation mechanism aimed toward the catheter distal end opening whereby the bend in the flexible member is straightened. The catheter body is inserted through the esophagus into the GI tract cavity to direct the catheter distal end to the site of implantation and fix the fixation mechanism to the GI tract wall. The IMD is ejected from the lumen, and the flexible member assumes its bent configuration and lodges the hermetically sealed housing against the mucosa. A first stimulation/sense electrode is preferably an exposed conductive portion of the housing that is aligned with the bend of the flexible member so that it is pressed against the mucosa. A second stimulation/sense electrode is located at the fixation site.

In some embodiments a reservoir for sensing one or more parameters of a patient is anchored to a tissue at a specific site and is released from a device, using a single actuator operated during a single motion. As an example, a delivery device may anchor the capsule to the tissue site and release the reservoir from the delivery device during a single motion of the actuator.

In some embodiments a device is provided comprising: a reservoir configured to contain a fluid, the reservoir having at least one outlet through which the fluid may exit the reservoir; a fluid contained within the reservoir; a primary material contained within the reservoir and having a controllable effective concentration in the fluid; and at least one electromagnetically responsive control element located in the reservoir or in a wall of the reservoir and adapted for modifying the distribution of the primary material between a first active form carried in the fluid and a second form within the reservoir in response to an incident electromagnetic control signal, the effective concentration being the concentration of the first active form in the fluid, whereby fluid exiting the reservoir carries the primary material in the first active form at the effective concentration.

In some embodiments systems and methods are provided for implementing or deploying medical or veterinary devices or reservoirs (a) operable for anchoring at least partly within a digestive tract, (b) small enough to pass through the tract per vias naturales and including a wireless-control component, (c) having one or more protrusions positionable adjacent to a mucous membrane, (d) configured to facilitate redundant modes of anchoring, (e) facilitating a "primary" material supply deployable within a stomach for an extended and/or controllable period, (f) anchored by one or more adaptable extender modules supported by a subject's head or neck, and/or (g) configured to facilitate supporting at least a sensor within a subject's body lumen for up to a day or more.

In certain embodiments, the reservoir is attachable to an ingestible device. In certain embodiments, the ingestible device comprises a housing and the reservoir is attachable to the housing. In certain embodiments, the attachable reservoir is also an anchorable reservoir, such as an anchorable reservoir comprising one or more anchor systems for anchoring the reservoir at a particular location in the GI tract as disclosed hereinabove.

Accordingly, in certain embodiments, provided herein is a JAK inhibitor for use in a method of treating a disease of the gastrointestinal tract as disclosed herein, wherein the JAK inhibitor is contained in a reservoir suitable for attachment to a device housing, and wherein the method comprises attaching the reservoir to the device housing to form the ingestible device, prior to orally administering the ingestible device to the subject.

In certain embodiments, provided herein is an attachable reservoir containing a JAK inhibitor for use in a method of treating a disease of the gastrointestinal tract, wherein the method comprises attaching the reservoir to a device housing to form an ingestible device and orally administering the ingestible device to a subject, wherein the JAK inhibitor is released by device at a location in the gastrointestinal tract of the subject that is proximate to one or more sites of disease.

In certain embodiments, provided herein is an attachable reservoir containing a JAK inhibitor, wherein the reservoir is attachable to a device housing to form an ingestible device that is suitable for oral administration to a subject and that is capable of releasing the JAK inhibitor at a location in the gastrointestinal tract of the subject that is proximate to one or more sites of disease.

In particular implementation the ingestible device includes cameras (e.g., video cameras) that affords inspection of the entire GI tract without discomfort or the need for sedation, thus avoiding many of the potential risks of conventional endoscopy. Video imaging can be used to help determine one or more characteristics of the GI tract, including the location of disease (e.g., presence or location of inflamed tissue and/or lesions associated with inflammatory bowel disease). In some embodiments, the ingestible device 101 may comprise a camera for generating video imaging data of the GI tract which can be used to determine, among other things, the location of the device. Examples of video imaging capsules include Medtronic's PillCam™, Olympus' Endocapsule®, and IntroMedic's MicroCam™. For a review of imaging capsules, see Basar et al. "Ingestible Wireless Capsule Technology: A Review of Development and Future Indication" International Journal of Antennas and Propagation (2012); 1-14). Other imaging technologies implemented with the device 101 can include thermal imaging cameras, and those that employ ultrasound or Doppler principles to generate different images (see Chinese patent application CN104473611: "Capsule endoscope system having ultrasonic positioning function".

Ingestible devices can be equipped with sources for generating reflected light, including light in the Ultraviolet, Visible, Near-infrared and/or Mid-infrared spectrum, and the corresponding detectors for spectroscopy and hyperspectral imaging. Likewise, autofluorescense may be used to characterize GI tissue (e.g., subsurface vessel information), or low-dose radiation (see Check-Cap™) can be used to obtain 3D reconstructed images.

Device Components

An ingestible device in accordance with particular embodiments of the present invention may comprise a component made of a non-digestible material and contain the JAK inhibitor. In some embodiments, the material is plastic.

It is envisaged that the device is single-use. The device is loaded with a drug prior to the time of administration. In some embodiments, it may be preferred that there is provided a medicinal product comprising the device pre-filled with the drug.

Anchoring Components

Several systems may actively actuate and control the capsule position and orientation in different sections of the GI tract. Examples include leg-like or anchor-like mechanisms that can be deployed by an ingestible device to resist peristaltic forces in narrowed sections of the GI tract, such as the intestine, and anchor the device to a location. Other systems employ magnetic shields of different shapes that can interact with external magnetic fields to move the device. These mechanisms may be particularly useful in areas outside of the small intestine, like the cecum and large intestine.

An anchoring mechanism may be a mechanical mechanism. For example, a device may be a capsule comprising a plurality of legs configured to steer the capsule. The number of legs in the capsule may be, for example, two, four, six, eight, ten or twelve. The aperture between the legs of the device may be up to about 35 mm; about 30 to about 35 mm; about 35 to about 75 mm; or about 70 to about 75 mm. The contact area of each leg may be varied to reduce impact on the tissue. One or more motors in the capsule may each actuate a set of legs independently from the other. The motors may be battery-powered motors.

An anchoring mechanism may be a non-mechanical mechanism. For example, a device may be a capsule comprising a permanent magnet located inside the capsule. The capsule may be anchored at the desired location of the GI tract by an external magnetic field.

An anchoring mechanism may comprise a non-mechanical mechanism and a mechanical mechanism. For example, a device may be a capsule comprising one or more legs, one or more of which are coated with an adhesive material.

Locomotion Components

Ingestible devices can be active or passive, depending on whether they have controlled or non-controlled locomotion. Passive (non-controlled) locomotion is more commonly used among ingestible devices given the challenges of implementing a locomotion module. Active (controlled) locomotion is more common in endoscopic ingestible capsules. For example, a capsule may comprise a miniaturized locomotion system (internal locomotion). Internal locomotion mechanisms may employ independent miniaturized propellers actuated by DC brushed motors, or the use of water jets. As an example, a mechanism may comprise flagellar or flap-based swimming mechanisms. As an example, a mechanism may comprise cyclic compression/extension shape-memory alloy (SMA) spring actuators and anchoring systems based on directional micro-needles. As an example, a mechanism may comprise six SMA actuated units, each provided with two SMA actuators for enabling bidirectional motion. As an example, a mechanism may comprise a motor adapted to electrically stimulating the GI muscles to generate a temporary restriction in the bowel.

As an example, a capsule may comprise a magnet and motion of the capsule is caused by an external magnetic field. For example, a locomotion system may comprise an ingestible capsule and an external magnetic field source. For example, the system may comprise an ingestible capsule and magnetic guidance equipment such as, for example, magnetic resonance imaging and computer tomography, coupled to a dedicated control interface. In some embodiments drug release mechanisms may also be triggered by an external condition, such as temperature, pH, movement, acoustics, or combinations thereof.

Use of an Endoscope or an Ingestible Device in Biopsy and Surgery

Sampling

Ingestible devices may comprise a mechanism adapted to permit the collection of tissue samples. In some examples, this is achieved using electro-mechanical solutions to collect and store the sample inside an ingestible device. As an example, a biopsy mechanism may include a rotational tissue cutting razor fixed to a torsional spring or the use of microgrippers to fold and collect small biopsies. As an example, Over-the-scope clips (OTSC®) may be used to perform endoscopic surgery and/or biopsy. As an example of the methods disclosed herein, the method may comprise releasing a JAK inhibitor and collecting a sample inside the device. As an example, the method may comprise releasing a JAK inhibitor and collecting a sample inside the device in a single procedure.

Figure 21:
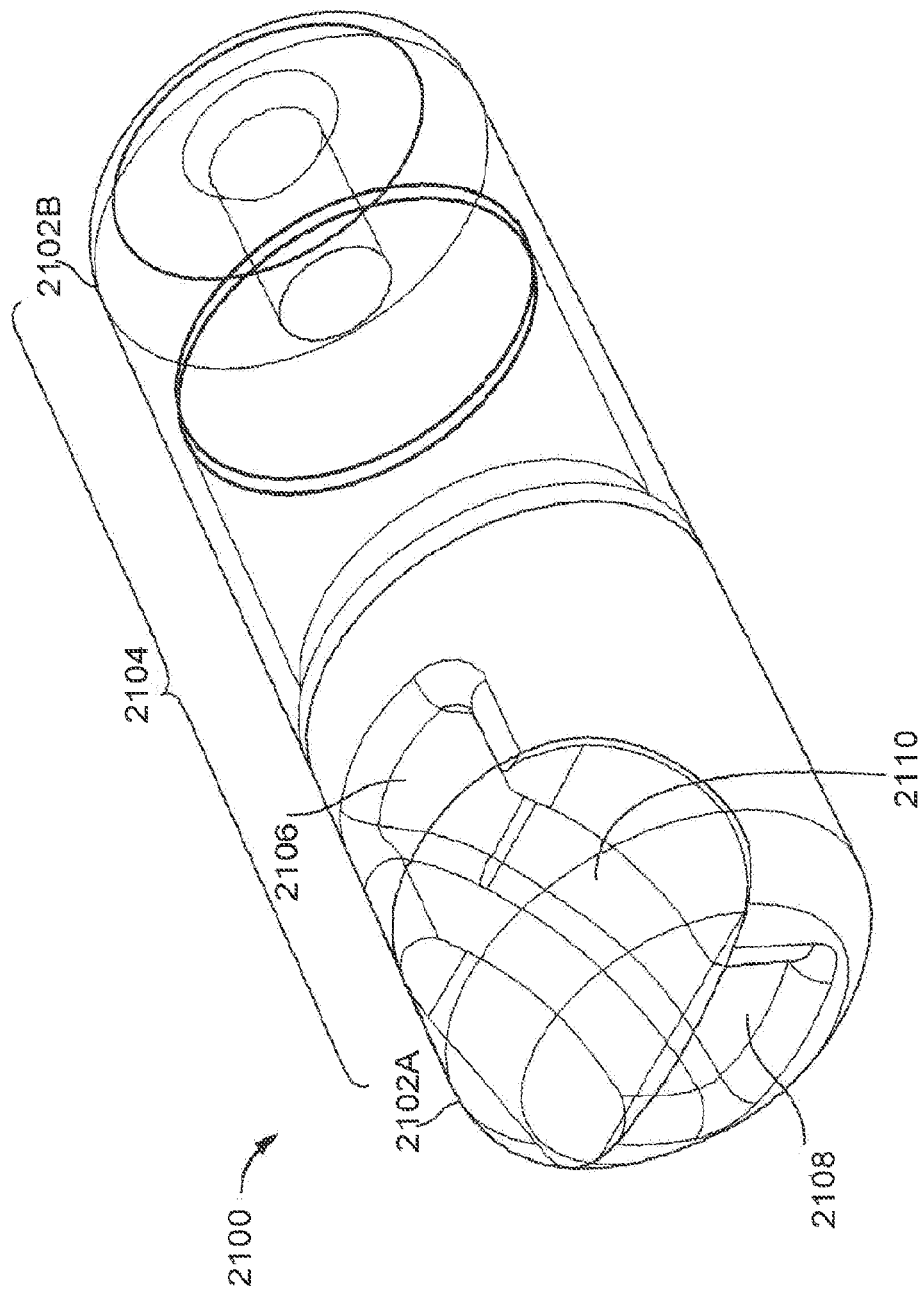
FIG. 21 shows an illustrative embodiment of an ingestible device with multiple openings in the housing.

FIG. 21 illustrates an example ingestible device 2100 with multiple openings in the housing. The ingestible device 2100 has an outer housing with a first end 2102A, a second end 2102B, and a wall 2104 extending longitudinally from the first end 2102A to the second end 2102B. Ingestible device 2100 has a first opening 2106 in the housing, which is connected to a second opening 2108 in the housing. The first opening 2106 of the ingestible device 2100 is oriented substantially perpendicular to the second opening 2108, and the connection between the first opening 2106 and the second opening 2108 forms a curved chamber 2110 within the ingestible device 2100.

The overall shape of the ingestible device 2100, or any of the other ingestible devices discussed in this disclosure, may be similar to an elongated pill or capsule.

In some embodiments, a portion of the curved chamber 2110 may be used as a sampling chamber, which may hold samples obtained from the GI tract. In some embodiments the curved chamber 2110 is subdivided into sub-chambers, each of which may be separated by a series of one or more valves or interlocks.

In some embodiments, the first opening 2106, the second opening 2108, or the curved chamber 2110 include one or more of a hydrophilic or hydrophobic material, a sponge, a valve, or an air permeable membrane.

The use of a hydrophilic material or sponge may allow samples to be retained within the curved chamber 2110, and may reduce the amount of pressure needed for fluid to enter through the first opening 2106 and dislodge air or gas in the curved chamber 2110. Examples of hydrophilic materials that may be incorporated into the ingestible device 2100 include hydrophilic polymers such as polyvinyl alcohol, polyvinyl pyrrolidone, and the like. Similarly, materials that have undergone various types of treatments, such as plasma treatments, may have suitable hydrophilic properties, and may be incorporated into the investible device 2100. Sponges may be made of any suitable material or combination of materials, such as fibers of cotton, rayon, glass, polyester, polyethylene, polyurethane, and the like. Sponges generally may be made from commercially available materials, such as those produced by Porex®.

As discussed in more detail below, in some embodiments, the sponges may be treated in order to change their absorbency or to help preserve samples.

In some embodiments, the sponges may be cut or abraded to change their absorbency or other physical properties.

Hydrophobic materials located near the second opening 2108 may repel liquids, discouraging liquid samples from entering or exiting the curved chamber 2110 through the second opening 2108. This may serve a similar function as an air permeable membrane. Examples of hydrophobic materials which may be incorporated into the ingestible device 2100 include polycarbonate, acrylics, fluorocarbons, styrenes, certain forms of vinyl, stainless steel, silicone, and the like.

The various materials listed above are provided as examples, and are not limiting. In practice, any type of suitable hydrophilic, hydrophobic, or sample preserving material may be used in the ingestible device 2100.

In some embodiments, an ingestible device includes a moveable valve as a diaphragm valve, which uses a mechanical actuator to move a flexible diaphragm in order to seal or unseal an aperture in a second portion of an inlet region, which may effectively block or unblock the inlet region. However, it will be understood that, in some embodiments, the moveable valve may be a different type of valve. For example, in some embodiments the moveable valve may be replaced by a pumping mechanism. As another example, in some embodiments the moveable valve is replaced with an osmotic valve A sampling chamber of an ingestible device can have an exit port to allow air or gas to exit the sampling chamber, while preventing at least a portion of the sample obtained by the ingestible device from exiting the sampling chamber. For example, the exit port may include a gas-permeable membrane. An ingestible device can include one-way valve as part of its exit port.

An ingestible device can include an outlet port connected to the volume within housing of the ingestible device. The outlet port may provide a path for the gas to exit the ingestible device and be released into the environment surrounding the ingestible device. This may prevent pressure from building up within the housing of the ingestible device. In some embodiments, an ingestible device does not include an outlet port, and the gas stays inside the volume of the ingestible device. In some embodiments, the outlet port may contain a gas permeable membrane, a one-way valve, a hydrophobic channel, or some other mechanism to avoid unwanted material, (e.g., fluids and solid particulates from within the GI tract), from entering the ingestible device through the outlet port.

In some embodiments, the ingestible device may include a sensor within or proximate to the sampling chamber. For example, this sensor may be used to detect various properties of a sample contained within the sampling chamber, or this sensor may be used to detect the results of an assay technique applied to the sample contained within the sampling chamber.

In some embodiments, a hydrophilic sponge is located within the sampling chamber, and the hydrophilic sponge may be configured to absorb the sample as the sample enters the sampling chamber. In some embodiments, the hydrophilic sponge fills a substantial portion of the sampling chamber, and holds the sample for an extended period of time. This may be particularly advantageous if the sample is collected from the ingestible device after the ingestible device exits the body. In some embodiments, the hydrophilic sponge is placed on only certain surfaces or fills only certain portions of the sampling chamber. For example, it may be possible to line certain walls (or all walls) of the sampling chamber with a hydrophilic sponge to assist in drawing in the sample, while leaving some (or none) of the walls of the sampling chamber uncovered. Leaving walls uncovered may allow the use of diagnostics or assay techniques that require a relatively un-obscured optical path.

In some embodiments, the ingestible device may include a sealed vacuum chamber connected to the exit port, or connected directly or indirectly to the sampling chamber. In some embodiments a pin valve may be used as a moveable valve (e.g., as moveable valve of ingestible device). In certain embodiments, a rotary valve may be used as a moveable valve (e.g., as moveable valve of ingestible device). In some embodiments, a flexible diaphragm, or diaphragm valve, may be used as a moveable valve (e.g., as moveable valve of ingestible device). In certain embodiments, a mechanism is near the diaphragm or in direct contact with the diaphragm. The spring mechanism may apply pressure to the diaphragm to oppose the pressure applied by the mechanical actuator, which may cause the flexible diaphragm to be moved into an open position when the mechanical actuator is not applying pressure to the flexible diaphragm. Additionally, this may ensure that the diaphragm valve remains open when the mechanical actuator is not applying pressure across the flexible diaphragm. In some embodiments, moving the mechanical actuator from a closed position to an open position causes a volume of the inlet region within the ingestible device to increase. This may cause the pressure within the inlet region to be reduced, generating suction to draw a sample into the inlet region. Similarly, moving the mechanical actuator from an open position to a closed position may cause the volume of the inlet region to be reduced. This may cause the pressure within the inlet region to be increased, pushing the sample out of the inlet region. Depending on the design of the inlet region, the mechanical actuator, and the moveable valve, this may push the sample into the sampling chamber rather than pushing the sample back through the opening in the ingestible device.

Figure 22:
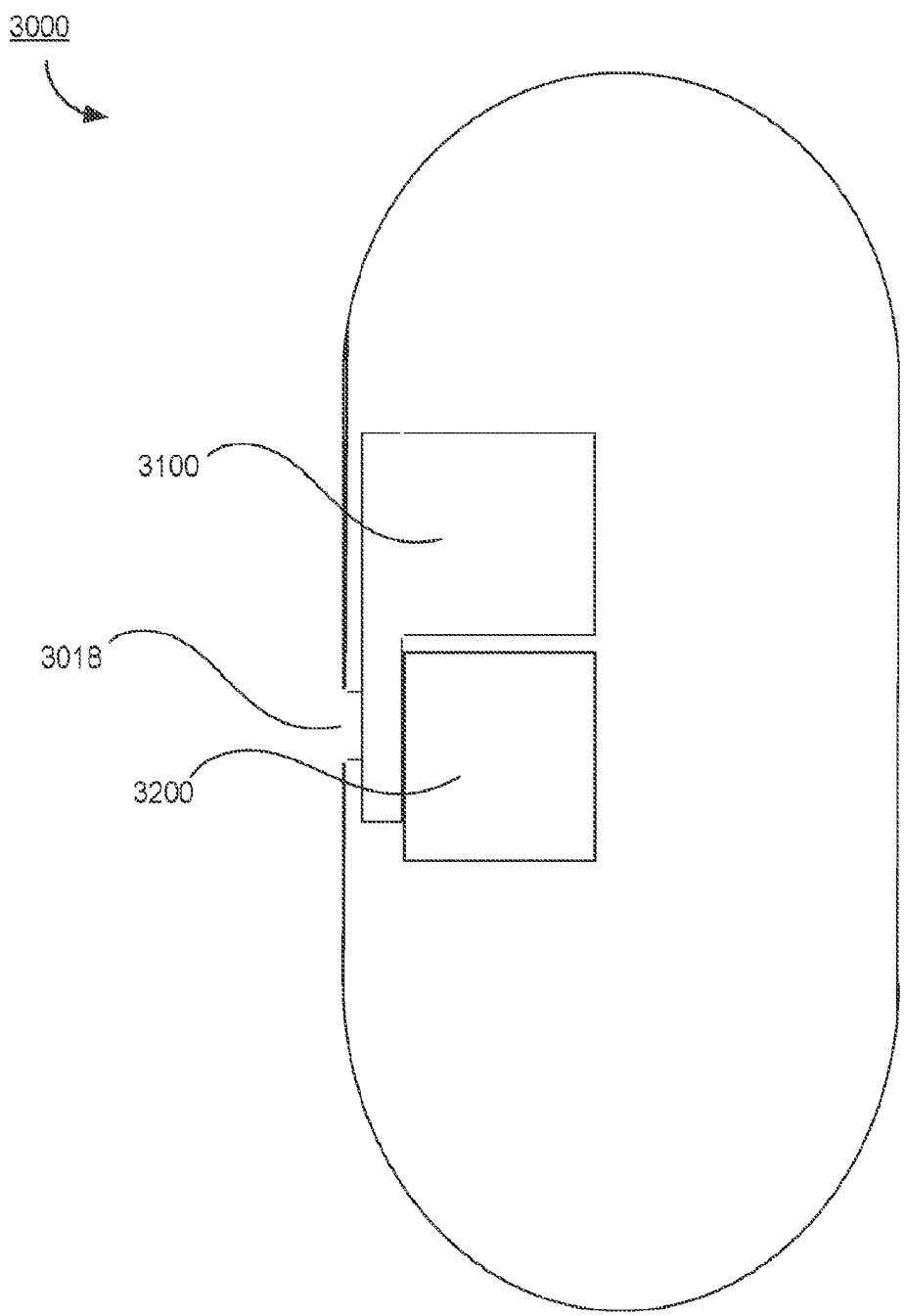
FIG. 22 shows a highly cross-section of an ingestible device including a valve system and a sampling system.

FIG. 22 depicts a cross-sectional view of a portion of the interior of ingestible device 3000. As shown in FIG. 22, the interior of ingestible device 3000 includes a valve system 3100 and a sampling system 3200. Valve system 3100 is depicted as having a portion that is flush with the opening 3018 so that valve system 3100 prevents fluid exterior to ingestible device 2000 from entering sampling system 3200. However, as described in more detail below with reference to FIGS. 22-27, valve system 3100 can change position so that valve system 3100 allows fluid exterior to ingestible device 3000 to enter sampling system 3200.

Figure 27:
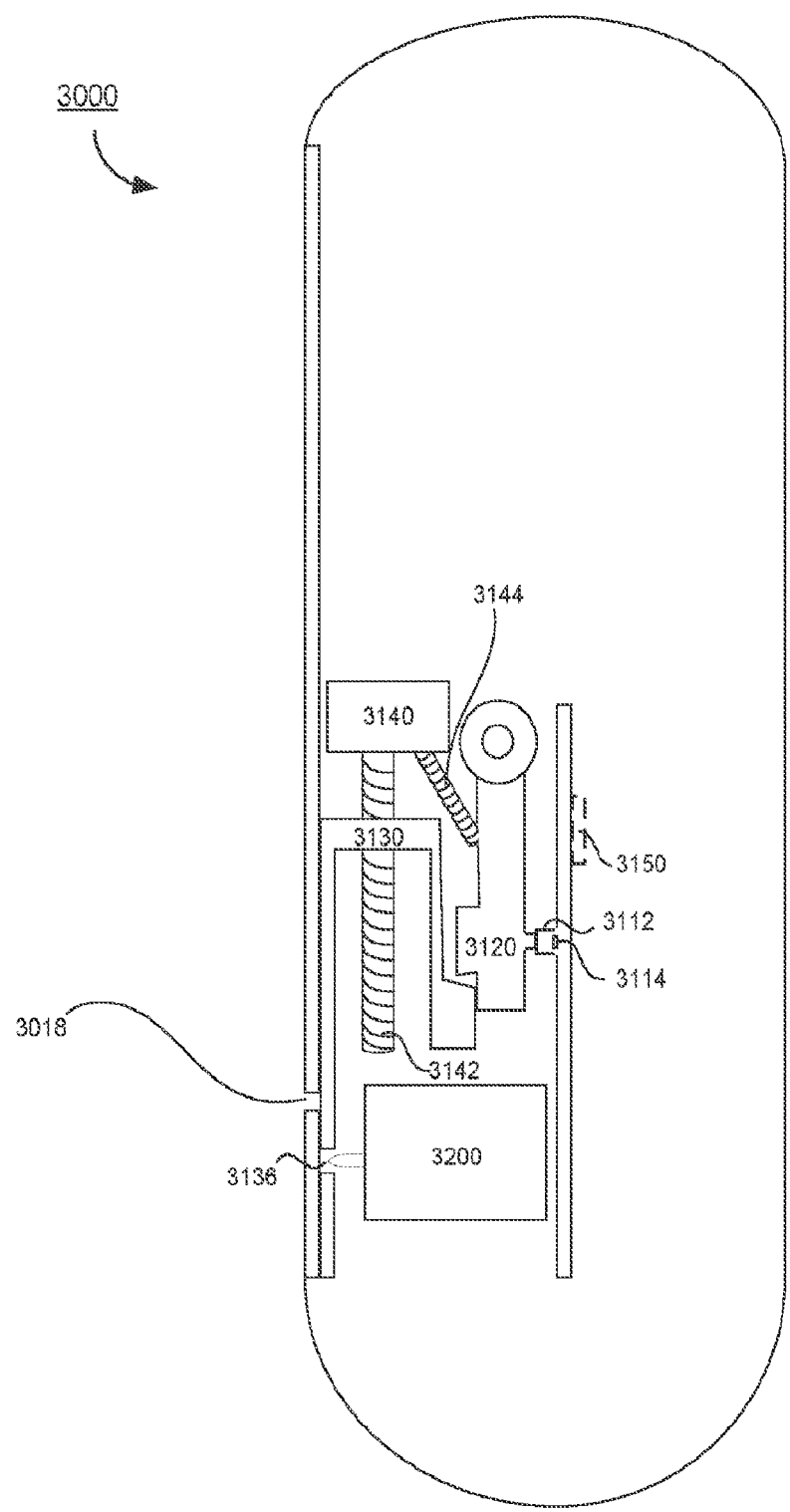
FIG. 27 illustrates a more detailed view of an ingestible device including a valve system and a sampling system.

FIGS. 23 and 27 illustrate valve system 3100 in more detail. As shown in FIG. 23, valve system 3100 includes an actuation mechanism 3110, a trigger 3120, and a gate 3130. In FIGS. 23 and 7, a leg 3132 of gate 3130 is flush against, and parallel with, housing wall 3016 so that gate leg 3132 covers opening 3018 to prevent fluid exterior to ingestible device 3000 (e.g., fluid in the GI tract) from entering the interior of ingestible device 3000. A protrusion 3134 of gate 3130 engages a lip 3122 of trigger 3120. A peg 3124 of trigger 3120 engages a wax pot 3112 of actuation mechanism 3110. Referring to FIG. 27, a biasing mechanism 3140 includes a compression spring 3142 that applies an upward force on gate 3130. Biasing mechanism 3140 also includes a torsion spring 3144 that applies a force on trigger 3120 in the counter-clockwise direction. In FIGS. 23 and 27, the force applied by torsion spring 3144 is counter-acted by the solid wax in pot 3112, and the force applied by compression spring 3142 is counter-acted by lip 3122.

FIG. 24A and FIG. 24B show an embodiment of the manner in which actuation mechanism 3110 actuates movement of trigger 3120. Similar to FIGS. 23 and 27, FIG. 24A shows a configuration in which peg 3124 applies a force against solid wax pot 3112 due to torsion spring 3144, and in which the solid nature of wax pot 3112 resists the force applied by peg 3124. A control unit 3150 is in signal communication with valve system 3100. During use of ingestible device 3000, a control unit 3150 receives a signal, indicating that the position of valve system 3100 should change, e.g., so that ingestible device 3000 can take a sample of a fluid in the GI tract. Control unit 3150 sends a signal that causes a heating system 3114 of actuation system 3100 to heat the wax in pot 3112 so that the wax melts. As shown in FIG. 24B, the melted wax is not able to resist the force applied by peg 3124 so that, under the force of torsion spring 3144, trigger 3120 moves in a counter-clockwise fashion.

Figure 25A:
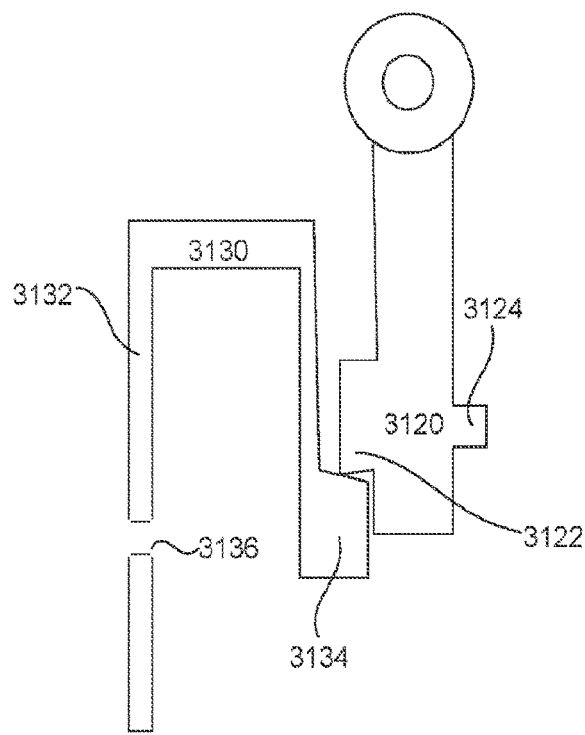
FIGS. 25A and 25B illustrate a portion of a two-stage valve system in its first and second stages, respectively.
Figure 25B:
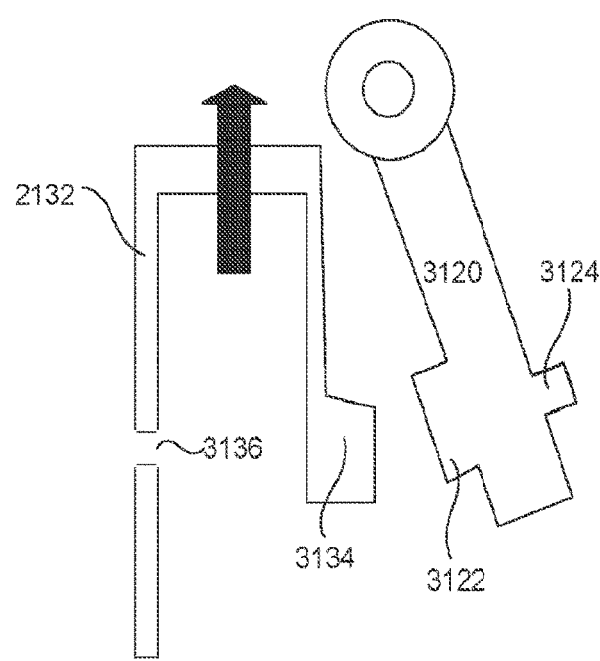

FIGS. 25A and 25B illustrate the interaction of trigger 3120 and gate 3130 before and after actuation. As shown in FIG. 25A, when wax pot 3112 is solid (corresponding to the configuration shown in FIG. 24A), protrusion 3134 engages lip 3122, which prevents the force of compression spring 3142 from moving gate 3130 upward. As shown in FIG. 25B, when the wax in pot 3112 melts (FIG. 24B), trigger 3120 moves counter-clockwise, and lip 3122 disengages from protrusion 3134. This allows the force of compression spring 3142 to move gate 3130 upward. As seen by comparing FIG. 25A to FIG. 25B, the upward movement of gate 3130 results in an upward movement of an opening 3136 in gate leg 3132.

Figures 26A, 26B:
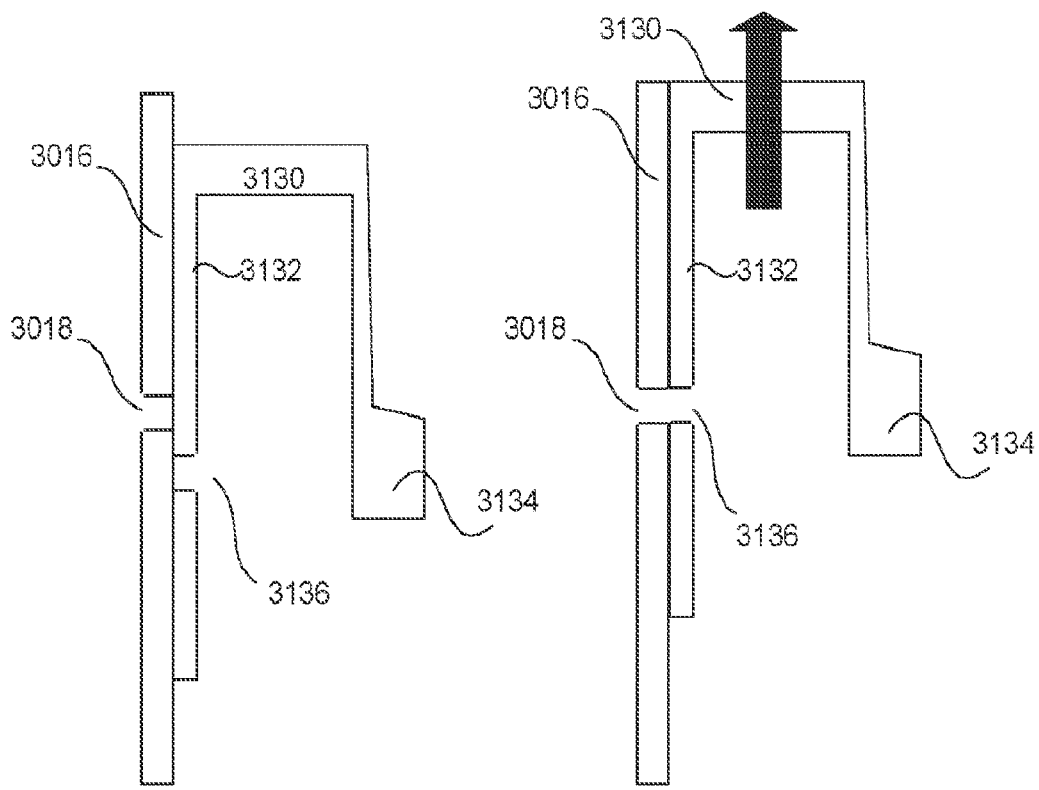
FIGS. 26A and 26B illustrate a portion of a two-stage valve system in its first and second stages, respectively.

FIGS. 26A and 26B illustrate the impact of the upward movement of opening 3136 on the ability of ingestible device 3000 to obtain a sample. As shown in FIG. 26A, when the wax in pot 3112 is solid (FIGS. 24A and 25A), opening 3136 in is not aligned with opening 3018 in wall 3016 of ingestible device 3000. Instead, gate leg 3132 covers opening 3018 and blocks fluid from entering the interior of ingestible device 3000. As shown in FIG. 26B, when the wax in pot 3112 is melted and trigger 3120 and gate 3130 have moved (FIGS. 24B and 42B), opening 3136 in gate 3130 is aligned with opening 3018 in wall 3016. In this configuration, fluid that is exterior to ingestible device 3000 (e.g., in the GI tract) can enter the interior of ingestible device 3000 via openings 3018 and 3036.

FIG. 27 illustrates a more detailed view of ingestible device 3000 including valve system 3100 and sampling system 3200.

While the foregoing description is made with regard to a valve system having one open position and one closed position (e.g., a two-stage valve system), the disclosure is not limited in this sense. Rather, the concepts described above with regard to a two stage valve system can be implemented with a valve system have more than two stages (e.g., three stages, four stages, five stages, etc.).

Figure 28:
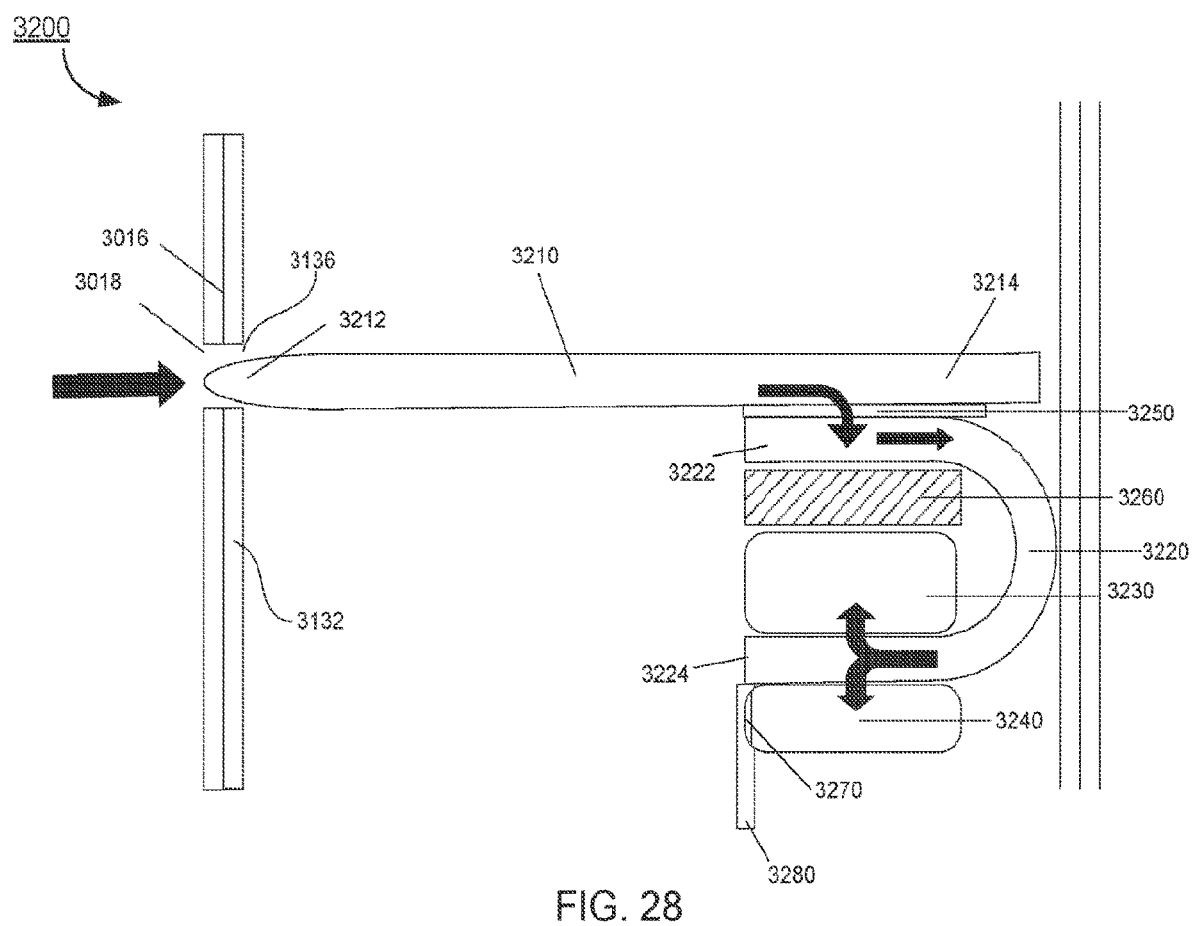
FIG. 28 illustrates a portion of an ingestible device including a sampling system and a two-stage valve system in its second stage.

As noted above in addition to a valve system, an ingestible device includes a sampling system. FIG. 28 illustrates a partial cross sectional view of ingestible device 3000 with sampling system 3200 and certain components of valve system 3100. Sampling system 3200 includes a series of sponges configured to absorb fluid from an opening, move the fluid to a location within the housing, and prepare the fluid for testing. Preparation for testing may include filtering the fluid and combining the fluid with a chemical assay. The assay may be configured to dye cells in the filtered sample. The series of sponges includes a wicking sponge 3210, a transfer sponge 3220, a volume sponge 3230, and an assay sponge 3240. Sampling system 3200 also includes a membrane 3270 located between assay sponge 3240 and a vent 3280 for gases to leave sampling system 3200. A cell filter 3250 is located between distal end 3214 of wicking sponge 3210 and a first end 3222 of transfer sponge 3220. Membrane 3270 is configured to allow one or more gases to leave sampling system 3200 via an opening 3280, while maintaining liquid in sampling system 3200.

Figure 29:
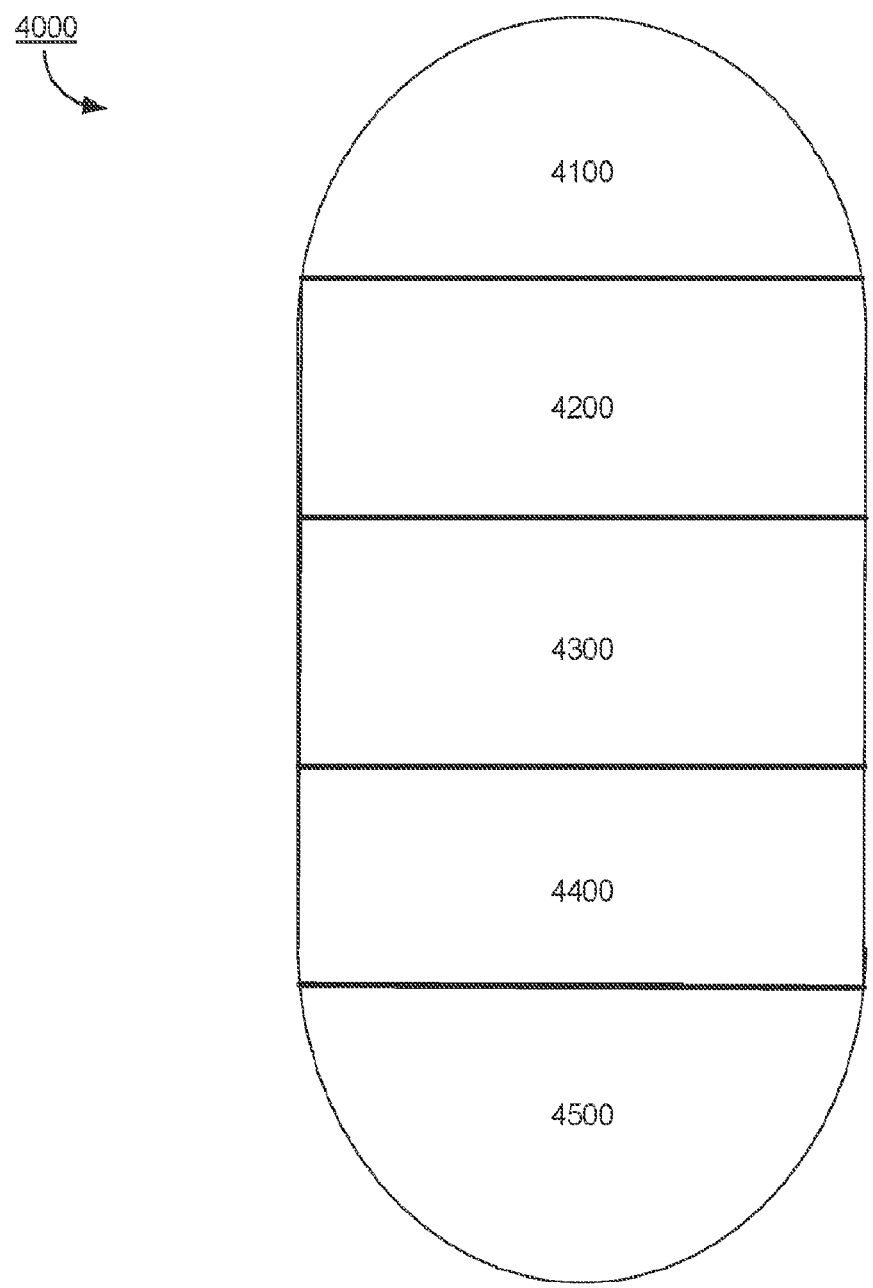
FIG. 29 is a highly schematic illustrate of an ingestible device.

FIG. 29 is a highly schematic illustration of an ingestible device 4000 that contains multiple different systems that cooperate for obtaining a sample and analyzing a sample, e.g., within the GI tract of a subject. Ingestible device 4000 includes a power system 4100 (e.g., one or more batteries), configured to power an electronics system 4200 (e.g., including a control system, optionally in signal communication with an external base station), a valve system 4300, a sampling system 4400, and an analytic system 4500. Exemplary analytical systems include assay systems, such as, for example, optical systems containing one or more sources of radiation and/or one or more detectors.

Some or all of the sponges of the above-described sampling systems may contain one or more preservatives (see discussion above). Typically, the assay sponge and/or the volume sponge 3230 and/or the transfer sponge contain one or more preservatives. Typically, the preservative(s) are selected based on the analyte of interest, e.g., an analyte (such as a protein biomarker) for a GI disorder.

Communication Systems

An ingestible device may be equipped with a communication system adapted to transmit and/or receive data, including imaging and/or localization data. As an example, a communication system may employ radiofrequency transmission. Ingestible devices using radiofrequency communication are attractive because of their efficient transmission through the layers of the skin. This is especially true for low frequency transmission (UHF-433 ISM and lower, including the Medical Device Radio Communication Service band (MDRS) band 402-406 MHz). In another embodiment, acoustics are used for communications, including the transmission of data. For example, an ingestible capsule may be able to transmit information by applying one or more base voltages to an electromechanical transducer or piezoelectric (e.g., PZT, PVDF, etc.) device to cause the piezoelectric device to ring at particular frequencies, resulting in an acoustic transmission. A multi-sensor array for receiving the acoustic transmission may include a plurality of acoustic transducers that receive the acoustic transmission from a movable device such as an ingestible capsule as described in U.S. patent application Ser. No. 11/851,214 filed Sep. 6, 2007, incorporated by reference herein in its entirety.

As an example, a communication system may employ human body communication technology. Human body communication technology uses the human body as a conductive medium, which generally requires a large number of sensor electrodes on the skin. As an example, a communication system may integrate a data storage system.

Environmental Sensors

In some embodiments the device may comprise environmental sensors to measure pH, temperature, transit times, or combinations thereof. Other examples of environmental sensors include, but are not limited to a capacitance sensor, an impedance sensor, a heart rate sensor, acoustic sensor such as a microphone or hydrophone, image sensor, and/or a movement sensor. In one embodiment, the ingestible device comprises a plurality of different environmental sensors for generating different kinds of environmental data.

In order to avoid the problem of capsule retention, a thorough past medical and surgical history should be undertaken. In addition, several other steps have been proposed, including performing investigations such as barium followthrough. In cases where it is suspected that there is a high risk of retention, the patient is given a patency capsule a few days before swallowing an ingestible device. Any dissolvable non-endoscopic capsule may be used to determine the patency of the GI tract. The patency capsule is usually the same size as the ingestible device and can be made of cellophane. In some embodiments, the patency capsule contains a mixture of barium and lactose, which allows visualization by x-ray. The patency capsule may also include a radiotag or other label, which allows for it to be detected by radio-scanner externally. The patency capsule may comprise wax plugs, which allow for intestinal fluid to enter and dissolve the content, thereby dividing the capsule into small particles.

Accordingly, in some embodiments, the methods herein comprise (a) identifying a subject having a disease of the gastrointestinal tract and (b) evaluating the subject for suitability to treatment. In some embodiments, the methods herein comprise evaluating for suitability to treatment a subject identified as having a disease of the gastrointestinal tract. In some embodiments, evaluating the subject for suitability to treatment comprises determining the patency of the subject's GI tract.

In some embodiments, an ingestible device comprises a tissue anchoring mechanism for anchoring the ingestible device to a subject's tissue. For example, an ingestible device could be administered to a subject and once it reaches the desired location, the tissue attachment mechanism can be activated or deployed such that the ingestible device, or a portion thereof, is anchored to the desired location. In some embodiments, the tissue anchoring mechanism is reversible such that after initial anchoring, the tissue attachment device is retracted, dissolved, detached, inactivated or otherwise rendered incapable of anchoring the ingestible device to the subject's tissue. In some embodiments the attachment mechanism is placed endoscopically.

In some embodiments, a tissue anchoring mechanism comprises an osmotically-driven sucker. In some embodiments, the osmotically-driven sucker comprises a first valve on the near side of the osmotically-driven sucker (e.g., near the subject's tissue) and a second one-way valve that is opened by osmotic pressure on the far side of the osmotically-driven sucker, and an internal osmotic pump system comprising salt crystals and semi-permeable membranes positioned between the two valves. In such embodiments, osmotic pressure is used to adhere the ingestible device to the subject's tissue without generating a vacuum within the ingestible capsule. After the osmotic system is activated by opening the first valve, fluid is drawn in through the sucker and expelled through the second burst valve. Fluid continues to flow until all the salt contained in the sucker is dissolved or until tissue is drawn into the sucker. As liminal fluid is drawn through the osmotic pump system, solutes build up between the tissue and the first valve, reducing osmotic pressure. In some embodiments, the solute buildup stalls the pump before the tissue contacts the valve, preventing tissue damage. In some embodiments, a burst valve is used on the far side of the osmotically-driven sucker rather than a one-way valve, such that luminal fluid eventually clears the saline chamber and the osmotic flow reverses, actively pushing the subject's tissue out of the sucker. In some embodiments, the ingestible device may be anchored to the interior surface of tissues forming the GI tract of a subject. In one embodiment, the ingestible device comprises a connector for anchoring the device to the interior surface of the GI tract. The connector may be operable to ingestible device to the interior surface of the GI tract using an adhesive, negative pressure and/or fastener.

In some embodiments a device comprises a tract stimulator and/or monitor IMD comprising a housing enclosing electrical stimulation and/or monitoring circuitry and a power source and an elongated flexible member extending from the housing to an active fixation mechanism adapted to be fixed into the GI tract wall is disclosed. After fixation is effected, the elongated flexible member bends into a pre-formed shape that presses the housing against the mucosa so that forces that would tend to dislodge the fixation mechanism are minimized. The IMD is fitted into an esophageal catheter lumen with the fixation mechanism aimed toward the catheter distal end opening whereby the bend in the flexible member is straightened. The catheter body is inserted through the esophagus into the GI tract cavity to direct the catheter distal end to the site of implantation and fix the fixation mechanism to the GI tract wall. The IMD is ejected from the lumen, and the flexible member assumes its bent configuration and lodges the hermetically sealed housing against the mucosa. A first stimulation/sense electrode is preferably an exposed conductive portion of the housing that is aligned with the bend of the flexible member so that it is pressed against the mucosa. A second stimulation/sense electrode is located at the fixation site.

In some embodiments a device includes a fixation mechanism to anchor the device to tissue within a body lumen, and a mechanism to permit selective de-anchoring of the device from the tissue anchoring site without the need for endoscopic or surgical intervention. An electromagnetic device may be provided to mechanically actuate the de-anchoring mechanism. Alternatively, a fuse link may be electrically blown to de-anchor the device. As a further alternative, a rapidly degradable bonding agent may be exposed to a degradation agent to de-anchor the device from a bonding surface within the body lumen.

In some embodiments a device is as disclosed in patent publication WO2015112575A1, incorporated by reference herein in its entirety. The patent publication is directed to a gastrointestinal sensor implantation system. In some embodiments an orally-administrable capsule comprises a tissue capture device or reservoir removably coupled to the orally-administrable capsule, where the tissue capture device including a plurality of fasteners for anchoring the tissue capture device to gastrointestinal tissue within a body In some embodiments, the ingestible device contains an electric energy emitting means, a radio signal transmitting means, a medicament storage means and a remote actuatable medicament releasing means. The capsule signals a remote receiver as it progresses through the alimentary tract in a previously mapped route and upon reaching a specified site is remotely triggered to release a dosage of medicament. Accordingly, in some embodiments, releasing the JAK inhibitor is triggered by a remote electromagnetic signal.

In some embodiments, the ingestible device includes a housing introducible into a body cavity and of a material insoluble in the body cavity fluids, but formed with an opening covered by a material which is soluble in body cavity fluids. A diaphragm divides the interior of the housing into a medication chamber including the opening, and a control chamber. An electrolytic cell in the control chamber generates a gas when electrical current is passed therethrough to deliver medication from the medication chamber through the opening into the body cavity at a rate controlled by the electrical current. Accordingly, in some embodiments, releasing the JAK inhibitor is triggered by generation in the composition of a gas in an amount sufficient to expel the JAK inhibitor.

In some embodiments, the ingestible device includes an oral drug delivery device having a housing with walls of water permeable material and having at least two chambers separated by a displaceable membrane. The first chamber receives drug and has an orifice through which the drug is expelled under pressure. The second chamber contains at least one of two spaced apart electrodes forming part of an electric circuit which is closed by the ingress of an aqueous ionic solution into the second chamber. When current flows through the circuit, gas is generated and acts on the displaceable membrane to compress the first chamber and expel the active ingredient through the orifice for progressive delivery to the gastrointestinal tract.

In some embodiments, the ingestible device includes an ingestible device for delivering a substance to a chosen location in the GI tract of a mammal includes a receiver of electromagnetic radiation for powering an openable part of the device to an opened position for dispensing of the substance. The receiver includes a coiled wire that couples the energy field, the wire having an air or ferrite core. In a further embodiment the invention includes an apparatus for generating the electromagnetic radiation, the apparatus including one or more pairs of field coils supported in a housing. The device optionally includes a latch defined by a heating resistor and a fusible restraint. The device may also include a flexible member that may serve one or both the functions of activating a transmitter circuit to indicate dispensing of the substance; and restraining of a piston used for expelling the substance.

In some embodiments, the ingestible device includes an ingestible device for delivering a substance to a chosen location in the GI tract of a mammal includes a receiver of electromagnetic radiation for powering an openable part of the device to an opened position for dispensing of the substance. The receiver includes a coiled wire that couples the energy field, the wire having an air or ferrite core. In a further embodiment the invention includes an apparatus for generating the electromagnetic radiation, the apparatus including one or more pairs of field coils supported in a housing. The device optionally includes a latch defined by a heating resistor and a fusible restraint. The device may also include a flexible member that may serve one or both the functions of activating a transmitter circuit to indicate dispensing of the substance; and restraining of a piston used for expelling the substance.

In some embodiments, the ingestible device is a device a swallowable capsule. A sensing module is disposed in the capsule. A bioactive substance dispenser is disposed in the capsule. A memory and logic component is disposed in the capsule and in communication with the sensing module and the dispenser.

In some embodiments, localized administration is implemented via an electronic probe which is introduced into the intestinal tract of a living organism and which operates autonomously therein, adapted to deliver one or more therapy agents. In one embodiment, the method includes loading the probe with one or more therapy agents, and selectively releasing the agents from the probe at a desired location of the intestinal tract in order to provide increased efficacy over traditional oral ingestion or intravenous introduction of the agent(s).

In some embodiments, the ingestible device includes electronic control means for dispensing the drug substantially to the diseased tissue sites of the GI tract, according to a pre-determined drug release profile obtained prior to administration from the specific mammal. Accordingly, in some embodiments, releasing the JAK inhibitor is triggered by an electromagnetic signal generated within the device. The releasing may occur according to a pre-determined drug release profile.

In some embodiments, the ingestible device can include at least one guide tube, one or more tissue penetrating members positioned in the guide tube, a delivery member, an actuating mechanism and a release element. The release element degrades upon exposure to various conditions in the intestine so as to release and actuate the actuating mechanism. Embodiments of the invention are particularly useful for the delivery of drugs which are poorly absorbed, tolerated and/or degraded within the GI tract.

In some embodiments, the ingestible device includes an electronic pill comprising at least one reservoir with a solid powder or granulate medicament or formulation, a discharge opening and an actuator responsive to control circuitry for displacing medicine from the reservoir to the discharge opening. The medicament or formulation comprises a dispersion of one or more active ingredients—e.g., solids in powder or granulate form—in an inert carrier matrix. Optionally, the active ingredients are dispersed using intestinal moisture absorbed into the pill via a semi-permeable wall section.

In some embodiments, the ingestible device includes a sensor comprising a plurality of electrodes having a miniature size and a lower power consumption and a coating exterior to the electrodes, wherein the coating interacts with a target condition thereby producing a change in an electrical property of the electrodes, wherein the change is transduced into an electrical signal by the electrodes. Accordingly, in some embodiments, releasing the JAK inhibitor is triggered by an electric signal by the electrodes resulting from the interaction of the coating with the one or more sites of disease. Further provided herein is a system for medication delivery comprising such sensor and a pill.

In some embodiments, the ingestible device includes an electronic pill comprising a plurality of reservoirs, each of the reservoirs comprising a discharge opening covered by a removable cover. The pill comprises at least one actuator responsive to control circuitry for removing the cover from the discharge opening. The actuator can for example be a spring loaded piston breaking a foil cover when dispensing the medicament. Alternatively, the cover can be a rotatable disk or cylinder with an opening which can be brought in line with the discharge opening of a reservoir under the action of the actuator.

In some embodiments, the ingestible device includes an electronically and remotely controlled pill or medicament delivery system. The pill includes a housing; a reservoir for storing a medicament; an electronically controlled release valve or hatch for dispensing one or more medicaments stored in the reservoir while traversing the gastrointestinal tract; control and timing circuitry for opening and closing the valve; and a battery. The control and timing circuitry opens and closes the valve throughout a dispensing time period in accordance with a preset dispensing timing pattern which is programmed within the control and timing circuitry. RF communication circuitry receives control signals for remotely overriding the preset dispensing timing pattern, reprogramming the control and timing circuitry or terminating the dispensing of the medicament within the body. The pill includes an RFID tag for tracking, identification, inventory and other purposes.

In some embodiments, the ingestible device includes an electronic capsule which has a discrete drive element comprising: a housing, electronics for making the electronic capsule operable, a pumping mechanism for dosing and displacing a substance, a power source for powering the electronic capsule and enabling the electronics and the pumping mechanism to operate, and a locking mechanism; and a discrete payload element comprising: a housing, a reservoir for storing the substance, one or more openings in the housing for releasing the substance from the reservoir and a locking mechanism for engaging the drive element locking mechanism. Engagement of the drive element locking mechanism with the payload element locking mechanism secures the drive element to the payload element, thereby making the electronic capsule operable and specific.

In some embodiments, the ingestible device may be a mucoadhesive device configured for release of an active agent.

In some embodiments, the ingestible device includes an apparatus that includes an ingestible medical treatment device, which is configured to initially assume a contracted state having a volume of less than 4 cm$^3$. The device includes a gastric anchor, which initially assumes a contracted size, and which is configured to, upon coming in contact with a liquid, expand sufficiently to prevent passage of the anchor through a round opening having a diameter of between 1 cm and 3 cm. The device also includes a duodenal unit, which is configured to pass through the opening, and which is coupled to the gastric anchor such that the duodenal unit is held between 1 cm and 20 cm from the gastric anchor.

In some embodiments, the ingestible device includes a medical robotic system and method of operating such comprises taking intraoperative external image data of a patient anatomy, and using that image data to generate a modeling adjustment for a control system of the medical robotic system (e.g., updating anatomic model and/or refining instrument registration), and/or adjust a procedure control aspect (e.g., regulating substance or therapy delivery, improving targeting, and/or tracking performance).

In one embodiment the ingestible device may also include one or more environmental sensors. Environmental sensor may be used to generate environmental data for the environment external to device in the gastrointestinal (GI) tract of the subject. In some embodiments, environmental data is generated at or near the location within the GI tract of the subject where a drug is delivered. Examples of environmental sensor include, but are not limited to a capacitance sensor, a temperature sensor, an impedance sensor, a pH sensor, a heart rate sensor, acoustic sensor, image sensor (e.g., a hydrophone), and/or a movement sensor (e.g., an accelerometer). In one embodiment, the ingestible device comprises a plurality of different environmental sensors for generating different kinds of environmental data.

In one embodiment, the image sensor is a video camera suitable for obtaining images in vivo of the tissues forming the GI tract of the subject. In one embodiment, the environmental data is used to help determine one or more characteristics of the GI tract, including the location of disease (e.g., presence or location of inflamed tissue and/or lesions associated with inflammatory bowel disease). In some embodiments, the ingestible device may comprise a camera for generating video imaging data of the GI tract which can be used to determine, among other things, the location of the device.

In another embodiment, the ingestible device described herein may be localized using a gamma scintigraphy technique or other radio-tracker technology as employed by Phaeton Research's Enterion™ capsule (See Teng, Renli, and Juan Maya. "Absolute bioavailability and regional absorption of ticagrelor in healthy volunteers." Journal of Drug Assessment 3.1 (2014): 43-50), or monitoring the magnetic field strength of permanent magnet in the ingestible device (see T. D. Than, et al., "A review of localization systems for robotic endoscopic capsules," IEEE Trans. Biomed. Eng., vol. 59, no. 9, pp. 2387-2399, September 2012).

In one embodiment, drug delivery is triggered when it encounters the site of disease in the GI tract.

In one embodiment, the one or more environmental sensors measure pH, temperature, transit times, or combinations thereof.

In some embodiments, releasing the JAK inhibitor is dependent on the pH at or in the vicinity of the location. In some embodiments the pH in the jejunum is from 6.1 to 7.2, such as 6.6. In some embodiments the pH in the mid small bowel is from 7.0 to 7.8, such as 7.4. In some embodiments the pH in the ileum is from 7.0 to 8.0, such as 7.5. In some embodiments the pH in the right colon is from 5.7 to 7.0, such as 6.4. In some embodiments the pH in the mid colon is from 5.7 to 7.4, such as 6.6. In some embodiments the pH in the left colon is from 6.3 to 7.7, such as 7.0. In some embodiments, the gastric pH in fasting subjects is from about 1.1 to 2.1, such as from 1.4 to 2.1, such as from 1.1 to 1.6, such as from 1.4 to 1.6. In some embodiments, the gastric pH in fed subjects is from 3.9 to 7.0, such as from 3.9 to 6.7, such as from 3.9 to 6.4, such as from 3.9 to 5.8, such as from 3.9 to 5.5, such as from 3.9 to 5.4, such as from 4.3 to 7.0, such as from 4.3 to 6.7, such as from 4.3 to 6.4, such as from 4.3 to 5.8, such as from 4.3 to 5.5, such as from 4.3 to 5.4. In some embodiments, the pH in the duodenum is from 5.8 to 6.8, such as from 6.0 to 6.8, such as from 6.1 to 6.8, such as from 6.2 to 6.8, such as from 5.8 to 6.7, such as from 6.0 to 6.7, such as from 6.1 to 6.7, such as from 6.2 to 6.7, such as from 5.8 to 6.6, such as from 6.0 to 6.6, such as from 6.1 to 6.6, such as from 6.2 to 6.6, such as from 5.8 to 6.5, such as from 6.0 to 6.5, such as from 6.1 to 6.5, such as from 6.2 to 6.5.

In some embodiments, releasing the JAK inhibitor is not dependent on the pH at or in the vicinity of the location. In some embodiments, releasing the JAK inhibitor is triggered by degradation of a release component located in the capsule. In some embodiments, the JAK inhibitor is not triggered by degradation of a release component located in the capsule. In some embodiments, wherein releasing the JAK inhibitor is not dependent on enzymatic activity at or in the vicinity of the location. In some embodiments, releasing the JAK inhibitor is not dependent on bacterial activity at or in the vicinity of the location.

In some embodiments, the pharmaceutical composition is an ingestible device, comprising:

a housing defined by a first end, a second end substantially opposite from the first end, and a wall extending longitudinally from the first end to the second end;

a reservoir located within the housing and containing the JAK inhibitor, wherein a first end of the reservoir is attached to the first end of the housing;

a mechanism for releasing the JAK inhibitor from the reservoir;

and;

an exit valve configured to allow the JAK inhibitor to be released out of the housing from the reservoir.

In some embodiments, the ingestible device further comprises:

an electronic component located within the housing; and a gas generating cell located within the housing and adjacent to the electronic component, wherein the electronic component is configured to activate the gas generating cell to generate gas.

In some embodiments, the ingestible device further comprises:

a safety device placed within or attached to the housing, wherein the safety device is configured to relieve an internal pressure within the housing when the internal pressure exceeds a threshold level.

In some embodiments, the pharmaceutical composition is an ingestible device, comprising:
a housing defined by a first end, a second end substantially opposite from the first end, and a wall extending longitudinally from the first end to the second end;
an electronic component located within the housing;
a gas generating cell located within the housing and adjacent to the electronic component,
wherein the electronic component is configured to activate the gas generating cell to generate gas;
a reservoir located within the housing,
wherein the reservoir stores a dispensable substance and a first end of the reservoir is attached to the first end of the housing;
an exit valve located at the first end of the housing,
wherein the exit valve is configured to allow the dispensable substance to be released out of the first end of the housing from the reservoir; and
a safety device placed within or attached to the housing, wherein the safety device is configured to relieve an internal pressure within the housing when the internal pressure exceeds a threshold level.

In some embodiments, the pharmaceutical composition is an ingestible device, comprising:
a housing defined by a first end, a second end substantially opposite from the first end, and a wall extending longitudinally from the first end to the second end;
an electronic component located within the housing,
a gas generating cell located within the housing and adjacent to the electronic component,
wherein the electronic component is configured to activate the gas generating cell to generate gas;
a reservoir located within the housing,
wherein the reservoir stores a dispensable substance and a first end of the reservoir is attached to the first end of the housing;
an injection device located at the first end of the housing,
wherein the jet injection device is configured to inject the dispensable substance out of the housing from the reservoir; and
a safety device placed within or attached to the housing, wherein the safety device is configured to relieve an internal pressure within the housing.

In some embodiments, the pharmaceutical composition is an ingestible device, comprising:
a housing defined by a first end, a second end substantially opposite from the first end, and a wall extending longitudinally from the first end to the second end;
an optical sensing unit located on a side of the housing, wherein the optical sensing unit is configured to detect a reflectance from an environment external to the housing;
an electronic component located within the housing;
a gas generating cell located within the housing and adjacent to the electronic component,
wherein the electronic component is configured to activate the gas generating cell to generate gas in response to identifying a location of the ingestible device based on the reflectance;
a reservoir located within the housing,
wherein the reservoir stores a dispensable substance and a first end of the reservoir is attached to the first end of the housing;
a membrane in contact with the gas generating cell and configured to move or deform into the reservoir by a pressure generated by the gas generating cell; and
a dispensing outlet placed at the first end of the housing, wherein the dispensing outlet is configured to deliver the dispensable substance out of the housing from the reservoir.

In one embodiment, drug delivery is triggered when it encounters the site of disease in the GI tract.

In one embodiment, the one or more environmental sensors measure pH, temperature, transit times, or combinations thereof.

In some embodiments, releasing the JAK inhibitor is dependent on the pH at or in the vicinity of the location. In some embodiments the pH in the jejunum is from 6.1 to 7.2, such as 6.6. In some embodiments the pH in the mid small bowel is from 7.0 to 7.8, such as 7.4. In some embodiments the pH in the ileum is from 7.0 to 8.0, such as 7.5. In some embodiments the pH in the right colon is from 5.7 to 7.0, such as 6.4. In some embodiments the pH in the mid colon is from 5.7 to 7.4, such as 6.6. In some embodiments the pH in the left colon is from 6.3 to 7.7, such as 7.0. In some embodiments, the gastric pH in fasting subjects is from about 1.1 to 2.1, such as from 1.4 to 2.1, such as from 1.1 to 1.6, such as from 1.4 to 1.6. In some embodiments, the gastric pH in fed subjects is from 3.9 to 7.0, such as from 3.9 to 6.7, such as from 3.9 to 6.4, such as from 3.9 to 5.8, such as from 3.9 to 5.5, such as from 3.9 to 5.4, such as from 4.3 to 7.0, such as from 4.3 to 6.7, such as from 4.3 to 6.4, such as from 4.3 to 5.8, such as from 4.3 to 5.5, such as from 4.3 to 5.4. In some embodiments, the pH in the duodenum is from 5.8 to 6.8, such as from 6.0 to 6.8, such as from 6.1 to 6.8, such as from 6.2 to 6.8, such as from 5.8 to 6.7, such as from 6.0 to 6.7, such as from 6.1 to 6.7, such as from 6.2 to 6.7, such as from 5.8 to 6.6, such as from 6.0 to 6.6, such as from 6.1 to 6.6, such as from 6.2 to 6.6, such as from 5.8 to 6.5, such as from 6.0 to 6.5, such as from 6.1 to 6.5, such as from 6.2 to 6.5.

In some embodiments, releasing the JAK inhibitor is not dependent on the pH at or in the vicinity of the location. In some embodiments, releasing the JAK inhibitor is triggered by degradation of a release component located in the capsule. In some embodiments, the JAK inhibitor is not triggered by degradation of a release component located in the capsule. In some embodiments, wherein releasing the JAK inhibitor is not dependent on enzymatic activity at or in the vicinity of the location. In some embodiments, releasing the JAK inhibitor is not dependent on bacterial activity at or in the vicinity of the location.

In some embodiments, the pharmaceutical composition is an ingestible device, comprising:
a housing defined by a first end, a second end substantially opposite from the first end, and a wall extending longitudinally from the first end to the second end;
a reservoir located within the housing and containing the JAK inhibitor,
wherein a first end of the reservoir is attached to the first end of the housing;
a mechanism for releasing the JAK inhibitor from the reservoir;
and;
an exit valve configured to allow the JAK inhibitor to be released out of the housing from the reservoir.

In some embodiments, the ingestible device further comprises:
an electronic component located within the housing; and a gas generating cell located within the housing and adjacent to the electronic component,
wherein the electronic component is configured to activate the gas generating cell to generate gas.

In some embodiments, the ingestible device further comprises:
a safety device placed within or attached to the housing,
wherein the safety device is configured to relieve an internal pressure within the housing when the internal pressure exceeds a threshold level.

In some embodiments, the pharmaceutical composition is an ingestible device, comprising:
a housing defined by a first end, a second end substantially opposite from the first end, and a wall extending longitudinally from the first end to the second end;
an electronic component located within the housing;
a gas generating cell located within the housing and adjacent to the electronic component,
wherein the electronic component is configured to activate the gas generating cell to generate gas;
a reservoir located within the housing,
wherein the reservoir stores a dispensable substance and a first end of the reservoir is attached to the first end of the housing;
an exit valve located at the first end of the housing,
wherein the exit valve is configured to allow the dispensable substance to be released out of the first end of the housing from the reservoir; and
a safety device placed within or attached to the housing,
wherein the safety device is configured to relieve an internal pressure within the housing when the internal pressure exceeds a threshold level.

In some embodiments, the pharmaceutical composition is an ingestible device, comprising:
a housing defined by a first end, a second end substantially opposite from the first end, and a wall extending longitudinally from the first end to the second end;
an electronic component located within the housing,
a gas generating cell located within the housing and adjacent to the electronic component,
wherein the electronic component is configured to activate the gas generating cell to generate gas;
a reservoir located within the housing,
wherein the reservoir stores a dispensable substance and a first end of the reservoir is attached to the first end of the housing;
an injection device located at the first end of the housing,
wherein the jet injection device is configured to inject the dispensable substance out of the housing from the reservoir; and
a safety device placed within or attached to the housing,
wherein the safety device is configured to relieve an internal pressure within the housing.

In some embodiments, the pharmaceutical composition is an ingestible device, comprising:
a housing defined by a first end, a second end substantially opposite from the first end, and a wall extending longitudinally from the first end to the second end;
an optical sensing unit located on a side of the housing,
wherein the optical sensing unit is configured to detect a reflectance from an environment external to the housing;
an electronic component located within the housing;
a gas generating cell located within the housing and adjacent to the electronic component,
wherein the electronic component is configured to activate the gas generating cell to generate gas in response to identifying a location of the ingestible device based on the reflectance;
a reservoir located within the housing,
wherein the reservoir stores a dispensable substance and a first end of the reservoir is attached to the first end of the housing;
a membrane in contact with the gas generating cell and configured to move or deform into the reservoir by a pressure generated by the gas generating cell; and
a dispensing outlet placed at the first end of the housing,
wherein the dispensing outlet is configured to deliver the dispensable substance out of the housing from the reservoir.

In some embodiments, the pharmaceutical composition is an ingestible device as disclosed in U.S. Patent Application Ser. No. 62/385,553, incorporated by reference herein in its entirety.

In some embodiments, the pharmaceutical composition is an ingestible device as disclosed in the following applications, each of which is incorporated by reference herein in its entirety:
U.S. Ser. Nos. 14/460,893; 15/514,413; 62/376,688; 62/385,344; 62/478,955; 62/434,188; 62/434,320; 62/431,297; 62/434,797; 62/480,187; 62/502,383; and 62/540,873.

In some embodiments, the pharmaceutical composition is an ingestible device comprising a localization mechanism as disclosed in international patent application PCT/US2015/052500, incorporated by reference herein in its entirety.

In some embodiments, the pharmaceutical composition is not a dart-like dosage form.

In some embodiments of any ingestible device disclosed herein comprising a JAK inhibitor, the JAK inhibitor is present in a therapeutically effective amount.

In case of conflict between the present specification and any subject matter incorporated by reference herein, the present specification, including definitions, will control.

Devices and Methods for Detection of Analytes in GI tract

Detection of certain analytes in the GI tract may be useful in the identification of the nature and severity of the disease, in accurately locating the site(s) of disease, and in assessing patient response to a therapeutic agent. The appropriate therapeutic agent may accordingly be released at the correct locations(s), dosage, or timing for the disease. As discussed further herein, analytes may include biomarkers associated with a disease or associated with patient response and/or therapeutic agents previously administered to treat the disease. In some embodiments, the disclosure provides an ingestible device for detecting an analyte in a sample, the ingestible device comprising a sampling chamber that is configured to hold a composition comprising: (1) a plurality of donor particles, each of the plurality of donor particles comprising a photosensitizer and having coupled thereto a first antigen-binding agent that binds to the analyte, wherein the photosensitizer, in its excited state, is capable of generating singlet oxygen; and (2) a plurality of acceptor particles, each of the plurality of acceptor particles comprising a chemiluminescent compound and having coupled thereto a second antigen-binding agent that binds to the analyte, wherein the chemiluminescent compound is capable of reacting with singlet oxygen to emit luminescence. In some embodiments, the first and the second analyte-binding agents are antigen-binding agents (e.g., antibodies). In some embodiments, the first and the second antigen-binding agents bind to the same epitope of the analyte (e.g., a protein). In some embodiments, the first and the second antigen-binding agents bind to separate epitopes of the analyte (e.g., a protein) that spatially overlap. In some embodiments, the first and the second antigen-binding agents bind to the separate epitopes of the analyte (e.g., a protein) that do not spatially overlap.

In some embodiments, this disclosure provides an ingestible device for detecting an analyte in a sample, the ingestible device comprising a sampling chamber that is configured to hold an absorbable material (e.g., an absorbable pad or sponge) having absorbed therein a composition comprising: (1) a plurality of donor particles, each of the plurality of donor particles comprising a photosensitizer and having coupled thereto a first antigen-binding agent that binds to the analyte, wherein the photosensitizer, in its excited state, is capable of generating singlet oxygen; and (2) a plurality of acceptor particles, each of the plurality of acceptor particles comprising a chemiluminescent compound and having coupled thereto a second antigen-binding agent that binds to the analyte, wherein the chemiluminescent compound is capable of reacting with singlet oxygen to emit luminescence. In some embodiments, the first and the second analyte-binding agents are antigen-binding agents (e.g., antibodies). In some embodiments, the first and the second antigen-binding agents bind to the same epitope of the analyte (e.g., a protein). In some embodiments, the first and the second antigen-binding agents bind to separate epitopes of the analyte (e.g., a protein) that spatially overlap. In some embodiments, the first and the second antigen-binding agents bind to the separate epitopes of the analyte (e.g., a protein) that do not spatially overlap.

In certain embodiments, the disclosure provides a kit comprising an ingestible device as described herein. In some embodiments, the kit further comprises instructions, e.g., for detecting or quantifying an analyte in a sample.

In some embodiments, the disclosure provides methods for determining an analyte in a sample. In certain embodiments, this disclosure provides a method of detecting an analyte in a fluid sample of a subject, comprising: (1) providing an ingestible device; (2) transferring the fluid sample of the subject into the sampling chamber of the ingestible device in vivo; (3) irradiating the composition held in the sampling chamber of the ingestible device with light to excite the photosensitizer; and (4) measuring total luminescence or rate of change of luminescence emitted from the composition held in the sampling chamber of the ingestible device as a function of time, thereby determining the level of the analyte in the fluid sample. In some embodiments, the method further comprises comparing the level of the analyte in the fluid sample with the level of analyte in a reference sample (e.g., a reference sample obtained from a healthy subject). In some embodiments, the level of the analyte in the sample is used to diagnose and/or monitor a disease or disorder in the subject.

In some embodiments, the disclosure provides a method of detecting an analyte in a fluid sample of a subject, comprising: (1) providing an ingestible device, the device comprising a sampling chamber that is configured to hold an absorbable material (e.g., an absorbable pad or sponge) having absorbed therein a composition, as described herein; (2) transferring the fluid sample of the subject into the sampling chamber of the ingestible device in vivo; (3) fully or partially saturating the absorbable material held in the sampling chamber of the ingestible device with the fluid sample; (4) irradiating the absorbable material held in the sampling chamber of the ingestible device with light to excite the photosensitizer; and (5) measuring total luminescence or rate of change of luminescence emitted from the composition held in the sampling chamber of the ingestible device as a function of time, thereby determining the level of the analyte in the fluid sample. In some embodiments, the method further comprises comparing the level of the analyte in the fluid sample with the level of analyte in a reference sample (e.g., a reference sample obtained from a healthy subject). In some embodiments, the level of the analyte in the sample is used to diagnose and/or monitor a disease or disorder in the subject.

In some embodiments, the disclosure provides a method of assessing or monitoring the need to treat a subject suffering from or at risk of overgrowth of bacterial cells in the gastrointestinal (GI) tract, comprising: (1) providing an ingestible device for detecting an analyte; (2) transferring a fluid sample from the GI tract of the subject into the sampling chamber of the ingestible device in vivo; (3) irradiating the composition held in the sampling chamber of the ingestible device with light to excite the photosensitizer; (4) measuring total luminescence or rate of change of luminescence emitted from the composition held in the sampling chamber of the ingestible device as a function of time; (5) correlating the total luminescence or the rate of change of luminescence as a function of time measured in step (4) to the amount of the analyte in the fluid sample; and (6) correlating the amount of the analyte in the fluid sample to the number of viable bacterial cells in the fluid sample. In some embodiments, a number of viable bacterial cells determined in step (6) greater than a control number of viable bacterial cells, indicates a need for treatment (e.g., with an antibiotic agent described herein). In some embodiments, the control number of viable bacterial cells is $10^3$, $10^4$, $10^5$, $10^6$, $10^7$, $10^8$, $10^9$, or more. For example, in some embodiments, a number of viable bacterial cells determined in step (6) greater that about $10^3$ CFU/mL indicates a need for treatment. In some embodiments, a number of viable bacterial cells determined in step (6) greater that about $10^4$ CFU/mL indicates a need for treatment. In some embodiments, a number of the viable bacterial cells determined in step (6) greater than about $10^5$ CFU/mL indicates a need for treatment, e.g., with an antibiotic agent as described herein. In some embodiments, a number of viable bacterial cells determined in step (6) greater that about $10^6$ or more CFU/mL indicates a need for treatment.

In some embodiments, the total luminescence or the rate of change of luminescence as a function of time of the sponge is measured over multiple time points for an extended period of time in step (4). For instance, in some embodiments, the total luminescence or rate of change of luminescence as a function of time of the sample is measured continuously for a period of 0-1800 minutes, 0-1600 minutes, 0-1500 minutes, 0-1440 minutes, 0-1320 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total luminescence or the rate of change of luminescence as a function of time of said sample is measured continuously for a period of 0-330 minutes. In some embodiments, the method is performed in vivo. In some embodiments, the method includes communicating the results of the onboard assay(s) to an ex vivo receiver. In some embodiments, the total luminescence or the rate of change of luminescence as a function of time of the sponge is measured over multiple time points for an extended period of time in step (5). For instance, in some embodiments, the total luminescence or rate of change of luminescence as a function of time of the sample is measured continuously for a period of 0-1800 minutes, 0-1600 minutes, 0-1500 minutes, 0-1440 minutes, 0-1320 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total luminescence or the rate of change of luminescence as a function of time of said sample is measured continuously for a period of 0-330 minutes. In some embodiments, the method is performed in vivo. In some embodiments, the method includes communicating the results of the onboard assay(s) to an ex vivo receiver.

In some embodiments, the disclosure provides a method of assessing or monitoring the need to treat a subject suffering from or at risk of overgrowth of bacterial cells in the gastrointestinal tract, comprising: (1) providing an ingestible device for detecting an analyte, the device comprising a sampling chamber that is configured to hold an absorbable material (e.g., an absorbable pad or sponge) having absorbed therein a composition, as described herein; (2) transferring a fluid sample from the GI tract of the subject into the sampling chamber of the ingestible device in vivo; (3) fully or partially saturating the absorbable material held in the sampling chamber of the ingestible device with the fluid sample; (4) irradiating the absorbable material held in the sampling chamber of the ingestible device with light to excite the photosensitizer; (5) measuring total luminescence or rate of change of luminescence emitted from the composition held in the sampling chamber of the ingestible device as a function of time; (6) correlating the total luminescence or the rate of change of luminescence as a function of time measured in step (5) to the amount of the analyte in the fluid sample; and (7) correlating the amount of the analyte in the fluid sample to the number of viable bacterial cells in the fluid sample. In some embodiments, a number of viable bacterial cells determined in step (7) greater than a control number of viable bacterial cells indicates a need for treatment (e.g., with an antibiotic agent described herein). In some embodiments, the control number of viable bacterial cells is $10^3$, $10^4$, $10^5$, $10^6$, $10^7$, $10^8$, $10^9$, or more. For example, in some embodiments, a number of viable bacterial cells determined in step (7) greater that about $10^3$ CFU/mL indicates a need for treatment. In some embodiments, a number of viable bacterial cells determined in step (7) greater that about $10^4$ CFU/mL indicates a need for treatment. In some embodiments, a number of the viable bacterial cells determined in step (7) greater than about $10^5$ CFU/mL indicates a need for treatment, e.g., with an antibiotic agent as described herein. In some embodiments, a number of viable bacterial cells determined in step (7) greater that about $10^6$ or more CFU/mL indicates a need for treatment.

In some embodiments, the disclosure, provides a method of measuring the presence, absence or amount of one or more analytes from one or more samples in the gastrointestinal tract. In some embodiments the one or more analytes are measured multiple times, for example, at different time points or at different locations. In one embodiment, a single device measures one or more analytes or more time points or locations; thereby creating a "molecular map" of a physiological region. Measurements can be taken at any location in the gastrointestinal tract. For example, in one aspect, analytes from samples from one or more of the duodenum, jejunum, ileum, ascending colon, transverse colon or descending colon can be measured to create a molecular map of the small and large intestine. In one aspect, the sample is from the duodenum. In one aspect, In one aspect, the sample is from the jejunum. In one aspect, the sample is from the ileum. In one aspect, the sample is from the ascending colon. In one aspect, the sample is from the transverse colon. In one aspect, the sample is from the descending colon.

In another aspect, a series of measurements can be taken over a shorter distance of the gastrointestinal tract (e.g., the ileum) to create a higher resolution molecular map. In some embodiments, previous endoscopic imaging may identify a diseased area for molecular mapping. For example, a gastroenterologist may use imaging (e.g., an endoscope equipped with a camera) to identify the presence of Crohn's Disease in the ileum and cecum of a patient, and the methods and techniques herein may be used to measure inflammation-associated analytes in this diseased area of the patient. In a related embodiment, the inflammation-associated analytes, or any analyte, may be measured every one or more days to monitor disease flare-ups, or response to therapeutics.

Analytes

The compositions and methods described herein can be used to detect, analyze, and/or quantitate a variety of analytes in a human subject. "Analyte" as used herein refers to a compound or composition to be detected in a sample. Exemplary analytes suitable for use herein include those described in U.S. Pat. No. 6,251,581, which is incorporated by reference herein in its entirety. Broadly speaking, an analyte can be any substance (e.g., a substance with one or more antigens) capable of being detected. An exemplary and non-limiting list of analytes includes ligands, proteins, blood clotting factors, hormones, cytokines, polysaccharides, mucopolysaccharides, microorganisms (e.g., bacteria), microbial antigens, and therapeutic agents (including fragments and metabolites thereof).

For instance, the analyte may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., a human leukocyte antigen (HLA), or other cell surface antigen, or a microorganism, e.g., bacterium (e.g. a pathogenic bacterium), a fungus, protozoan, or a virus (e.g., a protein, a nucleic acid, a lipid, or a hormone). In some embodiments, the analyte can be a part of an exosome (e.g., a bacterial exosome). In some embodiments, the analyte is derived from a subject (e.g., a human subject). In some embodiments, the analyte is derived from a microorganism present in the subject. In some embodiments, the analyte is a nucleic acid (e.g., a DNA molecule or a RNA molecule), a protein (e.g., a soluble protein, a cell surface protein), or a fragment thereof, that can be detected using any of the devices and methods provided herein.

The polyvalent ligand analytes will normally be poly (amino acids), i.e., a polypeptide (i.e., protein) or a peptide, polysaccharides, nucleic acids (e.g., DNA or RNA), and combinations thereof. Such combinations include components of bacteria, viruses, chromosomes, genes, mitochondria, nuclei, cell membranes, and the like.

In some embodiments, the polyepitopic ligand analytes have a molecular weight of at least about 5,000 Da, more usually at least about 10,000 Da. In the poly(amino acid) category, the poly(amino acids) of interest may generally have a molecular weight from about 5,000 Da to about 5,000,000 Da, more usually from about 20,000 Da to 1,000,000 Da; among the hormones of interest, the molecular weights will usually range from about 5,000 Da to 60,000 Da.

In some embodiments, the monoepitopic ligand analytes generally have a molecular weight of from about 100 to 2,000 Da, more usually from 125 to 1,000 Da.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

In some embodiments, the analyte is a protein. In some embodiments, the analyte is a protein, e.g., an enzyme (e.g., a hemolysin, a protease, a phospholipase), a soluble protein, an exotoxin. In some embodiments, the analyte is a fragment of a protein, a peptide, or an antigen. In some embodiments, the analyte is a peptide of at least 5 amino acids (e.g., at least 6, at least 7, at least 8, at least 9, at least 10, at least 25, at least, 50, or at least 100 amino acids). Exemplary lengths include 6, 7, 8, 9, 10, 11, 12, 13, 14, 15, 16, 17, 18, 19, 20, 21, 22, 23, 24, 25, 26, 27, 28, 29, 30, 50, 75, or 100 amino acids. Exemplary classes of protein analytes include, but are not limited to: protamines, histones, albumins, globulins, scleroproteins, phosphoproteins, mucoproteins, chromoproteins, lipoproteins, nucleoproteins, glycoproteins, T-cell receptors, proteoglycans, cell surface receptors, membrane-anchored proteins, transmembrane proteins, secreted proteins, HLA, and unclassified proteins.

In some embodiments, the analyte is an affimer (see, e.g., Tiede et al. (2017) *eLife* 6: e24903, which is expressly incorporated herein by reference).

Exemplary analytes include: Prealbumin, Albumin, $\alpha_1$-Lipoprotein, $\alpha_1$-Antitrypsin, $\alpha_1$-Glycoprotein, Transcortin, 4.6S-Postalbumin, $\alpha_1$-glycoprotein, $\alpha_{1X}$-Glycoprotein, Thyroxin-binding globulin, Inter-$\alpha$-trypsin-inhibitor, Gc-globulin (Gc 1-1, Gc 2-1, Gc 2-2), Haptoglobin (Hp 1-1, Hp 2-1, Hp 2-2), Ceruloplasmin, Cholinesterase, $\alpha_2$-Lipoprotein(s), Myoglobin, C-Reactive Protein, $\alpha_2$-Macroglobulin, $\alpha_2$-HS-glycoprotein, Zn-$\alpha_2$-glycoprotein, $\alpha_2$-Neuramino-glycoprotein, Erythropoietin, $\beta$-lipoprotein, Transferrin, Hemopexin, Fibrinogen, Plasminogen, $\beta_2$-glycoprotein I, $\beta_2$-glycoprotein II, Immunoglobulin G (IgG) or $\gamma$G-globulin, Immunoglobulin A (IgA) or $\gamma$A-globulin, Immunoglobulin M (IgM) or $\gamma$M-globulin, Immunoglobulin D (IgD) or $\gamma$D-Globulin ($\gamma$D), Immunoglobulin E (IgE) or $\gamma$E-Globulin ($\gamma$E), Free $\kappa$ and $\lambda$ light chains, and Complement factors: C'1, (C'1q, C'1r, C'1s, C'2, C'3 ($\beta_1$A, $\alpha_2$D), C'4, C'5, C'6, C'7, C'8, C'9.

Additional examples of analytes include tumor necrosis factor-$\alpha$ (TNF$\alpha$), interleukin-12 (IL-12), IL-23, IL-6, $\alpha 2\beta 1$ integrin, $\alpha 1\beta 1$ integrin, $\alpha 4\beta 7$ integrin, integrin $\alpha 4\beta 1$ (VLA-4), E-selectin, ICAM-1, $\alpha 5\beta 1$ integrin, $\alpha 4\beta 1$ integrin, VLA-4, $\alpha 2\beta 1$ integrin, $\alpha 5\beta 3$ integrin, $\alpha 5\beta 5$ integrin, $\alpha$IIb$\beta 3$ integrin, MAdCAM-1, SMAD7, JAK1, JAK2, JAK3, TYK-2, CHST15, IL-1, IL-1$\alpha$, IL-1$\beta$, IL-18, IL-36$\alpha$, IL-36$\beta$, IL-36$\gamma$, IL-38, IL-33, IL-13, CD40L, CD40, CD3$\gamma$, CD3$\delta$, CD3$\epsilon$, CD3$\zeta$, TCR, TCR$\alpha$, TCR$\beta$, TCR$\delta$, TCR$\gamma$, CD14, CD20, CD25, IL-2, IL-2$\beta$ chain, IL-2$\gamma$ chain, CD28, CD80, CD86, CD49, MMP1, CD89, IgA, CXCL10, CCL11, an ELR chemokine, CCR2, CCR9, CXCR3, CCR3, CCR5, CCL2, CCL8, CCL16, CCL25, CXCR1m CXCR2m CXCL1, CXCL2, CXCL3, CXCL4, CXCL5, CXCL6, CXCL7, and CXCL8, and a nucleic acid (e.g., mRNA) encoding any of the same.

In some embodiments, the analyte is a blood clotting factor. Exemplary blood clotting factors include, but are not limited to:

| International designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

In some embodiments, the analyte is a hormone. Exemplary hormones include, but are not limited to: Peptide and Protein Hormones, Parathyroid hormone, (parathromone), Thyrocalcitonin, Insulin, Glucagon, Relaxin, Erythropoietin, Melanotropin (melancyte-stimulating hormone; intermedin), Somatotropin (growth hormone), Corticotropin (adrenocorticotropic hormone), Thyrotropin, Follicle-stimulating hormone, Luteinizing hormone (interstitial cell-stimulating hormone), Luteomammotropic hormone (luteotropin, prolactin), Gonadotropin (chorionic gonadotropin), Secretin, Gastrin, Angiotensin I and II, Bradykinin, and Human placental lactogen, thyroxine, cortisol, triiodothyronine, testosterone, estradiol, estrone, progestrone, luteinizing hormone-releasing hormone (LHRH), and immunosuppressants such as cyclosporin, FK506, mycophenolic acid, and so forth.

In some embodiments, the analyte is a peptide hormone (e.g., a peptide hormone from the neurohypophysis). Exemplary peptide hormones from the neurohypophysis include, but are not limited to: Oxytocin, Vasopressin, and releasing factors (RF) (e.g., corticotropin releasing factor (CRF), luteinizing hormone releasing factor (LRF), thyrotropin releasing factor (TRF), Somatotropin-RF, growth hormone releasing factor (GRF), follicle stimulating hormone-releasing factor (FSH-RF), prolactin inhibiting factor (PIF), and melanocyte stimulating hormone inhibiting factor (MIF)).

In some embodiments, the analyte is a cytokine or a chemokine. Exemplary cytokines include, but are not limited to: interleukin-1 (IL-1), interleukin-2 (IL-2), interleukin-6 (IL-6), epidermal growth factor (EGF), tumor necrosis factor (TNF, e.g., TNF-$\alpha$ or TNF-$\beta$), and nerve growth factor (NGF).

In some embodiments, the analyte is a cancer antigen. Exemplary cancer antigens include, but are not limited to: prostate-specific antigen (PSA), carcinoembryonic antigen (CEA), $\alpha$-fetoprotein, Acid phosphatase, CA19.9, and CA125.

In some embodiments, the analyte is a tissue-specific antigen. Exemplary tissue specific antigens include, but are not limited to: alkaline phosphatase, myoglobin, CPK-MB, calcitonin, and myelin basic protein.

In some embodiments, the analyte is a mucopolysaccharide or a polysaccharide.

In some embodiments, the analyte is a microorganism, or a molecule derived from or produced by a microorganism (e.g., a bacteria, a virus, prion, or a protozoan). For example, in some embodiments, the analyte is a molecule (e.g., an protein or a nucleic acid) that is specific for a particular microbial genus, species, or strain (e.g., a specific bacterial genus, species, or strain). In some embodiments, the microorganism is pathogenic (i.e., causes disease). In some embodiments, the microorganism is non-pathogenic (e.g., a commensal microorganism). Exemplary microorganisms include, but are not limited to:

| | |
|---|---|
| Corynebacteria | |
| Corynebacterium diphtheria | |
| Pneumococci | |
| Diplococcus pneumoniae | |
| Streptococci | |
| Streptococcus pyrogenes | |
| Streptococcus salivarus | |
| Staphylococci | |
| Staphylococcus aureus | |
| Staphylococcus albus | |
| Neisseria | |
| Neisseria meningitidis | |
| Neisseria gonorrhea | |
| Enterobacteriaciae | |
| Escherichia coli | |
| Aerobacter aerogenes | The coliform |
| Klebsiella pneumoniae | bacteria |
| Salmonella typhosa | |
| Salmonella choleraesuis | The Salmonellae |
| Salmonella typhimurium | |
| Shigella dysenteria | |
| Shigella schmitzii | |
| Shigella arabinotarda | |
| | The Shigellae |
| Shigella flexneri | |
| Shigella boydii | |
| Shigella sonnei | |
| Other enteric bacilli | |
| Proteus vulgaris | |
| Proteus mirabilis | Proteus species |
| Proteus morgani | |
| Pseudomonas aeruginosa | |
| Alcaligenes faecalis | |
| Vibrio cholerae | |
| Hemophilus-Bordetella group | Rhizopus oryzae |
| Hemophilus influenza, H. ducryi | Rhizopus arrhizua |
| | Phycomycetes |
| Hemophilus hemophilus | Rhizopus nigricans |
| Hemophilus aegypticus | Sporotrichum schenkii |
| Hemophilus parainfluenza | Flonsecaea pedrosoi |
| Bordetella pertussis | Fonsecacea compact |
| Pasteurellae | Fonsecacea dermatidis |
| Pasteurella pestis | Cladosporium carrionii |
| Pasteurella tulareusis | Phialophora verrucosa |
| Brucellae | Aspergillus nidulans |
| Brucella melltensis | Madurella mycetomi |
| Brucella abortus | Madurella grisea |
| Brucella suis | Allescheria boydii |
| Aerobic Spore-forming Bacilli | Phialophora jeanselmei |
| Bacillus anthracis | Microsporum gypseum |
| Bacillus subtilis | Trichophyton mentagrophytes |
| Bacillus megaterium | Keratinomyces ajelloi |
| Bacillus cereus | Microsporum canis |
| Anaerobic Spore-forming Bacilli | Trichophyton rubrum |
| Clostridium botulinum | Microsporum adouini |
| Clostridium tetani | Viruses |
| Clostridium perfringens | Adenoviruses |
| Clostridium novyi | Herpes Viruses |
| Clostridium septicum | Herpes simplex |
| Clostridium histoyticum | Varicella (Chicken pox) |
| Clostridium tertium | Herpes Zoster (Shingles) |
| Clostridium bifermentans | Virus B |
| Clostridium sporogenes | Cytomegalovirus |
| Mycobacteria | Pox Viruses |
| Mycobacterium tuberculosis hominis | Variola (smallpox) |
| Mycobacterium bovis | Vaccinia |
| Mycobacterium avium | Poxvirus bovis |
| Mycobacterium leprae | Paravaccinia |
| Mycobacterium paratuberculosis | Molluscum contagiosum |
| Actinomycetes (fungus-ike bacteria) | Picornaviruses |
| Actinomyces Isaeli | Poliovirus |
| Actinomyces bovis | Coxsackievirus |

-continued

| | |
|---|---|
| Actinomyces naeslundii | Echoviruses |
| Nocardia asteroides | Rhinoviruses |
| Nocardia brasiliensis | Myxoviruses |
| The Spirochetes | Influenza(A, B, and C) |
| Treponema pallidum | Parainfluenza (1-4) |
| Treponema pertenue | Mumps Virus |
| Spirillum minus | |
| Streptobacillus monoiliformis | Newcastle Disease Virus |
| Treponema carateum | Measles Virus |
| Borrelia recurrentis | Rinderpest Virus |
| Leptospira icterohemorrhagiae | Canine Distemper Virus |
| Leptospira canicola | Respiratory Syncytial Virus |
| Trypanasomes | Rubella Virus |
| Mycoplasmas | Arboviruses |
| Mycoplasma pneumoniae | |
| Other pathogens | Eastern Equine Encephalitis Virus |
| Listeria monocytogenes | Western Equine Encephalitis Virus |
| Erysipeothrix rhusiopathiae | Sindbis Virus |
| Streptobacillus moniliformis | Chikugunya Virus |
| Donvania granulomatis | Semliki Forest Virus |
| Entamoeba histolytica | Mayora Virus |
| Plasmodium falciparum | St. Louis Encephalitis |
| Plasmodium japonicum | California Encephalitis Virus |
| Bartonella bacilliformis | Colorado Tick Fever Virus |
| Rickettsia (bacteria-like parasites) | Yellow Fever Virus |
| Rickettsia prowazekii | Dengue Virus |
| Rickettsia mooseri | Reoviruses |
| Rickettsia rickettsii | Reovirus Types 1-3 |
| Rickettsia conori | Retroviruses |
| Rickettsia australis | Human Immunodeficiency |
| Rickettsia sibiricus | Viruses I and II (HTLV) |
| Rickettsia akari | Human T-cell Lymphotrophic |
| Rickettsia tsutsugamushi | Virus I & II (HIV) |
| Rickettsia burnetti | Hepatitis |
| Rickettsia quintana | Hepatitis A Virus |
| Chlamydia (unclassifiable parasites bacterial/viral) | Hepatitis B Virus |
| | Hepatitis C Virus |
| Chlamydia agents (naming uncertain) | Tumor Viruses |
| Chlamydia trachomatis | |
| Fungi | Rauscher Leukemia Virus |
| Cryptococcus neoformans | Gross Virus |
| Blastomyces dermatidis | Maloney Leukemia Virus |
| Histoplasma capsulatum | |
| Coccidioides immitis | Human Papilloma Virus |
| Paracoccidioides brasliensis | |
| Candida albicans | |
| Aspergillus fumigatus | |
| Mucor corymbifer (Absidia corymbifera) | |

In some embodiments, the analyte is a bacterium. Exemplary bacteria include, but are not limited to: *Escherichia coli* (or *E. coli*), *Bacillus anthraces, Bacillus cereus, Clostridium botulinum, Clostridium difficile, Yersinia pestis, Yersinia enterocolitica, Francisella tularensis, Brucella* species, *Clostridium perfringens, Burkholderia mallei, Burkholderia pseudomallei, Staphylococcus* species, *Mycobacterium* species, Group A *Streptococcus*, Group B *Streptococcus, Streptococcus pneumoniae, Helicobacter pylori, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsia, Rickettsia akari, Rickettsia prowazekii, Rickettsia canada, Bacillus subtilis, Bacillus subtilis niger, Bacillus thuringiensis, Coxiella burnetti, Faecalibacterium prausnitzii* (also known as *Bacteroides praussnitzii*), *Roseburia hominis, Eubacterium rectale, Dialister invisus, Ruminococcus albus, Ruminococcus callidus,* and *Ruminococcus bromii*. Additional exemplary bacteria include bacteria of the phyla Firmicutes (e.g., *Clostridium* clusters XIVa and IV), bacteria of the phyla Bacteroidetes (e.g., *Bacteroides fragilis* or *Bacteroides vulgatus*), and bacteria of the phyla Actinobacteria (e.g., Coriobacteriaceae spp. or *Bifidobacterium adolescentis*). Bacteria of the *Clostridium* cluster XIVa includes species belonging to, for example, the *Clostridium, Ruminococcus, Lachnospira, Roseburia, Eubacterium, Coprococcus, Dorea,* and *Butyrivibrio* genera. Bacteria of the *Clostridium* cluster IV includes species belonging to, for example, the *Clostridium, Ruminococcus, Eubacterium* and *Anaerofilum* genera. In some embodiments, the analyte is *Candida*, e.g., *Candida albicans*. In some embodiments, the analyte is a byproduct from a bacterium or other microorganism, e.g., helminth ova, enterotoxin (*Clostridium difficile* toxin A; TcdA) or cytotoxin (*Clostridium difficile* toxin B; TcdB).

In some embodiments, the bacterium is a pathogenic bacterium. Non-limiting examples of pathogenic bacteria belong to the genera *Bacillus, Bordetella, Borrelia, Brucella, Campylobacter, Chlamydia, Chlamydophila, Clostridium, Corynebacterium, Enterobacter, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia*. Non-limiting examples of specific pathogenic bacterial species include a strain of *Bacillus anthraces*, a strain of a strain of *Bordetella pertussis*, a strain of a strain of *Borrelia burgdorferi*, a strain of a strain of *Brucella abortus*, a strain of a strain of *Brucella canis*, a strain of a strain of *Brucella melitensis*, a strain of a strain of *Brucella suis*, a strain of a strain of *Campylobacter jejuni*, a strain of *Chlamydia pneumoniae*, a strain of *Chlamydia trachomatis*, a strain of *Chlamydophila psittaci*, a strain of *Clostridium botulinum*, a strain of *Clostridium difficile*, a strain of *Clostridium perfringens*, a strain of *Clostridium tetani*, a strain of *Corynebacterium diphtheria*, a strain of *Enterobacter sakazakii*, a strain of *Enterococcus faecalis*, a strain of *Enterococcus faecium*, a strain of *Escherichia coli* (e.g., *E. coli* O157 H7), a strain of *Francisella tularensis*, a strain of *Haemophilus influenza*, a strain of *Helicobacter pylori*, a strain of *Legionella pneumophila*, a strain of *Leptospira interrogans*, a strain of *Listeria monocytogenes*, a strain of *Mycobacterium leprae*, a strain of *Mycobacterium tuberculosis*, a strain of *Mycobacterium ulcerans*, a strain of *Mycoplasma pneumonia*, a strain of *Neisseria gonorrhoeae*, a strain of *Neisseria meningitides*, a strain of *Pseudomonas aeruginosa*, a strain of *Rickettsia rickettsia*, a strain of *Salmonella typhi* and *Salmonella typhimurium*, a strain of *Shigella sonnei*, a strain of *Staphylococcus aureus*, a strain of *Staphylococcus epidermidis*, a strain of *Staphylococcus saprophyticus*, a strain of *Streptococcus agalactiae*, a strain of *Streptococcus pneumonia*, a strain of *Streptococcus pyogenes*, a strain of *Treponema pallidum*, a strain of *Vibrio cholera*, a strain of *Yersinia enterocolitica*, and, a strain of *Yersinia pestis*.

In some embodiments, the bacterium is a commensal bacterium (e.g., a probiotic). In some embodiments, the bacterium has been previously administered to a subject, e.g., as a live biotherapeutic agent. Exemplary commensal bacteria include, but are not limited to, *Faecalibacterium prausnitzii* (also referred to as *Bacteroides praussnitzii*), *Roseburia hominis, Eubacterium rectale, Dialister invisus, Ruminococcus albus, Ruminococcus gnavus, Ruminococcus torques, Ruminococcus callidus,* and *Ruminococcus bromii*.

In some embodiments, the analyte is a virus. In some embodiments, the virus is a pathogenic virus. Non-limiting examples of pathogenic viruses belong to the families Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae.

In some embodiments, the analyte is a fungus. In some embodiments, the fungi is a pathogenic fungus. Non-limiting examples of pathogenic fungi belong to the genera *Asperfillus, Canidia, Cryptococcus, Histoplasma, Pneumocystis,* and *Stachybotrys*. Non-limiting examples of specific pathogenic fungi species include a strain of *Aspergillus clavatus, Aspergillus fumigatus, Aspergillus flavus, Canidia albicans, Cryptococcus albidus, Cryptococcus gattii, Cryptococcus laurentii, Cryptococcus neoformans, Histoplasma capsulatum, Pneumocystis jirovecii, Pneumocystis carinii,* and *Stachybotrys chartarum*.

In some embodiments, the analyte is a protozoan. In some embodiments, the analyte is a pathogenic protozoan. Non-limiting examples of pathogenic protozoa belong to the genera *Acanthamoeba, Balamuthia, Cryptosporidium, Dientamoeba, Endolimax, Entamoeba, Giardia, Iodamoeba, Leishmania, Naegleria, Plasmodium, Sappinia, Toxoplasma, Trichomonas,* and *Trypanosoma*. Non-limiting examples of specific pathogenic protozoa species include a strain of *Acanthamoeba* spp., *Balamuthia mandrillaris, Cryptosporidium canis, Cryptosporidium fells, Cryptosporidium hominis, Cryptosporidium meleagridis, Cryptosporidium muris, Cryptosporidium parvum, Dientamoeba fragilis, Endolimax nana, Entamoeba dispar, Entamoeba hartmanni, Entamoeba histolytica, Entamoeba coli, Entamoeba moshkovskii, Giardia lamblia, Iodamoeba butschlii, Leishmania aethiopica, Leishmania braziliensis, Leishmania chagasi, Leishmania donovani, Leishmania infantum, Leishmania major, Leishmania mexicana, Leishmania tropica, Naegleria fowleri, Plasmodium falciparum, Plasmodium knowlesi, Plasmodium malariae, Plasmodium ovale, Plasmodium vivax, Sappinia diploidea, Toxoplasma gondii, Trichomonas vaginalis, Trypanosoma brucei,* and *Trypanosoma cruzi*.

In some embodiments, the analyte is secreted by or expressed on the cell surface of a microorganism (e.g., a bacterium, a colonic bacterium, a viable bacterium, a dead bacterium, a parasite (e.g., *Giardia lamblia, Cryptosporidium, Cystoisosporiasis belli,* and *Balantidium coli*), a virus (e.g., a herpes virus, a cytomegalovirus, a herpes simplex virus, an Epstein-Barr virus, a human papilloma virus, a rotavirus, a human herpesvirus-8; Goodgame (1999) Curr. Gastroenterol. Rep. 1(4): 292-300). In some embodiments, the analyte is secreted by or expressed on the cell surface of a Gram-negative bacterium (e.g., *E. coli, Helicobacter pylori*). In some embodiments, the analyte is secreted by or expressed on the cell surface (e.g., a bacterial surface epitope) of a Gram-positive bacterium (e.g., *Staphylococcus aureus, Clostridium botulinum, Clostridium difficile*).

In some embodiments, the analyte is a molecule expressed on the surface of a bacterial cell (e.g., a bacterial cell surface protein). In some embodiments, the analyte is a bacterial toxin (e.g., TcdA and/or TcdB from *Clostridium difficile*). In some embodiments, the analyte is CFA/I fimbriae, flagella, lipopolysaccharide (LPS), lipoteichoic acid, or a peptidoglycan. Non-limiting examples of bacterium that may express an analyte that can be detected using any of the devices and methods described herein include: *Bacillus anthraces, Bacillus cereus, Clostridium botulinum, Clostridium difficile, Escherichia coli, Yersinia pestis, Yersinia enterocolitica, Francisella tularensis, Brucella* species, *Clostridium perfringens, Burkholderia mallei, Burkholderia pseudomallei, Helicobacter pylori, Staphylococcus* species, *Mycobacterium* species, Group A *Streptococcus,*

Group B *Streptococcus, Streptococcus pneumoniae, Francisella tularensis, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsia, Rickettsia akari, Rickettsia prowazekii, Rickettsia canada, Bacillus subtilis, Bacillus subtilis niger, Bacillus thuringiensis, Coxiella bumetti, Candida albicans, Bacteroides fragilis, Leptospira interrogans, Listeria monocytogenes, Pasteurella multocida, Salmonella typhi, Salmonella typhimurium, Shigella dysenteriae, Shigella flexneria, Shigella sonnei, Vibrio cholera*, and *Vibrio parahaemolyticus*.

In some embodiments, the analyte is a byproduct from a bacterium or another microorganism, e.g., helminth ova, enterotoxin (*Clostridium difficile* toxin A; TcdA), cytotoxin (*Clostridium difficile* toxin B; TcdB), ammonia. In some embodiments, the analyte is an antigen from a microorganism (e.g., a bacteria, virus, prion, fungus, protozoan or a parasite).

In some embodiments, the analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

In some embodiments, the analyte is a steroid selected from the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

In some embodiments, the analyte is a bile acid. In some embodiments, the presence, absence, and/or a specific level of one or more bile acids in the GI tract of a subject is indicative of a condition or disease state (e.g., a GI disorder and/or a non-GI disorder (e.g., a systemic disorder). For example, in some embodiments, the compositions and methods described herein may be used to detect and/or quantify a bile acid in the GI tract of the subject to diagnose a condition such as bile acid malabsorption (also known as bile acid diarrhea). In some embodiments, the analyte is a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof 5-HT is a molecule that plays a role in the regulation of gastrointestinal motility, secretion, and sensation. Imbalances in the levels of 5-HT are associated with several diseases including inflammatory bowel syndrome (IBS), autism, gastric ulcer formation, non-cardiac chest pain, and functional dyspepsia (see, e.g., Faure et al. (2010) *Gastroenterology* 139(1): 249-58 and Muller et al. (2016) *Neuroscience* 321: 24-41, and International Publication No. WO 2014/188377, each of which are incorporated herein by reference). Conversion of metabolites within the serotonin, tryptophan and/or kynurenine pathways affects the levels of 5-HT in a subject. Therefore, measuring the levels of one or more of the metabolites in this pathway may be used for the diagnosis, management and treatment of a disease or disorder associated with 5-HT imbalance including but not limited to IBS, autism, carcinoid syndrome, depression, hypertension, Alzheimer's disease, constipation, migraine, and serotonin syndrome. One or more analytes in the serotonin, tryptophan and/or kynurenine pathways can be detected and/or quantitated using, for example, methods and analyte-binding agents that bind to these metabolites including, e.g., antibodies, known in the art (see, e.g., International Publication No. WO2014/188377, the entire contents of which are expressly incorporated herein by reference).

In some embodiments, the analyte is a lactam having from 5 to 6 annular members selected from barbituates, e.g., phenobarbital and secobarbital, diphenylhydantonin, primidone, ethosuximide, and metabolites thereof.

In some embodiments, the analyte is an aminoalkylbenzene, with alkyl of from 2 to 3 carbon atoms, selected from the amphetamines; catecholamines, which includes ephedrine, L-dopa, epinephrine; narceine; papaverine; and metabolites thereof.

In some embodiments, the analyte is a benzheterocyclic selected from oxazepam, chlorpromazine, tegretol, their derivatives and metabolites, the heterocyclic rings being azepines, diazepines and phenothiazines.

In some embodiments, the analyte is a purine selected from theophylline, caffeine, their metabolites and derivatives.

In some embodiments, the analyte is marijuana, cannabinol or tetrahydrocannabinol.

In some embodiments, the analyte is a vitamin such as vitamin A, vitamin B, e.g. vitamin $B_{12}$, vitamin C, vitamin D, vitamin E and vitamin K, folic acid, thiamine.

In some embodiments, the analyte is selected from prostaglandins, which differ by the degree and sites of hydroxylation and unsaturation.

In some embodiments, the analyte is a tricyclic antidepressant selected from imipramine, dismethylimipramine, amitriptyline, nortriptyline, protriptyline, trimipramine, chlomipramine, doxepine, and desmethyldoxepin.

In some embodiments, the analyte is selected from antineoplastics, including methotrexate.

In some embodiments, the analyte is an antibiotic as described herein, including, but not limited to, penicillin, chloromycetin, actinomycetin, tetracycline, terramycin, and metabolites and derivatives.

In some embodiments, the analyte is a nucleoside and nucleotide selected from ATP, NAD, FMN, adenosine, guanosine, thymidine, and cytidine with their appropriate sugar and phosphate substituents.

In some embodiments, the analyte is selected from methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

In some embodiments, the analyte is a metabolite related to a diseased state. Such metabolites include, but are not limited to spermine, galactose, phenylpyruvic acid, and porphyrin Type 1.

In some embodiments, the analyte is an aminoglycoside, such as gentamicin, kanamicin, tobramycin, or amikacin.

In some embodiments, the analyte is a pesticide. Among pesticides of interest are polyhalogenated biphenyls, phosphate esters, thiophosphates, carbamates, polyhalogenated sulfenamides, their metabolites and derivatives.

In some embodiments, the analyte has a molecular weight of about 500 Da to about 1,000,000 Da (e.g., about 500 to about 500,000 Da, about 1,000 to about 100,000 Da).

In some embodiments, the analyte is a receptor, with a molecular weight ranging from 10,000 to $2 \times 10^8$ Da, more usually from 10,000 to $10^6$ Da. For immunoglobulins, IgA, IgG, IgE and IgM, the molecular weights will generally vary from about 160,000 Da to about $10^6$ Da. Enzymes will normally range in molecular weight from about 10,000 Da to about 1,000,000 Da. Natural receptors vary widely, generally having a molecular weight of at least about 25,000 Da and may be $10^6$ or higher Da, including such materials as avidin, DNA, RNA, thyroxine binding globulin, thyroxine binding prealbumin, transcortin, etc.

In some embodiments, the term "analyte" further includes polynucleotide analytes such as those polynucleotides defined below. These include m-RNA, r-RNA, t-RNA, DNA, DNA-RNA duplexes, etc. The term analyte also includes polynucleotide-binding agents, such as, for example, restriction enzymes, trascription factors, transcription activators, transcription repressors, nucleases, polymerases, histones, DNA repair enzymes, intercalating gagents, chemotherapeutic agents, and the like.

In some embodiments, the analyte may be a molecule found directly in a sample such as a body fluid from a host. The sample can be examined directly or may be pretreated to render the analyte more readily detectable. Furthermore, the analyte of interest may be determined by detecting an agent probative of the analyte of interest (i.e., an analyte-binding agent), such as a specific binding pair member complementary to the analyte of interest, whose presence will be detected only when the analyte of interest is present in a sample. Thus, the agent probative of the analyte becomes the analyte that is detected in an assay.

In some embodiments, the analyte a nucleic acid (e.g., a bacterial DNA molecule or a bacterial RNA molecule (e.g., a bacterial tRNA, a transfer-messenger RNA (tmRNA)). See, e.g., Sjostrom et al. (2015) Scientific Reports 5: 15329; Ghosal (2017) Microbial Pathogenesis 104: 161-163; Shen et al. (2012) Cell Host Microbe. 12(4): 509-520.

In some embodiments, the analyte is a component of an outer membrane vesicle (OMV) (e.g., an OmpU protein, Elluri et al. (2014) PloS One 9: e106731). See, e.g., Kulp and Kuehn (2010) Annual Review of microbiology 64: 163-184; Berleman and Auer (2013) Environmental microbiology 15: 347-354; Wai et al. (1995) Microbiology and immunology 39: 451-456; Lindmark et al. (2009) BMC microbiology 9: 220; Sjostrom et al. (2015) Scientific Reports 5: 15329.

In some embodiments, the analyte is G-CSF, which can stimulate the bone marrow to produce granulocytes and stem cells and release them into the bloodstream.

In some embodiments, the analyte is an enzyme such as glutathione S-transferase. For example, the ingestible device can include P28GST, a 28 kDa helminth protein from *Schistosoma* with potent immunogenic and antioxidant properties. P28GST prevents intestinal inflammation in experimental colitis through a Th2-type response with mucosal eosinophils and can be recombinantly produced (e.g., in *S. cerevisiae*). See, for example, U.S. Pat. No. 9,593,313, Driss et al., *Mucosal Immunology,* 2016 9, 322-335; and Capron et al., *Gastroenterology,* 146(5):S-638.

In some embodiments, the analyte is a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof.

In some embodiments, analytes are therapeutic agents or drugs. In some embodiments, analytes are biomarkers. The therapeutic agents disclosed herein are can also be analytes. Examples of biomarkers are provided herein.

In some embodiments, analytes are therapeutic agents, fragments thereof, and metabolites thereof (e.g., antibiotics). In some embodiments, the analytes are antibodies. In some embodiments, the analytes are antibiotics. Additional exemplary analytes (e.g., antibodies and antibiotics) are provided below.

a. Antibodies

In some embodiments, the analyte or the analyte-binding agent is an antibody. An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv) and domain antibodies), and fusion proteins including an antibody portion, and any other modified configuration of the immunoglobulin molecule that includes an antigen recognition site. The term antibody includes antibody fragments (e.g., antigen-binding fragments) such as an Fv fragment, a Fab fragment, a F(ab')2 fragment, and a Fab' fragment. Additional examples of antigen-binding fragments include an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM). An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies including the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) that contain hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-Lazikani et al, 1997, J. Molec. Biol. 273:927-948). As used herein, a CDR may refer to CDRs defined by either approach or by a combination of both approaches.

As known in the art, a "constant region" of an antibody refers to the constant region of the antibody light chain or the constant region of the antibody heavy chain, either alone or in combination.

A "derivative" refers to any polypeptide (e.g., an antibody) having a substantially identical amino acid sequence to the naturally occurring polypeptide, in which one or more amino acids have been modified at side groups of the amino acids (e.g., an biotinylated protein or antibody). The term "derivative" shall also include any polypeptide (e.g., an antibody) which has one or more amino acids deleted from, added to, or substituted from the natural polypeptide sequence, but which retains a substantial amino acid sequence homology to the natural sequence. A substantial sequence homology is any homology greater than 50 percent.

In some embodiments, the antibody can be a humanized antibody, a chimeric antibody, a multivalent antibody, or a fragment thereof. In some embodiments, an antibody can be a scFv-Fc (Sokolowska-Wedzina et al., Mol. Cancer Res. 15(8):1040-1050, 2017), a VHH domain (Li et al., Immunol. Lett. 188:89-95, 2017), a VNAR domain (Hasler et al., Mol. Immunol. 75:28-37, 2016), a (scFv)$_2$, a minibody (Kim et al., PLoS One 10(1):e113442, 2014), or a BiTE. In some embodiments, an antibody can be a DVD-Ig (Wu et al., Nat. Biotechnol. 25(11):1290-1297, 2007; WO 08/024188; WO 07/024715), and a dual-affinity re-targeting antibody (DART) (Tsai et al., Mol. Ther. Oncolytics 3:15024, 2016), a triomab (Chelius et al., MAbs 2(3):309-319, 2010), kih IgG with a common LC (Kontermann et al., Drug Discovery Today 20(7):838-847, 2015), a crossmab (Regula et al., EMBO Mol. Med. 9(7):985, 2017), an ortho-Fab IgG (Kontermann et al., Drug Discovery Today 20(7):838-847, 2015), a 2-in-1-IgG (Kontermann et al., Drug Discovery Today 20(7):838-847, 2015), IgG-scFv (Cheal et al., Mol. Cancer Ther. 13(7):1803-1812, 2014), scFv2-Fc (Natsume et al., J. Biochem. 140(3):359-368, 2006), a bi-nanobody (Kontermann et al., Drug Discovery Today 20(7):838-847, 2015), tanden antibody (Kontermann et al., Drug Discovery Today 20(7):838-847, 2015), a DART-Fc (Kontermann et al., Drug Discovery Today 20(7):838-847, 2015), a scFv-HSA-scFv (Kontermann et al., Drug Discovery Today 20(7):838-847, 2015), DNL-Fab3 (Kontermann et al., Drug Discovery Today 20(7):838-847, 2015), DAF (two-in-one or four-in-one), DutaMab, DT-IgG, knobs-in-holes common LC, knobs-in-holes assembly, charge pair antibody, Fab-arm exchange antibody, SEEDbody, Triomab, LUZ-Y, Fcab, kλ-body, orthogonal Fab, DVD-IgG, IgG(H)-scFv, scFv-(H) IgG, IgG(L)-scFv, scFv-(L)-IgG, IgG (L,H)-Fc, IgG(H)-V, V(H)-IgG, IgG(L)-V, V(L)-IgG, KIH IgG-scFab, 2scFv-IgG, IgG-2scFv, scFv4-Ig, Zybody, DVI-IgG, nanobody (e.g., antibodies derived from Camelus bactriamus, Calelus dromaderius, or Lama paccos) (U.S. Pat. No. 5,759,808; Stijlemans et al., J. Biol. Chem. 279:1256-1261, 2004; Dumoulin et al., Nature 424:783-788, 2003; and Pleschberger et al., Bioconjugate Chem. 14:440-448, 2003), nanobody-HSA, a diabody (e.g., Poljak, Structure 2(12): 1121-1123, 1994; Hudson et al., J. Immunol. Methods 23(1-2):177-189, 1999), a TandAb (Reusch et al., mAbs 6(3):727-738, 2014), scDiabody (Cuesta et al., Trends in Biotechnol. 28(7):355-362, 2010), scDiabody-CH3 (Sanz et al., Trends in Immunol. 25(2):85-91, 2004), Diabody-CH3 (Guo et al.), Triple Body, miniantibody, minibody, TriBi minibody, scFv-CH3 KIH, Fab-scFv, scFv-CH-CL-scFv, F(ab')2-scFV2, scFv-KIH, Fab-scFv-Fc, tetravalent HCAb, scDiabody-Fc, diabody-Fc, tandem scFv-Fc, intrabody (Huston et al., Human Antibodies 10(3-4):127-142, 2001; Wheeler et al., Mol. Ther. 8(3):355-366, 2003; Stocks, Drug Discov. Today 9(22):960-966, 2004), dock and lock bispecific antibody, ImmTAC, HSAbody, scDiabody-HSA, tandem scFv, IgG-IgG, Cov-X-Body, and scFv1-PEG-scFv2.

In some embodiments, an antibody can be an IgNAR, a bispecific antibody (Milstein and Cuello, Nature 305:537-539, 1983; Suresh et al., Methods in Enzymology 121:210, 1986; WO 96/27011; Brennan et al., Science 229:81, 1985; Shalaby et al., J. Exp. Med. 175:217-225, 1992; Kolstelny et al., J. Immunol. 148(5):1547-1553, 1992; Hollinger et al., Proc. Natl. Acad. Sci. U.S.A. 90:6444-6448, 1993; Gruber et al., J. Immunol. 152:5368, 1994; Tuft et al., J. Immunol. 147:60, 1991), a bispecific diabody, a triabody (Schoonooghe et al., BMC Biotechnol. 9:70, 2009), a tetrabody, scFv-Fc knobs-into-holes, a scFv-Fc-scFv, a (Fab'scFv)$_2$, a V-IgG, a IvG-V, a dual V domain IgG, a heavy chain immunoglobulin or a camelid (Holt et al., Trends Biotechnol. 21(11):484-490, 2003), an intrabody, a monoclonal antibody (e.g., a human or humanized monoclonal antibody), a heteroconjugate antibody (e.g., U.S. Pat. No. 4,676,980), a linear antibody (Zapata et al., Protein Eng. 8(10: 1057-1062, 1995), a trispecific antibody (Tuft et al., J. Immunol. 147:60, 1991), a Fabs-in-Tandem immunoglobulin (WO 15/103072), or a humanized camelid antibody.

In some embodiments, the antibody binds specifically to a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid. Exemplary antibodies that bind to metabolites in these pathways are disclosed, for example, in International Publication No. WO2014/188377, the entire contents of which are incorporated herein by reference.

In some embodiments, the antibody is specific for a particular genus, species, or strain of a microorganism, and may therefore be used for the detection, analysis and/or quantitation of the microorganism using the detection methods described below. In some embodiments, the antibody specifically binds to a surface-specific biomolecule (e.g., a pilus subunit or a flagella protein) present in a particular genus, species or strain of microorganism, and does not cross-react with other microorganisms. In some embodiments, these antibodies may be used in the methods described herein to diagnose a subject with a particular infection or disease, or to monitor an infection (e.g., during or after treatment). In some embodiments, the antibody specifically binds to an antigen present in a particular genera, species or strain of a microorganism. Exemplary antigens, the corresponding microorganism that can be detected, and the disease caused by the microorganism (in parentheticals) include: outer membrane protein A OmpA (*Acinetobacter baumannii, Acinetobacter* infections)); HIV p24 antigen, HIV Eenvelope proteins (Gp120, Gp41, Gp160) (HIV (Human immunodeficiency virus), AIDS (Acquired immunodeficiency syndrome)); galactose-inhibitable adherence protein GIAP, 29 kDa antigen Eh29, GaVGalNAc lectin, protein CRT, 125 kDa immunodominant antigen, protein M17, adhesin ADH112, protein STIRP (*Entamoeba histolytica*, Amoebiasis); protective Antigen PA, edema factor EF, lethal factor LF, the S-layer homology proteins SLH (*Bacillus anthraces*, Anthrax); nucleocapsid protein NP, glycoprotein precursor GPC, glycoprotein GP1, glycoprotein GP2 (Junin virus, Argentine hemorrhagic fever); 41 kDa allergen Asp v13, allergen Asp f3, major conidial surface protein rodlet A, protease Pep1p, GPI-anchored protein Gel1p, GPI-anchored protein Crf1p (*Aspergillus* genus, Aspergillosis); outer surface protein A OspA, outer surface protein OspB, outer surface protein OspC, decorin binding protein A DbpA, flagellar filament 41 kDa core protein Fla, basic membrane protein A precursor BmpA (Immunodominant antigen P39), outer surface 22 kDa lipoprotein precursor (antigen IPLA7), variable surface lipoprotein vlsE (*Borrelia* genus, *Borrelia* infection); OmpA-like transmembrane domain-containing protein Omp31, immunogenic 39-kDa protein M5 P39, 25 kDa outer-membrane immunogenic protein precursor Omp25, outer membrane protein MotY Omp16, conserved outer membrane protein D15, malate dehydrogenase Mdh, component of the Type-IV secretion system (T4SS) VirJ, lipoprotein of unknown function BAB1-0187 (*Brucella* genus, Brucellosis); major outer membrane protein PorA, flagellin FlaA, surface antigen CjaA, fibronectin binding protein CadF, aspartate/glutamate-binding ABC transporter protein Peb1A, protein FspA1, protein FspA2 (*Campylobacter* genus, Campylobacteriosis); glycolytic enzyme enolase, secreted aspartyl proteinases SAP1-10, glycophosphatidylinositol (GPI)-linked cell wall protein, adhesin Als3p, cell surface hydrophobicity protein CSH (usually *Candida albicans* and other *Candida* species, Candidiasis); envelope glycoproteins (gB, gC, gE, gH, gI, gK, gL) (Varicella zoster virus (VZV), Chickenpox); major outer membrane protein MOMP, probable outer membrane protein PMPC, outer membrane complex protein B OmcB (*Chlamydia trachomatis, Chlamydia*); major outer membrane protein MOMP, outer membrane protein 2 Omp2, (*Chlamydophila pneumoniae, Chlamydophila pneumoniae* infection); outer membrane protein U Porin ompU, (*Vibrio cholerae*, Cholera); surface layer proteins SLPs, Cell Wall Protein CwpV, flagellar protein FliC, flagellar protein FliD (*Clostridium difficile, Clostridium difficile* infection); acidic ribosomal protein P2 CpP2, mucin antigens Muc1, Muc2, Muc3 Muc4, Muc5, Muc6, Muc7, surface adherence protein CP20, surface adherence protein CP23, surface protein CP12, surface protein CP21, surface protein CP40, surface protein CP60, surface protein CP15, surface-associated glycopeptides gp40, surface-associated glycopeptides gp15, oocyst wall protein AB, profilin PRF, apyrase (*Cryptosporidium* genus, Cryptosporidiosis); membrane protein pp15, capsid-proximal tegument protein pp150 (Cytomegalovirus, Cytomegalovirus infection); prion protein (vCJD prion, Variant Creutzfeldt-Jakob disease (vCJD, nvCJD)); cyst wall proteins CWP1, CWP2, CWP3, variant surface protein VSP, VSP1, VSP2, VSP3, VSP4, VSP5, VSP6, 56 kDa antigen (*Giardia intestinalis*, Giardiasis); minor pilin-associated subunit pilC, major pilin subunit and variants pilE, pilS (*Neisseria gonorrhoeae*, Gonorrhea); outer membrane protein A OmpA, outer membrane protein C OmpC, outer membrane protein K17 OmpK17 (*Klebsiella granulomatis, Granuloma inguinale* (Donovanosis)); fibronectin-binding protein Sfb (*Streptococcus pyogenes*, Group A streptococcal infection); outer membrane protein P6 (*Haemophilus influenzae, Haemophilus influenzae* infection); integral membrane proteins, aggregation-prone proteins, O-antigen, toxin-antigens Stx2B, toxin-antigen Stx1B, adhesion-antigen fragment Int28, protein EspA, protein EspB, Intimin, protein Tir, protein IntC300, protein Eae (*Escherichia coli* O157:H7, O111 and O104:H4, Hemolytic-uremic syndrome (HUS)); hepatitis A surface antigen HBAg (Hepatitis A Virus, Hepatitis A); hepatitis B surface antigen HBsAg (Hepatitis B Virus, Hepatitis B); envelope glycoprotein E1 gp32 gp35, envelope glycoprotein E2 NS1 gp68 gp70, capsid protein C, (Hepatitis C Virus, Hepatitis C); type IV pilin PilE, outer membrane protein MIP, major outer membrane protein MompS (*Legionella pneumophila*, Legionellosis (Legionnaires' disease, Pontiac fever)); minor pilin-associated subunit pilC, major pilin subunit and variants pilE, pilS (*Neisseria meningitidis*, Meningococcal disease); adhesin P1, adhesion P30 (*Mycoplasma pneumoniae, Mycoplasma* pneumonia); F1 capsule antigen, outer membrane protease Pla, (*Yersinia pestis*, Plague); surface adhesin PsaA, cell wall surface anchored protein psrP (*Streptococcus pneumoniae*, Pneumococcal infection); flagellin FliC, invasion protein SipC, glycoprotein gp43, outer membrane protein LamB, outer membrane protein PagC, outer membrane protein TolC, outer membrane protein NmpC, outer membrane protein FadL, transport protein SadA (*Salmonella* genus, Salmonellosis); collagen adhesin Cna, fibronectin-binding protein A FnbA, secretory antigen SssA (*Staphylococcus* genus, Staphylococcal food poisoning); collagen adhesin Can (*Staphylococcus* genus, Staphylococcal infection); fibronectin-binding protein A FbpA (Ag85A), fibronectin-binding protein D FbpD, fibronectin-binding protein C FbpC1, heat-shock protein HSP65, protein PST-S (*Mycobacterium tuberculosis*, Tuberculosis); and outer membrane protein FobA, outer membrane protein FobB, type IV pili glycosylation protein, outer membrane protein tolC, protein TolQ (*Francisella tularensis*, Tularemia). Additional exemplary microorganisms and corresponding antigens are disclosed, e.g., in U.S. Publication No. 2015/0118264, the entire contents of which are expressly incorporated herein by reference.

In some embodiments, a plurality of antibodies (e.g.,2, 3, 4, 5, 6, 7, 8, 9, 10, 15, 20, 25, 30, or more antibodies) are used as analyte-binding agents in any of the methods described herein (e.g., to detect the presence of one or more analytes in a sample). In some embodiments, the plurality of antibodies bind to the same analyte (e.g., an antigen). In some embodiments, the plurality of antibodes bind to the same epitope present on the analyte (e.g., an antigen). In some embodiments, the plurality of antibodies bind to different epitopes present on the same analyte. In some embodiments, the plurality of antibodies bind to overlapping epitopes present on the same analyte. In some embodiments, the plurality of antibodies bind to non-overlapping epitopes present on the same analyte.

b. Antibiotics

In some embodiments, the analyte or analyte-binding agent is an antibiotic. An "antibiotic" or "antibiotic agent" refers to a substance that has the capacity to inhibit or slow down the growth of, or to destroy bacteria and/or other microorganisms. In some embodiments, the antibiotic agent is a bacteriostatic antibiotic agent. In some embodiments, the antibiotic is a bacteriolytic antibiotic agent. Exemplary antibiotic agents are set forth in the U.S. Patent Publication US 2006/0269485, which is hereby incorporated by reference herein in its entirety.

In some embodiments, the antibiotic agent is selected from the classes consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds. In some embodiments, the antibiotic is rifaximin.

Beta-lactam antibiotics include, but are not limited to, 2-(3-alanyl)clavam, 2-hydroxymethylclavam, 8-epi-thienamycin, acetyl-thienamycin, amoxicillin, amoxicillin sodium, amoxicillin trihydrate, amoxicillin-potassium clavulanate combination, ampicillin, ampicillin sodium, ampicillin trihydrate, ampicillin-sulbactam, apalcillin, aspoxicillin, azidocillin, azlocillin, aztreonam, bacampicillin, biapenem, carbenicillin, carbenicillin disodium, carfecillin, carindacillin, carpetimycin, cefacetril, cefaclor, cefadroxil, cefalexin, cefaloridine, cefalotin, cefamandole, cefamandole, cefapirin, cefatrizine, cefatrizine propylene glycol, cefazedone, cefazolin, cefbuperazone, cefcapene, cefcapene pivoxil hydrochloride, cefdinir, cefditoren, cefditoren pivoxil, cefepime, cefetamet, cefetamet pivoxil, cefixime, cefmenoxime, cefinetazole, cefminox, cefminox, cefmolexin, cefodizime, cefonicid, cefoperazone, ceforanide, cefoselis, cefotaxime, cefotetan, cefotiam, cefoxitin, cefozopran, cefpiramide, cefpirome, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftriaxone, cefuroxime, cefuroxime axetil, cephalosporin, cephamycin, chitinovorin, ciclacillin, clavulanic acid, clometocillin, cloxacillin, cycloserine, deoxy pluracidomycin, dicloxacillin, dihydro pluracidomycin, epicillin, epithienamycin, ertapenem, faropenem, flomoxef, flucloxacillin, hetacillin, imipenem, lenampicillin, loracarbef, mecillinam, meropenem, metampicillin, meticillin, mezlocillin, moxalactam, nafcillin, northienamycin, oxacillin, panipenem, penamecillin, penicillin, phenethicillin, piperacillin, tazobactam, pivampicillin, pivcefalexin, pivmecillinam, pivmecillinam hydrochloride, pluracidomycin, propicillin, sarmoxicillin, sulbactam, sulbenicillin, talampicillin, temocillin, terconazole, thienamycin, ticarcillin and analogs, salts and derivatives thereof.

Aminoglycosides include, but are not limited to, 1,2'-N-DL-isoseryl-3',4'-dideoxykanamycin B, 1,2'-N-DL-isoserylkanamycin B, 1,2'-N-[(S)-4-amino-2-hydroxybutyryl]-3',4'-dideoxykanamycin B, 1,2'-N-[(S)-4-amino-2-hydroxybutyryl]-kanamycin B, 1-N-(2-Aminobutanesulfonyl) kanamycin A, 1-N-(2-aminoethanesulfonyl)3',4'-dideoxyribostamycin, 1-N-(2-Aminoethanesulfonyl)3'-deoxyribostamycin, 1-N-(2-aminoethanesulfonyl)3'4'-dideoxykanamycin B, 1-N-(2-aminoethanesulfonyl)kanamycin A, 1-N-(2-aminoethanesulfonyl)kanamycin B, 1-N-(2-aminoethanesulfonyl)ribostamycin, 1-N-(2-aminopropanesulfonyl)3'-deoxykanamycin B, 1-N-(2-aminopropanesulfonyl)3'4'-dideoxykanamycin B, 1-N-(2-aminopropanesulfonyl)kanamycin A, 1-N-(2-aminopropanesulfonyl)kanamycin B, 1-N-(L-4-amino-2-hydroxy-butyryl)2,'3'-dideoxy-2'-fluorokanamycin A, 1-N-(L-4-amino-2-hydroxy-propionyl)2,'3'-dideoxy-2'-fluorokanamycin A, 1-N-DL-3',4'-dideoxy-isoserylkanamycin B, 1-N-DL-isoserylkanamycin, 1-N-DL-isoserylkanamycin B, 1-N-[L-(−)-(alpha-hydroxy-gamma-aminobutyryl)]-XK-62-2,2',3'-dideoxy-2'-fluorokanamycin A,2-hydroxygentamycin A3,2-hydroxygentamycin B, 2-hydroxygentamycin B1, 2-hydroxygentamycin JI-20A, 2-hydroxygentamycin JI-20B, 3"-N-methyl-4"-C-methyl-3',4'-dodeoxy kanamycin A, 3"-N-methyl-4"-C-methyl-3',4'-dodeoxy kanamycin B, 3"-N-methyl-4"-C-methyl-3',4'-dodeoxy-6'-methyl kanamycin B, 3',4'-Dideoxy-3'-eno-ribostamycin,3',4'-dideoxyneamine,3',4'-dideoxyribostamycin, 3'-deoxy-6'-N-methyl-kanamycin B,3'-deoxyneamine,3'-deoxyribostamycin, 3'-oxysaccharocin,3,3'-nepotrehalosadiamine, 3-demethoxy-2"-N-formimidoylistamycin B disulfate tetrahydrate, 3-demethoxyistamycin B,3-O-demethyl-2-N-formimidoylistamycin B, 3-O-demethylistamycin B,3-trehalosamine,4",6"-dideoxydibekacin, 4-N-glycyl-KA-6606VI, 5"-Amino-3',4',5"-trideoxy-butirosin A, 6"-deoxydibekacin,6'-epifortimicin A, 6-deoxy-neomycin (structure 6-deoxy-neomycin B),6-deoxy-neomycin B, 6-deoxy-neomycin C, 6-deoxy-paromomycin, acmimycin, AHB-3',4'-dideoxyribostamycin, AHB-3'-deoxykanamycin B, AHB-3'-deoxyneamine, AHB-3'-deoxyribostamycin, AHB-4"-6"-dideoxydibekacin, AHB-6"-deoxydibekacin, AHB-dideoxyneamine, AHB-kanamycin B, AHB-methyl-3'-deoxykanamycin B, amikacin, amikacin sulfate, apramycin, arbekacin, astromicin, astromicin sulfate, bekanamycin, bluensomycin, boholmycin, butirosin, butirosin B, catenulin, coumamidine gamma1, coumamidine gamma2,D,L-1-N-(alpha-hydroxy-beta-aminopropionyl)-XK-62-2, dactimicin, de-O-methyl-4-N-glycyl-KA-6606VI, de-O-methyl-KA-6606I, de-O-methyl-KA-7038I, destomycin A, destomycin B, di-N6',O3-demethylistamycin A, dibekacin, dibekacin sulfate, dihydrostreptomycin, dihydrostreptomycin sulfate, epi-formamidoylglycidylfortimicin B, epihygromycin, formimidoyl-istamycin A, formimidoyl-istamycin B, fortimicin B, fortimicin C, fortimicin D, fortimicin KE, fortimicin KF, fortimicin KG, fortimicin KG1 (stereoisomer KG1/KG2), fortimicin KG2 (stereoisomer KG1/KG2), fortimicin KG3, framycetin, framycetin sulphate, gentamicin, gentamycin sulfate, globeomycin, hybrimycin A1, hybrimycin A2, hybrimycin B1, hybrimycin B2, hybrimycin C1, hybrimycin C2, hydroxystreptomycin, hygromycin, hygromycin B, isepamicin, isepamicin sulfate, istamycin, kanamycin, kanamycin sulphate, kasugamycin, lividomycin, marcomycin, micronomicin, micronomicin sulfate, mutamicin, myomycin, N-demethyl-7-O-demethylcelesticetin, demethylcelesticetin, methanesulfonic acid derivative of istamycin, nebramycin, nebramycin, neomycin, netilmicin, oligostatin, paromomycin, quintomycin, ribostamycin, saccharocin, seldomycin, sisomicin, sorbistin, spectinomycin, streptomycin, tobramycin, trehalosmaine, trestatin, validamycin, verdamycin, xylostasin, zygomycin and analogs, salts and derivatives thereof.

Ansa-type antibiotics include, but are not limited to, 21-hydroxy-25-demethyl-25-methylthioprotostreptovaricin, 3-methylthiorifamycin, ansamitocin, atropisostreptovaricin, awamycin, halomicin, maytansine, naphthomycin, rifabutin, rifamide, rifampicin, rifamycin, rifapentine, rifaximin (e.g., Xifaxan®), rubradirin, streptovaricin, tolypomycin and analogs, salts and derivatives thereof.

Antibiotic anthraquinones include, but are not limited to, auramycin, cinerubin, ditrisarubicin, ditrisarubicin C, figaroic acid fragilomycin, minomycin, rabelomycin, rudolfomycin, sulfurmycin and analogs, salts and derivatives thereof.

Antibiotic azoles include, but are not limited to, azanidazole, bifonazole, butoconazol, chlormidazole, chlormidazole hydrochloride, cloconazole, cloconazole monohydrochloride, clotrimazol, dimetridazole, econazole, econazole nitrate, enilconazole, fenticonazole, fenticonazole nitrate, fezatione, fluconazole, flutrimazole, isoconazole, isoconazole nitrate, itraconazole, ketoconazole, lanoconazole, metronidazole, metronidazole benzoate, miconazole, miconazole nitrate, neticonazole, nimorazole, niridazole, omoconazol, ornidazole, oxiconazole, oxiconazole nitrate, propenidazole, secnidazol, sertaconazole, sertaconazole nitrate, sulconazole, sulconazole nitrate, tinidazole, tioconazole, voriconazol and analogs, salts and derivatives thereof.

Antibiotic glycopeptides include, but are not limited to, acanthomycin, actaplanin, avoparcin, balhimycin, bleomycin B (copper bleomycin), chloroorienticin, chloropolysporin, demethylvancomycin, enduracidin, galacardin, guanidylfungin, hachimycin, demethylvancomycin, N-nonanoyl-teicoplanin, phleomycin, platomycin, ristocetin, staphylocidin, talisomycin, teicoplanin, vancomycin, victomycin, xylocandin, zorbamycin and analogs, salts and derivatives thereof.

Macrolides include, but are not limited to, acetylleucomycin, acetylkitasamycin, angolamycin, azithromycin, bafilomycin, brefeldin, carbomycin, chalcomycin, cirramycin, clarithromycin, concanamycin, deisovaleryl-niddamycin, demycinosyl-mycinamycin, Di-O-methyltiacumicidin, dirithromycin, erythromycin, erythromycin estolate, erythromycin ethyl succinate, erythromycin lactobionate, erythromycin stearate, flurithromycin, focusin, foromacidin, haterumalide, haterumalide, josamycin, josamycin ropionate, juvenimycin, juvenimycin, kitasamycin, ketotiacumicin, lankavacidin, lankavamycin, leucomycin, machecin, maridomycin, megalomicin, methylleucomycin, methymycin, midecamycin, miocamycin, mycaminosyltylactone, mycinomycin, neutramycin, niddamycin, nonactin, oleandomycin, phenylacetyideltamycin, pamamycin, picromycin, rokitamycin, rosaramicin, roxithromycin, sedecamycin, shincomycin, spiramycin, swalpamycin, tacrolimus, telithromycin, tiacumicin, tilmicosin, treponemycin, troleandomycin, tylosin, venturicidin and analogs, salts and derivatives thereof.

Antibiotic nucleosides include, but are not limited to, amicetin, angustmycin, azathymidine, blasticidin S, epiroprim, flucytosine, gougerotin, mildiomycin, nikkomycin, nucleocidin, oxanosine, oxanosine, puromycin, pyrazomycin, showdomycin, sinefungin, sparsogenin, spicamycin, tunicamycin, uracil polyoxin, vengicide and analogs, salts and derivatives thereof.

Antibiotic peptides include, but are not limited to, actinomycin, aculeacin, alazopeptin, amfomycin, amythiamycin, antifungal from Zalerion arboricola, antrimycin, apid, apidaecin, aspartocin, auromomycin, bacileucin, bacillomycin, bacillopeptin, bacitracin, bagacidin, beminamycin, beta-alanyl-L-tyrosine, bottromycin, capreomycin, caspofungine, cepacidine, cerexin, cilofungin, circulin, colistin, cyclodepsipeptide, cytophagin, dactinomycin, daptomycin, decapeptide, desoxymulundocandin, echanomycin, echinocandin B, echinomycin, ecomycin, enniatin, etamycin, fabatin, ferrimycin, ferrimycin, ficellomycin, fluoronocathiacin, fusaricidin, gardimycin, gatavalin, globopeptin, glyphomycin, gramicidin, herbicolin, iomycin, iturin, iyomycin, izupeptin, janiemycin, janthinocin, jolipeptin, katanosin, killertoxin, lipopeptide antibiotic, lipopeptide from Zalerion sp., lysobactin, lysozyme, macromomycin, magainin, melittin, mersacidin, mikamycin, mureidomycin, mycoplanecin, mycosubtilin, neopeptifluorin, neoviridogrisein, netropsin, nisin, nocathiacin, nocathiacin 6-deoxyglycoside, nosiheptide, octapeptin, pacidamycin, pentadecapeptide, peptifluorin, permetin, phytoactin, phytostreptin, planothiocin, plusbacin, polcillin, polymyxin antibiotic complex, polymyxin B, polymyxin B1, polymyxin F, preneocarzinostatin, quinomycin, quinupristin-dalfopristin, safracin, salmycin, salmycin, salmycin, sandramycin, saramycetin, siomycin, sperabillin, sporamycin, a Streptomyces compound, subtilin, teicoplanin aglycone, telomycin, thermothiocin, thiopeptin, thiostrepton, tridecaptin, tsushimycin, tuberactinomycin, tuberactinomycin, tyrothricin, valinomycin, viomycin, virginiamycin, zervacin and analogs, salts and derivatives thereof.

In some embodiments, the antibiotic peptide is a naturally-occurring peptide that possesses an antibacterial and/or an antifungal activity. Such peptide can be obtained from an herbal or a vertebrate source.

Polyenes include, but are not limited to, amphotericin, amphotericin, aureofungin, ayfactin, azalomycin, blasticidin, candicidin, candicidin methyl ester, candimycin, candimycin methyl ester, chinopricin, filipin, flavofungin, fradicin, hamycin, hydropricin, levorin, lucensomycin, lucknomycin, mediocidin, mediocidin methyl ester, mepartricin, methylamphotericin, natamycin, niphimycin, nystatin, nystatin methyl ester, oxypricin, partricin, pentamycin, perimycin, pimaricin, primycin, proticin, rimocidin, sistomycosin, sorangicin, trichomycin and analogs, salts and derivatives thereof.

Polyethers include, but are not limited to, 20-deoxy-epinarasin, 20-deoxysalinomycin, carriomycin, dianemycin, dihydrolonomycin, etheromycin, ionomycin, iso-lasalocid, lasalocid, lenoremycin, lonomycin, lysocellin, monensin, narasin, oxolonomycin, a polycyclic ether antibiotic, salinomycin and analogs, salts and derivatives thereof.

Quinolones include, but are not limited to, an alkyl-methylendioxy-4(1H)-oxocinnoline-3-carboxylic acid, alatrofloxacin, cinoxacin, ciprofloxacin, ciprofloxacin hydrochloride, danofloxacin, dermofongin A, enoxacin, enrofloxacin, fleroxacin, flumequine, gatifloxacin, gemifloxacin, grepafloxacin, levofloxacin, lomefloxacin, lomefloxacin, hydrochloride, miloxacin, moxifloxacin, nadifloxacin, nalidixic acid, nifuroquine, norfloxacin, ofloxacin, orbifloxacin, oxolinic acid, pazufloxacine, pefloxacin, pefloxacin mesylate, pipemidic acid, piromidic acid, premafloxacin, rosoxacin, rufloxacin, sparfloxacin, temafloxacin, tosufloxacin, trovafloxacin and analogs, salts and derivatives thereof.

Antibiotic steroids include, but are not limited to, aminosterol, ascosteroside, cladosporide A, dihydrofusidic acid, dehydro-dihydrofusidic acid, dehydrofusidic acid, fusidic acid, squalamine and analogs, salts and derivatives thereof.

Sulfonamides include, but are not limited to, chloramine, dapsone, mafenide, phthalylsulfathiazole, succinylsulfathiazole, sulfabenzamide, sulfacetamide, sulfachlorpyridazine, sulfadiazine, sulfadiazine silver, sulfadicramide, sulfadimethoxine, sulfadoxine, sulfaguanidine, sulfalene, sulfamazone, sulfamerazine, sulfamethazine, sulfamethizole, sulfamethoxazole, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfacarbamide and analogs, salts and derivatives thereof.

Tetracyclines include, but are not limited to, dihydrosteffimycin, demethyltetracycline, aclacinomycin, akrobomycin, baumycin, bromotetracycline, cetocyclin, chlortetracycline, clomocycline, daunorubicin, demeclocycline, doxorubicin, doxorubicin hydrochloride, doxycycline, lymecyclin, marcellomycin, meclocycline, meclocycline sulfosalicylate, methacycline, minocycline, minocycline hydrochloride, musettamycin, oxytetracycline, rhodirubin, rolitetracycline, rubomycin, serirubicin, steffimycin, tetracycline and analogs, salts and derivatives thereof.

Dicarboxylic acids, having between about 6 and about 14 carbon atoms in their carbon atom skeleton are particularly useful in the treatment of disorders of the skin and mucosal membranes that involve microbial. Suitable dicarboxylic acid moieties include, but are not limited to, adipic acid, pimelic acid, suberic acid, azelaic acid, sebacic acid, 1,11-undecanedioic acid, 1,12-dodecanedioic acid, 1,13-tridecanedioic acid and 1,14-tetradecanedioic acid. Thus, in one or more embodiments of the present disclosure, dicarboxylic acids, having between about 6 and about 14 carbon atoms in their carbon atom skeleton, as well as their salts and derivatives (e.g., esters, amides, mercapto-derivatives, anhydraides), are useful immunomodulators in the treatment of disorders of the skin and mucosal membranes that involve inflammation. Azelaic acid and its salts and derivatives are preferred. It has antibacterial effects on both aerobic and anaerobic organisms, particularly *Propionibacterium acnes* and *Staphylococcus epidermidis*, normalizes keratinization, and has a cytotoxic effect on malignant or hyperactive melanocytes. In a preferred embodiment, the dicarboxylic acid is azelaic acid in a concentration greater than 10%. Preferably, the concentration of azelaic acid is between about 10% and about 25%. In such concentrates, azelaic acid is suitable for the treatment of a variety of skin disorders, such as acne, rosacea and hyperpigmentation.

In some embodiments, the antibiotic agent is an antibiotic metal. A number of metals ions have been shown to possess antibiotic activity, including silver, copper, zinc, mercury, tin, lead, bismutin, cadmium, chromium and ions thereof. It has been theorized that these antibiotic metal ions exert their effects by disrupting respiration and electron transport systems upon absorption into bacterial or fungal cells. Antimicrobial metal ions of silver, copper, zinc, and gold, in particular, are considered safe for in vivo use. Anti-microbial silver and silver ions are particularly useful due to the fact that they are not substantially absorbed into the body. Thus, in one or more embodiment, the antibiotic metal consists of an elemental metal, selected from the group consisting of silver, copper, zinc, mercury, tin, lead, bismutin, cadmium, chromium and gold, which is suspended in the composition as particles, microparticles, nanoparticles or colloidal particles. The antibiotic metal can further be intercalated in a chelating substrate.

In further embodiments, the antibiotic metal is ionic. The ionic antibiotic metal can be presented as an inorganic or organic salt (coupled with a counterion), an organometallic complex or an intercalate. Non-binding examples of counter inorganic and organic ions are sulfadiazine, acetate, benzoate, carbonate, iodate, iodide, lactate, laurate, nitrate, oxide, and palmitate, a negatively charged protein. In preferred embodiments, the antibiotic metal salt is a silver salt, such as silver acetate, silver benzoate, silver carbonate, silver iodate, silver iodide, silver lactate, silver laurate, silver nitrate, silver oxide, silver palmitate, silver protein, and silver sulfadiazine.

In one or more embodiments, the antibiotic metal or metal ion is embedded into a substrate, such as a polymer, or a mineral (such as zeolite, clay and silica).

In one or more embodiments, the antibiotic agent includes strong oxidants and free radical liberating compounds, such as oxygen, hydrogen peroxide, benzoyl peroxide, elemental halogen species, as well as oxygenated halogen species, bleaching agents (e.g., sodium, calcium or magnesium hypochloride and the like), perchlorite species, iodine, iodate, and benzoyl peroxide. Organic oxidizing agents, such as quinones, are also included. Such agents possess a potent broad-spectrum activity.

In one or more embodiments, the antibiotic agent is a cationic antimicrobial agent. The outermost surface of bacterial cells universally carries a net negative charge, making them sensitive to cationic substances. Examples of cationic antibiotic agents include: quaternary ammonium compounds (QAC's)—QAC's are surfactants, generally containing one quaternary nitrogen associated with at least one major hydrophobic moiety; alkyltrimethyl ammonium bromides are mixtures of where the alkyl group is between 8 and 18 carbons long, such as cetrimide (tetradecyltrimethylammonium bromide); benzalkonium chloride, which is a mixture of n-alkyldimethylbenzyl ammonium chloride where the alkyl groups (the hydrophobic moiety) can be of variable length; dialkylmethyl ammonium halides; dialkylbenzyl ammonium halides; and QAC dimmers, which bear bi-polar positive charges in conjunction with interstitial hydrophobic regions.

In one or more embodiments, the cationic antimicrobial agent is a polymer. Cationic antimicrobial polymers include, for example, guanide polymers, biguanide polymers, or polymers having side chains containing biguanide moieties or other cationic functional groups, such as benzalkonium groups or quartemium groups (e.g., quaternary amine groups). It is understood that the term "polymer" as used herein includes any organic material including three or more repeating units, and includes oligomers, polymers, copolymers, block copolymers, terpolymers, etc. The polymer backbone may be, for example a polyethylene, polypropylene or polysilane polymer.

In one or more embodiments, the cationic antimicrobial polymer is a polymeric biguanide compound. When applied to a substrate, such a polymer is known to form a barrier film that can engage and disrupt a microorganism. An exemplary polymeric biguanide compound is polyhexamethylene biguanide (PHMB) salts. Other exemplary biguanide polymers include, but are not limited to poly(hexamethylenebiguanide), poly(hexamethylenebiguanide) hydrochloride, poly(hexamethylenebiguanide) gluconate, poly(hexamethylenebiguanide) stearate, or a derivative thereof. In one or more embodiments, the antimicrobial material is substantially water-insoluble.

In some embodiments, the antibiotic agent is selected from the group of biguanides, triguanides, bisbiguanides and analogs thereof.

Guanides, biguanides, biguanidines and triguanides are unsaturated nitrogen containing molecules that readily obtain one or more positive charges, which make them effective antimicrobial agents. The basic structures a guanide, a biguanide, a biguanidine and a triguanide are provided below.

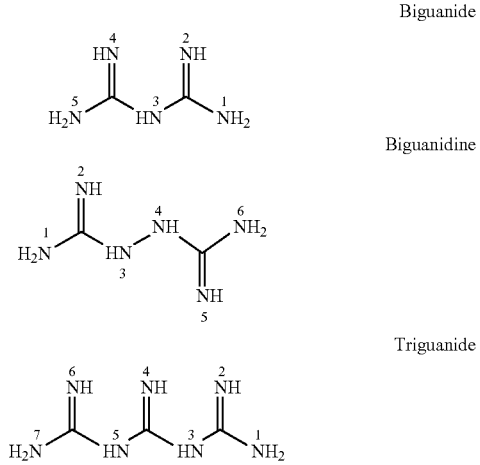

Biguanide

Biguanidine

Triguanide

In some embodiments, the guanide, biguanide, biguanidine or triguanide, provide bi-polar configurations of cationic and hydrophobic domains within a single molecule.

Examples of guanides, biguanides, biguanidines and triguanides that are currently been used as antibacterial agents include chlorhexidine and chlorohexidine salts, analogs and derivatives, such as chlorhexidine acetate, chlorhexidine gluconate and chlorhexidine hydrochloride, picloxydine, alexidine and polihexanide. Other examples of guanides, biguanides, biguanidines and triguanides that can conceivably be used according to the present disclosure are chlorproguanil hydrochloride, proguanil hydrochloride (currently used as antimalarial agents), mefformin hydrochloride, phenformin and buformin hydrochloride (currently used as antidiabetic agents).

Yet, in one or more embodiments, the antibiotic is a non-classified antibiotic agent, including, without limitation, aabomycin, acetomycin, acetoxycycloheximide, acetylnanaomycin, an *Actinoplanes* sp. compound, actinopyrone, aflastatin, albacarcin, albacarin, albofungin, albofungin, alisamycin, alpha-R,S-methoxycarbonylbenzylmonate, altromycin, amicetin, amycin, amycin demanoyl compound, amycine, amycomycin, anandimycin, anisomycin, anthramycin, anti-syphilis immune substance, anti-tuberculosis immune substance, an antibiotic from *Escherichia coli*, an antibiotic from *Streptomyces refuineus*, anticapsin, antimycin, aplasmomycin, aranorosin, aranorosinol, arugomycin, ascofuranone, ascomycin, ascosin, *Aspergillus flavus* antibiotic, asukamycin, aurantinin, an Aureolic acid antibiotic substance, aurodox, avilamycin, azidamfenicol, azidimycin, bacillaene, a *Bacillus larvae* antibiotic, bactobolin, benanomycin, benzanthrin, benzylmonate, bicozamycin, bravomicin, brodimoprim, butalactin, calcimycin, calvatic acid, candiplanecin, carumonam, carzinophilin, celesticetin, cepacin, cerulenin, cervinomycin, chartreusin, chloramphenicol, chloramphenicol palmitate, chloramphenicol succinate sodium, chlorflavonin, chlorobiocin, chlorocarcin, chromomycin, ciclopirox, ciclopirox olamine, citreamicin, cladosporin, clazamycin, clecarmycin, clindamycin, coliformin, collinomycin, copiamycin, corallopyronin, corynecandin, coumermycin, culpin, cuprimyxin, cycla-
midomycin, cycloheximide, dactylomycin, danomycin, danubomycin, delaminomycin, demethoxyrapamycin, demethylscytophycin, dermadin, desdamethine, dexylosylbenanomycin, pseudoaglycone, dihydromocimycin, dihydronancimycin, diumycin, dnacin, dorrigocin, dynemycin, dynemycin triacetate, ecteinascidin, efrotomycin, endomycin, ensanchomycin, equisetin, ericamycin, esperamicin, ethylmonate, everninomicin, feldamycin, flambamycin, flavensomycin, florfenicol, fluvomycin, fosfomycin, fosfonochlorin, fredericamycin, frenolicin, fumagillin, fumifungin, funginon, fusacandin, fusafungin, gelbecidine, glidobactin, grahamimycin, granaticin, griseofulvin, griseoviridin, grisonomycin, hayumicin, hayumicin, hazymicin, hedamycin, heneicomycin, heptelicid acid, holomycin, humidin, isohematinic acid, karnatakin, kazusamycin, kristenin, L-dihydrophenylalanine, a L-isoleucyl-L-2-amino-4-(4'-amino-2',5'-cyclohexadienyl) derivative, lanomycin, leinamycin, leptomycin, libanomycin, lincomycin, lomofungin, lysolipin, magnesidin, manumycin, melanomycin, methoxycarbonylmethylmonate, methoxycarbonylethylmonate, methoxycarbonylphenylmonate, methyl pseudomonate, methylmonate, microcin, mitomalcin, mocimycin, moenomycin, monoacetyl cladosporin, monomethyl cladosporin, mupirocin, mupirocin calcium, mycobacidin, myriocin, myxopyronin, pseudoaglycone, nanaomycin, nancimycin, nargenicin, neocarcinostatin, neoenactin, neothramycin, nifurtoinol, nocardicin, nogalamycin, novobiocin, octylmonate, olivomycin, orthosomycin, oudemansin, oxirapentyn, oxoglaucine methiodide, pactacin, pactamycin, papulacandin, paulomycin, phaeoramularia fungicide, phenelfamycin, phenyl, cerulenin, phenylmonate, pholipomycin, pirlimycin, pleuromutilin, a polylactone derivative, polynitroxin, polyoxin, porfiromycin, pradimicin, prenomycin, prop-2-enylmonate, protomycin, *Pseudomonas* antibiotic, pseudomonic acid, purpuromycin, pyrinodemin, pyrrolnitrin, pyrrolomycin, amino, chloro pentenedioic acid, rapamycin, rebeccamycin, resistomycin, reuterin, reveromycin, rhizocticin, roridin, rubiflavin, naphthyridinomycin, saframycin, saphenamycin, sarkomycin, sarkomycin, sclopularin, selenomycin, siccanin, spartanamicin, spectinomycin, spongistatin, stravidin, streptolydigin, *Streptomyces arenae* antibiotic complex, streptonigrin, streptothricins, streptovitacin, streptozotocine, a strobilurin derivative, stubomycin, sulfamethoxazol-trimethoprim, sakamycin, tejeramycin, terpentecin, tetrocarcin, thermorubin, thermozymocidin, thiamphenicol, thioaurin, thiolutin, thiomarinol, thiomarinol, tirandamycin, tolytoxin, trichodermin, trienomycin, trimethoprim, trioxacarcin, tyrissamycin, umbrinomycin, unphenelfamycin, urauchimycin, usnic acid, uredolysin, variotin, vermisporin, verrucarin and analogs, salts and derivatives thereof.

In one or more embodiments, the antibiotic agent is a naturally occurring antibiotic compound. As used herein, the term "naturally-occurring antibiotic agent" includes all antibiotics that are obtained, derived or extracted from plant or vertebrate sources. Non-limiting examples of families of naturally-occurring antibiotic agents include phenol, resorcinol, antibiotic aminoglycosides, anamycin, quinines, anthraquinones, antibiotic glycopeptides, azoles, macrolides, avilamycin, agropyrene, cnicin, aucubin antibioticsaponin fractions, berberine (isoquinoline alkaloid), arctiopicrin (sesquiterpene lactone), lupulone, humulone (bitter acids), allicin, hyperforin, echinacoside, coniosetin, tetramic acid, imanine and novoimanine.

Ciclopirox and ciclopiroxolamine possess fungicidal, fungistatic and sporicidal activity. They are active against a broad spectrum of dermatophytes, yeasts, moulds and other fungi, such as *Trichophytons* species, *Microsporum* species, *Epidermophyton* species and yeasts (*Candida albicans, Candida glabrata*, other candida species and *Cryptococcus neoformans*). Some *Aspergillus* species are sensitive to ciclopirox as are some *Penicillium*. Likewise, ciclopirox is effective against many Gram-positive and Gram-negative bacteria (e.g., *Escherichia coli, Proteus mirabilis, Pseudomonas aeruginosa, Staphylococcus* and *Streptococcus* species), as well as *Mycoplasma* species, *Trichomonas vaginalis* and *Actinomyces*.

Plant oils and extracts which contain antibiotic agents are also useful. Non-limiting examples of plants that contain agents include thyme, *Perilla*, lavender, tea tree, *Terfezia clayeryi, Micromonospora, Putterlickia verrucosa, Putterlickla pyracantha, Putterlickla retrospinosa, Maytenus ilicifolia, Maytenus evonymoides, Maytenus aquifolia, Faenia interjecta, Cordyceps sinensis*, couchgrass, holy thistle, plantain, burdock, hops, echinacea, buchu, chaparral, myrrh, red clover and yellow dock, garlic, and St. John's wort. Mixtures of the antibiotic agents as described herein may also be employed.

Combination Detection:

Any combination of the analytes disclosed herein can be detected using any of the methods described herein. In particular, any combination disclosed herein can be detected using any of the methods described herein.

A "photosensitizer" as used herein refers to a sensitizer for generation of singlet oxygen usually by excitation with light. Exemplary photosensitizers suitable for use include those described in U.S. Pat. Nos. 6,251,581, 5,516,636, 8,907,081, 6,545,012, 6,331,530, 8,247,180, 5,763,602, 5,705,622, 5,516,636, 7,217,531, and U.S. Patent Publication No. 2007/0059316, all of which are herein expressly incorporated by reference in their entireties. The photosensitizer can be photoactivatable (e.g., dyes and aromatic compounds) or chemiactivated (e.g., enzymes and metal salts). When excited by light the photosensitizer is usually a compound comprised of covalently bonded atoms, usually with multiple conjugated double or triple bonds. The compound should absorb light in the wavelength range of 200-1100 nm, usually 300-1000 nm, e.g., 450-950 nm, with an extinction coefficient at its absorbance maximum greater than 500 $M^{-1}$ $cm^{-1}$, e.g., at least 5000 $M^{-1}$ $cm^{-1}$, or at least 50,000 $M^{-1}$ $cm^{-1}$ at the excitation wavelength. The lifetime of an excited state produced following absorption of light in the absence of oxygen will usually be at least 100 nsec, e.g., at least 1 μsec. In general, the lifetime must be sufficiently long to permit energy transfer to oxygen, which will normally be present at concentrations in the range of $10^{-5}$ to $10^{-3}$ M depending on the medium. The sensitizer excited state will usually have a different spin quantum number (S) than its ground state and will usually be a triplet (S=1) when, as is usually the case, the ground state is a singlet (S=O). In some embodiments, the sensitizer will have a high intersystem crossing yield. That is, photoexcitation of a sensitizer will produce the long lived state (usually triplet) with an efficiency of at least 10%, at least 40%, e.g., greater than 80%. The photosensitizer will usually be at most weakly fluorescent under the assay conditions (quantum yield usually less that 0.5, or less that 0.1).

Photosensitizers that are to be excited by light will be relatively photostable and will not react efficiently with singlet oxygen. Several structural features are present in most useful sensitizers. Most sensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3-6 of the periodic table, especially iodine or bromine, or they may have extended aromatic structures. Typical sensitizers include acetone, benzophenone, 9-thioxanthone, eosin, 9,10-dibromoanthracene, methylene blue, metallo-porphyrins, such as hematoporphyrin, phthalocyanines, chlorophylls, rose bengal, buckminsterfullerene, etc., and derivatives of these compounds having substituents of 1 to 50 atoms for rendering such compounds more lipophilic or more hydrophilic and/or as attaching groups for attachment. Examples of other photosensitizers that may be utilized are those that have the above properties and are enumerated in N. J. Turro, "Molecular Photochemistry," page 132, W. A. Benjamin Inc., N.Y. 1965.

In some embodiments, the photosensitizers are relatively non-polar to assure dissolution into a lipophilic member when the photosensitizer is incorporated in an oil droplet, liposome, latex particle, etc.

In some embodiments, the photosensitizers suitable for use herein include other substances and compositions that can produce singlet oxygen with or without activation by an external light source. Thus, for example, molybdate ($MoO_4^-$) salts and chloroperoxidase and myeloperoxidase plus bromide or chloride ion (Kanofsky, *J. Biol. Chem.* (1983) 259 5596) have been shown to catalyze the conversion of hydrogen peroxide to singlet oxygen and water. Either of these compositions can, for example, be included in particles and used in the assay method wherein hydrogen peroxide is included as an ancillary reagebly, chloroperoxidase is bound to a surface and molybdate is incorporated in the aqueous phase of a liposome. Also included within the scope of the invention as photosensitizers are compounds that are not true sensitizers but which on excitation by heat, light, or chemical activation will release a molecule of singlet oxygen. The best known members of this class of compounds includes the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

A "chemiluminescent compound" as used herein refers to a substance that undergoes a chemical reaction with singlet oxygen to form a metastable intermediate that can decompose with the simultaneous or subsequent emission of light within the wavelength range of 250 to 1200 nm. Exemplary chemiluminescent compounds suitable for use include those described in U.S. Pat. Nos. 6,251,581 and 7,709,273, and Patent Cooperation Treaty (PCT) International Application Publication No. WO1999/042838. Examplery chemiluminescent compound includes the following:

| Chemiluminescer | Half-Life | Emission Max |
| --- | --- | --- |
| Thioxene + Diphenyl anthracence: | 0.6 seconds | 430 nm |
| Thioxene + Umbelliferone derivative | 0.6 seconds | 500 nm |
| Thioxene + Europium chelate | 0.6 seconds | 615 nm |
| Thioxene + Samarium Chelate | 0.6 seconds | 648 nm |
| Thioxene + terbium Chelate | 0.6 seconds | 540 nm |
| N-Phenyl Oxazine + Umbelliferone derivative | 30 seconds | 500 nm |
| N-Phenyl Oxazine + Europium chelate | 30 seconds | 613 nm |
| N-phenyl Oxazine + Samarium Chelate | 30 seconds | 648 nm |
| N-phenyl Oxazine + terbium Chelate | 30 seconds | 540 nm |
| Dioxene + Umbelliferone derivative | 300 seconds | 500 nm |
| Dioxene + Europium chelate | 300 seconds | 613 nm |
| Dioxene + Samarium Chelate | 300 seconds | 648 nm |
| N-phenyl Oxazine + terbium Chelate | 300 seconds | 540 nm |

All of the above mentioned applications are hereby expressly incorporated by reference herein in their entireties. Emission will usually occur without the presence of an energy acceptor or catalyst to cause decomposition and light emission. In some embodiments, the intermediate decomposes spontaneously without heating or addition of ancillary reagents following its formation. However, addition of a reagent after formation of the intermediate or the use of elevated temperature to accelerate decomposition will be required for some chemiluminescent compounds. The chemiluminescent compounds are usually electron rich compounds that react with singlet oxygen, frequently with formation of dioxetanes or dioxetanones. Exemplary of such compounds are enol ethers, enamines, 9-alkylidenexanthans, 9-alkylidene-N-alkylacridans, aryl vinyl ethers, dioxenes, arylimidazoles and lucigenin. Other chemiluminescent compounds give intermediates upon reaction with singlet oxygen, which subsequently react with another reagent with light emission. Exemplary compounds are hydrazides such as luminol and oxalate esters.

The chemiluminescent compounds of interest will generally emit at wavelengths above 300 nanometers and usually above 400 nm. Compounds that alone or together with a fluorescent molecule emit light at wavelengths beyond the region where serum components absorb light will be of particular use. The fluorescence of serum drops off rapidly above 500 nm and becomes relatively unimportant above 550 nm. Therefore, when the analyte is in serum, chemiluminescent compounds that emit light above 550 nm, e.g., above 600 nm may be suitable for use. In order to avoid autosensitization of the chemiluminescent compound, in some embodiments, the chemiluminescent compounds do not absorb light used to excite the photosensitizer. In some embodiments, the sensitizer is excited with light wavelengths longer than 500 nm, it will therefore be desirable that light absorption by the chemiluminescent compound be very low above 500 nm.

Where long wave length emission from the chemiluminescent compound is desired, a long wavelength emitter such as a pyrene, bound to the chemiluminescent compound can be used. Alternatively, a fluorescent molecule can be included in the medium containing the chemiluminescent compound. In some embodiments, fluorescent molecules will be excited by the activated chemiluminescent compound and emit at a wavelength longer than the emission wavelength of the chemiluminescent compound, usually greater that 550 nm. It is usually also desirable that the fluorescent molecules do not absorb at the wavelengths of light used to activate the photosensitizer. Examples of useful dyes include rhodamine, ethidium, dansyl, $Eu(fod)_3$, $Eu(TTA)_3$, $Ru(bpy)_3^{++}$ (wherein bpy=2,2'-dipyridyl, etc. In general these dyes act as acceptors in energy transfer processes and in some embodiments, have high fluorescent quantum yields and do not react rapidly with singlet oxygen. They can be incorporated into particles simultaneously with the incorporation of the chemiluminescent compound into the particles.

In some embodiments, the disclosure provides diffractive optics detection technology that can be used with, for example, ingestible device technology. In certain embodiments, an ingestible device includes the diffractive optics technology (e.g., diffractive optics detection system). In certain embodiments, the disclosure provides diffractive optics technology (e.g., diffractive optics detection systems) that are used outside the body of subject. As an example, an ingestible device can be used to obtain one more samples in the body (e.g., in the gastrointestinal tract) of a subject, and the diffractive optics technology can be used to analyze the sample(s). Such analysis can be performed in vivo (e.g., when the ingestible device contains the diffractive optics).

Diffraction is a phenomenon that occurs due to the wave nature of light. When light hits an edge or passes through a small aperture, it is scattered in different directions. But light waves can interfere to add (constructively) and subtract (destructively) from each other, so that if light hits a non-random pattern of obstacles, the subsequent constructive and destructive interference will result in a clear and distinct diffraction pattern. A specific example is that of a diffraction grating, which is of uniformly spaced lines, typically prepared by ruling straight, parallel grooves on a surface. Light incident on such a surface produces a pattern of evenly spaced spots of high light intensity. This is called Bragg scattering, and the distance between spots (or 'Bragg scattering peaks') is a unique function of the diffraction pattern and the wavelength of the light source. Diffraction gratings, like focusing optics, can be operated in both transmission and reflection modes.

In general, the light used in the diffractive optics can be of any appropriate wavelength. Exemplary wavelengths include visible light, infrared red (IR) and ultraviolet (UV). Optionally, the light can be monochromatic or polychromatic. The light can be coherent or incoherent. The light can be collimated or non-collimated. In some embodiments, the light is coherent and collimated. Generally, any appropriate light source may be used, such as, for example, a laser (e.g., a laser diode) or a light emitting diode. In some embodiments, the light source is a laser diode operating at 670 nm wavelength, e.g., at 3 mWatts power. Optionally, an operating wavelength of a laser diode can be 780 nm, e.g., when larger grating periods are used. In certain embodiments, the light source is a laser, such as, for example, a He—Ne laser, a Nd:YVO4 laser, or an argon-ion laser. In some embodiments, the light source is a low power, continuous waver laser.

The diffracted light can be detected using any appropriate light detector(s). Examples of light detectors include photodetectors, such as, for example, position sensitive photodiodes, photomultiplier tubes (PMTs), photodiodes (PDs), avalanche photodiodes (APDs), charged-coupled device (CCD) arrays, and CMOS detectors. In some embodiments, the diffracted light is detected via one or more individual photodiodes.

In general, the diffraction grating is made of a material that is transparent in the wavelength of the radiation used to illuminate the sensor. Any appropriate material may be used for the diffraction grating substrate, such as glass or a polymer. Exemplary polymers include polystyrene polymers (PSEs), cyclo-olefin polymers (COPs), polycarbonate polymers, polymethyl methacrylates, and methyl methacrylate styrene copolymers. Exemplary COPs include Zeonex (e.g., Zeonex E48R, Zeonex F52R).

The light may be incident on the diffraction grating any appropriate angle. In some embodiments, the light is incident on the diffraction grating with an angle of incidence of from 30° to 80° (e.g., from 40° to 80°, from 50° to 70°, from 55° to 65°, 60°). Optionally, the system is configured so that that diffractive grating and light source can move relative to each other In general, the light detector can be positioned with respect to the diffractive grating so that the diffraction grating can be illuminated at a desired angle of incidence and/or so that diffracted light can be detected at a desired angle and/or so that diffracted light of a desired order can be detected.

The period P of the diffraction grating can be selected as desired. In some embodiments, the period P is from 0.5 microns to 50 microns (e.g., from one micron to 15 microns, from one micron to five microns). In some embodiments, the grating is a repeating patter of 1.5 micron and 4.5 micron lines with a period of 15 microns.

The height h of the diffraction grating can be selected as desired. In certain embodiments, the height h is from one nanometer to about 1000 nanometers (e.g., from about five nanometers to about 250 nanometers, from five nanometers to 100 nanometers).

In general, the diffractive optics can be prepared using any appropriate method, such as, for example, surface ablation, photolithograph (e.g., UV photolithography), laser etching, electron beam etching, nano-imprint molding, or microcontact printing.

Optionally, the diffractive optics system can include one or more additional optical elements, such as, for example, one or more mirrors, filters and/or lenses. Such optical elements can, for example, be arranged between the light source and the diffractive grating and/or between the diffractive grating and the detector.

In some of the embodiments of the devices described herein, a primary binding partner specifically binds to a secondary binding partner through non-covalent interactions (e.g., electrostatic, van der Waals, hydrophobic effect). In some embodiments, a primary binding partner specifically binds to a secondary binding partner via a covalent bond (e.g., a polar covalent bond or a non-polar covalent bond). In some embodiments of any of the devices described herein, the primary and the secondary binding partner can be interchanged. For example, the primary binding partner can be biotin, or a derivative thereof, and the secondary binding partner is avidin, or a derivative thereof. In other examples, the primary binding partner can be avidin, or a derivative thereof, and the secondary binding partner is biotin.

In some embodiments, the binding of the primary and the secondary binding partner is essentially irreversible. In some embodiments, the binding of the primary and the secondary binding partner is reversible. In some embodiments, the primary binding partner is CaptAvidin™ biotin-binding protein and the secondary binding partner is biotin, or vice versa. In some embodiments, the primary binding partner is DSB-X™ biotin and the secondary binding partner is avidin, or vice versa. In some embodiments, the primary binding partner is desthiobiotin and the secondary binding partner is avidin, or vice versa (Hirsch et al., *Anal Biochem.* 308(2): 343-357, 2002). In some embodiments, the primary binding partner is glutathione (GSH) or a derivative thereof, and the secondary binding partner is glutathione-S-transferase (GST).

In some embodiments, the primary binding partner can bind to a target analyte that is a nucleic acid (e.g., a DNA molecule, a RNA molecule). In some embodiments, the primary binding partner comprises a portion of a nucleic acid that is complementary to the nucleic acid sequence of the target analyte.

In some embodiments of any of the devices described herein, the device can include a label that binds to the target analyte and does not prevent binding of the target analyte to the primary binding partner. In some embodiments, the label can amplify the diffraction signal of the target analyte.

In some embodiments, the label is from about 1 nm to 200 nm (e.g., about 50 nm to about 200 nm).

In some embodiments, the label (e.g., any of the labels described herein) includes one or more antibodies (e.g., any of the antibodies and/or antibody fragments described herein).

In some embodiments, the label is a nanoparticle (e.g., a gold nanoparticle) that includes the primary binding partner that has a nucleic acid sequence that is complementary to the target analyte, and is covalently linked to the nanoparticle.

One or more additional steps can be performed in any of the methods described herein. In some embodiments, the one or more additional steps are performed: prior to the binding of the primary binding partner to the secondary binding partner, after the binding of the primary binding partner to the secondary binding partner, prior to the binding of the primary binding partner to the target analyte, or after the binding of the primary binding partner to the target analyte.

In some embodiments of any of the methods described herein, the determining step (during which the primary binding partner binds to the target analyte is detected) can occur in at least 15 seconds. In some embodiments, the binding of the primary binding partner to the target analyte can occur during a period of time of, for example, five at least seconds.

In some embodiments, the one or more additional steps can include: a blocking of the sensors step, at least one wash step, a capturing step, and/or a filtering step. In some embodiments, the blocking step can include blocking a sensor within the ingestible device with a solution comprising at least 1% bovine serum albumin (BSA) in a buffered solution (e.g., phosphate buffered saline (PBS), Tris buffered saline (TBS)). In some embodiments, the at least one wash step can include washing with a buffered solution (e.g., phosphate buffered saline (PBS), Tris buffered saline (TBS)). In general, blocking is performed during capsule manufacture, rather than in vivo.

In some embodiments, the capturing step includes enriching the target analyte. In some embodiments, the capturing step includes physically separating the target analyte from the remaining sample using a filter, a pore, or a magnetic bead. In some embodiments, the target analyte is captured by size exclusion.

In some embodiments, the disclosure provides methods of obtaining, culturing, and/or detecting target cells and/or target analytes in vivo within the gastrointestinal (GI) tract or reproductive tract of a subject. Associated devices are also disclosed. The methods and devices described provide a number of advantages for obtaining and/or analyzing fluid samples from a subject. In some embodiments, diluting the fluid sample increases the dynamic range of analyte detection and/or reduces background signals or interference within the sample. For example, interference may be caused by the presence of non-target analytes or non-specific binding of a dye or label within the sample. In some embodiments, culturing the sample increases the concentration of target cells and/or target analytes produced by the target cells thereby facilitating their detection and/or characterization.

In certain embodiments, the methods and devices a described herein may be used to obtain information regarding bacteria populations in the GI tract of a subject. This has a number of advantages and is less invasive than surgical procedures such as intubation or endoscopy to obtain fluid samples from the GI tract. The use of an ingestible device as described herein also allows for fluid samples to be obtained and data to be generated on bacterial populations from specific regions of the GI tract.

In some embodiments, the methods and devices described herein may be used to generate data such as by analyzing the fluid sample, dilutions thereof or cultured samples for one or more target cells and/or target analytes. The data may include, but is not limited to, the types of bacteria present in the fluid sample or the concentration of bacteria in specific regions of the GI tract. Such data may be used to determine whether a subject has an infection, such as Small Intestinal Bacterial Overgrowth (SIBO), or to characterize bacterial populations within the GI tract for diagnostic or other purposes. Thus, in some embodiments, analytes disclosed herein are indicative of disorders of the gastrointestinal tract associated with anomalous bacterial populations.

For example, in one aspect, the data may include, but is not limited to, the concentration of bacteria in a specific region of the GI tract that is one or more of the duodenum, jejunum, ileum, ascending colon, transverse colon or descending colon. In one aspect, the specific region of the GI tract is the duodenum. In one aspect, the specific region of the GI tract is the jejunum. In one aspect, the specific region of the GI tract is the ileum. In one aspect, the specific region of the GI tract is the ascending colon. In one aspect, the specific region of the GI tract is the transverse colon. In one aspect, the specific region of the GI tract is the descending colon. In a related embodiment, the data may be generated every one or more days to monitor disease flare-ups, or response to the therapeutic agents disclosed herein.

Data may be generated after the device has exited the subject, or the data may be generated in vivo and stored on the device and recovered ex vivo. Alternatively, the data can be transmitted wirelessly from the device while the device is passing through the GI tract of the subject or in place within the reproductive tract of the subject.

In some embodiments, a method comprises: providing a device comprising one or more dilution chambers and dilution fluid; transferring all or part of a fluid sample obtained from the GI tract or reproductive tract of the subject into the one or more dilution chambers in vivo; and combining the fluid sample and the dilution fluid to produce one or more diluted samples in the one or more dilution chambers.

In certain embodiments, a method comprises: providing an ingestible device comprising one or more dilution chambers; transferring all or part of a fluid sample obtained from the GI tract into the one or more dilution chambers comprising sterile media; culturing the sample in vivo within the one or more dilution chambers to produce one or more cultured samples; and detecting bacteria in the one or more cultured samples.

In some embodiments, a method comprises: providing a device comprising one or more dilution chambers; transferring all or part of a fluid sample obtained from the GI tract or reproductive tract into the one or more dilution chambers; combining all or part of the fluid sample with a dilution fluid in the one or more dilution chambers; and detecting the target analyte in the one or more diluted samples.

In certain embodiments, a device comprises: one or more dilution chambers for diluting a fluid sample obtained from the GI tract or reproductive tract; and dilution fluid for diluting the sample within the one or more dilution chambers.

In some embodiments, the device comprises: one or more dilution chambers for culturing a fluid sample obtained from the GI tract; sterile media for culturing the sample within the one or more dilution chambers; and a detection system for detecting bacteria.

In certain embodiments, a device comprises: one or more dilution chambers for culturing a fluid sample obtained from the GI tract; sterile media for culturing the sample within the one or more dilution chambers; and a detection system for detecting bacteria.

Also provided is the use of a device as described herein for diluting one or more samples obtained from the GI tract or reproductive tract of a subject. In one embodiment, there is provided the use of an ingestible device as described herein for detecting target cells and/or target analytes in vivo within the gastrointestinal (GI) tract of a subject.

Further provided is a system comprising a device as described herein and a base station. In one embodiment, the device transmits data to the base station, such as data indicative of the concentration and/or types of bacteria in the GI tract of the subject. In one embodiment, the device receives operating parameters from the base station. Some embodiments described herein provide an ingestible device for obtaining one or more samples from the GI tract or reproductive tract of a subject and diluting and/or culturing all or part of the one or more samples. The ingestible device includes a cylindrical rotatable element having a port on the wall of the cylindrical rotatable element. The ingestible device further includes a shell element wrapping around the cylindrical rotatable element to form a first dilution chamber between the cylindrical rotatable element and the shell element. The shell element has an aperture that exposes a portion of the wall of the cylindrical rotatable element to an exterior of the ingestible device.

In certain embodiments, the medical device comprises one or more dilution chambers for receiving a fluid sample from the GI tract or reproductive tract of a subject or a dilution thereof. In some embodiments, one or more dilutions of the fluid sample are cultured in one or more dilution chambers. In certain embodiments, the dilution chambers each define a known volume, optionally the same volume or different volumes. In some embodiments, the dilution chambers define a fluid volume ranging from about 10 µL to about 1 mL. The dilution chambers may define a fluid volume less than or equal to about 500 µL, less than or equal to about 250 µL, less than or equal to about 100 µL, or less than or equal to about 50 µL. In certain embodiments, the dilution chambers define a fluid volume of greater than or equal to about 10 µL, greater than or equal to about 20 µL, greater than or equal to about 30 µL, or greater than or equal to about 50 µL. In some embodiments, the dilution chambers define a fluid volume between about 10 µL and 500 µL, between about 20 µL and 250 µL, between about 30 µL and 100 µL or about 50 µL.

In some embodiments, dilution fluid in the device is combined with all or part of the fluid sample, or dilution thereof, to produce one or more dilutions. In certain embodiments, the dilution fluid is sterile media suitable for culturing one or more target cells within the dilution chambers.

In certain embodiments, the one or more dilution chambers may be filled with the dilution fluid prior to a patient ingesting the ingestible device. In some embodiments, the dilution fluid may be added into the one or more dilution chambers in vivo from a reservoir of the ingestible device. Sampling and dilution of the GI fluid sample may take place in vivo. For example, an actuator of the ingestible device may pump the dilution fluid from the reservoir into a dilution chamber when it is determined that the ingestible device is located at a predetermined location within the GI tract. In some embodiments, the dilution chambers each contain a volume of sterile media suitable for culturing a fluid sample from the GI tract or reproductive tract. In certain embodiments, the dilution chambers are at least 95%, at least 97%, at least 98%, or at least 99% full of sterile media. In some embodiments, the dilution chambers each contain oxygen to facilitate aerobic bacteria growth. In certain embodiments, a non-dilution chamber comprises oxygen and is added to one or more of the dilution chambers to facilitate aerobic bacteria growth.

In some embodiments, the culturing may take place in vivo immediately after the GI fluid sample has been diluted. Or alternatively, the culturing may take place ex vivo, e.g., when the ingestible device has been evacuated and recovered such that the dilution chamber containing the diluted GI fluid sample may be extracted and the culturing may be performed in a laboratory. The recovery of the ingestible device may be performed in a similar manner as embodiments described in U.S. Provisional Application No. 62/434,188, filed on Dec. 14, 2016, which is herein expressly incorporated by reference in its entirety.

As used herein "culturing" refers to maintaining target cells in an environment that allows a population of one or more target cells to increase in number through cell division. For example, in some embodiments, "culturing" may include combining the cells with media in an dilution chamber at a temperature that permits cell growth, optionally a temperature found in vivo within the GI tract or reproductive tract of a subject. In certain embodiments, the cells are cultured at a temperature between about 35° C. and 42° C.

As used herein "dilution fluid" refers to a fluid within the device for diluting a fluid sample from the GI tract or reproductive tract. In some embodiments, the dilution fluid is an aqueous solution. In certain embodiments, the dilution fluid comprises one or more agents that promote or inhibit the growth of an organism, such as a fungus or bacteria. In some embodiments, the dilution fluid comprises one or more agents that facilitate the detection of a target analyte, such as dyes or binding agents for target analytes.

In some embodiments, the dilution fluid is a sterile media. As used herein, "sterile media" refers to media that does not contain any viable bacteria or other cells that would grow and increase in number through cell division. Media may be rendered sterile by various techniques known in the art such as, but not limited to, autoclaving and/or preparing the media using aseptic techniques. In certain embodiments, the media is a liquid media. Examples of media suitable for culturing bacteria include nutrient broth, Lysogeny Broth (LB) (also known as Luria Broth), Wilkins chalgren, and Tryptic Soy Broth (TSB). Other growth or culture media known in the art may also be used in the methods and devices described herein. In some embodiments, the media has a carbon source, such as glucose or glycerol, a nitrogen source such as ammonium salts or nitrates or amino acids, as well as salts and/or trace elements and vitamins required for microbial growth. In certain embodiments, the media is suitable for maintaining eukaryotic cells. In some embodiments, the media comprises one or more agents that promote or inhibit the growth of bacteria, optionally agents that promote or inhibit the growth of specific types of bacteria.

In certain embodiments, the media is a selective media. As used herein, "selective media" refers to a media that allows certain types of target cells to grow and inhibits the growth of other organisms. Accordingly, the growth of cells in a selective media indicates the presence of certain types of cells within the cultured sample. For example, in some embodiments, the media is selective for gram-positive or gram-negative bacteria. In certain embodiments, the media contains crystal violet and bile salts (such as found in MacConkey agar) that inhibit the growth of gram-positive organisms and allows for the selection and isolation of gram-negative bacteria. In some embodiments, the media contains a high concentration of salt (NaCl) (such as found in Mannitol salt agar) and is selective for Gram-positive bacteria. In some embodiments, the media selectively kills eukaryotic cells or only grows prokaryotic cells, for example, using a media comprising Triton™ X-100. In certain embodiments, the media selectively kills prokaryotic cells (or alternatively only grows eukaryotic cells), for example, using a media that comprises antibiotics.

In some embodiments, the media is an indicator media. As used herein, "indicator media" refers to a media that contains specific nutrients or indicators (such as, but not limited to neutral red, phenol red, eosin y, or methylene blue) that produce a detectable signal when a certain type of cells are cultured in the indicator media.

In some embodiments, the disclosure provides a composition comprising a dye and optionally a reagent for selective lysis of eukaryotic cells. In certain embodiments, the composition comprises both a dye and a reagent for selective lysis of eukaryotic cells. In some embodiments, the composition further comprises one or more reagents independently selected from the group consisting of: a second reagent for selective lysis of eukaryotic cells (e.g., Triton X-100), an electrolyte (e.g., $MgCl_2$), an anti-fungi reagent (e.g., amphotericin-B), and an antibiotic. In some embodiments, the composition comprises water and is in the form of an aqueous solution. In some embodiments, the composition is a solid or semi-solid. In some embodiments, the compositions described here are suitable for use in a kit or device for detecting or quantifying viable bacterial cells in a sample. In some embodiments, such a device is an ingestible device for detecting or quantifying viable bacterial cells in vivo (e.g., in the GI tract). In some embodiments, viable bacterial cells in a sample are detected or quantified in the presence of one or more antibiotics to determine antibiotic resistance of the bacteria in the sample. In some embodiments, anomalous bacterial populations in a sample may be detected or quantified, for example through the use of one a composition comprising a dye as disclosed herein, to determine whether a subject has an infection, such as Small Intestinal Bacterial Overgrowth (SIBO), or to characterize bacterial populations within the GI tract for diagnostic or other purposes.

In some embodiments, a method comprises: (a) contacting the sample with a composition as described herein; and (b) measuring total fluorescence or rate of change of fluorescence as a function of time of said sample, thereby detecting viable bacterial cells in said sample. In some embodiments, a control as described herein may be employed in the method. In some embodiments, the total fluorescence or the rate of change of fluorescence as a function of time of the sample is measured over multiple time points for an extended period of time in step (b), thereby detecting viable bacterial cells in said sample. In some embodiments, the method further comprises correlating the total fluorescence or the rate of change of fluorescence as a function of time determined in step (b) to the number of viable bacterial cells in the sample. In some embodiments, the rate of change of fluorescence as a function of time of the sample measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method comprises communicating the results of the onboard assay(s) to an ex vivo receiver.

In certain embodiments, a kit comprises a composition as described herein and instructions, e.g., for detecting or quantifying viable bacterial cells in a sample. In some embodiments, a device comprises a composition as described herein, e.g., for detecting or quantifying viable bacterial cells in a sample. The detection of live cells, as opposed to the detection of bacterial components (such as endotoxins) which can be present in the sample environment and lead to conflicting results, is the gold standard of viable plate counting and represents one of the advantages of the compositions and methods described herein.

The systems employ methods, compositions and detection systems found to accurately and reliably correlate fluorescence to total bacteria count (TBC) in an autonomous, ingestible device, or other similarly-sized device. The compositions include novel combinations of dyes, buffers and detergents that allow for the selective staining of viable bacterial cells in samples that comprise non-bacterial cells and other components that otherwise make detecting or quantifying live bacterial cells challenging. In some embodiments, the systems allow for bacteria to be quantified in near real-time and the results to be shared telemetrically outside of the device.

In certain embodiments, the disclosure provides a method of assessing or monitoring the need to treat a subject suffering from or at risk of overgrowth of bacterial cells in the gastrointestinal tract, which comprises: (a) obtaining a sample from the gastrointestinal tract of said subject; (b) contacting the sample with a composition as described herein; (c) measuring total fluorescence or rate of change of fluorescence as a function of time of said sample; and (d) correlating the total fluorescence or the rate of change of fluorescence as a function of time measured in step (c) to the number of viable bacterial cells in the sample, wherein the number of the viable bacterial cells determined in step (e) greater than about 105 CFU/mL indicates a need for treatment, e.g., with an antibiotic agent as described herein. In some embodiments, a control as described herein may be employed in the method. In some embodiments, the total fluorescence or the rate of change of fluorescence as a function of time of the sample is measured over multiple time points for an extended period of time in step (c). In some embodiments, the rate of change of fluorescence as a function of time of the sample measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method comprises communicating the results of the onboard assay(s) to an ex vivo receiver. In some embodiments, the method may be further used to monitor the subject after the treatment (e.g., with an antibiotic). In some embodiments, the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the method may be used to detect infection with antibiotic-resistant strains of bacteria in a subject. For instance, such infection may be indicated where the number of viable bacterial cells in a sample from the GI tract of the subject does not substantially decrease after antibiotic treatment.

In some embodiments, the disclosure provides an absorbable material, (e.g., absorbable sponge), having absorbed therein a composition as described herein. In some embodiments, the absorbable sponge is Ahlstrom Grade 6613H (Lot 150191) or Porex PSU-567, having absorbed therein a composition as described herein. In some embodiments, the absorbable sponge may be prepared by injecting into the absorbable sponge an aqueous solution comprising a composition as described herein, and optionally further comprising a step of drying the resulting absorbable sponge.

In certain embodiments, the disclosure provides a method for detecting the presence of viable bacterial cells in a sample, which comprises: (a) fully or partially saturating an absorbable sponge as described herein, or an absorbable sponge prepared as described herein, with the sample; and (b) measuring total fluorescence or rate of change of fluorescence as a function of time of the fully or partially saturated sponge prepared in step (a), thereby detecting viable bacterial cells. In some embodiments, a control as described herein may be employed in the method. In some embodiments, the total fluorescence or the rate of change of fluorescence as a function of time of the fully or partially saturated sponge is measured over multiple time points for an extended period of time in step (b), thereby detecting viable bacterial cells in said sample. In some embodiments, the method further comprises correlating the total fluorescence or the rate of change of fluorescence as a function of time measured in step (b) to the number of viable bacterial cells in the sample. In some embodiments, the rate of change of fluorescence as a function of time of the fully or partially saturated sponge measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method comprises communicating the results of the onboard assay(s) to an ex vivo receiver.

In one aspect, provided herein is a kit comprising an absorbable sponge as described herein and instructions, e.g., for detecting or quantifying viable bacterial cells in a sample. In another aspect, provided herein is a device comprising an absorbable sponge as described herein, e.g., for detecting or quantifying viable bacterial cells in a sample.

In certain embodiments, the disclosure provides a method of assessing or monitoring the need to treat a subject suffering from or at risk of overgrowth of bacterial cells in the gastrointestinal tract, which comprises: (a) obtaining a sample from the gastrointestinal tract of said subject; (b) fully or partially saturating an absorbable sponge described herein, or an absorbable sponge prepared as described herein, with the sample; (c) measuring total fluorescence or rate of change of fluorescence as a function of time of the fully or partially saturated sponge prepared in step (b); (d) correlating the total fluorescence or the rate of change of fluorescence as a function of time measured in step (c) to the number of viable bacterial cells in the sample, wherein the number of the viable bacterial cells as determined in step (e) greater than about $10^5$ CFU/mL indicates a need for treatment, e.g., with an antibiotic agent as described herein. In some embodiments, a control as described herein may be employed in the method. In some embodiments, the total fluorescence or the rate of change of fluorescence as a function of time of the fully or partially saturated sponge is measured over multiple time points for an extended period of time in step (c). In some embodiments, the rate of change of fluorescence as a function of time of the fully or partially saturated sponge measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method comprises communicating the results of the onboard assay(s) to an ex vivo receiver. In some embodiments, the method may be further used to monitor the subject after the treatment (e.g., with an antibiotic). In some embodiments, the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the method may be used to detect infection with antibiotic-resistant strains of bacteria in a subject. For instance, such infection may be indicated where the number of viable bacterial cells in a sample from the GI tract of the subject does not substantially decrease after antibiotic treatment In certain embodiments, the disclosure provides and ingestible device comprising a housing; a first opening in the wall of the housing; a second opening in the first end of the housing; and a chamber connecting the first opening and the second opening, wherein at least a portion of the chamber forms a sampling chamber within the ingestible device. In some embodiments, the sampling chamber is configured to hold an absorbable sponge described herein. In some embodiments, the sampling chamber is configured to hold a sample obtained from a gastrointestinal (GI) tract of a body. In some embodiments, the ingestible device is individually calibrated (for example, by comparing to a positive or negative control as described herein), wherein the fluorescent properties of the absorbable sponge held in the sampling chamber of the device are determined prior to the introduction of the sample. The ingestible device as described herein is useful for detecting or quantifying viable bacterial cells in vivo. In some embodiments, provided herein is a method for detecting or quantifying viable bacterial cells in a GI tract sample in vivo using an ingestible device as described herein. In some embodiments, provided herein is a method of assessing or monitoring the need to treat a subject suffering from or at risk of overgrowth of bacterial cells in the GI tract in vivo using an ingestible device as described herein. In some embodiments, provided herein is a method of altering the treatment regimen of a subject suffering from or at risk of overgrowth of bacterial cells in the GI tract in vivo using an ingestible device as described herein. In one aspect, the subject is a subject suffering from or at risk of overgrowth of bacterial cells in the duodenum. In one aspect, the subject is a subject suffering from or at risk of overgrowth of bacterial cells in the jejunum. In one aspect, the subject is a subject suffering from or at risk of overgrowth of bacterial cells in the ileum. In one aspect, the subject is a subject suffering from or at risk of overgrowth of bacterial cells in the ascending colon. In one aspect, the subject is a subject suffering from or at risk of overgrowth of bacterial cells in the transverse colon. In one aspect, the subject is a subject suffering from or at risk of overgrowth of bacterial cells in the descending colon. In some embodiments, the method may be further used to monitor the subject after the treatment (e.g., with an antibiotic). In some embodiments, the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the method may be used to detect infection with antibiotic-resistant strains of bacteria in a subject. For instance, such infection may be indicated where the number of viable bacterial cells in a sample from the GI tract of the subject does not substantially decrease after antibiotic treatment. In some embodiments, the method is performed autonomously and does not require instructions, triggers or other inputs from outside the body after the device has been ingested.

"Eukaryotic" as recited herein relates to any type of eukaryotic organism excluding fungi, such as animals, in particular animals containing blood, and comprises invertebrate animals such as crustaceans and vertebrates. Vertebrates comprise both cold-blooded (fish, reptiles, amphibians) and warm blooded animal (birds and mammals). Mammals comprise in particular primates and more particularly humans "Selective lysis" as used herein is obtained in a sample when the percentage of bacterial cells in that sample that remain intact is significantly higher (e.g. 2, 5, 10, 20, 50, 100, 250, 500, or 1,000 times more) than the percentage of the eukaryotic cells in that sample that remain intact, upon treatment of or contact with a composition or device as described herein.

In some embodiments, the dye suitable for use herein is a dye that is capable of being internalized by a viable cell, binding to or reacting with a target component of the viable cell, and having fluorescence properties that are measurably altered when the dye is bound to or reacted with the target component of the viable cell. In some embodiments, the dye herein is actively internalized by penetrating viable cells through a process other than passible diffusion across cell membranes. Such internalization includes, but is not limited to, internalization through cell receptors on cell surfaces or through channels in cell membranes. In some embodiments, the target component of a viable cell to which the dye is bound to or reacted with is selected from the group consisting of: nucleic acids, actin, tubulin, enzymes, nucleotide-binding proteins, ion-transport proteins, mitochondria, cytoplasmic components, and membrane components. In some embodiments, the dye suitable for use herein is a fluorogenic dye that is capable of being internalized and metabolized by a viable cell, and wherein said dye fluoresces when metabolized by the viable cell. In some embodiments, the dye is a chemiluminescent dye that is capable of being internalized and metabolized by a viable cell, and wherein said dye becomes chemiluminescent when metabolized by the viable cell.

In some embodiments, the composition comprises a dye that fluoresces when bond to nucleic acids. Examples of such dyes include, but are not limited to, acridine orange (U.S. Pat. No. 4,190,328); calcein-AM (U.S. Pat. No. 5,314,805); DAPI; Hoechst 33342; Hoechst 33258; PicoGreen™; SYTO® 16; SYBR® Green I; Texas Red®; Redmond Red™; Bodipy® Dyes; Oregon Green™; ethidium bromide; and propidium iodide.

In some embodiments, the composition comprises a lipophilic dye that fluoresces when metabolized by a cell. In some embodiments, the dye fluoresces when reduced by a cell or a cell component. Examples of dyes that fluoresce when reduced include, but are not limited to, resazurin; $C^{12}$-resazurin; 7-hydroxy-9H-(1,3 dichloro-9,9-dimethylacridin-2-ol) N-oxide; 6-chloro-9-nitro-5-oxo-5H-benzo[a]phenoxazine; and tetrazolium salts. In some embodiment, the dye fluoresces when oxidized by a cell or a cell component. Examples of such dyes include, but are not limited to, dihydrocalcein AM; dihydrorhodamine 123; dihydroethidium; 2,3,4,5,6-pentafluorotetramethyldihydrorosamine; and 3'-(p-aminophenyl) fluorescein.

In some embodiments, the composition comprises a dye that becomes chemiluminescent when oxidized by a cell or a cell component, such as luminol.

In some embodiments, the composition comprises a dye that fluoresces when de-acetylated and/or oxidized by a cell or a cell component. Examples of such dyes include, but are not limited to, dihydrorhodamines; dihydrofluoresceins; 2',7'-dichlorodihydrofluorescein diacetate; 5-(and 6-)carboxy-2',7'-dichlorodihydrofluorescein diacetate; and chloromethyl-2',7'-dichlorodihydrofluorescein diacetate acetyl ester.

In some embodiments, the composition comprises a dye that fluoresces when reacted with a peptidase. Examples of such dyes include, but are not limited to, (CBZ-Ala-Ala-Ala-Ala)2-R110 elastase 2; (CBZ-Ala-Ala-Asp)2-R110 granzyme B; and 7-amino-4-methylcoumarin, N-CBZ-L-aspartyl-L-glutamyl-L-valyl-L-aspartic acid amide.

In some embodiments, the composition comprises a dye selected from the group consisting of resazurin, FDA, Calcein AM, and SYTO® 9. In some embodiments, the dye is FDA or SYTO® 9.

SYTO® 9, when used alone, labels the nucleic acid of bacteria cells. The excitation/emission wavelengths for SYTO® 9 is 480/500 nm, with the background remaining non-fluorescent. See, e.g., J. Appl. Bacteriol. 72, 410 (1992); Lett. Appl. Microbiol. 13, 58 (1991); Curr. Microbiol. 4, 321 (1980); J. Microbiol. Methods 13, 87 (1991); and Microbiol. Rev. 51, 365 (1987); and J. Med. Microbiol. 39, 147 (1993).

FDA is a non-polar, non-fluorescent compound that can cross the membranes of mammalian and bacterial cells. The acetyl esterases (present only within viable cells) hydrolyze the FDA into the fluorescent compound fluorescein. Fluorescein is a fluorescent polar compound that is retained within these cells. Living cells can be visualized in a photospectrometer when assayed with an excitation wavelength of 494 nm and an emission wavelength of 518 nm. See, e.g., Brunius, G. (1980). *Technical aspects of the use of 3',6'-Diacetyl fluorescein for vital fluorescent staining of bacteria.* Current Microbiol. 4: 321-323; Jones, K. H. and Senft, J. A. (1985). *An improved method to determine cell viability by simultaneous staining with fluorescein diacetate-propidium iodide.* J. Histochem. Cytochem. 33: 77-79; Ross, R. D., Joneckis, C. C., Ordonez, J. V., Sisk, A. M., Wu, R. K., Hamburger, A. W., and Nora, R. E. (1989). *Estimation of cell survival by flow cytometric quantification of fluorescein diacetate/propidium iodide viable cell number.* Cancer Research. 49: 3776-3782.

Calcein-AM, which is an acetoxylmethyl ester of calcein, is highly lipophilic and cell permeable. Calcein-AM in itself is not fluorescent, but the calcein generated by esterase in a viable cell emits a green fluorescence with an excitation wavelength of 490 nm and an emission of 515 nm. Therefore, Calcein-AM can only stain viable cells. See, e.g., Kimura, K., et al., *Neurosci. Lett.,* 208, 53 (1998); Shimokawa, I., et al., *J. Geronto.,* 51a, b49 (1998); Yoshida, S., et al., *Clin. Nephrol.,* 49, 273 (1998); and Tominaga, H., et al., *Anal. Commun.,* 36, 47 (1999).

Resazuirn (also known as Alamar Blue) is a blue compound that can be reduced to pink resorufin which is fluorescent. This dye is mainly used in viability assays for mammalian cells. $C^{12}$-resazurin has better cell permeability than resazurin. When lipohilic $C^{12}$-resazurin crosses the cell membranes, it is subsequently reduced by living cells to make a red fluorescent resorufin. The adsorption/emission of $C^{12}$-resazurin is 563/587 nm. See, e.g., Appl Environ Microbiol 56, 3785 (1990); J Dairy Res 57, 239 (1990); J Neurosci Methods 70, 195 (1996); J Immunol Methods 210, 25 (1997); J Immunol Methods 213, 157 (1998); Antimicrob Agents Chemother 41, 1004 (1997).

In some embodiments, the composition optionally further comprises a reagent for selective lysis of eukaryotic cells. In some embodiments, the composition comprises a dye as described herein and a reagent for selective lysis of eukaryotic cells. In some embodiments, the reagent for selective lysis of eukaryotic cells is a detergent, such as a non-ionic or an ionic detergent. Examples of the reagent for selective lysis of eukaryotic cells include, but are not limited to, alkylglycosides, Brij 35 (C12E23 Polyoxyethyleneglycol dodecyl ether), Brij 58 (C16E20 Polyoxyethyleneglycol dodecyl ether), Genapol, glucanids such as MEGA-8, -9, -10, octylglucoside, Pluronic F127, Triton X-100 ($C_{14}H_{22}O$ ($C_2H_4O$)$_n$), Triton X-114 ($C_{24}H_{42}O_6$), Tween 20 (Polysorbate 20) and Tween 80 (Polysorbate 80), Nonidet P40, deoxycholate, reduced Triton X-100 and/or Igepal CA 630. In some embodiments, the composition comprises a dye as described herein and deoxycholate (e.g., sodium deoxycholate) as a reagent for selective lysis of eukaryotic cells. In some embodiments, the composition comprises deoxycholate at a concentration selected from 0.0001% to 1 wt %. In some embodiments, the composition comprises deoxycholate at a concentration of 0.005 wt %. In some embodiments, the composition may comprise more than one reagent for selective lysis of eukaryotic cells.

In some embodiments, the composition may comprise two different reagents for selective lysis of eukaryotic cells. In some instances, when more than one selective lysis reagents are used, more effective and/or complete selective lysis of eukaryotic cells in a sample may be achieved. For example, the composition may comprise deoxycholate (e.g., sodium deoxycholate) and Triton X-100 as two different reagents for selective lysis of eukaryotic cells. In some embodiments, the composition comprises deoxycholate (e.g., sodium deoxycholate) at a concentration selected from 0.0001% to 1 wt % (e.g., 0.005 wt %) and Triton X-100 at a concentration selected from 0.1 to 0.05 wt %.

In some embodiments, after a sample (e.g., a biological sample) is treated or contacted with a composition comprising a dye and one or more reagents for selective lysis of eukaryotic cells as described herein, the eukaryotic cells (e.g., animal cells) in the sample are selectively lysed whereby a substantial percentage (e.g., more than 20%, 40%, 60%, 80%, 90% or even more that 95%) of the bacterial cells in the same sample remains intact or alive.

In some embodiments, the composition does not comprise a reagent for selective lysis of eukaryotic cells, and such a composition is useful for detecting or quantifying viable bacterial cells in a sample (e.g., an environmental sample such as a water sample) that does not contain any eukaryotic cells.

In some embodiments, the composition further comprises an electrolyte, such as a divalent electrolyte (e.g., $MgCl_2$). In some embodiments, the composition comprises $MgCl_2$ at a concentration selected from 0.1 mM to 100 mM (e.g., a concentration selected from 0.5 mM to 50 mM).

In some embodiments, the composition further comprises water and is in a form of an aqueous solution. In some embodiments, the composition has a pH selected from 5-8 (e.g., a pH selected from 6-7.8, such as pH being 6.0). In some embodiments, the composition is a solid or a semi-solid.

In some embodiments, the composition further comprises an anti-fungal agent. Suitable anti-fungal agents for use herein include, but are not limited to, fungicidal and fungistatic agents including terbinafine, itraconazole, micronazole nitrate, thiapendazole, tolnaftate, clotrimazole and griseofulvin. In some embodiments, the anti-fungal agent is a polyene anti-fungal agent, such as amphotericin-B, nystatin, and pimaricin.

In some embodiments, the composition does not contain any anti-fungal agent. In some embodiments, the composition contains broad spectrum antibiotics but not any anti-fungal agent. Such compositions that do not contain anti-fungal agents but contain broad spectrum antibiotics may be useful in detecting or quantifying fungi (e.g., yeast) in a sample.

In some embodiments, the composition does not contain any anti-fungal agent, any antibiotics or any anti-mammalian agent. Such compositions that do not selectively lyse mammalian cells may be useful in detecting or quantifying mammalian cells (e.g., cells from the GI tract) in a sample since many dyes have a higher affinity for mammalian as compared to bacteria or fungi cells. In some embodiments, the composition contains broad spectrum antibiotics and one or more anti-fungal agents. Such compositions that contain anti-fungal agents and broad spectrum antibiotics may be useful in detecting or quantifying mammalian cells (e.g., cells from the GI tract) in a sample. The detection or quantification of mammalian cells may be useful for determining cell turnover in a subject. High cell turnover is sometimes associated with a GI injury (e.g., lesion), the presence of a tumor(s), or radiation-induced colitis or radiation enteropathy.

In some embodiments, the composition further comprises an antibiotic agent as described herein. Such a composition may be useful in detecting or quantifying antibiotic-resistant strains of bacteria in a sample.

In certain embodiments, the composition comprises Triton X-100, deoxycholate, resazurin, and $MgCl_2$. In some embodiments, the composition comprises Triton X-100, deoxycholate, resazurin, amphotericin-B and $MgCl_2$. In some embodiments, the composition comprises 0.1 wt % or 0.05 wt % Triton X-100; 0.005 wt % deoxycholate; 10 mM resazurin; 2.5 mg/L amphotericin-B and 50 mM $MgCl_2$. In some embodiments, the composition has a pH of 6.0.

In certain embodiments, the compositions are suitable for use in a kit or device, e.g., for detecting or quantifying viable bacterial cells in a sample. In some embodiments, such a device is an ingestible device for detecting or quantifying viable bacterial cells in vivo (e.g., in the GI tract).

Figure 62:
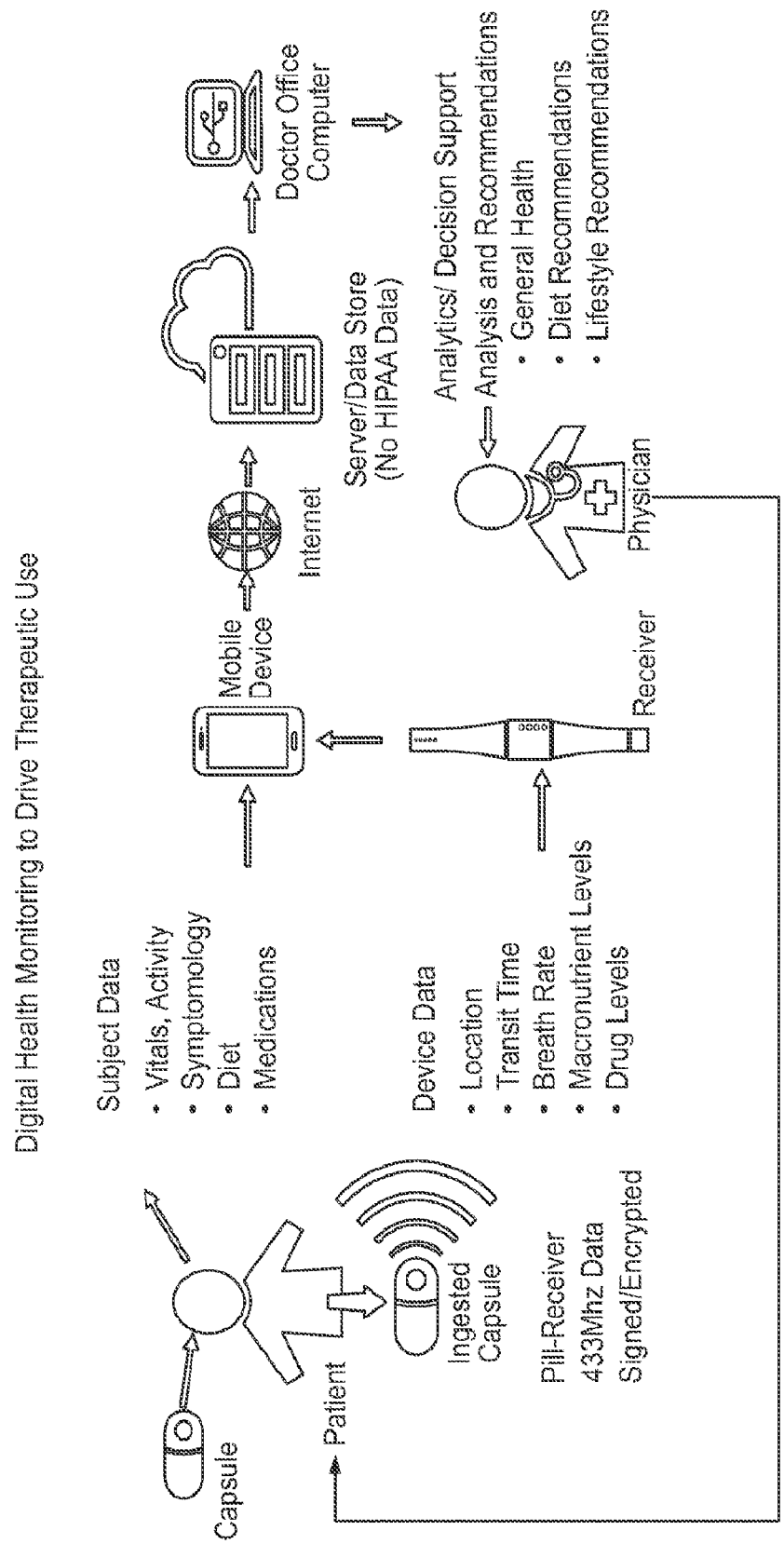
FIG. 62 illustrates a nonlimiting example of a system for collecting, communicating and/or analyzing data about a subject, using an ingestible device.
Figure 63A:
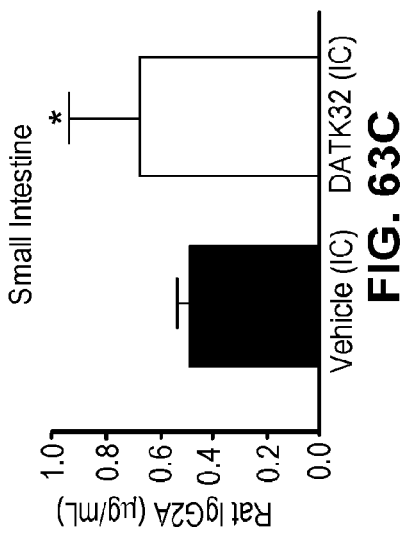
FIGS. 63A-F are graphs showing rat IgG2A concentration as measured in (A) colon homogenate, (B) mLN homogenate, (C) small intestine homogenate, (D) cecum contents, (E) colon contents, and (F) plasma by ELISA. Standards were prepared with plasma matrix. Samples were diluted 1:50 before analysis. Sample 20 was removed from cecum contents analysis graph (outlier). *p<0.05; p<0.01; **p<0.001 were determined using the unpaired t test.
Figure 63B:
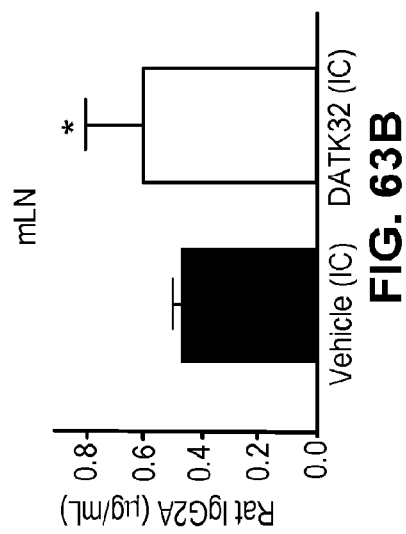
Figure 63C:
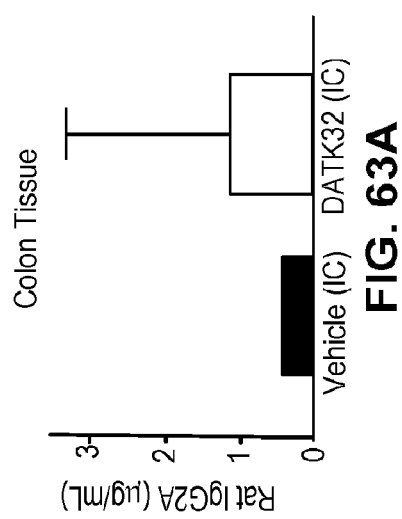
Figure 63D:
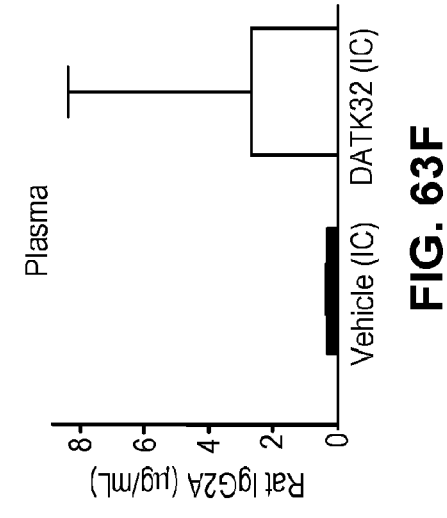
Figure 63E:
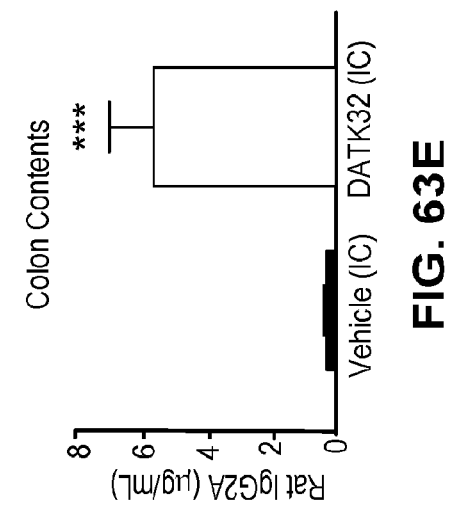
Figure 63F:
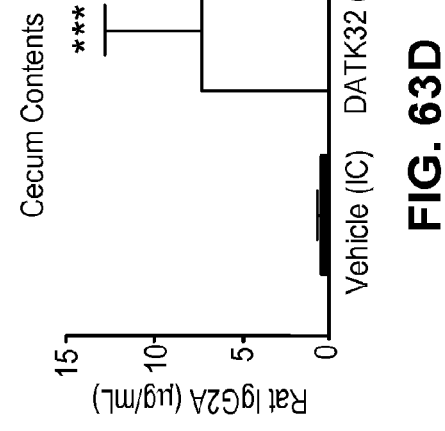

FIG. 62 illustrates a nonlimiting example of a system for collecting, communicating and/or analyzing data about a subject, using an ingestible device as disclosed herein. For example, an ingestible device may be configured to communicate with an external base station. As an example, an ingestible device can have a communications unit that communicates with an external base station which itself has a communications unit. FIG. 62 illustrates exemplary implementation of such an ingestible device. As shown in FIG. 62, a subject ingests an ingestible device as disclosed herein. Certain data about the subject (e.g., based on a collected sample) and/or the location of the ingestible device in the GI tract of the subject is collected or otherwise available and provided to a mobile device, which then forwards the data via the internet and a server/data store to a physician's office computer. The information collected by the ingestible device is communicated to a receiver, such as, for example, a watch or other object worn by the subject. The information is then communicated from the receiver to the mobile device which then forwards the data via the internet and a server/data store to a physician's office computer. The physician is then able to analyze some or all of the data about the subject to provide recommendations, such as, for example, delivery a therapeutic agent. While FIG. 62 shows a particular approach to collecting and transferring data about a subject, the disclosure is not limited. As an example, one or more of the receiver, mobile device, internet, and/or server/data store can be excluded from the data communication channel. For example, a mobile device can be used as the receiver of the device data, e.g., by using a dongle. In such embodiments, the item worn by the subject need not be part of the communication chain. As another example, one or more of the items in the data communication channel can be replaced with an alternative item. For example, rather than be provided to a physician's office computer, data may be provided to a service provider network, such as a hospital network, an HMO network, or the like. In some embodiments, subject data may be collected and/or stored in one location (e.g., a server/data store) while device data may be collected and/or stored in a different location (e.g., a different server/data store).

Locations of Treatment

In some embodiments, the JAK inhibitor is delivered at a location in the large intestine of the subject. In some embodiments, the location is in the proximal portion of the large intestine. In some embodiments, the location is in the distal portion of the large intestine.

In some embodiments, the JAK inhibitor is delivered at a location in the ascending colon of the subject. In some embodiments, the location is in the proximal portion of the ascending colon. In some embodiments, the location is in the distal portion of the ascending colon.

In some embodiments, the JAK inhibitor is delivered at a location in the cecum of the subject. In some embodiments, the location is in the proximal portion of the cecum. In some embodiments, the location is in the distal portion of the cecum.

In some embodiments, the JAK inhibitor is delivered at a location in the sigmoid colon of the subject. In some embodiments, the location is in the proximal portion of the sigmoid colon. In some embodiments, the location is in the distal portion of the sigmoid colon.

In some embodiments, the JAK inhibitor is delivered at a location in the transverse colon of the subject. In some embodiments, the location is in the proximal portion of the transverse colon. In some embodiments, the location is in the distal portion of the transverse colon.

In some embodiments, the JAK inhibitor is delivered at a location in the descending colon of the subject. In some embodiments, the location is in the proximal portion of the descending colon. In some embodiments, the location is in the distal portion of the descending colon.

In some embodiments, the JAK inhibitor is delivered at a location in the small intestine of the subject. In some embodiments, the location is in the proximal portion of the small intestine. In some embodiments, the location is in the distal portion of the small intestine.

In some embodiments, the JAK inhibitor is delivered at a location in the duodenum of the subject. In some embodiments, the location is in the proximal portion of the duodenum. In some embodiments, the location is in the distal portion of the duodenum.

In some embodiments, the JAK inhibitor is delivered at a location in the jejunum of the subject. In some embodiments, the location is in the proximal portion of the jejunum. In some embodiments, the location is in the distal portion of the jejunum.

In some embodiments, the JAK inhibitor is delivered at a location in the duodenum of the subject and is not delivered at other locations in the gastrointestinal tract. In some embodiments, the JAK inhibitor is delivered at a location in the duodenum of the subject and is not delivered at other locations in the gastrointestinal tract, wherein a site of disease is in the duodenum and no site of disease is present at other locations in the gastrointestinal tract.

In some embodiments, the JAK inhibitor is delivered at a location in the duodenum of the subject and is not delivered at other locations in the gastrointestinal tract, wherein a first site of disease is in the duodenum and a second site of disease is in the stomach and no site of disease is present at other locations in the gastrointestinal tract.

In some embodiments, the JAK inhibitor is delivered at a location in the proximal duodenum of the subject and is not delivered at other locations in the gastrointestinal tract. In some embodiments, the JAK inhibitor is delivered at a location in the proximal duodenum of the subject and is not delivered at other locations in the gastrointestinal tract, wherein a site of disease is in the duodenum and no site of disease is present at other locations in the gastrointestinal tract. In some embodiments, the JAK inhibitor is delivered at a location in the proximal duodenum of the subject and is not delivered at other locations in the gastrointestinal tract, wherein a first site of disease is in the duodenum and a second site of disease is in the stomach and no site of disease is present at other locations in the gastrointestinal tract.

In some embodiments, the JAK inhibitor is delivered at a location in the jejunum of the subject and is not delivered at other locations in the gastrointestinal tract. In some embodiments, the JAK inhibitor is delivered at a location in the jejunum of the subject and is not delivered at other locations in the gastrointestinal tract, wherein a site of disease is in the jejunum and no site of disease is present at other locations in the gastrointestinal tract. In some embodiments, the JAK inhibitor is delivered at a location in the jejunum of the subject and is not delivered at other locations in the gastrointestinal tract, wherein a first site of disease is in the jejunum and a second site of disease is in the ileum and no site of disease is present at other locations in the gastrointestinal tract.

In some embodiments, the JAK inhibitor is delivered at a location in the proximal portion of the jejunum of the subject and is not delivered at other locations in the gastrointestinal tract. In some embodiments, the JAK inhibitor is delivered at a location in the proximal portion of the jejunum of the subject and is not delivered at other locations in the gastrointestinal tract, wherein a site of disease is in the jejunum and no site of disease is present at other locations in the gastrointestinal tract. In some embodiments, the JAK inhibitor is delivered at a location in the proximal portion of the jejunum of the subject and is not delivered at other locations in the gastrointestinal tract, wherein a first site of disease is in the jejunum and a second site of disease is in the ileum and no site of disease is present at other locations in the gastrointestinal tract.

In some embodiments, the JAK inhibitor is delivered at a location in the distal portion of the jejunum of the subject and is not delivered at other locations in the gastrointestinal tract. In some embodiments, the JAK inhibitor is delivered at a location in the distal portion of the jejunum of the subject and is not delivered at other locations in the gastrointestinal tract, wherein a site of disease is in the jejunum and no site of disease is present at other locations in the gastrointestinal tract. In some embodiments, the JAK inhibitor is delivered at a location in the distal portion of the jejunum of the subject and is not delivered at other locations in the gastrointestinal tract, wherein a first site of disease is in the jejunum and a second site of disease is in the ileum and no site of disease is present at other locations in the gastrointestinal tract.

In some embodiments, the JAK inhibitor is delivered at a location in the ileum of the subject. In some embodiments, the location is in the proximal portion of the ileum. In some embodiments, the location is in the distal portion of the ileum.

In some embodiments, the JAK inhibitor is delivered at a location in the ileum of the subject and is not delivered at other locations in the gastrointestinal tract. In some embodiments, the JAK inhibitor is delivered at a location in the ileum of the subject and is not delivered at other locations in the gastrointestinal tract, wherein a site of disease is in the ileum and no site of disease is present at other locations in the gastrointestinal tract. In some embodiments, the JAK inhibitor is delivered at a location in the ileum of the subject and is not delivered at other locations in the gastrointestinal tract, wherein a first site of disease is in the ileum and a second site of disease is in the cecum and no site of disease is present at other locations in the gastrointestinal tract. In some embodiments, the JAK inhibitor is delivered at a location in the ileum of the subject and is not delivered at other locations in the gastrointestinal tract, wherein a first site of disease is in the ileum and a second site of disease is in the cecum and/or ascending colon, and no site of disease is present at other locations in the gastrointestinal tract.

In some embodiments, the JAK inhibitor is delivered at a location in the proximal portion of the ileum of the subject and is not delivered at other locations in the gastrointestinal tract. In some embodiments, the JAK inhibitor is delivered at a location in the proximal portion of the ileum of the subject and is not delivered at other locations in the gastrointestinal tract, wherein a site of disease is in the ileum and no site of disease is present at other locations in the gastrointestinal tract. In some embodiments, the JAK inhibitor is delivered at a location in the proximal portion of the ileum of the subject and is not delivered at other locations in the gastrointestinal tract, wherein a first site of disease is in the ileum and a second site of disease is in the cecum and no site of disease is present at other locations in the gastrointestinal tract. In some embodiments, the JAK inhibitor is delivered at a location in the proximal portion of the ileum of the subject and is not delivered at other locations in the gastrointestinal tract, wherein a first site of disease is in the ileum and a second site of disease is in the cecum and/or ascending colon, and no site of disease is present at other locations in the gastrointestinal tract.

In some embodiments, the JAK inhibitor is delivered at a location in the distal portion of the ileum of the subject and is not delivered at other locations in the gastrointestinal tract. In some embodiments, the JAK inhibitor is delivered at a location in the distal portion of the ileum of the subject and is not delivered at other locations in the gastrointestinal tract, wherein a site of disease is in the ileum and no site of disease is present at other locations in the gastrointestinal tract. In some embodiments, the JAK inhibitor is delivered at a location in the distal portion of the ileum of the subject and is not delivered at other locations in the gastrointestinal tract, wherein a first site of disease is in the ileum and a second site of disease is in the cecum and no site of disease is present at other locations in the gastrointestinal tract. In some embodiments, the JAK inhibitor is delivered at a location in the distal portion of the ileum of the subject and is not delivered at other locations in the gastrointestinal tract, wherein a first site of disease is in the ileum and a second site of disease is in the cecum and/or ascending colon, and no site of disease is present at other locations in the gastrointestinal tract.

In some embodiments, the JAK inhibitor is delivered at a location in the cecum of the subject and is not delivered at other locations in the gastrointestinal tract. In some embodiments, the JAK inhibitor is delivered at a location in the distal portion of the cecum of the subject and is not delivered at other locations in the gastrointestinal tract, wherein a site of disease is in the cecum and/or ascending colon, and no site of disease is present at other locations in the gastrointestinal tract. In some embodiments, the JAK inhibitor is delivered at a location in the distal portion of the ileum or the proximal portion of the ascending colon of the subject and is not delivered at other locations in the gastrointestinal tract, wherein a first site of disease is in the cecum and a second site of disease is in the ascending colon, and no site of disease is present at other locations in the gastrointestinal tract.

In some embodiments, a site of disease is in the colon and the JAK inhibitor is released in the colon, such as in the cecum. In some embodiments, a site of disease is in the ascending colon and the JAK inhibitor is released in the ascending colon, such as in the cecum. In some embodiments, a site of disease is in the ileum and the JAK inhibitor is released in the ileum.

In some embodiments the subject is diagnosed with ileal Crohn's disease and the JAK inhibitor is released in the ileum.

In some embodiments the subject is diagnosed with ileal colonic Crohn's disease and the JAK inhibitor is released in both the ileum and the colon. In some more particular embodiments, the JAK inhibitor is released in both the ileum and the colon from the same ingestible device. In some more particular embodiments, the JAK inhibitor is released in the ileum from a first ingestible device and in the colon from a second ingestible device, wherein the first ingestible device and the second ingestible device are ingested at substantially the same time or at different times.

In some embodiments the subject is diagnosed with colitis throughout the colon and the JAK inhibitor is released (a) in the cecum, (b) in the cecum and in the transverse colon, and/or release (c) in the descending colon.

In some embodiments the subject is diagnosed with right sided colitis and the JAK inhibitor is released in the transverse colon or in the descending colon.

In some embodiments the subject is diagnosed with rectosigmoidal colitis and the JAK inhibitor is released in the descending colon.

In some embodiments, the location at which the JAK inhibitor is delivered is proximate to a site of disease. The site of disease may be, for example, an injury, inflamed tissue, or one or more lesions. In some embodiments, the location at which the JAK inhibitor is delivered is proximate to one or more sites of disease. In some embodiments, the JAK inhibitor is delivered 150 cm or less from the one or more sites of disease. In some embodiments, the JAK inhibitor is delivered 125 cm or less from the one or more sites of disease. In some embodiments, the JAK inhibitor is delivered 100 cm or less from the one or more sites of disease. In some embodiments, the JAK inhibitor is delivered 50 cm or less from the one or more sites of disease. In some embodiments, the JAK inhibitor is delivered 40 cm or less from the one or more sites of disease. In some embodiments, the JAK inhibitor is delivered 30 cm or less from the one or more sites of disease. In some embodiments, the JAK inhibitor is delivered 20 cm or less from the one or more sites of disease. In some embodiments, the JAK inhibitor is delivered 10 cm or less from the one or more sites of disease. In some embodiments, the JAK inhibitor is delivered 5 cm or less from the one or more sites of disease. In some embodiments, the JAK inhibitor is delivered 2 cm or less from the one or more sites of disease. In some embodiments, the method further comprises using an ingestible device to deliver the JAK inhibitor and using localization methods disclosed herein (e.g., such as discussed in Example 13 below) to determine the location of the ingestible device within the GI tract (e.g., relative to the site of disease). In some embodiments, the method further comprises using an ingestible device to deliver the JAK inhibitor and determining the period of time since the ingestible device was ingested to determine the location of the ingestible device within the GI tract (e.g., relative to the site of disease). In some embodiments, the method further comprises identifying the one or more sites of disease by a method comprising imaging of the gastrointestinal tract. In some embodiments, imaging of the gastrointestinal tract comprises video imaging. In some embodiments, imaging of the gastrointestinal tract comprises thermal imaging. In some embodiments, imaging of the gastrointestinal tract comprises ultrasound imaging. In some embodiments, imaging of the gastrointestinal tract comprises Doppler imaging.

In some embodiments the method does not comprise releasing more than 20% of the JAK inhibitor at a location that is not proximate to a site of disease. In some embodiments the method does not comprise releasing more than 10% of the JAK inhibitor at a location that is not proximate to a site of disease. In some embodiments the method does not comprise releasing more than 5% of the JAK inhibitor at a location that is not proximate to a site of disease. In some embodiments the method does not comprise releasing more than 4% of the JAK inhibitor at a location that is not proximate to a site of disease. In some embodiments the method does not comprise releasing more than 3% of the JAK inhibitor at a location that is not proximate to a site of disease. In some embodiments the method does not comprise releasing more than 2% of the JAK inhibitor at a location that is not proximate to a site of disease.

In some embodiments the method comprises releasing at least 80% of the JAK inhibitor at a location proximate to a site of disease. In some embodiments the method comprise releasing at least 90% of the JAK inhibitor at a location proximate to a site of disease. In some embodiments the method comprises releasing at least 95% of the JAK inhibitor at a location proximate to a site of disease. In some embodiments the method comprises releasing at least 96% of the JAK inhibitor at a location proximate to a site of disease. In some embodiments the method comprises releasing at least 97% of the JAK inhibitor at a location proximate to a site of disease. In some embodiments the method comprises releasing at least 98% of the JAK inhibitor at a location proximate to a site of disease. In some embodiments, the at least 80%, at least 90%, at least 95%, at least 96%, at least 97%, or at least 98% of the JAK inhibitor is delivered 150 cm or less from the one or more sites of disease. In some embodiments, the at least 80%, at least 90%, at least 95%, at least 96%, at least 97%, or at least 98% of the JAK inhibitor is delivered 125 cm or less from the one or more sites of disease. In some embodiments, the at least 80%, at least 90%, at least 95%, at least 96%, at least 97%, or at least 98% of the JAK inhibitor is delivered 100 cm or less from the one or more sites of disease. In some embodiments, the at least 80%, at least 90%, at least 95%, at least 96%, at least 97%, or at least 98% of the JAK inhibitor is delivered 50 cm or less from the one or more sites of disease. In some embodiments, the at least 80%, at least 90%, at least 95%, at least 96%, at least 97%, or at least 98% of the JAK inhibitor is delivered 40 cm or less from the one or more sites of disease. In some embodiments, the at least 80%, at least 90%, at least 95%, at least 96%, at least 97%, or at least 98% of the JAK inhibitor is delivered 30 cm or less from the one or more sites of disease. In some embodiments, the at least 80%, at least 90%, at least 95%, at least 96%, at least 97%, or at least 98% of the JAK inhibitor is delivered 20 cm or less from the one or more sites of disease. In some embodiments, the at least 80%, at least 90%, at least 95%, at least 96%, at least 97%, or at least 98% of the JAK inhibitor is delivered 10 cm or less from the one or more sites of disease. In some embodiments, the at least 80%, at least 90%, at least 95%, at least 96%, at least 97%, or at least 98% of the JAK inhibitor is delivered 5 cm or less from the one or more sites of disease. In some embodiments, the at least 80%, at least 90%, at least 95%, at least 96%, at least 97%, or at least 98% of the JAK inhibitor is delivered 2 cm or less from the one or more sites of disease. In some embodiments, the method further comprises using an ingestible device to deliver the JAK inhibitor and using localization methods disclosed herein (e.g., such as discussed in Example 13 below) to determine the location of the ingestible device within the GI tract (e.g., relative to the site of disease). In some embodiments, the method further comprises using an ingestible device to deliver the JAK inhibitor and determining the period of time since the ingestible device was ingested to determine the location of the ingestible device within the GI tract (e.g., relative to the site of disease).

In some embodiments, the amount of JAK inhibitor that is delivered is a Human Equivalent Dose.

In some embodiments the method comprises releasing the JAK inhibitor at a location that is proximate to a site of disease, wherein the JAK inhibitor and, if applicable, any carriers, excipients or stabilizers admixed with the JAK inhibitor, are substantially unchanged, at the time of release of the JAK inhibitor at the location, relatively to the time of administration of the composition to the subject.

In some embodiments the method comprises releasing the JAK inhibitor at a location that is proximate to a site of disease, wherein the JAK inhibitor and, if applicable, any carriers, excipients or stabilizers admixed with the JAK inhibitor, are substantially unchanged by any physiological process (such as, but not limited to, degradation in the stomach), at the time of release of the JAK inhibitor at the location, relatively to the time of administration of the composition to the subject.

In some embodiments, the JAK inhibitor is delivered to the location by mucosal contact.

In some embodiments, a method of treatment disclosed herein includes determining the level of JAK inhibitor at a site of disease or a location in the gastrointestinal tract of the subject that is proximate to one or more sites of disease. In some examples, a method of treatment as described herein can include determining the level of JAK inhibitor at a site of disease or a location in the gastrointestinal tract of the subject that is proximate to one or more sites of disease within a time period of about 10 minutes to about 10 hours following administration of the device.

In some examples, a method of treatment disclosed herein includes determining the level of the JAK inhibitor at a site of disease or a location in the gastrointestinal tract of the subject that is proximate to one or more sites of disease at a time point following administration of the device that is elevated as compared to a level of the JAK inhibitor at the same site of disease or location at substantially the same time point in a subject following systemic administration of an equal amount of the JAK inhibitor.

In some examples where the JAK inhibitor is an antibody or an antigen-binding fragment thereof (e.g., any of the antibodies or antigen-binding antibody fragments described herein) are administered to a subject using any of the compositions or devices described herein, the antibody or antigen-binding antibody fragment can penetrate the GI tissue of the subject. As used herein, "GI tissue" refers to tissue in the gastrointestinal (GI) tract, such as tissue in one or more of duodenum, jejunum, ileum, cecum, ascending colon, transverse colon, descending colon, sigmoid colon, and rectum. In one particular embodiment, GI tissue refers to tissue in the proximal portion of one or more of duodenum, jejunum, ileum, cecum, ascending colon, transverse colon, descending colon, and sigmoid colon. In one particular embodiment, GI tissue refers to tissue in the distal portion of one or more of duodenum, jejunum, ileum, cecum, ascending colon, transverse colon, descending colon, and sigmoid colon. The GI tissue may be, for example, GI tissue proximate to one or more sites of disease. Accordingly, in some embodiments the antibody or antigen-binding antibody fragment can penetrate the dudodenum tissue proximate to one or more sites of disease. In some embodiments the antibody or antigen-binding antibody fragment can penetrate the jejunum tissue proximate to one or more sites of disease. In some embodiments the antibody or antigen-binding antibody fragment can penetrate the ileum tissue proximate to one or more sites of disease. In some embodiments the antibody or antigen-binding antibody fragment can penetrate the cecum tissue proximate to one or more sites of disease. In some embodiments the antibody or antigen-binding antibody fragment can penetrate the ascending colon tissue proximate to one or more sites of disease. In some embodiments the antibody or antigen-binding antibody fragment can penetrate the transverse colon tissue proximate to one or more sites of disease. In some embodiments the antibody or antigen-binding antibody fragment can penetrate the descending colon tissue proximate to one or more sites of disease. In some embodiments the antibody or antigen-binding antibody fragment can penetrate the sigmoid colon tissue proximate to one or more sites of disease. For example, an antibody or antigen-binding fragment thereof (e.g., a F(ab')$_2$, a Fv, or a scFv) can penetrate one or more (e.g., two, three, or four) of the lumen/superficial mucosa, the lamina propria, the submucosa, and the tunica muscularis/serosa. In some embodiments, any of the devices or compositions described herein can release a recombinant antibody (e.g., a humanized or fully human antibody, e.g., human or humanized IgG1, human or humanized IgG2, human or humanized IgG3, human or humanized IgG4, human or humanized IgA1, human or humanized IgA2, human or humanized IgD, human or humanized IgE, or human or humanized IgM), which is degraded into an antigen-binding antibody fragment (e.g., a Fab, a Fv, or a F(ab')$_2$), which in turn is able to penetrate GI tissue (e.g., one or more (e.g., two, three, or four) of the lumen/superficial mucosa, the lamina propria, the submucosa, and the tunica muscularis/serosa) of the subject. In some embodiments, the device releases an antigen-binding antibody fragment (e.g., any of the antigen-binding antibody fragments described herein).

In some examples, administration of an antibody or an antigen-binding fragment thereof using any of the compositions or devices described herein results in penetration (e.g., a detectable level of penetration) of GI tissue (e.g., one or more (e.g., two, three, or four) of the lumen/superficial mucosa, the lamina propria, the submucosa, and the tunica muscularis/serosa) within a time period of about 10 minutes to about 10 hours, about 10 minutes to about 9 hours, about 10 minutes to about 8 hours, about 10 minutes to about 7 hours, about 10 minutes to about 6 hours, about 10 minutes to about 5 hours, about 10 minutes to about 4.5 hours, about 10 minutes to about 4 hours, about 10 minutes to about 3.5 hours, about 10 minutes to about 3 hours, about 10 minutes to about 2.5 hours, about 10 minutes to about 2 hours, about 10 minutes to about 1.5 hours, about 10 minutes to about 1 hour, about 10 minutes to about 55 minutes, about 10 minutes to about 50 minutes, about 10 minutes to about 45 minutes, about 10 minutes to about 40 minutes, about 10 minutes to about 35 minutes, about 10 minutes to about 30 minutes, about 10 minutes to about 25 minutes, about 10 minutes to about 20 minutes, about 10 minutes to about 15 minutes, about 15 minutes to about 10 hours, about 15 minutes to about 9 hours, about 15 minutes to about 8 hours, about 15 minutes to about 7 hours, about 15 minutes to about 6 hours, about 15 minutes to about 5 hours, about 15 minutes to about 4.5 hours, about 15 minutes to about 4 hours, about 15 minutes to about 3.5 hours, about 15 minutes to about 3 hours, about 15 minutes to about 2.5 hours, about 15 minutes to about 2 hours, about 15 minutes to about 1.5 hours, about 15 minutes to about 1 hour, about 15 minutes to about 55 minutes, about 15 minutes to about 50 minutes, about 15 minutes to about 45 minutes, about 15 minutes to about 40 minutes, about 15 minutes to about 35 minutes, about 15 minutes to about 30 minutes, about 15 minutes to about 25 minutes, about 15 minutes to about 20 minutes, about 20 minutes to about 10 hours, about 20 minutes to about 9 hours, about 20 minutes to about 8 hours, about 20 minutes to about 7 hours, about 20 minutes to about 6 hours, about 20 minutes to about 5 hours, about 20 minutes to about 4.5 hours, about 20 minutes to about 4 hours, about 20 minutes to about 3.5 hours, about 20 minutes to about 3 hours, about 20 minutes to about 2.5 hours, about 20 minutes to about 2 hours, about 20 minutes to about 1.5 hours, about 20 minutes to about 1 hour, about 20 minutes to about 55 minutes, about 20 minutes to about 50 minutes, about 20 minutes to about 45 minutes, about 20 minutes to about 40 minutes, about 20 minutes to about 35 minutes, about 20 minutes to about 30 minutes, about 20 minutes to about 25 minutes, about 25 minutes to about 10 hours, about 25 minutes to about 9 hours, about 25 minutes to about 8 hours, about 25 minutes to about 7 hours, about 25 minutes to about 6 hours, about 25 minutes to about 5 hours, about 25 minutes to about 4.5 hours, about 25 minutes to about 4 hours, about 25 minutes to about 3.5 hours, about 25 minutes to about 3 hours, about 25 minutes to about 2.5 hours, about 25 minutes to about 2 hours, about 25 minutes to about 1.5 hours, about 25 minutes to about 1 hour, about 25 minutes to about 55 minutes, about 25 minutes to about 50 minutes, about 25 minutes to about 45 minutes, about 25 minutes to about 40 minutes, about 25 minutes to about 35 minutes, about 25 minutes to about 30 minutes, about 30 minutes to about 10 hours, about 30 minutes to about 9 hours, about 30 minutes to about 8 hours, about 30 minutes to about 7 hours, about 30 minutes to about 6 hours, about 30 minutes to about 5 hours, about 30 minutes to about 4.5 hours, about 30 minutes to about 4 hours, about 30 minutes to about 3.5 hours, about 30 minutes to about 3 hours, about 30 minutes to about 2.5 hours, about 30 minutes to about 2 hours, about 30 minutes to about 1.5 hours, about 30 minutes to about 1 hour, about 30 minutes to about 55 minutes, about 30 minutes to about 50 minutes, about 30 minutes to about 45 minutes, about 30 minutes to about 40 minutes, about 30 minutes to about 35 minutes, about 35 minutes to about 10 hours, about 35 minutes to about 9 hours, about 35 minutes to about 8 hours, about 35 minutes to about 7 hours, about 35 minutes to about 6 hours, about 35 minutes to about 5 hours, about 35 minutes to about 4.5 hours, about 35 minutes to about 4 hours, about 35 minutes to about 3.5 hours, about 35 minutes to about 3 hours, about 35 minutes to about 2.5 hours, about 35 minutes to about 2 hours, about 35 minutes to about 1.5 hours, about 35 minutes to about 1 hour, about 35 minutes to about 55 minutes, about 35 minutes to about 50 minutes, about 35 minutes to about 45 minutes, about 35 minutes to about 40 minutes, about 40 minutes to about 10 hours, about 40 minutes to about 9 hours, about 40 minutes to about 8 hours, about 40 minutes to about 7 hours, about 40 minutes to about 6 hours, about 40 minutes to about 5 hours, about 40 minutes to about 4.5 hours, about 40 minutes to about 4 hours, about 40 minutes to about 3.5 hours, about 40 minutes to about 3 hours, about 40 minutes to about 2.5 hours, about 40 minutes to about 2 hours, about 40 minutes to about 1.5 hours, about 40 minutes to about 1 hour, about 40 minutes to about 55 minutes, about 40 minutes to about 50 minutes, about 40 minutes to about 45 minutes, about 45 minutes to about 10 hours, about 45 minutes to about 9 hours, about 45 minutes to about 8 hours, about 45 minutes to about 7 hours, about 45 minutes to about 6 hours, about 45 minutes to about 5 hours, about 45 minutes to about 4.5 hours, about 45 minutes to about 4 hours, about 45 minutes to about 3.5 hours, about 45 minutes to about 3 hours, about 45 minutes to about 2.5 hours, about 45 minutes to about 2 hours, about 45 minutes to about 1.5 hours, about 45 minutes to about 1 hour, about 45 minutes to about 55 minutes, about 45 minutes to about 50 minutes, about 50 minutes to about 10 hours, about 50 minutes to about 9 hours, about 50 minutes to about 8 hours, about 50 minutes to about 7 hours, about 50 minutes to about 6 hours, about 50 minutes to about 5 hours, about 50 minutes to about 4.5 hours, about 50 minutes to about 4 hours, about 50 minutes to about 3.5 hours, about 50 minutes to about 3 hours, about 50 minutes to about 2.5 hours, about 50 minutes to about 2 hours, about 50 minutes to about 1.5 hours, about 50 minutes to about 1 hour, about 50 minutes to about 55 minutes, about 55 minutes to about 10 hours, about 55 minutes to about 9 hours, about 55 minutes to about 8 hours, about 55 minutes to about 7 hours, about 55 minutes to about 6 hours, about 55 minutes to about 5 hours, about 55 minutes to about 4.5 hours, about 55 minutes to about 4 hours, about 55 minutes to about 3.5 hours, about 55 minutes to about 3 hours, about 55 minutes to about 2.5 hours, about 55 minutes to about 2 hours, about 55 minutes to about 1.5 hours, about 55 minutes to about 1 hour, about 1 hour to about 10 hours, about 1 hour to about 9 hours, about 1 hour to about 8 hours, about 1 hour to about 7 hours, about 1 hour to about 6 hours, about 1 hour to about 5 hours, about 1 hour to about 4.5 hours, about 1 hour to about 4 hours, about 1 hour to about 3.5 hours, about 1 hour to about 3 hours, about 1 hour to about 2.5 hours, about 1 hour to about 2 hours, about 1 hour to about 1.5 hours, about 1.5 hours to about 10 hours, about 1.5 hours to about 9 hours, about 1.5 hours to about 8 hours, about 1.5 hours to about 7 hours, about 1.5 hours to about 6 hours, about 1.5 hours to about 5 hours, about 1.5 hours to about 4.5 hours, about 1.5 hours to about 4 hours, about 1.5 hours to about 3.5 hours, about 1.5 hours to about 3 hours, about 1.5 hours to about 2.5 hours, about 1.5 hours to about 2 hours, about 2 hours to about 10 hours, about 2 hours to about 9 hours, about 2 hours to about 8 hours, about 2 hours to about 7 hours, about 2 hours to about 6 hours, about 2 hours to about 5 hours, about 2 hours to about 4.5 hours, about 2 hours to about 4 hours, about 2 hours to about 3.5 hours, about 2 hours to about 3 hours, about 2 hours to about 2.5 hours, about 2.5 hours to about 10 hours, about 2.5 hours to about 9 hours, about 2.5 hours to about 8 hours, about 2.5 hours to about 7 hours, about 2.5 hours to about 6 hours, about 2.5 hours to about 5 hours, about 2.5 hours to about 4.5 hours, about 2.5 hours to about 4 hours, about 2.5 hours to about 3.5 hours, about 2.5 hours to about 3 hours, about 3 hours to about 10 hours, about 3 hours to about 9 hours, about 3 hours to about 8 hours, about 3 hours to about 7 hours, about 3 hours to about 6 hours, about 3 hours to about 5 hours, about 3 hours to about 4.5 hours, about 3 hours to about 4 hours, about 3 hours to about 3.5 hours, about 3.5 hours to about 10 hours, about 3.5 hours to about 9 hours, about 3.5 hours to about 8 hours, about 3.5 hours to about 7 hours, about 3.5 hours to about 6 hours, about 3.5 hours to about 5 hours, about 3.5 hours to about 4.5 hours, about 3.5 hours to about 4 hours, about 4 hours to about 10 hours, about 4 hours to about 9 hours, about 4 hours to about 8 hours, about 4 hours to about 7 hours, about 4 hours to about 6 hours, about 4 hours to about 5 hours, about 4 hours to about 4.5 hours, about 4.5 hours to about 10 hours, about 4.5 hours to about 9 hours, about 4.5 hours to about 8 hours, about 4.5 hours to about 7 hours, about 4.5 hours to about 6 hours, about 4.5 hours to about 5 hours, about 5 hours to about 10 hours, about 5 hours to about 9 hours, about 5 hours to about 8 hours, about 5 hours to about 7 hours, about 5 hours to about 6 hours, about 6 hours to about 10 hours, about 6 hours to about 9 hours, about 6 hours to about 8 hours, about 6 hours to about 7 hours, about 7 hours to about 10 hours, about 7 hours to about 9 hours, about 7 hours to about 8 hours, about 8 hours to about 10 hours, about 8 hours to about 9 hours, or about 9 hours to about 10 hours. Penetration of GI tissue by an antibody or an antigen-binding antibody fragment can be detected by administering a labeled antibody or labeled antigen-binding antibody fragment, and performing imaging on the subject (e.g., ultrasound, computed tomography, or magnetic resonance imaging). For example, the label can be a radioisotope, a heavy metal, a fluorophore, or a luminescent agent (e.g., any suitable radioisotopes, heavy metals, fluorophores, or luminescent agents used for imaging known in the art).

While not wishing to be bound to a particular theory, the inventors contemplate that at or near the site of release a concentration gradient of the JAK inhibitor is generated in the mucosa, and that administration of an JAK inhibitor using a device as described herein advantageously results in a "reverse" concentration gradient when compared to the concentration gradient resulting from systemic administration. In such "reverse" concentration gradient, the drug concentration is highest from superficial to deep with respect to the mucosal surface. Systemic administration instead typically results in concentrations of the drug being highest from deep to superficial. A "reverse" concentration gradient as described above aligns more favorably with the pathophysiology of IBD.

In some embodiments, administration of an antibody or an antigen-binding antibody fragment can provide for treatment (e.g., a reduction in the number, severity, and/or duration of one or more symptoms of any of the disorders described herein in a subject) for a time period of between about 1 hour to about 30 days, about 1 hour to about 28 days, about 1 hour to about 26 days, about 1 hour to about 24 days, about 1 hour to about 22 days, about 1 hour to about 20 days, about 1 hour to about 18 days, about 1 hour to about 16 days, about 1 hour to about 14 days, about 1 hour to about 12 days, about 1 hour to about 10 days, about 1 hour to about 8 days, about 1 hour to about 6 days, about 1 hour to about 5 days, about 1 hour to about 4 days, about 1 hour to about 3 days, about 1 hour to about 2 days, about 1 hour to about 1 day, about 1 hour to about 12 hours, about 1 hour to about 6 hours, about 1 hour to about 3 hours, about 3 hours to about 30 days, about 3 hours to about 28 days, about 3 hours to about 26 days, about 3 hours to about 24 days, about 3 hours to about 22 days, about 3 hours to about 20 days, about 3 hours to about 18 days, about 3 hours to about 16 days, about 3 hours to about 14 days, about 3 hours to about 12 days, about 3 hours to about 10 days, about 3 hours to about 8 days, about 3 hours to about 6 days, about 3 hours to about 5 days, about 3 hours to about 4 days, about 3 hours to about 3 days, about 3 hours to about 2 days, about 3 hours to about 1 day, about 3 hours to about 12 hours, about 3 hours to about 6 hours, about 6 hours to about 30 days, about 6 hours to about 28 days, about 6 hours to about 26 days, about 6 hours to about 24 days, about 6 hours to about 22 days, about 6 hours to about 20 days, about 6 hours to about 18 days, about 6 hours to about 16 days, about 6 hours to about 14 days, about 6 hours to about 12 days, about 6 hours to about 10 days, about 6 hours to about 8 days, about 6 hours to about 6 days, about 6 hours to about 5 days, about 6 hours to about 4 days, about 6 hours to about 3 days, about 6 hours to about 2 days, about 6 hours to about 1 day, about 6 hours to about 12 hours, about 12 hours to about 30 days, about 12 hours to about 28 days, about 12 hours to about 26 days, about 12 hours to about 24 days, about 12 hours to about 22 days, about 12 hours to about 20 days, about 12 hours to about 18 days, about 12 hours to about 16 days, about 12 hours to about 14 days, about 12 hours to about 12 days, about 12 hours to about 10 days, about 12 hours to about 8 days, about 12 hours to about 6 days, about 12 hours to about 5 days, about 12 hours to about 4 days, about 12 hours to about 3 days, about 12 hours to about 2 days, about 12 hours to about 1 day, about 1 day to about 30 days, about 1 day to about 28 days, about 1 day to about 26 days, about 1 day to about 24 days, about 1 day to about 22 days, about 1 day to about 20 days, about 1 day to about 18 days, about 1 day to about 16 days, about 1 day to about 14 days, about 1 day to about 12 days, about 1 day to about 10 days, about 1 day to about 8 days, about 1 day to about 6 days, about 1 day to about 5 days, about 1 day to about 4 days, about 1 day to about 3 days, about 1 day to about 2 days, about 2 days to about 30 days, about 2 days to about 28 days, about 2 days to about 26 days, about 2 days to about 24 days, about 2 days to about 22 days, about 2 days to about 20 days, about 2 days to about 18 days, about 2 days to about 16 days, about 2 days to about 14 days, about 2 days to about 12 days, about 2 days to about 10 days, about 2 days to about 8 days, about 2 days to about 6 days, about 2 days to about 5 days, about 2 days to about 4 days, about 2 days to about 3 days, about 3 days to about 30 days, about 3 days to about 28 days, about 3 days to about 26 days, about 3 days to about 24 days, about 3 days to about 22 days, about 3 days to about 20 days, about 3 days to about 18 days, about 3 days to about 16 days, about 3 days to about 14 days, about 3 days to about 12 days, about 3 days to about 10 days, about 3 days to about 8 days, about 3 days to about 6 days, about 3 days to about 5 days, about 3 days to about 4 days, about 4 days to about 30 days, about 4 days to about 28 days, about 4 days to about 26 days, about 4 days to about 24 days, about 4 days to about 22 days, about 4 days to about 20 days, about 4 days to about 18 days, about 4 days to about 16 days, about 4 days to about 14 days, about 4 days to about 12 days, about 4 days to about 10 days, about 4 days to about 8 days, about 4 days to about 6 days, about 4 days to about 5 days, about 5 days to about 30 days, about 5 days to about 28 days, about 5 days to about 26 days, about 5 days to about 24 days, about 5 days to about 22 days, about 5 days to about 20 days, about 5 days to about 18 days, about 5 days to about 16 days, about 5 days to about 14 days, about 5 days to about 12 days, about 5 days to about 10 days, about 5 days to about 8 days, about 5 days to about 6 days, about 6 days to about 30 days, about 6 days to about 28 days, about 6 days to about 26 days, about 6 days to about 24 days, about 6 days to about 22 days, about 6 days to about 20 days, about 6 days to about 18 days, about 6 days to about 16 days, about 6 days to about 14 days, about 6 days to about 12 days, about 6 days to about 10 days, about 6 days to about 8 days, about 8 days to about 30 days, about 8 days to about 28 days, about 8 days to about 26 days, about 8 days to about 24 days, about 8 days to about 22 days, about 8 days to about 20 days, about 8 days to about 18 days, about 8 days to about 16 days, about 8 days to about 14 days, about 8 days to about 12 days, about 10 days, about 10 days to about 30 days, about 10 days to about 28 days, about 10 days to about 26 days, about 10 days to about 24 days, about 10 days to about 22 days, about 10 days to about 20 days, about 10 days to about 18 days, about 10 days to about 16 days, about 10 days to about 14 days, about 10 days to about 12 days, about 12 days to about 30 days, about 12 days to about 28 days, about 12 days to about 26 days, about 12 days to about 24 days, about 12 days to about 22 days, about 12 days to about 20 days, about 12 days to about 18 days, about 12 days to about 16 days, about 12 days to about 14 days, about 14 days to about 30 days, about 14 days to about 28 days, about 14 days to about 26 days, about 14 days to about 24 days, about 14 days to about 22 days, about 14 days to about 20 days, about 14 days to about 18 days, about 14 days to about 16 days, about 16 days to about 30 days, about 16 days to about 28 days, about 16 days to about 26 days, about 16 days to about 24 days, about 16 days to about 22 days, about 16 days to about 20 days, about 16 days to about 18 days, about 18 days to about 30 days, about 18 days to about 28 days, about 18 days to about 26 days, about 18 days to about 24 days, about 18 days to about 22 days, about 18 days to about 20 days, about 20 days to about 30 days, about 20 days to about 28 days, about 20 days to about 26 days, about 20 days to about 24 days, about 20 days to about 22 days, about 22 days to about 30 days, about 22 days to about 28 days, about 22 days to about 26 days, about 22 days to about 24 days, about 24 days to about 30 days, about 24 days to about 28 days, about 24 days to about 26 days, about 26 days to about 30 days, about 26 days to about 28 days, or about 28 days to about 30 days in a subject following first administration of an antibody or antigen-binding antibody fragment using any of the compositions or devices described herein. Non-limiting examples of symptoms of a disease described herein are described below.

For example, treatment can result in a decrease (e.g., about 1% to about 99% decrease, about 1% to about 95% decrease, about 1% to about 90% decrease, about 1% to about 85% decrease, about 1% to about 80% decrease, about 1% to about 75% decrease, about 1% to about 70% decrease, about 1% to about 65% decrease, about 1% to about 60% decrease, about 1% to about 55% decrease, about 1% to about 50% decrease, about 1% to about 45% decrease, about 1% to about 40% decrease, about 1% to about 35% decrease, about 1% to about 30% decrease, about 1% to about 25% decrease, about 1% to about 20% decrease, about 1% to about 15% decrease, about 1% to about 10% decrease, about 1% to about 5% decrease, about 5% to about 99% decrease, about 5% to about 95% decrease, about 5% to about 90% decrease, about 5% to about 85% decrease, about 5% to about 80% decrease, about 5% to about 75% decrease, about 5% to about 70% decrease, about 5% to about 65% decrease, about 5% to about 60% decrease, about 5% to about 55% decrease, about 5% to about 50% decrease, about 5% to about 45% decrease, about 5% to about 40% decrease, about 5% to about 35% decrease, about 5% to about 30% decrease, about 5% to about 25% decrease, about 5% to about 20% decrease, about 5% to about 15% decrease, about 5% to about 10% decrease, about 10% to about 99% decrease, about 10% to about 95% decrease, about 10% to about 90% decrease, about 10% to about 85% decrease, about 10% to about 80% decrease, about 10% to about 75% decrease, about 10% to about 70% decrease, about 10% to about 65% decrease, about 10% to about 60% decrease, about 10% to about 55% decrease, about 10% to about 50% decrease, about 10% to about 45% decrease, about 10% to about 40% decrease, about 10% to about 35% decrease, about 10% to about 30% decrease, about 10% to about 25% decrease, about 10% to about 20% decrease, about 10% to about 15% decrease, about 15% to about 99% decrease, about 15% to about 95% decrease, about 15% to about 90% decrease, about 15% to about 85% decrease, about 15% to about 80% decrease, about 15% to about 75% decrease, about 15% to about 70% decrease, about 15% to about 65% decrease, about 15% to about 60% decrease, about 15% to about 55% decrease, about 15% to about 50% decrease, about 15% to about 45% decrease, about 15% to about 40% decrease, about 15% to about 35% decrease, about 15% to about 30% decrease, about 15% to about 25% decrease, about 15% to about 20% decrease, about 20% to about 99% decrease, about 20% to about 95% decrease, about 20% to about 90% decrease, about 20% to about 85% decrease, about 20% to about 80% decrease, about 20% to about 75% decrease, about 20% to about 70% decrease, about 20% to about 65% decrease, about 20% to about 60% decrease, about 20% to about 55% decrease, about 20% to about 50% decrease, about 20% to about 45% decrease, about 20% to about 40% decrease, about 20% to about 35% decrease, about 20% to about 30% decrease, about 20% to about 25% decrease, about 25% to about 99% decrease, about 25% to about 95% decrease, about 25% to about 90% decrease, about 25% to about 85% decrease, about 25% to about 80% decrease, about 25% to about 75% decrease, about 25% to about 70% decrease, about 25% to about 65% decrease, about 25% to about 60% decrease, about 25% to about 55% decrease, about 25% to about 50% decrease, about 25% to about 45% decrease, about 25% to about 40% decrease, about 25% to about 35% decrease, about 25% to about 30% decrease, about 30% to about 99% decrease, about 30% to about 95% decrease, about 30% to about 90% decrease, about 30% to about 85% decrease, about 30% to about 80% decrease, about 30% to about 75% decrease, about 30% to about 70% decrease, about 30% to about 65% decrease, about 30% to about 60% decrease, about 30% to about 55% decrease, about 30% to about 50% decrease, about 30% to about 45% decrease, about 30% to about 40% decrease, about 30% to about 35% decrease, about 35% to about 99% decrease, about 35% to about 95% decrease, about 35% to about 90% decrease, about 35% to about 85% decrease, about 35% to about 80% decrease, about 35% to about 75% decrease, about 35% to about 70% decrease, about 35% to about 65% decrease, about 35% to about 60% decrease, about 35% to about 55% decrease, about 35% to about 50% decrease, about 35% to about 45% decrease, about 35% to about 40% decrease, about 40% to about 99% decrease, about 40% to about 95% decrease, about 40% to about 90% decrease, about 40% to about 85% decrease, about 40% to about 80% decrease, about 40% to about 75% decrease, about 40% to about 70% decrease, about 40% to about 65% decrease, about 40% to about 60% decrease, about 40% to about 55% decrease, about 40% to about 50% decrease, about 40% to about 45% decrease, about 45% to about 99% decrease, about 45% to about 95% decrease, about 45% to about 90% decrease, about 45% to about 85% decrease, about 45% to about 80% decrease, about 45% to about 75% decrease, about 45% to about 70% decrease, about 45% to about 65% decrease, about 45% to about 60% decrease, about 45% to about 55% decrease, about 45% to about 50% decrease, about 50% to about 99% decrease, about 50% to about 95% decrease, about 50% to about 90% decrease, about 50% to about 85% decrease, about 50% to about 80% decrease, about 50% to about 75% decrease, about 50% to about 70% decrease, about 50% to about 65% decrease, about 50% to about 60% decrease, about 50% to about 55% decrease, about 55% to about 99% decrease, about 55% to about 95% decrease, about 55% to about 90% decrease, about 55% to about 85% decrease, about 55% to about 80% decrease, about 55% to about 75% decrease, about 55% to about 70% decrease, about 55% to about 65% decrease, about 55% to about 60% decrease, about 60% to about 99% decrease, about 60% to about 95% decrease, about 60% to about 90% decrease, about 60% to about 85% decrease, about 60% to about 80% decrease, about 60% to about 75% decrease, about 60% to about 70% decrease, about 60% to about 65% decrease, about 65% to about 99% decrease, about 65% to about 95% decrease, about 65% to about 90% decrease, about 65% to about 85% decrease, about 65% to about 80% decrease, about 65% to about 75% decrease, about 65% to about 70% decrease, about 70% to about 99% decrease, about 70% to about 95% decrease, about 70% to about 90% decrease, about 70% to about 85% decrease, about 70% to about 80% decrease, about 70% to about 75% decrease, about 75% to about 99% decrease, about 75% to about 95% decrease, about 75% to about 90% decrease, about 75% to about 85% decrease, about 75% to about 80% decrease, about 80% to about 99% decrease, about 80% to about 95% decrease, about 80% to about 90% decrease, about 80% to about 85% decrease, about 85% to about 99% decrease, about 85% to about 95% decrease, about 85% to about 90% decrease, about 90% to about 99% decrease, about 90% to about 95% decrease, or about 95% to about 99% decrease) in one or more (e.g., two, three, four, five, six, seven, eight, or nine) of: the level of interferon-γ in GI tissue, the level of IL-1β in GI tissue, the level of IL-6 in GI tissue, the level of IL-22 in GI tissue, the level of IL-17A in the GI tissue, the level of TNFα in GI tissue, the level of IL-2 in GI tissue, and endoscopy score in a subject (e.g., as compared to the level in the subject prior to treatment or compared to a subject or population of subjects having a similar disease but receiving a placebo or a different treatment) (e.g., for a time period of between about 1 hour to about 30 days (e.g., or any of the subranges herein) following the first administration of an antibody or antigen-binding antibody fragment using any of the compositions or devices described herein. Exemplary methods for determining the endoscopy score are described herein and other methods for determining the endoscopy score are known in the art. Exemplary methods for determining the levels of interferon-γ, IL-1β, IL-6, IL-22, IL-17A, TNFα, and IL-2 are described herein. Additional methods for determining the levels of these cytokines are known in the art.

In some examples, treatment can result in an increase (e.g., about 1% to about 500% increase, about 1% to about 400% increase, about 1% to about 300% increase, about 1% to about 200% increase, about 1% to about 150% increase, about 1% to about 100% increase, about 1% to about 90% increase, about 1% to about 80% increase, about 1% to about 70% increase, about 1% to about 60% increase, about 1% to about 50% increase, about 1% to about 40% increase, about 1% to about 30% increase, about 1% to about 20% increase, about 1% to about 10% increase, a 10% to about 500% increase, about 10% to about 400% increase, about 10% to about 300% increase, about 10% to about 200% increase, about 10% to about 150% increase, about 10% to about 100% increase, about 10% to about 90% increase, about 10% to about 80% increase, about 10% to about 70% increase, about 10% to about 60% increase, about 10% to about 50% increase, about 10% to about 40% increase, about 10% to about 30% increase, about 10% to about 20% increase, about 20% to about 500% increase, about 20% to about 400% increase, about 20% to about 300% increase, about 20% to about 200% increase, about 20% to about 150% increase, about 20% to about 100% increase, about 20% to about 90% increase, about 20% to about 80% increase, about 20% to about 70% increase, about 20% to about 60% increase, about 20% to about 50% increase, about 20% to about 40% increase, about 20% to about 30% increase, about 30% to about 500% increase, about 30% to about 400% increase, about 30% to about 300% increase, about 30% to about 200% increase, about 30% to about 150% increase, about 30% to about 100% increase, about 30% to about 90% increase, about 30% to about 80% increase, about 30% to about 70% increase, about 30% to about 60% increase, about 30% to about 50% increase, about 30% to about 40% increase, about 40% to about 500% increase, about 40% to about 400% increase, about 40% to about 300% increase, about 40% to about 200% increase, about 40% to about 150% increase, about 40% to about 100% increase, about 40% to about 90% increase, about 40% to about 80% increase, about 40% to about 70% increase, about 40% to about 60% increase, about 40% to about 50% increase, about 50% to about 500% increase, about 50% to about 400% increase, about 50% to about 300% increase, about 50% to about 200% increase, about 50% to about 150% increase, about 50% to about 100% increase, about 50% to about 90% increase, about 50% to about 80% increase, about 50% to about 70% increase, about 50% to about 60% increase, about 60% to about 500% increase, about 60% to about 400% increase, about 60% to about 300% increase, about 60% to about 200% increase, about 60% to about 150% increase, about 60% to about 100% increase, about 60% to about 90% increase, about 60% to about 80% increase, about 60% to about 70% increase, about 70% to about 500% increase, about 70% to about 400% increase, about 70% to about 300% increase, about 70% to about 200% increase, about 70% to about 150% increase, about 70% to about 100% increase, about 70% to about 90% increase, about 70% to about 80% increase, about 80% to about 500% increase, about 80% to about 400% increase, about 80% to about 300% increase, about 80% to about 200% increase, about 80% to about 150% increase, about 80% to about 100% increase, about 80% to about 90% increase, about 90% to about 500% increase, about 90% to about 400% increase, about 90% to about 300% increase, about 90% to about 200% increase, about 90% to about 150% increase, about 90% to about 100% increase, about 100% to about 500% increase, about 100% to about 400% increase, about 100% to about 300% increase, about 100% to about 200% increase, about 100% to about 150% increase, about 150% to about 500% increase, about 150% to about 400% increase, about 150% to about 300% increase, about 150% to about 200% increase, about 200% to about 500% increase, about 200% to about 400% increase, about 200% to about 300% increase, about 300% to about 500% increase, about 300% to about 400% increase, or about 400% to about 500% increase) in one or both of stool consistency score and weight of a subject (e.g., as compared to the level in the subject prior to treatment or compared to a subject or population of subjects having a similar disease but receiving a placebo or a different treatment) (e.g., for a time period of between about 1 hour to about 30 days (e.g., or any of the subranges herein) following the first administration of an antibody or antigen-binding antibody fragment using any of the compositions or devices described herein. Exemplary methods for determining stool consistency score are described herein. Additional methods for determining a stool consistency score are known in the art.

In some examples, administration of an antibody or an antigen-binding antibody fragment using any of the devices or compositions described herein can result in a ratio of GI tissue concentration of the antibody or the antigen-binding antibody fragment to the blood, serum, or plasma concentration of the antibody or the antigen-binding antibody fragment of, e.g., about 2.8 to about 6.0, about 2.8 to about 5.8, about 2.8 to about 5.6, about 2.8 to about 5.4, about 2.8 to about 5.2, about 2.8 to about 5.0, about 2.8 to about 4.8, about 2.8 to about 4.6, about 2.8 to about 4.4, about 2.8 to about 4.2, about 2.8 to about 4.0, about 2.8 to about 3.8, about 2.8 to about 3.6, about 2.8 to about 3.4, about 2.8 to about 3.2, about 2.8 to about 3.0, about 3.0 to about 6.0, about 3.0 to about 5.8, about 3.0 to about 5.6, about 3.0 to about 5.4, about 3.0 to about 5.2, about 3.0 to about 5.0, about 3.0 to about 4.8, about 3.0 to about 4.6, about 3.0 to about 4.4, about 3.0 to about 4.2, about 3.0 to about 4.0, about 3.0 to about 3.8, about 3.0 to about 3.6, about 3.0 to about 3.4, about 3.0 to about 3.2, about 3.2 to about 6.0, about 3.2 to about 5.8, about 3.2 to about 5.6, about 3.2 to about 5.4, about 3.2 to about 5.2, about 3.2 to about 5.0, about 3.2 to about 4.8, about 3.2 to about 4.6, about 3.2 to about 4.4, about 3.2 to about 4.2, about 3.2 to about 4.0, about 3.2 to about 3.8, about 3.2 to about 3.6, about 3.2 to about 3.4, about 3.4 to about 6.0, about 3.4 to about 5.8, about 3.4 to about 5.6, about 3.4 to about 5.4, about 3.4 to about 5.2, about 3.4 to about 5.0, about 3.4 to about 4.8, about 3.4 to about 4.6, about 3.4 to about 4.4, about 3.4 to about 4.2, about 3.4 to about 4.0, about 3.4 to about 3.8, about 3.4 to about 3.6, about 3.6 to about 6.0, about 3.6 to about 5.8, about 3.6 to about 5.6, about 3.6 to about 5.4, about 3.6 to about 5.2, about 3.6 to about 5.0, about 3.6 to about 4.8, about 3.6 to about 4.6, about 3.6 to about 4.4, about 3.6 to about 4.2, about 3.6 to about 4.0, about 3.6 to about 3.8, about 3.8 to about 6.0, about 3.8 to about 5.8, about 3.8 to about 5.6, about 3.8 to about 5.4, about 3.8 to about 5.2, about 3.8 to about 5.0, about 3.8 to about 4.8, about 3.8 to about 4.6, about 3.8 to about 4.4, about 3.8 to about 4.2, about 3.8 to about 4.0, about 4.0 to about 6.0, about 4.0 to about 5.8, about 4.0 to about 5.6, about 4.0 to about 5.4, about 4.0 to about 5.2, about 4.0 to about 5.0, about 4.0 to about 4.8, about 4.0 to about 4.6, about 4.0 to about 4.4, about 4.0 to about 4.2, about 4.2 to about 6.0, about 4.2 to about 5.8, about 4.2 to about 5.6, about 4.2 to about 5.4, about 4.2 to about 5.2, about 4.2 to about 5.0, about 4.2 to about 4.8, about 4.2 to about 4.6, about 4.2 to about 4.4, about 4.4 to about 6.0, about 4.4 to about 5.8, about 4.4 to about 5.6, about 4.4 to about 5.4, about 4.4 to about 5.2, about 4.4 to about 5.0, about 4.4 to about 4.8, about 4.4 to about 4.6, about 4.6 to about 6.0, about 4.6 to about 5.8, about 4.6 to about 5.6, about 4.6 to about 5.4, about 4.6 to about 5.2, about 4.6 to about 5.0, about 4.6 to about 4.8, about 4.8 to about 6.0, about 4.8 to about 5.8, about 4.8 to about 5.6, about 4.8 to about 5.4, about 4.8 to about 5.2, about 4.8 to about 5.0, about 5.0 to about 6.0, about 5.0 to about 5.8, about 5.0 to about 5.6, about 5.0 to about 5.4, about 5.0 to about 5.2, about 5.2 to about 6.0, about 5.2 to about 5.8, about 5.2 to about 5.6, about 5.2 to about 5.4, about 5.4 to about 6.0, about 5.4 to about 5.8, about 5.4 to about 5.6, about 5.6 to about 6.0, about 5.6 to about 5.8, or about 5.8 to about 6.0. Accordingly, in some embodiments, a method of treatment disclosed herein can include determining the ratio of the level of the JAK inhibitor in the GI tissue to the level of the JAK inhibitor in the blood, serum, or plasma of a subject at substantially the same time point following administration of the device is about 2.8 to about 6.0. Exemplary methods for measuring the concentration of an antibody or an antigen-binding antibody fragment in the plasma or the GI tissue of a subject are described herein. Additional methods for measuring the concentration of an antibody or an antigen-binding antibody fragment in the plasma or the GI tissue of a subject are known in the art.

Accordingly, in some embodiments, a method of treatment disclosed herein includes determining the level of the JAK inhibitor in the GI tissue (e.g., one or more of any of the exemplary GI tissues described herein). In some embodiments, a method of treatment disclosed herein can include determining the level of JAK inhibitor in one or more (e.g., two, three, or four) of the lumen/superficial mucosa, the lamina propria, the submucosa, and the tunica muscularis/serosa.

In some embodiments, a method of treatment disclosed herein includes determining that the level of the JAK inhibitor in the GI tissue (e.g., one or more of any of the exemplary types of GI tissues described herein) at a time point following administration of the device is higher than the level of JAK inhibitor in the GI tissue at substantially the same time point following systemic administration of an equal amount of the JAK inhibitor. In some embodiments, a method of treatment disclosed herein can include determining that the level of the JAK inhibitor in one or more (e.g., two, three, or four) of the lumen/superficial mucosa, the lamina propria, the submucosa, and the tunica muscularis/serosa at a time point following administration of the device is higher than the level of the JAK inhibitor in one or more (e.g., two, three, or four) of the lumen/superficial mucosa, the lamina propria, the submucosa, and the tunica muscularis/serosa at substantially the same time point following systemic administration of an equal amount of the JAK inhibitor.

In some embodiments, a method of treatment disclosed herein includes determining the level of JAK inhibitor in the feces of the subject. In some embodiments, a method of treatment disclosed herein includes determining the level of JAK inhibitor in the GI tissue, e.g., in one or more (e.g., two, three, or four) of the lumen/superficial mucosa, the lamina propria, the submucosa, and the tunica muscularis/serosa within a time period of about 10 minutes to about 10 hours following administration of the device.

In some embodiments, a method of treatment as disclosed herein comprises determining the level of the JAK inhibitor at the location of disease following administration of the device.

In some embodiments, a method of treatment as disclosed herein comprises determining that the level of JAK inhibitor at the location of disease at a time point following administration of the device is higher than the level of the JAK inhibitor at the same location of disease at substantially the same time point following systemic administration of an equal amount of the JAK inhibitor.

In some embodiments, a method of treatment as disclosed herein comprises determining that the level of JAK inhibitor in plasma in a subject at a time point following administration of the device is lower than the level of the JAK inhibitor in plasma in a subject at substantially the same time point following systemic administration of an equal amount of the JAK inhibitor.

In some embodiments, a method of treatment as disclosed herein comprises determining the level of the JAK inhibitor in the tissue of the subject within a time period of about 10 minutes to 10 hours following administration of the device.

Some examples of any of the methods described herein can, e.g., result in a selective suppression of a local inflammatory response (e.g., an inflammatory response in local GI tissue), while maintaining the systemic immune response (e.g., blood). The GI tissue may be, for example, GI tissue proximate to one or more sites of disease. FAs used herein, "GI content" refers to the content of the gastrointestinal (GI) tract, such as the content of one or more of duodenum, jejunum, ileum, cecum, ascending colon, transverse colon, descending colon, sigmoid colon, and rectum, more particularly of the proximal portion of one or more of duodenum, jejunum, ileum, cecum, ascending colon, transverse colon, descending colon, and sigmoid colon, or of the distal portion of one or more of duodenum, jejunum, ileum, cecum, ascending colon, transverse colon, descending colon, and sigmoid colon. Accordingly, in some embodiments, the methods described herein can result in a selective suppression of the inflammatory response in the dudodenum tissue proximate to one or more sites of disease, while maintaining the systemic immune response. In some embodiments, the methods described herein can result in a selective suppression of the inflammatory response in the jejunum tissue proximate to one or more sites of disease, while maintaining the systemic immune response. In some embodiments, the methods described herein can result in a selective suppression of the inflammatory response in the ileum tissue proximate to one or more sites of disease, while maintaining the systemic immune response. In some embodiments, the methods described herein can result in a selective suppression of the inflammatory response in the cecum tissue proximate to one or more sites of disease, while maintaining the systemic immune response. In some embodiments, the methods described herein can result in a selective suppression of the inflammatory response in the ascending colon tissue proximate to one or more sites of disease, while maintaining the systemic immune response. In some embodiments, the methods described herein can result in a selective suppression of the inflammatory response in the transverse colon tissue proximate to one or more sites of disease, while maintaining the systemic immune response. In some embodiments, the methods described herein can result in a selective suppression of the inflammatory response in the descending colon tissue proximate to one or more sites of disease, while maintaining the systemic immune response. In some embodiments, the methods described herein can result in a selective suppression of the inflammatory response in the sigmoid colon tissue proximate to one or more sites of disease, while maintaining the systemic immune response. In some examples, the methods described herein can result in a 1% increase to 500% increase (e.g., a 1% increase to 450% increase, a 1% increase to 400% increase, a 1% increase to 350% increase, a 1% increase to 300% increase, a 1% increase to 250% increase, a 1% increase to 200% increase, a 1% increase to 190% increase, a 1% increase to 180% increase, a 1% increase to 170% increase, a 1% increase to 160% increase, a 1% increase to 150% increase, a 1% increase to 140% increase, a 1% increase to 130% increase, a 1% increase to 120% increase, a 1% increase to 110% increase, a 1% increase to 100% increase, a 1% increase to 90% increase, a 1% increase to 80% increase, a 1% increase to 70% increase, a 1% increase to 60% increase, a 1% increase to 50% increase, a 1% increase to 40% increase, a 1% increase to 30% increase, a 1% increase to 25% increase, a 1% increase to 20% increase, a 1% increase to 15% increase, a 1% increase to 10% increase, a 1% increase to 5% increase, a 5% increase to 500% increase, a 5% increase to 450% increase, a 5% increase to 400% increase, a 5% increase to 350% increase, a 5% increase to 300% increase, a 5% increase to 250% increase, a 5% increase to 200% increase, a 5% increase to 190% increase, a 5% increase to 180% increase, a 5% increase to 170% increase, a 5% increase to 160% increase, a 5% increase to 150% increase, a 5% increase to 140% increase, a 5% increase to 130% increase, a 5% increase to 120% increase, a 5% increase to 110% increase, a 5% increase to 100% increase, a 5% increase to 90% increase, a 5% increase to 80% increase, a 5% increase to 70% increase, a 5% increase to 60% increase, a 5% increase to 50% increase, a 5% increase to 40% increase, a 5% increase to 30% increase, a 5% increase to 25% increase, a 5% increase to 20% increase, a 5% increase to 15% increase, a 5% increase to 10% increase, a 10% increase to 500% increase, a 10% increase to 450% increase, a 10% increase to 400% increase, a 10% increase to 350% increase, a 10% increase to 300% increase, a 10% increase to 250% increase, a 10% increase to 200% increase, a 10% increase to 190% increase, a 10% increase to 180% increase, a 10% increase to 170% increase, a 10% increase to 160% increase, a 10% increase to 150% increase, a 10% increase to 140% increase, a 10% increase to 130% increase, a 10% increase to 120% increase, a 10% increase to 110% increase, a 10% increase to 100% increase, a 10% increase to 90% increase, a 10% increase to 80% increase, a 10% increase to 70% increase, a 10% increase to 60% increase, a 10% increase to 50% increase, a 10% increase to 40% increase, a 10% increase to 30% increase, a 10% increase to 25% increase, a 10% increase to 20% increase, a 10% increase to 15% increase, a 15% increase to 500% increase, a 15% increase to 450% increase, a 15% increase to 400% increase, a 15% increase to 350% increase, a 15% increase to 300% increase, a 15% increase to 250% increase, a 15% increase to 200% increase, a 15% increase to 190% increase, a 15% increase to 180% increase, a 15% increase to 170% increase, a 15% increase to 160% increase, a 15% increase to 150% increase, a 15% increase to 140% increase, a 15% increase to 130% increase, a 15% increase to 120% increase, a 15% increase to 110% increase, a 15% increase to 100% increase, a 15% increase to 90% increase, a 15% increase to 80% increase, a 15% increase to 70% increase, a 15% increase to 60% increase, a 15% increase to 50% increase, a 15% increase to 40% increase, a 15% increase to 30% increase, a 15% increase to 25% increase, a 15% increase to 20% increase, a 20% increase to 500% increase, a 20% increase to 450% increase, a 20% increase to 400% increase, a 20% increase to 350% increase, a 20% increase to 300% increase, a 20% increase to 250% increase, a 20% increase to 200% increase, a 20% increase to 190% increase, a 20% increase to 180% increase, a 20% increase to 170% increase, a 20% increase to 160% increase, a 20% increase to 150% increase, a 20% increase to 140% increase, a 20% increase to 130% increase, a 20% increase to 120% increase, a 20% increase to 110% increase, a 20% increase to 100% increase, a 20% increase to 90% increase, a 20% increase to 80% increase, a 20% increase to 70% increase, a 20% increase to 60% increase, a 20% increase to 50% increase, a 20% increase to 40% increase, a 20% increase to 30% increase, a 20% increase to 25% increase, a 25% increase to 500% increase, a 25% increase to 450% increase, a 25% increase to 400% increase, a 25% increase to 350% increase, a 25% increase to 300% increase, a 25% increase to 250% increase, a 25% increase to 200% increase, a 25% increase to 190% increase, a 25% increase to 180% increase, a 25% increase to 170% increase, a 25% increase to 160% increase, a 25% increase to 150% increase, a 25% increase to 140% increase, a 25% increase to 130% increase, a 25% increase to 120% increase, a 25% increase to 110% increase, a 25% increase to 100% increase, a 25% increase to 90% increase, a 25% increase to 80% increase, a 25% increase to 70% increase, a 25% increase to 60% increase, a 25% increase to 50% increase, a 25% increase to 40% increase, a 25% increase to 30% increase, a 30% increase to 500% increase, a 30% increase to 450% increase, a 30% increase to 400% increase, a 30% increase to 350% increase, a 30% increase to 300% increase, a 30% increase to 250% increase, a 30% increase to 200% increase, a 30% increase to 190% increase, a 30% increase to 180% increase, a 30% increase to 170% increase, a 30% increase to 160% increase, a 30% increase to 150% increase, a 30% increase to 140% increase, a 30% increase to 130% increase, a 30% increase to 120% increase, a 30% increase to 110% increase, a 30% increase to 100% increase, a 30% increase to 90% increase, a 30% increase to 80% increase, a 30% increase to 70% increase, a 30% increase to 60% increase, a 30% increase to 50% increase, a 30% increase to 40% increase, a 40% increase to 500% increase, a 40% increase to 450% increase, a 40% increase to 400% increase, a 40% increase to 350% increase, a 40% increase to 300% increase, a 40% increase to 250% increase, a 40% increase to 200% increase, a 40% increase to 190% increase, a 40% increase to 180% increase, a 40% increase to 170% increase, a 40% increase to 160% increase, a 40% increase to 150% increase, a 40% increase to 140% increase, a 40% increase to 130% increase, a 40% increase to 120% increase, a 40% increase to 110% increase, a 40% increase to 100% increase, a 40% increase to 90% increase, a 40% increase to 80% increase, a 40% increase to 70% increase, a 40% increase to 60% increase, a 40% increase to 50% increase, a 50% increase to 500% increase, a 50% increase to 450% increase, a 50% increase to 400% increase, a 50% increase to 350% increase, a 50% increase to 300% increase, a 50% increase to 250% increase, a 50% increase to 200% increase, a 50% increase to 190% increase, a 50% increase to 180% increase, a 50% increase to 170% increase, a 50% increase to 160% increase, a 50% increase to 150% increase, a 50% increase to 140% increase, a 50% increase to 130% increase, a 50% increase to 120% increase, a 50% increase to 110% increase, a 50% increase to 100% increase, a 50% increase to 90% increase, a 50% increase to 80% increase, a 50% increase to 70% increase, a 50% increase to 60% increase, a 60% increase to 500% increase, a 60% increase to 450% increase, a 60% increase to 400% increase, a 60% increase to 350% increase, a 60% increase to 300% increase, a 60% increase to 250% increase, a 60% increase to 200% increase, a 60% increase to 190% increase, a 60% increase to 180% increase, a 60% increase to 170% increase, a 60% increase to 160% increase, a 60% increase to 150% increase, a 60% increase to 140% increase, a 60% increase to 130% increase, a 60% increase to 120% increase, a 60% increase to 110% increase, a 60% increase to 100% increase, a 60% increase to 90% increase, a 60% increase to 80% increase, a 60% increase to 70% increase, a 70% increase to 500% increase, a 70% increase to 450% increase, a 70% increase to 400% increase, a 70% increase to 350% increase, a 70% increase to 300% increase, a 70% increase to 250% increase, a 70% increase to 200% increase, a 70% increase to 190% increase, a 70% increase to 180% increase, a 70% increase to 170% increase, a 70% increase to 160% increase, a 70% increase to 150% increase, a 70% increase to 140% increase, a 70% increase to 130% increase, a 70% increase to 120% increase, a 70% increase to 110% increase, a 70% increase to 100% increase, a 70% increase to 90% increase, a 70% increase to 80% increase, a 80% increase to 500% increase, a 80% increase to 450% increase, a 80% increase to 400% increase, a 80% increase to 350% increase, a 80% increase to 300% increase, a 80% increase to 250% increase, a 80% increase to 200% increase, a 80% increase to 190% increase, a 80% increase to 180% increase, a 80% increase to 170% increase, a 80% increase to 160% increase, a 80% increase to 150% increase, a 80% increase to 140% increase, a 80% increase to 130% increase, a 80% increase to 120% increase, a 80% increase to 110% increase, a 80% increase to 100% increase, a 80% increase to 90% increase, a 90% increase to 500% increase, a 90% increase to 450% increase, a 90% increase to 400% increase, a 90% increase to 350% increase, a 90% increase to 300% increase, a 90% increase to 250% increase, a 90% increase to 200% increase, a 90% increase to 190% increase, a 90% increase to 180% increase, a 90% increase to 170% increase, a 90% increase to 160% increase, a 90% increase to 150% increase, a 90% increase to 140% increase, a 90% increase to 130% increase, a 90% increase to 120% increase, a 90% increase to 110% increase, a 90% increase to 100% increase, a 100% increase to 500% increase, a 100% increase to 450% increase, a 100% increase to 400% increase, a 100% increase to 350% increase, a 100% increase to 300% increase, a 100% increase to 250% increase, a 100% increase to 200% increase, a 100% increase to 190% increase, a 100% increase to 180% increase, a 100% increase to 170% increase, a 100% increase to 160% increase, a 100% increase to 150% increase, a 100% increase to 140% increase, a 100% increase to 130% increase, a 100% increase to 120% increase, a 100% increase to 110% increase, a 110% increase to 500% increase, a 110% increase to 450% increase, a 110% increase to 400% increase, a 110% increase to 350% increase, a 110% increase to 300% increase, a 110% increase to 250% increase, a 110% increase to 200% increase, a 110% increase to 190% increase, a 110% increase to 180% increase, a 110% increase to 170% increase, a 110% increase to 160% increase, a 110% increase to 150% increase, a 110% increase to 140% increase, a 110% increase to 130% increase, a 110% increase to 120% increase, a 120% increase to 500% increase, a 120% increase to 450% increase, a 120% increase to 400% increase, a 120% increase to 350% increase, a 120% increase to 300% increase, a 120% increase to 250% increase, a 120% increase to 200% increase, a 120% increase to 190% increase, a 120% increase to 180% increase, a 120% increase to 170% increase, a 120% increase to 160% increase, a 120% increase to 150% increase, a 120% increase to 140% increase, a 120% increase to 130% increase, a 130% increase to 500% increase, a 130% increase to 450% increase, a 130% increase to 400% increase, a 130% increase to 350% increase, a 130% increase to 300% increase, a 130% increase to 250% increase, a 130% increase to 200% increase, a 130% increase to 190% increase, a 130% increase to 180% increase, a 130% increase to 170% increase, a 130% increase to 160% increase, a 130% increase to 150% increase, a 130% increase to 140% increase, a 140% increase to 500% increase, a 140% increase to 450% increase, a 140% increase to 400% increase, a 140% increase to 350% increase, a 140% increase to 300% increase, a 140% increase to 250% increase, a 140% increase to 200% increase, a 140% increase to 190% increase, a 140% increase to 180% increase, a 140% increase to 170% increase, a 140% increase to 160% increase, a 140% increase to 150% increase, a 150% increase to 500% increase, a 150% increase to 450% increase, a 150% increase to 400% increase, a 150% increase to 350% increase, a 150% increase to 300% increase, a 150% increase to 250% increase, a 150% increase to 200% increase, a 150% increase to 190% increase, a 150% increase to 180% increase, a 150% increase to 170% increase, a 150% increase to 160% increase, a 160% increase to 500% increase, a 160% increase to 450% increase, a 160% increase to 400% increase, a 160% increase to 350% increase, a 160% increase to 300% increase, a 160% increase to 250% increase, a 160% increase to 200% increase, a 160% increase to 190% increase, a 160% increase to 180% increase, a 170% increase to 500% increase, a 170% increase to 450% increase, a 170% increase to 400% increase, a 170% increase to 350% increase, a 170% increase to 300% increase, a 170% increase to 250% increase, a 170% increase to 200% increase, a 170% increase to 190% increase, a 180% increase to 500% increase, a 180% increase to 450% increase, a 180% increase to 400% increase, a 180% increase to 350% increase, a 180% increase to 300% increase, a 180% increase to 250% increase, a 180% increase to 200% increase, a 180% increase to 190% increase, a 190% increase to 500% increase, a 190% increase to 450% increase, a 190% increase to 400% increase, a 190% increase to 350% increase, a 190% increase to 300% increase, a 190% increase to 250% increase, a 190% increase to 200% increase, a 200% increase to 500% increase, a 200% increase to 450% increase, a 200% increase to 400% increase, a 200% increase to 350% increase, a 200% increase to 300% increase, a 200% increase to 250% increase, a 250% increase to 500% increase, a 250% increase to 450% increase, a 250% increase to 400% increase, a 250% increase to 350% increase, a 250% increase to 300% increase, a 300% increase to 500% increase, a 300% increase to 450% increase, a 300% increase to 400% increase, a 300% increase to 350% increase, a 350% increase to 500% increase, a 350% increase to 450% increase, a 350% increase to 400% increase, a 400% increase to 500% increase, a 400% increase to 450% increase, or a 450% increase to 500% increase) in one or more (e.g., two, three, four, five, six, seven, eight, nine, or ten) of: the plasma, serum, or blood level of IL-6; the plasma, serum, or blood level of IL-2; the plasma, serum, or blood level of IL-1β; the plasma, serum, or blood level of TNFα; the plasma, serum, or blood level of IL-17A; the plasma, serum, or blood level of IL-22; the plasma, serum, or blood level of interferon-γ; the level of blood Th memory cells (CD44$^+$CD45RB$^-$CD4$^+$ cells); and the level of α4β7 expression in blood cells; e.g., each as compared to the corresponding level in a subject systemically administered the same dose of the same JAK inhibitor. Methods for determining the plasma, serum, or blood level of IL-6; the plasma, serum, or blood level of IL-2; the plasma, serum, or blood level of IL-1β; the plasma, serum, or blood level of TNFα; the plasma, serum, or blood level of IL-17A; the plasma, serum, or blood level of IL-22; the plasma, serum, or blood level of interferon-γ; the level of blood Th memory cells (CD44$^+$CD45RB$^-$CD4$^+$ cells); and the level of α4β7 expression in blood cells are known in the art.

In some examples of any of the methods described herein can result, e.g., in a 1% to 99% decrease (or any of the subranges of this range described herein) in one or more (e.g., two, three, four, five, six, or seven) of: the level of interferon-γ in GI tissue or GI content; the level of IL-1β in GI tissue or GI content; the level of IL-6 in GI tissue or GI content; the level of IL-22 in GI tissue or GI content; the level of IL-17A in GI tissue or GI content; the level of TNFα in GI tissue or GI content; and the level of IL-2 in GI tissue or GI content, e.g., as compared to the corresponding level in a subject not administered a treatment, or not administered a JAK inhibitor locally as disclosed herein. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the duodenum tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the ileum tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the jejunum tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the cecum tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the ascending colon tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the transverse colon tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the decending colon tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the sigmoid colon tissue proximate to one or more sites of disease.

In some embodiments, the JAK inhibitor is delivered to the location by a process that does not comprise systemic transport of the JAK inhibitor.

In some embodiments, the amount of the JAK inhibitor that is administered is from about 1 mg to about 500 mg. In some embodiments, the amount of the JAK inhibitor that is administered is from about 1 mg to about 100 mg. In some embodiments, the amount of the JAK inhibitor that is administered is from about 10 mg to about 300 mg. In some embodiments, the amount of the JAK inhibitor that is administered is from about 5 mg to about 50 mg. In some embodiments, the amount of the JAK inhibitor that is administered is from about 10 mg to about 50 mg. In some embodiments, the amount of the JAK inhibitor that is administered is from about 5 mg to about 40 mg.

In some embodiments, the amount of the JAK inhibitor that is administered is less than an amount that is effective when the JAK inhibitor is delivered systemically.

In some embodiments, the amount of the JAK inhibitor that is administered is an induction dose. In some embodiments, such induction dose is effective to induce remission of the TNF and cytokine storm and healing of acute inflammation and lesions. In some embodiments, the induction dose is administered once a day. In some embodiments, the induction dose is administered once every three days. In some embodiments, the induction dose is administered once a week. In some embodiments, the induction dose is administered once a day, once every three days, or once a week, over a period of about 6-8 weeks.

In some embodiments, the method comprises administering (i) an amount of the JAK inhibitor that is an induction dose, and (ii) an amount of the JAK inhibitor that is a maintenance dose, in this order. In some embodiments, step (ii) is repeated one or more times. In some embodiments, the induction dose is equal to the maintenance dose. In some embodiments, the induction dose is greater than the maintenance dose. In some embodiments, the induction dose is five times greater than the maintenance dose. In some embodiments, the induction dose is two times greater than the maintenance dose.

In some embodiments, the induction dose is the same as or higher than an induction dose administered systemically for treatment of the same disorder to a subject. In more particular embodiments, the induction dose is the same as or higher than an induction dose administered systemically for treatment of the same disorder to a subject, and the maintenance dose is lower than the maintenance dose administered systemically for treatment of the same disorder to a subject. In some embodiments, the induction dose is the same as or higher than an induction dose administered systemically for treatment of the same disorder to a subject, and the maintenance dose is higher than the maintenance dose administered systemically for treatment of the same disorder to a subject.

In some embodiments an induction dose of JAK inhibitor and a maintenance dose of JAK inhibitor are each administered to the subject by administering a pharmaceutical composition comprising a therapeutically effective amount of the JAK inhibitor, wherein the pharmaceutical composition is a device. In some embodiments an induction dose of JAK inhibitor is administered to the subject in a different manner from the maintenance dose. As an example, the induction dose may be administered systemically. In some embodiments, the induction dose may be administered other than orally. As an example, the induction dose may be administered rectally. As an example, the induction dose may be administered intravenously. As an example, the induction dose may be administered subcutaneously. In some embodiments, the induction dose may be administered by spray catheter.

In some embodiments, the concentration of the JAK inhibitor delivered at the location in the gastrointestinal tract is 10%, 25%, 50%, 75%, 100%, 200%, 300%, 400%, 500%, 1000%, 2000% greater than the concentration of JAK inhibitor in plasma.

In some embodiments, the method provides a concentration of the JAK inhibitor at a location that is a site of disease or proximate to a site of disease that is 2-100 times greater than at a location that is not a site of disease or proximate to a site of disease.

In some embodiments, the method comprises delivering the JAK inhibitor at the location in the gastrointestinal tract as a single bolus.

In some embodiments, the method comprises delivering the JAK inhibitor at the location in the gastrointestinal tract as more than one bolus.

In some embodiments, the method comprises delivering the JAK inhibitor at the location in the gastrointestinal tract in a continuous manner.

In some embodiments, the method comprises delivering the JAK inhibitor at the location in the gastrointestinal tract over a time period of 20 or more minutes.

In some embodiments, the method provides a concentration of the JAK inhibitor in the plasma of the subject that is less than 10 µg/ml. In some embodiments, the method provides a concentration of the JAK inhibitor in the plasma of the subject that is less than 3 µg/ml. In some embodiments, the method provides a concentration of the JAK inhibitor in the plasma of the subject that is less than 1 µg/ml. In some embodiments, the method provides a concentration of the JAK inhibitor in the plasma of the subject that is less than 0.3 µg/ml. In some embodiments, the method provides a concentration of the JAK inhibitor in the plasma of the subject that is less than 0.1 µg/ml. In some embodiments, the method provides a concentration of the JAK inhibitor in the plasma of the subject that is less than 0.01 µg/ml. In some embodiments, the values of the concentration of the JAK inhibitor in the plasma of the subject provided herein refer to $C_{trough}$, that is, the lowest value of the concentration prior to administration of the next dose.

In some embodiments, the method provides a concentration $C_{max}$ of the JAK inhibitor in the plasma of the subject that is less than 10 µg/ml. In some embodiments, the method provides a concentration $C_{max}$ of the JAK inhibitor in the plasma of the subject that is less than 3 µg/ml. In some embodiments, the method provides a concentration $C_{max}$ of the JAK inhibitor in the plasma of the subject that is less than 1 µg/ml. In some embodiments, the method provides a concentration $C_{max}$ of the JAK inhibitor in the plasma of the subject that is less than 0.3 µg/ml. In some embodiments, the method provides a concentration $C_{max}$ of the JAK inhibitor in the plasma of the subject that is less than 0.1 µg/ml. In some embodiments, the method provides a concentration $C_{max}$ of the JAK inhibitor in the plasma of the subject that is less than 0.01 µg/ml.

In some embodiments, the method does not comprise delivering a JAK inhibitor rectally to the subject.

In some embodiments, the method does not comprise delivering a JAK inhibitor via an enema to the subject.

In some embodiments, the method does not comprise delivering a JAK inhibitor via suppository to the subject.

In some embodiments, the method does not comprise delivering a JAK inhibitor via instillation to the rectum of a subject.

In some embodiments, the methods disclosed herein comprise producing a therapeutically effective degradation product of the JAK inhibitor in the gastrointestinal tract. In some embodiments, the degradation product is a therapeutic antibody fragment. In some embodiments, a therapeutically effective amount of the degradation product is produced.

In some embodiments, the antibody can be a humanized antibody, a chimeric antibody, a multivalent antibody, or a fragment thereof. In some embodiments, an antibody can be a scFv-Fc (Sokolowska-Wedzina et al., Mol. Cancer Res. 15(8):1040-1050, 2017), a VHH domain (Li et al., Immunol. Lett. 188:89-95, 2017), a VNAR domain (Hasler et al., Mol. Immunol. 75:28-37, 2016), a (scFv)$_2$, a minibody (Kim et al., PLoS One 10(1):e113442, 2014), or a BiTE. In some embodiments, an antibody can be a DVD-Ig (Wu et al., Nat. Biotechnol. 25(11):1290-1297, 2007; WO 08/024188; WO 07/024715), and a dual-affinity re-targeting antibody (DART) (Tsai et al., Mol. Ther. Oncolytics 3:15024, 2016), a triomab (Chelius et al., MAbs 2(3):309-319, 2010), kih IgG with a common LC (Kontermann et al., Drug Discovery Today 20(7):838-847, 2015), a crossmab (Regula et al., EMBO Mol. Med. 9(7):985, 2017), an ortho-Fab IgG (Kontermann et al., Drug Discovery Today 20(7):838-847, 2015), a 2-in-1-IgG (Kontermann et al., Drug Discovery Today 20(7):838-847, 2015), IgG-scFv (Cheal et al., Mol. Cancer Ther. 13(7):1803-1812, 2014), scFv2-Fc (Natsume et al., J. Biochem. 140(3):359-368, 2006), a bi-nanobody (Kontermann et al., Drug Discovery Today 20(7):838-847, 2015), tanden antibody (Kontermann et al., Drug Discovery Today 20(7):838-847, 2015), a DART-Fc (Kontermann et al., Drug Discovery Today 20(7):838-847, 2015), a scFv-HSA-scFv (Kontermann et al., Drug Discovery Today 20(7):838-847, 2015), DNL-Fab3 (Kontermann et al., Drug Discovery Today 20(7):838-847, 2015), DAF (two-in-one or four-in-one), DutaMab, DT-IgG, knobs-in-holes common LC, knobs-in-holes assembly, charge pair antibody, Fab-arm exchange antibody, SEEDbody, Triomab, LUZ-Y, Fcab, kλ-body, orthogonal Fab, DVD-IgG, IgG(H)-scFv, scFv-(H) IgG, IgG(L)-scFv, scFv-(L)-IgG, IgG (L,H)-Fc, IgG(H)-V, V(H)-IgG, IgG(L)-V, V(L)-IgG, KIH IgG-scFab, 2scFv-IgG, IgG-2scFv, scFv4-Ig, Zybody, DVI-IgG, nanobody (e.g., antibodies derived from Camelus bactriamus, Calelus dromaderius, or Lama paccos) (U.S. Pat. No. 5,759,808; Stijlemans et al., J. Biol. Chem. 279:1256-1261, 2004; Dumoulin et al., Nature 424:783-788, 2003; and Pleschberger et al., Bioconjugate Chem. 14:440-448, 2003), nanobody-HSA, a diabody (e.g., Poljak, Structure 2(12): 1121-1123, 1994; Hudson et al., J. Immunol. Methods 23(1-2):177-189, 1999), a TandAb (Reusch et al., mAbs 6(3):727-738, 2014), scDiabody (Cuesta et al., Trends in Biotechnol. 28(7):355-362, 2010), scDiabody-CH3 (Sanz et al., Trends in Immunol. 25(2):85-91, 2004), Diabody-CH3 (Guo et al., Triple Body, miniantibody, minibody, TriBi minibody, scFv-CH3 KIH, Fab-scFv, scFv-CH-CL-scFv, F(ab')2-scFV2, scFv-KIH, Fab-scFv-Fc, tetravalent HCAb, scDiabody-Fc, diabody-Fc, tandem scFv-Fc, intrabody (Huston et al., Human Antibodies 10(3-4):127-142, 2001; Wheeler et al., Mol. Ther. 8(3):355-366, 2003; Stocks, Drug Discov. Today 9(22):960-966, 2004), dock and lock bispecific antibody, ImmTAC, HSAbody, scDiabody-HSA, tandem scFv, IgG-IgG, Cov-X-Body, and scFv1-PEG-scFv2.

Non-limiting examples of an antigen-binding fragment of an antibody include an Fv fragment, a Fab fragment, a F(ab')$_2$ fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

In some embodiments, an antibody can be an IgNAR, a bispecific antibody (Milstein and Cuello, Nature 305:537-539, 1983; Suresh et al., Methods in Enzymology 121:210, 1986; WO 96/27011; Brennan et al., Science 229:81, 1985; Shalaby et al., J. Exp. Med. 175:217-225, 1992; Kolstelny et al., J. Immunol. 148(5):1547-1553, 1992; Hollinger et al., Proc. Natl. Acad. Sci. U.S.A. 90:6444-6448, 1993; Gruber et al., J. Immunol. 152:5368, 1994; Tuft et al., J. Immunol. 147:60, 1991), a bispecific diabody, a triabody (Schoonooghe et al., BMC Biotechnol. 9:70, 2009), a tetrabody, scFv-Fc knobs-into-holes, a scFv-Fc-scFv, a (Fab'scFv)$_2$, a V-IgG, a IvG-V, a dual V domain IgG, a heavy chain immunoglobulin or a camelid (Holt et al., Trends Biotechnol. 21(11):484-490, 2003), an intrabody, a monoclonal antibody (e.g., a human or humanized monoclonal antibody), a heteroconjugate antibody (e.g., U.S. Pat. No. 4,676, 980), a linear antibody (Zapata et al., *Protein Eng.* 8(10: 1057-1062, 1995), a trispecific antibody (Tuft et al., *J. Immunol.* 147:60, 1991), a Fabs-in-Tandem immunoglobulin (WO 15/103072), or a humanized camelid antibody.

In some embodiments, the methods comprising administering the JAK inhibitor in the manner disclosed herein disclosed herein result in a reduced immunosuppressive properties relative to methods of administration of the JAK inhibitor systemically.

In some embodiments, the methods comprising administering the JAK inhibitor in the manner disclosed herein disclosed herein result in reduced immunogenicity relative to methods of administration of the JAK inhibitor systemically.

Methods for Treating Colitis in Subjects in Immune-Oncology Therapy

In some embodiments, provided herein is a method for treating colitis as disclosed herein in a subject, comprising releasing a JAK inhibitor at a location in the gastrointestinal tract of the subject that is proximate to one or more sites of disease, wherein the method comprises administering to the subject a pharmaceutical composition comprising a therapeutically effective amount of the JAK inhibitor, wherein the colitis is associated with treatment of the subject with one or more immuno-oncology agents. In some embodiments, the pharmaceutical composition is an ingestible device. In some embodiments, the pharmaceutical composition is an ingestible device and the method comprises administering orally to the subject the pharmaceutical composition.

In some embodiments, at least one of the one or more immuno-oncology agents is a chemotherapeutic agent. In some embodiments, the chemotherapeutic agent is a chemotherapeutic immunomodulator. In some embodiments, the chemotherapeutic immunomodulator is an immune checkpoint inhibitor.

In some embodiments, the immune checkpoint inhibitor targets an immune checkpoint protein or decreases an activity of an immune checkpoint protein selected from the group of CTLA-4, PD-1, PD-L1, PD-1-PD-L1, PD-1-PD-L2, interleukin 2 (IL 2), indoleamine 2,3-dioxygenase (IDO), IL 10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4 1BB-4 1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7 H3, B7 H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155.

In some examples, the immune checkpoint inhibitor is selected from the group consisting of: Urelumab, PF 05082566, MEDI6469, TRX518, Varlilumab, CP 870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS 986016, MGA271, Lirilumab, IPH2201, Emactuzumab, INCB024360, Galunisertib, Ulocuplumab, BKT140, Bavituximab, CC 90002, Bevacizumab, and MNRP1685A, and MGA271.

In some examples, the immune checkpoint inhibitor targets or decreases an activity of CTLA-4. In some embodiments, the immune checkpoint inhibitor is an antibody. In some embodiments, the antibody is ipilimumab or tremelimumab.

In some examples, the immune checkpoint inhibitor targets PD1 or PD-L1. In some examples, the immune checkpoint inhibitor is selected from nivolumab, lambroizumab, and BMS-936559.

In some embodiments, at least one of the one or more immuno-oncology agents is a T-cell capable of expressing a chimeric antigen receptor (CAR). In some embodiments, at least one of the one or more immuno-oncology agents is a PI-3-kinase inhibitor.

In some embodiments, the treatment of the subject with one or more immuno-oncology agents further comprises treatment of the subject with an immunosuppressant.

In some embodiments, provided herein is a method for reducing the development of colitis in a subject administered an immuno-oncology agent, comprising releasing a JAK inhibitor at a location in the gastrointestinal tract of the subject that is proximate to one or more sites of disease, wherein the method comprises administering to the subject a pharmaceutical composition comprising a therapeutically effective amount of the JAK inhibitor. In some embodiments, the pharmaceutical composition is an ingestible device. In some embodiments, the pharmaceutical composition is an ingestible device and the method comprises administering orally to the subject the pharmaceutical composition.

In some embodiments of these methods, a subject is administered at least one dose of an immuno-oncology agent prior to administering a pharmaceutical composition comprising any of the devices described herein as described herein to the subject. In some embodiments of these methods, a subject is first administered any of the devices as described herein, prior to administration of the first dose of the immuno-oncology agent. In some embodiments of these methods, the immuno-oncology agent is administered at substantially the same time as the device described herein.

Also provided herein are methods of treating a subject having a cancer that include: administering a first dose of an immuno-oncology agent to the subject; monitoring one or more biomarkers, markers, or symptoms of colitis (e.g., any of the biomarkers, markers, or symptoms of colitis described herein or known in the art); identifying a subject having a level of a biomarker or marker, or having a symptom of colitis; and releasing a JAK inhibitor at a location in the gastrointestinal tract of the subject that is proximate to one or more sites of disease, wherein the method comprises administering to the subject a pharmaceutical composition comprising a therapeutically effective amount of the JAK inhibitor. In some embodiments, the pharmaceutical composition is an ingestible device. In some embodiments, the pharmaceutical composition is an ingestible device and the method comprises administering orally to the subject the pharmaceutical composition.

Also provided herein are methods of reducing the severity of colitis in a subject having a cancer and administered an immuno-oncology agent that include administering to the subject any of the devices described herein.

In some embodiments, provided herein is a method for treating colitis in a subject comprising:

determining that the subject has colitis associated with treatment of the subject with one or more immuno-oncology agents; and releasing a JAK inhibitor at a location in the gastrointestinal tract of the subject that is proximate to one or more sites of colitis, wherein the method comprises administering to the subject a pharmaceutical composition comprising a therapeutically effective amount of the JAK inhibitor. In some embodiments, the pharmaceutical composition is an ingestible device. In some embodiments, the pharmaceutical composition is an ingestible device and the method comprises administering orally to the subject the pharmaceutical composition.

In some embodiments, provided herein is a method for treating colitis in a subject comprising:

determining that the subject has colitis associated with treatment of the subject with one or more immuno-oncology agents; and administering to the subject an ingestible device comprisingany of the JAK inhibitors described herein, to treat the colitis.

In some embodiments, provided herein is a method for treating colitis, comprising releasing a JAK inhibitor at a location in the gastrointestinal tract of a subject who has been determined to have colitis associated with treatment of the subject with one or more immuno-oncology agents, wherein the location is proximate to one or more sites of colitis, wherein the method comprises administering to the subject a pharmaceutical composition comprising a therapeutically effective amount of the JAK inhibitor. In some embodiments, the pharmaceutical composition is an ingestible device. In some embodiments, the pharmaceutical composition is an ingestible device and the method comprises administering orally to the subject the pharmaceutical composition.

In some embodiments, provided herein is a method for treating colitis, comprising administering an ingestible device comprising any of the JAK inhibitors described herein to a subject who has been determined to have colitis associated with treatment of the subject with one or more immuno-oncology agents.

In some embodiments, provided herein is an ingestible device comprising any of the JAK inhibitors described herein for treating colitis associated with treatment of a subject with one or more immuno-oncology agents.

Monitoring Progress of Disease

In some embodiments, the methods provided herein comprise monitoring the progress of the disease. In some embodiments, monitoring the progress of the disease comprises measuring the levels of IBD serological markers. In some embodiments, monitoring the progress of the disease comprises determining mucosal healing at the location of release. In some embodiments, monitoring the progress of the disease comprises determining the Crohn's Disease Activity Index (CDAI) over a period of about 6-8 weeks, or over a period of about 52 weeks, following administration of the JAK inhibitor. In some embodiments, monitoring the progress of the disease comprises determining the Harvey-Bradshaw Index (HBI) following administration of the JAK inhibitor. Possible markers may include the following: anti-glycan antibodies: anti-*Saccharomices cerevisiae* (ASCA); anti-laminaribioside (ALCA); anti-chitobioside (ACCA); anti-mannobioside (AMCA); anti-laminarin (anti-L); anti-chitin (anti-C) antibodies: anti-outer membrane porin C (anti-OmpC), anti-Cbir1 flagellin; anti-12 antibody; autoantibodies targeting the exocrine pancreas (PAB); perinuclear anti-neutrophil antibody (pANCA). In some embodiments, monitoring the progress of the disease comprises measuring JAK inhibitor levels in serum over a period of about 1-14 weeks, such as about 6-8 weeks following administration of the JAK inhibitor, including at the 6-8 week time point. In some embodiments, monitoring the progress of the disease comprises measuring JAK inhibitor levels in serum over a period of about 52 weeks following administration of the JAK inhibitor, including at the 52 week time point.

Patients Condition, Diagnosis and Treatment

In some embodiments herein, the method of treating a disease of the gastrointestinal tract that comprises releasing a JAK inhibitor at a location in the gastrointestinal tract that is proximate to one or more sites of disease comprises one or more of the following:

a) identifying a subject having a disease of the gastrointestinal tract, for example by endoscopy or colonoscopy;

b) determination of the severity of the disease, for example with reference to the Mayo Clinic Score, the Crohn's Disease Activity Index (CDAI), the Harvey-Bradshaw Index (HBI), or a combination of the above;

c) determination of the location of the disease, for example as determined by the presence of lesions indicative of the disease;

d) evaluating the subject for suitability to treatment, for example by determining the patency of the subject's GI tract, for example if the indication is small intestinal diseases, pancolitis, Crohn's disease, or if the patients has strictures or fistulae;

e) administration of an induction dose or of a maintenance dose of a drug, such as the JAK inhibitor or such as another drug that is effective in the treatment of IBD conditions;

f) monitoring the progress of the disease, for example with reference to the Mayo Clinic Score, the Crohn's Disease Activity Index (CDAI), the Harvey-Bradshaw Index (HBI), the PRO, PRO2 or PRO3 tools, or a combination of the above; and/or g) optionally repeating steps e) and f) one or more times, for example over a period of about 1-14 weeks, such as about 6-8 weeks following administration of the JAK inhibitor, including at the 6-8 week time point, or over a period of about 52 weeks following administration of the JAK inhibitor, including at the 52 week time point.

As used herein, an induction dose is a dose of drug that may be administered, for example, at the beginning of a course of treatment, and that is higher than the maintenance dose administered during treatment. An induction dose may also be administered during treatment, for example if the condition of the patients becomes worse.

As used herein, a maintenance dose is a dose of drug that is provided on a repetitive basis, for example at regular dosing intervals.

In some embodiments the JAK inhibitor is released from an ingestible device.

In some embodiments herein, the method of treating a disease of the gastrointestinal tract that comprises releasing a JAK inhibitor at a location in the gastrointestinal tract that is proximate to one or more sites of disease comprises a) hereinabove.

In some embodiments herein, the method of treating a disease of the gastrointestinal tract that comprises releasing a JAK inhibitor at a location in the gastrointestinal tract that is proximate to one or more sites of disease comprises b) hereinabove.

In some embodiments herein, the method of treating a disease of the gastrointestinal tract that comprises releasing a JAK inhibitor at a location in the gastrointestinal tract that is proximate to one or more sites of disease comprises c) hereinabove.

In some embodiments herein, the method of treating a disease of the gastrointestinal tract that comprises releasing a JAK inhibitor at a location in the gastrointestinal tract that is proximate to one or more sites of disease comprises d) hereinabove.

In some embodiments herein, the method of treating a disease of the gastrointestinal tract that comprises releasing a JAK inhibitor at a location in the gastrointestinal tract that is proximate to one or more sites of disease comprises e) hereinabove.

In some embodiments herein, the method of treating a disease of the gastrointestinal tract that comprises releasing a JAK inhibitor at a location in the gastrointestinal tract that is proximate to one or more sites of disease comprises f) hereinabove.

In some embodiments herein, the method of treating a disease of the gastrointestinal tract that comprises releasing a JAK inhibitor at a location in the gastrointestinal tract that is proximate to one or more sites of disease comprises g) hereinabove.

In some embodiments herein, the method of treating a disease of the gastrointestinal tract that comprises releasing a JAK inhibitor at a location in the gastrointestinal tract that is proximate to one or more sites of disease comprises a) and b) hereinabove. In some embodiments herein, the method of treating a disease of the gastrointestinal tract that comprises releasing a JAK inhibitor at a location in the gastrointestinal tract that is proximate to one or more sites of disease comprises a) and c) hereinabove. In some embodiments herein, the method of treating a disease of the gastrointestinal tract that comprises releasing a JAK inhibitor at a location in the gastrointestinal tract that is proximate to one or more sites of disease comprises a) and d) hereinabove. In some embodiments herein, the method of treating a disease of the gastrointestinal tract that comprises releasing a JAK inhibitor at a location in the gastrointestinal tract that is proximate to one or more sites of disease comprises a) and e) hereinabove. In some embodiments herein, the method of treating a disease of the gastrointestinal tract that comprises releasing a JAK inhibitor at a location in the gastrointestinal tract that is proximate to one or more sites of disease comprises a) and f) hereinabove. In some embodiments herein, the method of treating a disease of the gastrointestinal tract that comprises releasing a JAK inhibitor at a location in the gastrointestinal tract that is proximate to one or more sites of disease comprises a) and g) hereinabove. In some embodiments herein, the method of treating a disease of the gastrointestinal tract that comprises releasing a JAK inhibitor at a location in the gastrointestinal tract that is proximate to one or more sites of disease comprises b) and c) hereinabove. In some embodiments herein, the method of treating a disease of the gastrointestinal tract that comprises releasing a JAK inhibitor at a location in the gastrointestinal tract that is proximate to one or more sites of disease comprises b) and d) hereinabove. In some embodiments herein, the method of treating a disease of the gastrointestinal tract that comprises releasing a JAK inhibitor at a location in the gastrointestinal tract that is proximate to one or more sites of disease comprises b) and e) hereinabove. In some embodiments herein, the method of treating a disease of the gastrointestinal tract that comprises releasing a JAK inhibitor at a location in the gastrointestinal tract that is proximate to one or more sites of disease comprises b) and f) hereinabove. In some embodiments herein, the method of treating a disease of the gastrointestinal tract that comprises releasing a JAK inhibitor at a location in the gastrointestinal tract that is proximate to one or more sites of disease comprises b) and g) hereinabove. In some embodiments herein, the method of treating a disease of the gastrointestinal tract that comprises releasing a JAK inhibitor at a location in the gastrointestinal tract that is proximate to one or more sites of disease comprises c) and d) hereinabove. In some embodiments herein, the method of treating a disease of the gastrointestinal tract that comprises releasing a JAK inhibitor at a location in the gastrointestinal tract that is proximate to one or more sites of disease comprises c) and e) hereinabove. In some embodiments herein, the method of treating a disease of the gastrointestinal tract that comprises releasing a JAK inhibitor at a location in the gastrointestinal tract that is proximate to one or more sites of disease comprises c) and f) hereinabove. In some embodiments herein, the method of treating a disease of the gastrointestinal tract that comprises releasing a JAK inhibitor at a location in the gastrointestinal tract that is proximate to one or more sites of disease comprises c) and g) hereinabove. In some embodiments herein, the method of treating a disease of the gastrointestinal tract that comprises releasing a JAK inhibitor at a location in the gastrointestinal tract that is proximate to one or more sites of disease comprises d) and e) hereinabove. In some embodiments herein, the method of treating a disease of the gastrointestinal tract that comprises releasing a JAK inhibitor at a location in the gastrointestinal tract that is proximate to one or more sites of disease comprises d) and f) hereinabove. In some embodiments herein, the method of treating a disease of the gastrointestinal tract that comprises releasing a JAK inhibitor at a location in the gastrointestinal tract that is proximate to one or more sites of disease comprises d) and g) hereinabove. In some embodiments herein, the method of treating a disease of the gastrointestinal tract that comprises releasing a JAK inhibitor at a location in the gastrointestinal tract that is proximate to one or more sites of disease comprises e) and f) hereinabove. In some embodiments herein, the method of treating a disease of the gastrointestinal tract that comprises releasing a JAK inhibitor at a location in the gastrointestinal tract that is proximate to one or more sites of disease comprises g) hereinabove.

In some embodiments, one or more steps a) to e) herein comprise endoscopy of the gastrointestinal tract. In some embodiments, one or more steps a) to e) herein comprise colonoscopy of the gastrointestinal tract. In some embodiments, one or more steps a) to e) herein is performed one or more times. In some embodiments, such one or more of such one or more steps a) to e) is performed after releasing the JAK inhibitor at the location in the gastrointestinal tract that is proximate to one or more sites of disease.

In some embodiments, the method comprises administering one or more maintenance doses following administration of the induction dose in step e). In some embodiments an induction dose of JAK inhibitor and a maintenance dose of JAK inhibitor are each administered to the subject by administering a pharmaceutical composition comprising a therapeutically effective amount of the JAK inhibitor. In some embodiments an induction dose of JAK inhibitor is administered to the subject in a different manner from the maintenance dose. As an example, the maintenance dose may be administered systemically, while the maintenance dose is administered locally using a device. In one embodiment, a maintenance dose is administered systemically, and an induction dose is administered using a device every 1, 2, 3, 4, 5, 6, 7, 10, 15, 20, 25, 30, 35, 40, or 45 days. In another embodiment, a maintenance dose is administered systemically, and an induction dose is administered when a disease flares up is detected or suspected.

In some embodiments, the induction dose is a dose of the JAK inhibitor administered in an ingestible device as disclosed herein. In some embodiments, the maintenance dose is a dose of the JAK inhibitor administered in an ingestible device as disclosed herein.

In some embodiments, the induction dose is a dose of the JAK inhibitor administered in an ingestible device as disclosed herein. In some embodiments, the maintenance dose is a dose of the JAK inhibitor delivered systemically, such as orally with a tablet or capsule, or subcutaneously, or intravenously.

In some embodiments, the induction dose is a dose of the JAK inhibitor delivered systemically, such as orally with a tablet or capsule, or subcutaneously, or intravenously. In some embodiments, the maintenance dose is a dose of the JAK inhibitor administered in an ingestible device as disclosed herein.

In some embodiments, the induction dose is a dose of the JAK inhibitor administered in an ingestible device as disclosed herein. In some embodiments, the maintenance dose is a dose of a second agent as disclosed herein delivered systemically, such as orally with a tablet or capsule, or subcutaneously, or intravenously.

In some embodiments, the induction dose is a dose of a second agent as disclosed herein delivered systemically, such as orally with a tablet or capsule, or subcutaneously, or intravenously. In some embodiments, the maintenance dose is a dose of the JAK inhibitor administered in an ingestible device as disclosed herein.

In one embodiment of the methods provided herein, the patient is not previously treated with a JAK inhibitor. In one embodiment, the gastrointestinal inflammatory disorder is an inflammatory bowel disease. In one embodiment, the inflammatory bowel disease is ulcerative colitis or Crohn's disease. In one embodiment, the inflammatory bowel disease is ulcerative colitis and the response is selected from clinical response, mucosal healing and remission. In certain embodiments, remission in the patient is determined to be induced when the Mayo Clinic Score<2 and no individual subscore>1, which is also referred to as clinical remission. In certain embodiments, mucosal healing is determined to have occurred when the patient is determined to have an endoscopy subscore of 0 or 1 as assessed by flexible sigmoidoscopy. In certain such embodiments, patients who experience mucosal healing are determined to have an endoscopy subscore of 0. In certain embodiments, clinical response is determined to have occurred when the patient experiences a 3-point decrease and 30% reduction from baseline in MCS and >1-point decrease in rectal bleeding subscore or absolute rectal bleeding score of 0 or 1.

In some embodiments, the method comprises identifying the disease site substantially at the same time as releasing the JAK inhibitor.

In some embodiments, the method comprises monitoring the progress of the disease. In some embodiments, monitoring the progress of the disease comprises measuring the weight of the subject over a period of about 1-14 weeks, such as about 6-8 weeks following administration of the JAK inhibitor, including at the 6-8 week time point, or over a period of about 52 weeks following administration of the JAK inhibitor, including at the 52 week time point. In some embodiments, monitoring the progress of the disease comprises measuring the food intake of the subject; measuring the level of blood in the feces of the subject; measuring the level of abdominal pain of the subject; and/or a combination of the above, for example over a period of about 1-14 weeks, such as about 6-8 weeks following administration of the JAK inhibitor, including at the 6-8 week time point, or over a period of about 52 weeks following administration of the JAK inhibitor, including at the 52 week time point.

In some embodiments, the method comprises administering a JAK inhibitor with a spray catheter. For example, administering a JAK inhibitor with a spray catheter may be performed in step (e) hereinabove.

In some embodiments, the method does not comprise administering a JAK inhibitor with a spray catheter.

In some embodiments, data obtained from cell culture assays and animal studies can be used in formulating an appropriate dosage of any given JAK inhibitor. The effectiveness and dosing of any JAK inhibitor can be determined by a health care professional or veterinary professional using methods known in the art, as well as by the observation of one or more disease symptoms in a subject (e.g., a human). Certain factors may influence the dosage and timing required to effectively treat a subject (e.g., the severity of the disease or disorder, previous treatments, the general health and/or age of the subject, and the presence of other diseases).

In some embodiments, the subject is further administered an additional therapeutic agent (e.g., any of the additional therapeutic agents described herein). The additional therapeutic agent can be administered to the subject at substantially the same time as the JAK inhibitor or pharmaceutical composition comprising it is administered and/or at one or more other time points. In some embodiments, the additional therapeutic agent is formulated together with the JAK inhibitor (e.g., using any of the examples of formulations described herein).

In some embodiments, the subject is administered a dose of the JAK inhibitor at least once a month (e.g., at least twice a month, at least three times a month, at least four times a month, at least once a week, at least twice a week, three times a week, once a day, or twice a day). The JAK inhibitor may be administered to a subject chronically. Chronic treatments include any form of repeated administration for an extended period of time, such as repeated administrations for one or more months, between a month and a year, one or more years, more than five years, more than 10 years, more than 15 years, more than 20 years, more than 25 years, more than 30 years, more than 35 years, more than 40 years, more than 45 years, or longer. Alternatively, or in addition, chronic treatments may be administered. Chronic treatments can involve regular administrations, for example one or more times a day, one or more times a week, or one or more times a month. For example, chronic treatment can include administration (e.g., intravenous administration) about every two weeks (e.g., between about every 10 to 18 days).

A suitable dose may be the amount that is the lowest dose effective to produce a desired therapeutic effect. Such an effective dose will generally depend upon the factors described herein. If desired, an effective daily dose of JAK inhibitor can be administered as two, three, four, five, or six or more sub-doses administered separately at appropriate intervals throughout the day, optionally, in unit dosage forms.

In some examples, administration of an JAK inhibitorusing any of the compositions or devices described herein can result in the onset of treatment (e.g., a reduction in the number, severity, or duration of one or more symptoms and/or markers of any of the diseases described herein) or drug-target engagement in a subject within a time period of about 10 minutes to about 10 hours, about 10 minutes to about 9 hours, about 10 minutes to about 8 hours, about 10 minutes to about 7 hours, about 10 minutes to about 6 hours, about 10 minutes to about 5 hours, about 10 minutes to about 4.5 hours, about 10 minutes to about 4 hours, about 10 minutes to about 3.5 hours, about 10 minutes to about 3 hours, about 10 minutes to about 2.5 hours, about 10 minutes to about 2 hours, about 10 minutes to about 1.5 hours, about 10 minutes to about 1 hour, about 10 minutes to about 55 minutes, about 10 minutes to about 50 minutes, about 10 minutes to about 45 minutes, about 10 minutes to about 40 minutes, about 10 minutes to about 35 minutes, about 10 minutes to about 30 minutes, about 10 minutes to about 25 minutes, about 10 minutes to about 20 minutes, about 10 minutes to about 15 minutes, about 15 minutes to about 10 hours, about 15 minutes to about 9 hours, about 15 minutes to about 8 hours, about 15 minutes to about 7 hours, about 15 minutes to about 6 hours, about 15 minutes to about 5 hours, about 15 minutes to about 4.5 hours, about 15 minutes to about 4 hours, about 15 minutes to about 3.5 hours, about 15 minutes to about 3 hours, about 15 minutes to about 2.5 hours, about 15 minutes to about 2 hours, about 15 minutes to about 1.5 hours, about 15 minutes to about 1 hour, about 15 minutes to about 55 minutes, about 15 minutes to about 50 minutes, about 15 minutes to about 45 minutes, about 15 minutes to about 40 minutes, about 15 minutes to about 35 minutes, about 15 minutes to about 30 minutes, about 15 minutes to about 25 minutes, about 15 minutes to about 20 minutes, about 20 minutes to about 10 hours, about 20 minutes to about 9 hours, about 20 minutes to about 8 hours, about 20 minutes to about 7 hours, about 20 minutes to about 6 hours, about 20 minutes to about 5 hours, about 20 minutes to about 4.5 hours, about 20 minutes to about 4 hours, about 20 minutes to about 3.5 hours, about 20 minutes to about 3 hours, about 20 minutes to about 2.5 hours, about 20 minutes to about 2 hours, about 20 minutes to about 1.5 hours, about 20 minutes to about 1 hour, about 20 minutes to about 55 minutes, about 20 minutes to about 50 minutes, about 20 minutes to about 45 minutes, about 20 minutes to about 40 minutes, about 20 minutes to about 35 minutes, about 20 minutes to about 30 minutes, about 20 minutes to about 25 minutes, about 25 minutes to about 10 hours, about 25 minutes to about 9 hours, about 25 minutes to about 8 hours, about 25 minutes to about 7 hours, about 25 minutes to about 6 hours, about 25 minutes to about 5 hours, about 25 minutes to about 4.5 hours, about 25 minutes to about 4 hours, about 25 minutes to about 3.5 hours, about 25 minutes to about 3 hours, about 25 minutes to about 2.5 hours, about 25 minutes to about 2 hours, about 25 minutes to about 1.5 hours, about 25 minutes to about 1 hour, about 25 minutes to about 55 minutes, about 25 minutes to about 50 minutes, about 25 minutes to about 45 minutes, about 25 minutes to about 40 minutes, about 25 minutes to about 35 minutes, about 25 minutes to about 30 minutes, about 30 minutes to about 10 hours, about 30 minutes to about 9 hours, about 30 minutes to about 8 hours, about 30 minutes to about 7 hours, about 30 minutes to about 6 hours, about 30 minutes to about 5 hours, about 30 minutes to about 4.5 hours, about 30 minutes to about 4 hours, about 30 minutes to about 3.5 hours, about 30 minutes to about 3 hours, about 30 minutes to about 2.5 hours, about 30 minutes to about 2 hours, about 30 minutes to about 1.5 hours, about 30 minutes to about 1 hour, about 30 minutes to about 55 minutes, about 30 minutes to about 50 minutes, about 30 minutes to about 45 minutes, about 30 minutes to about 40 minutes, about 30 minutes to about 35 minutes, about 35 minutes to about 10 hours, about 35 minutes to about 9 hours, about 35 minutes to about 8 hours, about 35 minutes to about 7 hours, about 35 minutes to about 6 hours, about 35 minutes to about 5 hours, about 35 minutes to about 4.5 hours, about 35 minutes to about 4 hours, about 35 minutes to about 3.5 hours, about 35 minutes to about 3 hours, about 35 minutes to about 2.5 hours, about 35 minutes to about 2 hours, about 35 minutes to about 1.5 hours, about 35 minutes to about 1 hour, about 35 minutes to about 55 minutes, about 35 minutes to about 50 minutes, about 35 minutes to about 45 minutes, about 35 minutes to about 40 minutes, about 40 minutes to about 10 hours, about 40 minutes to about 9 hours, about 40 minutes to about 8 hours, about 40 minutes to about 7 hours, about 40 minutes to about 6 hours, about 40 minutes to about 5 hours, about 40 minutes to about 4.5 hours, about 40 minutes to about 4 hours, about 40 minutes to about 3.5 hours, about 40 minutes to about 3 hours, about 40 minutes to about 2.5 hours, about 40 minutes to about 2 hours, about 40 minutes to about 1.5 hours, about 40 minutes to about 1 hour, about 40 minutes to about 55 minutes, about 40 minutes to about 50 minutes, about 40 minutes to about 45 minutes, about 45 minutes to about 10 hours, about 45 minutes to about 9 hours, about 45 minutes to about 8 hours, about 45 minutes to about 7 hours, about 45 minutes to about 6 hours, about 45 minutes to about 5 hours, about 45 minutes to about 4.5 hours, about 45 minutes to about 4 hours, about 45 minutes to about 3.5 hours, about 45 minutes to about 3 hours, about 45 minutes to about 2.5 hours, about 45 minutes to about 2 hours, about 45 minutes to about 1.5 hours, about 45 minutes to about 1 hour, about 45 minutes to about 55 minutes, about 45 minutes to about 50 minutes, about 50 minutes to about 10 hours, about 50 minutes to about 9 hours, about 50 minutes to about 8 hours, about 50 minutes to about 7 hours, about 50 minutes to about 6 hours, about 50 minutes to about 5 hours, about 50 minutes to about 4.5 hours, about 50 minutes to about 4 hours, about 50 minutes to about 3.5 hours, about 50 minutes to about 3 hours, about 50 minutes to about 2.5 hours, about 50 minutes to about 2 hours, about 50 minutes to about 1.5 hours, about 50 minutes to about 1 hour, about 50 minutes to about 55 minutes, about 55 minutes to about 10 hours, about 55 minutes to about 9 hours, about 55 minutes to about 8 hours, about 55 minutes to about 7 hours, about 55 minutes to about 6 hours, about 55 minutes to about 5 hours, about 55 minutes to about 4.5 hours, about 55 minutes to about 4 hours, about 55 minutes to about 3.5 hours, about 55 minutes to about 3 hours, about 55 minutes to about 2.5 hours, about 55 minutes to about 2 hours, about 55 minutes to about 1.5 hours, about 55 minutes to about 1 hour, about 1 hour to about 10 hours, about 1 hour to about 9 hours, about 1 hour to about 8 hours, about 1 hour to about 7 hours, about 1 hour to about 6 hours, about 1 hour to about 5 hours, about 1 hour to about 4.5 hours, about 1 hour to about 4 hours, about 1 hour to about 3.5 hours, about 1 hour to about 3 hours, about 1 hour to about 2.5 hours, about 1 hour to about 2 hours, about 1 hour to about 1.5 hours, about 1.5 hours to about 10 hours, about 1.5 hours to about 9 hours, about 1.5 hours to about 8 hours, about 1.5 hours to about 7 hours, about 1.5 hours to about 6 hours, about 1.5 hours to about 5 hours, about 1.5 hours to about 4.5 hours, about 1.5 hours to about 4 hours, about 1.5 hours to about 3.5 hours, about 1.5 hours to about 3 hours, about 1.5 hours to about 2.5 hours, about 1.5 hours to about 2 hours, about 2 hours to about 10 hours, about 2 hours to about 9 hours, about 2 hours to about 8 hours, about 2 hours to about 7 hours, about 2 hours to about 6 hours, about 2 hours to about 5 hours, about 2 hours to about 4.5 hours, about 2 hours to about 4 hours, about 2 hours to about 3.5 hours, about 2 hours to about 3 hours, about 2 hours to about 2.5 hours, about 2.5 hours to about 10 hours, about 2.5 hours to about 9 hours, about 2.5 hours to about 8 hours, about 2.5 hours to about 7 hours, about 2.5 hours to about 6 hours, about 2.5 hours to about 5 hours, about 2.5 hours to about 4.5 hours, about 2.5 hours to about 4 hours, about 2.5 hours to about 3.5 hours, about 2.5 hours to about 3 hours, about 3 hours to about 10 hours, about 3 hours to about 9 hours, about 3 hours to about 8 hours, about 3 hours to about 7 hours, about 3 hours to about 6 hours, about 3 hours to about 5 hours, about 3 hours to about 4.5 hours, about 3 hours to about 4 hours, about 3 hours to about 3.5 hours, about 3.5 hours to about 10 hours, about 3.5 hours to about 9 hours, about 3.5 hours to about 8 hours, about 3.5 hours to about 7 hours, about 3.5 hours to about 6 hours, about 3.5 hours to about 5 hours, about 3.5 hours to about 4.5 hours, about 3.5 hours to about 4 hours, about 4 hours to about 10 hours, about 4 hours to about 9 hours, about 4 hours to about 8 hours, about 4 hours to about 7 hours, about 4 hours to about 6 hours, about 4 hours to about 5 hours, about 4 hours to about 4.5 hours, about 4.5 hours to about 10 hours, about 4.5 hours to about 9 hours, about 4.5 hours to about 8 hours, about 4.5 hours to about 7 hours, about 4.5 hours to about 6 hours, about 4.5 hours to about 5 hours, about 5 hours to about 10 hours, about 5 hours to about 9 hours, about 5 hours to about 8 hours, about 5 hours to about 7 hours, about 5 hours to about 6 hours, about 6 hours to about 10 hours, about 6 hours to about 9 hours, about 6 hours to about 8 hours, about 6 hours to about 7 hours, about 7 hours to about 10 hours, about 7 hours to about 9 hours, about 7 hours to about 8 hours, about 8 hours to about 10 hours, about 8 hours to about 9 hours, or about 9 hours to about 10 hours of administration of a dose of an JAK inhibitor using any of the devices or compositions described herein. Drug-target engagement may be determined, for example, as disclosed in Simon G M, Niphakis M J, Cravat B F, Nature chemical biology. 2013; 9(4):200-205, incorporated by reference herein in its entirety.

In some embodiments, administration of an JAK inhibitor using any of the devices or compositions described herein can provide for treatment (e.g., a reduction in the number, severity, and/or duration of one or more symptoms and/or markers of any of the disorders described herein in a subject) for a time period of between about 1 hour to about 30 days, about 1 hour to about 28 days, about 1 hour to about 26 days, about 1 hour to about 24 days, about 1 hour to about 22 days, about 1 hour to about 20 days, about 1 hour to about 18 days, about 1 hour to about 16 days, about 1 hour to about 14 days, about 1 hour to about 12 days, about 1 hour to about 10 days, about 1 hour to about 8 days, about 1 hour to about 6 days, about 1 hour to about 5 days, about 1 hour to about 4 days, about 1 hour to about 3 days, about 1 hour to about 2 days, about 1 hour to about 1 day, about 1 hour to about 12 hours, about 1 hour to about 6 hours, about 1 hour to about 3 hours, about 3 hours to about 30 days, about 3 hours to about 28 days, about 3 hours to about 26 days, about 3 hours to about 24 days, about 3 hours to about 22 days, about 3 hours to about 20 days, about 3 hours to about 18 days, about 3 hours to about 16 days, about 3 hours to about 14 days, about 3 hours to about 12 days, about 3 hours to about 10 days, about 3 hours to about 8 days, about 3 hours to about 6 days, about 3 hours to about 5 days, about 3 hours to about 4 days, about 3 hours to about 3 days, about 3 hours to about 2 days, about 3 hours to about 1 day, about 3 hours to about 12 hours, about 3 hours to about 6 hours, about 6 hours to about 30 days, about 6 hours to about 28 days, about 6 hours to about 26 days, about 6 hours to about 24 days, about 6 hours to about 22 days, about 6 hours to about 20 days, about 6 hours to about 18 days, about 6 hours to about 16 days, about 6 hours to about 14 days, about 6 hours to about 12 days, about 6 hours to about 10 days, about 6 hours to about 8 days, about 6 hours to about 6 days, about 6 hours to about 5 days, about 6 hours to about 4 days, about 6 hours to about 3 days, about 6 hours to about 2 days, about 6 hours to about 1 day, about 6 hours to about 12 hours, about 12 hours to about 30 days, about 12 hours to about 28 days, about 12 hours to about 26 days, about 12 hours to about 24 days, about 12 hours to about 22 days, about 12 hours to about 20 days, about 12 hours to about 18 days, about 12 hours to about 16 days, about 12 hours to about 14 days, about 12 hours to about 12 days, about 12 hours to about 10 days, about 12 hours to about 8 days, about 12 hours to about 6 days, about 12 hours to about 5 days, about 12 hours to about 4 days, about 12 hours to about 3 days, about 12 hours to about 2 days, about 12 hours to about 1 day, about 1 day to about 30 days, about 1 day to about 28 days, about 1 day to about 26 days, about 1 day to about 24 days, about 1 day to about 22 days, about 1 day to about 20 days, about 1 day to about 18 days, about 1 day to about 16 days, about 1 day to about 14 days, about 1 day to about 12 days, about 1 day to about 10 days, about 1 day to about 8 days, about 1 day to about 6 days, about 1 day to about 5 days, about 1 day to about 4 days, about 1 day to about 3 days, about 1 day to about 2 days, about 2 days to about 30 days, about 2 days to about 28 days, about 2 days to about 26 days, about 2 days to about 24 days, about 2 days to about 22 days, about 2 days to about 20 days, about 2 days to about 18 days, about 2 days to about 16 days, about 2 days to about 14 days, about 2 days to about 12 days, about 2 days to about 10 days, about 2 days to about 8 days, about 2 days to about 6 days, about 2 days to about 5 days, about 2 days to about 4 days, about 2 days to about 3 days, about 3 days to about 30 days, about 3 days to about 28 days, about 3 days to about 26 days, about 3 days to about 24 days, about 3 days to about 22 days, about 3 days to about 20 days, about 3 days to about 18 days, about 3 days to about 16 days, about 3 days to about 14 days, about 3 days to about 12 days, about 3 days to about 10 days, about 3 days to about 8 days, about 3 days to about 6 days, about 3 days to about 5 days, about 3 days to about 4 days, about 4 days to about 30 days, about 4 days to about 28 days, about 4 days to about 26 days, about 4 days to about 24 days, about 4 days to about 22 days, about 4 days to about 20 days, about 4 days to about 18 days, about 4 days to about 16 days, about 4 days to about 14 days, about 4 days to about 12 days, about 4 days to about 10 days, about 4 days to about 8 days, about 4 days to about 6 days, about 4 days to about 5 days, about 5 days to about 30 days, about 5 days to about 28 days, about 5 days to about 26 days, about 5 days to about 24 days, about 5 days to about 22 days, about 5 days to about 20 days, about 5 days to about 18 days, about 5 days to about 16 days, about 5 days to about 14 days, about 5 days to about 12 days, about 5 days to about 10 days, about 5 days to about 8 days, about 5 days to about 6 days, about 6 days to about 30 days, about 6 days to about 28 days, about 6 days to about 26 days, about 6 days to about 24 days, about 6 days to about 22 days, about 6 days to about 20 days, about 6 days to about 18 days, about 6 days to about 16 days, about 6 days to about 14 days, about 6 days to about 12 days, about 6 days to about 10 days, about 6 days to about 8 days, about 8 days to about 30 days, about 8 days to about 28 days, about 8 days to about 26 days, about 8 days to about 24 days, about 8 days to about 22 days, about 8 days to about 20 days, about 8 days to about 18 days, about 8 days to about 16 days, about 8 days to about 14 days, about 8 days to about 12 days, about 8 days to about 10 days, about 10 days to about 30 days, about 10 days to about 28 days, about 10 days to about 26 days, about 10 days to about 24 days, about 10 days to about 22 days, about 10 days to about 20 days, about 10 days to about 18 days, about 10 days to about 16 days, about 10 days to about 14 days, about 10 days to about 12 days, about 12 days to about 30 days, about 12 days to about 28 days, about 12 days to about 26 days, about 12 days to about 24 days, about 12 days to about 22 days, about 12 days to about 20 days, about 12 days to about 18 days, about 12 days to about 16 days, about 12 days to about 14 days, about 14 days to about 30 days, about 14 days to about 28 days, about 14 days to about 26 days, about 14 days to about 24 days, about 14 days to about 22 days, about 14 days to about 20 days, about 14 days to about 18 days, about 14 days to about 16 days, about 16 days to about 30 days, about 16 days to about 28 days, about 16 days to about 26 days, about 16 days to about 24 days, about 16 days to about 22 days, about 16 days to about 20 days, about 16 days to about 18 days, about 18 days to about 30 days, about 18 days to about 28 days, about 18 days to about 26 days, about 18 days to about 24 days, about 18 days to about 22 days, about 18 days to about 20 days, about 20 days to about 30 days, about 20 days to about 28 days, about 20 days to about 26 days, about 20 days to about 24 days, about 20 days to about 22 days, about 22 days to about 30 days, about 22 days to about 28 days, about 22 days to about 26 days, about 22 days to about 24 days, about 24 days to about 30 days, about 24 days to about 28 days, about 24 days to about 26 days, about 26 days to about 30 days, about 26 days to about 28 days, or about 28 days to about 30 days in a subject following first administration of an JAK inhibitor using any of the compositions or devices described herein. Non-limiting examples of symptoms and/or markers of a disease described herein are described below.

For example, treatment can result in a decrease (e.g., about 1% to about 99% decrease, about 1% to about 95% decrease, about 1% to about 90% decrease, about 1% to about 85% decrease, about 1% to about 80% decrease, about 1% to about 75% decrease, about 1% to about 70% decrease, about 1% to about 65% decrease, about 1% to about 60% decrease, about 1% to about 55% decrease, about 1% to about 50% decrease, about 1% to about 45% decrease, about 1% to about 40% decrease, about 1% to about 35% decrease, about 1% to about 30% decrease, about 1% to about 25% decrease, about 1% to about 20% decrease, about 1% to about 15% decrease, about 1% to about 10% decrease, about 1% to about 5% decrease, about 5% to about 99% decrease, about 5% to about 95% decrease, about 5% to about 90% decrease, about 5% to about 85% decrease, about 5% to about 80% decrease, about 5% to about 75% decrease, about 5% to about 70% decrease, about 5% to about 65% decrease, about 5% to about 60% decrease, about 5% to about 55% decrease, about 5% to about 50% decrease, about 5% to about 45% decrease, about 5% to about 40% decrease, about 5% to about 35% decrease, about 5% to about 30% decrease, about 5% to about 25% decrease, about 5% to about 20% decrease, about 5% to about 15% decrease, about 5% to about 10% decrease, about 10% to about 99% decrease, about 10% to about 95% decrease, about 10% to about 90% decrease, about 10% to about 85% decrease, about 10% to about 80% decrease, about 10% to about 75% decrease, about 10% to about 70% decrease, about 10% to about 65% decrease, about 10% to about 60% decrease, about 10% to about 55% decrease, about 10% to about 50% decrease, about 10% to about 45% decrease, about 10% to about 40% decrease, about 10% to about 35% decrease, about 10% to about 30% decrease, about 10% to about 25% decrease, about 10% to about 20% decrease, about 10% to about 15% decrease, about 15% to about 99% decrease, about 15% to about 95% decrease, about 15% to about 90% decrease, about 15% to about 85% decrease, about 15% to about 80% decrease, about 15% to about 75% decrease, about 15% to about 70% decrease, about 15% to about 65% decrease, about 15% to about 60% decrease, about 15% to about 55% decrease, about 15% to about 50% decrease, about 15% to about 45% decrease, about 15% to about 40% decrease, about 15% to about 35% decrease, about 15% to about 30% decrease, about 15% to about 25% decrease, about 15% to about 20% decrease, about 20% to about 99% decrease, about 20% to about 95% decrease, about 20% to about 90% decrease, about 20% to about 85% decrease, about 20% to about 80% decrease, about 20% to about 75% decrease, about 20% to about 70% decrease, about 20% to about 65% decrease, about 20% to about 60% decrease, about 20% to about 55% decrease, about 20% to about 50% decrease, about 20% to about 45% decrease, about 20% to about 40% decrease, about 20% to about 35% decrease, about 20% to about 30% decrease, about 20% to about 25% decrease, about 25% to about 99% decrease, about 25% to about 95% decrease, about 25% to about 90% decrease, about 25% to about 85% decrease, about 25% to about 80% decrease, about 25% to about 75% decrease, about 25% to about 70% decrease, about 25% to about 65% decrease, about 25% to about 60% decrease, about 25% to about 55% decrease, about 25% to about 50% decrease, about 25% to about 45% decrease, about 25% to about 40% decrease, about 25% to about 35% decrease, about 25% to about 30% decrease, about 30% to about 99% decrease, about 30% to about 95% decrease, about 30% to about 90% decrease, about 30% to about 85% decrease, about 30% to about 80% decrease, about 30% to about 75% decrease, about 30% to about 70% decrease, about 30% to about 65% decrease, about 30% to about 60% decrease, about 30% to about 55% decrease, about 30% to about 50% decrease, about 30% to about 45% decrease, about 30% to about 40% decrease, about 30% to about 35% decrease, about 35% to about 99% decrease, about 35% to about 95% decrease, about 35% to about 90% decrease, about 35% to about 85% decrease, about 35% to about 80% decrease, about 35% to about 75% decrease, about 35% to about 70% decrease, about 35% to about 65% decrease, about 35% to about 60% decrease, about 35% to about 55% decrease, about 35% to about 50% decrease, about 35% to about 45% decrease, about 35% to about 40% decrease, about 40% to about 99% decrease, about 40% to about 95% decrease, about 40% to about 90% decrease, about 40% to about 85% decrease, about 40% to about 80% decrease, about 40% to about 75% decrease, about 40% to about 70% decrease, about 40% to about 65% decrease, about 40% to about 60% decrease, about 40% to about 55% decrease, about 40% to about 50% decrease, about 40% to about 45% decrease, about 45% to about 99% decrease, about 45% to about 95% decrease, about 45% to about 90% decrease, about 45% to about 85% decrease, about 45% to about 80% decrease, about 45% to about 75% decrease, about 45% to about 70% decrease, about 45% to about 65% decrease, about 45% to about 60% decrease, about 45% to about 55% decrease, about 45% to about 50% decrease, about 50% to about 99% decrease, about 50% to about 95% decrease, about 50% to about 90% decrease, about 50% to about 85% decrease, about 50% to about 80% decrease, about 50% to about 75% decrease, about 50% to about 70% decrease, about 50% to about 65% decrease, about 50% to about 60% decrease, about 50% to about 55% decrease, about 55% to about 99% decrease, about 55% to about 95% decrease, about 55% to about 90% decrease, about 55% to about 85% decrease, about 55% to about 80% decrease, about 55% to about 75% decrease, about 55% to about 70% decrease, about 55% to about 65% decrease, about 55% to about 60% decrease, about 60% to about 99% decrease, about 60% to about 95% decrease, about 60% to about 90% decrease, about 60% to about 85% decrease, about 60% to about 80% decrease, about 60% to about 75% decrease, about 60% to about 70% decrease, about 60% to about 65% decrease, about 65% to about 99% decrease, about 65% to about 95% decrease, about 65% to about 90% decrease, about 65% to about 85% decrease, about 65% to about 80% decrease, about 65% to about 75% decrease, about 65% to about 70% decrease, about 70% to about 99% decrease, about 70% to about 95% decrease, about 70% to about 90% decrease, about 70% to about 85% decrease, about 70% to about 80% decrease, about 70% to about 75% decrease, about 75% to about 99% decrease, about 75% to about 95% decrease, about 75% to about 90% decrease, about 75% to about 85% decrease, about 75% to about 80% decrease, about 80% to about 99% decrease, about 80% to about 95% decrease, about 80% to about 90% decrease, about 80% to about 85% decrease, about 85% to about 99% decrease, about 85% to about 95% decrease, about 85% to about 90% decrease, about 90% to about 99% decrease, about 90% to about 95% decrease, or about 95% to about 99% decrease) in one or more (e.g., two, three, four, five, six, seven, eight, or nine) of: the level of interferon-γ in GI tissue, the level of IL-1γ in GI tissue, the level of IL-6 in GI tissue, the level of IL-22 in GI tissue, the level of IL-17A in the GI tissue, the level of TNFα in GI tissue, the level of IL-2 in GI tissue, and endoscopy score in a subject (e.g., as compared to the level in the subject prior to treatment or compared to a subject or population of subjects having a similar disease but receiving a placebo or a different treatment) (e.g., for a time period of between about 1 hour to about 30 days (e.g., or any of the subranges herein) following the first administration of an JAK inhibitor using any of the compositions or devices described herein. As used herein, "GI tissue" refers to tissue in the gastrointestinal (GI) tract, such as tissue in one or more of duodenum, jejunum, ileum, cecum, ascending colon, transverse colon, descending colon, sigmoid colon, and rectum, more particularly in the proximal portion of one or more of duodenum, jejunum, ileum, cecum, ascending colon, transverse colon, descending colon, and sigmoid colon, or in the distal portion of one or more of duodenum, jejunum, ileum, cecum, ascending colon, transverse colon, descending colon, and sigmoid colon. The GI tissue may be, for example, GI tissue proximate to one or more sites of disease. Exemplary methods for determining the endoscopy score are described herein and other methods for determining the endoscopy score are known in the art. Exemplary methods for determining the levels of interferon-γ, IL-1β, IL-6, IL-22, IL-17A, TNFα, and IL-2 are described herein. Additional methods for determining the levels of these cytokines are known in the art.

In some examples, treatment can result in an increase (e.g., about 1% to about 500% increase, about 1% to about 400% increase, about 1% to about 300% increase, about 1% to about 200% increase, about 1% to about 150% increase, about 1% to about 100% increase, about 1% to about 90% increase, about 1% to about 80% increase, about 1% to about 70% increase, about 1% to about 60% increase, about 1% to about 50% increase, about 1% to about 40% increase, about 1% to about 30% increase, about 1% to about 20% increase, about 1% to about 10% increase, a 10% to about 500% increase, about 10% to about 400% increase, about 10% to about 300% increase, about 10% to about 200% increase, about 10% to about 150% increase, about 10% to about 100% increase, about 10% to about 90% increase, about 10% to about 80% increase, about 10% to about 70% increase, about 10% to about 60% increase, about 10% to about 50% increase, about 10% to about 40% increase, about 10% to about 30% increase, about 10% to about 20% increase, about 20% to about 500% increase, about 20% to about 400% increase, about 20% to about 300% increase, about 20% to about 200% increase, about 20% to about 150% increase, about 20% to about 100% increase, about 20% to about 90% increase, about 20% to about 80% increase, about 20% to about 70% increase, about 20% to about 60% increase, about 20% to about 50% increase, about 20% to about 40% increase, about 20% to about 30% increase, about 30% to about 500% increase, about 30% to about 400% increase, about 30% to about 300% increase, about 30% to about 200% increase, about 30% to about 150% increase, about 30% to about 100% increase, about 30% to about 90% increase, about 30% to about 80% increase, about 30% to about 70% increase, about 30% to about 60% increase, about 30% to about 50% increase, about 30% to about 40% increase, about 40% to about 500% increase, about 40% to about 400% increase, about 40% to about 300% increase, about 40% to about 200% increase, about 40% to about 150% increase, about 40% to about 100% increase, about 40% to about 90% increase, about 40% to about 80% increase, about 40% to about 70% increase, about 40% to about 60% increase, about 40% to about 50% increase, about 50% to about 500% increase, about 50% to about 400% increase, about 50% to about 300% increase, about 50% to about 200% increase, about 50% to about 150% increase, about 50% to about 100% increase, about 50% to about 90% increase, about 50% to about 80% increase, about 50% to about 70% increase, about 50% to about 60% increase, about 60% to about 500% increase, about 60% to about 400% increase, about 60% to about 300% increase, about 60% to about 200% increase, about 60% to about 150% increase, about 60% to about 100% increase, about 60% to about 90% increase, about 60% to about 80% increase, about 60% to about 70% increase, about 70% to about 500% increase, about 70% to about 400% increase, about 70% to about 300% increase, about 70% to about 200% increase, about 70% to about 150% increase, about 70% to about 100% increase, about 70% to about 90% increase, about 70% to about 80% increase, about 80% to about 500% increase, about 80% to about 400% increase, about 80% to about 300% increase, about 80% to about 200% increase, about 80% to about 150% increase, about 80% to about 100% increase, about 80% to about 90% increase, about 90% to about 500% increase, about 90% to about 400% increase, about 90% to about 300% increase, about 90% to about 200% increase, about 90% to about 150% increase, about 90% to about 100% increase, about 100% to about 500% increase, about 100% to about 400% increase, about 100% to about 300% increase, about 100% to about 200% increase, about 100% to about 150% increase, about 150% to about 500% increase, about 150% to about 400% increase, about 150% to about 300% increase, about 150% to about 200% increase, about 200% to about 500% increase, about 200% to about 400% increase, about 200% to about 300% increase, about 300% to about 500% increase, about 300% to about 400% increase, or about 400% to about 500% increase) in one or both of stool consistency score and weight of a subject (e.g., as compared to the level in the subject prior to treatment or compared to a subject or population of subjects having a similar disease but receiving a placebo or a different treatment) (e.g., for a time period of between about 1 hour to about 30 days (e.g., or any of the subranges herein) following the first administration of an JAK inhibitor using any of the compositions or devices described herein. Exemplary methods for determining stool consistency score are described herein. Additional methods for determining a stool consistency score are known in the art.

Accordingly, in some embodiments, a method of treatment disclosed herein includes determining the level of a marker at the location of disease in a subject (e.g., either before and/or after administration of the device). In some embodiments, the marker is a biomarker and the method of treatment disclosed herein comprises determining that the level of a biomarker at the location of disease is a subject following administration of the device is decreased as compared to the level of the biomarker at the same location of disease in a subject either before administration or at the same time point following systemic administration of an equal amount of the JAK inhibitor. In some examples, the level of the biomarker at the same location of disease following administration of the device is 1% decreased to 99% decreased as compared to the level of the biomarker at the same location of disease in a subject either before administration or at the same time point following systemic administration of an equal amount of the JAK inhibitor. In some embodiments, the level of the marker is one or more of: the level of interferon-γ in GI tissue, the level of IL-17A in the GI tissue, the level of TNFα in the GI tissue, the level of IL-2 in the GI tissue, and the endoscopy score in a subject.

In some embodiments, the method of treatment disclosed herein includes determining that the level of a marker at a time point following administration of a device is lower than the level of the marker at a time point following administration of the device is lower than the level of the marker in a subject prior to administration of the device or in a subject at substantially the same time point following systemic administration of an equal amount of the JAK inhibitor. In some examples, the level of the marker following administration of the device is 1% decreased to 99% decreased as compared to the level of the marker in a subject prior to administration of the device or in a subject at the same time point following systemic administration of an equal amount of the JAK inhibitor. In some examples, a method of treatment disclosed herein includes determining the level of the biomarker at the location of disease in a subject within a time period of about 10 minutes to 10 hours following administration of the device.

In some embodiments, a method of treatment described herein includes: (i) determining the ratio $R_B$ of the level $L_{1B}$ of a biomarker at the location of disease at a first time point following administration of the device and the level $L_{2B}$ of the biomarker at the same location of disease in a subject at substantially the same time point following systemic administration of an equal amount of the JAK inhibitor; (ii) determining the ratio of $R_D$ of the level of $L_{1D}$ of the JAK inhibitor at the same location and the substantially the same time point as in (i) and the level $L_{2D}$ of the JAK inhibitor at the same location of disease in a subject at substantially the same time point following systemic administration of an equal amount of the JAK inhibitor; and (iii) determining the ratio of $R_B/R_D$.

In some embodiments, a method of treatment disclosed herein can include: (i) determining the ratio $R_B$ of the level $L_{1B}$ of a biomarker at the location of disease at a time point following administration of the device and the level $L_{2B}$ of the biomarker at the same location of disease in a subject at substantially the same time point following systemic administration of an equal amount of the JAK inhibitor; (ii) determining the ratio $R_D$ of the level $L_{1D}$ of the JAK inhibitor at the same location and at substantially the time point as in (i) and the level $L_{2D}$ of the JAK inhibitor in a subject at the same location of disease at substantially the same time point following systemic administration of an equal amount of the JAK inhibitor; and (iii) determining the product $R_B \times R_D$.

In some embodiments, a method of treatment disclosed herein can include determining that the level of a marker in a subject at a time point following administration of the device is elevated as compared to a level of the marker in a subject prior to administration of the device or a level at substantially the same time point in a subject following systemic administration of an equal amount of the JAK inhibitor. In some examples, the level of the marker at a time point following administration of the device is 1% increased or 400% increased as compared to the level of the marker in a subject prior to administration of the device or a level at substantially the same time point in a subject following systemic administration of an equal amount of the JAK inhibitor. In some examples, the level of the marker is one or more of subject weight and stool consistency (e.g., stool consistency score). In some examples, a method of treatment disclosed herein includes determining the level of the marker in a subject within a period of about 10 minutes to about 10 hours following administration of the device.

In some embodiments, a method of treatment disclosed herein can include determining the level of a marker in a subject's blood, serum or plasma.

An illustrative list of examples of biomarkers for GI disorders includes interferon-γ, IL-1β, IL-6, IL-22, IL-17A, TNFα, IL-2, memory cells (CD44$^+$CD45RB$^-$CD4$^+$ cells); α4β7; VEGF; ICAM; VCAM; SAA; Calprotectin; lactoferrin; FGF2; TGFb; ANG-1; ANG-2; PLGF; Biologics (Infliximab; Humira; Stelara; Vedolizumab; Simponi; Jak inhibitors; Others); EGF; IL12/23p40; GMCSF; A4 B7; AeB7; CRP; SAA; ICAM; VCAM; AREG; EREG; HB-EGF; HRG; BTC; TGFα; SCF; TWEAK; MMP-9; MMP-6; Ceacam CD66; IL10; ADA; Madcam-1; CD166 (ALCAM); FGF2; FGF7; FGF9; FGF19; ANCA Antineutrophil cytoplasmic antibody; ASCAA Anti-*Saccharomyces Cerevisiae* Antibody IgA; ASCAG Anti-*Saccharomyces Cerevisiae* Antibody IgG; CBir1 Anti-*Clostridium* cluster XIVa flagellin CBir1 antibody; A4-Fla2 Anti-*Clostridium* cluster XIVa flagellin 2 antibody; FlaX Anti-*Clostridium* cluster XIVa flagellin X antibody; OmpC Anti-Escherichia coli Outer Membrane Protein C; ANCA Perinuclear AntiNeutrophil Cytoplasmic Antibody; AREG Amphiregulin Protein; BTC Betacellulin Protein; EGF Epidermal Growth Factor EREG Epiregulin Protein; HBEGF Heparin Binding Epidermal Growth Factors; HGF Hepatocyte Growth Factor; HRG Neuregulin-1; TGFA Transforming Growth Factor alpha; CRP C-Reactive Protein; SAA Serum Amyloid A; ICAM-1 Intercellular Adhesion Molecule 1; VCAM-1 Vascular Cell Adhesion Molecule 1; fibroblasts underlying the intestinal epithelium; and HGF.

In some embodiments, a marker is an IBD biomarker, such as, for example: anti-glycan; anti-*Saccharomices cerevisiae* (ASCA); anti-laminaribioside (ALCA); anti-chitobioside (ACCA); anti-mannobioside (AMCA); anti-laminarin (anti-L); anti-chitin (anti-C) antibodies: anti-outer membrane porin C (anti-OmpC), anti-Cbir1 flagellin; anti-12 antibody; autoantibodies targeting the exocrine pancreas (PAB); and perinuclear anti-neutrophil antibody (pANCA); and calprotectin.

In some embodiments, a biomarker is associated with membrane repair, fibrosis, angiogenesis. In certain embodiments, a biomarker is an inflammatory biomarker, an anti-inflammatory biomarker, an MMP biomarker, an immune marker, or a TNF pathway biomarker. In some embodiments, a biomarker is gut specific.

For tissue samples, HER2 can be used as a biomarker relating to cytotoxic T cells. Additionally, other cytokine levels can be used as biomarkers in tissue (e.g., phospho STAT 1, STAT 3 and STAT 5), in plasma (e.g., VEGF, VCAM, ICAM, IL-6), or both. In some embodiments, the biomarkers include one or more immunoglobulins, such as, for example, immunoglobulin M (IgM), immunoglobulin D (IgD), immunoglobulin G (IgG), immunoglobulin E (IgE) and/or immunoglobulin A (IgA). In some embodiments, IgM is a biomarker of infection and/or inflammation. In some embodiments, IgD is a biomarker of autoimmune disease. In some embodiments, IgG is a biomarker of Alzheimer's disease and/or for cancer. In some embodiments, IgE is a biomarker of asthma and/or allergen immunotherapy. In some embodiments, IgA is a biomarker of kidney disease.

In some embodiments, the biomarker is High Sensitivity C-reactive Protein (hsCRP); 7 α-hydroxy-4-cholesten-3-one (7C4); Anti-Endomysial IgA (EMA IgA); Anti-Human Tissue Transglutaminase IgA (tTG IgA); Total Serum IgA by Nephelometry; Fecal Calprotectin; or Fecal Gastrointestinal Pathogens.

In some embodiments, the biomarker is
a) an anti-gliadin IgA antibody, an anti-gliadin IgG antibody, an anti-tissue transglutaminase (tTG) antibody, an anti-endomysial antibody;
b)i) a serological marker that is ASCA-A, ASCA-G, ANCA, pANCA, anti-OmpC antibody, anti-CBir1 antibody, anti-FlaX antibody, or anti-A4-Fla2 antibody;
b)ii) an inflammation marker that is VEGF, ICAM, VCAM, SAA, or CRP;
b)iii) the genotype of the genetic markers ATG16L1, ECM1, NKX2-3, or STAT3;
c) a bacterial antigen antibody marker;
d) a mast cell marker;
e) an inflammatory cell marker;
f) a bile acid malabsorption (BAM) marker;
g) a kynurenine marker;
or
h) a serotonin marker.

In some embodiments, the bacterial antigen antibody marker is selected from the group consisting of an anti-Fla1 antibody, anti-Fla2 antibody, anti-FlaA antibody, anti-FliC antibody, anti-FliC2 antibody, anti-FliC3 antibody, anti-YBaN1 antibody, anti-ECFliC antibody, anti-Ec0FliC antibody, anti-SeFljB antibody, anti-CjFlaA antibody, anti-CjFlaB antibody, anti-SfFliC antibody, anti-CjCgtA antibody, anti-Cjdmh antibody, anti-CjGT-A antibody, anti-EcYidX antibody, anti-EcEra antibody, anti-EcFrvX antibody, anti-EcGabT antibody, anti-EcYedK antibody, anti-EcYbaN antibody, anti-EcYhgN antibody, anti-RtMaga antibody, anti-RbCpaF antibody, anti-RgPilD antibody, anti-LaFrc antibody, anti-LaEno antibody, anti-LjEFTu antibody, anti-BfOmpa antibody, anti-PrOmpA antibody, anti-Cp10bA antibody, anti-CpSpA antibody, anti-EfSant antibody, anti-LmOsp antibody, anti-SfET-2 antibody, anti-Cpatox antibody, anti-Cpbtox antibody, anti-EcSta2 antibody, anti-Ec0Stx2A antibody, anti-CjcdtB/C antibody, anti-CdtcdA/B antibody, and combinations thereof.

In some embodiments, the mast cell marker is selected from the group consisting of beta-tryptase, histamine, prostaglandin E2 (PGE2), and combinations thereof.

In some embodiments, the inflammatory marker is selected from the group consisting of CRP, ICAM, VCAM, SAA, GRO.alpha., and combinations thereof.

In some embodiments, the bile acid malabsorption marker is selected from the group consisting of 7α-hydroxy-4-cholesten-3-one, FGF19, and a combination thereof.

In some embodiments, the kynurenine marker is selected from the group consisting of kynurenine (K), kynurenic acid (KyA), anthranilic acid (AA), 3-hydroxykynurenine (3-HK), 3-hydroxyanthranilic acid (3-HAA), xanthurenic acid (XA), quinolinic acid (QA), tryptophan, 5-hydroxytryptophan (5-HTP), and combinations thereof.

In some embodiments, the serotonin marker is selected from the group consisting of serotonin (5-HT), 5-hydroxyindoleacetic acid (5-HIAA), serotonin-O-sulfate, serotonin-O-phosphate, and combinations thereof.

In some embodiments, the biomarker is a biomarker as disclosed in U.S. Pat. No. 9,739,786, incorporated by reference herein in its entirety.

The following markers can be expressed by mesenchymal stem cells (MSC): CD105, CD73, CD90, CD13, CD29, CD44, CD10, Stro-1, CD271, SSEA-4, CD146, CD49f, CD349, GD2, 3G5, SSEA-3, SISD2, Stro-4, MSCA-1, CD56, CD200, PODX1, Sox11, or TM4SF1 (e.g., 2 or more, 3 or more, 4 or more, 5 or more, 6 or more, 7 or more, 8 or more, 9 or more, or 10 or more of such markers), and lack expression of one or more of CD45, CD34, CD14, CD19, and HLA-DR (e.g., lack expression of two or more, three or more, four or more, or five or more such markers). In some embodiments, MSC can express CD105, CD73, and CD90. In some embodiments, MSC can express CD105, CD73, CD90, CD13, CD29, CD44, and CD10. In some embodiments, MSC can express CD105, CD73, and CD90 and one or more sternness markers such as Stro-1, CD271, SSEA-4, CD146, CD49f, CD349, GD2, 3G5, SSEA-3. SISD2, Stro-4, MSCA-1, CD56, CD200, PODX1, Sox11, or TM4SF1. In some embodiments, MSC can express CD105, CD73, CD90, CD13, CD29, CD44, and CD10 and one or more sternness markers such as Stro-1, CD271, SSEA-4, CD146, CD49f, CD349, GD2, 3G5, SSEA-3. SISD2, Stro-4, MSCA-1, CD56, CD200, PODX1, Sox11, or TM4SF1. See, e.g., Lv, et al., *Stem Cells,* 2014, 32:1408-1419.

Intestinal stem cells (ISC) can be positive for one or more markers such as Musashi-1 (Msi-1), Asc12, Bmi-1, Doublecortin and Ca2+/calmodulin-dependent kinase-like 1 (DCAMKL1), and Leucin-rich repeat-containing G-protein-coupled receptor 5 (Lgrs). See, e.g., Mohamed, et al., Cytotechnology, 2015 67(2): 177-189.

Any of the foregoing biomarkers can be used as a biomarker for one or more of other conditions as appropriate.

In some embodiments of the methods herein, the methods comprise determining the time period of onset of treatment following administration of the device.
Combination Therapy:

The JAK inhibitors disclosed herein may be optionally be used with additional agents in the treatment of the diseases disclosed herein. Nonlimiting examples of such agents for treating or preventing inflammatory bowel disease in such adjunct therapy (e.g., Crohn's disease, ulcerative colitis) include substances that suppress cytokine production, down-regulate or suppress self-antigen expression, or mask the MHC antigens. Examples of such agents include 2-amino-6-aryl-5-substituted pyrimidines (see U.S. Pat. No. 4,665, 077); non-steroidal antiinflammatory drugs (NSAIDs); ganciclovir; tacrolimus; lucocorticoids such as Cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); alkylating agents such as cyclophosphamide; bromocriptine; danazol; dapsone; glutaraldehyde (which masks the MHC antigens, as described in U.S. Pat. No. 4,120,649); anti-idiotypic antibodies for MHC antigens and MHC fragments; cyclosporine; 6-mercaptopurine; steroids such as corticosteroids or glucocorticosteroids or glucocorticoid analogs, e.g., prednisone, methylprednisolone, including SOLU-MEDROL®, methylprednisolone sodium succinate, and dexamethasone; dihydrofolate reductase inhibitors such as methotrexate (oral or subcutaneous); antimalarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor(TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD 1 la and anti-CD 18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al, U.S. Pat. No. 5,114,721); T-cell receptor fragments (Offner et al, Science, 251: 430-432 (1991); WO 90/11294; Ianeway, Nature, 341: 482 (1989); and WO 91/01133); BAFF antagonists such as BAFF or BR3 antibodies or immunoadhesins and zTNF4 antagonists (for review, see Mackay and Mackay, Trends Immunol, 23: 113-5 (2002) and see also definition below); biologic agents that interfere with T cell helper signals, such as anti-CD40 receptor or anti-CD40 ligand (CD 154), including blocking antibodies to CD40-CD40 ligand. (e.g., Durie et al, Science, 261: 1328-30 (1993); Mohan et al, J. Immunol, 154: 1470-80 (1995)) and CTLA4-Ig (Finck et al, Science, 265: 1225-7 (1994)); and T-cell receptor antibodies (EP 340,109) such as T10B9. Non-limiting examples of adjunct agents also include the following: budenoside; epidermal growth factor; aminosalicylates; metronidazole; mesalamine; olsalazine; balsalazide; antioxidants; thromboxane inhibitors; IL-1 receptor antagonists; anti-IL-1 monoclonal antibodies; growth factors; elastase inhibitors; pyridinyl-imidazole compounds; TNF antagonists; IL-4, IL-10, IL-13 and/or TGFβ cytokines or agonists thereof (e.g., agonist antibodies); IL-11; glucuronide- or dextran-conjugated prodrugs of prednisolone, dexamethasone or budesonide; ICAM-I antisense phosphorothioate oligodeoxynucleotides (ISIS 2302; Isis Pharmaceuticals, Inc.); soluble complement receptor 1 (TPlO; T Cell Sciences, Inc.); slow-release mesalazine; antagonists of platelet activating factor (PAF); ciprofloxacin; and lignocaine. Examples of agents for UC are sulfasalazine and related salicylate-containing drugs for mild cases and corticosteroid drugs in severe cases. Topical administration of either salicylates or corticosteroids is sometimes effective, particularly when the disease is limited to the distal bowel, and is associated with decreased side effects compared with systemic use. Supportive measures such as administration of iron and antidiarrheal agents are sometimes indicated. Azathioprine, 6-mercaptopurine and methotrexate are sometimes also prescribed for use in refractory corticosteroid-dependent cases.

In other embodiments, a JAK inhibitor as described herein can be administered with one or more of: a CHST15 inhibitor, a IL-6 receptor inhibitor, a TNF inhibitor, an integrin inhibitor, an IL-12/IL-23 inhibitor, a SMAD7 inhibitor, a IL-13 inhibitor, an IL-1 receptor inhibitor, a TLR agonist, an immunosuppressant, a live biotherapeutic such as a stem cell, IL-10 or an IL-10 agonist, copaxone, a CD40 inhibitor, an S1P-inhibitor, or a chemokine/chemokine receptor inhibitor. In other embodiments, a JAK inhibitor as described herein can be administered with a vitamin C infusion, one or more corticosteroids, and optionally thiamine.

Examples of particular combinations include the following.
Unless otherwise specified, the first component (component (1)) is administered in an ingestible device, while the second component (component (2)) is administered either in an ingestible device, which may be the same or different ingestible device as the first component, or by another form of administration.
(1) JAK inhibitor; (2) TNF inhibitor.
(1) JAK inhibitor; (2) TNF inhibitor in an ingestible device.
(1) JAK inhibitor; (2) TNF inhibitor intravenously or subcutaneously.
(1) TNF inhibitor; (2) JAK inhibitor
(1) TNF inhibitor; (2) JAK inhibitor in an ingestible device.
(1) TNF inhibitor; (2) JAK inhibitor orally.
(1) Neoregulin-4; (2) JAK inhibitor.
(1) Neoregulin-4; (2) JAK inhibitor in an ingestible device.
(1) Neoregulin-4; (2) JAK inhibitor intravenously or subcutaneously.

In some embodiments, the methods disclosed herein comprise administering (i) the JAK inhibitor as disclosed herein, and (ii) a second agent orally, intravenously or subcutaneously, wherein the second agent in (ii) is the same JAK inhibitor in (i); a different JAK inhibitor; or an agent having a different biological target from the JAK inhibitor.

In some embodiments, the methods disclosed herein comprise administering (i) the JAK inhibitor in the manner disclosed herein, and (ii) a second agent orally, intravenously or subcutaneously, wherein the second agent in (ii) is an agent suitable for treating an inflammatory bowel disease.

In some embodiments, the JAK inhibitor is administered prior to the second agent. In some embodiments, the JAK inhibitor is administered after the second agent. In some embodiments, the JAK inhibitor and the second agent are administered substantially at the same time. In some embodiments, the JAK inhibitor is delivered prior to the second agent. In some embodiments, the JAK inhibitor is delivered after the second agent. In some embodiments, the JAK inhibitor and the second agent are delivered substantially at the same time.

In some embodiments, the second agent is an agent suitable for the treatment of a disease of the gastrointestinal tract. In some embodiments, the second agent is an agent suitable for the treatment of an inflammatory bowel disease. In some embodiments, the second agent is administered intravenously. In some embodiments, the second agent is administered subcutaneously. In some embodiments, the second agent is methotrexate.

In some embodiments, delivery of the JAK inhibitor to the location, such as delivery to the location by mucosal contact, results in systemic immunogenicity levels at or below systemic immunogenicity levels resulting from administration of the JAK inhibitor systemically. In some embodiments comprising administering the JAK inhibitor in the manner disclosed herein and a second agent systemically, delivery of the JAK inhibitor to the location, such as delivery to the location by mucosal contact, results in systemic immunogenicity levels at or below systemic immunogenicity levels resulting from administration of the JAK inhibitor systemically and the second agent systemically. In some embodiments, the method comprises administering the JAK inhibitor in the manner disclosed herein and a second agent, wherein the amount of the second agent is less than the amount of the second agent when the JAK inhibitor and second agent are both administered systemically. In some aspects of these embodiments, the second agent is a JAK inhibitor.

In some embodiments, the method comprises administering the JAK inhibitor in the manner disclosed herein and does not comprise administering a second agent.

Example 1—Preclinical Murine Colitis Model

Experimental Induction of Colitis

Colitis is experimentally induced to mice via the dextran sulfate sodium (DSS)-induced colitis model. This model is widely used because of its simplicity and many similarities with human ulcerative colitis. Briefly, mice are subjected to DSS via cecal catheterization, which is thought to be directly toxic to colonic epithelial cells of the basal crypts, for several days until colitis is induced.

Groups

Mice are allocated to one of seven cohorts, depending on the agent that is administered:
1. Control (no agent)
2. Adalimumab (2.5 mg/kg)
3. Adalimumab (5 mg/kg)
4. Adalimumab (10 mg/kg)

The control or agent is applied to a damaged mucosal surface of the bowel via administration through a cecal catheter at the dose levels described above.

Additionally, for each cohort, the animals are separated into two groups. One group receives a single dose of the control or agent on day 10 or 12. The other group receives daily (or similar) dosing of the control or agent.

Analysis

For each animal, efficacy is determined (e.g., by endoscopy, histology, etc.), and cytotoxic T-cell levels are determined in blood, feces, and tissue (tissue levels are determined after animal sacrifice). For tissue samples, levels HER2 are additionally determined, and the level of cytotoxic T cells is normalized to the level of HER2. Additionally, other cytokine levels are determined in tissue (e.g., phospho STAT 1, STAT 3 and STAT 5), in plasma (e.g., VEGF, VCAM, ICAM, IL-6), or both.

Pharmacokinetics are determined both systemically (e.g., in the plasma) and locally (e.g., in colon tissue). For systemic pharmacokinetic analysis, blood and/or feces is collected from the animals at one or more timepoints after administration (e.g., plasma samples are collected at 15 minutes, 30 minutes, 1 hour, 2 hours, 4 hours, and/or 8 hours after administration). Local/colon tissue samples are collected once after animal sacrifice.

Example 2A—Development of Preclinical Porcine Colitis Model

Experimental Induction of Colitis

Female swine weighing approximately 35 to 45 kg at study start are fasted at least 24 hours prior to intra-rectal administration of trinitrobenzene sulfonic acid (TNBS). Animals are lightly anesthetized during the dosing and endoscopy procedure. An enema to clean the colon is used, if necessary. One animal is administered 40 ml of 100% EtOH mixed with 5 grams of TNBS diluted in 10 ml of water via an enema using a ball-tipped catheter. The enema is deposited in the proximal portion of the descending colon just past the bend of the transverse colon. The TNBS is retained at the dose site for 12 minutes by use of two Foley catheters with 60-ml balloons placed in the mid-section of the descending colon below the dose site. A second animal is similarly treated, but with a solution containing 10 grams of TNBS. An Endoscope is employed to positively identify the dose site in both animals prior to TNBS administration. Dosing and endoscopy are performed by a veterinary surgeon Seven (7) days after TNBS administration, after light anesthesia, the dose site and mucosal tissues above and below the dose site are evaluated by the veterinary surgeon using an endoscope. Pinch Biopsies are obtained necessary, as determined by the surgeon. Based on the endoscopy findings, the animals may be euthanized for tissue collection on that day, or may proceed on study pending the results of subsequent endoscopy exams for 1 to 4 more days. Macroscopic and microscopic alterations of colonic architecture, possible necrosis, thickening of the colon, and substantial histologic changes are observed at the proper TNBS dose.

Clinical signs (e.g., ill health, behavioral changes, etc.) are recorded at least daily during acclimation and throughout the study. Additional pen-side observations are conducted twice daily (once-daily on weekends). Body weight is measured for both animals Days 1 and 7 (and on the day of euthanasia if after Day 7).

On the day of necropsy, the animals are euthanized via injection of a veterinarian-approved euthanasia solution. Immediately after euthanasia in order to avoid autolytic changes, colon tissues are collected, opened, rinsed with saline, and a detailed macroscopic examination of the colon is performed to identify macroscopic finings related to TNBS-damage. Photos are taken. Tissue samples are taken from the proximal, mid, and distal transverse colon; the dose site; the distal colon; the rectum; and the anal canal. Samples are placed into NBF and evaluated by a board certified veterinary pathologist.

Example 2B—Pharmacokinetic/Pharmacodynamic and Bioavailability of Adalimumab After Topical Application Groups Sixteen (16) swine (approximately 35 to 45 kg at study start) are allocated to one of five groups:
1. Vehicle Control: (3.2 mL saline); intra-rectal; (n=2)
2. Treated Control: Adalimumab (40 mg in 3.2 mL saline); subcutaneous; (n=2)
3. Adalimumab (low): Adalimumab (40 mg in 3.2 mL saline); intra-rectal; (n=4)
4. Adalimumab (med): Adalimumab (80 mg in 3.2 mL saline); intra-rectal; (n=4)
5. Adalimumab (high): Adalimumab (160 mg in 3.2 mL saline); intra-rectal; (n=4)

On Day 0, the test article is applied to a damaged mucosal surface of the bowel via intra-rectal administration or subcutaneous injection by a veterinary surgeon at the dose levels and volume described above.

Clinical Observations and Body Weight

Clinical observations are conducted at least once daily. Clinical signs (e.g., ill health, behavioral changes, etc.) are recorded on all appropriate animals at least daily prior to the initiation of experiment and throughout the study until termination. Additional clinical observations may be performed if deemed necessary. Animals whose health condition warrants further evaluation are examined by a Clinical Veterinarian. Body weight is measured for all animals Days −6, 0, and after the last blood collections.

Samples

Blood:

Blood is collected (cephalic, jugular, and/or catheter) into EDTA tubes during acclimation on Day−7, just prior to dose on Day 0, and 0.5, 1, 2, 4, 6, 8, 12, 24, and 48 hours post-dose. The EDTA samples are split into two aliquots and one is centrifuged for pharmacokinetic plasma and either analyzed immediately, or stored frozen (−80° C.) for later on liquid nitrogen and stored frozen at −70° C. pending later analysis of drug concentration, inflammatory cytokines and histology.

Samples are analyzed for adalimumab levels (local mucosal tissue levels and systemic circulation levels), and for levels of inflammatory cytokines including TNF-alpha.

Terminal Procedures

Animals are euthanized as per the schedule in Table AA, where one animal each of Vehicle and Treated Control groups is euthanized at 6 and 48 hours post-dose, and one animal of each the adalimumab groups are euthanized at 6, 12, 24 and 48 hours post-dose. Animals are discarded after the last blood collection unless retained for a subsequent study.

TABLE AA

| General | Sample size | Dose | Route | Days −7 | −6 | −5 | −4 | −3 | −2 | −1 | 0 | Hours 0.5 | 1 | 2 | 4 | 6 | 8 | 12 | 24 | 48 |
|---|---|---|---|---|---|---|---|---|---|---|---|---|---|---|---|---|---|---|---|---|
| Fast | | | | • | | | | | | | | | | | | | | | | |
| Food/Water | | ad libitum | oral | | | | | | | | | | | | | | | | | |
| Observations | | | | | | | | | | | | | | | | | | | | |
| clinical observations | | | | | • | • | • | • | • | • | • | | | | | | | | • | • |
| body weight | | | | | • | | | | | | • | | | | | | | | • | • |
| Treatments (groups) | | | | | | | | | | | | | | | | | | | | |
| TNBS (all animals) | | | intra rectal | • | | | | | | | | | | | | | | | | |
| 1. Vehicle control | n = 2 | 1.6 mL saline (vehicle) | intra rectal | | | | | | | | | | | | | • | | | | |
| euthanized | | | | | | | | | | | | | | | | n = 1 | | | | n = 1 |
| 2. Treated control | n = 2 | 40 mg in 1.6 mL saline | sub-cutaneous | | | | | | | | | | | | | • | | | | |
| euthanized | | | | | | | | | | | | | | | | n = 1 | | | | n = 1 |
| 3. Adalimumab (low) | n = 4 | 40 mg in 1.6 mL saline | intra rectal | | | | | | | | | | | | | • | | | | |
| euthanized | | | | | | | | | | | | | | | | n = 1 | | n = 1 | n = 1 | n = 1 |
| 4. Adalimumab (med) | n = 4 | 80 mg in 1.6 mL saline | intra rectal | | | | | | | | | | | | | • | | | | |
| euthanized | | | | | | | | | | | | | | | | n = 1 | | n = 1 | n = 1 | n = 1 |
| 5. Adalimumab (high) | n = 4 | 160 mg in 1.6 mL saline | intra rectal | | | | | | | | | | | | | • | | | | |
| euthanized | | | | | | | | | | | | | | | | n = 1 | | n = 1 | n = 1 | n = 1 |
| Adalimumab (required) Samples | | 1200 | | | | | | | | | | | | | | | | | | |
| Blood | | | cephalic, jugular or catheter | • | | | | | | | | • | • | • | • | • | • | • | • | • |
| Fecal | | | rectal | • | | | | | | | | • | • | • | • | • | • | • | • | • |
| Tissue | | | necropsy | • | | | | | | | | | | | | • | | | • | • | pharmacokinetic analyses. The remaining sample of whole blood is used for pharmacodynamic analyses.

Feces:

Feces is collected Day −7, 0 and 0.5, 1, 2, 4, 6, 8, 12, 24 and 48 hours post-dose, and either analyzed immediately, or flash-frozen on liquid nitrogen and stored frozen at −70° C. pending later analysis of drug levels and inflammatory cytokines.

Tissue:

Immediately after euthanasia in order to avoid autolytic changes, colon tissues are collected, opened, rinsed with saline, and a detailed macroscopic examination of the colon is performed to identify macroscopic finings related to TNBS-damage. Triplicate samples of normal and damaged tissues are either analyzed immediately, or are flash-frozen Example 2C—Pharmacokinetic/Pharmacodynamic and Bioavailability of Adalimumab After Topical Application Groups DSS-induced colitis Yorkshire-Cross Farm Swine (approximately 5-10 kg at study start) are allocated to one of five groups:
1. Vehicle Control: (saline); intra-rectal;
2. Treated Control: Adalimumab (13 mg in saline); sub-cutaneous;
3. Adalimumab: Adalimumab (13 mg in saline); intra-rectal;

At t=0, the test article is applied to a damaged mucosal surface of the bowel via intra-rectal administration or sub-cutaneous injection by a veterinary surgeon at the dose levels and volume described above.

Clinical Observations

Clinical signs (e.g., ill health, behavioral changes, etc.) are recorded on all appropriate animals at least daily prior to the initiation of experiment and throughout the study until termination. Additional clinical observations may be performed if deemed necessary. Animals whose health condition warrants further evaluation are examined by a Clinical Veterinarian.

Samples

Blood:

Blood is collected (cephalic, jugular, and/or catheter) into EDTA tubes during acclimation on Day−7, just prior to dose on Day 0, and 12 hours post-dose. The EDTA samples are split into two aliquots and one is centrifuged for pharmacokinetic plasma and either analyzed immediately, or stored frozen (−80° C.) for later pharmacokinetic analyses. The remaining sample of whole blood is used for pharmacodynamic analyses.

Feces:

Feces is collected Day −7, 0 and 12 hours post-dose, and either analyzed immediately, or flash-frozen on liquid nitrogen and stored frozen at −70° C. pending later analysis of drug levels and inflammatory cytokines.

Tissue:

Immediately after euthanasia (12 hours after dosing) in order to avoid autolytic changes, colon tissues are collected, opened, rinsed with saline, and a detailed macroscopic examination of the colon is performed to identify macroscopic finings related to DSS-damage. Triplicate samples of normal and damaged tissues are either analyzed immediately, or are flash-frozen on liquid nitrogen and stored frozen at −70° C. pending later analysis of drug concentration, inflammatory cytokines and histology.

Samples are analyzed for adalimumab levels (local mucosal tissue levels and systemic circulation levels), and for levels of inflammatory cytokines including TNF-alpha.

Terminal Procedures

Animals are euthanized at 12 hours post-dose.

Example 3. Comparison of Systemic Versus Intracecal Delivery of an Anti-IL-12 Antibody The objective of this study was to compare the efficacy of an IL-12 inhibitor (anti-IL-12 p40; anti-p40 mAb; BioXCell (Cat #: BE0051)), when dosed systemically versus intracecally, to the treat dextran sulfate sodium salt (DSS)-induced colitis in male C57Bl/6 mice.

Materials and Methods

Mice

Normal male C57Bl/6 mice between the ages of 6-8 weeks old, weighing 20-24 g, were obtained from Charles River Laboratories. The mice were randomized into thirteen groups of twelve animals and two groups of eight animals, and housed in groups of 6-8 per cage, and acclimatized for at least three days prior to entering the study. Animal rooms were set to maintain a minimum of 12 to 15 air changes per hour, with an automatic timer for a light/dark cycle of 12 hours on/off, and fed with Labdiet 5053 sterile rodent chow, with water administered ad libitum.

Cecal Cannulation

Animals were placed under isoflurane anesthesia, with the cecum exposed via a midline incision in the abdomen. A small point incision was made in the distal cecum where 1-2 cm of the cannula was inserted. The incision was closed with a purse string suture using 5-0 silk. An incision was then made in the left abdominal wall through which the distal end of the cannula was inserted and pushed subcutaneously to the dorsal aspect of the back. The site was then washed copiously with warmed saline prior to closing the abdominal wall. A small incision was also made in the skin of the back between the shoulder blades, exposing the tip of the cannula. The cannula was secured in place using suture, wound clips, and tissue glue. All animals received 1 mL of warm sterile saline (subcutaneous injection) and were monitored closely until recovery before returning to their cage. All animals received 0.6 mg/kg BID buprenorphine for the first 3 days, and Baytril® at 10 mg/Kg every day for the first 5 days post surgery.

Induction of Colitis

Colitis was induced in male C57Bl/6 mice by exposure to 3% DSS drinking water (MP Biomedicals #0260110) from Day 0 to Day 5. Fresh DSS/water solutions were made again on Day 3 and any of the remaining original DSS solution will be discarded.

Assessment of Colitis

All animals were weighed daily and visually assessed for the presence of diarrhea and/or bloody stool at the time of dosing. The mice underwent two video endoscopies, one on day 10 and one on day 14, to assess colitis severity. Images were captured from each animal at the most severe region of disease identified during the endoscopy, and assessed using the rubric demonstrated in Table 1.1. Additionally, stool consistency was scored during the endoscopy using this rubric (Table 1.2) (0=Normal, well-formed pellet, 1=Loose stool, soft, staying in shape, 2=Loose stool, abnormal form with excess moisture, 3=Watery or diarrhea, 4=Bloody diarrhea). At necropsy, intestinal contents, peripheral blood, and tissue, and cecum/colon contents were collected for analysis.

TABLE 1.1

Endoscopy Scoring

| Score | Description of Endoscopy Score |
|---|---|
| 0 | Normal |
| 1 | Loss of vascularity |
| 2 | Loss of vascularity and friability |
| 3 | Friability and erosions |
| 4 | Ulcerations and bleeding |

TABLE 1.2

Stool Consistency Score

| Score | Description of Stool Consistency |
|---|---|
| 0 | Normal, well-formed pellet |
| 1 | Loose stool, soft, staying in shape |
| 2 | Loose stool, abnormal form with excess moisture |
| 3 | Watery or diarrhea |
| 4 | Bloody diarrhea |

Treatment of Colitis

Mice were treated with anti-IL-12 p40 during the acute phase of colitis due to its efficacy in the treatment of DSS-induced colitis. The test article was dosed at a volume of 0.1 mL/20 g from days 0 to 14. Anti-IL-12 p40 was administered intraperitoneally at a dose of 10 mg/kg every 3 days, and intracecally at a dose of 10 mg/kg, either every 3 days or every day. There was also a lower dose of 1 mg/kg given every day intracecally. The control groups were not administered drugs, and the vehicles (sterile PBS) were administered the placebo drug intraperitoneally and intracecally every day. These drugs were given from days 5-14, which is 9 days of administration. A more detailed explanation of dosing and groups can be seen in Table 1.3.

TABLE 1.3

Groups of Animals

| Group # | # of Animals | DSS | Cecal Cannula | Treatment | Dose (mg/kg) | Route | Dosing Schedule |
|---|---|---|---|---|---|---|---|
| 1 | 8 males | — | NO | — | — | — | — |
| 2 | 8 males | — | YES | — | — | — | — |
| 3 | 12 males | 3% DSS (day 0-5) | NO | Vehicle | — | PO | QD day 0-14 |
| 4 | 12 males | 3% DSS (day 0-5) | YES | Vehicle | — | IC | QD day 0-14 |
| 5 | 12 males | 3% DSS (day 0-5) | NO | Anti-p40 | 10 | IP | Q3 0, 3, 6, 9, 12 |
| 6 | 12 males | 3% DSS (day 0-5) | YES | Anti-p40 | 10 | IC | Q3 0, 3, 6, 9, 12 |
| 7 | 12 males | 3% DSS (day 0-5) | YES | Anti-p40 | 10 | IC | QD day 0-14 |
| 8 | 12 males | 3% DSS (day 0-5) | YES | Anti-p40 | 1 | IC | QD day 0-14 |

Sample Collection

Intestinal contents, peripheral blood, and tissue were collected at sacrifice on day 14, as follows: at the end of each study period, mice were euthanized by $CO_2$ inhalation immediately following endoscopy on day 14. The blood was collected via cardiac puncture into $K_2$EDTA-coated tubes and centrifuged at 4000×g for 10 minutes. The blood cell pellet was retained and snapped frozen. The resulting plasma was then split into two separate cryotubes, with 100 μL in one tube and the remainder in the second. Plasma and cell pellet were also collected, flash frozen, and stored at −80 degrees Celsius.

The cecum and colon were removed from each animal and contents were collected, weighed, and snap frozen in separate cryovials. The colon was excised, rinsed, measured, weighed, and then trimmed to 6 cm in length and divided into 5 pieces. The most proximal 1 cm of colon was snapped frozen for subsequent bioanalysis of test article levels. Of the remaining 5 cm of colon, the most distal and proximal 1.5-cm sections was placed in formalin for 24 hours then transferred to 70% ethanol for subsequent histological evaluation. The middle 2-cm portion was bisected longitudinally and placed into two separate cryotubes, weighed, and snap frozen in liquid nitrogen.

Results

Figure 30:
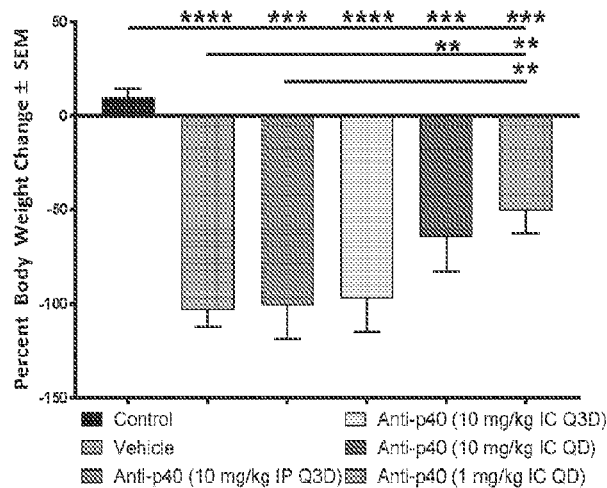
FIG. 30 is a graph showing the percentage (%) change in body weight at day 14 (±SEM) for DSS mice treated with anti-IL-12 p40 antibody intraperitoneally (10 mg/kg) every third day (Q3D) or intracecally (10 mg/kg or 1 mg/kg) daily (QD), when compared to mice treated with anti-IL-12 p40 antibody intraperitoneally (10 mg/kg) every third day (Q3D) and vehicle control (Vehicle). Mann-Whitney's U¬-test and Student's t-test were used for statistical analysis on non-Gaussian and Gaussian data respectively. A value of $p<0.05$ was considered significant (Graph Pad Software, Inc.).

The data in FIG. 30 show that the DSS mice that were intracecally administered an anti-IL-12 p40 (IgG2A) antibody had decreased weight loss as compared to DSS mice that were intraperitoneally administered the anti-IL-12 p40 antibody.

Figure 31:
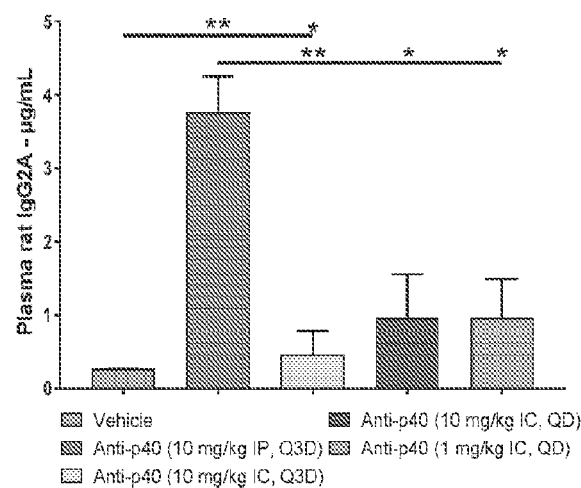
FIG. 31 is a graph showing the concentration of anti-IL-12 p40 rat IgG2A (μg/mL) in plasma of anti-IL-12 p40 intraperitoneally (10 mg/kg) and intracecally (10 mg/kg and 1 mg/kg) administered treatment groups given daily (QD) or every third day (Q3D) when compared to vehicle control (Vehicle) and when IP is compared to IC. ELISA analysis was used to determine the concentration of anti-IL-12 p40 (IgG2A). Data presented as mean±SEM. Mann-Whitney's U¬-test and Student's t-test were used for statistical analysis on non-Gaussian and Gaussian data respectively. A value of $p<0.05$ was considered significant (Graph Pad Software, Inc.).
Figure 32:
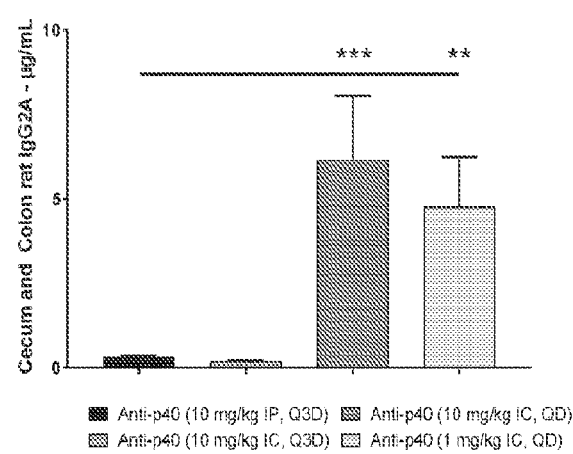
FIG. 32 is a graph showing the concentration of anti-IL-12 p40 antibody (IgG2A) (μg/mL) in the cecum and colon content of anti-IL-12 p40 antibody intraperitoneally (10 mg/kg) and intracecally (10 mg/kg and 1 mg/kg) administered treatment groups given daily (QD) or every third day (Q3D), when compared to vehicle control (Vehicle) and when IP is compared to IC. ELISA analysis was used to determine the concentration of rat IgG2A. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

The data in FIG. 31 show that the plasma concentration of the anti-IL-12 p40 antibody was decreased in DSS mice that were intracecally administered the anti-IL-12 p40 antibody as compared to DSS mice that were intraperitoneally administered the anti-IL-12 p40 antibody. The data in FIG. 32 show that the cecum and colon concentration of the anti-IL-12 p40 antibody is increased in DSS mice that were intracecally administered the anti-IL-12 p40 antibody as compared to the DSS mice that were intraperitoneally administered the anti-IL-12 p40 antibody.

Figure 33:
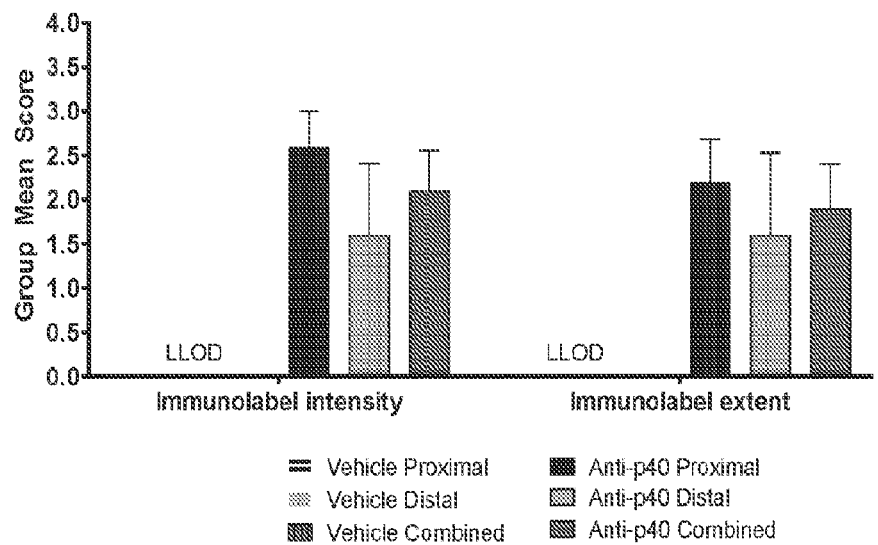
FIG. 33 is a graph showing the mean overall tissue immunolabel scores (intensity and extent) in acute DSS colitis mouse colon of anti-IL-12 p40 antibody intracecally-treated versus vehicle control-treated DSS mice. Data presented as mean±SEM.
Figure 34:
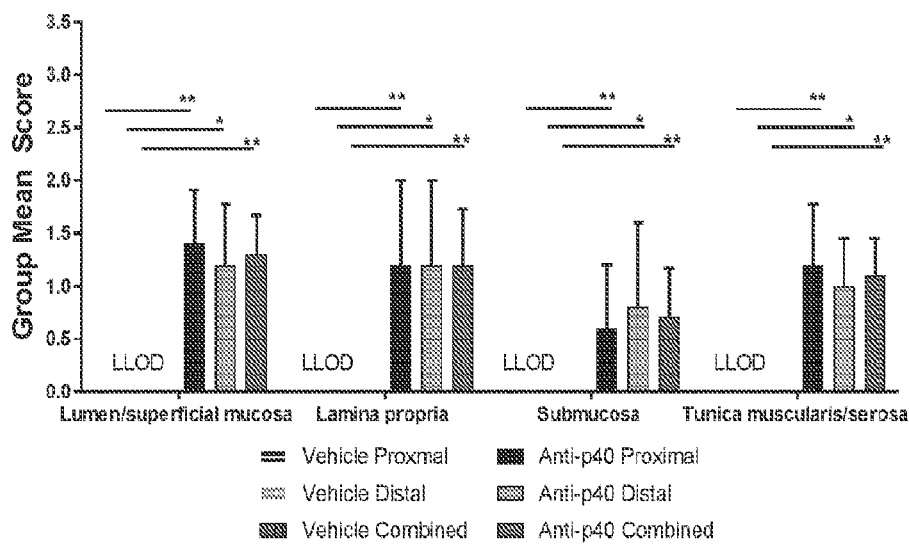
FIG. 34 is a graph showing the mean location-specific immunolabel scores in acute DSS colitis mouse colon of anti-IL-12 p40 intracecally-treated versus vehicle control-treated DSS mice. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

The data in FIGS. 33 and 34 show that the anti-IL-12 p40 antibody is able to penetrate colon tissues (the lumen superficial, lamina propria, submucosa, and tunica muscularis/serosa) in DSS mice intracecally administered the anti-IL-12 p40 antibody, while the anti-IL-12 p40 antibody did not detectably penetrate the colon tissues of DSS mice intraperitoneally administered the anti-IL-12 p40 antibody.

Figure 35:
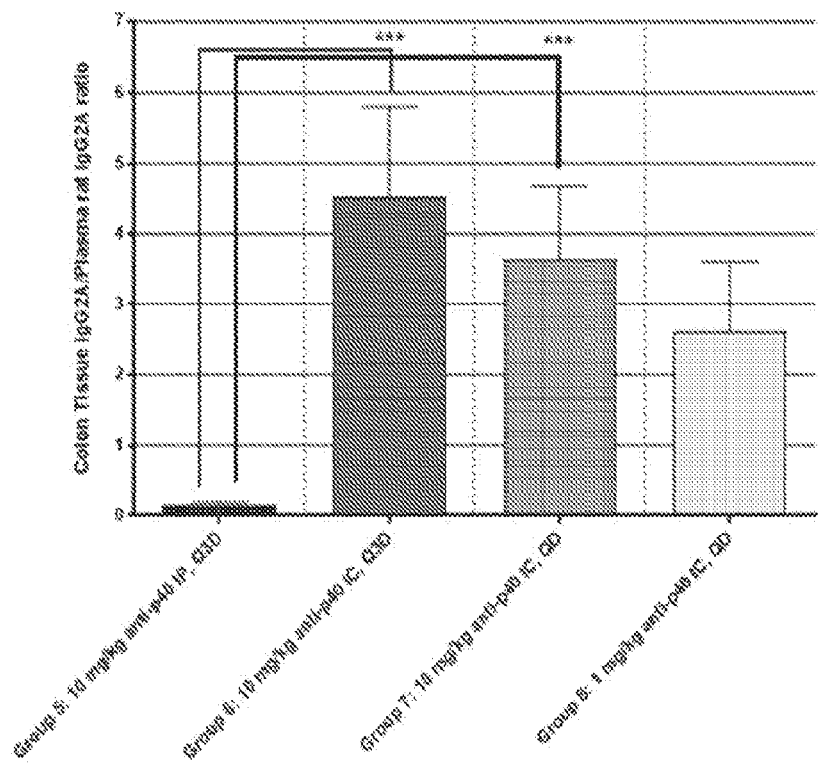
FIG. 35 is a graph showing the ratio of anti-IL-12 p40 antibody in the colon tissue to the plasma concentration of the anti-IL-12 p40 antibody in mice treated with the anti-IL-12 p40 antibody on day 0 (Q0) or day 3 (Q3D) of the study, when measured at the same time point after the initial dosing. An outlier animal was removed from Group 5.

The data in FIG. 35 also show that the ratio of the concentration of anti-IL-12 p40 antibody in colon tissue to the concentration of the anti-IL-12 p40 antibody in plasma is increased in DSS mice intracecally administered the anti-IL-12 p40 antibody as compared to the ratio in DSS mice intraperitoneally administered the anti-IL-12 p40 antibody.

Figure 36:
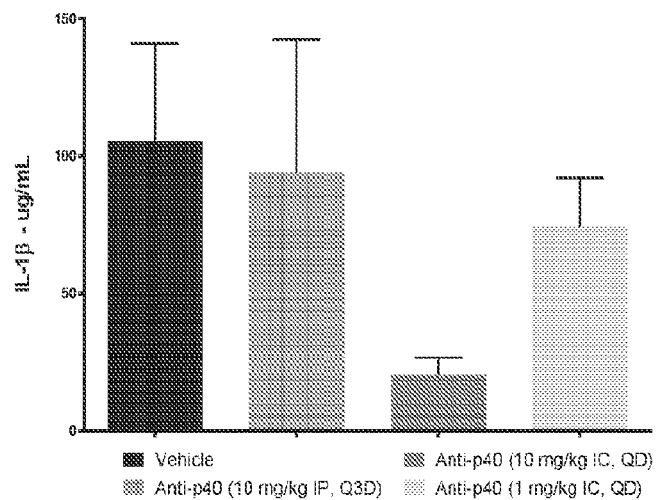
FIG. 36 is a graph showing the concentration of Il-1β (μg/mL) in colon tissue lysate of acute DSS colitis mice treated with anti-IL-12 p40 intraperitoneally (10 mg/kg) every third day (Q3D) or intracecally (10 mg/kg or 1 mg/kg) administered daily (QD), when compared to vehicle control (Vehicle). Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).
Figure 37:
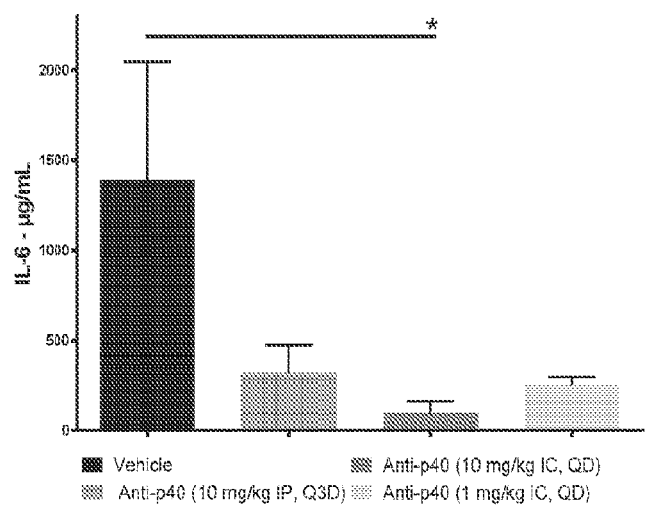
FIG. 37 is a graph showing the concentration of Il-6 (μg/mL) in colon tissue lysate of acute DSS colitis mice treated with anti-IL-12 p40 intraperitoneally (10 mg/kg) every third day (Q3D) or intracecally (10 mg/kg or 1 mg/kg) administered daily (QD), when compared to vehicle control (Vehicle). Data presented as mean±SEM. Mann-Whitney's U-test and Student's t-test were used for statistical analysis on non-Gaussian and Gaussian data respectively. A value of $p<0.05$ was considered significant (Graph Pad Software, Inc.
Figure 38:
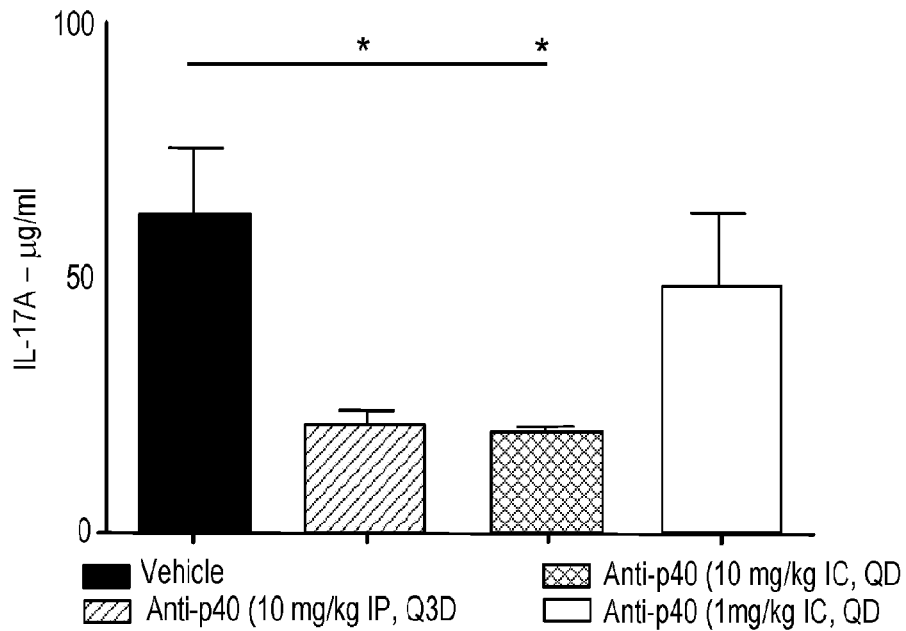
FIG. 38 is a graph showing the concentration of Il-17A (μg/mL) in colon tissue lysate of acute DSS colitis mice treated with anti-IL-12 p40 intraperitoneally (10 mg/kg) every third day (Q3D) or intracecally (10 mg/kg and 1 mg/kg) administered daily (QD), when compared to vehicle control (Vehicle). Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

The data in FIG. 36 show that the concentration of IL-10 in colon tissue is decreased in DSS mice intracecally administered the anti-IL-12 p40 antibody as compared to the concentration of IL-10 in colon tissue in DSS mice intraperitoneally administered the anti-IL-12 p40 antibody. The data in FIG. 37 show that the concentration of IL-6 in colon tissue is decreased in DSS mice intracecally administered the anti-IL-12 p40 antibody as compared to the concentration of IL-6 in colon tissue in DSS mice intraperitoneally administered the anti-IL-12 p40 antibody. The data in FIG. 38 show that the concentration of IL-17A in colon tissue is decreased in DSS mice intracecally administered the anti-IL-12 p40 antibody as compared to the concentration of IL-17A in colon tissue in DSS mice intraperitoneally administered the anti-IL-12 p40 antibody.

No significant differences in clinical observations or gastrointestinal-specific adverse effects, including stool consistency and/or bloody stool, were observed due to cannulation or intra-cecal treatments when compared with vehicle. No toxicity resulting from the treatments was reported. A significant reduction in body weight-loss (AUC) was found in groups treated with anti-IL-12 p40 antibody (10 mg/kg and 1 mg/kg, QD) via intra-cecal delivery when compared with vehicle control and intraperitoneal delivery (10 mg/kg, Q3D). The immunohistochemistry staining in anti-IL-12 p40 antibody (10 mg/kg, QD) treatment groups showed penetration of the antibody in all layers of colon tissue, including lumen mucosa, lamina propria, submucosa, tunica muscularis, via intra-cecal delivery. The distribution of anti-IL-12 p40 antibody was found in all segments of the colon, however, higher levels were detected in the proximal region. A significantly higher mean concentration of anti-IL-12 p40 antibody was found in the gastrointestinal contents and colon tissues when delivered via intra-cecal administration (Anti-p40: 10 mg/kg and 1 mg/kg, QD) compared with intraperitoneal administration (anti-p40: 10 mg/kg, Q3D). The blood level of anti-IL-12 p40 antibody was significantly higher when delivered via intraperitoneal administration (Q3D) as compared to intra-cecal administration (Q3D & QD). The concentrations of inflammatory cytokines, including IL-1β, IL-6, and IL-17, were significantly reduced by anti-IL-12 p40 antibody (10 mg/kg, QD) treatment when delivered via intra-cecal administration as compared to vehicle controls.

In sum, these data show that the compositions and devices provided herein can suppress the local immune response in the intestine, while having less of a suppressive effect on the systemic immune response of an animal. These data also suggest that the presently claimed compositions and devices will provide for treatment of colitis and other pro-inflammatory disorders of the intestine.

Example 4. Comparison of Systemic Versus Intracecal Delivery of an Anti-Integrin α4β7 Antibody The objective of this study was to compare the efficacy of an integrin inhibitor (anti-integrin α4β7; anti-LPAM1; DATK-32 mAb; BioXCell (Cat #: BE0034)) when dosed systemically versus intracecally for treating dextran sulfate sodium salt (DSS)-induced colitis in male C57Bl/6 mice.

Materials and Methods

Mice

Normal male C57Bl/6 mice between the ages of 6-8 weeks old, weighing 20-24 g, were obtained from Charles River Laboratories. The mice were randomized into thirteen groups of twelve animals and two groups of eight animals, and housed in groups of 6-8 per cage, and acclimatized for at least three days prior to entering the study. Animal rooms were set to maintain a minimum of 12 to 15 air changes per hour, with an automatic timer for a light/dark cycle of 12 hours on/off, and fed with Labdiet 5053 sterile rodent chow, with water administered ad libitum.

Cecal Cannulation

The animals were placed under isoflurane anesthesia, with the cecum exposed via a midline incision in the abdomen. A small point incision was made in the distal cecum where 1-2 cm of the cannula was inserted. The incision was closed with a purse string suture using 5-0 silk. An incision was then made in the left abdominal wall through which the distal end of the cannula was inserted and pushed subcutaneously to the dorsal aspect of the back. The site was then washed copiously with warmed saline prior to closing the abdominal wall. A small incision was also made in the skin of the back between the shoulder blades, exposing the tip of the cannula. The cannula was secured in place using suture, wound clips, and tissue glue. All animals received 1 mL of warm sterile saline (subcutaneous injection) and were monitored closely until recovery before returning to their cage. All animals received 0.6 mg/kg BID buprenorphine for the first 3 days, and Baytril® at 10 mg/Kg every day for the first 5 days post-surgery.

Induction of Colitis

Colitis was induced in male C57Bl/6 mice by exposure to 3% DSS drinking water (MP Biomedicals #0260110) from day 0 to day 5. Fresh DSS/water solutions were made again on day 3 and any of the remaining original DSS solution will be discarded.

Assessment of Colitis

All animals were weighed daily and visually assessed for the presence of diarrhea and/or bloody stool at the time of dosing. Mice underwent two video endoscopies, one on day 10 and one on day 14, to assess colitis severity. Images were captured from each animal at the most severe region of disease identified during the endoscopy, and assessed using the rubric demonstrated in Table 2.1. Additionally, stool consistency was scored during the endoscopy using this rubric (Table 2.2) (0=Normal, well-formed pellet, 1=Loose stool, soft, staying in shape, 2=Loose stool, abnormal form with excess moisture, 3=Watery or diarrhea, 4=Bloody diarrhea). At necropsy, intestinal contents, peripheral blood and tissue, and cecum/colon contents were collected for analysis.

TABLE 2.1

| Endoscopy Score | |
| --- | --- |
| Score | Description of Endoscopy Score |
| 0 | Normal |
| 1 | Loss of vascularity |
| 2 | Loss of vascularity and friability |
| 3 | Friability and erosions |
| 4 | Ulcerations and bleeding |

TABLE 2.2

| Stool Consistency Score | |
| --- | --- |
| Score | Description of Stool Consistency |
| 0 | Normal, well-formed pellet |
| 1 | Loose stool, soft, staying in shape |
| 2 | Loose stool, abnormal form with excess moisture |
| 3 | Watery or diarrhea |
| 4 | Bloody diarrhea |

Treatment of Colitis

Mice were treated with DATK32 during the acute phase of colitis due to its efficacy in the treatment of DSS-induced colitis. The test article was dosed at a volume of 0.1 mL/20 g from days 0 to 14. DATK32 was administered intraperitoneally at a dose of 25 mg/kg every 3 days, and intracecally at a dose of 25 mg/kg, either every 3 days or every day. There was also a lower dose of 5 mg/kg given every day intracecally. The control groups were not administered drugs, and the vehicle (sterile PBS) was administered as the placebo drug intraperitoneally and intracecally every day. These drugs were given from days 5-14, which is 9 days of administration. A more detailed explanation of dosing and groups can be seen in Table 2.3.

TABLE 2.3

| Groups of Mice | | | | | | | |
| --- | --- | --- | --- | --- | --- | --- | --- |
| Group # | # of Animals | DSS | Cecal Cannula | Treatment | Dose (mg/kg) | Route | Dosing Schedule |
| 1 | 8 males | — | NO | — | — | — | — |
| 2 | 8 males | — | YES | — | — | — | — |
| 3 | 12 males | 3% DSS (day 0-5) | NO | Vehicle | — | PO | QD day 0-14 |

TABLE 2.3-continued

| | | | Groups of Mice | | | | |
|---|---|---|---|---|---|---|---|
| Group # | # of Animals | DSS | Cecal Cannula | Treatment | Dose (mg/kg) | Route | Dosing Schedule |
| 4 | 12 males | 3% DSS (day 0-5) | YES | Vehicle | — | IC | QD day 0-14 |
| 9 | 12 males | 3% DSS (day 0-5) | NO | DATK32 | 25 | IP | Q3 0, 3, 6, 9, 12 |
| 10 | 12 males | 3% DSS (day 0-5) | YES | DATK32 | 25 | IC | Q3 0, 3, 6, 9, 12 |
| 11 | 12 males | 3% DSS (day 0-5) | YES | DATK32 | 25 | IC | QD |
| 12 | 12 males | 3% DSS (day 0-5) | YES | DATK32 | 5 | IC | QD day 0-14 |

Sample Collection

Intestinal contents, peripheral blood, and tissue were collected at sacrifice on day 14, as follows: at the end of each study period, mice were euthanized by $CO_2$ inhalation immediately following endoscopy on day 14. The blood was collected via cardiac puncture into $K_2$EDTA-coated tubes and centrifuged at 4000×g for 10 minutes. The blood cell pellet was retained and snapped frozen. The resulting plasma was then split into two separate cryotubes, with 100 μL in one tube and the remainder in the second. Plasma and the cell pellet were also collected, flash frozen, and stored at −80 degrees Celsius. An ELISA was used to determine the level of rat IgG2A.

The cecum and colon were removed from each animal and contents were collected, weighed, and snap frozen in separate cryovials. The colon was excised, rinsed, measured, weighed, and then trimmed to 6 cm in length and divided into 5 pieces. The most proximal 1 cm of colon was snapped frozen for subsequent bioanalysis of anti-DATK32 levels. Of the remaining 5 cm of colon, the most distal and proximal 1.5-cm sections was placed in formalin for 24 hours then transferred to 70% ethanol for subsequent histological evaluation. The middle 2-cm portion was bisected longitudinally and placed into two separate cryotubes, weighed, and snap frozen in liquid nitrogen.

There was an additional collection of 100 μL of whole blood from all animals and processed for FACS analysis of α4 and β7 expression on T-helper memory cells. Tissue and blood were immediately placed in FACS buffer (1×PBS containing 2.5% fetal calf serum) and analyzed using the following antibody panel (Table 2.4).

TABLE 2.4

| Fluorophore Labelled Antibodies Used in FACS Analysis | | |
|---|---|---|
| Antibody Target | Flurochrome | Purpose |
| CD4 | APC-Vio770 | Defines T-Helper Cells |
| CD44 | VioBlue | Memory/Naive Discrimination |
| CD45RB | FITC | Memory/Naive Discrimination |
| α4 | APC | Defines T-helper memory subset of interest |
| β7 | PE | Defines T-helper memory subset of interest |
| CD16/32 | — | Fc Block |

Results

Figure 39:
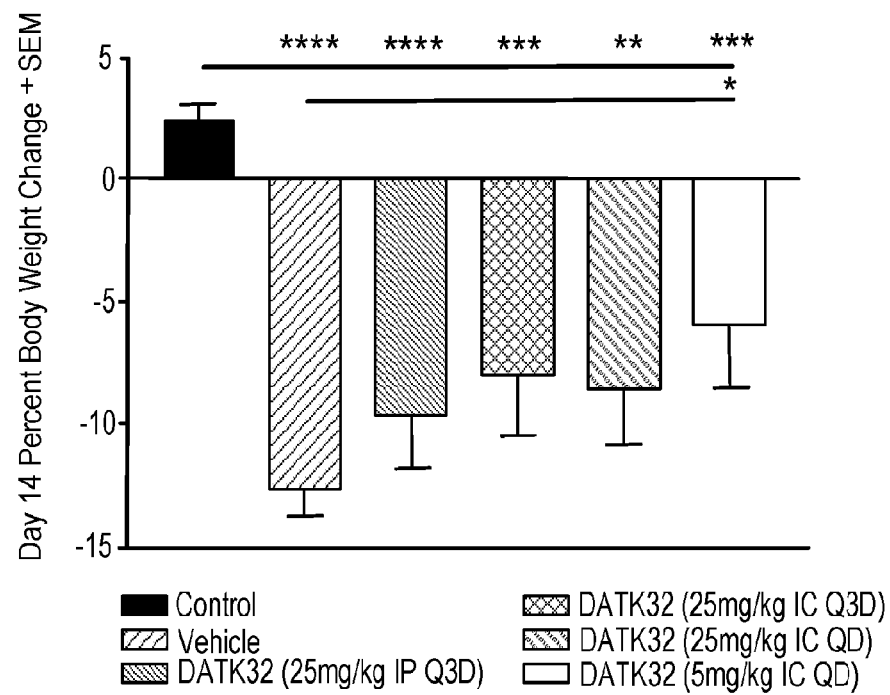
FIG. 39 is a graph showing the percentage (%) change in body weight at day 14 (±SEM) for DSS mice treated with DATK32 (anti-α4β7) antibody intraperitoneally (25 mg/kg) every third day (Q3D) or intracecally (25 mg/kg or 5 mg/kg) administered daily (QD), when compared to vehicle control (Vehicle) and when IC is compared to IP. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).
Figure 40:
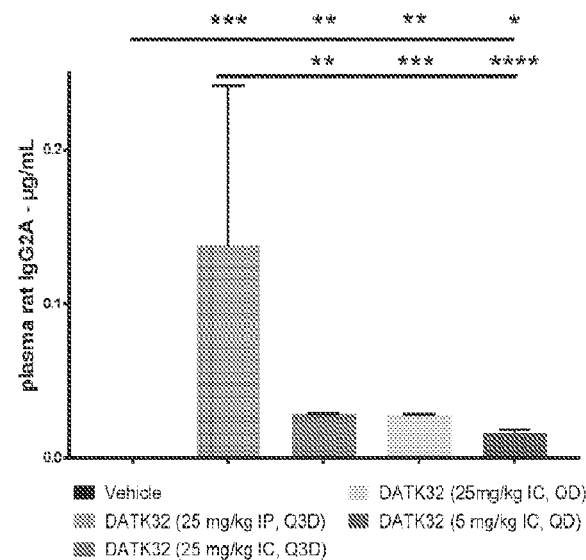
FIG. 40 is a graph showing the plasma concentration of DATK32 rat IgG2A (μg/mL) of intraperitoneally (25 mg/kg) and intracecally (25 mg/kg and 5 mg/kg) administered treatment groups given daily (QD) or every third day (Q3D), where IP is compared to IC. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).
Figure 41:
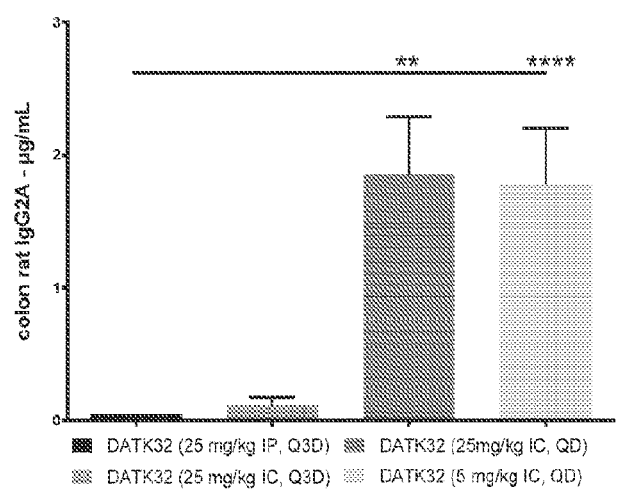
FIG. 41 is a graph showing the concentration of DATK32 rat IgG2A antibody (μg/mL) in cecum and colon content of intraperitoneally (25 mg/kg) or intracecally (25 mg/kg and 5 mg/kg) administered treatment groups given daily (QD) or every third day (Q3D), where IP is compared to IC. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).
Figure 42:
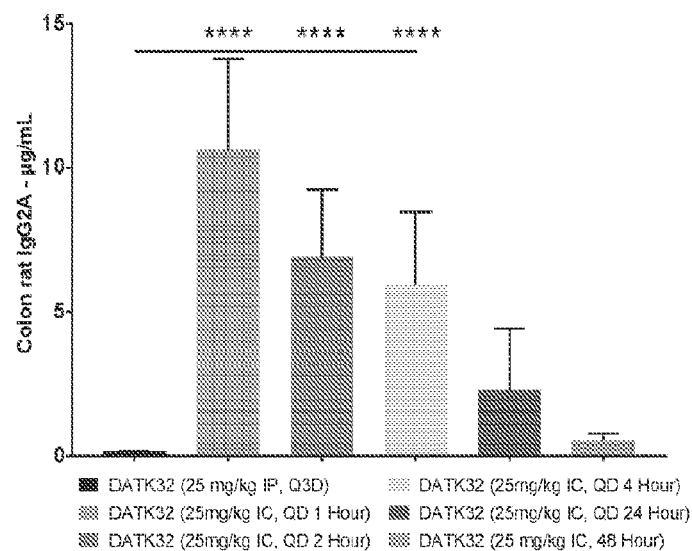
FIG. 42 is a graph showing the concentration of DATK32 rat IgG2A (μg/mL) in the colon content of intraperitoneally (25 mg/kg) or intracecally (25 mg/kg and 5 mg/kg) administered treatment groups given daily (QD), and concentration over time (1, 2, 4, 24, and 48 hours), where IP is compared to IC. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).
Figure 43:
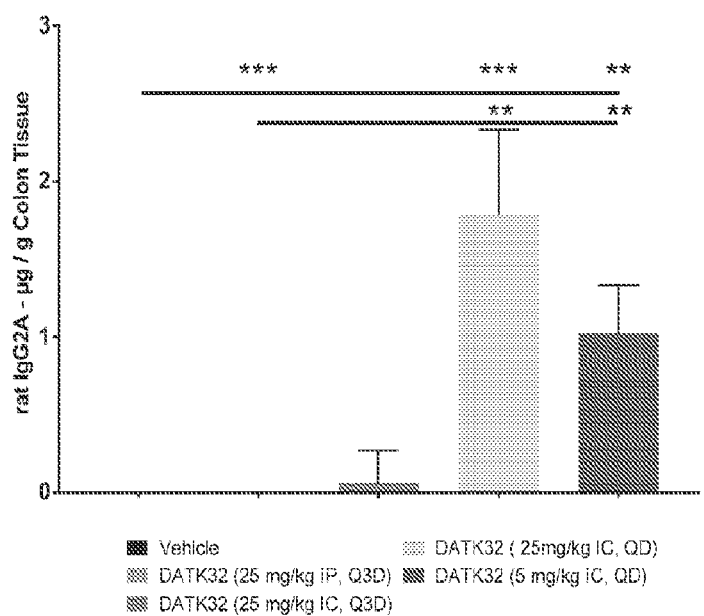
FIG. 43 is a graph showing the concentration of DATK32 rat IgG2A (μg/g) in colon tissue of intraperitoneally (25 mg/kg) or intracecally (25 mg/kg and 5 mg/kg) administered treatment groups given daily (QD) or every third day (Q3D), where IP is compared to IC. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).
Figure 44:
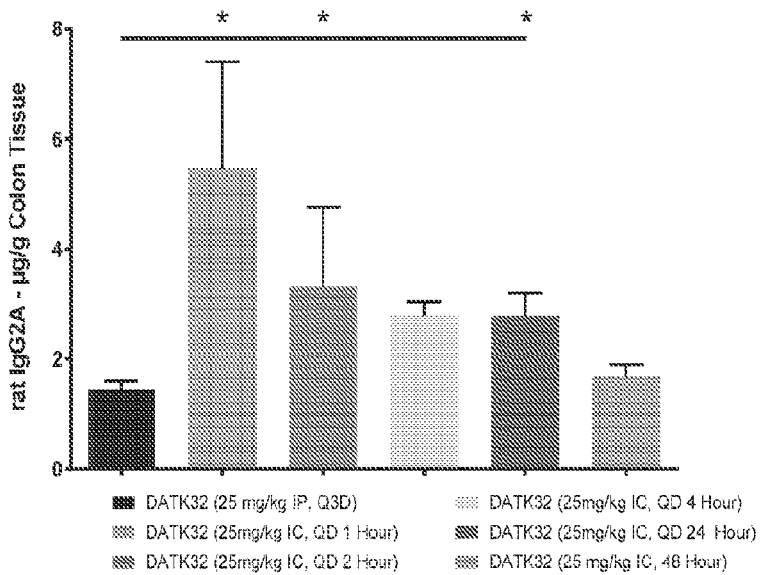
FIG. 44 is a graph showing the concentration of DATK32 rat IgG2A (μg/g) in the colon tissue of intraperitoneally (25 mg/kg) or intracecally (25 mg/kg and 5 mg/kg) administered treatment groups given daily (QD), and the concentration over time (1, 2, 4, 24, and 48 hours) was determined, where IP is compared to IC. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).
Figure 45:
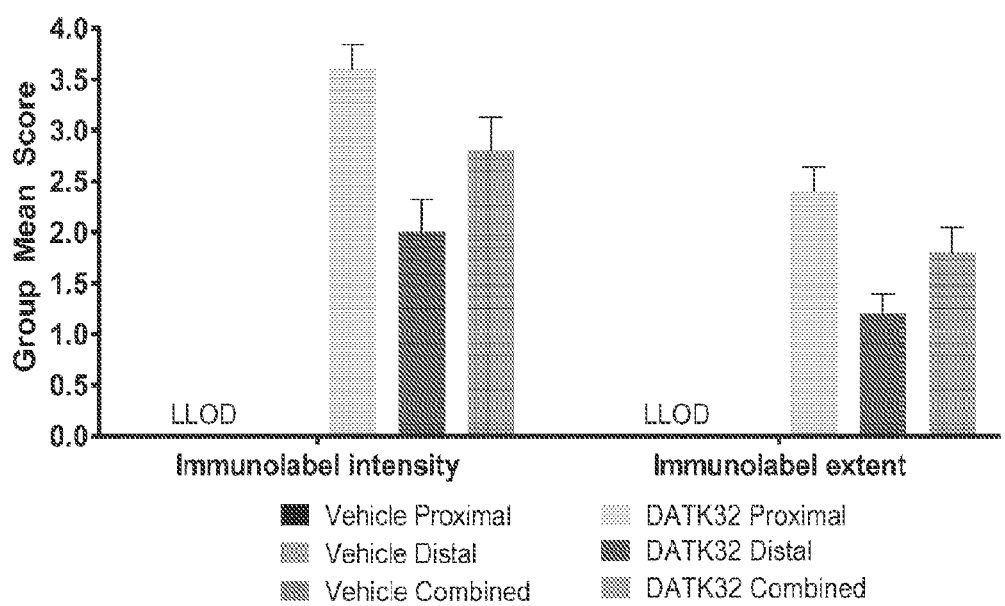
FIG. 45 is a graph showing the mean overall tissue immunolabel scores (intensity and extent) in acute DSS colitis mouse colon of DATK32 (anti-α4β7) antibody treated versus vehicle control (Vehicle) treated DSS mice. The data are presented as mean±SEM.
Figure 46:
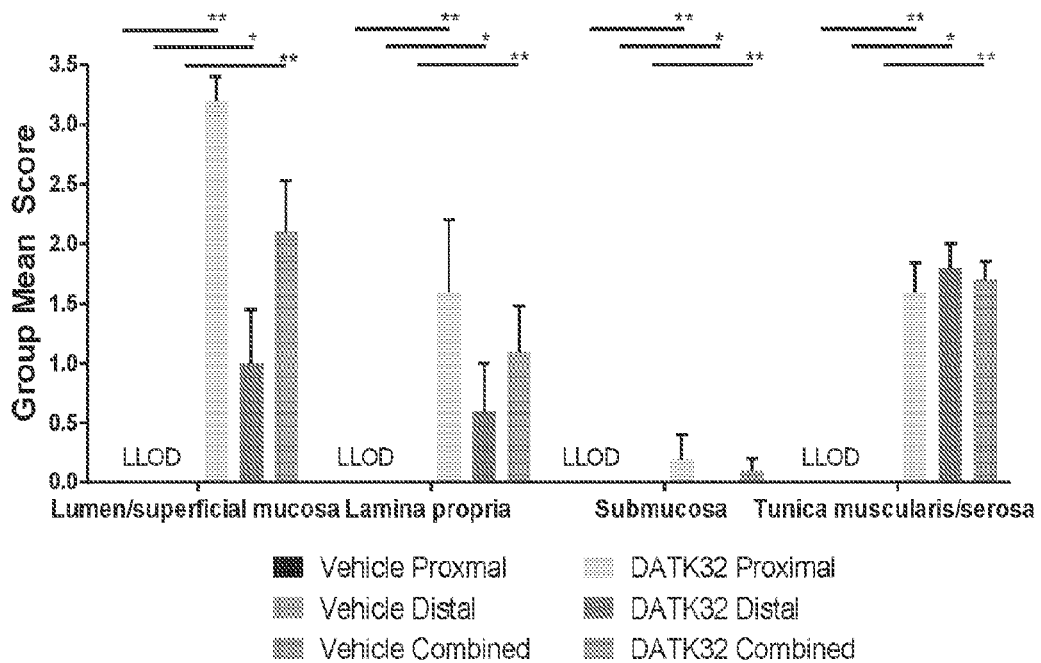
FIG. 46 is a graph showing the mean location-specific immunolabel scores in acute DSS colitis mouse colon of DATK32 (anti-α4β7) antibody-treated versus vehicle control (Vehicle)-treated DSS mice. Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 47:
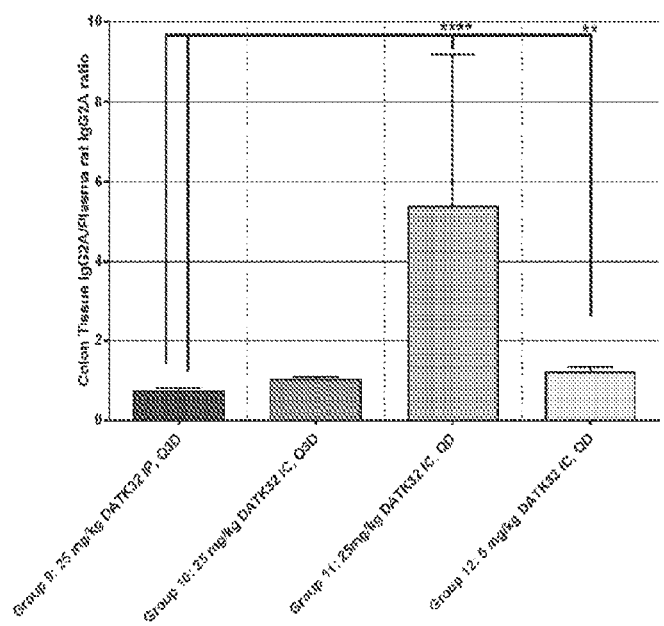
FIG. 47 is a graph showing the ratio of the DATK-32 antibody in the colon tissue to the plasma concentration of the DATK-32 antibody in mice treated with the DATK-32 antibody on day 0 (Q0) or day 3 (Q3D) of the study (Groups 9-12), when measured after initial dosing.

The data in FIG. 39 show decreased weight loss in DSS mice intracecally administered DATK antibody as compared to DSS mice that were intraperitoneally administered the DATK antibody. The data in FIG. 40 show that DSS mice intracecally administered DATK antibody have a decreased plasma concentration of DATK antibody as compared to DSS mice that were intraperitoneally administered DATK antibody. The data in FIGS. 41 and 42 show that DSS mice intracecally administered DATK antibody have an increased concentration of DATK antibody in the cecum and colon content as compared to DSS mice intraperitoneally administered DATK antibody. The data in FIGS. 43 and 44 show that DSS mice intracecally administered DATK antibody have an increased concentration of DATK antibody in colon tissue as compared to DSS mice intraperitoneally administered DATK antibody. The data in FIGS. 45 and 46 show an increased level of penetration of DATK antibody into colon tissue in DSS mice intracecally administered the DATK antibody as compared to an intracecal vehicle control (PBS). The data in FIG. 47 show that DSS mice intracecally administered DATK antibody have an increased ratio of the concentration of DATK antibody in colon tissue to the plasma concentration of the DATK antibody, as compared to the same ratio in DSS mice intraperitoneally administered the DATK antibody.

Figure 48:
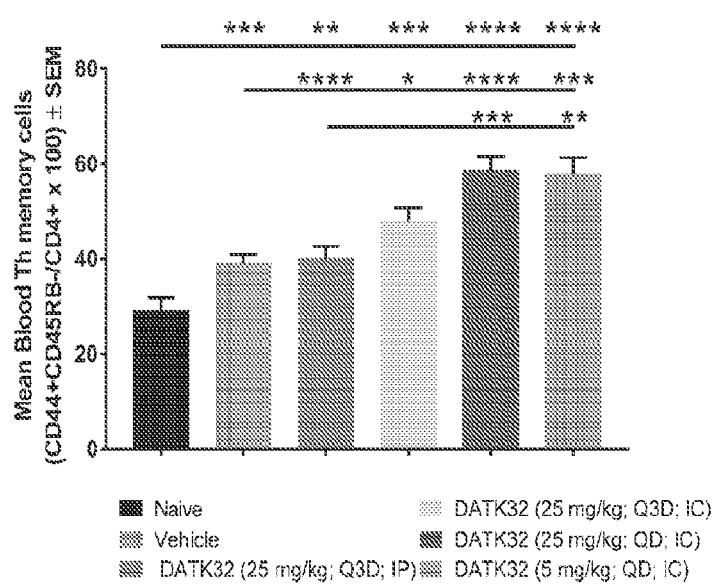
FIG. 48 is a graph showing the mean percentage of Th memory cells (mean±SEM) in blood for DATK32 (anti-α4β7) antibody intraperitoneally (25 mg/kg) or intracecally (25 mg/kg or 5 mg/kg) administered treatment groups given daily (QD) or every third day (Q3D), when compared to vehicle control (Vehicle) and when IP is compared to IC. Mean percentage Th memory cells were measured using FACS analysis. Data presented as mean±SEM. Mann-Whitney's U-test and Student's t-test were used for statistical analysis on non-Gaussian and Gaussian data respectively. A value of p<0.05 was considered significant (Graph Pad Software, Inc.).

The data in FIG. 48 show that DSS mice intracecally administered the DATK antibody have an increased percentage of blood Th memory cells as compared to DSS mice intraperitoneally administered the DATK antibody.

No significant differences in clinical observations or gastrointestinal-specific adverse effects, including stool consistency and/or bloody stool, were observed due to cannulation or intra-cecal treatments when compared with vehicle. No toxicity resulting from the treatments was reported. A significant reduction in body weight-loss was also found with DATK32 (5 mg/kg, QD) treatment (IC) when compared to vehicle control at the endpoint (day 14). The immunohistochemistry staining in DATK32 (25 mg/kg, QD) treatment groups showed penetration of DATK32 in all layers of colon tissue, including lumen mucosa, lamina propria, submucosa, tunica muscularis, via intra-cecal delivery. The distribution of DATK32 was found in all segments of the colon, however, higher levels were detected in the proximal region. A significantly higher mean concentration of DATK32 was found in gastrointestinal contents and colon tissues when delivered via intra-cecal administration (DATK32: 25 mg/kg and 5 mg/kg, QD) as compared to intraperitoneal administration (DATK32: 25 mg/kg, Q3D). The blood level of DATK32 was significantly higher when delivered via intraperitoneal administration (Q3D) as compared to intra-cecal administration (Q3D & QD). The pharmacokinetics of DATK32 (25 mg/kg, QD) showed significantly higher mean concentrations of DATK32 when delivered via intra-cecal administration at 1, 2, and 4 h post-dose in the gastrointestinal contents, and 1, 2, 4 and 24 h in colon tissue as compared with the mean concentrations of DATK32 following intraperitoneal administration. The mean number of gut-homing T cells (Th memory cells) was significantly higher in the blood of groups treated with DATK32 via intra-cecal administration (QD 25 mg/kg and QD 5 mg/kg) as compared to the groups treated with DATK32 via intraperitoneal administration (Q3D 25 mg/kg). The mean number of Th memory cells was significantly lower in the Peyer's Patches of groups treated with DATK32 via intracecal administration (QD 25 mg/kg and 5 mg/kg) as compared to the groups treated with DATK32 via intraperitoneal administration (Q3D 25 mg/kg). The mean number of Th memory cells in mesenteric lymph nodes (MLN) was significantly lower in groups treated with DATK32 via intracecal administratoin (QD and Q3D 25 mg/kg and QD 5 mg/kg) as compared to the groups treated with DATK32 via intraperitoneal administration (Q3D 25 mg/kg).

In sum, these data show that the compositions and devices provided herein can suppress the local immune response in the intestine, while having less of a suppressive effect on the systemic immune response of an animal. These data also show that the release of DATK-32 antibody in the colon can result in a suppression of leukocyte recruitment and may provide for the treatment of colitis and other pro-inflammatory diseases of the intestine.

Example 5. An Assessment of DATK32 Bio-Distribution Following Intracecal Administration in Male C57Bl/6 Mice The objective of this study is to assess DATK32 bio-distribution when dosed intracecally in male C57Bl/6 mice. A minimum of 10 days prior to the start of the experiment a cohort of animals will undergo surgical implantation of a cecal cannula. A sufficient number of animals will undergo implantation to allow for 24 cannulated animals to be enrolled in the main study (e.g., 31 animals). Animals were dosed with vehicle or test article via intracecal injection (IC) on Day 0 as indicated in Table 3. Animals from all groups were sacrificed for terminal sample collection three hours following test article administration.

Materials and Methods

Mice

Normal male C57Bl/6 mice between the ages of 6-8 weeks old, weighing 20-24 g, were obtained from Charles River Laboratories. The mice were randomized into two groups of twelve animals, and housed in groups of 12 per cage, and acclimatized for at least three days prior to entering the study. Animal rooms were set to maintain a minimum of 12 to 15 air changes per hour, with an automatic timer for a light/dark cycle of 12 hours on/off, and fed with Labdiet 5053 sterile rodent chow, with water administered ad libitum.

Cecal Cannulation

The animals were placed under isoflurane anesthesia, with the cecum exposed via a midline incision in the abdomen. A small point incision was made in the distal cecum where 1-2 cm of the cannula was inserted. The incision was closed with a purse string suture using 5-0 silk. An incision was then made in the left abdominal wall through which the distal end of the cannula was inserted and pushed subcutaneously to the dorsal aspect of the back. The site was then washed copiously with warmed saline prior to closing the abdominal wall. A small incision was also made in the skin of the back between the shoulder blades, exposing the tip of the cannula. The cannula was secured in place using suture, wound clips, and tissue glue. All animals received 1 mL of warm sterile saline (subcutaneous injection) and were monitored closely until recovery before returning to their cage. All animals received 0.6 mg/kg BID buprenorphine for the first 3 days, and Baytril® at 10 mg/Kg every day for the first 5 days post-surgery.

Dosing

Animals were dosed IC at a volume of 0.075 mL/animal on Days 0 as indicated in Table 3.

Sacrifice

All animals were euthanized by CO2 inhalation three hours after dosing on Day 0.

Sample Collection

Terminal blood was collected and prepared for plasma using $K_2$EDTA as the anti-coagulant. The plasma will be split into two cryotubes, with 50 μL in one tube (PK analysis) and the remainder in another (other). Both samples were flash-frozen in liquid nitrogen. Plasma was stored at −80° C. for downstream analysis. Mesenteric lymph nodes (mLN) were collected, weighed, and flash-frozen in liquid nitrogen. Mesenteric lymph nodes were stored at −80° C. for downstream analysis. The small intestine was excised and rinsed, and the most distal 1 cm of ilium was dissected, weighed, and flash-frozen in liquid nitrogen. The samples were stored at −80° C. for downstream analysis. The cecum and colon were removed from each animal and contents collected, weighed, and snap frozen in separate cryovials. The samples were stored at −80° C. for downstream analysis. The colon was rinsed, and the most proximal 1 cm of colon was weighed and flash-frozen in liquid nitrogen. The snap frozen tissues were stored at −80° C.

TABLE 3

Study Design

| Group | N° Animals | Treatment | Route | Schedule | Terminal Collections Day 0 |
|---|---|---|---|---|---|
| 1 | 12 | Vehicle (PBS) | IC | Day 0 ** | Blood (plasma) Small intestine mLN Colon Colon Contents Cecum Contents |
| 2 | 12 | DATK32 (625 μg)* | | | |

*Per mouse. TA was administered in 0.075 mL/animal. DATK32 was delivered in sterile PBS.
**Animals were dosed on Day 0 and collections were performed 3 hours later.

Results

The data in FIGS. 63A-F show no significant differences in clinical observations. No gastrointestinal-specific or adverse effects were found in the group administered DATK32 via intra-cecal administration as compared to the group administered a vehicle control. No toxicity resulting from the treatments was reported. The level of DATK32 in the group intra-cecally administered DATK32 was significantly higher in cecum and colon content, and colon tissue compared to the group administered a vehicle control at 3 h post-dose. A small amount of DATK32 was also detected in plasma, small intestine, and mesenteric lymph node in the group intra-cecally administered DATK32.

Example 6. Pharmacokinectics/Pharmacodynamics and Bioavailability of Adalimumab When Applied to a TNBS-damaged Mucosal Surface (Induced Colitis) in Swine The purpose of this non-Good Laboratory Practice (GLP) study was to explore the PK/PD, and bioavailability of adalimumab when applied to a TNBS-damaged mucosal surface (induced colitis) in Yorkshire-Cross farm swine, and to determine an appropriate dose and frequency for studies where a drug will be delivered by the ingestible device system. The ingestible device system will be capable of delivering a TNF inhibitor (adalimumab) topically and locally to damaged mucosa in human patients with inflammatory bowel disease (IBD). The TNBS-induced colitis model was validated when a single administration on Day 1 of 40 mL of 100% ethanol (EtOH) mixed with 5 grams of TNBS diluted in 10 mL of water via an enema using a rubber catheter resulted in the intended reproducible induction of damaged mucosal surface (induced colitis) in Yorkshire-Cross farm swine.

This study investigated whether topical delivery of adalimumab would result in increased local mucosal tissue levels with limited drug reaching systemic circulation, as compared to subcutaneous administration; whether local mucosal tissue levels of drug would be greater in damaged tissues when compared to normal tissues; whether increasing the dose of drug would result in increased mucosal tissue levels in local and distal TNBS-damaged tissues; and whether topical delivery of adalimumab would result in reductions in inflammatory cytokines such as TNF-α in damaged tissues, feces, and possibly blood.

Figure 49:
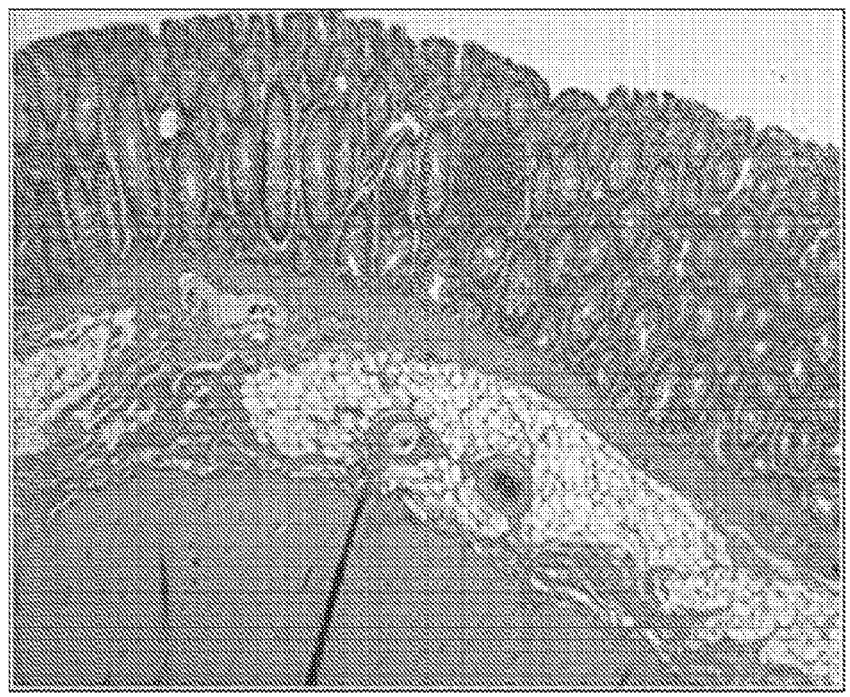
FIG. 49 is an exemplary image of a histological section of a distal transverse colon of Animal 1501 showing no significant lesions (i.e., normal colon).
Figure 50:
FIG. 50 is an exemplary image of a histological section of a distal transverse colon of Animal 2501 (treated with TNBS) showing areas of necrosis and inflammation.

All animals were subjected to intra-rectal administration of trinitrobenzene sulfonic acid (TNBS) to induce chronic colitis on day −2. All animals were fasted prior to colitis induction. Bedding was removed and replaced with rubber mats on day −3 to prevent ingestion of straw bedding material. The dose was 40 mL of 100% EtOH mixed with 5 grams of TNBS diluted in 10 mL of water, then instilled into the colon intra-rectally using a flexible gavage tube by a veterinary surgeon (deposited in a 10-cm portion of the distal colon and proximal rectum, and retained for 12 minutes by use of two Foley catheters with 60-mL balloons). Approximately 3 days after induction, macroscopic and microscopic alterations of colonic architecture were apparent: some necrosis, thickening of the colon, and substantial histologic changes were observed (FIGS. 49 and 50). The study employed 15 female swine (approximately 35 to 45 kg at study start) allocated to one of five groups. Group 1 employed three animals that were the treated controls. Each animal in Group 1 was administered adalimumab by subcutaneous injection at 40 mg in 0.8 mL saline. Groups 2, 3, 4, and 5 employed 3 animals in each group. Animals in these groups were administered intra-rectal adalimumab at 40 mg in 0.8 mL saline. The test drug (adalimumab) was administered to all groups on study day 1. The intra-rectal administrations (Groups 2-5) were applied to damaged mucosal surface of the bowel vial intra-rectal administration by a veterinary surgeon. Blood (EDTA) was collected from all animals (cephalic, jugular, or catheter) on day −3 (n=15), −1 (n=15), and 6 (n=15), 12 (n=12), 24 (n=9), and 48 (n=6) hours post-dose (87 bleeds total). The EDTA samples were split into two aliquots, and one was centrifuged for PK plasma, and stored frozen (−80° C.) for PK analyses and reporting. Fecal samples were collected for the same time-points (87 fecal collections). Fecal samples were flash-frozen in liquid nitrogen and then stored at −80° C. for analysis of drug levels and inflammatory cytokines. Groups 2, 3, 4, and 5 were euthanized and subjected to gross necropsy and tissue collection 6, 12, 24, and 48 hours post-dose, respectively. Group 1 was similarly euthanized and necropsied 48 hours post-dose. The animals were euthanized via injection of a veterinarian-approved euthanasia solution as per the schedule. Immediately after euthanasia in order to avoid autolytic changes, colon tissues were collected, opened, rinsed with saline, and a detailed macroscopic examination of the colon were performed to identify macroscopic findings related to TNBS-damage. Tissue samples were taken from the proximal, mid, and distal transverse colon; the dose site; and the distal colon. Each tissue sample was divided into two approximate halves; one tissue section was placed into 10% neutral buffered formalin (NBF) and evaluated by a Board certified veterinary pathologist, and the remaining tissue section was flash frozen in liquid nitrogen and stored frozen at −80° C. Clinical signs (ill health, behavioral changes, etc.) were recorded daily beginning on day −3. Additional pen-side observations were conducted once or twice daily. Animals observed to be in ill health were examined by a veterinarian. Body weight was measured for all animals on day −3, and prior to scheduled euthanasia. Table 4.1, depicted below, shows the study design.

Materials and Methods

Test Article

Adalimumab (EXEMPTIA™) is a Tumour Necrosis Factor (TNF) inhibitor. A single dose was pre-filled in a syringe (40 mg in a volume of 0.8 mL).

TABLE 4.1

Study Design Table

| General | Sample size | Dose | Route | Days | | | | Hours | | | | | | | |
|---|---|---|---|---|---|---|---|---|---|---|---|---|---|---|---|
| | | | | −3 | −2 | −1 | 1 | 0.5 | 1 | 2 | 4 | 6 | 8 | 12 | 24 | 48 |
| Fast | ad libidum | | oral | • | | | | | | | | | | | | |
| Food/Water | | | | | • | • | • | • | • | • | • | • | • | • | • | • |
| Observations | | | | | | | | | | | | | | | | |
| clinical observations | | | | | | | • | • | • | • | | | | | • | • |
| body weight | | | | | | | • | | | • | | | | | • | • |
| Treatments (groups) | | | | | | | | | | | | | | | | |
| TNBS (all animals) | | | intra rectal | | • | | | | | | | | | | | |
| 1. Vehicle control | n = 3 | 40 mg in 0.8 mL saline | sub-cutaneous | | | | • | | | | | | | | | |
| euthanized | | | | | | | | | | | | | | | | n = 3 |
| 2. Adalimumab | n = 3 | 40 mg in 0.8 mL saline | intra rectal | | | | • | | | | | | | | | |
| euthanized | | | | | | | | | | | | | n = 3 | | | |
| 3. Adalimumab | n = 3 | 40 mg in 0.8 mL saline | intra rectal | | | | • | | | | | | | | | |
| euthanized | | | | | | | | | | | | | | | n = 3 | |

TABLE 4.1-continued

Study Design Table

| General | Sample size | Dose | Route | Days -3 | -2 | -1 | 1 | Hours 0.5 | 1 | 2 | 4 | 6 | 8 | 12 | 24 | 48 |
|---|---|---|---|---|---|---|---|---|---|---|---|---|---|---|---|---|
| 4. Adalimumab euthanized | n = 3 | 40 mg in 0.8 mL saline | intra rectal | | | | • | | | | | | | | n = 3 | |
| 5. Adalimumab euthanized | n = 3 | 40 mg in 0.8 mL saline | intra rectal | | | | • | | | | | | | | | n = 3 |
| Adalimumab (required) Samples | | 600 | | | | | | | | | | | | | | |
| PBMCs | | | cephalic, jugular or catheter | | | | • | | | | | • | | • | • | • |
| Serum | | | cephalic, jugular or catheter | • | • | • | | | | | | • | | • | • | • |
| Fecal | | | rectal | • | • | • | | | | | | • | | • | • | • |
| Tissue Analysis | | | necropsy | | | | | | | | | • | | • | • | • |
| Histopathology | 1 location | 4 locations | | | | | | | | | | | | | | |
| inflammed | 45 | 180 | H&E | | | | | | | | | | | | | |
| normal | 45 | 180 | H&E | | | | | | | | | | | | | |
| Blood | | | | | | | | | | | | | | | | |
| adalimumab | 57 | | pbl | | | | 15 | | | | | 15 | | 12 | 9 | 6 |
| TNFα | 87 | | pbl | 15 | | 15 | 15 | | | | | 15 | | 12 | 9 | 6 |
| Feces | | | | | | | | | | | | | | | | |
| adalimumab | 57 | | pbl | | | | 15 | | | | | 15 | | 12 | 9 | 6 |
| TNFα | 87 | | pbl | 15 | | 15 | 15 | | | | | 15 | | 12 | 9 | 6 |
| Tissue Inflammed | | | | | | | | | | | | | | | | |
| adalimumab | 45 | 180 | pbl | | | | | | | | | 3 | | 3 | 3 | 6 |
| TNFα | 45 | 180 | pbl | | | | | | | | | 3 | | 3 | 3 | 6 |
| HER2 | 45 | 180 | pbl | | | | | | | | | 3 | | 3 | 3 | 6 |
| Normal | | | | | | | | | | | | | | | | |
| adalimumab | 45 | 180 | pbl | | | | | | | | | 3 | | 3 | 3 | 6 |
| TNFα | 45 | 180 | pbl | | | | | | | | | 3 | | 3 | 3 | 6 |
| HER2 | 45 | 180 | pbl | | | | | | | | | 3 | | 3 | 3 | 6 |

Results

Figure 51:
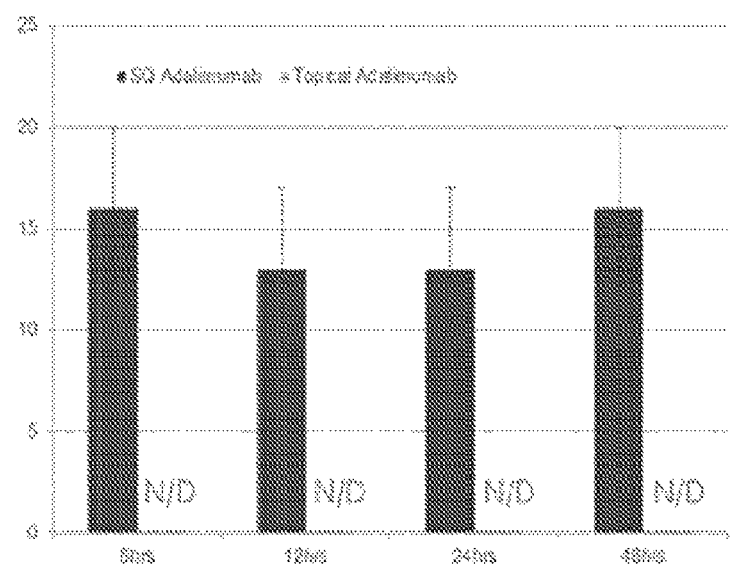
FIG. 51 is a representative graph of plasma adalimumab concentrations over time following a single subcutaneous (SQ) or topical administration of adalimumab. The plasma concentrations of adalimumab were determined 6, 12, 24, and 48 hours after administration of adalimumab. N/D=not detectable.
Figure 53:
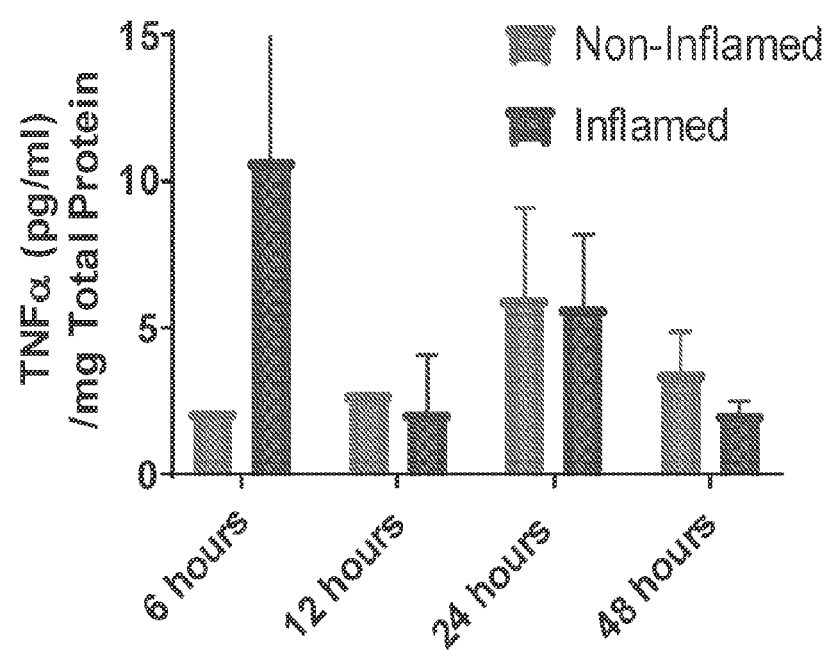
FIG. 53 is a graph showing the concentration of TNFα (pg/mL per mg of total protein) in non-inflamed and inflamed colon tissue after intracecal administration of adalimumab, as measured 6, 12, 24, and 24 hours after the initial dosing.
Figure 54:
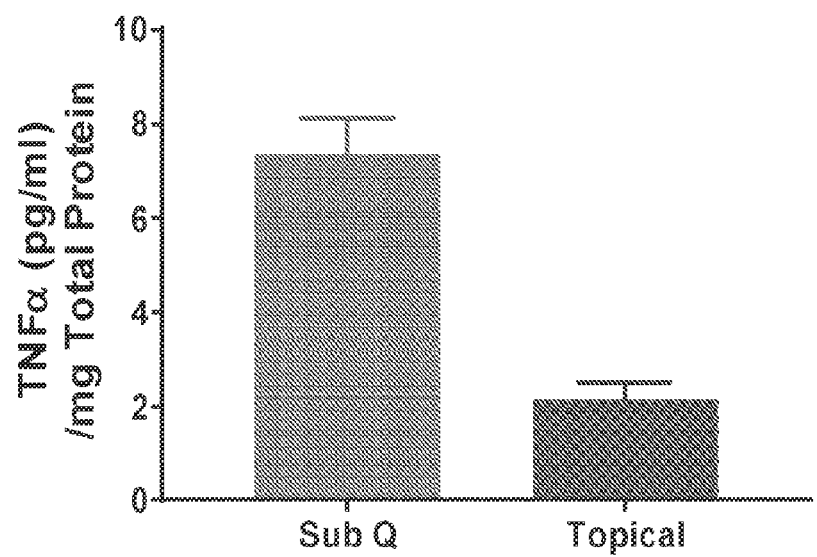
FIG. 54 is a graph showing the concentration of TNFα (pg/mL per mg of total protein) in colon tissue after subcutaneous or intracecal (topical) administration of adalimumab, as measured 48 hours after the initial dosing.

While subcutaneously administered adalimumab was detected at all times points tested in plasma, topically administered adalimumab was barely detectable in plasma (FIGS. 51 and 52). Both topical delivery and subcutaneous delivery of adalimumab resulted in reduced levels of TNF-α in colon tissue of TNBS-induced colitis animals, yet topical delivery of adalimumab was able to achieve a greater reduction in TNF-α levels (FIGS. 53 and 54).

Either subcutaneous or intra-rectal administration of adalimumab was well tolerated and did not result in death, morbidity, adverse clinical observations, or body weight changes. A decreased level of total TNBS-related inflammatory response was observed by adalimumab treatment via intra-rectal administration when applied to the damaged mucosal surface of the bowel when compared to subcutaneous delivery. A significantly higher concentration of adalimumab was measured in blood following subcutaneous delivery as compared to the blood concentration following intra-rectal administration. Intra-rectal administration of adalimumab decreased the total and normalized TNFα concentration over time (6-48 h) and was more effective at reducing TNFα at the endpoint (48 h) as compared to groups administered adalimumab subcutaneously.

In sum, these data show that the compositions and devices provided herein can suppress the local immune response in the intestine, while having less of a suppressive effect on the systemic immune response of an animal. For example, these data show that intracecal administration of adalimumab using a device as described herein can provide for local delivery of adalimumab to the site of disease, without suppressing the systemic immune response. These data also show that local administration of adalimumab using a device as described herein can result in a significant reduction of the levels of TNFα in diseases animals.

Example 7. Comparison of Systemic Versus Intracecal Delivery of Cyclosporine A

The objective of this study was to compare the efficacy of an immunosuppressant agent (cyclosporine A; CsA) when dosed systemically versus intracecally to treat dextran sulfate sodium salt (DSS)-induced colitis in male C57Bl/6 mice.

Experimental Design

A minimum of 10 days prior to the start of the experiment a cohort of animals underwent surgical implantation of a cecal cannula. A sufficient number of animals underwent implantation to allow for 44 cannulated animals to be enrolled in the main study (e.g., 76 animals). Colitis was induced in 60 male C5Bl/6 mice by exposure to 3% DSS-treated drinking water from day 0 to day 5. Two groups of eight additional animals (cannulated and non-cannulated) served as no-disease controls (Groups 1 and 2). Animals were dosed with cyclosporine A via intraperitoneal injection (IP), oral gavage (PO), or intracecal injection (IC) from day 0 to 14 as indicated in Table 5.1. All animals were weighed daily and assessed visually for the presence of diarrhea and/or bloody stool at the time of dosing. Mice underwent video endoscopy on days 10 and 14 to assess colitis severity. Images were captured from each animal at the most severe region of disease identified during endoscopy. Additionally, stool consistency was scored during endoscopy using the parameters defined in Table 5.2. Following endoscopy on day 14, animals from all groups were sacrificed and underwent terminal sample collection.

Specifically, animals in all treatment groups dosed on day 14 were sacrificed at a pre-dosing time point, or 1, 2, and 4 hours after dosing (n=3/group/time point). Terminal blood was collected via cardiac puncture and prepared for plasma using K$_2$EDTA as the anti-coagulant. The blood cell pellet was retained and snap frozen while the resulting plasma was split into two separate cryotubes, with 100 μL in one tube and the remainder in the second. Additionally, the cecum and colon were removed from all animals; the contents were collected, weighed, and snap frozen in separate cyrovials. The colon was then rinsed, measured, weighed, and then trimmed to 6 cm in length and divided into five pieces. The most proximal 1 cm of colon was snap frozen for subsequent bioanalysis of cyclosporine A levels. Of the remaining 5 cm of colon, the most distal and proximal 1.5-cm sections were each placed in formalin for 24 hours, then transferred to 70% ethanol for subsequent histological evaluation. The middle 2-cm portion was bisected longitudinally and placed into two separate cryotubes, weighed, and snap frozen in liquid nitrogen. All plasma and frozen colon tissue were stored at −80° C. for selected end point analysis. For all control animals in Groups 1-4, there was an additional collection of 100 μL of whole blood from all animals which was then processed for FACS analysis of α4 and β7 expression on T$_H$ memory cells. The details of the study are shown in Table 5.1.

TABLE 5.1

| Study Design | | | | | | | |
|---|---|---|---|---|---|---|---|
| Group Number | 1 | 2 | 3 | 4 | 13 | 14 | 15 |
| Number of Animals | 8 | 8 | 12 | 12 | 12 | 12 | 12 |
| Cecal Cannula | NO | YES | NO | YES | NO | YES | YES |
| DSS | N/A | N/A | 3% DSS on Day 0 to Day 5 | | | | |
| Treatment | none | none | vehicle | vehicle | CsA | CsA | CsA |
| Dose (mg/kg) | N/A | N/A | N/A | N/A | 10 | 10 | 3 |
| Route | N/A | N/A | N/A | N/A | PO | IC | IC |
| Dosing Schedule | N/A | N/A | QD: Day 0 to 14 | QD: Day 0 to 14 | QD: Day 0 to 14 | QD: Day 0 to 14 | QD: Day 0 to 14 |
| Endoscopy Schedule* | Days 10 and 14 | | | | | | |
| Endpoints Day 14 | Endoscopy, Colon weight/ length, stool score Terminal Collection (all groups): Cecal contents, colon contents, plasma, and colon tissue FACS analysis collection of Groups 1-4: Whole blood for the following FACS panel: CD4, CD44, CD45RB, α4, β7, CD16/32 | | | | | | |
| PK Sacrifice (Day 14) | N = 3/time points At pre-dose and 1, 2, and 4 hours post-dosing | | | | | | |

*Animals were dosed once (QD) on Day 14 and plasma collected (K2EDTA) at pre-dosing, 1, 2, and 4 hours post-dosing from n = 3/group/time point. Each collection was terminal.

Experimental Procedures

Cecal Cannulation

Animals were placed under isoflurance anesthesia, and the cecum exposed via a midline incision in the abdomen. A small point incision was made in the distal cecum through which 1-2 cm of the cannula was inserted. The incision was closed with a purse-string suture using 5-0 silk. An incision was made in the left abdominal wall through which the distal end of the cannula was inserted and pushed subcutaneously to the dorsal aspect of the back. The site was washed copiously with warmed saline prior to closing the abdominal wall. A small incision was made in the skin of the back between the shoulder blades, exposing the tip of the cannula. The cannula was secured in place using suture, wound clips, and tissue glue. All animals received 1 mL of warm sterile saline (subcutaneous injection) and were monitored closely until fully recovered before returning to the cage. All animals received buprenorphine at 0.6 mg/kg BID for the first 3 days, and Baytril® at 10 mg/kg QD for the first 5 days following surgery.

Disease Induction

Colitis was induced on day 0 via addition of 3% DSS (MP Biomedicals, Cat #0260110) to the drinking water. Fresh DSS/water solutions were made on day 3 and any of the remaining original DSS solution was discarded.

Dosing

Animals were dosed by oral gavage (PO), intraperitoneal injection (IP), or intracecal injection (IC) at a volume of 0.1 mL/20 g on days 0 to 14 as indicated in Table 5.1.

Body Weight and Survival

Animals were observed daily (weight, morbidity, survival, presence of diarrhea, and/or bloody stool) in order to assess possible differences among treatment groups and/or possible toxicity resulting from the treatments.

Animals Found Dead or Moribund

Animals were monitored on a daily basis and those exhibiting weight loss greater than 30% were euthanized, and samples were not collected from these animals.

Endoscopy

Each mouse underwent video endoscopy on days 10 and 14 using a small animal endoscope (Karl Storz Endoskope, Germany) under isoflurane anesthesia. During each endoscopic procedure still images as well as video were recorded to evaluate the extent of colitis and the response to treatment. Additionally, we attempted to capture an image from each animal at the most severe region of disease identified during endoscopy. Colitis severity was scored using a 0-4 scale (0=normal; 1=loss of vascularity; 2=loss of vascularity and friability; 3=friability and erosions; 4=ulcerations and bleeding). Additionally, stool consistency was scored during endoscopy using the parameters defined in Table 5.2.

TABLE 5.2

Stool Consistency

| Score | Description |
|---|---|
| 0 | Normal, well-formed pellet |
| 1 | Loose stool, soft, staying in shape |
| 2 | Loose stool, abnormal form with excess moisture |
| 3 | Watery or diarrhea |
| 4 | Bloody diarrhea |

Tissue/Blood for FACS

Tissue and blood were immediately placed in FACS buffer (1× phosphate-buffered saline (PBS) containing 2.5% fetal calf serum (FCS)) and analyzed using the antibody panel in Table 5.3.

TABLE 5.3

FACS Antibody Panel

| Antibody Target | Fluorochrome | Purpose |
|---|---|---|
| CD4 | APC-Vio770 | Defines $T_H$ cells |
| CD44 | VioBlue | Memory/Naïve discrimination |
| CD45RB | FITC | Memory/Naïve discrimination |
| α4 | APC | Defines $T_H$-memory subset of interest |
| β7 | PE | Defines $T_H$-memory subset of interest |
| CD16/32 | — | Fc block |

Results

Figure 55:
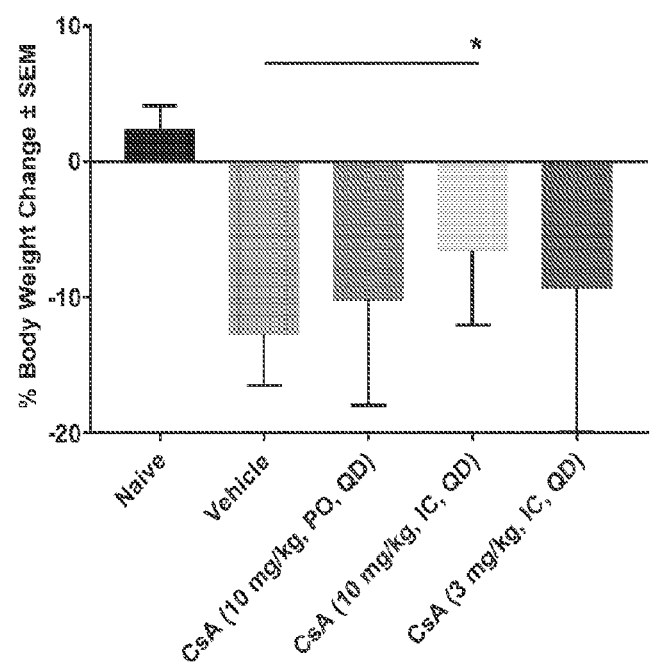
FIG. 55 is a graph showing the percentage (%) change in body weight at day 14 (±SEM) in acute DSS colitis mice treated with cyclosporine A orally (10 mg/kg) every third day (Q3D) or intracecally (10 mg/kg or 3 mg/kg) daily (QD), when compared to vehicle control (Vehicle). Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 56:
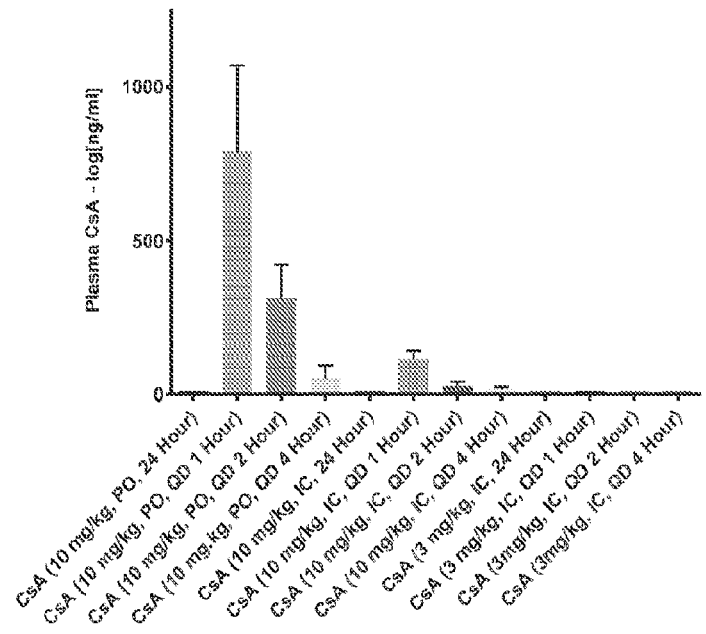
FIG. 56 is a graph showing the plasma cyclosporine A (CsA) (ng/mL) concentration over time (1 h, 2 h, 4 h, and 24 h) in acute DSS colitis mice treated daily (QD) with orally (PO) (10 mg/kg) or intracecally (IC) (10 mg/kg or 3 mg/kg) administered CsA. Data presented as mean±SEM.
Figure 57:
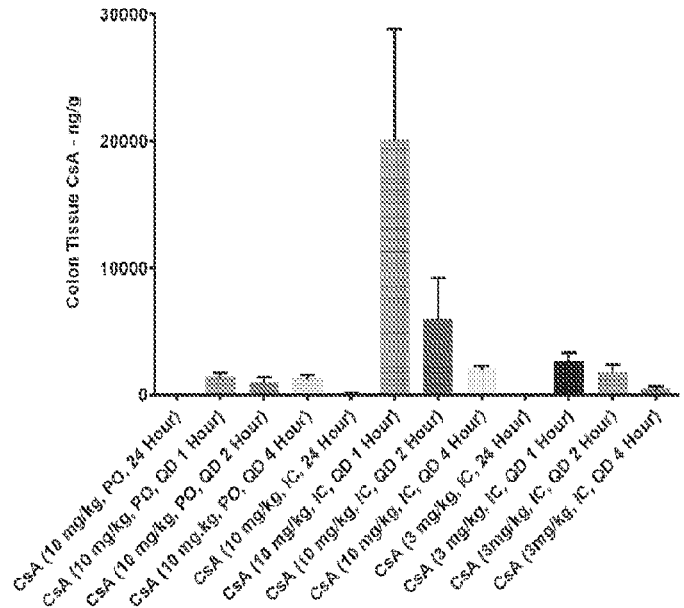
FIG. 57 is a graph showing the colon tissue cyclosporine A (CsA) (ng/g) concentration over time (1 h, 2 h, 4 h and 24 h) in acute DSS colitis mice treated daily (QD) with orally (PO) (10 mg/kg) or intracecally (IC) (10 mg/kg or 3 mg/kg) administered CsA. Data presented as mean±SEM.
Figure 58:
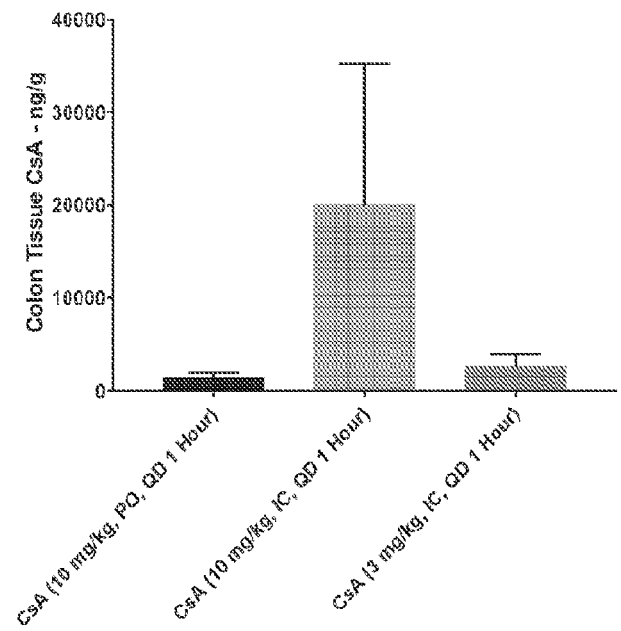
FIG. 58 is a graph showing the peak colon tissue cyclosporine A (CsA) (ng/g) concentration in acute DSS colitis mice treated daily (QD) with orally (PO) (10 mg/kg) or intracecally (IC) (10 mg/kg or 3 mg/kg) administered CsA. Data presented as mean±SEM.
Figure 59:
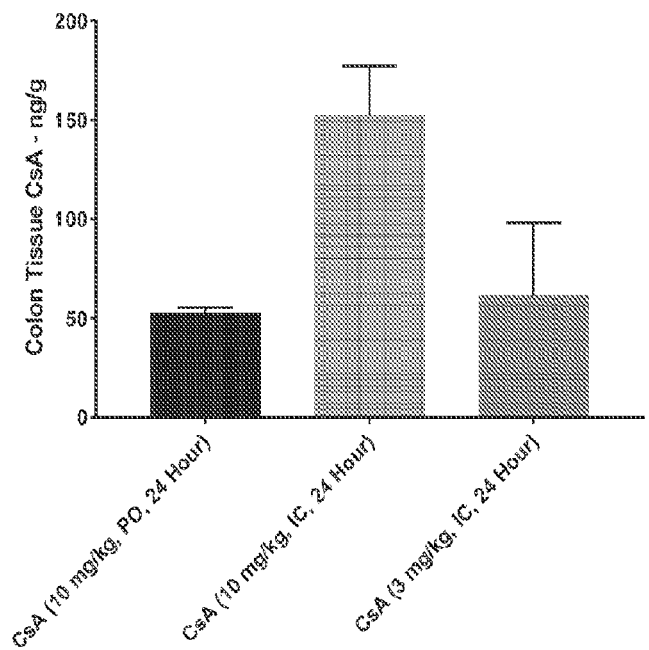
FIG. 59 is a graph showing the trough tissue concentration of cyclosporine (CsA) (ng/g) in colon of acute DSS colitis mice treated daily (QD) with orally (PO) (10 mg/kg) or intracecally (IC) (10 mg/kg or 3 mg/kg) administered CsA. Data presented as mean±SEM.

The data in FIG. 55 show a decrease in weight loss is observed in DSS mice intracecally administered cyclosporine A as compared to DSS mice orally administered cyclosporine A. The data in FIG. 56 show a decrease in plasma concentration of cyclosporine A in DSS mice intracecally administered cyclosporine A as compared to DSS mice orally administered cyclosporine A. The data in FIGS. 57-59 show an increased concentration of cyclosporine A in the colon tissue of DSS mice intracecally administered cyclosporine A as compared to the concentration of cyclosporine A in the colon tissue of DSS mice orally administered cyclosporine A.

Figure 60:
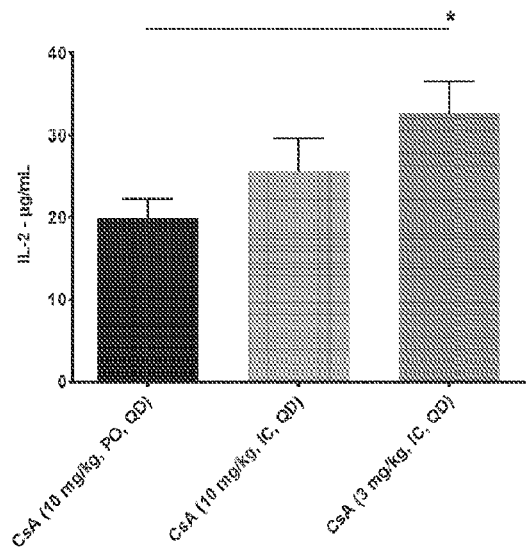
FIG. 60 is a graph showing the interleukin-2 (Il-2) concentration (μg/mL) in colon tissue of acute DSS colitis mice treated daily (QD) with orally (PO) (10 mg/kg) or intracecally (IC) (10 mg/kg or 3 mg/kg) administered CsA, where PO is compared to IC. Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 61:
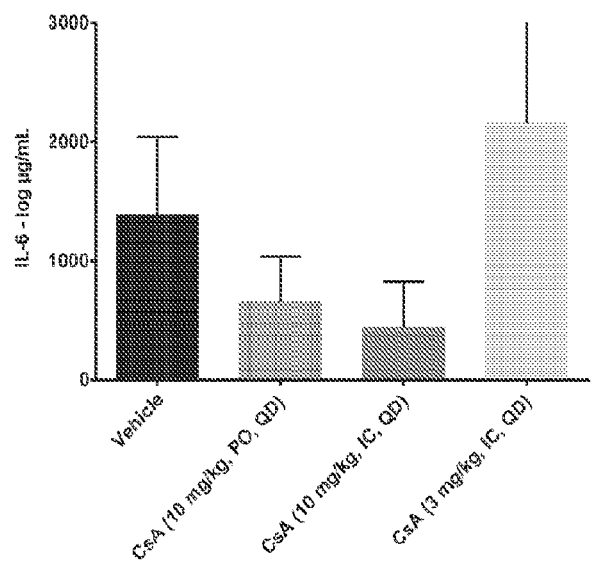
FIG. 61 is a graph showing the interleukin-6 (Il-6) concentration (μg/mL) in colon tissue of acute DSS colitis mice treated daily (QD) with orally (PO) (10 mg/kg) or intracecally (IC) (10 mg/kg or 3 mg/kg) administered CsA. Data presented as mean±SEM.

The data in FIG. 60 show that DSS mice intracecally administered cyclosporine A have an increased concentration of IL-2 in colon tissue as compared to DSS mice orally administered cyclosporine A. The data in FIG. 61 show that DSS mice intracecally administered cyclosporine A have a decreased concentration of IL-6 in colon tissue as compared to DSS mice orally administered cyclosporine A.

In sum, these data show that the compositions and devices provided herein can suppress the local immune response in the intestine, while having less of a suppressive effect on the systemic immune response of an animal. For example, these data demonstrate that the present compositions and devices can be used to release cyclosporine A to the intestine and that this results in a selective immune suppression in the colon, while having less of an effect on the immune system outside of the intesting. These data also suggest that the present compositions and devices will provide for the treatment of colitis and other pro-inflammatory disorders of the intestine.

Example 8. Bellows Testing: Drug Stability Bench Test

Experiments were run to evaluate the effects that bellows material would have on the function of a drug used as the dispensable substance. The experiments also evaluated the effects on drug function due to shelf life in the bellows.

Figure 64:
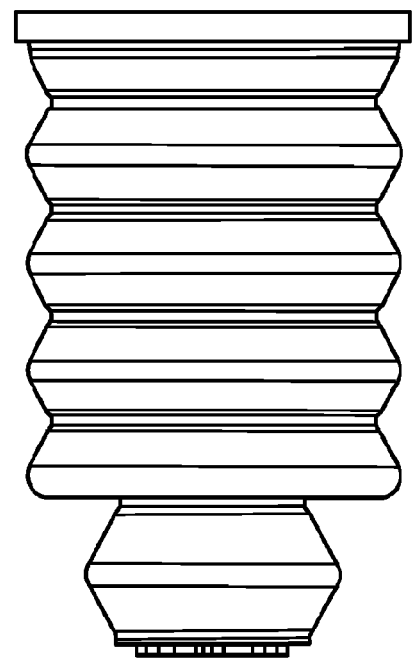
FIG. 64 illustrates a tapered silicon bellows.
Figure 65:
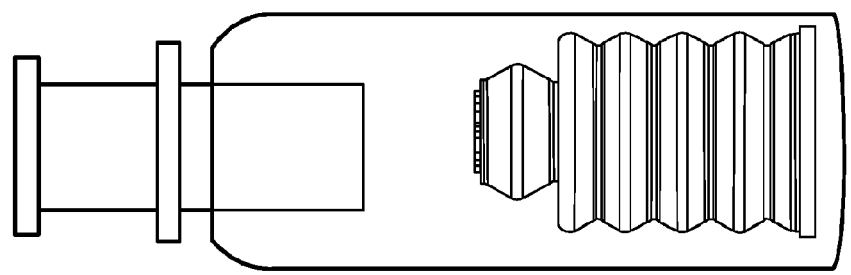
FIG. 65 illustrates a tapered silicone bellows in the simulated device jig.
Figure 66:
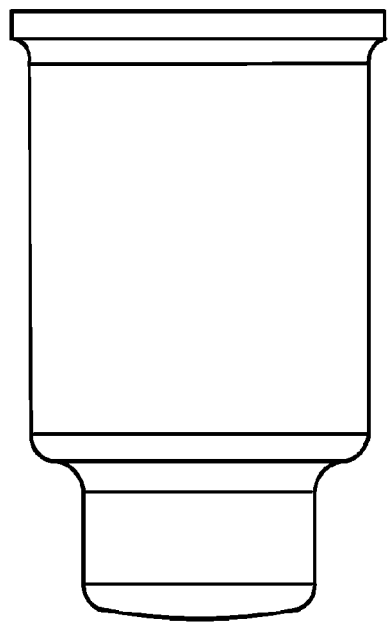
FIG. 66 illustrates a smooth PVC bellows.
Figure 67:
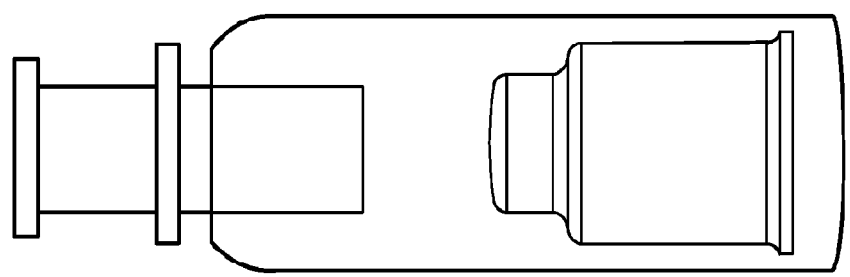
FIG. 67 illustrates a smooth PVC bellows in the simulated device jig.

The adalimumab was loaded into simulated device jigs containing either tapered silicone bellows or smooth PVC bellows and allowed to incubate for 4, 24, or 336 hours at room temperature while protected from light. FIG. 64 illustrates the tapered silicone bellows, and FIG. 65 illustrates the tapered silicone bellows in the simulated device jig. FIG. 66 illustrates the smooth PVC bellows, and FIG. 67 illustrates the smooth PVC in the simulated device jig.

Figure 68:
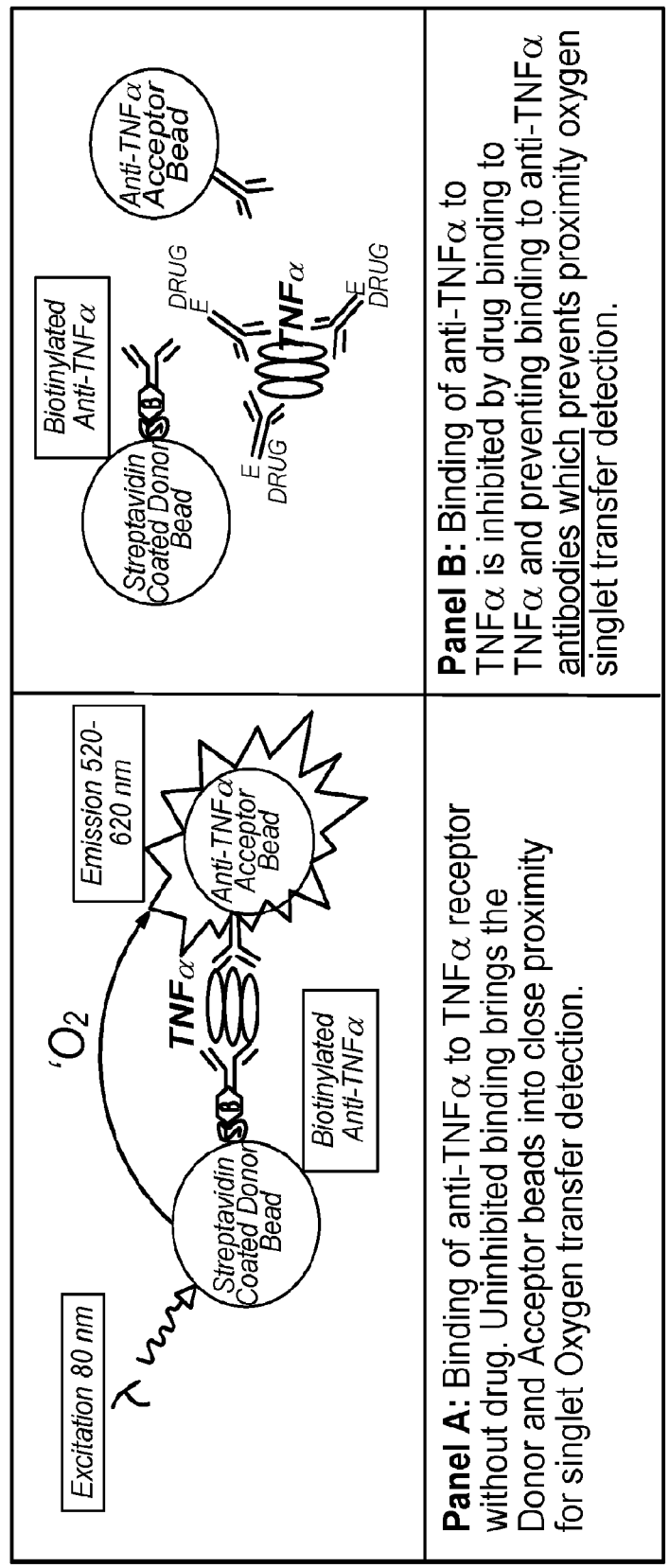
FIG. 68 demonstrates a principle of a competition assay performed in an experiment.

The drug was subsequently extracted using the respective dispensing systems and tested by a competitive inhibition assay. The test method has been developed from the literature (Velayudhan et al., "Demonstration of functional similarity of proposed biosimilar ABP501 to adalimumab" *BioDrugs* 30:339-351 (2016) and Barbeauet al., "Application Note: Screening for inhibitors of TNFα/s TNFR1 Binding using AlphaScreen™ Technology". PerkinElmer Technical Note ASC-016. (2002)), as well as pre-testing development work using control drug and experiments using the provided AlphaLISA test kits. FIG. 68 demonstrates the principle of the competition assay performed in the experiment.

The bellows were loaded as follows: aseptically wiped the dispensing port of the simulated ingestible device jig with 70% ethanol; allowed to air dry for one minute; used an adalimumab delivery syringe to load each set of bellows with 200 μL of drug; took a photo of the loaded device; gently rotated the device such that the drug is allowed to come in contact with all bellows surfaces; protected the bellows from light; and incubate at room temperature for the predetermined time period to allow full contact of the drug with all bellows' surfaces.

The drug was extracted as follows: after completion of the incubation period; the device jig was inverted such that the dispensing port was positioned over a sterile collection microfuge tube and petri dish below; five cubic centimeters of air was drawn into an appropriate syringe; the lure lock was attached to the device jig; the syringe was used to gently apply positive pressure to the bellow with air such that the drug was recovered in the collection microfuge tube; where possible, a video of drug dispensing was taken; samples were collected from each bellows type; a control drug sample was collected by directly dispensing 200 μL of drug from the commercial dispensing syringe into a sterile microfuge tube; the control drug-free sample was collected by directly dispensing 200 μL of PBS using a sterile pipette into a sterile microfuge tube; the collected drug was protected from light; and the drug was diluted over the following dilution range (250, 125, 25, 2.5, 0.25, 0.025, 0.0125, 0.0025 μg) in sterile PBS to determine the $IC_{50}$ range of the drug.

To determine any effects storage conditions may have on drug efficacy in the device, the drug (stored either in the syringe, silicon bellows, PVC bellows) was stored at room temperature while protected from light for 24 hours and 72 hours. Samples were then extracted and the steps in the preceding paragraph were repeated.

The AlphaLISA (LOCI™) test method was used. Human TNFα standard dilution ranges were prepared as described in Table 6.

TABLE 6

| Tube | Vol. of human TNFα (μL) | Vol. of diluent (μL)* | [human TNFα] in standard curve (g/mL in 5 μL) | [human TNFα] in standard curve (pg/mL in 5 μL) |
| --- | --- | --- | --- | --- |
| A | 10 μL of reconstituted human TNFα | 90 | 1E−07 | 100 000 |
| B | 60 μL of tube A | 140 | 3E−08 | 30 000 |
| C | 60 μL of tube B | 120 | 1E−08 | 10 000 |
| D | 60 μL of tube C | 140 | 3E−09 | 3 000 |
| E | 60 μL of tube D | 120 | 1E−09 | 1 000 |
| F | 60 μL of tube E | 140 | 3E−10 | 300 |
| G | 60 μL of tube F | 120 | 1E−10 | 100 |
| H | 60 μL of tube G | 140 | 3E−11 | 30 |
| I | 60 μL of tube H | 120 | 1E−11 | 10 |
| J | 60 μL of tube I | 140 | 3E−12 | 3 |
| K | 60 μL of tube J | 120 | 1E−12 | 1 |
| L | 60 μL of tube K | 140 | 3E−13 | 0.3 |
| M**(background) | 0 | 100 | 0 | 0 |
| N**(background) | 0 | 100 | 0 | 0 |
| O**(background) | 0 | 100 | 0 | 0 |
| P**(background) | 0 | 100 | 0 | 0 |

The test was performed as follows: the above standard dilution ranges were in a separate 96-well plate; to ensure consistent mixing, samples were mixed up and down gently with a pipette five times; a 384-well test plate was prepared according to the test layout diagram depicted Table 7; five microliters of 10,000 pg/mL TNFα standard from the previously made dilution plate was added to each corresponding concentration as shown in Table 6; five microliters of recovered drug (directly from the commercial syringe (A), from the silicone bellows (B Si), from the PVC bellows (B PVC), or from the PBS control (C) was added into the corresponding wells described in Table 5; the test plate was incubated for one hour at room temperature while protected from light; 10 microliters of acceptor beads were added to each previously accessed well; the wells were incubated for 30 minutes at room temperature while protected from light; 10 μL of biotinylated antibody was added to each previously accessed well; the wells were incubated for 15 minutes at room temperature, while protected from light; the room lights were darkened and 25 microliters of streptavidin (SA) donor beads were added to each previously accessed well; the wells were incubated for 30 minutes at room temperature while protected from light; the plate was read in Alpha Mode; and the results were recorded. Upon addition of reagent(s) in the various steps, each well was pipetted up and down three times to achieve good mixing.

TABLE 7

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| A | STD2 1.00E+05 | STD10 10 | 250 A | 250 A | 250 A | 250 A | 250 A | 250 A | 250 B Si | 250 B Si | 250 B Si | 250 B Si | 250 B Si | 250 B PVC | 250 B PVC | 250 B PVC | 250 B PVC | 250 B PVC | 250 C | 250 C | 250 C | 250 C | 250 C |
| B | | | | | | | | | | | | | | | | | | | | | | | |
| C | STD3 30000 | STD11 3 | 125 A | 125 A | 125 A | 125 A | 125 A | 125 A | 125 B Si | 125 B Si | 125 B Si | 125 B Si | 125 B Si | 125 B PVC | 125 B PVC | 125 B PVC | 125 B PVC | 125 B PVC | 125 C | 125 C | 125 C | 125 C | 125 C |
| D | | | | | | | | | | | | | | | | | | | | | | | |
| E | STD4 10000 | STD12 1 | 25 A | 25 A | 25 A | 25 A | 25 A | 25 A | 25 B Si | 25 B Si | 25 B Si | 25 B Si | 25 B Si | 25 B PVC | 25 B PVC | 25 B PVC | 25 B PVC | 25 B PVC | 25 C | 25 C | 25 C | 25 C | 25 C |
| F | | | | | | | | | | | | | | | | | | | | | | | |
| G | STD5 3000 | STD13 0.333 | 2.5 A | 2.5 A | 2.5 A | 2.5 A | 2.5 A | 2.5 A | 2.5 B Si | 2.5 B Si | 2.5 B Si | 2.5 B Si | 2.5 B Si | 2.5 B PVC | 2.5 B PVC | 2.5 B PVC | 2.5 B PVC | 2.5 B PVC | 2.5 C | 2.5 C | 2.5 C | 2.5 C | 2.5 C |
| H | | | | | | | | | | | | | | | | | | | | | | | |
| I | STD6 1000 | Blank 0 | 0.25 A | 0.25 A | 0.25 A | 0.25 A | 0.25 A | 0.25 A | 0.25 B Si | 0.25 B Si | 0.25 B Si | 0.25 B Si | 0.25 B Si | 0.25 B PVC | 0.25 B PVC | 0.25 B PVC | 0.25 B PVC | 0.25 B PVC | 0.25 C | 0.25 C | 0.25 C | 0.25 C | 0.25 C |
| J | | | | | | | | | | | | | | | | | | | | | | | |
| K | SID7 300 | Blank 0 | 0.025 A | 0.025 A | 0.025 A | 0.025 A | 0.025 A | 0.025 A | 0.025 B Si | 0.025 B Si | 0.025 B Si | 0.025 B Si | 0.025 B Si | 0.025 B PVC | 0.025 B PVC | 0.025 B PVC | 0.025 B PVC | 0.025 B PVC | 0.025 C | 0.025 C | 0.025 C | 0.025 C | 0.025 C |
| L | | | | | | | | | | | | | | | | | | | | | | | |
| M | STD8 100 | Blank 0 | 0.013 A | 0.013 A | 0.013 A | 0.013 A | 0.013 A | 0.013 A | 0.013 B Si | 0.013 B Si | 0.013 B Si | 0.013 B Si | 0.013 B Si | 0.013 B PVC | 0.013 B PVC | 0.013 B PVC | 0.013 B PVC | 0.013 B PVC | 0.013 C | 0.013 C | 0.013 C | 0.013 C | 0.013 C |
| N | | | | | | | | | | | | | | | | | | | | | | | |
| O | STD9 30 | Blank 0 | 0.003 A | 0.003 A | 0.003 A | 0.003 A | 0.003 A | 0.003 A | 0.003 B Si | 0.003 B Si | 0.003 B Si | 0.003 B Si | 0.003 B Si | 0.003 B PVC | 0.003 B PVC | 0.003 B PVC | 0.003 B PVC | 0.003 B PVC | 0.003 C | 0.003 C | 0.003 C | 0.003 C | 0.003 C |
| P | | | | | | | | | | | | | | | | | | | | | | | |

Figure 69:
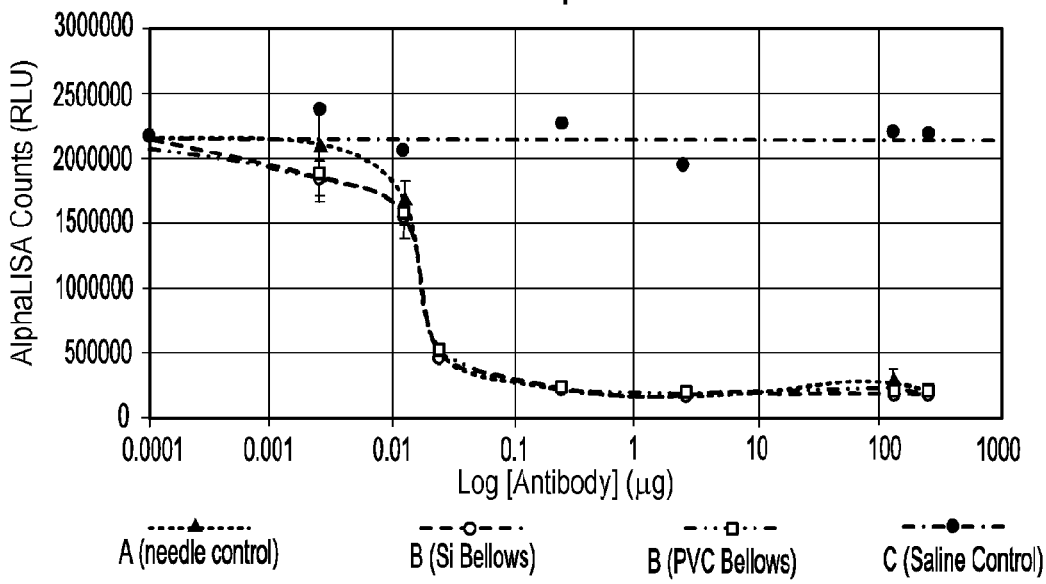
FIG. 69 shows AlphaLISA data.
Figure 70:
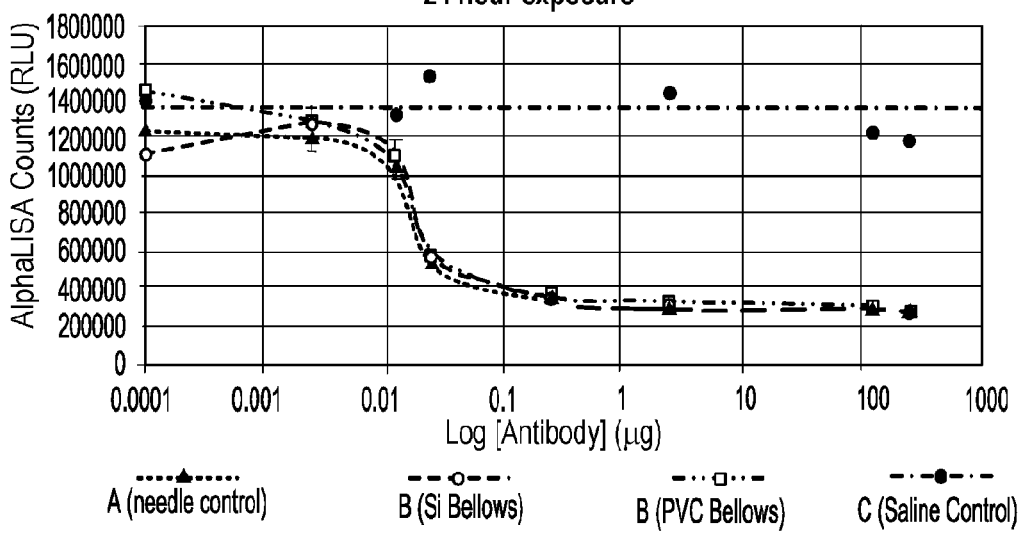
FIG. 70 shows AlphaLISA data.
Figure 71:
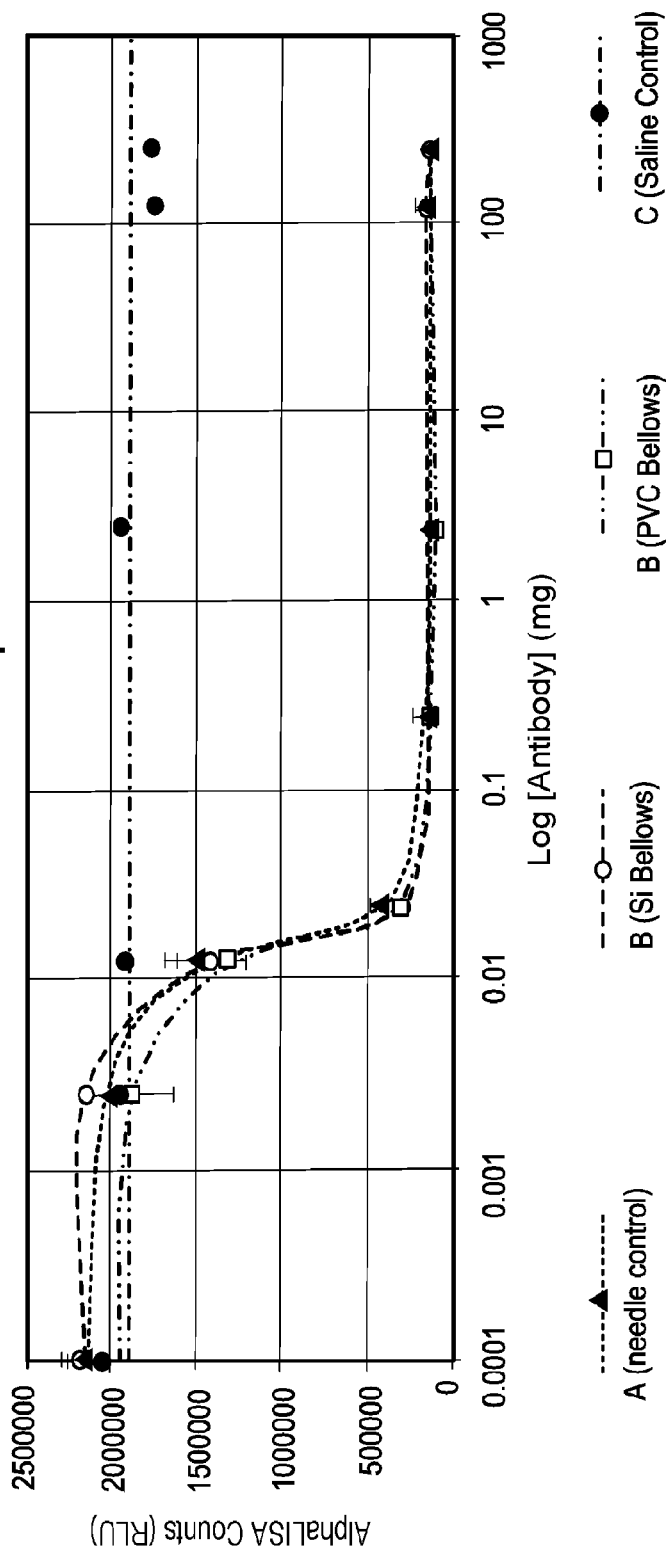
FIG. 71 shows AlphaLISA data.

The data are shown in FIGS. 69-71. The data demonstrate that the bellows do not negatively impact the drug function after shelf lives of 4 hours, 24 hours, or 336 hours. The $IC_{50}$ values of the drug dispensed from the bellows were comparable to the $IC_{50}$ values of the standard dispensation method (Table 6). A slight right shift was noted in the bellows curves after 24 hours (FIG. 70), but this shift was well within the error bars of the curves. Tables 8-11 represent data of FIGS. 69-71, respectively. Of note, when comparing mean (n=5) RFU data between test articles over the concentration ranges significant differences (p<0.05) were discerned. However, these significant differences did not favor either test article over time, suggesting that they were not related to the performance of the material in response to the drug (FIGS. 69-71).

TABLE 8

|  | Needle control (A) | Silicone Bellows (B) | PVC Bellows (C) |
|---|---|---|---|
| 4 Hours | 0.0174 | 0.0169 | 0.0172 |
| 24 Hours | 0.0180 | 0.0180 | 0.0180 |
| 336 Hours | 0.0144 | 0.0159 | 0.0163 |

TABLE 9

Statistics (Student's T-test, 2 tailed, non-pair-wise, for significance $p < 0.05$)

| Drug (micrograms) | Needle control (A) vs. Silicone (B) | Needle control (A) vs. PVC | Silicone vs. PVC |
|---|---|---|---|
| 0.0001 | 0.911 | 0.008* | 0.268 |
| 0.0025 | 0.138 | 0.390 | 0.822 |
| 0.0125 | 0.122 | 0.118 | 0.771 |
| 0.025 | 0.143 | 0.465 | 0.020* |
| 0.25 | 0.591 | 0.984 | 0.350 |
| 2.5 | 0.243 | 0.124 | 0.169 |
| 125 | 0.867 | 0.688 | 0.182 |
| 250 | 0.681 | 0.184 | 0.108 |

*$p < 0.5$ data set

TABLE 10

Statistics (Student's T-test, 2 tailed, non-pair-wise, for significance $p < 0.05$)

| Drug (micrograms) | Needle control (A) vs. Silicone (B) | Needle control (A) vs. PVC | Silicone vs. PVC |
|---|---|---|---|
| 0.0001 | 0.132 | 0.038* | 0.292 |
| 0.0025 | 0.003* | 0.076 | 0.575 |
| 0.0125 | 0.161 | 0.022* | 0.783 |
| 0.025 | 0.058 | 0.078 | 0.538 |
| 0.25 | 0.974 | 0.384 | 0.198 |
| 2.5 | 0.714 | 0.080 | 0.017* |
| 125 | 0.873 | 0.731 | 0.269 |
| 250 | 0.798 | 0.956 | 0.903 |

*$p < 0.5$ data set

TABLE 11

Statistics (Student's T-test, 2 tailed, non-pair-wise, for significance $p < 0.05$)

| Drug (micrograms) | Needle control (A) vs. Silicone (B) | Needle control (A) vs. PVC | Silicone vs. PVC |
|---|---|---|---|
| 0.0001 | 0.858449 | 0.036847* | 0.026444* |
| 0.0025 | 0.087379 | 0.280302 | 0.046767* |
| 0.0125 | 0.469282 | 0.057232 | 0.117194 |
| 0.025 | 0.02758* | 0.078234 | 0.373419 |
| 0.25 | 0.411548 | 0.258928 | 0.400498 |
| 2.5 | 0.368959 | 0.156574 | 0.006719* |
| 125 | 0.948649 | 0.246702 | 0.463735 |
| 250 | 0.485046 | 0.128993 | 0.705543 |

*$p < 0.5$ data set

Example 9. A Comparison Study of Systemic vs Intracecal Delivery of SMAD7 Bio-Distribution in DSS-Induced Colitis in Male C57Bl/6 Mice The objective of this study was to compare the efficacy of novel test articles, e.g., fluorescent SMAD7 antisense oligonucleotides (SMAD7 AS), when dosed systemically versus intracecally in the treatment of DSS-induced colitis, in male C57Bl/6 mice.

Experimental Design

A minimum of 10 days prior to the start of the experiment a cohort of animals underwent surgical implantation of a cecal cannula. A sufficient number of animals underwent implantation to allow for 12 cannulated animals to be enrolled in the main study (i.e., 16 animals).

Colitis was induced in 12 male C57Bl/6 mice (Groups 4-5) by exposure to 3% DSS-treated drinking water from Day 0 to Day 5. Three groups of six additional animals per group (n=6 cannulated; n=12 non-cannulated; Groups 1-3) served as no-disease controls (Groups 1-3). All animals were weighed daily and assessed visually for the presence of diarrhea and/or bloody stool during this time.

Animals were dosed with test-article via oral gavage (PO) or intracecal injection (IC) once on Day 9 as indicated in Table 12. The animals in Group 0 were not dosed. The animals in Groups 2 and 4 were dosed PO with SMAD7 antisense. The animals in Groups 3 and 5 were dosed IC with SMAD7 antisense.

All animals were euthanized by $CO_2$ inhalation 12 hours after dosing, on Day 10. Terminal blood was collected into two $K_2$EDTA tubes and processed for plasma. Both plasma and pellet samples were snap-frozen in liquid nitrogen and stored at $-80°$ C. Cecum contents were removed and the contents were split into two aliquots. Both aliquots were weighed and snap frozen in separate cryovials in liquid nitrogen. The cecum was excised and bisected longitudinally; each piece is separately weighed and flash-frozen in liquid nitrogen. The colon contents were removed and the contents were split into two aliquots. Both aliquots were weighed and snap frozen in separate cryovials in liquid nitrogen. The colon was then rinsed, and the most proximal 2 cm of colon was collected. This 2-cm portion was bisected longitudinally; each piece was separately weighed and flash-frozen in liquid nitrogen. Snap-frozen blood pellet, cecum/colon contents, and tissue samples were used for downstream fluorometry or RP-HPLC. The details of the study design are shown in Table 12.

TABLE 12

Study design

| Group | No Animals | Cecal Cannula | Colitis Induction | Treatment | Route | Schedule | Terminal Collections Day 10 |
|---|---|---|---|---|---|---|---|
| 1 | 6 | NO | — | — | — | — | Whole blood, plasma, cecal contents, colon contents, cecal tissue, colon tissue |
| 2 | 6 | NO | — | Fluorescently labeled SMAD7 antisense 50 µg* | PO | QD | |
| 3 | 6 | YES | — | | IC | Day 9** | |
| 4 | 6 | NO | 3% DSS Days 0-5 | | PO | | |
| 5 | 6 | YES | | | IC | | |

*Per mouse. TA is administered in 0.075 mL/animal.
**Animals are dosed on Day 9 and collections are performed 12 hours later.

Materials and Methods

Mice

Normal male C57Bl/6 mice between the ages of 6-8 weeks old, weighing 20-24 g, were obtained from Charles River Laboratories. The mice were randomized into five groups of six mice each, and housed in groups of 8-15 per cage, and acclimatized for at least three days prior to entering the study. Animal rooms were set to maintain a minimum of 12 to 15 air changes per hour, with an automatic timer for a light/dark cycle of 12 hours on/off, and fed with Labdiet 5053 sterile rodent chow, with water administered ad libitum.

Cecal Cannulation

The animals were placed under isoflurane anesthesia, with the cecum exposed via a midline incision in the abdomen. A small point incision was made in the distal cecum, where 1-2 cm of the cannula was inserted. The incision was closed with a purse string suture using 5-0 silk. An incision was then made in the left abdominal wall through which the distal end of the cannula was inserted and pushed subcutaneously to the dorsal aspect of the back. The site was then washed copiously with warmed saline prior to closing the abdominal wall. A small incision was also made in the skin of the back between the shoulder blades, exposing the tip of the cannula. The cannula was secured in place using suture, wound clips, and tissue glue. All animals were administered 1 mL of warm sterile saline (subcutaneous injection) and were monitored closely until recovery before returning to their cage. All animals were administered 0.6 mg/kg BID buprenorphine for the first 3 days, and Baytril® at 10 mg/Kg every day for the first 5 days post-surgery.

Disease Induction

Colitis was induced on Day 0 via addition of 3% DSS (MP Biomedicals, Cat #0260110) to the drinking water. Fresh DSS/water solutions was provided on Day 3 and any of the remaining original DSS solution is discarded.

Body Weight and Survival

Animals were observed daily (weight, morbidity, survival, presence of diarrhea and/or bloody stool) in order to assess possible differences among treatment groups and/or possible toxicity resulting from the treatments.

Animals Found Dead or Moribund

Animals were monitored on a daily basis. Animals exhibiting weight loss greater than 30% were euthanized, and samples were not collected from these animals.

Dosing

Animals were dosed with test-article via oral gavage (PO) or intracecal injection (IC) once on Day 9 as indicated in Table 12. Animals in Group 0 were not dosed. Animals in Groups 2 and 4 were dosed PO with SMAD7 antisense. Animals in Groups 3 and 5 were dosed IC with SMAD7 antisense.

Sacrifice

All animals were euthanized by $CO_2$ inhalation 12 hours after dosing, on Day 10.

Sample Collection

Intestinal contents, peripheral blood and tissue were collected at sacrifice on Day 10, as follows:

Blood/Plasma

Terminal blood was collected into two $K_2$EDTA tubes and processed for plasma. The approximate volume of each blood sample was recorded prior to centrifugation. Both plasma and pellet samples were snap-frozen in liquid nitrogen and stored at −80° C. The first pellet sample (sample 1) was used for fluorometry. The second pellet sample (sample 2) was used for RP-HPLC.

Cecum Contents

Cecum contents was removed and contents were split into two aliquots. Both aliquots were weighed and snap frozen in separate cryovials in liquid nitrogen. The first sample (sample 1) was used for fluorometry. The second sample (sample 2) was used for RP-HPLC.

Cecum

The cecum was excised and bisected longitudinally; each piece was separately weighed and snap-frozen. The first sample (sample 1) was used for fluorometry. The second sample (sample 2) was used for RP-HPLC.

Colon Contents

Colon contents were removed and contents were split into two aliquots. Both aliquots were weighed and snap frozen in separate cryovials in liquid nitrogen. The first sample (sample 1) was used for fluorometry. The second sample (sample 2) was used for RP-HPLC.

Colon

The colon was rinsed, and the most proximal 2 cm of colon was collected and bisected longitudinally. Each piece was separately weighed and flash-frozen in liquid nitrogen. The first sample (sample 1) was used for fluorometry. The second sample (sample 2) was used for RP-HPLC.

SMAD7 Antisense Bioanalysis

Samples flash-frozen for fluorometry were homogenized in 0.5 mL buffer RLT+ (Qiagen). Homogenate was centrifuged (4000×g; 10 minutes), and supernatant was collected. Forty microliters of the sample was diluted 1:6 in 200 µL of bicarbonate solution and 100 µL of diluted supernatant was analyzed on a fluorescent plate reader (485 excitation; 535 emission) in duplicate.

Prior to the above, assay development was performed as follows. Samples (as indicated in Sample Collection) were harvested from a naïve animal and flash-frozen. Samples were then homogenized in 0.5 mL buffer RLT+, homogenate was centrifuged (4000×g; 10 minutes) and supernatant was collected and diluted 1:6 with bicarbonate solution (i.e., 0.5 mL supernatant was added to 2.5 mL of PBS). An aliquot (0.200 mL (90 µL for each duplicate) of each diluted sample was pipetted into 15 (14 dilution of FAM-AS-SAMD7+ blank control) Eppendorf tubes. One tube was set-aside to be used as a blank sample. Ten microliters of fluorescently-labeled SMAD7 antisense was then spiked into all other sample to achieve final concentrations of 50 µg/mL, 16.67 µg/mL, 5.56 µg/mL, 1.85 µg/mL, 0.62 µg/mL, 0.21 µg/mL, 0.069 µg/mL, 0.023 µg/mL, 7.6 ng/mL, 2.5 ng/mL, 0.847 ng/mL, 0.282 ng/mL, 0.094 ng/mL, and 0.024 ng/mL respectively. The fluorescently-labeled SMAD7 antisense was prepared and serially diluted such that the volume added to each organ homogenate sample was the same for each of the above concentrations. These samples were analyzed on a fluorescent plate reader (485 excitation; 535 emission) in duplicate.

Processing for RP-HPLC

Samples flash-frozen for RP-HPLC were homogenized in buffer RLT+ (Qiagen). Homogenate was centrifuged (4000× g; 10 minutes), and supernatant was used to perform RP-HPLC analysis.

Results

Figure 73:
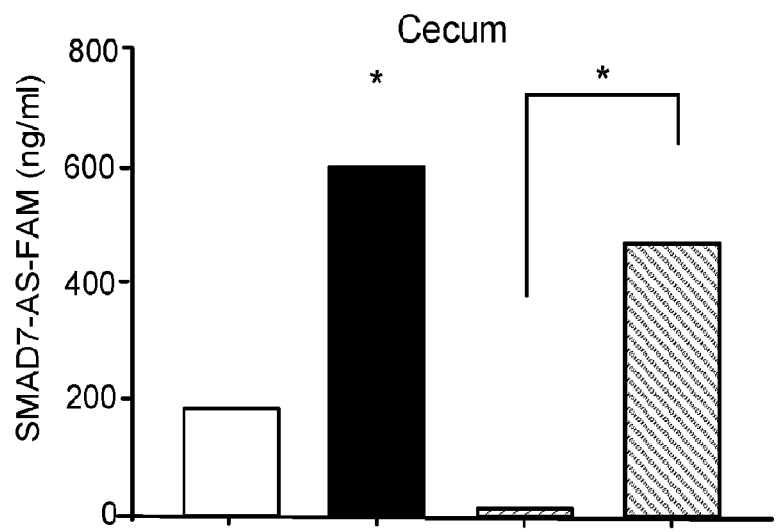
FIG. 73 is a graph showing the level of FAM-SMAD7-AS oligonucleotide in the cecum tissue of DSS-induced colitis mice at 12-hours. The bars represent from left to right, Groups 2 through 5 in the experiment described in Example 9.
Figure 74:
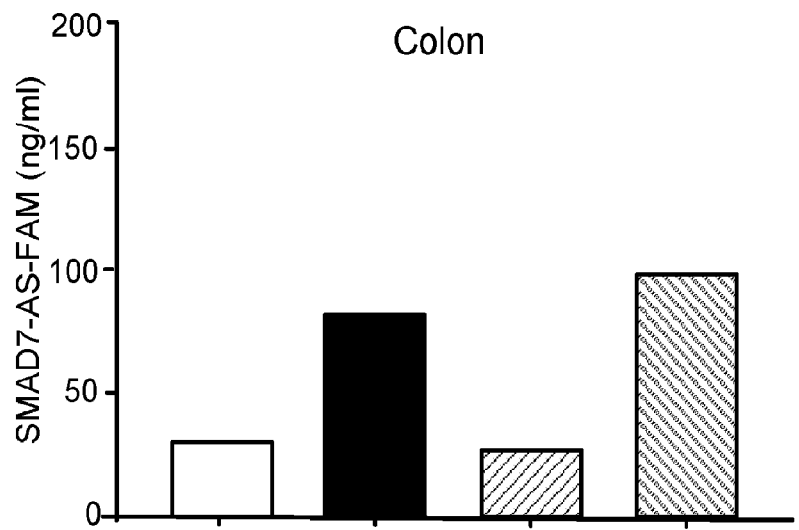
FIG. 74 is a graph showing the level of FAM-SMAD7-AS oligonucleotide in the colon tissue of DSS-induced colitis mice at 12-hours. The bars represent from left to right, Groups 2 through 5 in the experiment described in Example 9.
Figure 75:
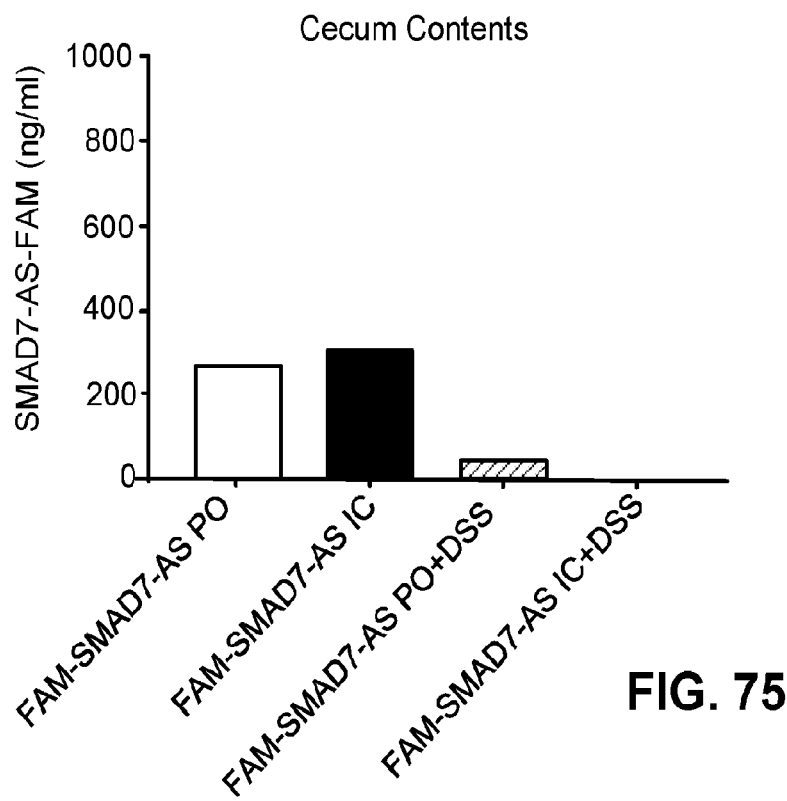
FIG. 75 is a graph showing the level of FAM-SMAD7-AS oligonucleotide in the cecum contents of DSS-induced colitis mice at 12-hours. The bars represent from left to right, Groups 2 through 5 in the experiment described in Example 9.

The data in FIGS. 73 and 74 show that significantly more SMAD7 anstisense oligonucleotide was present in cecum tissue and colon tissue for mice with or without DSS treatment that were intra-cecally administered the SMAD7 antisense oligonucleotide as compared to mice with or without DSS treatment that were orally administered the SMAD7 antisense oligonucleotide. The data in FIG. 75 show that there is about the same level of SMAD7 antisense oligonucleotide in the cecum contents of mice with or without DSS treatment that were orally or intra-cecally administered the SMAD7 antisense oligonucleotide. No SMAD7 antisense oligonucleotide was found in the plasma or white blood cell pellet of SMAD7 antisense oligonucleotide treated mice.

Example 10. Comparison of the Tissue, Plasma, and GI Content Pharmacokinetics of Tacrolimus through Oral vs. Intra-Cecal Ingestible Device Delivery in Yorkshire-Cross Farm Swine The primary objective of this study was to compare the tissue, plasma, rectal sample, and GI content pharmacokinetics of tacrolimus through oral versus intra-cecal ingestible device delivery in normal Yorkshire-Cross farm swine.

This study compares the effects of administration of: a single intra-cecal administration of an ingestible device containing 0.8 mL sterile vehicle solution (80% alcohol, 20% castor oil (HCO-60)); a single oral dose of tacrolimus at 4 mg/0.8 mL (in sterile vehicle solution); and a single intra-cecal administration of an ingestible device containing either 1 mg/0.8 mL (in sterile vehicle solution), 2 mg/0.8 mL (in sterile vehicle solution), or 4 mg/0.8 mL (in sterile vehicle solution).

This study employed five groups of three female swine weighing approximately 45 to 50 kg at study start. Swine were randomly placed into animal rooms/pens as they are transferred from the delivery vehicle without regard to group. Group numbers were assigned to the rooms in order of room number. No further randomization procedure was employed. The study design is provided in Table 13.

TABLE 13

Study Design Table

| General | Group size | Dose | Route | Days Pre-Dose | | | | | Hours Post-dose | | | | | | |
|---|---|---|---|---|---|---|---|---|---|---|---|---|---|---|---|
| | | | | -11 | -10 | -5 | -1 | 1 | 0.5 | 1 | 2 | 3 | 4 | 6 | 12 |
| Fast | | | | • | | | • | | | | | | | | |
| Food/Water | | ad libidum | | | | | | | | | | | | | |
| Observations | | | | | | | | | | | | | | | |
| clinical observations | | Day -10~-5 & | | • | • | | • | • | • | • | • | • | • | • | • |
| body weight* | | Day 1 | | • | • | | • | | | | | | | | • |
| Treatments (Groups) | | | | | | | | | | | | | | | |
| 1. Vehicle control | n = 3 | 0.8 mL (20% HCO-60, 80% EtOH) | IC | | | | | | | | | | | | |
| Surgical placement of IC port** | | | | | | | • | | | | | | | | |
| Euthanized | | (1 Ingestible Device) | | | | | | | | | | | | | n = 3 |
| 2. Tacrolimus (PO) | n = 3 | 4 mg in 0.8 mL 0.08mg/kg | Oral | | | | | | • | | | | | | |
| Surgical placement of IC port** | | | | | | | • | | | | | | | | |
| Euthanized | | (solution) | | | | | | | | | | | | | n = 3 |
| 3. Tacrolimus (IC) | n = 3 | 1 mg in 0.8 mL 0.02 mg/kg | IC | | | | | | • | | | | | | |
| Surgical placement of IC port** | | | | | | | • | | | | | | | | |
| Euthanized | | (1 Ingestible Device) | | | | | | | | | | | | | n = 3 |
| 4. Tacrolimus (IC) | n = 3 | 2 mg in 0.8 mL 0.04 mg/kg | IC | | | | | | • | | | | | | |
| Surgical placement of IC port** | | | | | | | • | | | | | | | | |
| Euthanized | | (1 Ingestible Device) | | | | | | | | | | | | | n = 3 |
| 5. Tacrolimus (IC) | n = 3 | 4 mg in 0.8 mL 0.08 mg/kg | IC | | | | | | • | | | | | | |
| Surgical placement of IC port** | | | | | | | • | | | | | | | | |
| Euthanized | | (1 Ingestible Device) | | | | | | | | | | | | | n = 3 |
| Tacrolimus (required) Samples***** | | 20 mg | | | | | | | | | | | | | |

TABLE 13-continued

Study Design Table

| General | Group size | Dose | Route | Days Pre-Dose | | | | | Hours Post-dose | | | | | | |
|---|---|---|---|---|---|---|---|---|---|---|---|---|---|---|---|
| | | | | -11 | -10 | -5 | -1 | 1 | 0.5 | 1 | 2 | 3 | 4 | 6 | 12 |
| Plasma | | | cephalic, jugular or catheter rectal necropsy necropsy | | | | | • | • | • | • | • | • | • | • |
| Rectal contents | | | | | | | | | | • | | • | | • | • |
| Tissue*** | x5 | | | | | | | | | | | | | | • |
| Luminal contents**** | x5 | | | | | | | | | | | | | | • |
| Analysis (Agrilux Charles River) | Total Samples | | | | | | | | | | | | | | |
| Plasma [Tacrolimus] | 105 | | | | | | | 15 | | 15 | 15 | 15 | 15 | 15 | 15 |
| Rectal contents [Tacrolimus] | 60 | | | | | | | | | 15 | | 15 | | 15 | 15 |
| Tissue (intact)*** [Tacrolimus] | 105 | | | | | | | | | | | | | | 105 |
| Luminal contents [Tacrolimus] | 75 | | | | | | | | | | | | | | 75 |
| Tissue after removing luminal content [Tacrolimus] | 75 | | | | | | | | | | | | | | 75 |

Notes:
*Animal weight was ~45-50 kg for drug doses proposed.
**Surgical placement of IC port in all animals to control.
***Tissue samples (five GI section cecum (CAC); proximal colon (PCN); transverse colon (TCN); distal colon (DCN); rectum (RTM), plus mesenteric lymph nodes and Peyer's Patch).
****Luminal contents (cecum (CAC); proximal colon (PCN); transverse colon (TCN); distal colon (DCN); rectum (RTM)).

Animals in Group 1 received an ingestible device containing 0.8 mL of vehicle solution (80% alcohol, 20% HCO-60). Animals in Group 2 received orally 4 mL liquid formulation of tacrolimus at 4 mg/0.8 mL per animal (Prograf: 5 mg/mL). Animals in Group 3 received intra-cecally an ingestible device containing tacrolimus at 1 mg in 0.8 mL per ingestible device. Animals in Group 4 received intra-cecally an ingestible device containing tacrolimus at 2 mg in 0.8 mL per ingestible device. Animals in Group 5 received intra-cecally an ingestible device containing tacrolimus at 4 mg in 0.8 mL per ingestible device. To control for potential confounding effects of the surgery, all groups fast on Day −11 at least 24 hr before being subjected to anesthesia followed by surgical placements of a cecal port by a veterinary surgeon at Day −10. All animals were fasted for at least 12 hr prior to dosing on Day 1. Animals were dosed via either intra-cecal dosing (IC) or oral dosing (PO) at Day 1 (between 6-8 p.m.). All animals resumed feeding at approximately 4 hours after dose (11-12 p.m. after dosing).

Animals in Group 1 (Vehicle Control) were administered a single intra-cecal ingestible device containing 0.8 mL Vehicle solution (80% alcohol, 20% castor oil (HCO-60)) on Day 1. On Day −10 the animals were anesthetized, and a veterinary surgeon surgically placed an intra-cecal port in each animal. On Day 1, each animal was placed into a sling then a single intra-cecal ingestible device containing 0.8 mL vehicle solution (80% alcohol, 20% castor oil (HCO-60)) is introduced by the veterinary surgeon into the cecum via the cecal port in each animal. Following ingestible device placement, the animals were removed from the slings and placed back into their pens with water. All animals resumed feeding at approximately 4 hours after dose. Samples of rectal contents were collected for pharmacokinetic analyses from each animal at each of 1, 3, 6, and 12 hours post-ingestible device placement using a fecal swab (rectal swab). A total of 60 samples were collected.

Approximately 200~400 mg of rectal content were collected, if available, with a fecal swab (Copan Diagnostics Nylon Flocked Dry Swabs, 502CS01). The fecal swab was pre-weighed and weighed after collection in the collection tube (Sterile Tube and Cap No Media, PFPM913S), and the sample weight was recorded. The fecal swab was broken via the breakpoint, and was stored in the collection tube, and immediately frozen at −70° C. Whole blood (2 mL) was collected into $K_2$EDTA coated tubes for pharmacokinetics at each time-point of pre-dose and 1, 2, 3, 4, 6 and 12 hours post-dose. Immediately following euthanasia, tissue was collected. A total of 105 samples were collected.

For tissue necropsy, small intestine fluid and cecal fluid were collected separately from all the animals into two separate square plastic bottles, and stored at −20° C. The length and diameter of the cecum and the colon was measured from one animal in each group and recorded for reference. Tissues were collected for pharmacokinetic analyses and include mesenteric lymph nodes, a Peyer's Patch, and five gastrointestinal sections, including cecum, proximal colon, transverse colon, distal colon, and rectum. All samples were weighed, and the tissue sample weights were recorded. In each of the five gastrointestinal sections, tissue samples were collected in three different areas where the mucosal surface was visible and not covered by luminal content by using an 8.0-mm punch biopsy tool. Around 3 grams of the total punched sample were collected into a pre-weighed 15-mL conical tube, and the tissue weight was recorded. Three mesenteric lymph nodes were collected from different areas and weighed. At least one Peyer's Patch was collected and weighed. Tissues were snap-frozen in liquid nitrogen and stored frozen at approximately −70° C. or below (total of 105 samples).

Luminal contents were collected for pharmacokinetic analyses from the surface of the tissue from each of five gastrointestinal sections: cecum, proximal colon, transverse colon, distal colon, and rectum (total of 75). The contents were collected in pre-weighed 15-mL conical tubes and the sample weights were recorded. Samples were snap-frozen in liquid nitrogen stored frozen at approximately −70° C. or below.

After removing the luminal content, another set of tissue samples from 3 different areas were collected via an 8.0-mm punch biopsy in each section of the five tissue gastrointestinal sections described above. Around 3 grams of the total punched sample were collected into a pre-weighed 15-mL conical tube, and the tissue weight was recorded (total of 75). Tissues were snap-frozen in liquid nitrogen and stored frozen at approximately −70° C. or below.

A 30-cm length of jejunum (separated into two 15 cm lengths), and the remaining distal and transverse colon tissue sample (after tissue and luminal content were collected for PK) were collected in one animal in each group of treatment, snap-frozen in liquid nitrogen and stored frozen at approximately −70° C. or below. All samples for pharmacokinetic analyses were stored on dry ice before analyses.

Group 2 animals were administered a single oral dose of tacrolimus at 1 mg/0.8 mL (in the vehicle solution) on Day 1. Plasma, rectal content sample, tissue collection, GI content collection and related procedures/storage/shipments was the same as those employed in Group 1.

Group 3 animals were administered a single intra-cecal ingestible device containing tacrolimus at 0.5 mg/0.8 mL (in the vehicle solution) on Day 1 by a veterinary surgeon. Plasma, rectal content sample, tissue collection, GI content collection and related procedures/storage/shipments was the same as those employed in Group 1. All samples wereanalyzed for tacrolimus.

Group 4 animals were administered a single intra-cecal ingestible device of tacrolimus at 2 mg/0.8 mL (in sterile vehicle solution) on Day 1 by a veterinary surgeon. Plasma, rectal content sample, tissue collection, GI content collection and related procedures/storage/shipments were the same as those employed in Group 1. All samples were analyzed for tacrolimus.

Group 5 animals are administered a single intra-cecal ingestible device containing tacrolimus at 4 mg/0.8 mL (in the vehicle solution) on Day 1 by a veterinary surgeon. Plasma, rectal content sample, tissue collection, GI content collection and related procedures/storage/shipments were the same as those employed in Group 1. All samples were analyzed for tacrolimus.

Detailed clinical observations were conducted daily from Day −10 to −5, and on Day 1. Additional pen-side observations were conducted at least once each day. The animals remained under constant clinical observation for the entire 12 hours from dose until euthanasia. Body weights were collected on Day −10, Day −5, and pre-dose on Day 1. Animals were euthanized via injection of a veterinarian-approved euthanasia.

Test Article and Formulation
1. Vehicle solution, 20 mL
Description: 80% alcohol, 20% PEG-60 castor oil
Physical characteristics: clear liquid solution.
2. Prograf (tacrolimus injection), 10 ampules
Description: A sterile solution containing the equivalent of 5 mg anhydrous tacrolimus in 1 mL. Tacrolimus is macrolide immunosuppressant and the active ingredient of Prograf 0.8 mL of Prograf (5 mg/mL) was administered through oral gavage per animal in group 2. Prograf (5 mg/mL) was diluted 2× folds (2.5 mg/mL) and 4× folds (1.25 mg/mL) by using vehicle solution. 0.8 mL of each concentration, 1.25 mg/mL, 2.5 mg/mL, and 5 mg/mL of Prograf, was injected into a DSS ingestible device for group 3, 4, and 5.
Formulation: Each mL contained polyoxyl 60 hydrogenated castor oil (HCO-60), 200 mg, and dehydrated alcohol, USP, 80.0% v/v.
Physical characteristics: clear liquid solution.
3. DDS ingestible device containing Tacrolimus
Description: Three (3) DDS ingestible devices containing vehicle solution for Group 1, three (3) DSS ingestible devices containing 1 mg tacrolimus for Group 3, three (3) DDS ingestible devices containing 2 mg tacrolimus for Group 4, and three (3) DDS ingestible devices containing 4 mg tacrolimus for Group 5.

Acclimation
Animals were acclimated prior to study initiation for at least 7 days. Animals in obvious poor health were not placed on study.

Concurrent Medication
Other than veterinary-approved anesthetics and medications used during surgery to install the ileocecal ports, or for vehicle or test article administration, and analgesia and antibiotics post-surgery, no further medications were employed.

Feed
All swine were fasted at least 24 hours before being anesthetized and properly medicated for surgery or overnight before dosing. Otherwise, animals were fed ad-libitum. Tap water was pressure-reduced and passed through a particulate filter, then a carbon filter prior to supply to an automatic watering system. Water was supplied ad libitum. There were no known contaminants in the feed or water that would be expected to interfere with this study.

Figure 76:
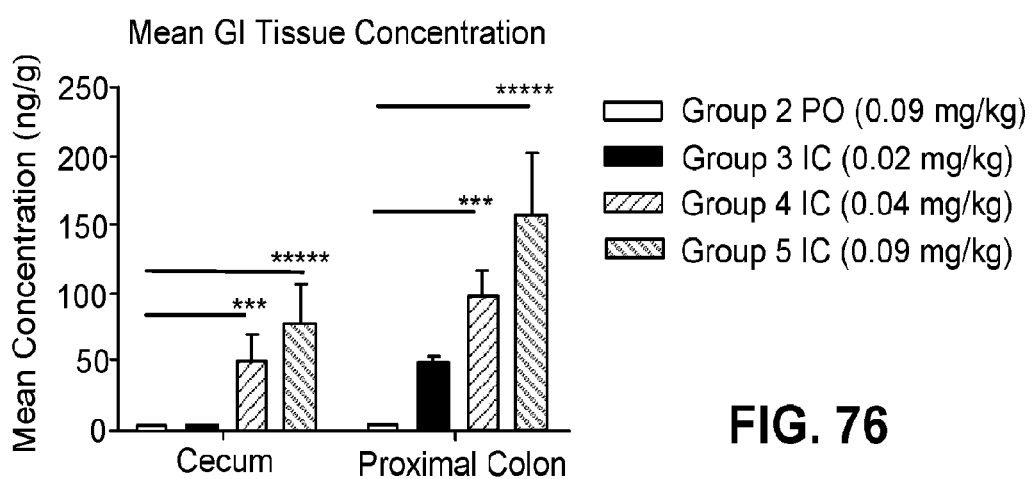
FIG. 76 is a graph showing the mean concentration of tacrolimus in the cecum tissue and the proximal colon tissue 12 hours after intra-cecal or oral administration of tacrolimus to swine as described in Example 10.

Results
The data in FIG. 76 show that the mean concentration of tacrolimus in the cecum tissue and the proximate colon tissue were higher in swine that were inta-cecally administered tacrolimus as compared to swine that were orally administered tacrolimus. These data suggest that intra-cecal administration of tacrolimus is able to locally deliver tacrolimus to the tissues in the GI tract of a mammal, while not decreasing the systemic immune system of a mammal.

Example 11. Comparison of the Tissue, Plasma, and GI Content Pharmacokinetics of Adalimumab Through SC vs. Intra-Cecal Ingestible Device Delivery in Yorkshire-Cross Farm Swine in DSS-Induced Colitis The purpose of this non-Good Laboratory Practice (GLP) study is to explore the PK/PD and bioavailability of adalimumab when applied to DSS-induced colitis in Yorkshire-cross farm swine. All animals are randomized into groups of three. Animals are dosed once with adalimumab via subcutaneous (SC), perirectal (PR), or intracecal (IC) administration.

The concentration of adalimumab and TNFα is measured in plasma at 1, 2, 3, 4, 6, and 12 hours post-dose. The concentration of adalimumab is measured in rectal contents at 1, 3, 6, and 12 hours post-dose and in luminal content at 12 hours post-dose. Concentration of adalimumab and TNFα, HER2, and total protein is measured in gastrointestinal tissue, e.g., cecum sample (CAC), proximal colon sample (PCN), transverse colon sample (TCN), distal colon sample (DCNi) inflamed, distal colon non-inflamed sample (DCNn), and rectum sample (RTM), at 12 hours post-dose.

Example 12. Human Clinical Trial of Treatment of Ulcerative Colitis Using Adalimumab As a proof of concept, the patient population of this study is patients that (1) have moderate to severe ulcerative colitis, regardless of extent, and (2) have had an insufficient response to a previous treatment, e.g., a conventional therapy (e.g., 5-ASA, corticosteroid, and/or immunosuppressant) or a FDA-approved treatment. In this placebo-controlled eight-week study, patients are randomized. All patient undergo a colonoscopy at the start of the study (baseline) and at week 8. Patients enrolled in the study are assessed for clinical status of disease by stool frequency, rectal bleeding, abdominal pain, physician's global assessment, and biomarker levels such as fecal calprotectin and hsCRP. The primary endpoint is a shift in endoscopy scores from Baseline to Week 8. Secondary and exploratory endpoints include safety and tolerability, change in rectal bleeding score, change in abdominal pain score, change in stool frequency, change in partial Mayo score, change in Mayo score, proportion of subjects achieving endoscopy remission, proportion of subjects achieving clinical remission, change in histology score, change in biomarkers of disease such as fecal calprotectin and hsCRP, level of adalimumab in the blood/tissue/stool, change in cytokine levels (e.g., TNFα, IL-6) in the blood and tissue.

Figure 72:
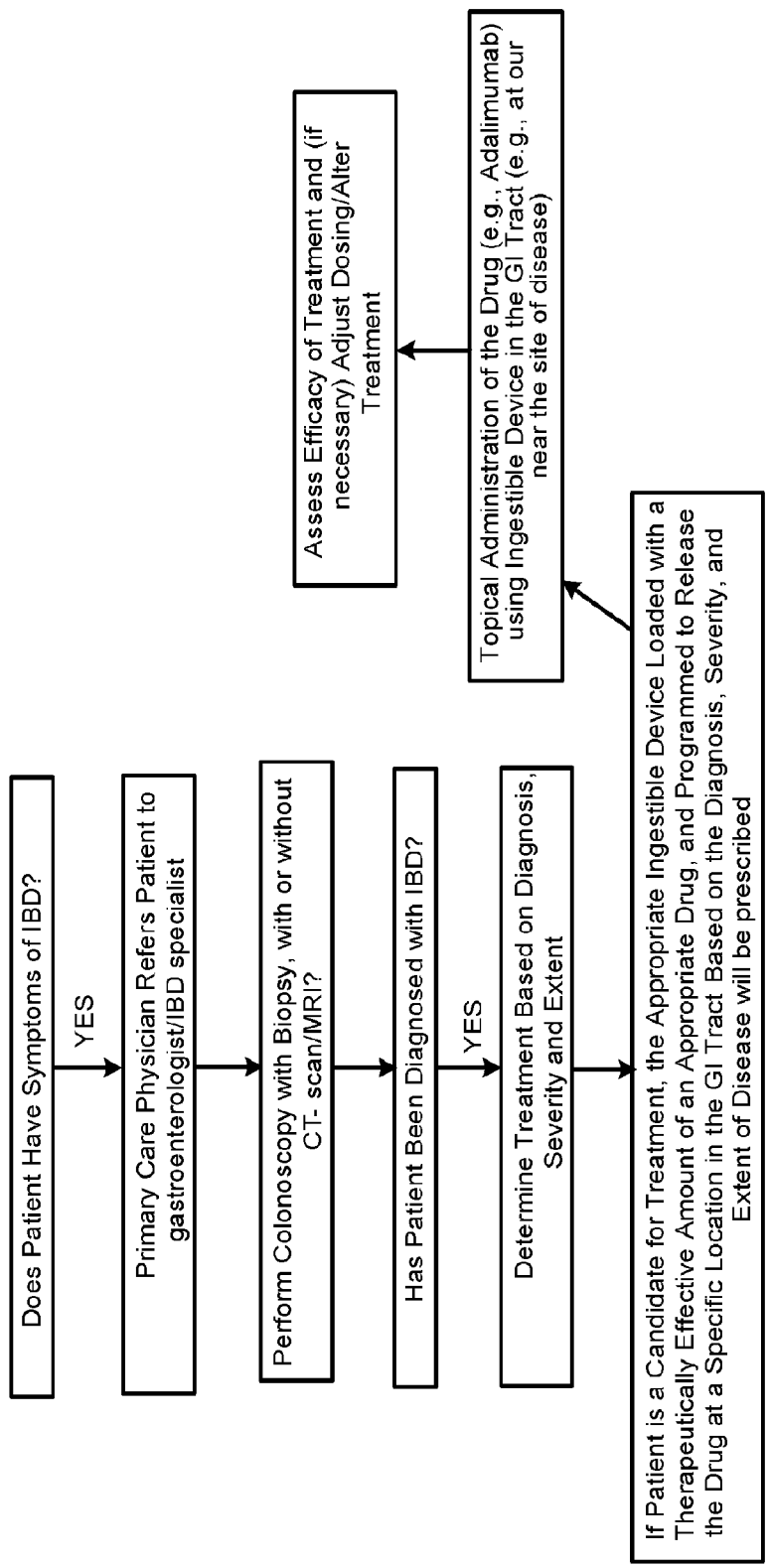
FIG. 72 is a flowchart of illustrative steps of a clinical protocol, in accordance with some embodiments of the disclosure.

FIG. 72 describes an exemplary process of what would occur in clinical practice, and when, where, and how the ingestible device will be used. Briefly, a patient displays symptoms of ulcerative colitis, including but not limited to: diarrhea, bloody stool, abdominal pain, high c-reactive protein (CRP), and/or high fecal calprotectin. A patient may or may not have undergone a colonoscopy with diagnosis of ulcerative colitis at this time. The patient's primary care physician refers the patient. The patient undergoes a colonoscopy with a biopsy, CT scan, and/or MRI. Based on this testing, the patient is diagnosed with ulcerative colitis. Most patients are diagnosed with ulcerative colitis by colonoscopy with biopsy. The severity based on clinical symptoms and endoscopic appearance, and the extent, based on the area of involvement on colonoscopy with or without CT/MRI is documented. Treatment is determined based on diagnosis, severity and extent.

For example, treatment for a patient that is diagnosed with ulcerative colitis is an ingestible device programmed to release a single bolus of a therapeutic agent, e.g., 40 mg adalimumab, in the cecum or proximal to the cecum. Prior to administration of the treatment, the patient is fasted overnight and is allowed to drink clear fluids. Four hours after swallowing the ingestible device, the patient can resume a normal diet. An ingestible device is swallowed at the same time each day. The ingestible device is not recovered.

In some embodiments, there may be two different ingestible devices: one including an induction dose (first 8 to 12 weeks) and a different ingestible device including a different dose or a different dosing interval.

In some examples, the ingestible device can include a mapping tool, which can be used after 8 to 12 weeks of induction therapy, to assess the response status (e.g., based on one or more of the following: drug level, drug antibody level, biomarker level, and mucosal healing status). Depending on the response status determined by the mapping tool, a subject may continue to receive an induction regimen or maintenance regimen of adalimumab.

In different clinical studies, the patients may be diagnosed with Crohn's disease and the ingestible devices (including adalimumab) can be programmed to release adalimumab in the cecum, or in both the cecum and transverse colon.

In different clinical studies, the patients may be diagnosed with illeocolonic Crohn's disease and the ingestible devices (including adalimumab) can be programmed to release adalimumab in the late jejunum or in the jejunum and transverse colon.

Example 13

An ingestible medical device according to the disclosure ("TLC1") was tested on 20 subjects to investigate its localization ability. TLC1 was a biocompatible polycarbonate ingestible device that contained a power supply, electronics and software. An onboard software algorithm used time, temperature and reflected light spectral data to determine the location of the ingestible device as it traveled the GI tract. The ingestible device is 0.51×1.22 inches which is larger than a vitamin pill which is 0.4×0.85 inches. The subjects fasted overnight before participating in the study. Computerized tomography ("CT") were used as a basis for determining the accuracy of the localization data collected with TLC1. One of the 20 subjects did not follow the fasting rule. CT data was lacking for another one of the 20 subjects. Thus, these two subjects were excluded from further analysis. TLC1 sampled RGB data (radially transmitted) every 15 seconds for the first 14 hours after it entered the subject's stomach, and then samples every five minutes after that until battery dies. TLC1 did not start to record optical data until it reached the subject's stomach. Thus, there was no RGB-based data for the mouth-esophagus transition for any of the subjects.

In addition, a PillCam® SB (Given Imaging) device was tested on 57 subjects. The subjects fasted overnight before joining the study. PillCam videos were recorded within each subject. The sampling frequency of PillCam is velocity dependent. The faster PillCam travels, the faster it would sample data. Each video is about seven to eight hours long, starting from when the ingestible device was administrated into the subject's mouth. RGB optical data were recorded in a table. A physician provided notes on where stomach-duodenum transition and ileum-cecum transition occured in each video. Computerized tomography ("CT") was used as a basis for determining the accuracy of the localization data collected with PillCam.

Esophagus-Stomach Transition

For TLC1, it was assumed that this transition occurred one minute after the patient ingested the device. For PillCam, the algorithm was as follows:
1. Start mouth-esophagus transition detection after ingestible device is activated/administrated
2. Check whether Green<102.3 and Blue<94.6
   a. If yes, mark as mouth-esophagus transition
   b. If no, continue to scan the data
3. After detecting mouth-esophagus transition, continue to monitor Green and Blue signals for another 30 seconds, in case of location reversal
   a. If either Green>110.1 or Blue>105.5, mark it as mouth-esophagus location reversal
   b. Reset the mouth-esophagus flag and loop through step 2 and 3 until the confirmed mouth-esophagus transition detected
4. Add one minute to the confirmed mouth-esophagus transition and mark it as esophagus-stomach transition For one of the PillCam subjects, there was not a clear cut difference between the esophagus and stomach, so this subject was excluded from future analysis of stomach localization. Among the 56 valid subjects, 54 of them have correct esophagus-stomach transition localization. The total agreement is 54/56=96%. Each of the two failed cases had prolonged esophageal of greater than one minute. Thus, adding one minute to mouth-esophagus transition was not enough to cover the transition in esophagus for these two subjects.

Stomach-Duodenum

For both TLC1 and PillCam, a sliding window analysis was used. The algorithm used a dumbbell shape two-sliding-window approach with a two-minute gap between the front (first) and back (second) windows. The two-minute gap was designed, at least in part, to skip the rapid transition from stomach to small intestine and capture the small intestine signal after ingestible device settles down in small intestine. The algorithm was as follows:

1. Start to check for stomach-duodenum transition after ingestible device enters stomach
2. Setup the two windows (front and back)
   a. Time length of each window: 3 minutes for TLC1; 30 seconds for PillCam
   b. Time gap between two windows: 2 minutes for both devices
   c. Window sliding step size: 0.5 minute for both devices
3. Compare signals in the two sliding windows
   a. If difference in mean is higher than 3 times the standard deviation of Green/Blue signal in the back window
      i. If this is the first time ever, record the mean and standard deviation of signals in the back window as stomach reference
      ii. If mean signal in the front window is higher than stomach reference signal by a certain threshold (0.3 for TLC1 and 0.18 for PillCam), mark this as a possible stomach-duodenum transition
   b. If a possible pyloric transition is detected, continue to scan for another 10 minutes in case of false positive flag
      i. If within this 10 minutes, location reversal is detected, the previous pyloric transition flag is a false positive flag. Clear the flag and continue to check
      ii. If no location reversal has been identified within 10 minutes following the possible pyloric transition flag, mark it as a confirmed pyloric transition
   c. Continue monitoring Green/Blue data for another 2 hours after the confirmed pyloric transition, in case of location reversal
      i. If a location reversal is identified, flag the timestamp when reversal happened and then repeat steps a-c to look for the next pyloric transition
      ii. If the ingestible device has not gone back to stomach 2 hours after previously confirmed pyloric transition, stops location reversal monitoring and assume the ingestible device would stay in intestinal area For TLC1, one of the 18 subjects had too few samples (<3 minutes) taken in the stomach due to the delayed esophagus-stomach transition identification by previously developed localization algorithm. Thus, this subject was excluded from the stomach-duodenum transition algorithm test. For the rest of the TLC1 subjects, CT images confirmed that the detected pyloric transitions for all the subjects were located somewhere between stomach and jejunum. Two out of the 17 subjects showed that the ingestible device went back to stomach after first the first stomach-duodenum transition. The total agreement between the TLC1 algorithm detection and CT scans was 17/17=100%.

For one of the PillCam subjects, the ingestible device stayed in the subject's stomach all the time before the video ended. For another two of the PillCam subjects, too few samples were taken in the stomach to run the localization algorithm. These three PillCam subjects were excluded from the stomach-duodenum transition localization algorithm performance test. The performance summary of pyloric transition localization algorithm for PillCam was as follows:

1. Good cases (48 subjects):
   a. For 25 subjects, our detection matches exactly with the physician's notes
   b. For 19 subjects, the difference between the two detections is less than five minutes
   c. For four subjects, the difference between the two detections is less than 10 minutes (The full transition could take up to 10 minutes before the G/B signal settled)
2. Failed cases (6 subjects):
   a. Four subjects had high standard deviation of Green/Blue signal in the stomach
   b. One subject had bile in the stomach, which greatly affected Green/Blue in stomach
   c. One subject had no Green/Blue change at pyloric transition The total agreement for the PillCam stomach-duodenum transition localization algorithm detection and physician's notes was 48/54=89%.

Duodenum-Jejenum Transition

For TLC1, it was assumed that the device left the duodenum and entered the jejenum three minutes after it was determined that the device entered the duodenum. Of the 17 subjects noted above with respect to the TLC1 investigation of the stomach-duodenum transition, 16 of the subjects mentioned had CT images that confirmed that the duodenum-jejenum transition was located somewhere between stomach and jejunum. One of the 17 subjects had a prolonged transit time in duodenum. The total agreement between algorithm detection and CT scans was 16/17=94%.

For PillCam, the duodenum-jejenum transition was not determined.

Jejenum-Ileum Transition

It is to be noted that the jejunum is redder and more vascular than ileum, and that the jejunum has a thicker intestine wall with more mesentery fat. These differences can cause various optical responses between jejunum and ileum, particularly for the reflected red light signal. For both TLC1 and PillCam, two different approaches were explored to track the change of red signal at the jejunum-ileum transition. The first approach was a single-sliding-window analysis, where the window is 10 minutes long, and the mean signal was compared with a threshold value while the window was moving along. The second approach was a two-sliding-window analysis, where each window was 10 minutes long with a 20 minute spacing between the two windows. The algorithm for the jejunum-ileum transition localization was as follows:

1. Obtain 20 minutes of Red signal after the duodenum-jejenum transition, average the data and record it as the jejunum reference signal
2. Start to check the jejunum-ileum transition 20 minutes after the device enters the jejunum
   a. Normalize the newly received data by the jejunum reference signal
   b. Two approaches:
      i. Single-sliding-window analysis
         Set the transition flag if the mean of reflected red signal is less than 0.8
      ii. Two-sliding-window analysis:
         Set the transition flag if the mean difference in reflected red is higher than 2× the standard deviation of the reflected red signal in the front window For TLC1, 16 of the 18 subjects had CT images that confirmed that the detected jejunum-ileum transition fell between jejunum and cecum. The total agreement between algorithm and CT scans was 16/18=89%. This was true for both the single-sliding-window and double-sliding-window approaches, and the same two subjects failed in both approaches.

The performance summary of the jejunum-ileum transition detection for PillCam is listed below:
1. Single-sliding-window analysis:
    a. 11 cases having jejunum-ileum transition detected somewhere between jejunum and cecum
    b. 24 cases having jejunum-ileum transition detected after cecum
    c. 19 cases having no jejunum-ileum transition detected
    d. Total agreement: 11/54=20%
2. Two-sliding-window analysis:
    a. 30 cases having jejunum-ileum transition detected somewhere between jejunum and cecum
    b. 24 cases having jejunum-ileum transition detected after cecum
    c. Total agreement: 30/54=56%

Ileum-Cecum Transition

Data demonstrated that, for TLC1, mean signal of reflected red/green provided the most statistical difference before and after the ileum-cecum transition. Data also demonstrated that, for TLC1, the coefficient of variation of reflected green/blue provided the most statistical contrast at ileum-cecum transition. The analysis based on PillCam videos showed very similar statistical trends to those results obtained with TLC1 device. Thus, the algortithm utilized changes in mean value of reflected red/green and the coefficient of variation of reflected green/blue. The algorithm was as follows:
1. Start to monitor ileum-cecum transition after the ingestible device enters the stomach
2. Setup the two windows (front (first) and back (second))
    a. Use a five-minute time length for each window
    b. Use a 10-minute gap between the two windows
    c. Use a one-minute window sliding step size
3. Compare signals in the two sliding windows
    a. Set ileum-cecum transition flag if
        i. Reflected red/green has a significant change or is lower than a threshold
        ii. Coefficient of variation of reflected green/blue is lower than a threshold
    b. If this is the first ileum-cecum transition detected, record average reflected red/green signal in small intestine as small intestine reference signal
    c. Mark location reversal (i.e. ingestible device returns to terminal ileum) if
        i. Reflected red/green is statistically comparable with small intestine reference signal
        ii. Coefficient of variation of reflected green/blue is higher than a threshold
    d. If a possible ileum-cecum transition is detected, continue to scan for another 10 minutes for TLC1 (15 minutes for PillCam) in case of false positive flag
        i. If within this time frame (10 minutes for TLC1, 15 minutes for PillCam), location reversal is detected, the previous ileum-cecum transition flag is a false positive flag. Clear the flag and continue to check
        ii. If no location reversal has been identified within this time frame (10 minutes for TLC1, 15 minutes for PillCam) following the possible ileum-cecum transition flag, mark it as a confirmed ileum-cecum transition
    e. Continue monitoring data for another 2 hours after the confirmed ileum-cecum transition, in case of location reversal
        i. If a location reversal is identified, flag the timestamp when reversal happened and then repeat steps a-d to look for the next ileum-cecum transition
        ii. If the ingestible device has not gone back to small intestine 2 hours after previously confirmed ileum-cecum transition, stop location reversal monitoring and assume the ingestible device would stay in large intestinal area The flag setting and location reversal criteria particularly designed for TLC1 device were as follows:
1. Set ileum-cecum transition flag if
    a. The average reflected red/Green in the front window is less than 0.7 or mean difference between the two windows is higher than 0.6
    b. And the coefficient of variation of reflected green/blue is less than 0.02
2. Define as location reversal if
    a. The average reflected red/green in the front window is higher than small intestine reference signal
    b. And the coefficient of variation of reflected green/blue is higher than 0.086

For TLC1, 16 of the 18 subjects had CT images that confirmed that the detected ileum-cecum transition fell between terminal ileum and colon. The total agreement between algorithm and CT scans was 16/18=89%. Regarding those two subject where the ileum-cecum transition localization algorithm failed, for one subject the ileum-cecum transition was detected while TLC1 was still in the subject's terminal ileum, and for the other subject the ileum-cecum transition was detected when the device was in the colon.

Among the 57 available PillCam endoscopy videos, for three subjects the endoscopy video ended before PillCam reached cecum, and another two subjects had only very limited video data (less than five minutes) in the large intestine. These five subjects were excluded from ileum-cecum transition localization algorithm performance test. The performance summary of ileum-cecum transition detection for PillCam is listed below:
1. Good cases (39 subjects):
    a. For 31 subjects, the difference between the PillCam detection and the physician's notes was less than five minutes
    b. For 3 subjects, the difference between the PillCam detection and the physician's notes was less than 10 minutes
    c. For 5 subjects, the difference between the PillCam detection and the physician's notes was less than 20 minutes (the full transition can take up to 20 minutes before the signal settles)
2. Marginal/bad cases (13 subjects):
    a. Marginal cases (9 subjects)
        i. The PillCam ileum-cecum transition detection appeared in the terminal ileum or colon, but the difference between the two detections was within one hour
    b. Failed cases (4 subjects)
        i. Reasons of failure:
            1. The signal already stabilized in the terminal ileum 2. The signal was highly variable from the entrance to exit
3. There was no statistically significant change in reflected red/green at ileum-cecum transition The total agreement between ileocecal transition localization algorithm detection and the physician's notes is 39/52=75% if considering good cases only. Total agreement including possibly acceptable cases is 48/52=92.3%

Cecum-Colon Transition

Data demonstrated that, for TLC1, mean signal of reflected red/green provided the most statistical difference before and after the cecum-colon transition. Data also demonstrated that, for TLC1, the coefficient of variation of reflected bluee provided the most statistical contrast at cecum-colon transition. The same signals were used for PillCam. The cecum-colon transition localization algorithm was as follows:
1. Obtain 10 minutes of reflected red/green and reflected blue signals after ileum-cecum transition, average the data and record it as the cecum reference signals
2. Start to check cecum-colon transition after ingestible device enters cecum (The cecum-colon transition algorithm is dependent on the ileum-cecum transition flag)
   a. Normalize the newly received data by the cecum reference signals
   b. Two-sliding-window analysis:
      i. Use two adjacent 10 minute windows
      ii. Set the transition flag if any of the following criteria were met
         The mean difference in reflected red/green was more than 4× the standard deviation of reflected red/green in the back (second) window
         The mean of reflected red/green in the front (first) window was higher than 1.03
         The coefficient of variation of reflected blue signal in the front (first) window was greater than 0.23

The threshold values above were chosen based on a statistical analysis of data taken by TLC1.

For TLC1, 15 of the 18 subjects had the cecum-colon transition detected somewhere between cecum and colon. One of the subjects had the cecum-colon transition detected while TLC1 was still in cecum. The other two subjects had both wrong ileum-cecum transition detection and wrong cecum-colon transition detection. The total agreement between algorithm and CT scans was 15/18=83%.

For PillCam, for three subjects the endoscopy video ended before PillCam reached cecum, and for another two subjects there was very limited video data (less than five minutes) in the large intestine. These five subjects were excluded from cecum-colon transition localization algorithm performance test. The performance summary of cecum-colon transition detection for PillCam is listed below:
1. 27 cases had the cecum-colon transition detected somewhere between the cecum and the colon
2. one case had the cecum-colon transition detected in the ileum
3. 24 cases had no cecum-colon transition localized The total agreement: 27/52=52%.
The following table summarizes the localization accuracy results.

| Transition | TLC1 | PillCam |
| --- | --- | --- |
| Stomach-Duodenum | 100% (17/17) | 89% (48/54) |
| Duodenum-Jejenum | 94% (16/17) | N/A |
| Ileum-Cecum | 89% (16/18) | 75% (39/52) |
| Ileum-terminal ileum/cecum/colon | 100% (18/18) | 92% (48/52) |

Exemplary Embodiments

The following exemplary embodiments 1)-94) are provided herein:

1) A method of treating a disease of the gastro-intestinal tract in a subject, comprising:
delivering a JAK inhibitor at a location in the gastrointestinal tract of the subject, wherein the method comprises administering orally to the subject a pharmaceutical composition comprising a therapeutically effective amount of the JAK inhibitor.

2) The method of exemplary embodiment 1, wherein the disease of the GI tract is an inflammatory bowel disease.

3) The method of exemplary embodiment 1, wherein the disease of the GI tract is ulcerative colitis.

4) The method of exemplary embodiment 1, wherein the disease of the GI tract is Crohn's disease.

5) The method of any one of exemplary embodiments 1, 2, or 3, 4, wherein the JAK inhibitor is delivered at a location in the large intestine of the subject.

6) The method of exemplary embodiment 5, wherein the location is in the proximal portion of the large intestine.

7) The method of exemplary embodiment 5, wherein the location is in the distal portion of the large intestine.

8) The method of any one of exemplary embodiments 1, 2, or 3, 4, wherein the JAK inhibitor is delivered at a location in the ascending colon of the subject.

9) The method of exemplary embodiment 8, wherein the location is in the proximal portion of the ascending colon.

10) The method of exemplary embodiment 8, wherein the location is in the distal portion of the ascending colon.

11) The method of any one of exemplary embodiments 1, 2, or 3, 4, wherein the JAK inhibitor is delivered at a location in the cecum of the subject.

12) The method of exemplary embodiment 11, wherein the location is in the proximal portion of the cecum.

13) The method of exemplary embodiment 11, wherein the location is in the distal portion of the cecum.

14) The method of any one of exemplary embodiments 1, 2, or 3, 4, wherein the JAK inhibitor is delivered at a location in the sigmoid colon of the subject.

15) The method of exemplary embodiment 14, wherein the location is in the proximal portion of the sigmoid colon.

16) The method of exemplary embodiment 14, wherein the location is in the distal portion of the sigmoid colon.

17) The method of any one of exemplary embodiments 1, 2, or 3, 4, wherein the JAK inhibitor is delivered at a location in the transverse colon of the subject.

18) The method of exemplary embodiment 17, wherein the location is in the proximal portion of the transverse colon.

19) The method of exemplary embodiment 17, wherein the location is in the distal portion of the transverse colon.

20) The method of any one of exemplary embodiments 1, 2, or 3, 4, wherein the JAK inhibitor is delivered at a location in the descending colon of the subject.

21) The method of exemplary embodiment 20, wherein the location is in the proximal portion of the descending colon.

22) The method of exemplary embodiment 20, wherein the location is in the distal portion of the descending colon.

23) The method of any one of exemplary embodiments 1, 2, or 3, 4, wherein the JAK inhibitor is delivered at a location in the small intestine of the subject.

24) The method of exemplary embodiment 23, wherein the location is in the proximal portion of the small intestine.

25) The method of exemplary embodiment 23, wherein the location is in the distal portion of the small intestine.

26) The method of any one of exemplary embodiments 1, 2, or 3, 4, wherein the JAK inhibitor is delivered at a location in the duodenum of the subject.

27) The method of exemplary embodiment 26, wherein the location is in the proximal portion of the duodenum.

28) The method of exemplary embodiment 26, wherein the location is in the distal portion of the duodenum.

29) The method of any one of exemplary embodiments 1, 2, or 3, 4, wherein the JAK inhibitor is delivered at a location in the jejunum of the subject.

30) The method of exemplary embodiment 29, wherein the location is in the proximal portion of the jejunum.

31) The method of exemplary embodiment 29, wherein the location is in the distal portion of the jejunum.

32) The method of any one of exemplary embodiments 1, 2, or 3, 4, wherein the JAK inhibitor is delivered at a location in the ileum of the subject.

33) The method of exemplary embodiment 32, wherein the location is in the proximal portion of the ileum.

34) The method of exemplary embodiment 32, wherein the location is in the distal portion of the ileum.

35) The method of any one of the preceding exemplary embodiments, wherein the location is proximate to one or more sites of disease.

36) The method of exemplary embodiment 35, further comprising identifying the one or more sites of disease by a method comprising imaging of the gastrointestinal tract.

37) The method of any one of the preceding exemplary embodiments, wherein the JAK inhibitor is delivered to the location by mucosal contact.

38) The method of any one of the preceding exemplary embodiments, wherein the JAK inhibitor is delivered to the location by a process that does not comprise systemic transport of the JAK inhibitor.

39) The method of any one of the preceding exemplary embodiments, wherein the amount of the JAK inhibitor that is administered is from about 1 mg to about 300 mg.

40) The method of exemplary embodiment 39, wherein the amount of the JAK inhibitor that is administered is from about 1 mg to about 100 mg.

41) The method of exemplary embodiment 40, wherein the amount of the JAK inhibitor that is administered is from about 5 mg to about 40 mg.

42) The method of any one of exemplary embodiments 1 to 41, wherein the amount of the JAK inhibitor is less than an amount that is effective when the JAK inhibitor is administered systemically.

43) The method of any one of the preceding exemplary embodiments, comprising administering (i) an amount of the JAK inhibitor that is an induction dose.

44) The method of exemplary embodiment 43, further comprising (ii) administering an amount of the JAK inhibitor that is a maintenance dose following the administration of the induction dose.

45) The method of exemplary embodiment 43 or 44, wherein the induction dose is administered once a day.

46) The method of exemplary embodiment 43 or 44, wherein the induction dose is administered once every three days.

47) The method of exemplary embodiment 43 or 44, wherein the induction dose is administered once a week.

48) The method of exemplary embodiment 44, wherein step (ii) is repeated one or more times.

49) The method of exemplary embodiment 44, wherein the induction dose is equal to the maintenance dose.

50) The method of exemplary embodiment 44, wherein the induction dose is greater than the maintenance dose.

51) The method of exemplary embodiment 44, wherein the induction dose is 5 greater than the maintenance dose.

52) The method of exemplary embodiment 44, wherein the induction dose is 2 greater than the maintenance dose.

53) The method of any one of the preceding exemplary embodiments, wherein the method comprises delivering the JAK inhibitor at the location in the gastrointestinal tract as a single bolus.

54) The method of any one of exemplary embodiments 1 to 52, wherein the method comprises delivering the JAK inhibitor at the location in the gastrointestinal tract as more than one bolus.

55) The method of any one of exemplary embodiments 1 to 52, wherein the method comprises delivering the JAK inhibitor at the location in the gastrointestinal tract in a continuous manner.

56) The method of exemplary embodiment 55, wherein the method comprises delivering the JAK inhibitor at the location in the gastrointestinal tract over a time period of 20 or more minutes.

57) The method of any one of the preceding exemplary embodiments, wherein the method provides a concentration of the JAK inhibitor in the plasma of the subject that is less than 3 µg/ml.

58) The method of exemplary embodiment 57, wherein the method provides a concentration of the JAK inhibitor in the plasma of the subject that is less than 0.3 µg/ml.

59) The method of exemplary embodiment 58, wherein the method provides a concentration of the JAK inhibitor in the plasma of the subject that is less than 0.01 µg/ml.

60) The method of any one of exemplary embodiments 1 to 59, wherein the method does not comprise delivering a JAK inhibitor rectally to the subject.

61) The method of any one of exemplary embodiments 1 to 59, wherein the method does not comprise delivering a JAK inhibitor via an enema to the subject.

62) The method of any one of exemplary embodiments 1 to 59, wherein the method does not comprise delivering a JAK inhibitor via suppository to the subject.

63) The method of any one of exemplary embodiments 1 to 59, wherein the method does not comprise delivering a JAK inhibitor via instillation to the rectum of the subject.

64) The method of exemplary embodiment 63, wherein the JAK inhibitor is a JAK1 inhibitor.

65) The method of exemplary embodiment 63, wherein the JAK inhibitor is selected from tofacitinib (Xeljanz®), filgotinib (GLPG0634, Galapagos NV); TD-1473 (Theravance Biopharma, Inc.); ruxolitinib; and generic equivalents thereof.

66) The method of any one of the preceding exemplary embodiments, wherein the pharmaceutical composition is an ingestible device, comprising:

a housing defined by a first end, a second end substantially opposite from the first end, and a wall extending longitudinally from the first end to the second end;

a storage reservoir located within the housing and containing the JAK inhibitor,
a first end of the storage reservoir is connected to the first end of the housing;
a mechanism for releasing the JAK inhibitor from the storage reservoir;
and;
an exit valve configured to allow the JAK inhibitor to be released out of the housing from the storage reservoir.

67) The method of exemplary embodiment 66, wherein the ingestible device further comprises:
an electronic component located within the housing; and
a gas generating cell located within the housing and adjacent to the electronic component,
wherein the electronic component is configured to activate the gas generating cell to generate gas.

68) The method of exemplary embodiment 66 or 67, wherein the ingestible device further comprises:
a safety device placed within or attached to the housing,
wherein the safety device is configured to relieve an internal pressure within the housing when the internal pressure exceeds a threshold level.

69) The method of exemplary embodiment 66, wherein the pharmaceutical composition is an ingestible device, comprising:
a housing defined by a first end, a second end substantially opposite from the first end, and a wall extending longitudinally from the first end to the second end;
an electronic component located within the housing;
a gas generating cell located within the housing and adjacent to the electronic component,
wherein the electronic component is configured to activate the gas generating cell to generate gas;
a storage reservoir located within the housing,
wherein the storage reservoir stores a dispensable substance and a first end of the storage reservoir is connected to the first end of the housing;
an exit valve located at the first end of the housing,
wherein the exit valve is configured to allow the dispensable substance to be released out of the first end of the housing from the storage reservoir; and
a safety device placed within or attached to the housing,
wherein the safety device is configured to relieve an internal pressure within the housing when the internal pressure exceeds a threshold level.

70) The method of exemplary embodiment 66, wherein the pharmaceutical composition is an ingestible device, comprising:
a housing defined by a first end, a second end substantially opposite from the first end, and a wall extending longitudinally from the first end to the second end;
an electronic component located within the housing,
a gas generating cell located within the housing and adjacent to the electronic component,
wherein the electronic component is configured to activate the gas generating cell to generate gas;
a storage reservoir located within the housing,
wherein the storage reservoir stores a dispensable substance and a first end of the storage reservoir is connected to the first end of the housing;
an injection device located at the first end of the housing,
wherein the jet injection device is configured to inject the dispensable substance out of the housing from the storage reservoir; and
a safety device placed within or attached to the housing,
wherein the safety device is configured to relieve an internal pressure within the housing.

71) The method of exemplary embodiment 66, wherein the pharmaceutical composition is an ingestible device, comprising:
a housing defined by a first end, a second end substantially opposite from the first end, and a wall extending longitudinally from the first end to the second end;
an optical sensing unit located on a side of the housing,
wherein the optical sensing unit is configured to detect a reflectance from an environment external to the housing;
an electronic component located within the housing;
a gas generating cell located within the housing and adjacent to the electronic component,
wherein the electronic component is configured to activate the gas generating cell to generate gas in response to identifying a location of the ingestible device based on the reflectance;
a storage reservoir located within the housing,
wherein the storage reservoir stores a dispensable substance and a first end of the storage reservoir is connected to the first end of the housing;
a membrane in contact with the gas generating cell and configured to move or deform into the storage reservoir by a pressure generated by the gas generating cell; and
a dispensing outlet placed at the first end of the housing,
wherein the dispensing outlet is configured to deliver the dispensable substance out of the housing from the storage reservoir.

72) The method of any one of exemplary embodiments 1-71, wherein the pharmaceutical composition is an ingestible device as disclosed in U.S. Patent Application Ser. No. 62/385,553, incorporated by reference herein in its entirety.

73) The method of any one of exemplary embodiments 1-71, wherein the pharmaceutical composition is an ingestible device comprising a localization mechanism as disclosed in international patent application PCT/US2015/052500, incorporated by reference herein in its entirety.

74) The method of any one of exemplary embodiments 1-73, wherein the pharmaceutical composition is not a dart-like dosage form.

75) A method of treating a disease of the large intestine of a subject, comprising:
delivering of a JAK inhibitor at a location in the proximal portion of the large intestine of the subject,
wherein the method comprises administering endoscopically to the subject a therapeutically effective amount of the JAK inhibitor.

76) The method of exemplary embodiment 75, wherein the disease of the large intestine is an inflammatory bowel disease.

77) The method of exemplary embodiment 75, wherein the disease of the large intestine is ulcerative colitis.

78) The method of exemplary embodiment 75, wherein the disease the large intestine is Crohn's disease.

79) The method of any one of exemplary embodiments 75 to 78, wherein the JAK inhibitor is delivered at a location in the proximal portion of the ascending colon.

80) The method of any one of exemplary embodiments 75 to 78, wherein the JAK inhibitor is delivered at a location in the proximal portion of the cecum.

81) The method of any one of exemplary embodiments 75 to 78, wherein the JAK inhibitor is delivered at a location in the proximal portion of the sigmoid colon.

82) The method of any one of exemplary embodiments 75 to 78, wherein the JAK inhibitor is delivered at a location in the proximal portion of the transverse colon.

83) The method of any one of exemplary embodiments 75 to 78, wherein the JAK inhibitor is delivered at a location in the proximal portion of the descending colon.

84) The method of any one of the preceding exemplary embodiments, further comprising administering a second agent orally, intravenously or subcutaneously, wherein the second agent is the same JAK inhibitor as in exemplary embodiment 1 or 75; a different JAK inhibitor; or an agent having a different biological target from JAK.

85) The method of any one of the preceding exemplary embodiments, further comprising administering a second agent orally, intravenously or subcutaneously, wherein the second agent is an agent suitable for treating an inflammatory bowel disease.

86) The method of exemplary embodiment 84 or 85, wherein the JAK inhibitor is administered prior to the second agent.

87) The method of exemplary embodiment 84 or 85, wherein the JAK inhibitor is administered after the second agent.

88) The method of exemplary embodiment 84 or 85, wherein the JAK inhibitor and the second agent are administered substantially at the same time.

89) The method of any one of exemplary embodiments 84 to 88, wherein the second agent is administered intravenously.

90) The method of any one of exemplary embodiments 84 to 88, wherein the second agent is administered subcutaneously.

91) The method of any one of exemplary embodiments 84 to 90, wherein the amount of the second agent is less than the amount of the second agent when the JAK inhibitor and the second agent are both administered systemically.

92) The method of exemplary embodiment 91, wherein the second agent is an immunosuppressant.

93) In some aspects of these embodiments, the second agent is methotrexate.

94) The method of any one of exemplary embodiments 1 to 83, wherein the method does not comprise Other Embodiments The various embodiments of systems, processes and apparatuses have been described herein by way of example only. It is contemplated that the features and limitations described in any one embodiment may be applied to any other embodiment herein, and flowcharts or examples relating to one embodiment may be combined with any other embodiment in a suitable manner, done in different orders, or done in parallel. It should be noted, the systems and/or methods described above may be applied to, or used in accordance with, other systems and/or methods. Various modifications and variations may be made to these example embodiments without departing from the spirit and scope of the embodiments, and the appended listing of embodiments should be given the broadest interpretation consistent with the description as a whole.

The invention claimed is:

1. A method of treating ulcerative colitis in a subject, the method comprising:

orally administering to the subject an ingestible device comprising:

an ingestible housing comprising a reservoir, the reservoir containing a pharmaceutical formulation comprising a therapeutically effective amount of a Janus Kinase (JAK) inhibitor;

a release mechanism having a closed state wherein the pharmaceutical formulation is retained in the reservoir and an open state which allows for the release of the pharmaceutical formulation from the reservoir to the exterior of the ingestible device;

an actuator which controls the transition of the release mechanism from the closed state to the open state;

a light source configured to produce light that interacts with the subject's gastrointestinal (GI) tract to provide light reflectance;

a detector configured to detect the light reflectance to detect the GI tract; and a processor coupled to the detector and to the actuator, wherein the processor triggers the actuator to cause the release mechanism to transition from the closed state to the open state when the ingestible device is located in the cecum based on the detected light reflectance, wherein the cecum has been predetermined to be proximal to one or more disease sites, thereby releasing the pharmaceutical formulation comprising the JAK inhibitor from the ingestible device when the ingestible device is located in the cecum of the subject, wherein the JAK inhibitor is selected from the group consisting of tofacitinib, filgotinib, TD-1473, ruxolitinib, cerdulatinib, momelotinib, oclacitinib, upadacitinib, lestaurtinib, decernotinib, pacritinib, cucurbitacin I, PF-06700841, PF-06651600, PF-04965842, and BMS-986165; and generic equivalents thereof.

2. The method of claim 1, wherein the one or more disease sites is in the colon.

3. The method of claim 1, wherein the JAK inhibitor is selected from the group consisting of tofacitinib, filgotinib, TD-1473 and ruxolitinib; and generic equivalents thereof.

4. The method of claim 1, wherein the JAK inhibitor is tofacitinib or a generic equivalent thereof.

5. The method of claim 1, wherein the ingestible device further comprises one or more machine-readable hardware storage devices that stores instructions that are executable by the processor to determine that the ingestible device is in the cecum of the subject to an accuracy of at least 70%.

6. The method of claim 1, wherein the method further comprises determining the location of the ingestible device in the cecum of the subject to an accuracy of at least 85%.

7. The method of claim 1, wherein the detected reflectance autonomously triggers the release of the pharmaceutical formulation comprising the JAK inhibitor from the ingestible device.

8. The method of claim 1, wherein the detected reflectance comprises light of at least two different wavelengths.

9. The method of claim 1, wherein determining the location of the ingestible device in the cecum comprises detecting a transition of the ingestible device from the ileum to the cecum.

10. The method of claim 9, wherein detecting the transition of the ingestible device from the ileum to the cecum comprises detecting a change in the ratio of reflected red light to reflected green light.

11. The method of claim 10, wherein detecting the transition of the ingestible device from the ileum to the cecum further comprises detecting a change in the ratio of reflected green light to reflected blue light.

12. The method of claim 1, wherein the ingestible device comprises a gas generating cell located within the housing, wherein the gas generating cell is capable of generating a gas; and the ingestible device is configured so that, when the gas generating cell generates the gas, the gas creates an internal pressure that forces a release mechanism from a closed state, which retains the JAK inhibitor in the reservoir, to an open state, thereby allowing for the release of the JAK inhibitor from the reservoir to the exterior of the device.

13. The method of claim 12, wherein the reservoir is configured to friction fit with the ingestible device.

14. The method of claim 12, wherein the reservoir is configured to attach to the housing of the ingestible device.

15. The method of claim 12, wherein the ingestible device comprises a safety device placed within or attached to the housing, wherein the safety device is configured to relieve the internal pressure within the housing when the internal pressure exceeds a threshold level.

16. The method of claim 1, further comprising releasing the pharmaceutical formulation comprising the JAK inhibitor to the cecum as a bolus.

17. The method of claim 1, further comprising determining the level of JAK inhibitor in the plasma of the subject following the oral administration of the ingestible device, wherein the level of JAK inhibitor is lower than the level of the JAK inhibitor in the plasma of a subject at substantially the same time point following systemic administration of an equal amount of the JAK inhibitor.

18. The method of claim 1, wherein releasing the JAK inhibitor from the ingestible device is not dependent on pH, enzymatic activity or bacterial activity at or in the vicinity of the predetermined location.

* * * * *